US012630547B2

(12) United States Patent
Chan et al.

(10) Patent No.: US 12,630,547 B2
(45) Date of Patent: May 19, 2026

(54) RAS PROTEIN DEGRADERS, PHARMACEUTICAL COMPOSITIONS THEREOF, AND THEIR THERAPEUTIC APPLICATIONS

(71) Applicant: BioTheryX, Inc., San Diego, CA (US)

(72) Inventors: Kyle W.H. Chan, San Diego, CA (US); Aparajita Hoskote Chourasia, San Diego, CA (US); Paul E. Erdman, San Diego, CA (US); Leah M. Fung, San Diego, CA (US); David Aaron Hecht, Chula Vista, CA (US); Imelda Lam, San Diego, CA (US); Frank Mercurio, Rancho Santa Fe, CA (US); Robert W. Sullivan, Vista, CA (US); Eduardo Torres, San Diego, CA (US)

(73) Assignee: BioTheryX, Inc., San Diego, CA (US)

( * ) Notice: Subject to any disclaimer, the term of this patent is extended or adjusted under 35 U.S.C. 154(b) by 1036 days.

(21) Appl. No.: 17/753,686

(22) PCT Filed: Sep. 14, 2020

(86) PCT No.: PCT/US2020/050611
§ 371 (c)(1),
(2) Date: Mar. 11, 2022

(87) PCT Pub. No.: WO2021/051034
PCT Pub. Date: Mar. 18, 2021

(65) Prior Publication Data

US 2023/0002371 A1 Jan. 5, 2023

Related U.S. Application Data

(60) Provisional application No. 62/941,599, filed on Nov. 27, 2019, provisional application No. 62/900,249, filed on Sep. 13, 2019.

(51) Int. Cl.

| | |
|---|---|
| ***C07D 471/04*** | (2006.01) |
| ***A61P 11/00*** | (2006.01) |
| ***A61P 35/00*** | (2006.01) |
| ***C07D 401/14*** | (2006.01) |
| ***C07D 405/14*** | (2006.01) |
| ***C07D 417/14*** | (2006.01) |
| ***C07D 471/14*** | (2006.01) |
| ***C07D 495/04*** | (2006.01) |

(52) U.S. Cl.
CPC ............ *C07D 471/04* (2013.01); *A61P 11/00* (2018.01); *A61P 35/00* (2018.01); *C07D 401/14* (2013.01); *C07D 405/14* (2013.01); *C07D 417/14* (2013.01); *C07D 471/14* (2013.01); *C07D 495/04* (2013.01)

(58) Field of Classification Search
CPC .. C07D 471/04; C07D 401/14; C07D 405/14; C07D 417/14; C07D 471/14; C07D 495/04; A61P 11/00; A61P 35/00
See application file for complete search history.

(56) References Cited

U.S. PATENT DOCUMENTS

| | | | | |
|---|---|---|---|---|
| 2018/0015087 | A1* | 1/2018 | Liu | A61K 31/517 |
| 2018/0170948 | A1* | 6/2018 | Chan | A61P 25/28 |
| 2019/0315732 | A1 | 10/2019 | Crew et al. | |
| 2020/0109149 | A1 | 4/2020 | Wang et al. | |

FOREIGN PATENT DOCUMENTS

| | | | | |
|---|---|---|---|---|
| CN | 101805390 A | | 8/2010 | |
| WO | 2018006801 A1 | | 1/2018 | |
| WO | 2018006804 A1 | | 1/2018 | |
| WO | WO-2018068017 A1 | * | 4/2018 | C07D 401/04 |
| WO | WO-2018140514 A1 | * | 8/2018 | A61P 35/00 |
| WO | WO-2019195609 A2 | * | 10/2019 | A61P 35/00 |

OTHER PUBLICATIONS

Bondeson et al., Annu Rev Pharmacol Toxicol, 2017, 57:107-123 (Year: 2017).*
Pettersson et al., Drug Discov Today Technol, 2019, 31:15-27 (Year: 2019).*
Cyrus et al., Chem Med Chem, 2010, 5:979-985 (Year: 2010).*
Berge et al., "Pharmaceutical salts," J. Pharm. Sci. 1977, 66, 1-19.
Cox et al., "Drugging the undruggable RAS: Mission possible?" Nat. Rev. Drug Discov. 2014, 13, 828-51.
Fang et al., "Small-molecule MDM2/X inhibitors and PROTAC degraders for cancer therapy: advances and perspectives," Acta Pharm. Sin. B 2020, 10, 1253-78.
Janes et al., "Targeting KRAS mutant cancers with a covalent G12C-specific inhibitor," Cell 2018, 172, 578-89.
Milburn et al., "Molecular switch for signal transduction: structural differences between active and inactive forms of protooncogenic ras proteins," Science 1990, 247, 939-45.
Papke and Der, "Drugging RAS: Know the enemy," Science 2017, 355, 1158-63.
Rebocho and Marais, "New insight puts CRAF in sight as a therapeutic target," Cancer Discov. 2011, 1, 98-9.
Santana-Codina et al., "Defining and targeting adaptations to oncogenic Kras G12C inhibition using quantitative temporal proteomics," Cell Rep. 2020, 30, 4584-99.
Simanshu et al., "RAS proteins and their regulators in human disease," Cell 2017, 170, 17-33.

(Continued)

*Primary Examiner* — Andrew D Kosar
*Assistant Examiner* — Jonathan D Mahlum
(74) *Attorney, Agent, or Firm* — Juniv LLP; Lin Yu

(57) ABSTRACT

Provided herein are RAS protein degraders, e.g., a compound of Formula (I), and pharmaceutical compositions thereof. Also provided herein are methods of their use for treating, preventing, or ameliorating one or more symptoms of a RAS-mediated disorder, disease, or condition.

$$R^{Het}\text{-}L^2\text{-}X\text{-}L^1\text{-}R^1 \quad (I)$$

29 Claims, No Drawings

(56) References Cited

OTHER PUBLICATIONS

Uras et al., ", Targeting KRAS mutant non-small-cell lung cancer: past, present and future," Int. J. Mol. Sci. 2020, 21, 4325.
Wang et al., "Degradation of proteins by PROTACs and other strategies," Acta Pharm. Sin. B 2020, 10, 207-38.
Zeng et al., "Exploring targeted degradation strategy for oncogenic KRAS G12C," Cell Chem. Biol. 2020, 27, 19-31.
Chen et al., "SAR study of celastrol analogs targeting Nur77-mediated inflammatory pathway," Eur. J. Med. Chem. 2019, 177, 171-87.
Cho et al., "Nur77 agonists induce proapoptotic genes and responses in colon cancer cells through nuclear receptor-dependent and nuclear receptor-independent pathways," Cancer Res. 2007, 67, 674-83.
Lee et al., "The nuclear receptor TR3 regulates mTORC1 signaling in lung cancer cells expressing wild-type p53," Oncogene 2012, 31, 3265-76.
Pearen and Muscat, "Minireview: Nuclear hormone receptor 4A signaling: implications for metabolic disease," Mol. Endocrinol. 2010, 24, 1891-903.
Safe et al., "Minireview: role of orphan nuclear receptors in cancer and potential as drug targets," Mol. Endocrinol. 2014, 28, 157-72.
Wang et al., "Orphan nuclear receptor Nur77 promotes colorectal cancer invasion and metastasis by regulating MMP-9 and E-cadherin," Carcinogenesis 2014, 35, 2474-84.
Wu and Chen, "Characteristics of Nur77 and its ligands as potential anticancer compounds (Review)," Mol. Med. Rep. 2018, 18, 4793-801.
Zhang, "Targeting Nur77 translocation," Expert Opin. Ther. Targets 2007, 11, 69-79.
Zheng et al., "Orphan nuclear receptor TR3/Nur77 is a specific therapeutic target for hepatic cancers," J. Clin. Exp. Oncol. 2017, 6, 184.
Zhou et al., "Nuclear receptor NR4A1 promotes breast cancer invasion and metastasis by activating TGF-β signalling," Nat. Commun. 2014, 5, 3388.

* cited by examiner

RAS PROTEIN DEGRADERS, PHARMACEUTICAL COMPOSITIONS THEREOF, AND THEIR THERAPEUTIC APPLICATIONS

CROSS REFERENCE TO RELATED APPLICATIONS

This application is a National Stage of International Application No. PCT/US2020/050611, filed Sep. 14, 2020; which claims the benefit of U.S. Provisional Application Nos. 62/900,249, filed Sep. 13, 2019, and 62/941,599, filed Nov. 27, 2019; the disclosure of each of which is incorporated herein by reference in its entirety.

FIELD

Provided herein are RAS protein degraders and pharmaceutical compositions thereof. Also provided herein are methods of their use for treating, preventing, or ameliorating one or more symptoms of a RAS-mediated disorder, disease, or condition.

BACKGROUND

The three RAS oncogenes, KRAS, NRAS, and NRAS, are from the most frequently mutated oncogene family in cancer. Milburn et al, *Science* 1990, 247, 939-945; Cox et al., *Nat. Rev. Drug Discov.* 2014, 13, 828-851; Papke and Der, *Science* 2017, 355, 1158-1163. RAS mutations have been detected in up to 30% of all human cancer. Cox et al., *Nat. Rev. Drug Discov.* 2014. RAS mutations are found in about 95% of pancreatic ductal adenocarcinomas (PDACs), about 50% of colorectal adenocarcinomas (CRCs), and about 30% of lung adenocarcinomas (CACs). Papke and Der, *Science* 2017, 355, 1158-1163. Among the three, KRAS mutations are the most common and alone account for about a million death per year worldwide. Cox et al., *Nat. Rev. Drug Discov.* 2014, 13, 828-851; Simanshu et al., *Cell* 2017, 170, 17-33. KRAS G12C, in particular, accounts for 44% of all non-small cell lung cancer (NSCLC) bearing a KRAS mutation. Santana-Codina et al., *Cell Rep.* 2020, 30, 4584-99.

A RAS protein is a small GTPase encoded by a RAS oncogene. Papke and Der, *Science* 2017, 355, 1158-1163. The RAS protein functions as a molecular switch cycling between the active guanosine triphosphate (GTP)-bound and inactive guanosine diphosphate (GDP)-bound states. Milburn et al, *Science* 1990, 247, 939-945. The GTP-bound active RAS activates downstream effector pathways, including rat fibrosarcoma/mitogen-activated protein kinase kinase/extracellular regulated kinase (RAF/MEK/ERK) and phosphoinositide 3-kinase/protein kinase B/mechanistic target of rapamycin kinase (PI3K/AKT/mTOR). Rebocho and Marais, *Cancer Discov.* 2011, 1, 98-99. Oncogenic mutations in RAS proteins impair their ability for GTP hydrolysis, resulting in the accumulation of GTP-bound active RAS and hyperactivation of downstream signaling cascades that lead to uncontrolled cell proliferation and survival. Uras et al., *Int. J. Mol. Sci.* 2020, 21, 4325.

Despite the recognition of the prevalence of RAS mutations in cancer and intensive drug discovery efforts for decades, no RAS-targeted therapy has been approved. Cox et al., *Nat. Rev. Drug Discov.* 2014, 13, 828-851. Therefore, there is a need for an effective therapy for cancer treatment.

SUMMARY OF THE DISCLOSURE

Provided herein are bifunctional compounds that are useful to reduce the cellular level of a RAS (such as KRAS, HRAS, and NRAS) and/or inhibit the activities of the RAS. In addition, the compounds provided herein are capable of modulating protein function and/or protein levels to restore protein homeostasis.

Provided herein is a compound of Formula (I):

$$R^{Het}\text{-}L^2\text{-}X\text{-}L^1\text{-}R^1 \quad (I)$$

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is

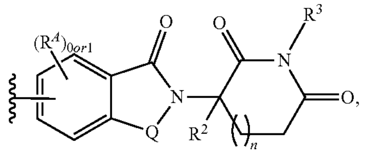

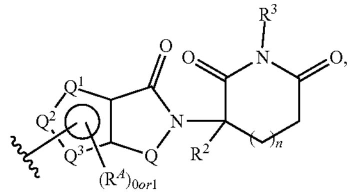

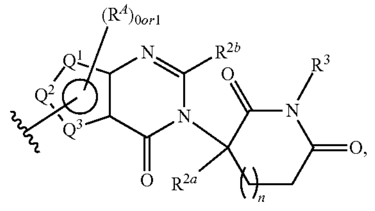

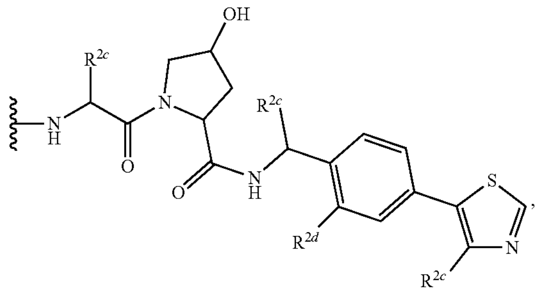

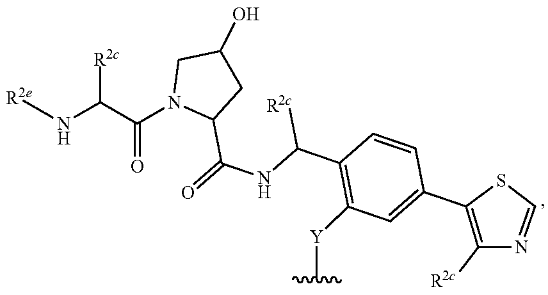

, or

-continued
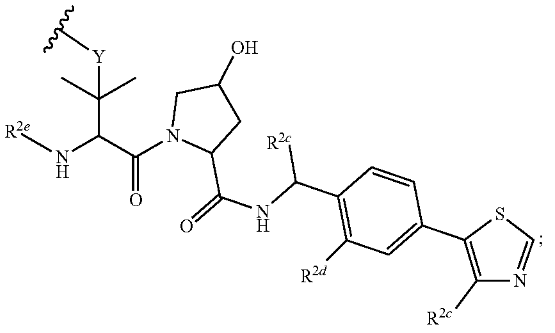
$R^{Het}$ is
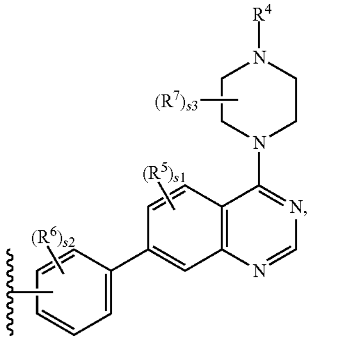
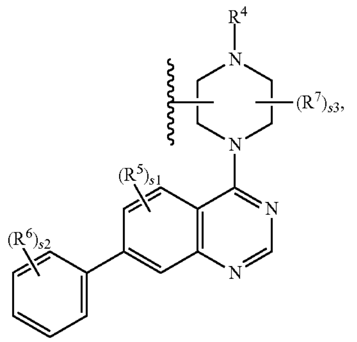
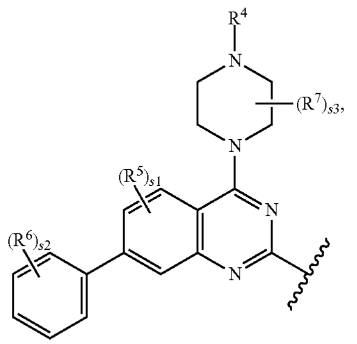
-continued
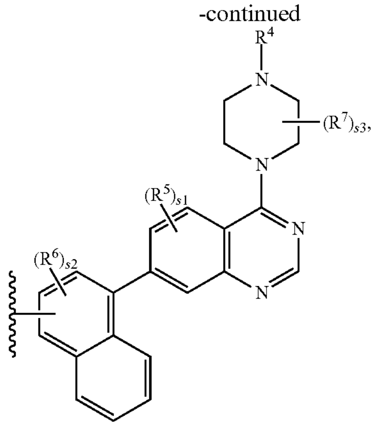
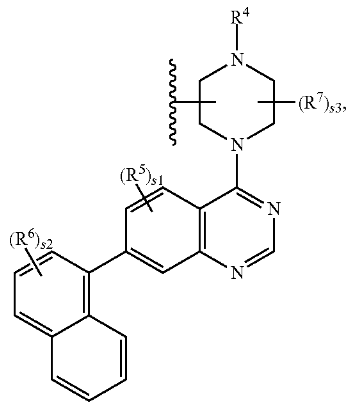
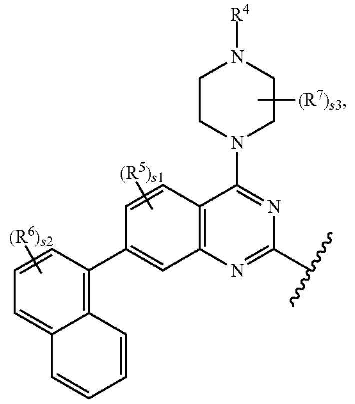
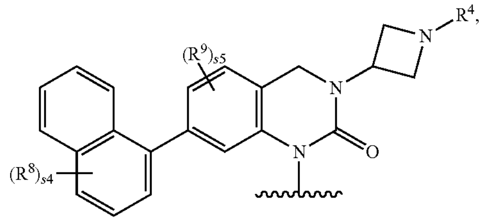
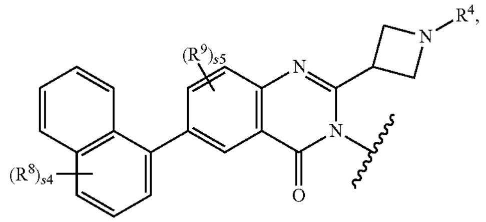

-continued
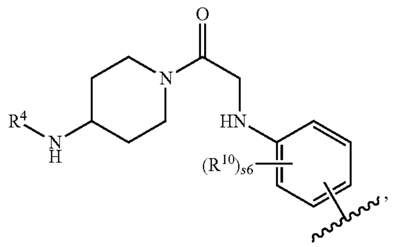
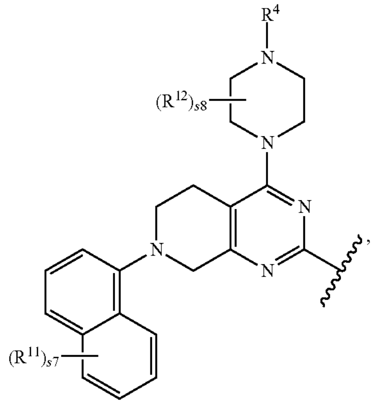
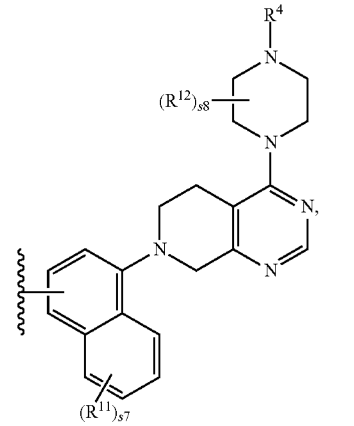
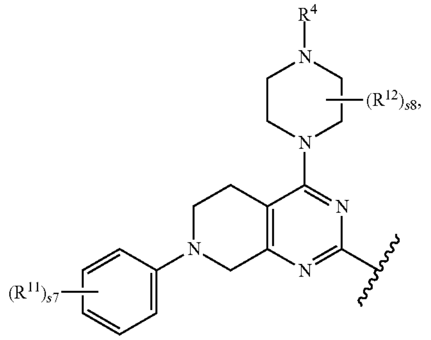
-continued
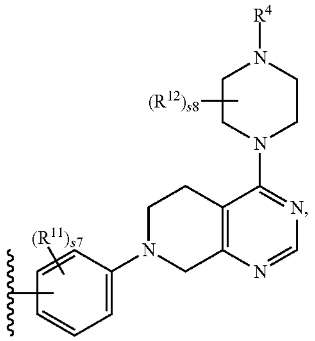
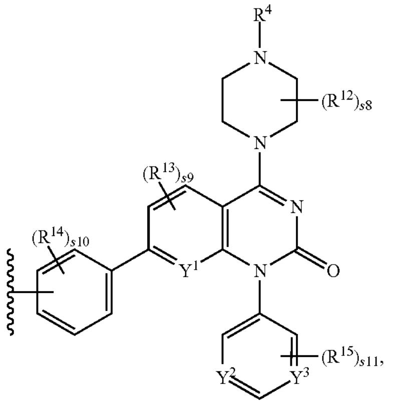
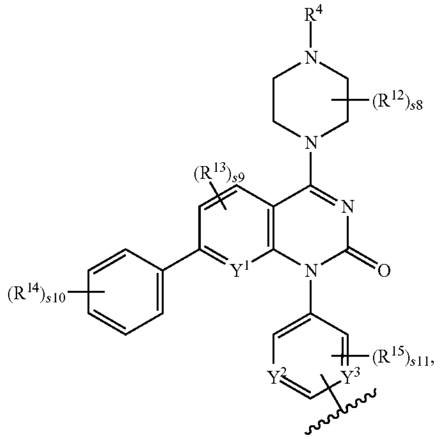
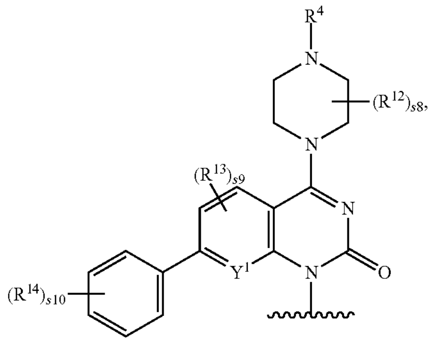

-continued

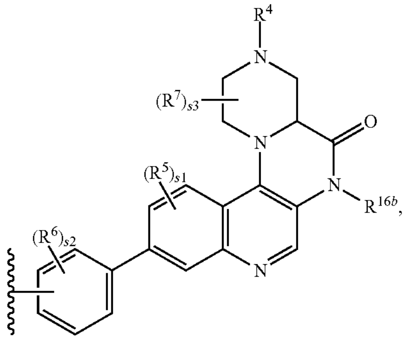

,

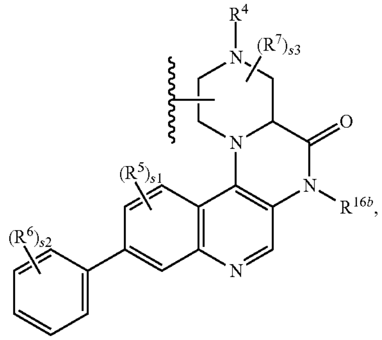

,

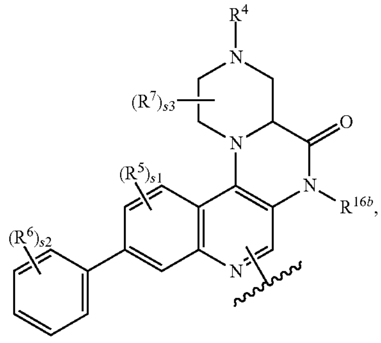

, or

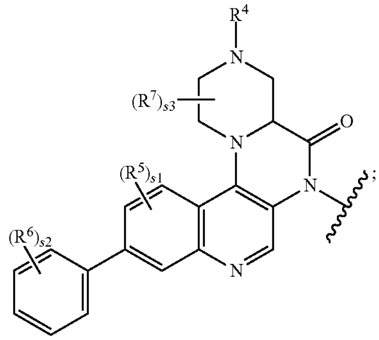

;

X is $C_1$-$C_{15}$ alkylene, heteroalkylene, $C_2$-$C_{10}$ alkenylene, $C_2$-$C_{10}$ alkynylene, phenylene, five to six membered heteroarylene, five to six membered heterocyclylene, or $C_3$-$C_5$ cycloalkylene, each of which is optionally substituted with one or more $R^{18}$; or X is $C_1$-$C_{15}$ alkylene, heteroalkylene, $C_2$-$C_{10}$ alkenylene, or $C_2$-$C_{10}$ alkynylene, wherein one or more methylene repeating units is replaced by a ring structure, each ring structure independently selected from the group consisting of phenylene, five to six membered heteroarylene, five to six membered heterocyclylene, and $C_3$-$C_8$ cycloalkylene, and wherein each ring structure is independently and optionally substituted with one or more $R^{18}$;

Y is $CH_2$, O, S, or NH;

$L^1$ is a bond,

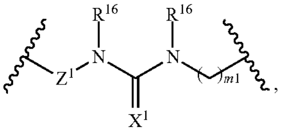

,

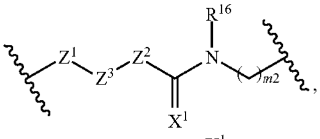

,

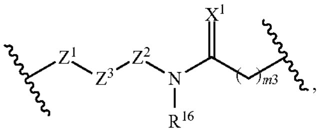

,

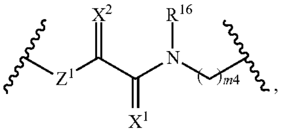

,

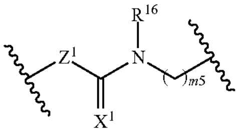

,

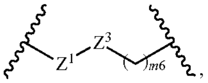

,

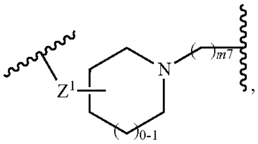

,

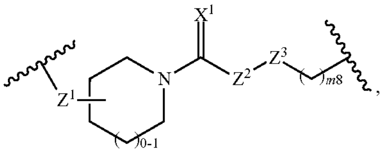

,

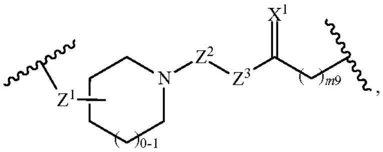

,

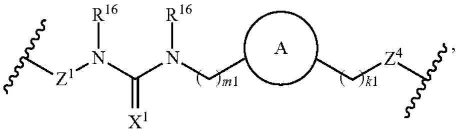

,

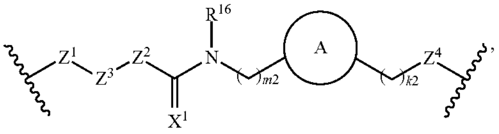

,

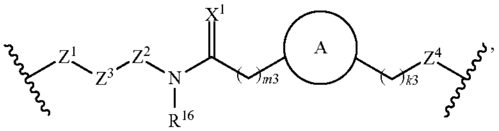

,

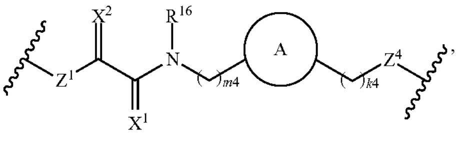

,

-continued

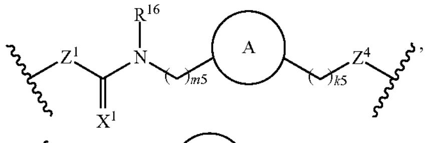

,

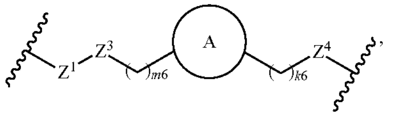

,

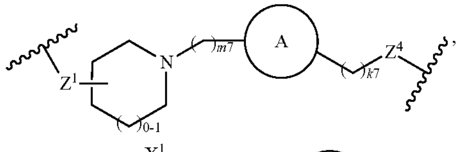

,

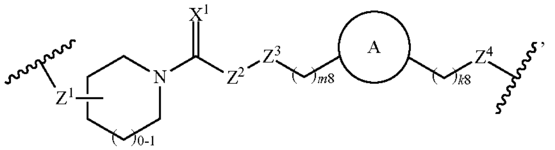

, or

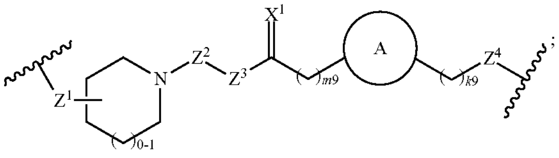

;

$L^2$ is a bond. —O—, —S—, —$NR^{16a}$— —$(CH_2)_{1-3}$—, —C(=O)—, or —$(CH_2)_{0-3}C(=O)NR^{16a}$;

each of $Q^1$, $Q^2$, and $Q^3$ is independently S or CH, provided that one of $Q^1$, $Q^2$, and $Q^3$ is S;

Q is $CH_2$ or C(O);

n is an integer of 0, 1, or 2;

each $R^A$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, (amino)$C_1$-$C_6$ alkyl, —(C=O)$NR^{17a}R^{17b}$, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl;

each of $R^2$, $R^{2a}$, and $R^{2b}$ is independently H, deuterium, halogen, or $C_1$-$C_6$ alkyl;

each $R^{2c}$ is independently H, $C_1$-$C_6$ alkyl, or $C_3$-$C_8$ cycloalkyl, wherein the $C_3$-$C_8$ cycloalkyl is optionally substituted with $C_1$-$C_6$ alkyl, halogen, or $C_1$-$C_6$ haloalkyl;

each $R^{2d}$ is independently H, OH, halogen, —O—$C_1$-$C_6$ alkyl, —O—$C_1$-$C_6$ haloalkyl, or —O—$C_3$-$C_8$ cycloalkyl, wherein the cycloalkyl is optionally substituted with $C_1$-$C_6$ alkyl, halogen, or $C_1$-$C_6$ haloalkyl;

each $R^{2e}$ is independently —C(=O)—$C_1$-$C_6$ alkyl or —C(=O)—$C_3$-$C_8$ cycloalkyl, each optionally substituted with one or more substituents, each independently selected from the group consisting of cyano, halogen, hydroxyl, amino, and $C_1$-$C_6$ haloalkyl;

each $R^3$ is independently H, deuterium, $C_1$-$C_6$ alkyl,

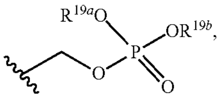

, or

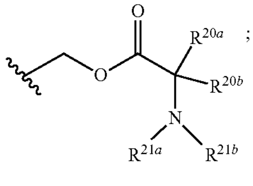

;

each $R^4$ is independently H, $C_1$-$C_6$ alkyl, —C(O)$C_1$-$C_6$ alkyl, —C(O)$C_2$-$C_6$ alkenyl, —C(O)$C_3$-$C_8$ cycloalkyl, —C(O)($C_3$-$C_8$ cycloalkyl)$C_1$-$C_6$ alkyl, —C(O)—(3 to 7 membered heteroaryl), —C(O)—(3 to 7 membered heterocyclyl), —C(O)—(3 to 7 membered heterocyclyl)$C_1$-$C_6$ alkyl, —C(O)$NR^{17a}R^{17b}$, —$S(O)_2C_1$-$C_6$ alkyl, —$S(O)_2C_2$-$C_6$ alkenyl, —$S(O)_2C_3$-$C_8$ cycloalkyl, —$S(O)_2$($C_3$-$C_8$ cycloalkyl)$C_1$-$C_6$ alkyl, —$S(O)_2$-(3 to 7 membered heterocyclyl), —$S(O)_2$-(3 to 7 membered heterocyclyl)$C_1$-$C_6$ alkyl, or —$S(O)_2NR^{17a}R^{17b}$, wherein, when $R^4$ is not H, $R^4$ is optionally substituted with one or more $R^{18}$;

each of $R^5$, $R^6$, $R^7$, $R^8$, $R^9$, $R^{10}$, $R^{11}$, $R^{12}$, $R^{13}$, $R^{14}$, and $R^{15}$ is independently halogen, hydroxyl, cyano, nitro, optionally substituted $C_1$-$C_6$ alkyl, optionally substituted $C_1$-$C_6$ haloalkyl, optionally substituted $C_1$-$C_6$ alkoxy, optionally substituted $C_1$-$C_6$ haloalkoxy, optionally substituted amino, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl;

each of $R^{16}$, $R^{16a}$, and $R^{16b}$ is independently H or $C_1$-$C_6$ alkyl;

each $R^{17a}$ and $R^{17b}$ is independently H or $C_1$-$C_6$ alkyl; or $R^{17a}$ and $R^{17b}$ together with the nitrogen atom to which they are attached form 5 or 6 membered heterocyclyl, each optionally substituted with one or more $R^{18}$;

each $R^{18}$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, —O—($C_1$-$C_6$ alkoxy)$C_1$-$C_6$ alkyl, optionally substituted amino, halogen, or cyano; or two geminal $R^{18}$ form oxo;

each of $R^{19a}$ and $R^{19b}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each of $R^{20a}$ and $R^{20b}$ is independently H, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl;

each of $R^{21a}$ and $R^{21b}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl;

each of s1, s2, s3, s4, s5, s6, s7, s8, s9, s10, and s11 is independently an integer of 0, 1, 2 or 3;

each of $Y^1$, $Y^2$, and $Y^3$ is independently N or CH;

each $Z^1$ is independently a bond, —$(CR^aR^b)_{q1}$—, —C(=O)—, —CH=CH—, or —C≡C—;

each $Z^2$ is independently —$(CR^cR^d)_{q2}$—;

each of $Z^3$ and $Z^4$ is independently $NR^{16}$, O, S, or a bond;

each of $R^a$, $R^b$, $R^c$, and $R^d$ is independently H, halogen, hydroxyl, $C_1$-$C_6$ alkyl, $C_1$-$C_6$ haloalkyl, $C_1$-$C_6$ alkoxy, $C_1$-$C_6$ haloalkoxy, or optionally substituted $C_3$-$C_6$ cycloalkyl;

q1 and q2 are each independently an integer of 1, 2, or 3;

each of $X^1$ and $X^2$ is independently O or S;

each ring A is independently phenylene, five to six membered heteroarylene, five to six membered heterocyclylene, or $C_3$-$C_8$ cycloalkylene, each of which is optionally substituted with one or more $R^{18}$; and each of m1, m2, m3, m4, m5, m6, m7, m8, m9, k1, k2, k3, k4, k5, k6, k7, k8, and k9 is independently an integer of 0, 1, 2, 3, 4, or 5.

Also provided herein is a pharmaceutical composition, comprising a compound of Formula (I) or a pharmaceutically acceptable salt thereof, and a pharmaceutically acceptable excipient.

Additionally, provided herein is a method of inhibiting the activity of a RAS in a biological sample, comprising contacting the biological sample with an effective amount of a compound of Formula (I) or a pharmaceutically acceptable salt thereof.

Furthermore, provided herein is a method of treating or ameliorating a disease, disorder, or condition associated with RAS malfunction, comprising administering to a subject in need thereof a pharmaceutically effective amount of a compound of Formula (I) or a pharmaceutically acceptable salt thereof, or a pharmaceutical composition thereof.

Provided herein is a method or treating or ameliorating cancer, comprising administering to a subject in need thereof a pharmaceutically effective amount of a compound of Formula (I) or a pharmaceutically acceptable salt thereof, or a pharmaceutical composition thereof.

DETAILED DESCRIPTION

Unless otherwise defined, all terms (including technical and scientific terms) are to be given their ordinary and customary meanings to a person of ordinary skill in the art and are not to be limited to a special or customized meaning unless expressly so defined herein. It should be noted that the use of a particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limits, and each intervening value between the upper and lower limits of the range are encompassed.

Whenever a group is described as being "optionally substituted," that group may be unsubstituted or substituted with one or more of the substituents specified. Likewise, when a group is described as being "substituted," the substituent may be selected from one or more of the substituents specified. If no substituents are specified, it is meant that the "optionally substituted" or "substituted" group may be substituted with one or more groups, each of which is individually and independently selected from alkyl (e.g., $C_1$-$C_6$ alkyl); alkenyl (e.g., $C_2$-$C_6$ alkenyl); alkynyl (e.g., $C_2$-$C_6$ alkynyl); $C_3$-$C_8$ carbocyclyl (e.g., $C_3$-$C_8$ cycloalkyl, $C_3$-$C_8$ cycloalkenyl, or $C_3$-$C_8$ cycloalkynyl, each of which is further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); ($C_3$-$C_7$ carbocyclyl)$C_1$-$C_6$ alkyl, each of which is further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl; 5-10 membered heterocyclyl, each of which is further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl; (5-10 membered heterocyclyl)$C_1$-$C_6$ alkyl, each of which is further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl; aryl, which is further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl; (aryl)$C_1$-$C_6$ alkyl, each of which is further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl; 5-10 membered heteroaryl, each of which is further optionally substituted with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl; (5-10 membered heteroaryl)$C_1$-$C_6$ alkyl, each of which is further optionally substituted with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$alkoxy)$C_1$-$C_6$ alkyl, or —O($C_1$-$C_6$ alkoxy)$C_1$-$C_6$ alkyl; halo (e.g., fluoro, chloro, bromo, or iodo); cyano; hydroxyl; protected hydroxy; alkoxy (e.g., $C_1$-$C_6$ alkoxy); haloalkyl (e.g., $C_1$-$C_6$ haloalkyl, such as —$CF_3$); haloalkyl (e.g., $C_1$-$C_6$ haloalkoxy, such as —$OCF_3$); ($C_1$-$C_6$ alkoxy) $C_1$-$C_6$ alkyl; —O($C_1$-$C_6$ alkoxy)$C_1$-$C_6$ alkyl; ($C_1$-$C_6$ haloalkoxy)$C_1$-$C_6$ alkyl; —O($C_1$-$C_6$ haloalkoxy)$C_1$-$C_6$ alkyl; aryloxy; sulfhydryl (mercapto); alkylthio (e.g., $C_1$-$C_6$ alkylthio); arylthio; azido; nitro; O-carbamyl; N-carbamyl; O-thiocarbamyl; N-thiocarbamyl; C-amido; N-amido; S-sulfonamido; N-sulfonamido; C-carboxy; protected C-carboxy; O-carboxy; acyl; cyanate; isocyanato; thiocyanato; isothiocyanato; silyl; sulfenyl; sulfinyl; sulfonyl; trihalomethanesulfonyl; trihalomethanesulfonamido; amino (including protected derivatives thereof); mono-substituted amino (e.g., NH($C_1$-$C_6$ alkyl); di-substituted amino (e.g., N($C_1$-$C_6$ alkyl)$_2$); oxo (=O); and thioxo (=S).

As used herein, the term "$C_a$ to $C_b$," in which "a" and "b" are each an integer, refers to, for example, the number of carbon atoms in an alkyl, alkenyl, or alkynyl group, or the number of ring atoms of a cycloalkyl, aryl, heteroaryl, or heterocyclyl group. That is, the alkyl, the ring of the cycloalkyl, or the ring of the aryl, contains from "a" to "b," inclusive, carbon atoms. Likewise, the ring of the heteroaryl or the ring of the heterocyclyl contains from "a" to "b," inclusive, total ring atoms. Thus, for example, a "$C_1$ to $C_4$ alkyl" group refers to all alkyl groups having from 1 to 4 carbons, e.g., —$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, and —C($CH_3$)$_3$; a $C_3$ to $C_4$ cycloalkyl group refers to all cycloalkyl groups having from 3 to 4 carbon atoms, e.g., cyclopropyl and cyclobutyl. Similarly, a "4 to 6 membered heterocyclyl" group refers to all heterocyclyl groups with 4 to 6 total ring atoms, e.g., azetidinyl, oxetanyl, oxazolinyl, pyrrolidinyl, piperidinyl, piperazinyl, and morpholinyl. If no "a" and "b" are designated with regard to an alkyl, cycloalkyl, aryl, heteroaryl, or heterocyclyl group, the broadest range described in these definitions is to be assumed. As used herein, the term "$C_1$-$C_6$" includes $C_1$, $C_2$, $C_3$, $C_4$, $C_5$, and $C_6$, and a range defined by any of the two numbers. For example, $C_1$-$C_6$ alkyl includes $C_1$, $C_2$, $C_3$, $C_4$, $C_5$, and $C_6$ alkyl, $C_2$-$C_6$ alkyl, $C_1$-$C_3$ alkyl, etc. Similarly, $C_3$-$C_8$ carbocyclyl or cycloalkyl each includes hydrocarbon ring containing 3, 4, 5, 6, 7, and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that comprises a fully saturated (no double or triple bonds) hydrocarbon group. The alkyl group can have 1 to 20 carbon atoms (whenever it appears herein, a numerical range such as "1 to 20" refers to each integer in the given range; e.g., "1 to 20 carbon atoms" means that the alkyl group can consist of 1 carbon atom, 2 carbon atoms, 3 carbon atoms, etc., up to and including 20 carbon atoms, although the present definition also covers the occurrence of the term "alkyl" where no numerical range is designated). The alkyl group can be a medium size alkyl having 1 to 10 carbon atoms. The alkyl group can be a lower alkyl having 1 to 6 carbon atoms. By way of example only, "$C_1$-$C_4$ alkyl" indicates that there are one to four carbon atoms in the alkyl chain, i.e., the alkyl chain is selected from methyl, ethyl, propyl, isopropyl, n-butyl, isobutyl, sec-butyl, and t-butyl. Exemplary alkyl groups include, but are not limited to, methyl, ethyl, n-propyl, isopropyl, butyl, isobutyl, tertiary butyl, pentyl (straight chain or branched), and hexyl (straight chain or branched). The alkyl group can be substituted or unsubstituted.

As used herein, "alkenyl" refers to a straight or branched hydrocarbon chain containing one or more double bonds. The alkenyl group can have 2 to 20 carbon atoms. By way of example only, "$C_2$-$C_6$ alkenyl" indicates that there are two to six carbon atoms in the alkenyl chain, e.g., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2, -dienyl, and buta-1,2-dien-4-yl. Exemplary alkenyl groups include, but are not limited to, ethenyl, propenyl, butenyl, pentenyl, and hexenyl. The alkenyl group can be substituted or unsubstituted.

As used herein, "alkynyl" refers to a straight or branched hydrocarbon chain containing one or more triple bonds. The alkynyl group can have 2 to 20 carbon atoms. By way of example only, "$C_2$-$C_6$ alkynyl" indicates that there are two to six carbon atoms in the alkynyl chain, e.g., the alkynyl chain is selected from the group consisting of ethynyl, propyn-1-yl, propyn-2-yl, butyn-1-yl, butyn-3-yl, butyn-4-yl, and 2-butynyl. Exemplary alkynyl groups include, but are not limited to, ethynyl, propynyl, butynyl, pentynyl, and hexynyl. The alkynyl group can be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused, bridged, or spiro fashion. As used herein, the term "fused" refers to two rings that have two atoms and one bond in common. As used herein, the term "bridged" refers to a cycloalkyl that contains a linkage of one or more atoms connecting non-adjacent atoms. As used herein, the term "spiro" refers to two rings that have one atom in common and the two rings are not linked by a bridge. A cycloalkyl group can contain 3 to 10 atoms in the ring(s), 3 to 8 atoms in the ring(s), or 3 to 6 atoms in the ring(s). A cycloalkyl group can be unsubstituted or substituted. Examples of monocyclic cycloalkyl groups include, but are not limited to, cyclopropyl, cyclobutyl, cyclopentyl, cyclohexyl, cycloheptyl, and cyclooctyl. Examples of bicyclic fused cycloalkyl groups include, but are not limited to, decahydronaphthalenyl, dodecahydro-1H-phenalenyl, and tetradecahydroanthracenyl. Examples of bicyclic bridged cycloalkyl groups include, but are not limited to, bicyclo[1.1.1]pentyl, adamantanyl, and norbornenyl. Examples of bicyclic spiro cycloalkyl groups include, but are not limited to, spiro[3.3]heptanyl and spiro[4.5]decanyl.

As used herein, "carbocyclyl" refers to a non-aromatic mono- or multi-cyclic hydrocarbon ring system. When composed of two or more rings, the rings may be joined together in a fused, bridged, or spiro fashion. A carbocyclyl group can contain 3 to 30 atoms in the ring(s), 3 to 20 atoms in the ring(s), 3 to 10 atoms in the ring(s), 3 to 8 atoms in the ring(s), or 3 to 6 atoms in the ring(s). A carbocyclyl group can be unsubstituted or substituted. Examples of carbocyclyl groups include, but are not limited to, cycloalkyl groups, and the non-aromatic portions of 1,2,3,4-tetrahydronaphthyl, 2,3-dihydro-1H-indenyl, 5,6,7,8-tetrahydroquinolinyl, and 6,7-dihydro-5H-cyclopenta[b]pyridinyl.

As used herein, "aryl" refers to a carbocyclic (all carbon) monocyclic or multicyclic aromatic ring system (including fused ring systems where two carbocyclic rings share a chemical bond). For example, the aryl group can be a $C_6$ aryl group or a $C_{10}$ aryl group. Examples of aryl groups include, but are not limited to, phenyl and naphthyl. An aryl group can be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2, or 3 heteroatoms), that is, an element other than carbon, including, but not limited to, nitrogen, oxygen, and sulfur. For example, the heteroaryl group can contain 5 to 10 atoms in the ring(s), 6 to 10 atoms in the ring(s), or 5 to 6 atoms in the ring(s); such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems, where two rings, such as at least one aryl ring and at least one heteroaryl ring, or at least two heteroaryl rings, share at least one chemical bond. Examples of heteroaryl rings include, but are not limited to, furanyl, furazanyl, thiophenyl, benzothiophenyl, phthalazinyl, pyrrolyl, oxazolyl, benzoxazolyl, 1,2,3-oxadiazolyl, 1,2,4-oxadiazolyl, thiazolyl, 1,2,3-thiadiazolyl, 1,2,4-thiadiazolyl, benzothiazolyl, imidazolyl, benzimidazolyl, indolyl, indazolyl, pyrazolyl, benzopyrazolyl, isoxazolyl, benzoisoxazolyl, isothiazolyl, triazolyl, benzotriazolyl, thiadiazolyl, tetrazolyl, pyridinyl, pyridazinyl, pyrimidinyl, pyrazinyl, purinyl, pteridinyl, quinolinyl, isoquinolinyl, quinazolinyl, quinoxalinyl, cinnolinyl, and triazinyl. A heteroaryl group can be substituted or unsubstituted.

As used herein, "heterocyclyl" refers to a three-, four-, five-, six-, seven-, eight-, nine-, or ten-membered monocyclic, bicyclic, or tricyclic ring system, wherein carbon atoms together with from 1 to 5 heteroatoms constitute the ring system. A heterocyclyl group may optionally contain one or more unsaturated bonds situated in such a way, however, that a fully delocalized pi-electron system does not occur throughout all the rings (i.e., heterocyclyl groups are not aromatic). The heteroatom(s) is an element other than carbon, including, but not limited to, oxygen, sulfur, and nitrogen. A heterocyclyl group can further contain one or more carbonyl functionalities so as to make the definition to include oxo-systems such as lactams, lactones, and cyclic carbamates. When composed of two or more rings, the rings can be joined together in a fused, bridged, or spiro fashion. As used herein, the term "fused" refers to two rings that have two atoms and one bond in common. As used herein, the term "bridged heterocyclyl" refers to a heterocyclyl that contains a linkage of one or more atoms connecting non-adjacent atoms. As used herein, the term "spiro" refers to two rings that have one atom in common and the two rings are not linked by a bridge. A heterocyclyl group can contain 3 to 10 atoms in the ring(s), 3 to 8 atoms in the ring(s), 3 to 6 atoms in the ring(s), or 5 to 6 atoms in the ring(s); for example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogen in a heterocyclyl group can be quaternized. A heterocyclyl group can be linked to the rest of a molecule via a carbon atom in the heterocyclyl group (C-linked) or via a heteroatom in the heterocyclyl group, such as a nitrogen atom (N-linked). Heterocyclyl groups can be unsubstituted or substituted. Examples of heterocyclyl groups include, but are not limited to, aziridinyl, oxiranyl, thiiranyl, azetidinyl, oxetanyl, 1,3-dioxinyl, 1,3-dioxanyl, 1,4-dioxanyl, 1,2-dioxolanyl, 1,3-dioxolanyl, 1,4-dioxolanyl, 1,3-oxathianyl, 1,4-oxathiinyl, 1,3-oxathiolanyl, 1,3-dithiolyl, 1,3-dithiolanyl, 1,4-oxathianyl, tetrahydro-1,4-thiazinyl, 2H-1,2-oxazinyl, maleimidyl, succinimidyl, barbituryl, thiobarbituryl, dioxopiperazinyl, hydantoinyl, dihydrouracyl, trioxanyl, hexahydro-1,3,5-triazinyl, imidazolinyl, imidazolidinyl, isoxazolinyl, isoxazolidinyl, oxazolinyl, oxazolidinyl, oxazolidinonyl, thiazolinyl, thiazolidinyl, morpholinyl, oxiranyl, N-oxypiperidinyl, piperidinyl, piperazinyl, pyrrolidinyl, azepanyl, pyrrolidonyl, pyrrolidionyl, 4-piperidonyl, pyrazolinyl, pyrazolidinyl, 2-oxopyrrolidinyl, tetrahydropyranyl, 4H-pyranyl, tetrahydrothiopyranyl, thiamorpholinyl, benzimidazolidinonyl, tetrahydroquinolinyl, and 3,4-methylenedioxyphenyl. Examples of spiro heterocyclyl groups include, but are not limited to, 2-azaspiro[3.3]heptanyl, 2-oxaspiro[3.3]heptanyl, 2-oxa-6-azaspiro[3.3]heptanyl, 2,6-diazaspiro[3.3]heptanyl, 2-oxaspiro[3.4]octanyl, and 2-azaspiro[3.4]octanyl.

As used herein, "alkylene" refers to a branched or straight chain fully saturated di-radical hydrocarbon group, which is attached to the rest of a molecule via two points of attachment. By way of example only, "$C_1$-$C_{10}$ alkylene" indicates that there are one to ten carbon atoms in the alkylene chain. Non-limiting examples include ethylene ($-CH_2CH_2-$), propylene ($-CH_2CH_2CH_2-$), butylene ($-CH_2CH_2CH_2CH_2-$), and pentylene ($-CH_2CH_2CH_2CH_2CH_2-$).

As used herein, "alkenylene" refers to a straight or branched chain di-radical hydrocarbon group containing at least one carbon-carbon double bond, which is attached to the rest of a molecule via two points of attachment. By way of example only, "$C_2$-$C_{10}$ alkenylene" indicates that there are two to ten carbon atoms in the alkenylene chain.

As used herein, "alkynylene" refers to a straight or branched chain di-radical hydrocarbon group containing at least one carbon-carbon triple bond, which is attached to the rest of a molecule via two points of attachment. By way of example only, "$C_2$-$C_{10}$ alkynylene" indicates that there are two to ten carbon atoms in the alkynylene chain.

As used herein, "heteroalkylene" refers to an alkylene group as defined herein that contains one or more heteroatoms in the carbon backbone (i.e., an alkylene group in which one or more carbon atoms is replaced with a heteroatom, for example, a nitrogen atom, oxygen atom, or sulfur atom). Heteroalkylene groups include, but are not limited to, ether, thioether, amino-alkylene, and alkylene-amino-alkylene moieties.

As used herein, "aralkyl" and "(aryl)alkyl" refer to an aryl group as defined herein, connected, as a substituent, via an alkylene group as defined herein. The alkylene and aryl groups of an aralkyl can each be independently substituted or unsubstituted. Examples include, but are not limited to, benzyl, 2-phenylalkyl, 3-phenylalkyl, and naphthylalkyl.

As used herein, "heteroaralkyl" and "(heteroaryl)alkyl" refer to a heteroaryl group as defined herein, connected, as a substituent, via an alkylene group as defined herein. The alkylene and heteroaryl groups of heteroaralkyl can each be independently substituted or unsubstituted. Examples include, but are not limited to 2-thienylalkyl, 3-thienylalkyl, furylalkyl, thienylalkyl, pyrrolylalkyl, pyridylalkyl, isoxazolylalkyl, and imidazolylalkyl.

As used herein, "(heterocyclyl)alkyl" refer to a heterocyclic or heterocyclyl group as defined herein, connected, as a substituent, via an alkylene group as defined herein. The alkylene and heterocyclyl groups of (heterocyclyl)alkyl can each be independently substituted or unsubstituted. Examples include, but are not limited to, (tetrahydro-2H-pyran-4-yl)methyl, (piperidin-4-yl)ethyl, (piperidin-4-yl) propyl, (tetrahydro-2H-thiopyran-4-yl)methyl, and (1,3-thiazinan-4-yl)methyl.

As used herein, "cycloalkylalkyl" and "(cycloalkyl)alkyl" refer to a cycloalkyl group as defined herein, connected, as a substituent, via an alkylene group. The alkylene and cycloalkyl groups of (cycloalkyl)alkyl can each be independently substituted or unsubstituted. Examples include, but are not limited to, cyclopropylmethyl, cyclobutylmethyl, cyclopentylethyl, and cyclohexylpropyl.

As used herein, "alkoxy" refers to the formula —OR, wherein R is an alkyl group as defined herein. Examples include, but are not limited to, methoxy, ethoxy, n-propoxy, 1-methylethoxy (isopropoxy), n-butoxy, isobutoxy, sec-butoxy, and tert-butoxy. An alkoxy can be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Examples include, but are not limited to, chloromethyl, fluoromethyl, difluoromethyl, trifluoromethyl, 1-chloro-2-fluoromethyl, and 2-fluoroisobutyl. A haloalkyl can be substituted or unsubstituted.

As used herein, "haloalkoxy" refers to an alkoxy group in which one or more of the hydrogen atoms are replaced by a halogen (e.g., mono-haloalkoxy, di-haloalkoxy, and tri-haloalkoxy). Examples include, but are not limited to, chloromethoxy, fluoromethoxy, difluoromethoxy, trifluoromethoxy, 1-chloro-2-fluoromethoxy, and 2-fluoroisobutoxy. A haloalkoxy can be substituted or unsubstituted.

As used herein, "amino" refer to an $-NH_2$ group. The term "mono-substituted amino group" as used herein refers to an amino ($-NH_2$) group, where one of the hydrogen atom is replaced by a substituent. The term "di-substituted amino group" as used herein refers to an amino ($-NH_2$) group, where each of the two hydrogen atoms is independently replaced by a substituent. The term "optionally substituted amino" as used herein refer to an $-NR_AR_B$ group, where $R_A$ and $R_B$ are each independently hydrogen, alkyl, cycloalkyl, aryl, heteroaryl, heterocyclyl, aralkyl, or heterocyclyl(alkyl), each as defined herein.

As used herein, "alkylamino" or "(alkyl)amino" refers to a $-NR_AR_B$ group, where $R_A$ is hydrogen or alkyl and $R_B$ is alkyl. Examples of alkylamino groups include, but are not limited to, methylamino (—NHMe), ethylamino (—NHEt), dimethylamino ($-N(Me)_2$), methylethylamino (—N(Me)(Et)), and isopropylamino (—NHiPr).

As used herein, "aminoalkyl" or "(amino)alkyl" refers to an alkyl group in which one or more of the hydrogen atoms are replaced by an amino group or "$-NR_AR_B$" group as defined herein. Examples of aminoalkyl groups include, but are not limited to, $-(CH_2)_{1-4}NH_2$, $-(CH_2)_{1-4}-NHCH_3$, $-(CH_2)_{1-4}-NHC_2H_5$, $-(CH_2)_{1-4}-N(CH_3)_2$, $-(CH_2)_{1-4}-N(C_2H_5)_2$, $-(CH_2)_{1-4}-NH-CH(CH_3)_2$, $-(CH_2)_{1-4}N(CH_3)C_2H_5$, and $-CH(NH_2)CH_3$.

The term "halogen atom" or "halogen" as used herein refers to fluorine, chlorine, bromine, or iodine.

As used herein, "alkoxyalkyl" or "(alkoxy)alkyl" refers to an alkoxy group connected via an alkylene group, such as $C_2$-$C_8$ alkoxyalkyl or ($C_1$-$C_6$ alkoxy)$C_1$-$C_6$ alkyl, for example, $-(CH_2)_{1-3}-OCH_3$.

As used herein, "—O-alkoxyalkyl" or "—O-(alkoxy) alkyl" refers to an alkoxy group connected via an —O-(alkylene) group, such as —O—($C_1$-$C_6$ alkoxy)$C_1$-$C_6$ alkyl, for example, $-O-(CH_2)_{1-3}-OCH_3$.

As used herein, "aryloxy" and "arylthio" refers to —OR and —SR, respectively, wherein R is an aryl as defined herein, e.g., phenyl. An aryloxy and arylthio can each be independently substituted or unsubstituted.

A "sulfenyl" group refers to an "—SR" group in which R is hydrogen, alkyl, alkenyl, alkynyl, carbocyclyl, aryl, heteroaryl, heterocyclyl, aralkyl, or heterocyclyl(alkyl), each as defined herein. A sulfenyl can be substituted or unsubstituted.

A "sulfinyl" group refers to an "—S(=O)R" group in which R is hydrogen, alkyl, alkenyl, alkynyl, carbocyclyl, aryl, heteroaryl, heterocyclyl, aralkyl, or heterocyclyl(alkyl), each as defined herein. A sulfinyl can be substituted or unsubstituted.

A "sulfonyl" group refers to an "$-SO_2R$" group in which R is hydrogen, alkyl, alkenyl, alkynyl, carbocyclyl, aryl, heteroaryl, heterocyclyl, aralkyl, or heterocyclyl(alkyl), each as defined herein. A sulfonyl can be substituted or unsubstituted.

An "O-carboxy" group refers to an "—OC(=O)R" group in which R is hydrogen, alkyl, alkenyl, alkynyl, carbocyclyl, aryl, heteroaryl, heterocyclyl, aralkyl, or heterocyclyl(alkyl), each as defined herein. An O-carboxy can be substituted or unsubstituted.

The terms "ester" and "C-carboxy" refer to a "—C(=O)OR" group in which R is hydrogen, alkyl, alkenyl, alkynyl, carbocyclyl, aryl, heteroaryl, heterocyclyl, aralkyl, or heterocyclyl(alkyl), each as defined herein. An ester or C-carboxy can be substituted or unsubstituted.

A "trihalomethanesulfonyl" group refers to an "$-O_2SCX'_3$" group, wherein X' is a halogen.

A "trihalomethanesulfonamido" group refers to an "$-N(R)S(O)_2CX'_3$" group, wherein X' is a halogen and R is hydrogen, alkyl, alkenyl, alkynyl, carbocyclyl, aryl, heteroaryl, heterocyclyl, aralkyl, or heterocyclyl(alkyl), each as defined herein.

A "mercapto" group refers to an "—SH" group.

An "S-sulfonamido" group refers to an "$-SO_2N(R_AR_B)$" group in which $R_A$ and $R_B$ can each be independently hydrogen, alkyl, alkenyl, alkynyl, carbocyclyl, aryl, heteroaryl, heterocyclyl, aralkyl, or heterocyclyl(alkyl), each as defined herein. An S-sulfonamido can be substituted or unsubstituted.

An "N-sulfonamido" group refers to an "$-N(R_A)SO_2R$" group in which R and $R_A$ can each be independently hydrogen, alkyl, alkenyl, alkynyl, carbocyclyl, aryl, heteroaryl, heterocyclyl, aralkyl, or heterocyclyl(alkyl), each as defined herein. An N-sulfonamido can be substituted or unsubstituted.

An "O-carbamyl" group refers to an "$-OC(=O)N(R_AR_B)$" group in which $R_A$ and $R_B$ can each be independently hydrogen, alkyl, alkenyl, alkynyl, carbocyclyl, aryl, heteroaryl, heterocyclyl, aralkyl, or heterocyclyl(alkyl), each as defined herein. An O-carbamyl can be substituted or unsubstituted.

An "N-carbamyl" group refers to an "$-N(R_A)C(=O)OR$" group in which R and $R_A$ can each be independently hydrogen, alkyl, alkenyl, alkynyl, carbocyclyl, aryl, heteroaryl, heterocyclyl, aralkyl, or heterocyclyl(alkyl), each as defined herein. An N-carbamyl can be substituted or unsubstituted.

An "O-thiocarbamyl" group refers to an "$-OC(=S)N(R_AR_B)$" group in which $R_A$ and $R_B$ can each be independently hydrogen, alkyl, alkenyl, alkynyl, carbocyclyl, aryl, heteroaryl, heterocyclyl, aralkyl, or heterocyclyl(alkyl), each as defined herein. An O-thiocarbamyl can be substituted or unsubstituted.

An "N-thiocarbamyl" group refers to an "$-N(R_A)C(=S)OR$" group in which R and $R_A$ can each be independently hydrogen, alkyl, alkenyl, alkynyl, carbocyclyl, aryl, heteroaryl, heterocyclyl, aralkyl, or heterocyclyl(alkyl), each as defined herein. An N-thiocarbamyl can be substituted or unsubstituted.

A "C-amido" group refers to a "$-C(=O)N(R_AR_B)$" group in which $R_A$ and $R_B$ can each be independently hydrogen, alkyl, alkenyl, alkynyl, carbocyclyl, aryl, heteroaryl, heterocyclyl, aralkyl, or heterocyclyl(alkyl), each as defined herein. A C-amido can be substituted or unsubstituted.

An "N-amido" group refers to an "$-N(R_A)C(=O)R$" group in which R and $R_A$ can each be independently hydrogen, alkyl, alkenyl, alkynyl, carbocyclyl, aryl, heteroaryl, heterocyclyl, aralkyl, or heterocyclyl(alkyl), each as defined herein. An N-amido can be substituted or unsubstituted.

Where the number of substituents is not specified (e.g., haloalkyl), there can be one or more substituents present. For example, "haloalkyl" can include one or more of the same or different halogens.

The term "solvate" refers to a complex or aggregate formed by one or more molecules of a solute, e.g., a compound provided herein, and one or more molecules of a solvent, which are present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

It is understood that, in any compound described herein having one or more chiral centers, if an absolute stereochemistry is not expressly indicated, then each center may independently be of R-configuration or S-configuration or a mixture thereof. Thus, the compounds provided herein can be enantiomerically pure or enantiomerically enriched, or can be stereoisomeric mixtures, and include all diastereomeric and enantiomeric forms. In addition, it is understood that, in any compound described herein having one or more double bond(s) generating geometrical isomers that can be defined as E or Z, each double bond can independently be E or Z or a mixture thereof. Stereoisomers are obtained, if desired, by methods such as, stereoselective synthesis and/or the separation of stereoisomers by chiral chromatographic columns. Likewise, it is understood that, in any compound described, all tautomeric forms are also intended to be included.

Wherever a substituent is depicted as a di-radical (i.e., has two points of attachment to the rest of a molecule), it is to be understood that the substituent can be attached in any directional configuration unless otherwise indicated. For example, unless a particular orientation is specified, the formula -AE- represents both -AE- and -EA-. In addition, if a group or substituent is depicted as

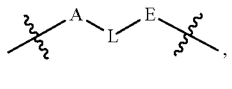

and when L is defined as a bond or absent; such group or substituent is equivalent to

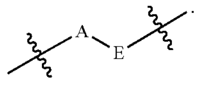

In addition, when a group is depicted as a di-radical, such as X or ring A in Formula (I), one of ordinary skill in the art understands that the definition of such a group should also be di-radical. For example, when X is defined as phenyl, 5 to 6 membered heteroaryl, 5 to 6 membered heterocyclyl, or $C_3$-$C_8$ cycloalkyl, one skilled in the art understands that X is a phenylene, 5 to 6 membered heteroarylene, 5 to 6 membered heterocyclylene, or $C_3$-$C_8$ cycloalkylene.

It is to be understood that, where a compound disclosed herein has an unfilled valency, the valency is to be filled with hydrogen or deuterium.

It is understood that the compounds described herein can be labeled isotopically or by another other means, including, but not limited to, the use of chromophores or fluorescent moieties, bioluminescent labels, or chemiluminescent labels. Substitution with isotopes such as deuterium can afford certain therapeutic advantages from greater metabolic stability, such as, for example, increased in vivo half-life or reduced dosage requirements. Each chemical element as represented in a compound structure may include any isotope of said element. For example, in a compound structure, a hydrogen atom may be explicitly disclosed or understood to be present in the compound. At any position of the compound that a hydrogen atom may be present, the hydrogen atom can be any isotope of hydrogen, including, but not limited to, hydrogen-1 (protium), hydrogen-2 (deuterium), and hydrogen-3 (tritium). Thus, a reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of the compounds provided herein, as well as metabolites and active metabolites of these compounds having the same type of activity. A conformer is a structure that is a conformational isomer. Conformational isomerism is the phenomenon of a molecule with the same structural formula but different conformations (conformers) of atoms about a rotating bond. In certain embodiments, the compounds described herein exist in solvated forms with pharmaceutically acceptable solvents such as water or ethanol. In certain embodiments, the compounds provided herein exist in unsolvated form. Solvates contain either stoichiometric or non-stoichiometric amounts of a solvent and may be formed during the process of crystallization with pharmaceutically acceptable solvents such as water or ethanol. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds provided herein can be provided include amorphous forms, milled forms, and nano-particulate forms.

Likewise, it is understood that a compound described herein include the compound in any of the forms described herein (e.g., pharmaceutically acceptable salts, crystalline forms, amorphous form, solvated forms, enantiomeric forms, and tautomeric forms).

As used herein, the abbreviations for any protective groups, amino acids, and other compounds are, unless indicated otherwise, in accord with their common usage, recognized abbreviations, or the IUPAC-IUB Commission on Biochemical Nomenclature (See, *Eur. J. Biochem.* 1992, 204, 1-3).

The term "protecting group" as used herein refer to any atom or group of atoms that is added to a molecule in order to prevent existing groups in the molecule from undergoing unwanted chemical reactions. Examples of protecting group moieties are described in Greene and Wuts, *Protective Groups in Organic Synthesis,* 3rd. Ed. John Wiley & Sons, 1999; and in McOmie, *Protective Groups in Organic Chemistry*, Plenum Press, 1973; each of which is hereby incorporated by reference for the limited purpose of disclosing suitable protecting groups. The protecting group moiety may be chosen in such a way that they are stable to certain reaction conditions and readily removed at a convenient stage using methodology known in the art.

The term "RAS" or "RAS protein," as used herein, refers to one or more protein in the RAS protein family. The most common RAS proteins are KRAS, HRAS and NRAS. Other members include, but are not limited to, DIRAS1; DIRAS2; DIRAS3; ERAS; GEM; MRAS; NKIRAS1; NKIRAS2; NRAS; RALA; RALB; RAPlA; RAP1B; RAP2A; RAP2B; RAP2C; RASD1; RASD2; RASL10A; RASLiOB; RASLi1A; RASL11B; RASL12; REM1; REM2; RERG; RERGL; RRAD; RRAS; and RRAS2. In certain embodiments, the RAS protein is wild-type. In certain embodiments, the RAS protein is overexpressed. In certain embodiments, the RAS protein is a RAS with a mutation, for example, a KRAS with a G12C mutation.

Generally, the nomenclature used herein and the laboratory procedures in organic chemistry, medicinal chemistry, biochemistry, biology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and a biological molecule (e.g., a protein, enzyme, RNA, or DNA), cell, or tissue such that a physiological and/or chemical effect takes place as a result of such contact. Contacting can take place in vitro, ex vivo, or in vivo. In one embodiment, a therapeutic agent is contacted with a biological molecule in vitro to determine the effect of the therapeutic agent on the biological molecule. In another embodiment, a therapeutic agent is contacted with a cell in cell culture (in vitro) to determine the effect of the therapeutic agent on the cell. In yet another embodiment, the contacting of a therapeutic agent with a biological molecule, cell, or tissue includes the administration of a therapeutic agent to a subject having the biological molecule, cell, or tissue to be contacted.

The term "therapeutically effective amount" or "effective amount" is meant to include the amount of a compound that, when administered, is sufficient to prevent development of, or alleviate to some extent, one or more of the symptoms of the disorder, disease, or condition being treated.

The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "$IC_{50}$" or "$EC_{50}$" refers to an amount, concentration, or dosage of a compound that is required for 50% inhibition of a maximal response in an assay that measures such a response.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, and commensurate with a reasonable benefit/risk ratio. See, e.g., *Remington: The Science and Practice of Pharmacy,* 22nd ed.; Allen Ed.; Pharmaceutical Press: London, 2012*; Handbook of Pharmaceutical Excipients,* 8th ed.; Sheskey et al., *Eds.; Pharmaceutical Press: London,* 2017*; Handbook of Pharmaceutical Additives,* 3rd ed.; Ash and Ash Eds.; Synapse Information Resources: 2007*; Pharmaceutical Preformulation and Formulation,* 2nd ed.; Gibson Ed.; Drugs and the Pharmaceutical Sciences 199; Informa Healthcare: New York, NY, 2009.

The term "about" or "approximately" means an acceptable error for a particular value as determined by one of ordinary skill in the art, which depends in part on how the value is measured or determined. In certain embodiments, the term "about" or "approximately" means within 1, 2, or 3 standard deviations. In certain embodiments, the term "about" or "approximately" means within 25%, 20%, 15%, 10%, 9%, 8%, 7%, 6%, 5%, 4%, 3%, 2%, 1%, 0.5%, or 0.05% of a given value or range.

Compounds

In one embodiment, provided herein is a compound of Formula (I):

$$R^{Het}\text{-}L^2\text{-}X\text{-}L^1\text{-}R^1 \quad (I)$$

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is

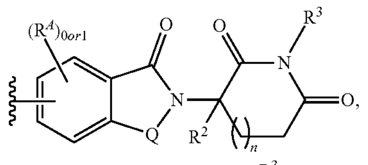

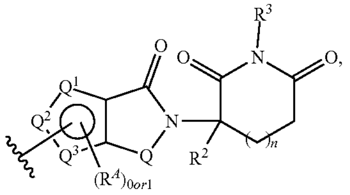

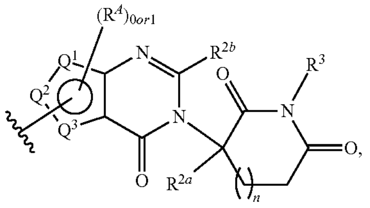

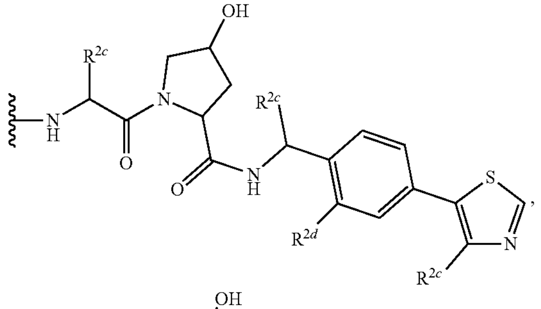

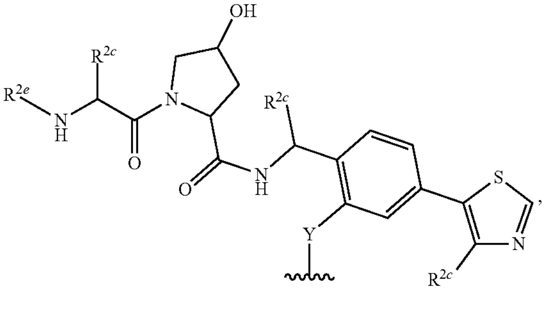

or

-continued
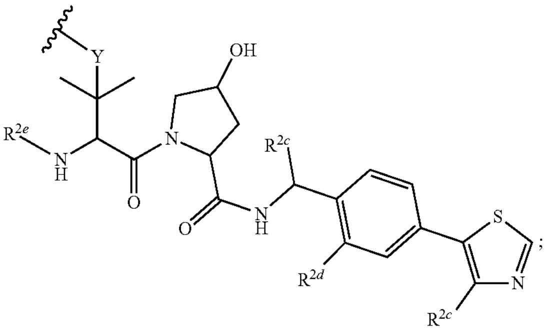
$R^{Het}$ is
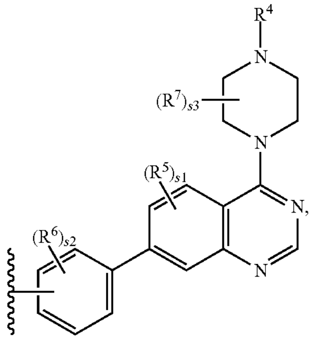
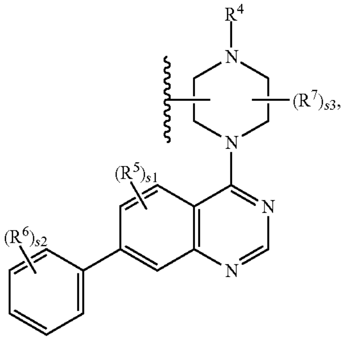
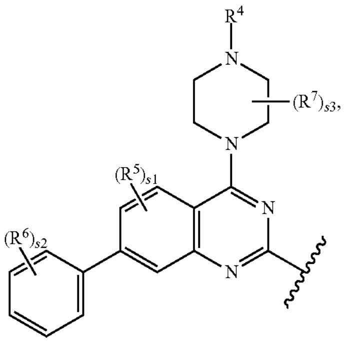
-continued
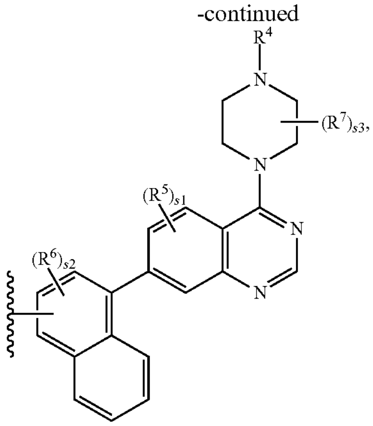
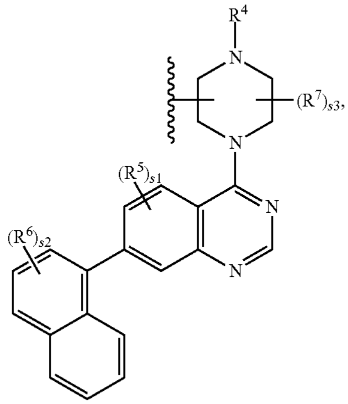
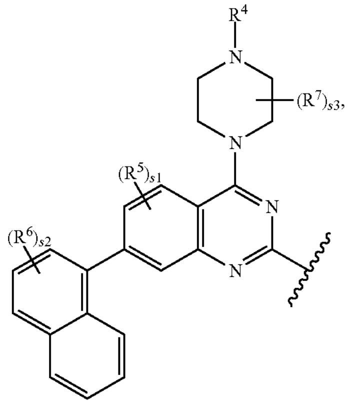
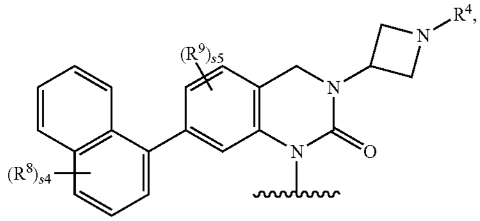
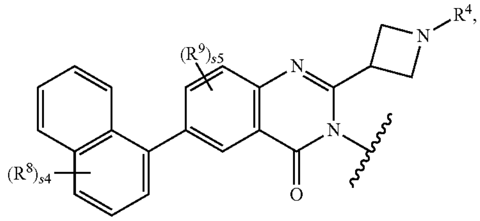

-continued
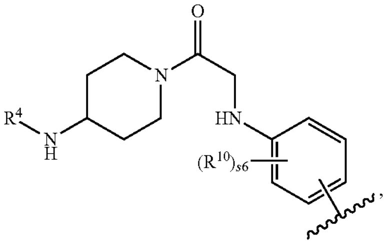
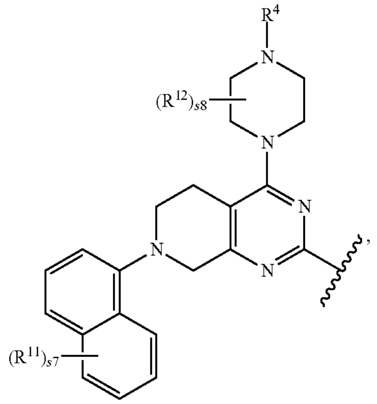
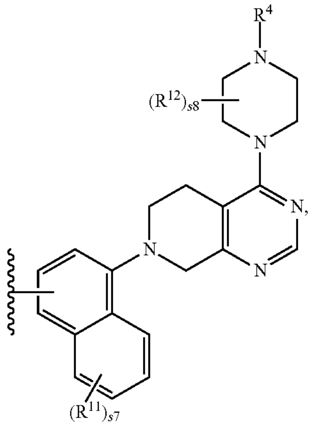
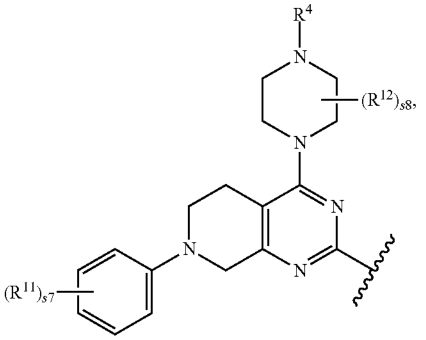
-continued
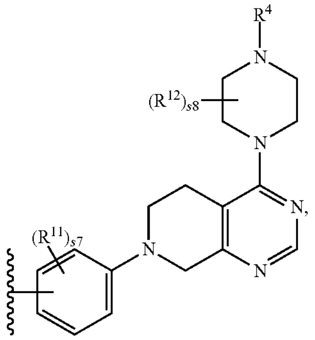
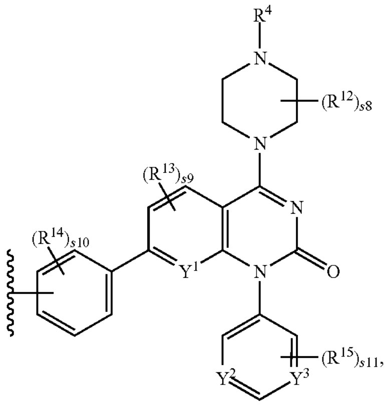
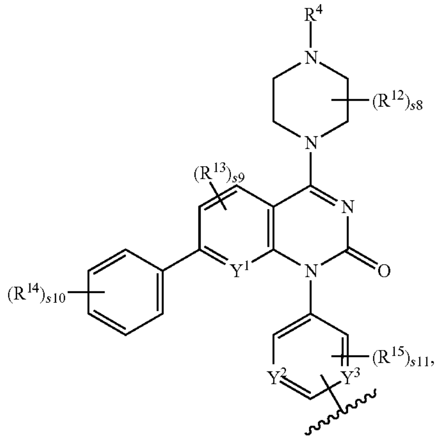
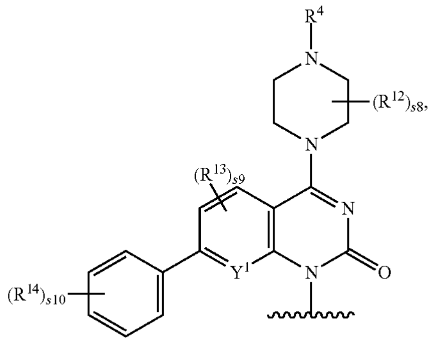

-continued

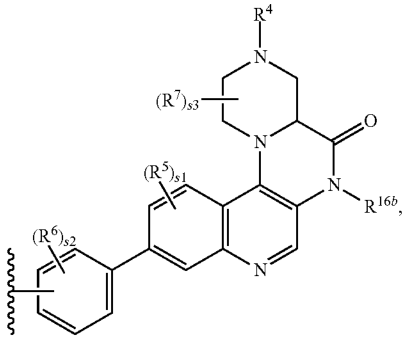

,

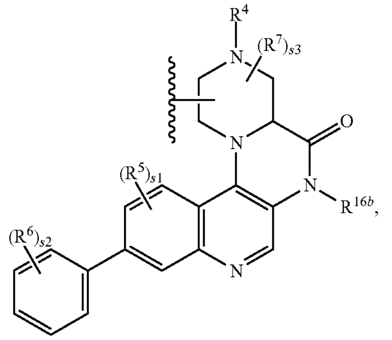

,

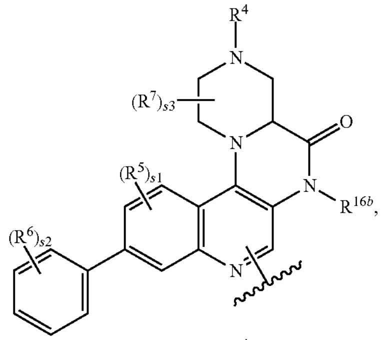

or

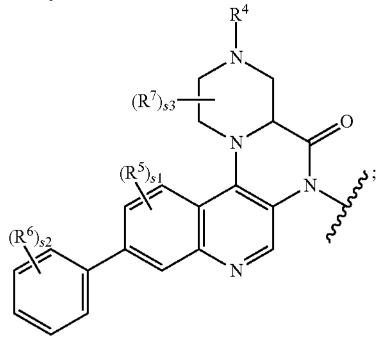

;

X is $C_1$-$C_{15}$ alkylene, heteroalkylene, $C_2$-$C_{10}$ alkenylene, $C_2$-$C_{10}$ alkynylene, phenylene, five to six membered heteroarylene, five to six membered heterocyclylene, or $C_3$-$C_8$ cycloalkylene, each of which is optionally substituted with one or more $R^{18}$; or X is $C_1$-$C_{15}$ alkylene, heteroalkylene, $C_2$-$C_{10}$ alkenylene, or $C_2$-$C_{10}$ alkynylene, wherein one or more methylene repeating units is replaced by a ring structure, each independently selected from the group consisting of phenylene, five to six membered heteroarylene, five to six membered heterocyclylene, and $C_3$-$C_8$ cycloalkylene, and wherein each ring structure is independently and optionally substituted with one or more $R^{18}$;

Y is $CH_2$, O, S, or NH;

$L^1$ is a bond,

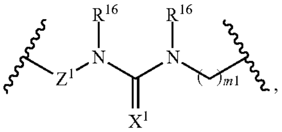

,

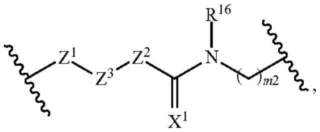

,

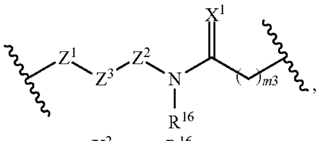

,

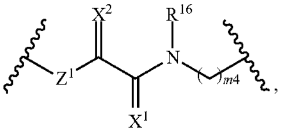

,

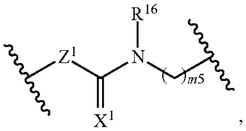

,

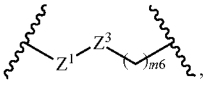

,

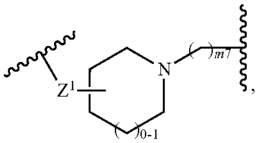

,

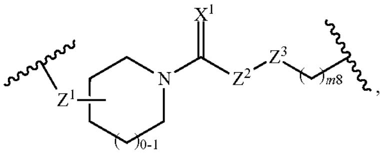

,

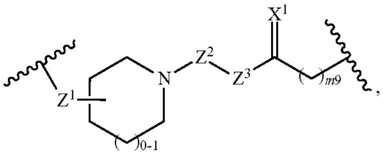

,

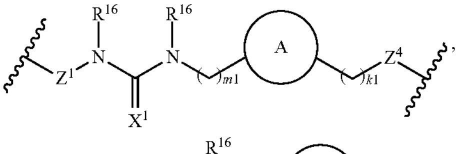

,

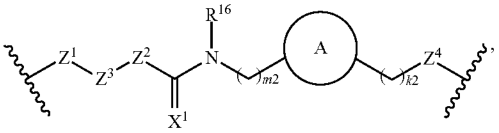

,

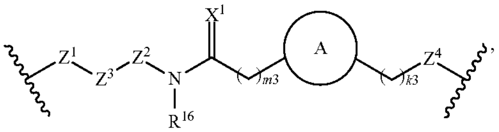

,

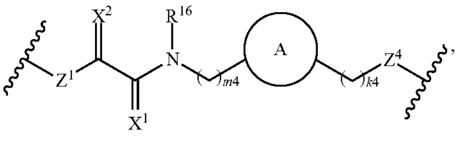

,

-continued

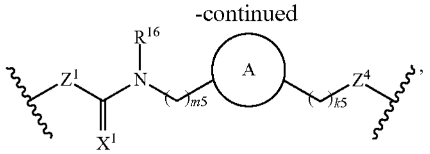,

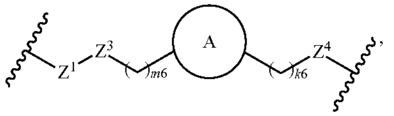,

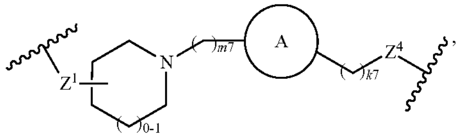,

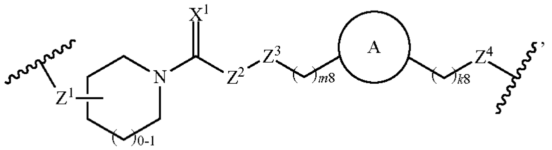, or

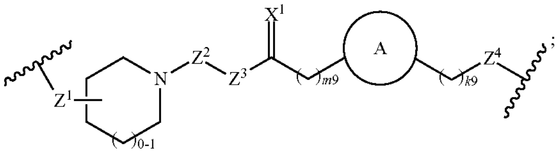;

$L^2$ is a bond, —O—, —S—, —$NR^{16a}$—, —$(CH_2)_{1-3}$—, —C(=O)—, or —$(CH_2)_{0-3}C(=O)NR^{16a}$—;

each of $Q^1$, $Q^2$, and $Q^3$ is independently S or CH, provided that one of $Q^1$, $Q^2$, and $Q^3$ is S;

Q is $CH_2$ or C(O);

n is an integer of 0, 1, or 2;

each $R^A$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, (amino)$C_1$-$C_6$ alkyl, —(C=O)$NR^{17a}R^{17b}$, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl;

each of $R^2$, $R^{2a}$, and $R^{2b}$ is independently H, deuterium, halogen, or $C_1$-$C_6$ alkyl;

each $R^{2e}$ is independently H, $C_1$-$C_6$ alkyl, or $C_3$-$C_8$ cycloalkyl, wherein the $C_3$-$C_8$ cycloalkyl is optionally substituted with $C_1$-$C_6$ alkyl, halogen, or $C_1$-$C_6$ haloalkyl;

each $R^{2d}$ is independently H, OH, halogen, —O—$C_1$-$C_6$ alkyl, —O—$C_1$-$C_6$ haloalkyl, or —O—$C_3$-$C_8$ cycloalkyl, wherein the cycloalkyl is optionally substituted with $C_1$-$C_6$ alkyl, halogen, or $C_1$-$C_6$ haloalkyl;

each $R^{2e}$ is independently —C(=O)—$C_1$-$C_6$ alkyl or —C(=O)—$C_3$-$C_5$ cycloalkyl, each optionally substituted with one or more substituents, each independently selected from the group consisting of cyano, halogen, hydroxyl, amino, and $C_1$-$C_6$ haloalkyl;

each $R^3$ is independently H, deuterium, $C_1$-$C_6$ alkyl,

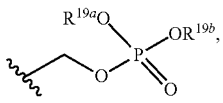, or 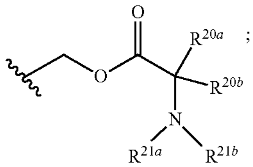;

each $R^4$ is independently H, $C_1$-$C_6$ alkyl, —C(O)$C_1$-$C_6$ alkyl, —C(O)$C_2$-$C_6$ alkenyl, —C(O)$C_3$-$C_5$ cycloalkyl, —C(O)($C_3$-$C_5$ cycloalkyl)$C_1$-$C_6$ alkyl, —C(O)—(3 to 7 membered heteroaryl), —C(O)—(3 to 7 membered heterocyclyl), —C(O)—(3 to 7 membered heterocyclyl)$C_1$-$C_6$ alkyl, —C(O)$NR^{17a}R^{17b}$, —$S(O)_2C_1$-$C_6$ alkyl, —$S(O)_2C_2$-$C_6$ alkenyl, —$S(O)_2C_3$-$C_8$ cycloalkyl, —$S(O)_2$($C_3$-$C_8$ cycloalkyl)$C_1$-$C_6$ alkyl, —$S(O)_2$-(3 to 7 membered heterocyclyl), —$S(O)_2$-(3 to 7 membered heterocyclyl)$C_1$-$C_6$ alkyl, or —$S(O)_2NR^{17a}R^{17b}$, wherein, when $R^4$ is not H, $R^4$ is optionally substituted with one or more $R^{18}$;

each of $R^5$, $R^6$, $R^7$, $R^8$, $R^9$, $R^{10}$, $R^{11}$, $R^{12}$, $R^{13}$, $R^{14}$, and $R^{15}$ is independently halogen, hydroxyl, cyano, nitro, optionally substituted $C_1$-$C_6$ alkyl, optionally substituted $C_1$-$C_6$ haloalkyl, optionally substituted $C_1$-$C_6$ alkoxy, optionally substituted $C_1$-$C_6$ haloalkoxy, optionally substituted amino, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl;

each of $R^{16}$, $R^{16a}$, and $R^{16b}$ is independently H or $C_1$-$C_6$ alkyl;

each $R^{17a}$ and $R^{17b}$ is independently H or $C_1$-$C_6$ alkyl; or $R^{17a}$ and $R^{17b}$ together with the nitrogen atom to which they are attached form 5 or 6 membered heterocyclyl, each optionally substituted with one or more $R^{18}$;

each $R^{18}$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$alkoxy)$C_1$-$C_6$ alkyl, —O—($C_1$-$C_6$ alkoxy)$C_1$-$C_6$ alkyl, optionally substituted amino, halogen, or cyano; or two geminal $R^{18}$ form oxo;

each of $R^{19a}$ and $R^{19b}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each of $R^{20a}$ and $R^{20b}$ is independently H, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl;

each of $R^{21a}$ and $R^{21b}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl;

each of s1, s2, s3, s4, s5, s6, s7, s8, s9, s10, and s11 is independently an integer of 0, 1, 2 or 3;

each of $Y^1$, $Y^2$, and $Y^3$ is independently N or CH;

each $Z^1$ is independently a bond, —$(CR^aR^b)_{q1}$—, —C(=O)—, —CH=CH—, or —C≡C—;

each $Z^2$ is independently —$(CR^cR^d)_{q2}$—;

each of $Z^3$ and $Z^4$ is independently $NR^{16}$, O, S, or a bond;

each of $R^a$, $R^b$, $R^c$, and $R^d$ is independently H, halogen, hydroxyl, $C_1$-$C_6$ alkyl, $C_1$-$C_6$ haloalkyl, $C_1$-$C_6$ alkoxy, $C_1$-$C_6$ haloalkoxy, or optionally substituted $C_3$-$C_6$ cycloalkyl;

q1 and q2 are each independently an integer of 1, 2, or 3;

each of $X^1$ and $X^2$ is independently O or S;

each ring A is independently phenylene, five to six membered heteroarylene, five to six membered heterocyclylene, or $C_3$-$C_8$ cycloalkylene, each of which is optionally substituted with one or more $R^{18}$; and each of m1, m2, m3, m4, m5, m6, m7, m8, m9, k1, k2, k3, k4, k5, k6, k7, k8, and k9 is independently an integer of 0, 1, 2, 3, 4, or 5.

In another embodiment, provided herein is a compound of Formula (I):
$$R^{Het}\text{-}L^2\text{-}X\text{-}L^1\text{-}R^1 \quad (1$$
or a pharmaceutically acceptable salt thereof; wherein:
$R^1$ is
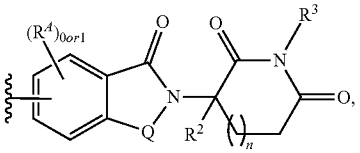
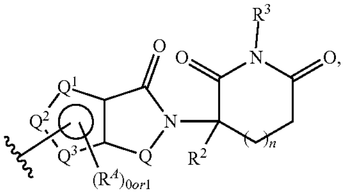
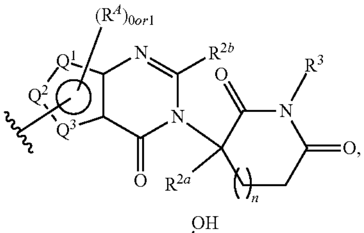
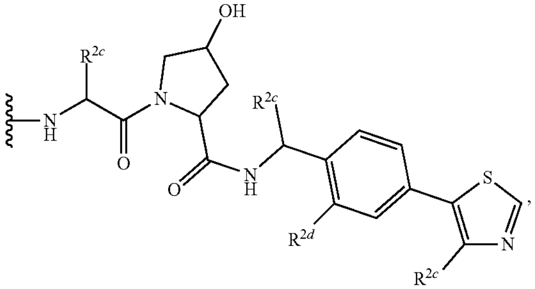
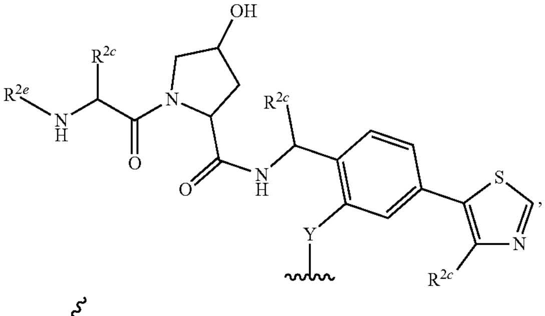
or
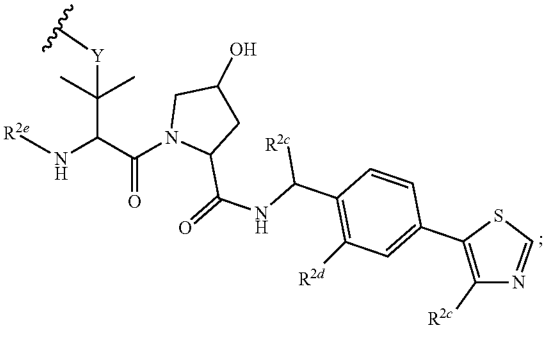
$R^{Het}$ is
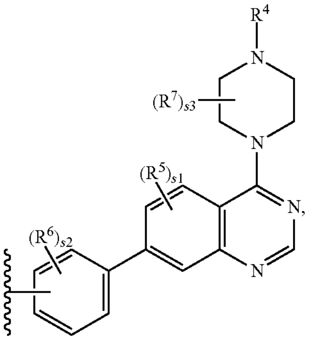
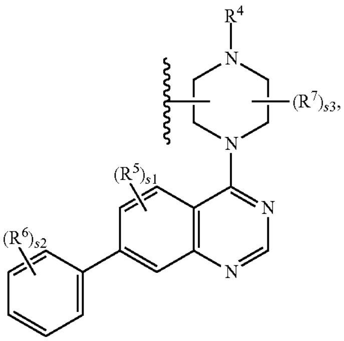
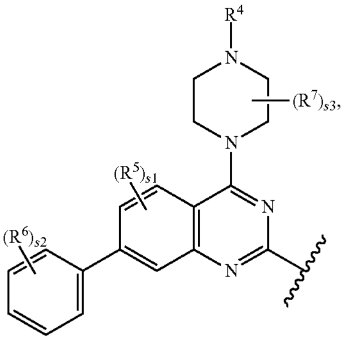
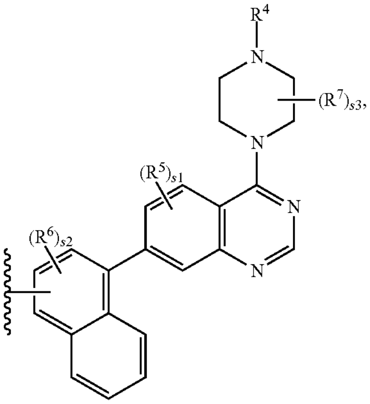

-continued
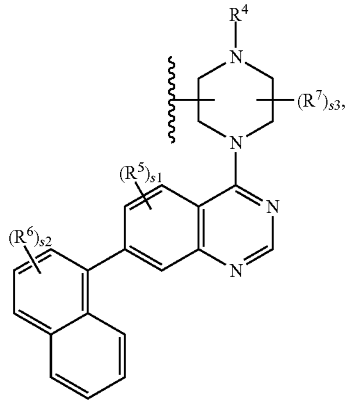
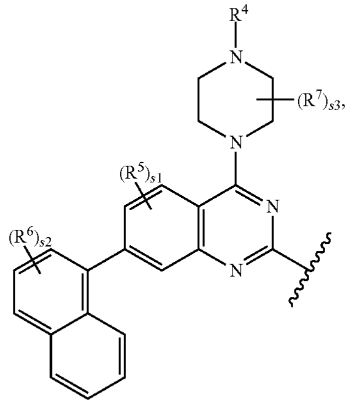
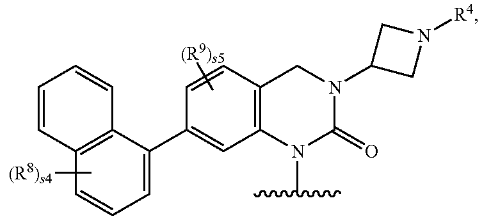
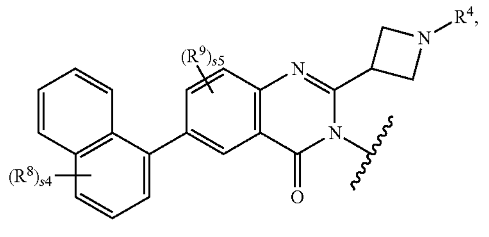
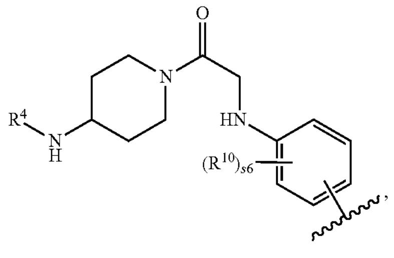
-continued
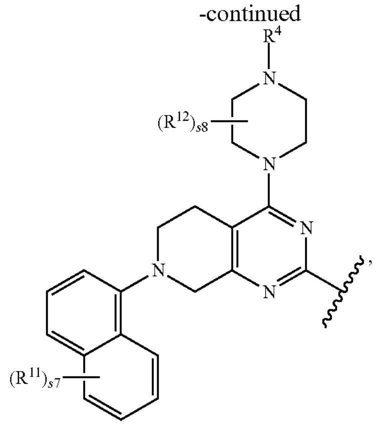
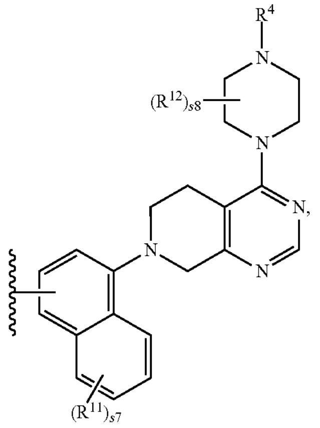
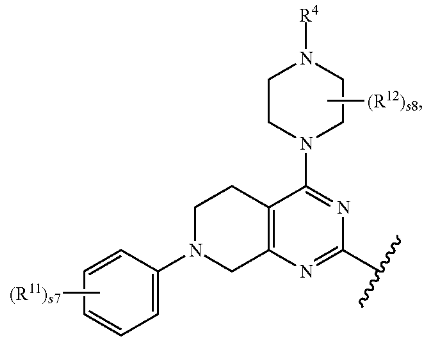
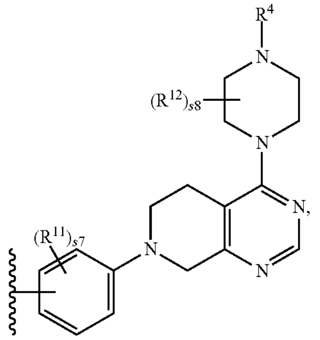

-continued

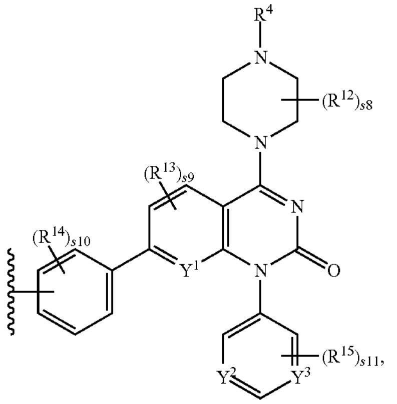

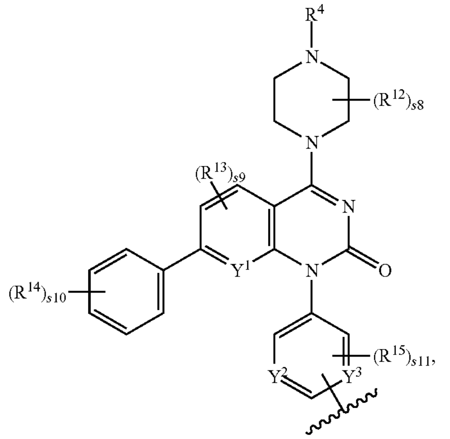

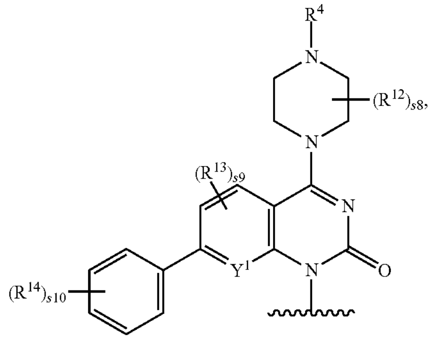

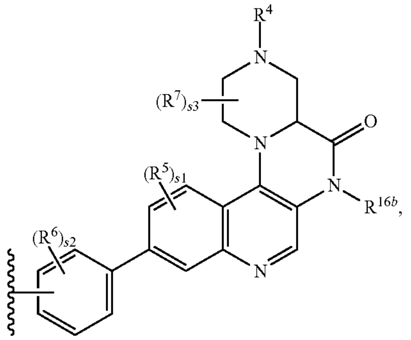

-continued

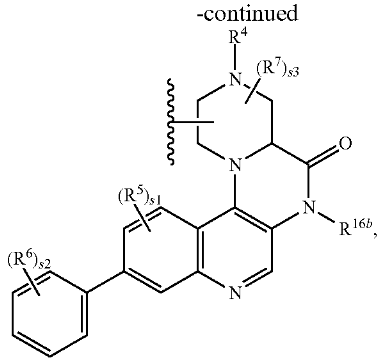

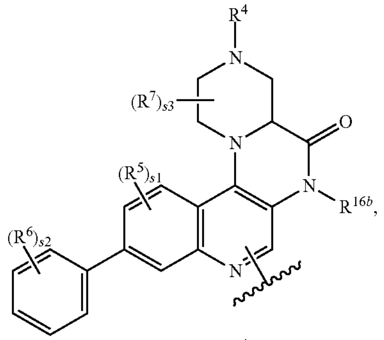

or

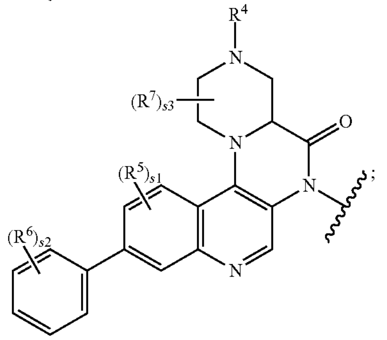

X is $C_1$-$C_{15}$ alkylene, heteroalkylene, $C_2$-$C_{10}$ alkenylene, $C_2$-$C_{10}$ alkynylene, phenylene, five to six membered heteroarylene, five to six membered heterocyclylene, or $C_3$-$C_5$ cycloalkylene, wherein each of the phenylene, five to six membered heteroarylene, five to six membered heterocyclylene, and $C_3$-$C_8$ cycloalkylene is optionally substituted with one or more $R^{18}$; or X is $C_1$-$C_{15}$ alkylene, heteroalkylene, $C_2$-$C_{10}$ alkenylene, or $C_2$-$C_{10}$ alkynylene, wherein one or more methylene repeating units is replaced by a ring structure, each independently selected from the group consisting of phenylene, five to six membered heteroarylene, five to six membered heterocyclylene, and $C_3$-$C_8$ cycloalkylene, and wherein each ring structure is independently and optionally substituted with one or more $R^{18}$;

Y is $CH_2$, O, S, or NH;

$L^1$ is a bond

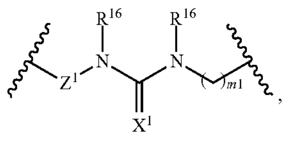

-continued

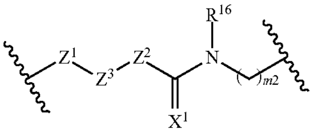
,

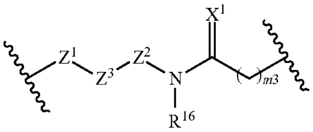
,

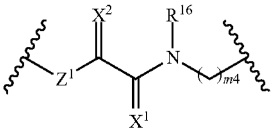
,

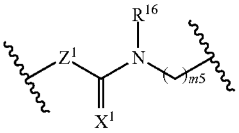
,
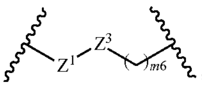
,

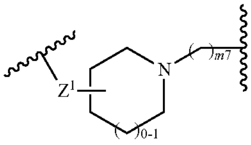
,

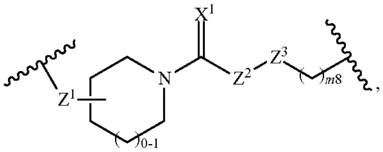
,

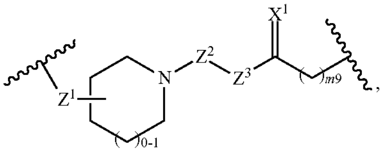
,

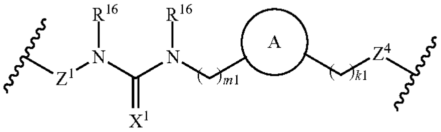
,

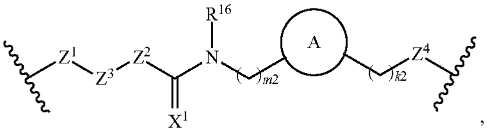
,

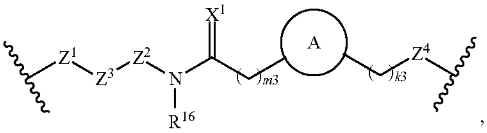
,

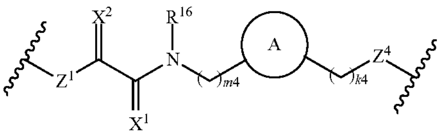
,

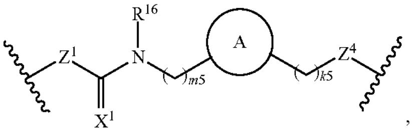
,

-continued

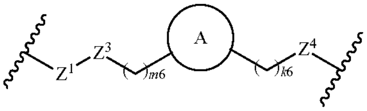
,

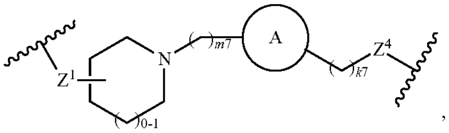
,

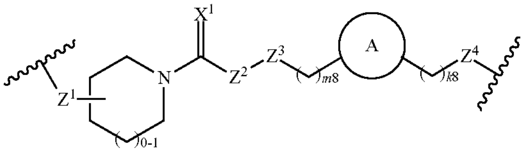
, or

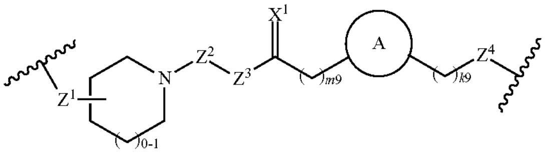
;

$L^2$ is a bond, —O—, —S—, —$NR^{16a}$—, —$(CH_2)_{1-3}$—, —C(=O)—, or —$(CH_2)$—$_3C$(=O)$NR^{16a}$ each of $Q^1$, $Q^2$, and $Q^3$ is independently S or CH, provided that one of $Q^1$, $Q^2$, and $Q^3$ is S;

Q is $CH_2$ or C(O);

n is an integer of 0, 1, or 2;

each $R^A$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, (amino)$C_1$—C, alkyl, —(C=O)$NR^{17a}R^{17b}$, ($C_1$—C alkoxy)$C_1$-$C_6$ alkyl, —O—($C_1$-$C_6$ alkoxy)$C_1$-$C_6$ alkyl, or optionally substituted $C_3$-$C_7$ cycloalkyl;

each of $R^2$, $R^{2a}$, and $R^{2b}$ is independently H, deuterium, halogen, or $C_1$-$C_6$ alkyl;

each $R^{2c}$ is independently H, $C_1$-$C_6$ alkyl, or $C_3$-$C_8$ cycloalkyl, wherein the $C_3$-$C_8$ cycloalkyl is optionally substituted with $C_1$-$C_6$ alkyl, halogen, or $C_1$-$C_6$ haloalkyl;

each $R^{2d}$ is independently H, OH, halogen, —O—$C_1$-$C_6$ alkyl, —O—$C_1$-$C_6$ haloalkyl, or —O—$C_3$-$C_8$ cycloalkyl, wherein the cycloalkyl is optionally substituted with $C_1$-$C_6$ alkyl, halogen, or $C_1$-$C_6$ haloalkyl;

each $R^{2e}$ is independently —C(=O)—$C_1$-$C_6$ alkyl or —C(=O)—$C_3$-$C_8$ cycloalkyl, each optionally substituted with one or more substituents, each independently selected from the group consisting of cyano, halogen, hydroxyl, amino, and $C_1$-$C_6$ haloalkyl;

each $R^3$ is independently H, deuterium, $C_1$-$C_6$ alkyl,

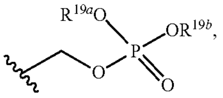
, or
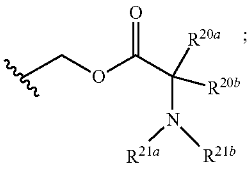
;

each $R^4$ is independently H, $C_1$-$C_6$ alkyl, —C(O)$C_1$-$C_6$ alkyl, —C(O)$C_2$-$C_6$ alkenyl, —C(O)$C_3$-$C_5$ cycloalkyl, —C(O)($C_3$-$C_5$ cycloalkyl)$C_1$-$C_6$ alkyl, —C(O)—(3 to 7 membered heterocyclyl), —C(O)—(3 to 7 membered heterocyclyl)$C_1$-$C_6$ alkyl, —C(O)$NR^{17a}R^{17b}$, —$S(O)_2$ $C_1$-$C_6$ alkyl, —$S(O)_2C_2$-$C_6$ alkenyl, —$S(O)_2C_3$-$C_8$ cycloalkyl, —$S(O)_2$($C_3$-$C_5$ cycloalkyl)$C_1$-$C_6$ alkyl, —$S(O)_2$-(3 to 7 membered heterocyclyl), —$S(O)_2$-(3 to 7 membered heterocyclyl)$C_1$-$C_6$ alkyl, or —$S(O)_2$ $NR^{17a}R^{17b}$, wherein, when $R^4$ is not H, $R^4$ is optionally substituted with one or more $R^{18}$;

each of $R^5$, $R^6$, $R^7$, $R^8$, $R^9$, $R^{10}$, $R^{11}$, $R^{12}$, $R^{13}$, $R^{14}$, and $R^{15}$ is independently halogen, hydroxyl, cyano, nitro, optionally substituted $C_1$-$C_6$ alkyl, $C_1$-$C_6$ haloalkyl, $C_1$-$C_6$ alkoxy, $C_1$-$C_6$ haloalkoxy, optionally substituted amino, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl;

each of $R^{16}$, $R^{16a}$, and $R^{16b}$ is independently H or $C_1$-$C_6$ alkyl;

each $R^{17a}$ and $R^{17b}$ is independently H or $C_1$-$C_6$ alkyl; or $R^{17a}$ and $R^{17b}$ together with the nitrogen atom to which they are attached form 5 or 6 membered heterocyclyl, each optionally substituted with one or more $R^{18}$;

each $R^{18}$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, —O—($C_1$-$C_6$ alkoxy)$C_1$-$C_6$ alkyl, optionally substituted amino, halogen, or cyano; or two geminal $R^{18}$ form oxo;

each of $R^{19a}$ and $R^{19b}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each of $R^{20a}$ and $R^{20b}$ is independently H, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl;

each of $R^{21a}$ and $R^{21b}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl;

each of s1, s2, s3, s4, s5, s6, s7, s8, s9, s10, and s11 is independently an integer of 0, 1, 2 or 3;

each of $Y^1$, $Y^2$, and $Y^3$ is independently N or CH;

each $Z^1$ is independently a bond, —$(CR^aR^b)_{q1}$—, —C(=O)—, —CH=CH—, or —C≡C—;

each $Z^2$ is independently —$(CR^cR^d)_{q2}$—;

each of $Z^3$ and $Z^4$ is independently $NR^{16}$, O, S, or a bond;

each of $R^a$, $R^b$, $R^c$, and $R^d$ is independently H, halogen, hydroxyl, $C_1$-$C_6$ alkyl, $C_1$-$C_6$ haloalkyl, $C_1$-$C_6$ alkoxy, $C_1$-$C_6$ haloalkoxy, or optionally substituted $C_3$-$C_6$ cycloalkyl;

q1 and q2 are each independently an integer of 1, 2, or 3;

each of $X^1$ and $X^2$ is independently O or S;

each ring A is independently phenylene, five to six membered heteroarylene, five to six membered heterocyclylene, or $C_3$-$C_8$ cycloalkylene, each of which is optionally substituted with one or more $R^{18}$; and each of m1, m2, m3, m4, m5, m6, m7, m8, m9, k1, k2, k3, k4, k5, k6, k7, k8, and k9 is independently an integer of 0, 1, 2, 3, 4, or 5.

In one embodiment, when $R^1$ is 2-(2,6-dioxopiperidin-3-yl)-1,3-dioxoisoindolin-4-yl, $R^{Het}$ is 4-((2S,5R)-4-acryloyl-2,5-dimethylpiperazin-1-yl)-6-chloro-8-fluoro-7-(2-fluoro-6-hydroxyphenyl)quinazolin-2-yl, X is $C_2$-$C_{12}$ alkylene, $L^2$ is O, and $L^1$ is

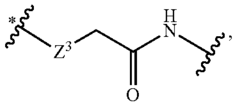

where * indicates the point of connection to $R^1$; then $Z^3$ is $NR^{16}$ or S. In another embodiment, when $R^{Het}$ is

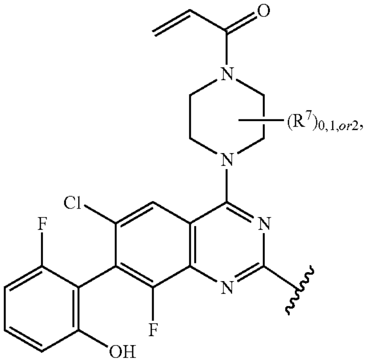

$R^7$ is methyl, X is $C_1$-$C_{12}$ alkylene or —$(CH_2CH_2O)_{1-11}$—, $L^2$ is O or a bond, and $L^1$ is

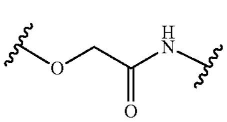

or

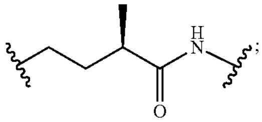

;

then R is

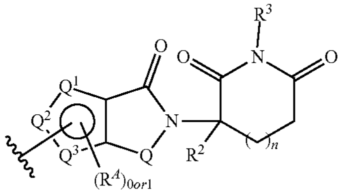

or

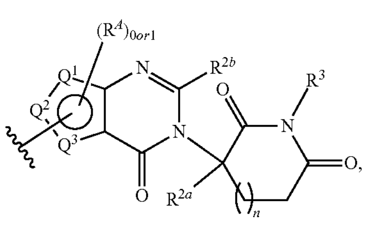

, wherein $R^2$, $R^3$, $R^{2a}$, $R^{2b}$, $R^A$, Q, $Q^1$, $Q^2$, $Q^3$, and n are each as defined herein. In yet another embodiment, $R^{Het}$ is neither

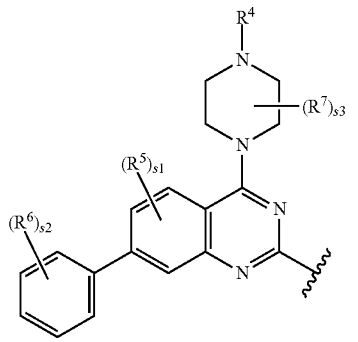

nor

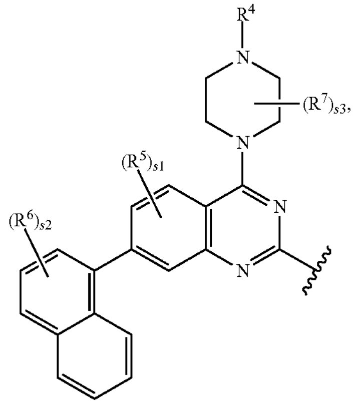

wherein $R^4$, $R^5$, $R^6$, $R^7$, s1, s2, and s3 are each as defined herein. In certain embodiments, $R^{Het}$ is not any one of 4-((2S,5R)-4-acryloyl-2,5-dimethylpiperazin-1-yl)-6-chloro-8-fluoro-7-(2-fluoro-6-hydroxyphenyl)quinazolin-2-yl, 4-(4-acryloylpiperazin-1-yl)-6-chloro-8-fluoro-7-(2-fluoro-6-hydroxyphenyl)quinazolin-2-yl, and 4-(4-acryloylpiperazin-1-yl)-6-chloro-8-fluoro-7-(3-hydroxynaphthalen-1-yl)quinazolin-2-yl.

In certain embodiments, in Formula (I), n is an integer of 1. In certain embodiments, in Formula (I), $R^1$ is

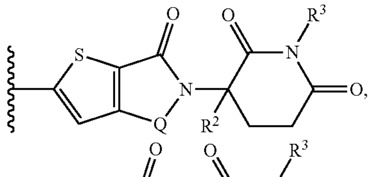

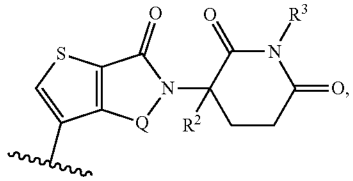

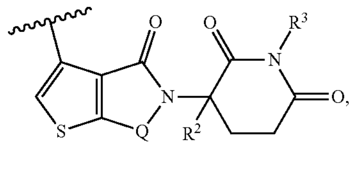

-continued

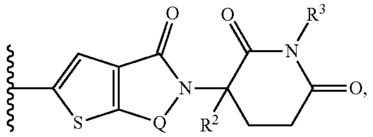

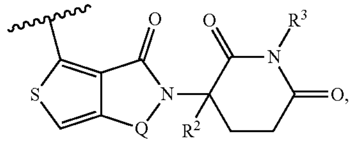

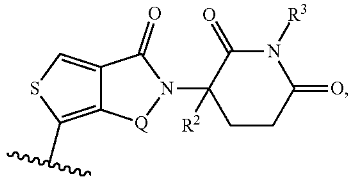

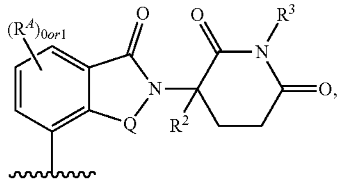

or

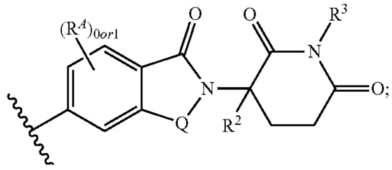

wherein $R^2$, $R^3$, $R^A$, and Q are each as defined herein. In certain embodiments, in Formula (I), n is an integer of 0 or 2. In certain embodiments, in Formula (I), $R^1$ is

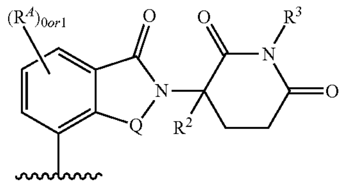

or

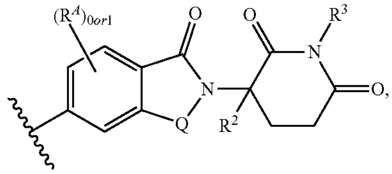

wherein $R^2$, $R^3$, $R^A$, and Q are each as defined herein. In certain embodiments, in Formula (I), $R^1$ is unsubstituted. In certain embodiments, in Formula (I), $R^1$ is substituted with one $R^A$. In certain embodiments, $R^A$ is halogen or optionally substituted $C_1$-$C_6$ alkyl. In certain embodiments, $R^A$ is fluoro.

In certain embodiments, in Formula (I), $R^1$ is

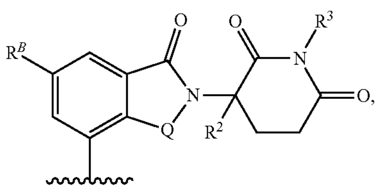

wherein $R^B$ is H or $R^A$; and $R^2$, $R^3$, $R^A$, and Q are each as defined herein. In certain embodiments, in Formula (I), $R^1$ is

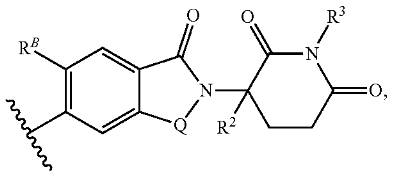

wherein $R^2$, $R^3$, $R^B$, and Q are as defined herein. In certain embodiments, $R^B$ is H, halogen, or optionally substituted $C_1$-$C_6$ alkyl. In certain embodiments, $R^B$ is fluoro. In certain embodiments, in Formula (I), $R^1$ is

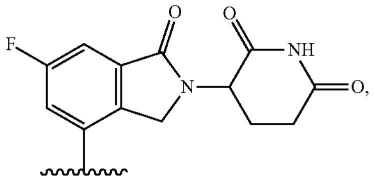

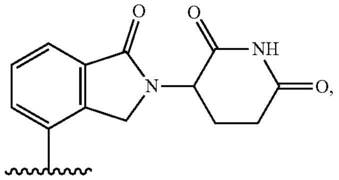

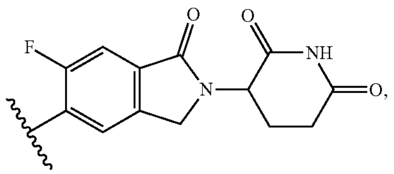

or

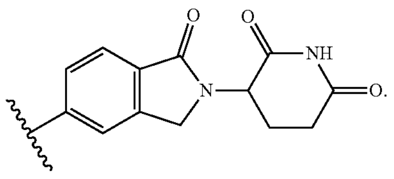

In certain embodiments, in Formula (I), $R^1$ is

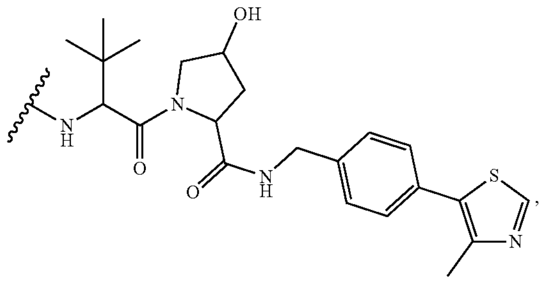

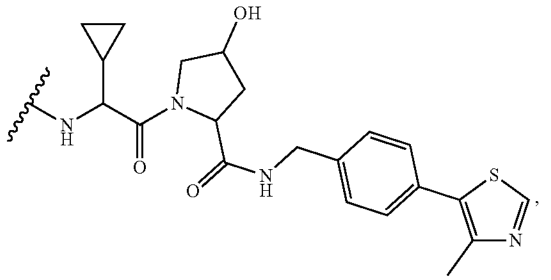

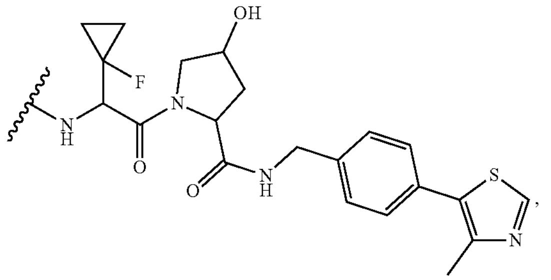

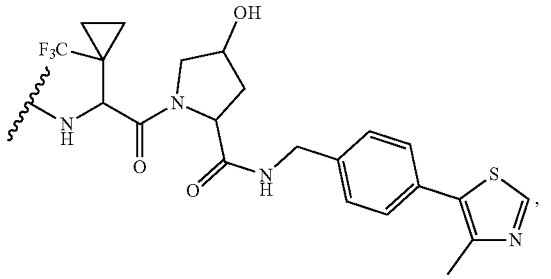

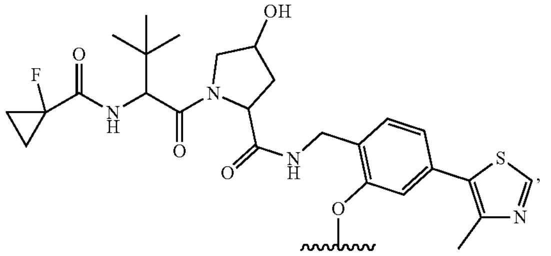

or

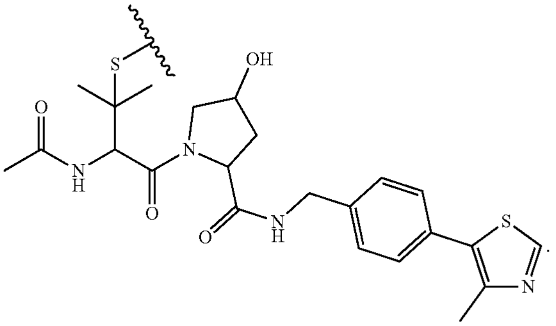

In certain embodiments, in Formula (I), $R^1$ is
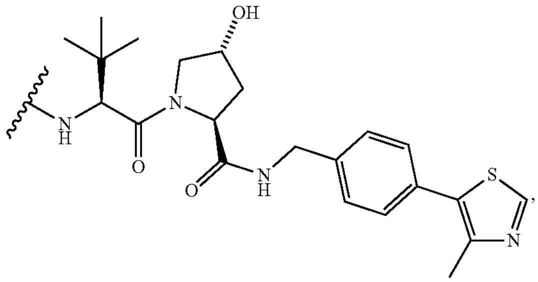 [SMILES: *N[C@H](C(=O)N1C[C@H](O)C[C@H]1C(=O)NCc1ccc(-c2scnc2C)cc1)C(C)(C)C]
,
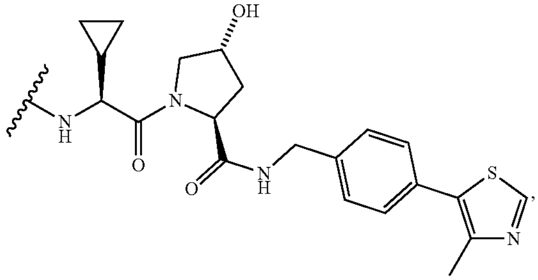
,
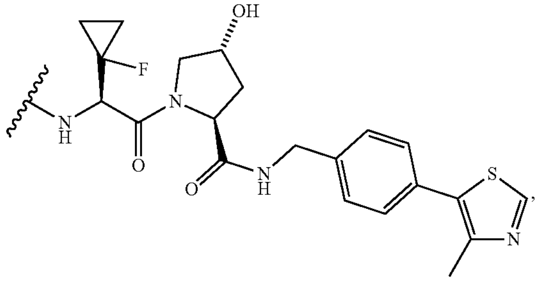
,
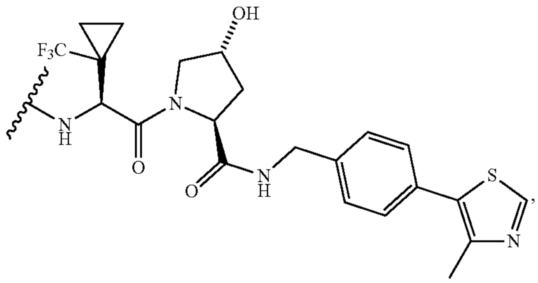
,
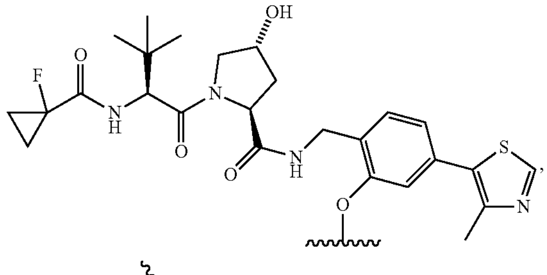
, or
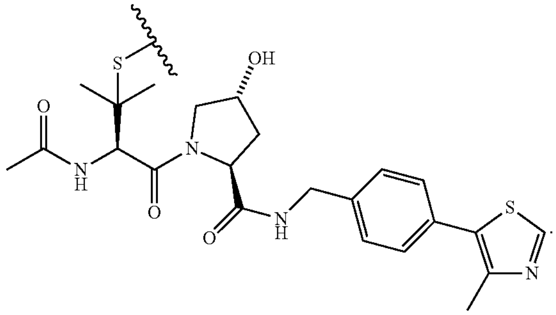
.
In certain embodiments, in Formula (I), $R^1$ is
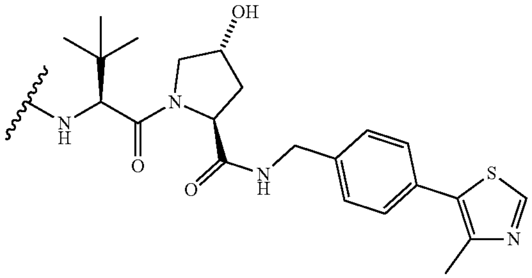
.
In certain embodiments, in Formula (I), $R^2$ is H. In certain embodiments, in Formula (I), $R^3$ is H.
In certain embodiments, in Formula (I), $L^1$ is a bond,
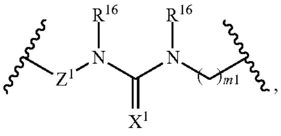
,
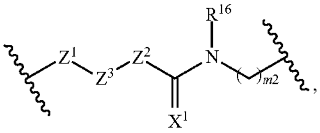
,
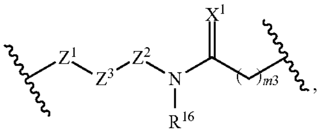
,
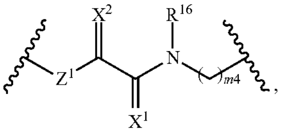
,
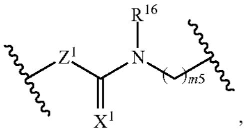
,
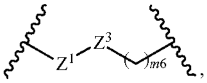
,
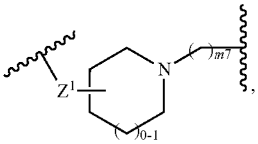
,
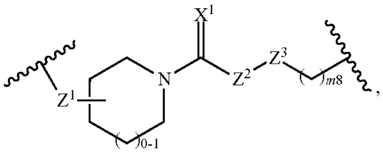
,
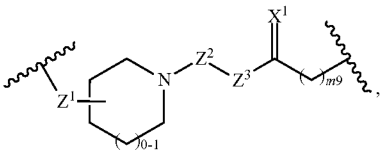
,
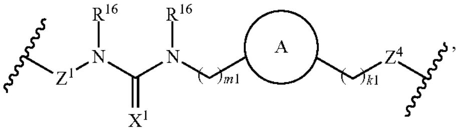
, -continued

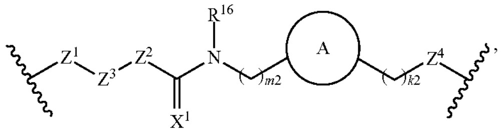

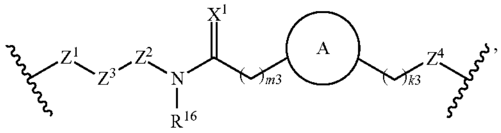

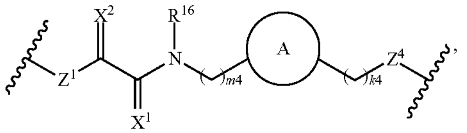

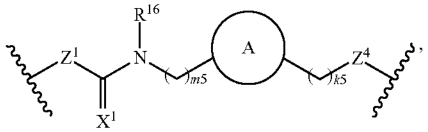

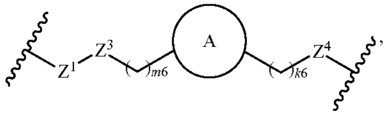

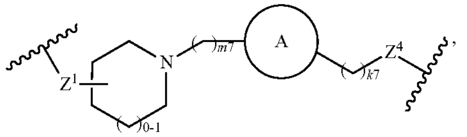

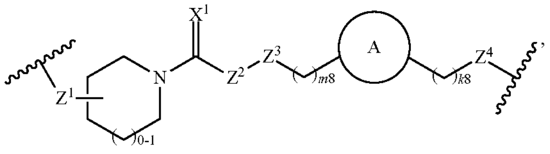

or

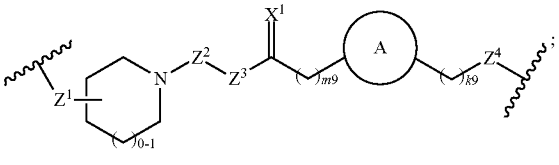

wherein $R^1$ is attached to $Z^1$; and ring A, $R^{16}$, $X^1$, $X^2$, $Z^1$, $Z^2$, $Z^3$, $Z^3$, k1, k2, k3, k4, k5, k6, k7, k8, k9, m1, m2, m3, m4, m5, m6, m7, m8, and m9 are each as defined herein.

In certain embodiments, in Formula (I), $L^1$ is

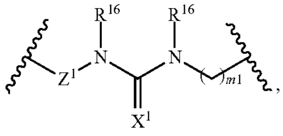

wherein $R^{16}$, $X^1$, $Z^1$, and m1 are each as defined herein; in one embodiment, each $R^{16}$ is H; $X^1$ is O; $Z^1$ is a bond or $-(CH_2)_{1-3}-$; and m1 is an integer of 0 or 1. In one embodiment, in Formula (I), $L^1$ is

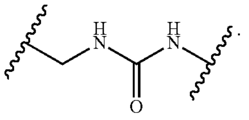 [SMILES: *CNC(=O)N*]

In certain embodiments, in Formula (I), $L^1$ is

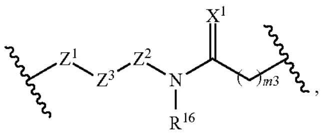

wherein $R^{16}$, $X^1$, $Z^1$, $Z^2$, $Z^3$, and m3 are each as defined herein; in one embodiment, $Z^3$ is O or $NR^{16}$; in another embodiment, each $R^{16}$ is H; $X^1$ is O; $Z^2$ is $-(CH_2)_{1-2}-$; $Z^1$ is a bond or $-(CH_2)_{1-3}-$; and m3 is an integer of 0 or 1. In certain embodiments, in Formula (I), $L^1$ is

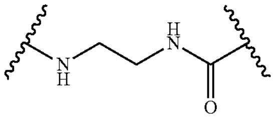

or

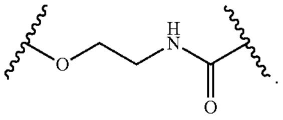

In certain embodiments, in Formula (I), $L^1$ is

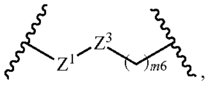

wherein $Z^1$, $Z^3$, and m6 are each as defined herein; in one embodiment, $Z^3$ is O or $NR^{16}$; in another embodiment, $R^{16}$ is H; $Z^1$ is a bond or $-(CH_2)_{1-3}-$; and m6 is an integer of 0 or 1; in yet another embodiment, $Z^1$ is $-C(O)-$; $Z^3$ is a bond; and m6 is an integer of 0 or 1. In certain embodiments, in Formula (I), $L^1$ is

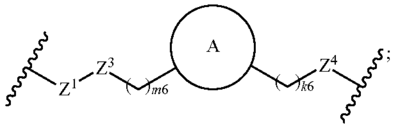

wherein ring A, $Z^1$, $Z^3$, $Z^4$, k6, and m6 are each as defined herein; in one embodiment, $Z^3$ is O or $NR^{16}$; in another embodiment, ring A is phenylene optionally substituted with $R^{18}$; $Z^1$ is a bond or $-(CH_2)_{1-3}-$; $Z^4$ is $-O-$ or $-NR^{16}-$; each $R^{16}$ is H; k6 and m6 are each independently an integer of 0 or 1. In certain embodiments, in Formula (I), $L^1$ is

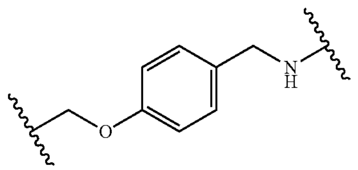
or

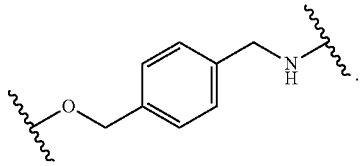
.

In certain embodiments, in Formula (I), $L^1$ is

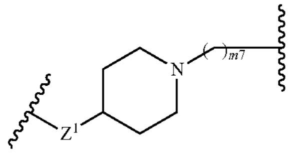
or

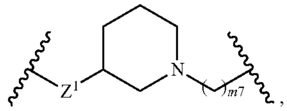
, wherein $Z^1$ and m7 are each as defined herein; in one embodiment, each $Z^1$ is independently a bond or $-(CH_2)_{1-3}-$; and each m7 is independently an integer of 0 or 1. In one embodiment, $L^1$ is

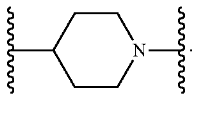 [SMILES: *C1CCN(*)CC1]
.

In certain embodiments, in Formula (I), $L^1$ is

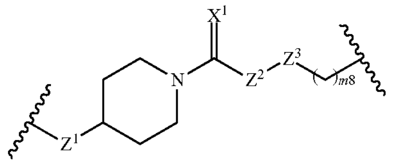
or

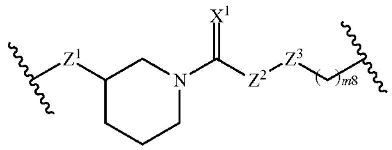
, wherein each $Z^3$ is independently $NR^{16}$; and $R^{16}$, $X^1$, $Z^1$, $Z^2$, and m8 are each as defined herein; in one embodiment, $Z^1$ is $-C\equiv C-$; in another embodiment, $X^1$ is O; $Z^2$ is $-CH_2-$; $R^{16}$ is H; and each m8 is independently an integer of 0 or 1. In certain embodiments, in Formula (I), $L^1$ is

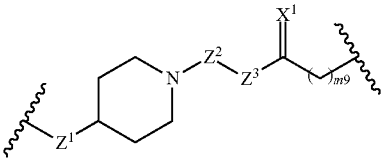
or

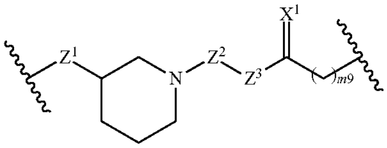
, wherein $X^1$, $Z^1$, $Z^2$, $Z^3$, and m9 are each as defined herein; in one embodiment, $Z^1$ is a bond; $X^1$ is 0; and each m9 is independently an integer of 0 or 1. In one embodiment, in Formula (I), $L^1$ is

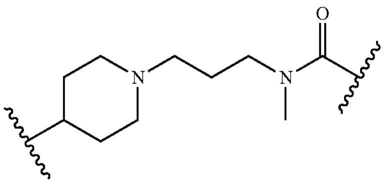
.

In certain embodiments, in Formula (I), $L^1$ is

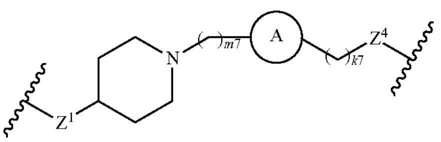
or

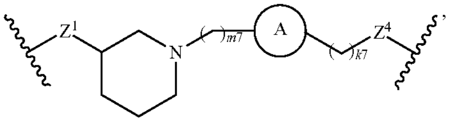
, wherein each $Z^4$ is independently O or $NR^{16}$; and ring A, $R^{16}$, $Z^1$, m7, and m7 are each as defined herein; in one embodiment, each ring A is independently phenylene, 6 membered heterocyclylene, or $C_6$-$C_8$ cycloalkylene; each $R^{16}$ is independently H or methyl; $Z^1$ is a bond; each m7 is independently an integer of 0, 1, or 2; and each k7 is independently an integer of 0 or 1. In certain embodiments, in Formula I, $L^1$ is

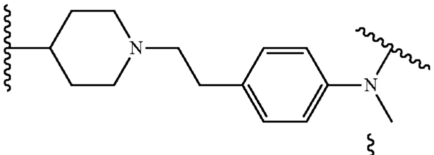
,

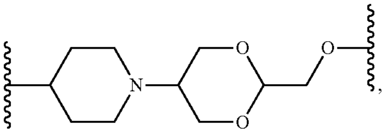
, or

-continued

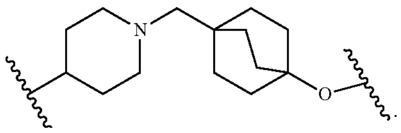

In any embodiments of $L^1$ that contains ring A, ring A can be a phenylene; five or six membered heteroarylene containing one, two, or three heteroatoms, each independently selected from the group consisting of N, O, and S; five or six membered heterocyclylene containing one or two heteroatoms, each independently selected from the group consisting of N, O and S; or $C_3$-$C_8$ cycloalkylene (in one embodiment, cyclopropyl, cyclobutyl, cyclopentyl, cyclohexyl, cycloheptyl, bicyclo[2.2.1]heptanyl, or bicyclo[2.2.2]octanyl). In certain embodiments, ring A is optionally substituted with one or more $R^{18}$.

In one embodiment, in Formula (I), $L^1$ is —$NH(CH_2)_2NHC(=O)$—, —$O(CH_2)_2NHC(=O)$—, —NH—, —$CH_2NHC(O)NH$—, or

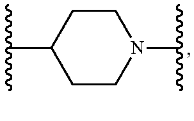,
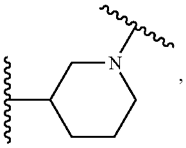,

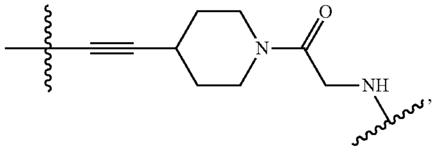, or

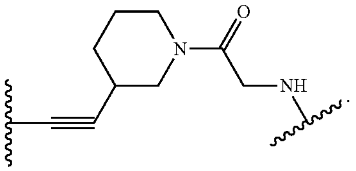.

In another embodiment, $L^1$ is *—$NH(CH_2)_2NHC(=O)$—, *—$O(CH_2)_2NHC(=O)$—,

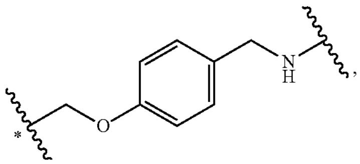,

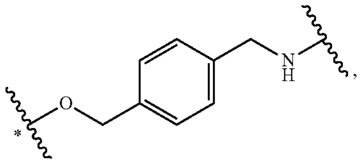,

*—$CH_2NHC(O)NH$—,

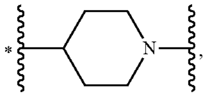,
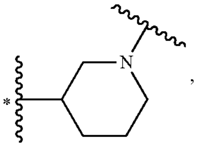,

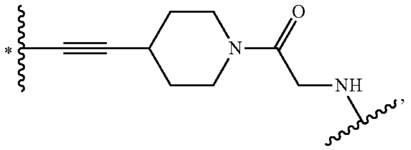,

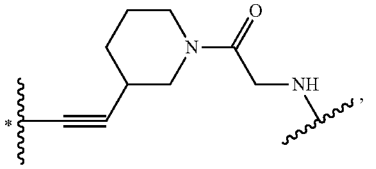,

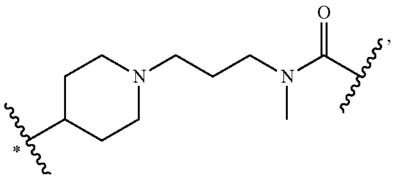,

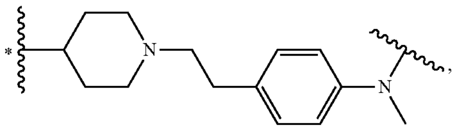,

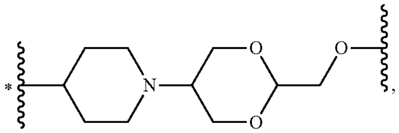, or

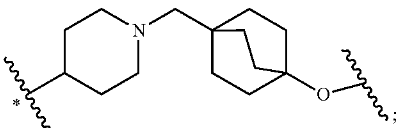;

where * indicates the point of connection to $R^1$.

In certain embodiments, in Formula (I), $R^1$-$L^1$ is

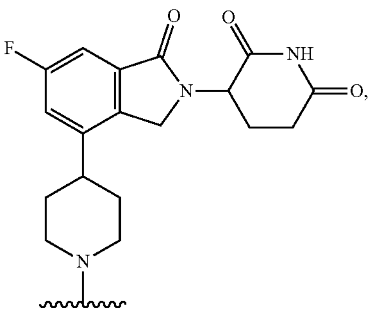,

-continued

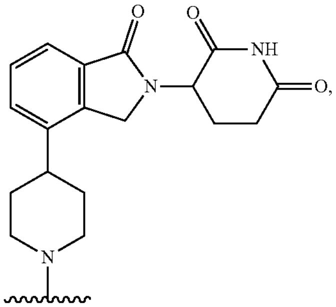

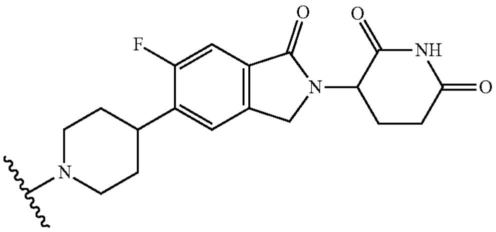

or

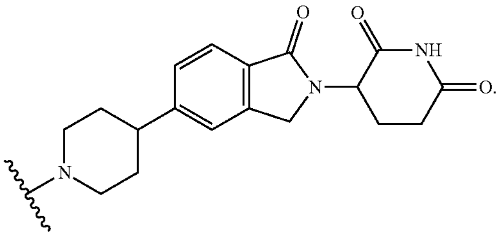

In certain embodiments, provided herein is a compound of Formula (Ia), (Ib), (Ic), or (Id):

(Ia)

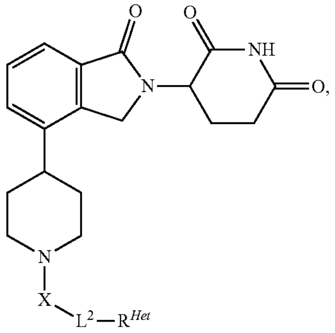

(Ib)

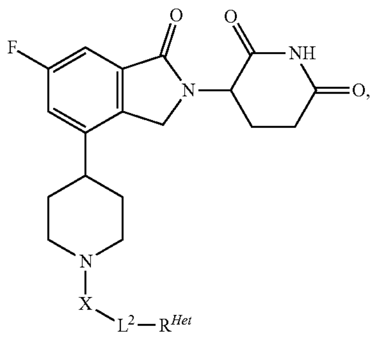

-continued (Ic)

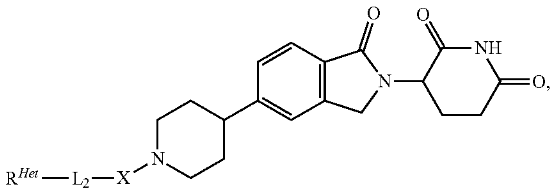

or (Id)

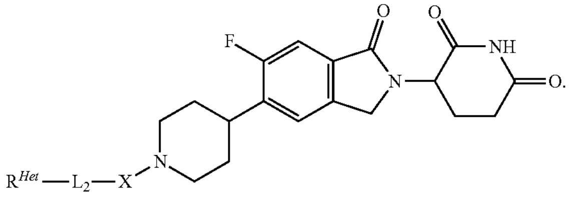

In certain embodiments, in Formula (I), (Ia), (Ib), (Ic), or (Id), $L^2$ is a bond. In certain embodiments, in Formula (I), (Ia), (Ib), (Ic), or (Id), $L^2$ is —O—. In certain embodiments, in Formula (I), (Ia), (Ib), (Ic), or (Id), $L^2$ is —$NR^{16a}$—, wherein $R^{16a}$ is as defined herein. In certain embodiments, in Formula (I), (Ia), (Ib), (Ic), or (Id), $L^2$ is —$(CH_2)_{1-2}$—. In certain embodiments, in Formula (I), (Ia), (Ib), (Ic), or (Id), $L^2$ is-C(═O)—. In certain embodiments, in Formula (I), (Ia), (Ib), (Ic), or (Id), $L^2$ is —$CH_2C$(═O)$NR^{16a}$—, wherein $R^{16a}$ is as defined herein. In certain embodiments, $R^{16a}$ is H. In certain embodiments, $R^{16a}$ is methyl. In certain embodiments, in Formula (I), (Ia), (Ib), (Ic), or (Id), $L^2$ is —$CH_2C$(═O)NH—*, where * indicates the point of connection to X. In certain embodiments, in Formula (I), (Ia), (Ib), (Ic), or (Id), $L^1$ and $L^2$ cannot both be a bond.

In certain embodiments, in Formula (I), (Ia), (Ib), (Ic) or (Id), X is alkylene. In certain embodiments, in Formula (I), (Ia), (Ib), (Ic) or (Id), X is $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ alkylene. In certain embodiments, in Formula (I), (Ia), (Ib), (Ic) or (Id), X is $C_1$-$C_8$alkylene. In certain embodiments, in Formula (I), (Ia), (Ib), (Ic) or (Id), X is methylene, ethylene, propylene, butylene, pentylene, hexylene, heptylene, or octylene. In certain embodiments, in Formula (I), (Ia), (Ib), (Ic) or (Id), X is straight-chained alkylene. In certain embodiments, in Formula (I), (Ia), (Tb), (Ic) or (Id), X is straight-chained $C_1$-$C_8$ alkylene. In certain embodiments, in Formula (I), (Ia), (Tb), (Ic) or (Id), X is unsubstituted. In certain embodiments, in Formula (I), (Ia), (Ib), (Ic) or (Id), X is unsubstituted $C_7$ alkylene. In certain embodiments, in Formula (I), (Ia), (Tb), (Ic) or (Id), X is —$(CH_2)_5$—, —$(CH_2)_6$—, —$(CH_2)_7$—, or —$(CH_2)_8$—.

In certain embodiments, in Formula (I), (Ia), (Tb), (Ic), or (Id), X is heteroalkylene. In certain embodiments, in Formula (I), (Ia), (Ib), (Ic), or (Id), X is $C_1$-$C_{15}$ alkylene, wherein one or more methylene units are replaced by a heteroatom. In certain embodiments, the heteroatom in the heteroalkylene is oxygen (O), nitrogen (N), or sulfur (S). In certain embodiments, in Formula (I), (Ia), (Ib), (Ic), or (Id), X is a heteroalkylene containing carbon, hydrogen, and oxygen atoms, wherein at least one methylene unit is replaced by oxygen. In certain embodiments, in Formula (I), (Ia), (Ib), (Ic), or (Id), X is —$(CH_2CH_2O)_{1-5}$— or —$(CH_2CH_2O)_{1-5}CH_2CH_2$—. In certain embodiments, in Formula (I), (Ia), (Ib), (Ic), or (Id), X is heteroalkylene containing carbon, hydrogen, and nitrogen atoms, wherein at least one methylene unit is replaced by $NR^{16c}$, and $R^{16c}$ is as defined herein. In certain embodiments, in Formula (I), (Ia), (Ib), (Ic), or (Id), X is $—(CH_2)_{1-5}—NR^{16c}—(CH_2)_{1-5}—$, wherein $R^{16c}$ is H or $C_1$-$C_6$ alkyl, in one embodiment, methyl. In certain embodiments, in Formula (I), (Ia), (Ib), (Ic), or (Id), X is unsubstituted heteroalkylene containing carbon, hydrogen, and oxygen and/or nitrogen atoms. In certain embodiments, in Formula (I), (Ia), (Ib), (Ic), or (Id), X is straight-chained heteroalkylene. In certain embodiments, in Formula (I), (Ia), (Ib), (Ic), or (Id), X is $—CH_2CH_2O—$, $—(CH_2CH_2O)_2—$, $—(CH_2CH_2O)_3—$, $—CH_2CH_2OCH_2CH_2—$, $—(CH_2CH_2O)_2CH_2CH_2—$, $—(CH_2CH_2O)_3CH_2CH_2—$, $—(CH_2CH_2O)_4CH_2CH_2—$, $—CH_2NR^{16c}$ $CH_2—$, $—CH_2CH_2NR^{16c}CH_2CH_2—$, $—(CH_2)_2OCH_2(CH_2)_3—$, or $—(CH_2)_3NR^{16}$, $(CH_2)_3—$, wherein $R^{16c}$ is as defined herein. In certain embodiments, $R^{16c}$ is H or methyl. In certain embodiments, in Formula (I), (Ia), (Ib), (Ic), or (Id), X is phenylene; five or six membered heteroarylene containing one, two, or three heteroatoms, each independently selected from the group consisting of N, O, and S; five or six membered heterocyclylene containing one or two heteroatoms, each independently selected from the group consisting of N, O, and S; or $C_3$-$C_8$ cycloalkylene (in one embodiment, cyclopropyl, cyclobutylene, cyclopentylene, cyclohexylene, or cycloheptylene); each of which is optionally substituted with one or more $R^{18}$, wherein $R^{18}$ is as defined herein. In certain embodiments, in Formula (I), (Ia), (Ib), (Ic), or (Id), X is $C_1$-$C_8$ alkylene or heteroalkylene, wherein at least one methylene unit is replaced by a ring structure selected from 5 or 6 membered heteroarylene containing one, two or three heteroatoms, each independently selected from the group consisting of N, O, and S; five or six membered heterocyclylene containing one or two heteroatoms, each independently selected from the group consisting of N, O, and S; and $C_3$-$C_8$ cycloalkylene (in one embodiment, cyclopropylene, cyclobutylene, cyclopentylene, cyclohexylene, or cycloheptylene); each of which is optionally substituted with one or more $R^{18}$, wherein $R^{15}$ is as defined herein.

In certain embodiments, in Formula (I), (Ia), (Ib), (Ic), or (Id), $R^{Het}$ is:

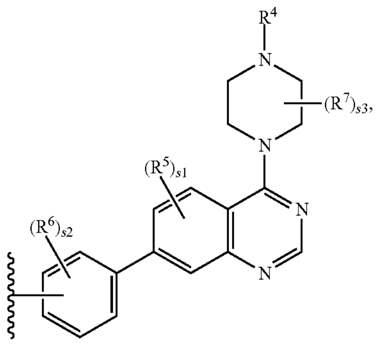

-continued

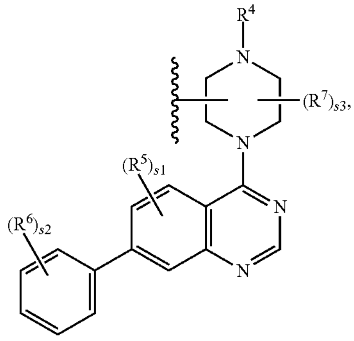

or

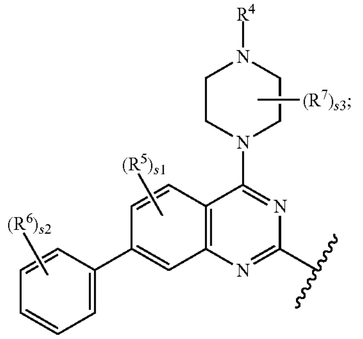

wherein $R^4$, $R^5$, $R^6$, $R^7$, s1, s2, and s3 are each as defined herein. In certain embodiments, each $R^4$ is independently $—C(O)C_1$-$C_6$ alkyl (in one embodiment, $—C(O)CH_3$ or $—C(O)C_2H_5$), $—C(O)C_2$-$C_6$ alkenyl (in one embodiment, $—C(O)CH{=}CH_2$), $—C(O)C_3$-$C_5$ cycloalkyl, $—C(O)(C_3$-$C_5$ cycloalkyl)$C_1$-$C_6$ alkyl, —C(O)—(3 to 7 membered heterocyclyl), or $—C(O)NH_2$. In certain embodiments, each $R^4$ is independently $—C(O)C_1$-$C_6$ alkyl, $—C(O)C_2$-$C_6$ alkenyl, $—C(O)C_3$-$C_5$ cycloalkyl, $—C(O)(C_3$-$C_5$ cycloalkyl)$C_1$-$C_6$ alkyl, —C(O)—(3 to 7 membered heteroaryl), —C(O)—(3 to 7 membered heterocyclyl), or $—C(O)NH_2$. In certain embodiments, each $R^4$ is independently and optionally substituted with halogen or cyano. In certain embodiments, each $R^4$ is independently $—C(O)C_2$-$C_6$ alkenyl, optionally substituted with halogen or cyano. In certain embodiments, each $R^4$ is independently

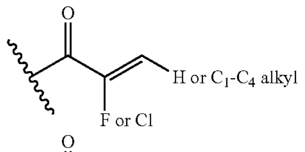

or

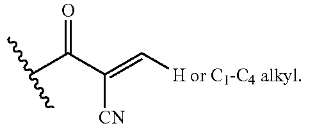

In certain embodiments, each $R^4$ is independently

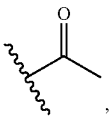

,

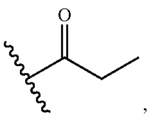

,

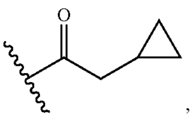

,

-continued

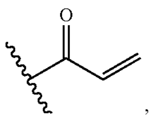 , 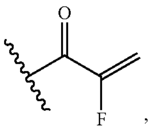 , 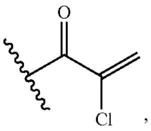 ,

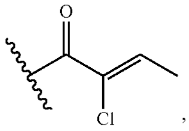 , 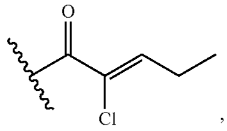 ,

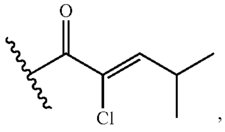 , 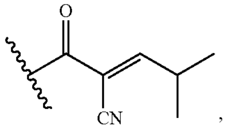 ,

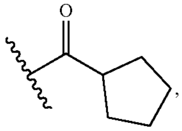 , 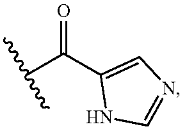

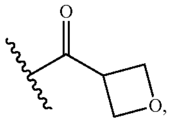 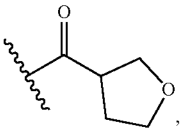 ,

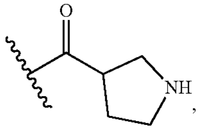 , 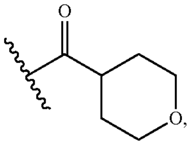

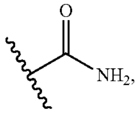 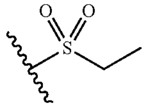 , or 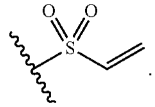 .

In certain embodiments, s1 is an integer of 1 or 2, and each $R^5$ is independently halogen, hydroxyl, or $C_1$-$C_6$ alkyl. In certain embodiments, s1 is an integer of 1; and $R^5$ is F or Cl. In certain embodiments, s1 is an integer of 3. In certain embodiments, s1 is an integer of 2; and each $R^5$ is independently F or Cl. In certain embodiments, s2 is an integer of 1 or 2; and each $R^6$ is independently halogen, hydroxyl, or $C_1$-$C_6$ alkyl. In certain embodiments, s2 is an integer of 1; and $R^6$ is F. In certain embodiments, s2 is an integer of 2 and each $R^6$ is independently F and —OH. In certain embodiments, s3 is 1 or 2, and each $R^7$ is independently $C_1$-$C_6$ alkyl. In certain embodiments, s3 is 1 or 2, and $R^7$ is methyl. In certain embodiments, s3 is 0.

In certain embodiments, in Formula (I), (Ia), (Ib), (Ic), or (Id), $R^{Het}$ is

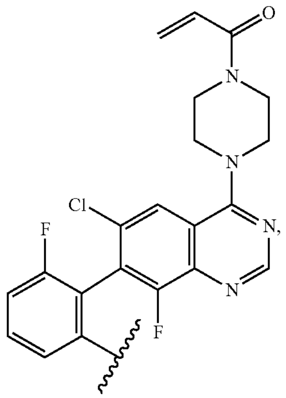

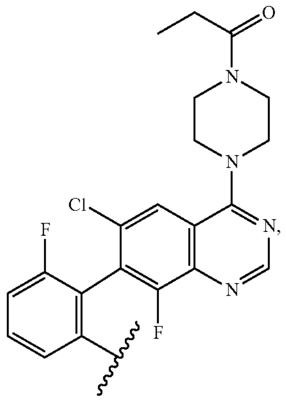

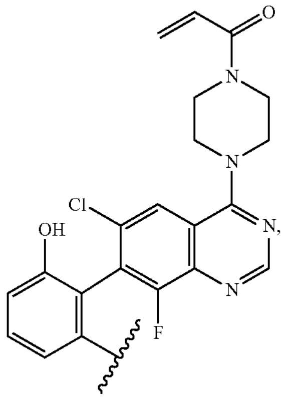

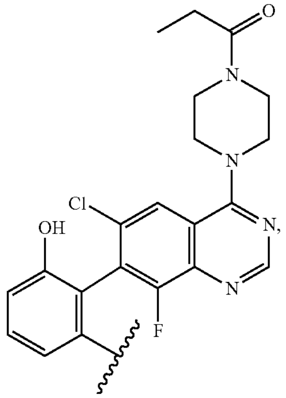

-continued
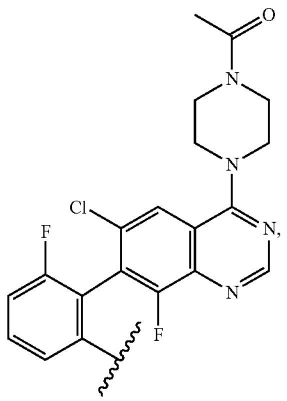
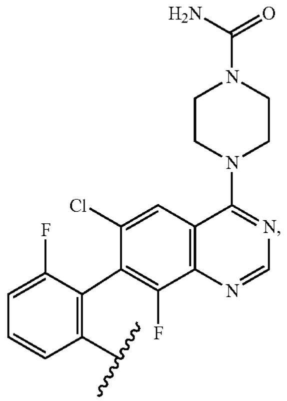
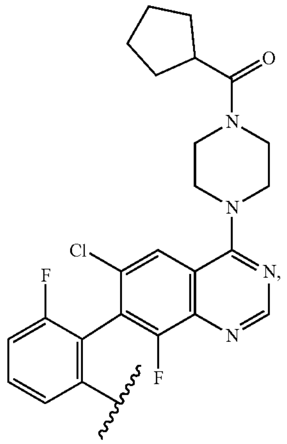
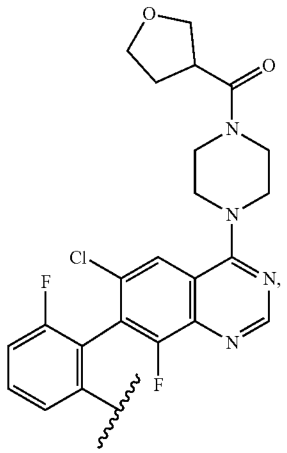
-continued
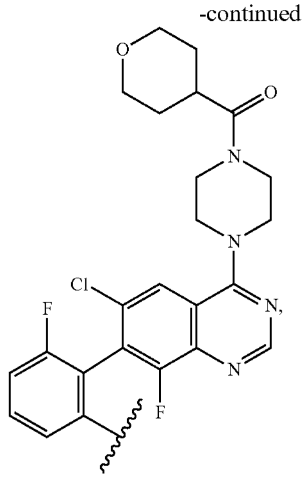
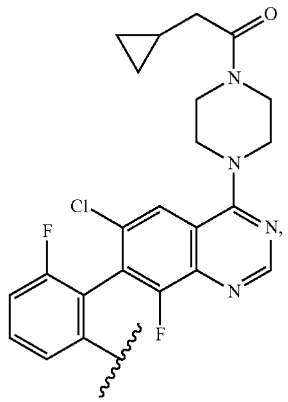
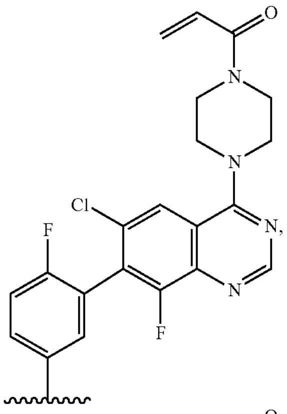
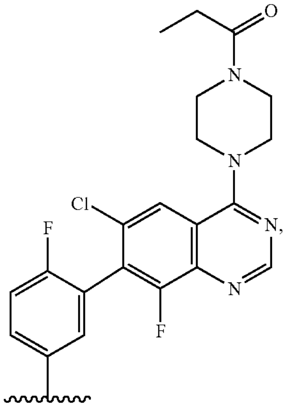

-continued

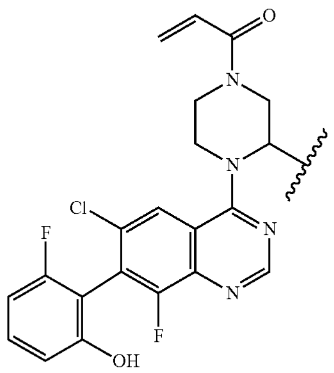

,

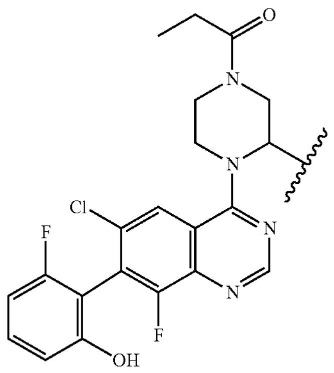

,

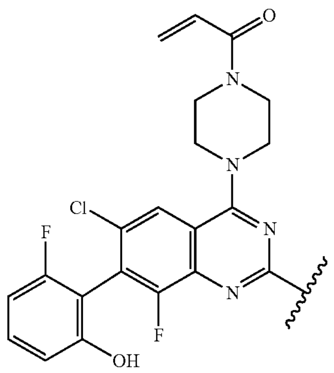

, or

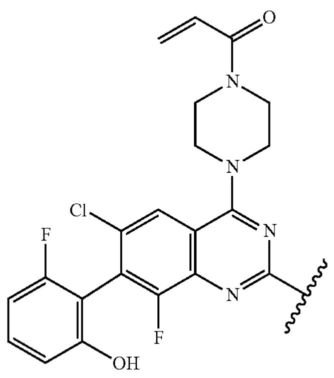

.

In certain embodiments, $R^{Het}$ is an R or S atropisomer, or a mixture thereof. In one embodiment, $R^{Het}$ is an R-atropisomer. In another embodiment, $R^{Het}$ is an S-atropisomer.

In one embodiment, provided herein is a compound of Formula (II):

(II)

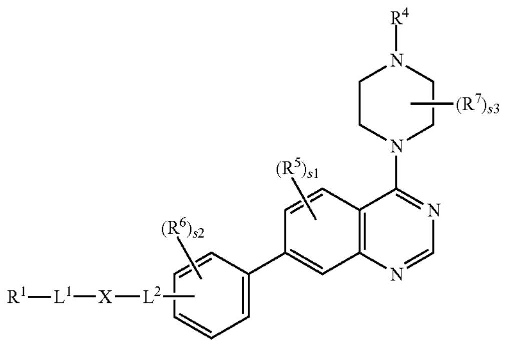

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^4$, $R^5$, $R^6$, $R^7$, $L^1$, $L^2$, X, s1, s2, and s3 are each as defined herein.

In another embodiment, provided herein is a compound of Formula (III):

(III)

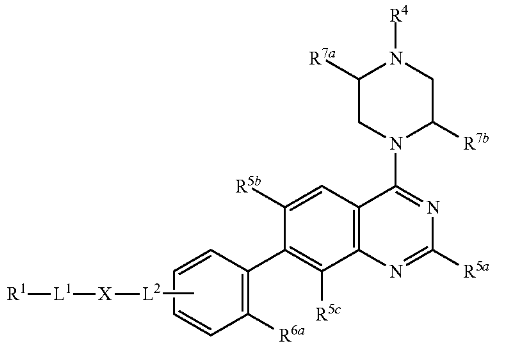

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^{5a}$, $R^{5b}$, and $R^{5C}$ are each independently H or $R^5$;

$R^{6a}$ is H or $R^6$.

$R^{7a}$ and $R^{7b}$ are each independently H or $R^7$; and $R^1$, $R^4$, $R^5$, $R^6$, $R^7$, $L^1$, $L^2$, and X are each as defined herein.

In yet another embodiment, provided herein is a compound of Formula (IV):

(IV)

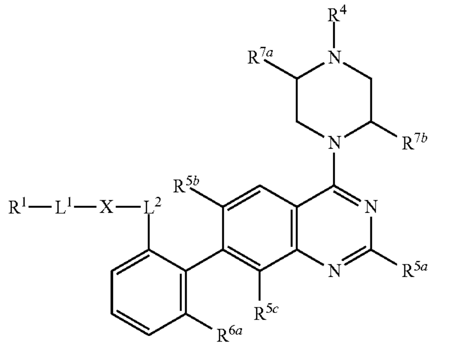

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^4$, $R^{5a}$, $R^{5b}$, $R^{5c}$, $R^{6a}$, $R^{7a}R^{7b}$, $L^1$, $L^2$, and X are each as defined herein.

In yet another embodiment, provided herein is a compound of Formula (V):

(V)

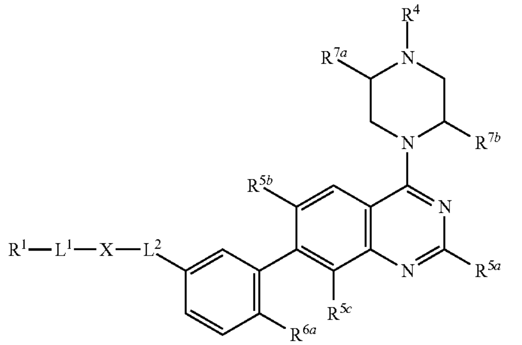

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^4$, $R^{5a}$, $R^{5b}$, $R^{5c}$, $R^{6a}$, $R^{7a}$, $R^{7b}$, $L^1$, $L^2$, and X are each as defined herein.

In yet another embodiment, provided herein is a compound of Formula (VI):

(VI)

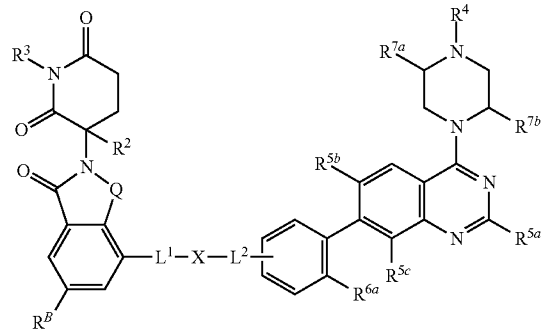

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^1$, $L^2$, Q, and X are each as defined herein.

In yet another embodiment, provided herein is a compound of Formula (VII):

(VII)

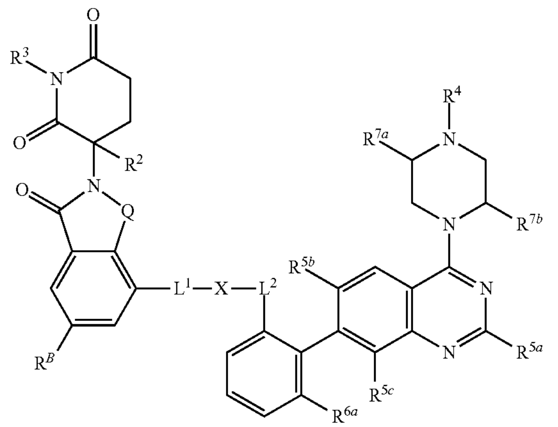

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^1$, $L^2$, Q, and X are each as defined herein.

In yet another embodiment, provided herein is a compound of Formula (VIIa):

(VIIa)

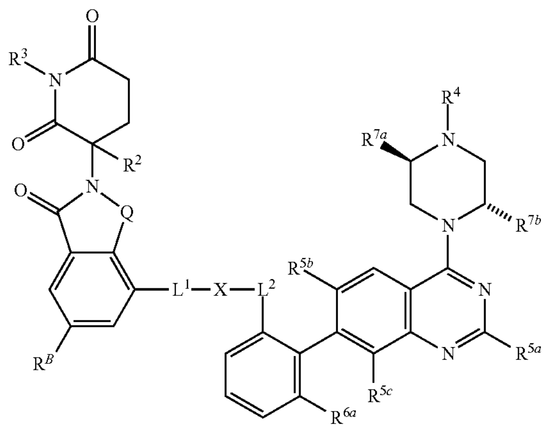

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^1$, $L^2$, Q, and X are each as defined herein.

In yet another embodiment, provided herein is a compound of Formula (VIII):

(VIII)

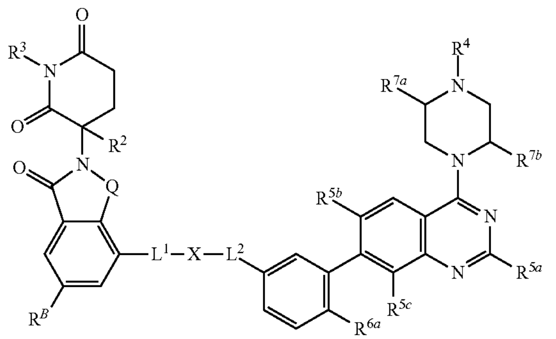

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^1$, $L^2$, Q, and X are each as defined herein.

In yet another embodiment, provided herein is a compound of Formula (VIIIa):

(VIIIa)

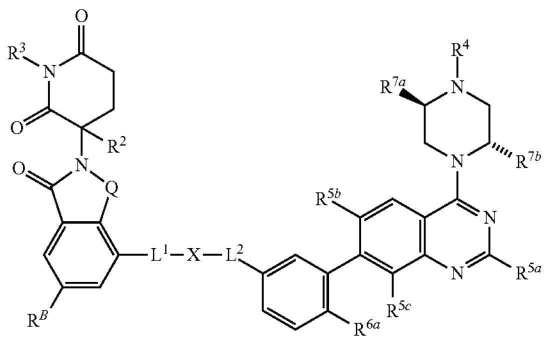

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^1$, $L^2$, Q, and X are each as defined herein.

In yet another embodiment, provided herein is a compound of Formula (IX):

(IX)

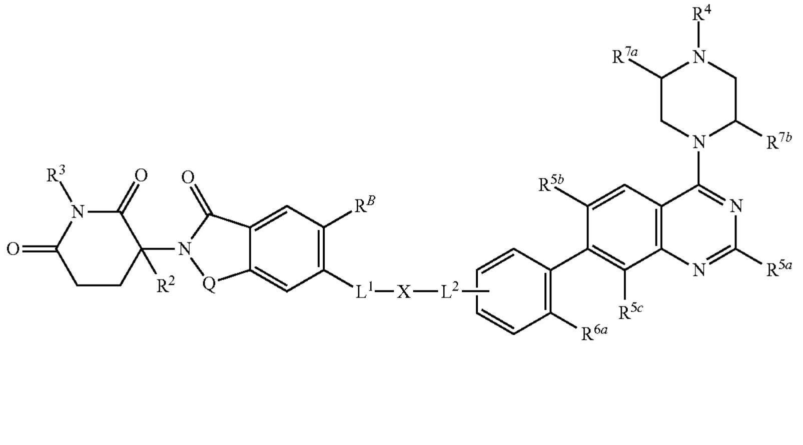

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^1$, $L^2$, Q, and X are each as defined herein.

In yet another embodiment, provided herein is a compound of Formula (X):

(X)

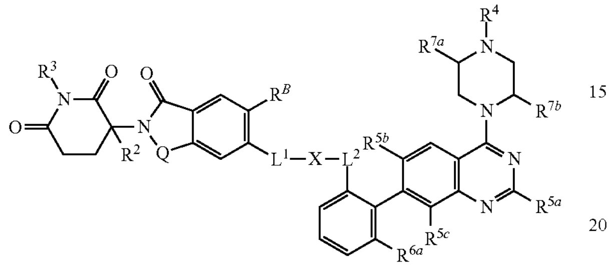

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5s}$, $R^{5b}$, $R^{5c}$, $R^{6a}$, $R^{7a}$, $R^{7b}$, $R^B$, $L^1$, $L^2$, Q, and X are each as defined herein.

In yet another embodiment, provided herein is a compound of Formula (Xa):

(Xa)

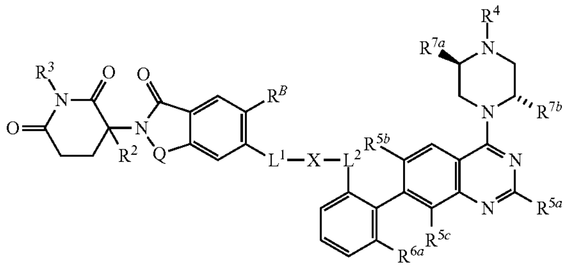

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^1$, $L^2$, Q, and X are each as defined herein.

In yet another embodiment, provided herein is a compound of Formula (XI):

(XI)

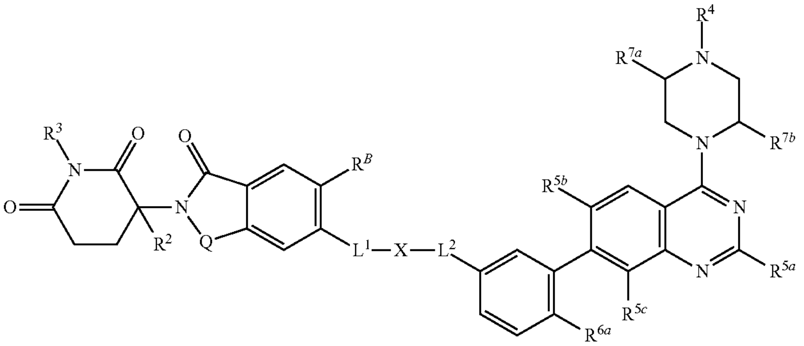

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^1$, $L^2$, Q, and X are each as defined herein.

In yet another embodiment, provided herein is a compound of Formula (XIa):

(XIa)

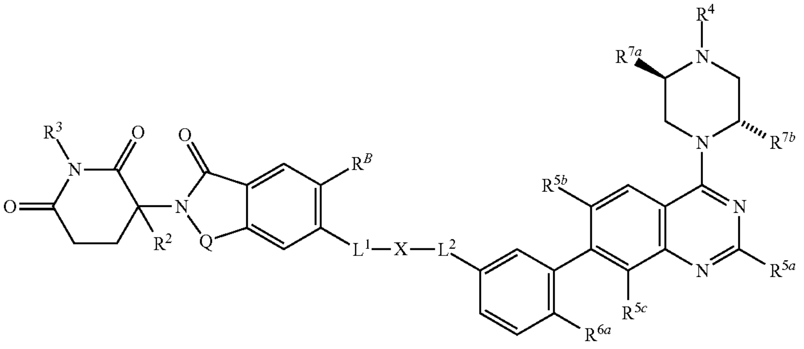

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^1$, $L^2$, Q, and X are each as defined herein.

In yet another embodiment, provided herein is a compound of Formula (XII):

(XII)

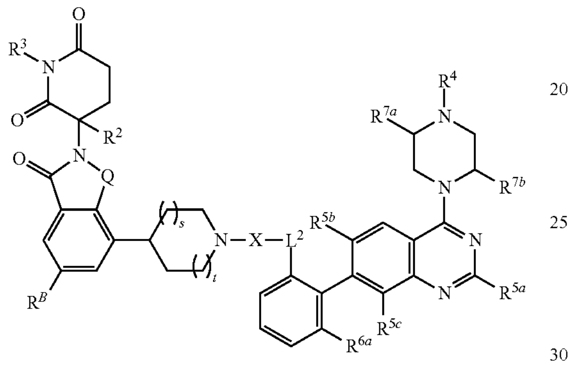

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein s and t are each independently an integer of 0, 1, 2, or 3; and $R^2$, $R^3$, $R^4$, $R^{5a}$, $R^{5b}$, $R^{5c}$, $R^{6a}$, $R^{7a}$, $R^{7b}$, $R^B$, $L^2$, Q, and X are each as defined herein.

In yet another embodiment, provided herein is a compound of Formula (XIIa):

(XIIa)

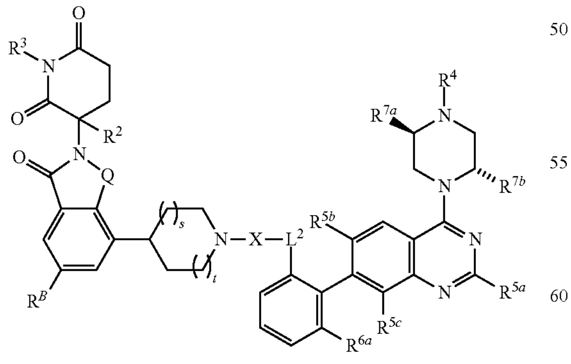

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein s and t are each independently an integer of 0, 1, 2, or 3; and $R^2$, $R^3$, $R^4$, $R^{5s}$, $R^{5b}$, $R^{5c}$, $R^{6a}$, $R^{7a}$, $R^{7b}$, $R^B$, $L^2$, Q, and X are each as defined herein.

In yet another embodiment, provided herein is a compound of Formula (XIII):

(XIII)

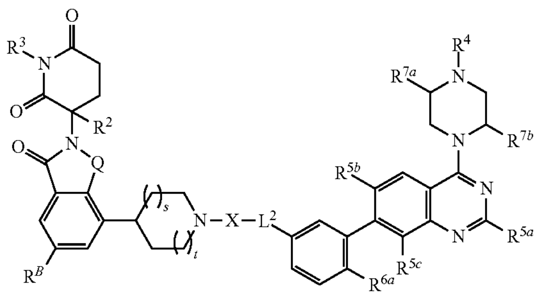

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^2$, Q, X, s, and t are each as defined herein.

In yet another embodiment, provided herein is a compound of Formula (XIIIa):

(XIIIa)

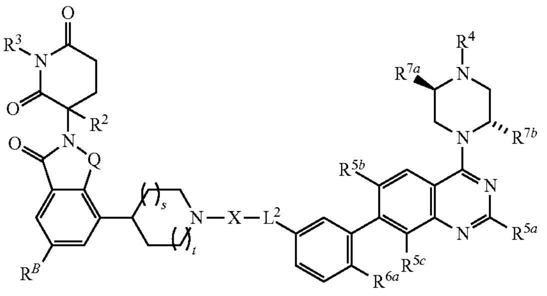

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^2$, Q, X, s, and t are each as defined herein.

In yet another embodiment, provided herein is a compound of Formula (XIV):

(XIV)

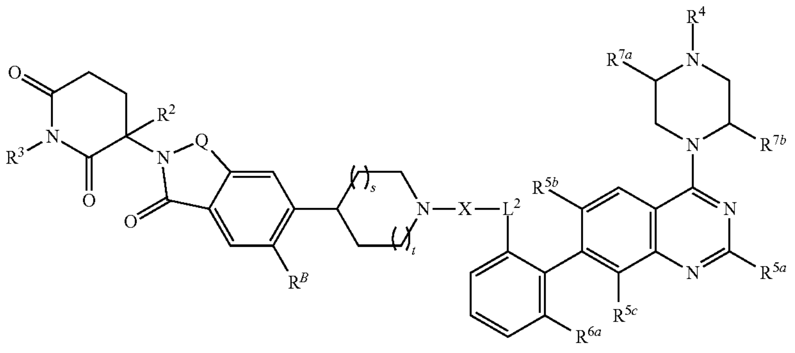

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^2$, Q, X, s, and t are each as defined herein.

In yet another embodiment, provided herein is a compound of Formula (XIVa):

(XIVa)

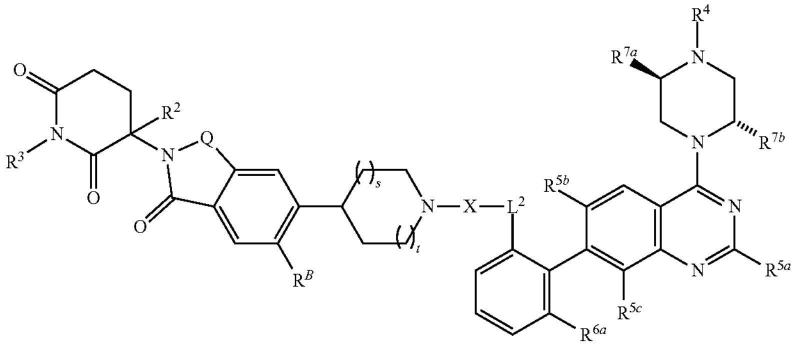

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^2$, Q, X, s, and t are each as defined herein.

In yet another embodiment, provided herein is a compound of Formula (XV):

(XV)

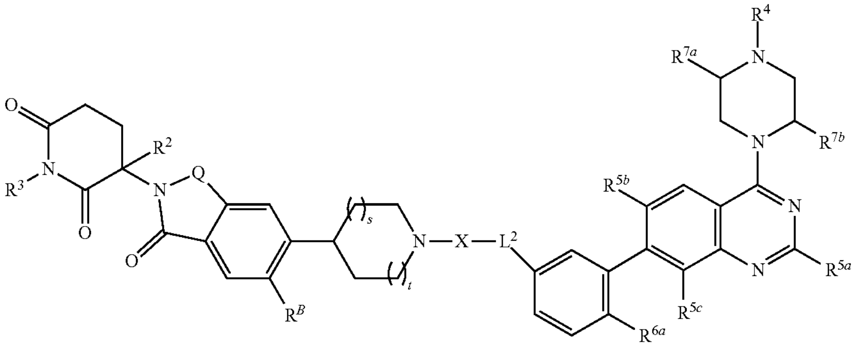

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^2$, Q, and X are each as defined herein.

In still another embodiment, provided herein is a compound of Formula (XVa):

(XVa)

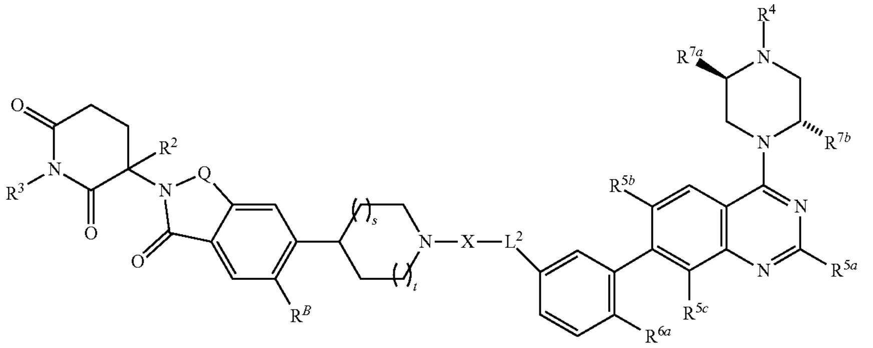

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $R^B$, $L^2$, Q, and X are each as defined herein.

In one embodiment, in any one of Formulae (II) to (XV), (VIIa), (VIIIa), and (Xa) to (XVa), $R^2$ and $R^3$ are each H;

$R^4$ is acetyl, propionoyl, 2-cyclopropylacetyl, acryloyl, 2-fluoroacryloyl, 2-chloroacryloyl, (Z)-2-chlorobut-2-enoyl, (Z)-2-chloropent-2-enoyl, (Z)-2-chloro-4-methylpent-2-enoyl, (E)-2-cyano-4-methylpent-2-enoyl, cyclopentylcarbonyl, imidaz-4-ylcarbonyl, oxetan-3-ylcarbonyl, tetrahydrofuran-3-ylcarbonyl, pyrrolidin-3-ylcarbonyl, tetrahydropyran-4-ylcarbonyl, carbamoyl, ethylsulfonyl, or ethenylsulfonyl;

$R^{5a}$ is H, 2-dimethylaminoethoxy, (S)-1-methylpyrrolidin-2-ylmethoxy, or 2-dimethylcarbamoylethylamino;

$R^{5b}$ is fluoro or chloro;

$R^{5c}$ is H, fluoro, or chloro;

$R^{6a}$ is fluoro;

$R^{7a}$ is H, methyl, or cyanomethyl;

$R^{7b}$ is H or methyl;

$R^B$ is H or fluoro;

$L^1$, if present, is a bond, —NH—, pyrrolidin-1,3-diyl, piperidin-1,3-diyl, piperidin-1,4-diyl,

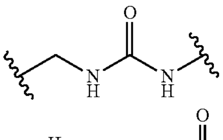,
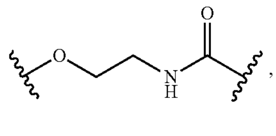,
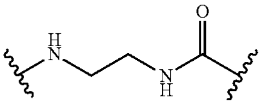, or

-continued

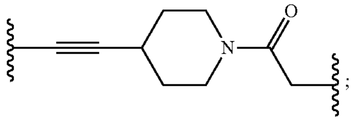;

$L^2$ is O;

Q is $CH_2$ or C(O);

X is pentan-1,5-diyl, hexan-1,6-diyl, heptan-1,7-diyl, octan-1,8-diyl, nonan-1,9-diyl, decan-1,10-diyl, undecan-1,11-diyl, piperazin-1,4-diyl,

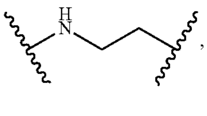,
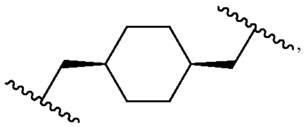,
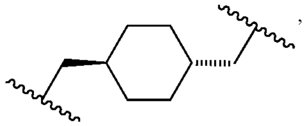,
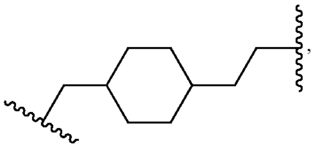,
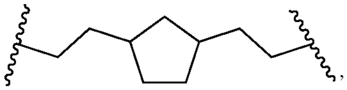,
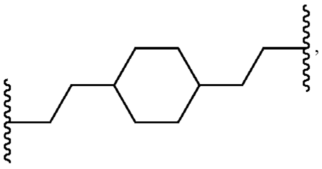,

-continued

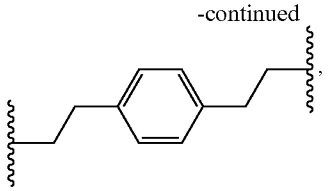,

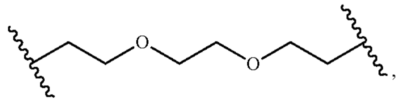,

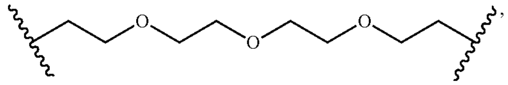,

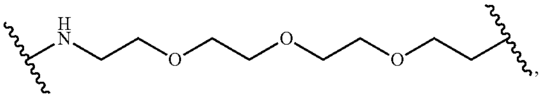,

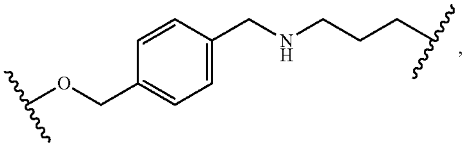,

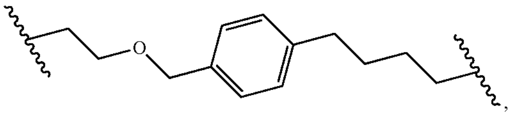,

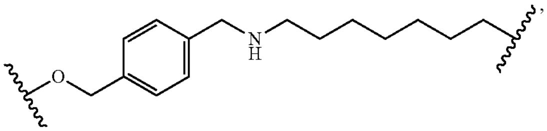,

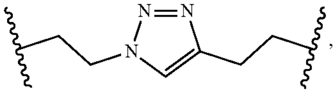, or

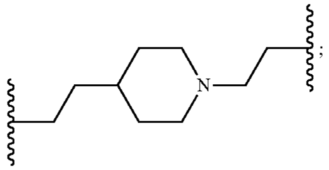 [SMILES: *CCC1CCN(CC*)CC1];

s, if present, is an integer of 0 or 1; and t, if present, is an integer of 1.

In another embodiment, in any one of Formulae (II) to (XV), (VIIa), (VIIIa), and (Xa) to (XVa), $R^2$ and $R^3$ are each H;

$R^4$ is acetyl, propionoyl, 2-cyclopropylacetyl, acryloyl, 2-fluoroacryloyl, 2-chloroacryloyl, (Z)-2-chlorobut-2-enoyl, (Z)-2-chloropent-2-enoyl, (Z)-2-chloro-4-methylpent-2-enoyl, (E)-2-cyano-4-methylpent-2-enoyl, cyclopentylcarbonyl, imidaz-4-ylcarbonyl, oxetan-3-ylcarbonyl, tetrahydrofuran-3-ylcarbonyl, pyrrolidin-3-ylcarbonyl, tetrahydropyran-4-ylcarbonyl, or carbamoyl;

$R^{5a}$ is H, 2-dimethylaminoethoxy, (S)-1-methylpyrrolidin-2-ylmethoxy, or 2-dimethylcarbamoylethylamino;

$R^{5b}$ is fluoro or chloro;

$R^{5c}$ is H, fluoro, or chloro;

$R^{6a}$ is fluoro;

$R^{7a}$ is H, methyl, or cyanomethyl;

$R^{7b}$ is H or methyl;

$R^B$ is H or fluoro;

$L^1$, if present, is a bond, —NH—, pyrrolidin-1,3-diyl, piperidin-1,3-diyl, piperidin-1,4-diyl,

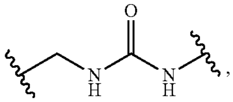, 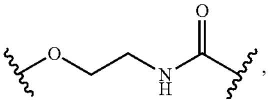,

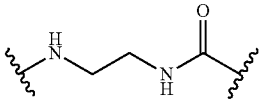, or

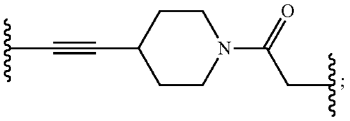;

$L^2$ is O;

Q is $CH_2$;

X is pentan-1,5-diyl, hexan-1,6-diyl, heptan-1,7-diyl, octan-1,8-diyl, nonan-1,9-diyl, decan-1,10-diyl, undecan-1,11-diyl, piperazin-1,4-dyl,

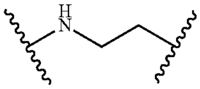,

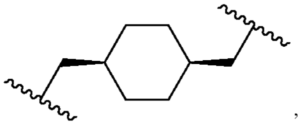,

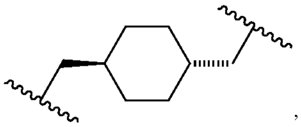,

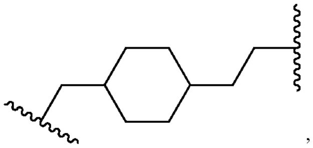,

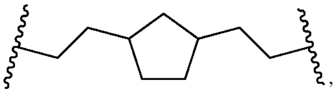,

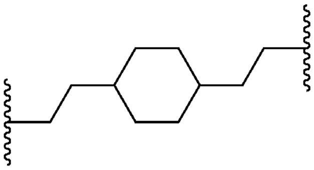,

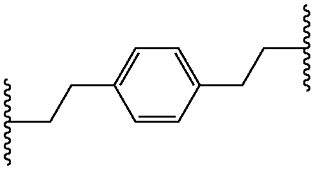,

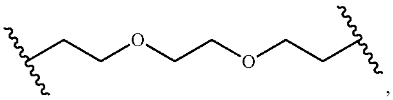,

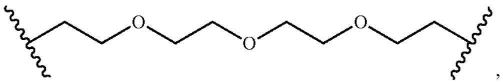,

-continued

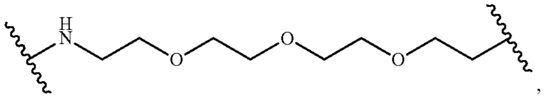

,

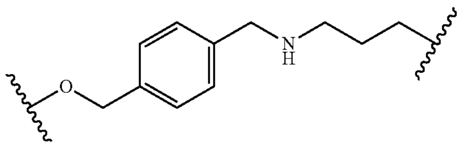

,

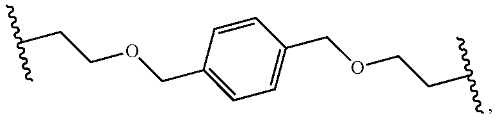

,

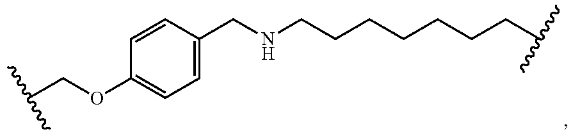

,

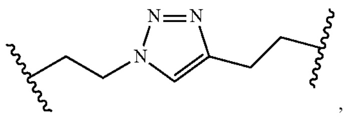

, or

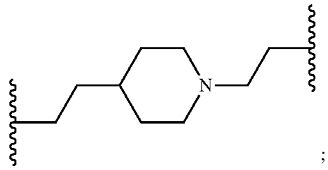 [SMILES: *CCC1CCN(CC*)CC1]

;

s, if present, is an integer of 0 or 1; and t, if present, is an integer of 1.

In one embodiment, provided herein is a compound of Formula (XVI):

(XVI)

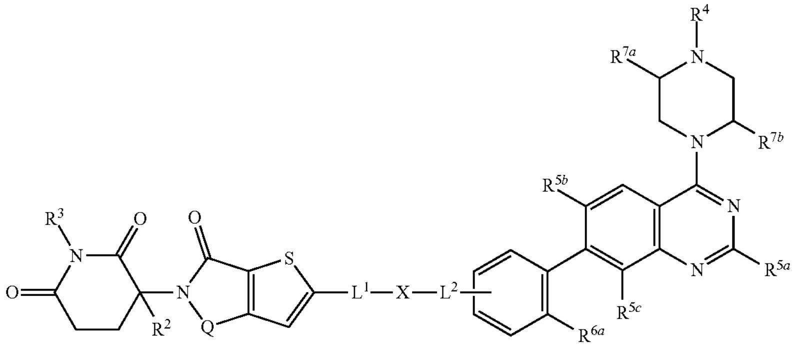

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $L^1$, $L^2$, Q, and X are each as defined herein.

In another embodiment, provided herein is a compound of Formula (XVII):

(XVII)

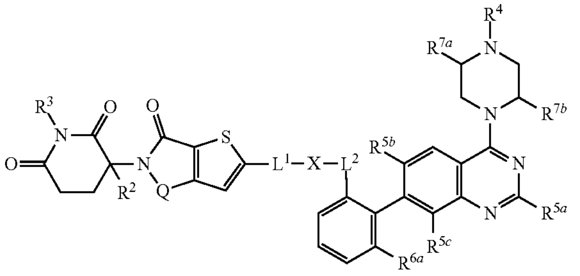

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $L^1$, $L^2$, Q, and X are each as defined herein.

In one embodiment, provided herein is a compound of Formula (XVIII):

(XVIII)

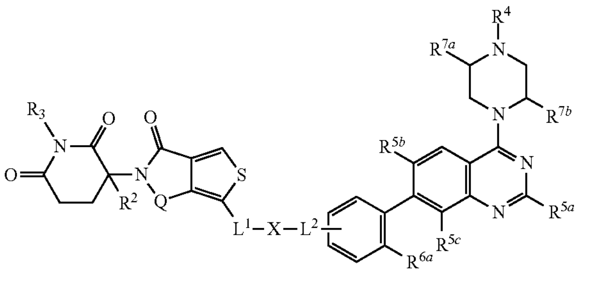

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $L^1$, $L^2$, Q, and X are each as defined herein.

In another embodiment, provided herein is a compound of Formula (XIX):

(XIX)

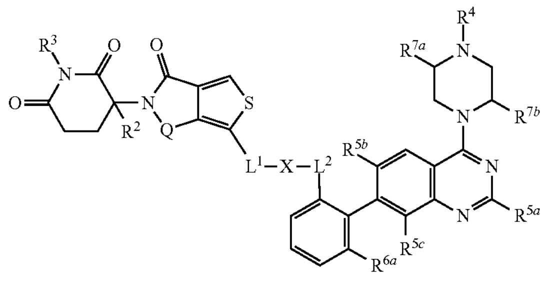

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $L^1$, $L^2$, Q, and X are each as defined herein.

In one embodiment, provided herein is a compound of Formula (XX):

(XX)

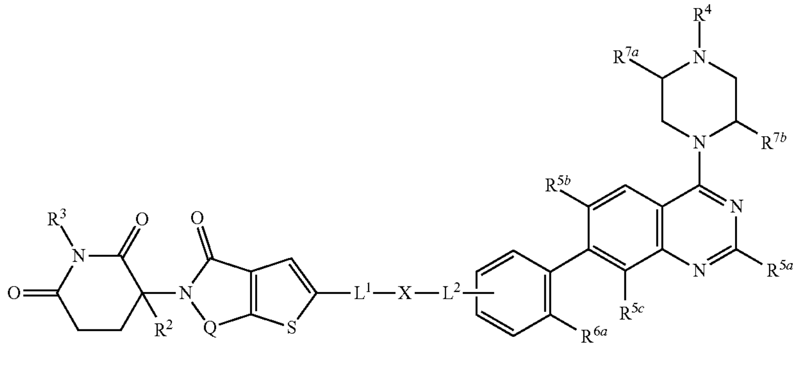

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $L^1$, $L^2$, Q, and X are each as defined herein.

In another embodiment, provided herein is a compound of Formula (XXI):

(XXI)

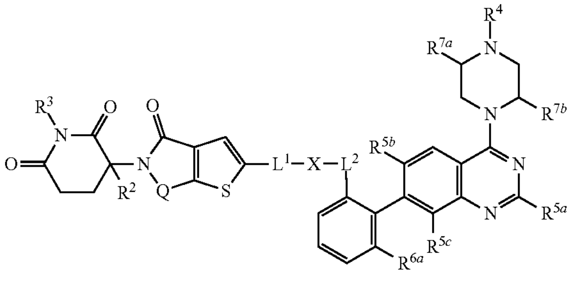

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^{5a}$, $R^{5b}$, $R^{5c}$, $R^{6a}$, $R^{7a}$, $R^{7b}$, $L^1$, $L^2$, Q, and X are each as defined herein.

In one embodiment, in any one of Formulae (XVI) to (XXI), $R^2$ and $R^3$ are each H;

$R^4$ is acetyl, propionoyl, 2-cyclopropylacetyl, acryloyl, 2-fluoroacryloyl, 2-chloroacryloyl, (Z)-2-chlorobut-2-enoyl, (Z)-2-chloropent-2-enoyl, (Z)-2-chloro-4-methylpent-2-enoyl, (E)-2-cyano-4-methylpent-2-enoyl, cyclopentylcarbonyl, imidaz-4-ylcarbonyl, oxetan-3-ylcarbonyl, tetrahydrofuran-3-ylcarbonyl, pyrrolidin-3-ylcarbonyl, tetrahydropyran-4-ylcarbonyl, carbamoyl, ethylsulfonyl, or ethenylsulfonyl;

$R^{5a}$ is H, 2-dimethylaminoethoxy, (S)-1-methylpyrrolidin-2-ylmethoxy, or 2-dimethylcarbamoylethylamino;

$R^{5b}$ is fluoro or chloro;

$R^{5c}$ is H, fluoro, or chloro;

$R^{6a}$ is fluoro;

$R^{7a}$ is H, methyl, or cyanomethyl;

$R^{7b}$ is H or methyl;

$L^1$, if present, is a bond, —NH—, pyrrolidin-1,3-diyl, piperidin-1,3-diyl, piperidin-1,4-diyl,

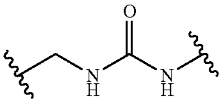,
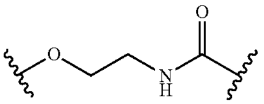,

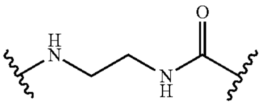, or

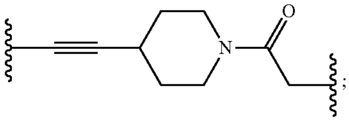;

$L^2$ is O;

Q is $CH_2$ or C(O);

X is pentan-1,5-diyl, hexan-1,6-diyl, heptan-1,7-diyl, octan-1,8-diyl, nonan-1,9-diyl, decan-1,10-diyl, undecan-1,11-diyl, piperazin-1,4-diyl, G

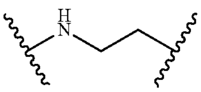,

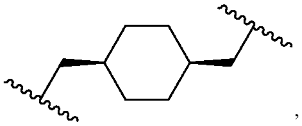,

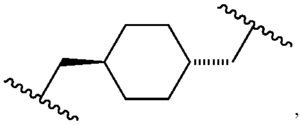,

-continued

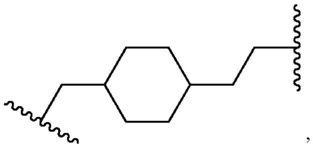,

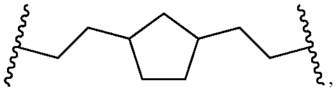,

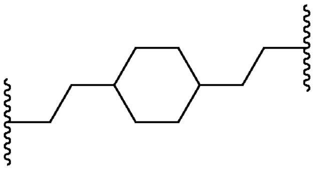,

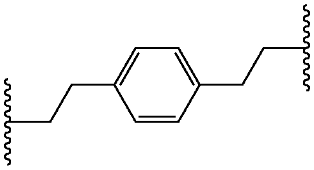,

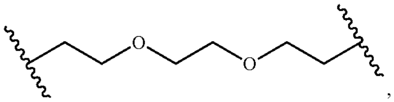,

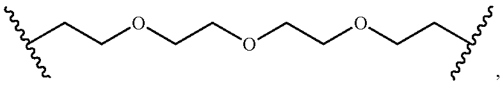,

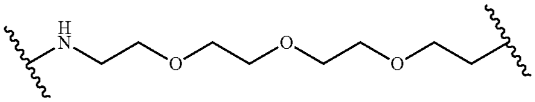,

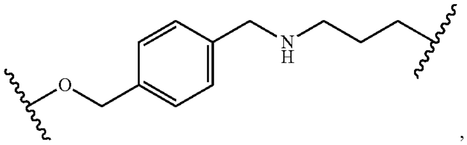,

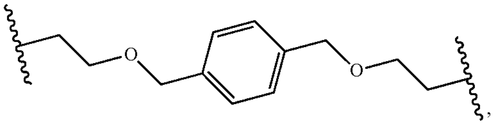,

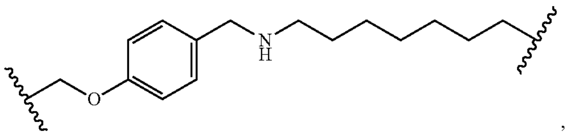,

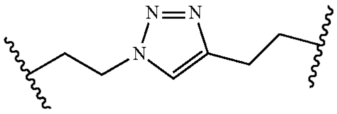, or

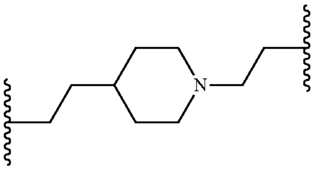;

s, if present, is an integer of 0 or 1; and t, if present, is an integer of 1.

In another embodiment, in any one of Formulae (XVI) to (XXI), $R^2$ and $R^3$ are each H;

$R^4$ is acetyl, propionoyl, 2-cyclopropylacetyl, acryloyl, 2-fluoroacryloyl, 2-chloroacryloyl, (Z)-2-chlorobut-2-enoyl, (Z)-2-chloropent-2-enoyl, (Z)-2-chloro-4-methylpent-2-enoyl, (E)-2-cyano-4-methylpent-2-enoyl, cyclopentylcarbonyl, imidaz-4-ylcarbonyl, oxetan-3-ylcarbonyl, tetrahydrofuran-3-ylcarbonyl, pyrrolidin-3-ylcarbonyl, tetrahydropyran-4-ylcarbonyl, or carbamoyl;

$R^{5a}$ is H, 2-dimethylaminoethoxy, (S)-1-methylpyrrolidin-2-ylmethoxy, or 2-dimethylcarbamoylethylamino;

$R^{5b}$ is fluoro or chloro;

$R^{5c}$ is H, fluoro, or chloro;

$R^{6a}$ is fluoro;

$R^{7a}$ is H, methyl, or cyanomethyl;

$R^{7b}$ is H or methyl;

$L^1$, if present, is a bond, —NH—, pyrrolidin-1,3-diyl, piperidin-1,3-diyl, piperidin-1,4-diyl,

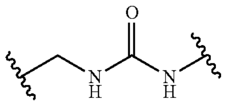
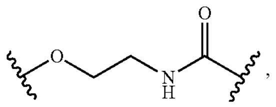
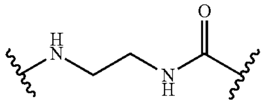
, or
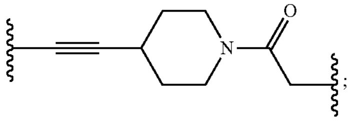

$L^2$ is O;

Q is $CH_2$;

X is pentan-1,5-diyl, hexan-1,6-diyl, heptan-1,7-diyl, octan-1,8-diyl, nonan-1,9-diyl, decan-1,10-diyl, undecan-1,11-diyl, piperazin-1,4-diyl,

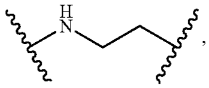
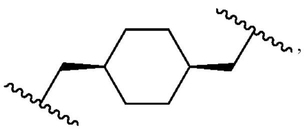
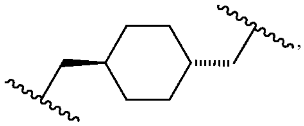
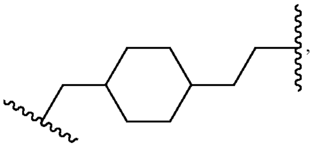
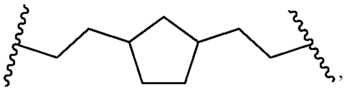

-continued

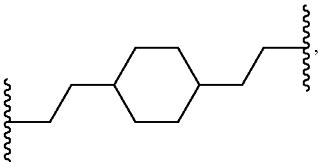
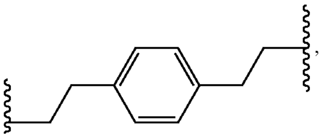
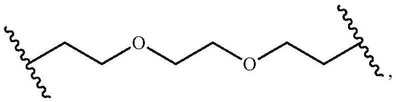
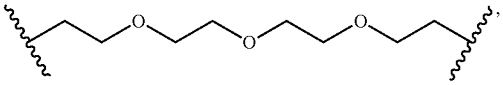
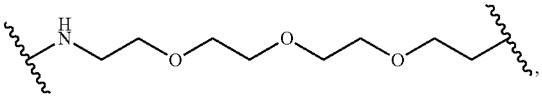
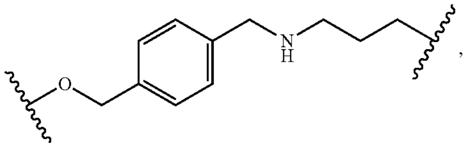
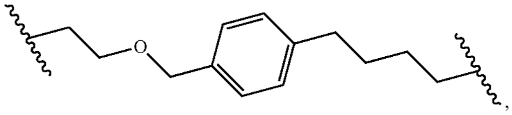
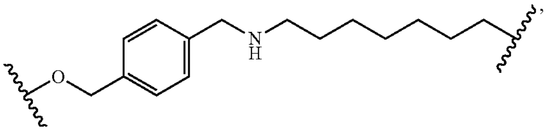
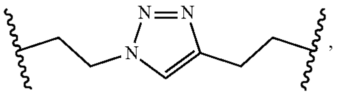
, or
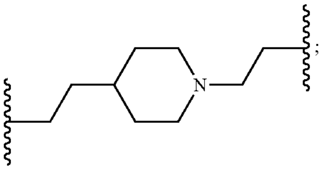 [SMILES: *CCC1CCN(CC*)CC1]

s, if present, is an integer of 0 or 1; and t, if present, is an integer of 1.

In one embodiment, provided herein is a compound of Formula (XXII):

(XXII)

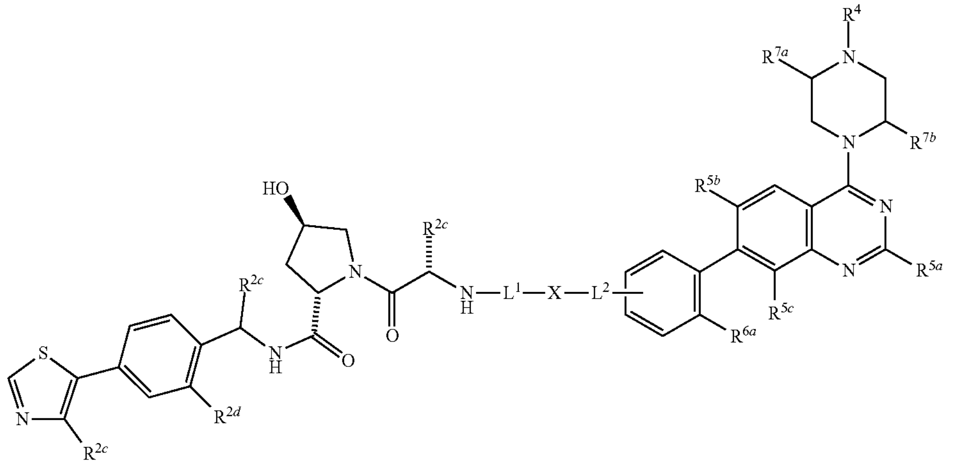

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^{2c}$, $R^{2d}$, $R^{5a}$, $R^{5b}$, $R^{5c}$, $R^{6a}$, $R^{7a}R^{7b}$, $L^1$, $L^2$, and X are each as defined herein.

In another embodiment, provided herein is a compound of Formula (XXIII):

(XXIII)

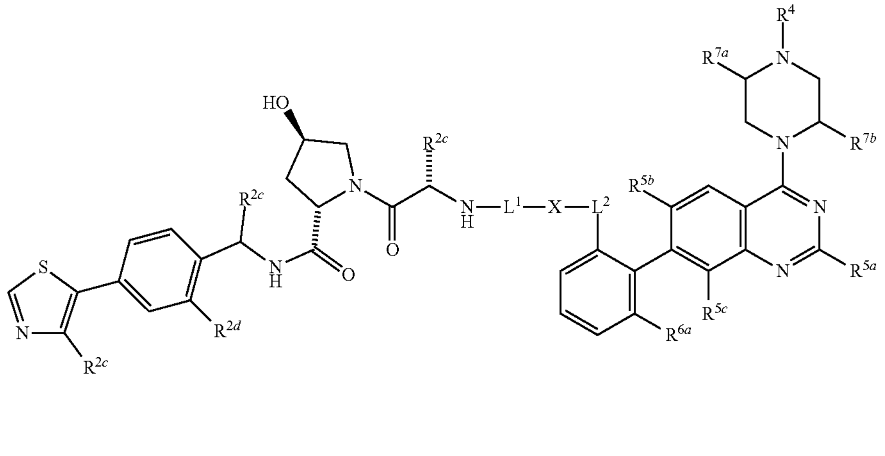

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^{2c}$, $R^{2d}$, $R^{5a}$, $R^{5b}$, $R^{5c}$, $R^{6a}$, $R^{7a}R^{7b}$, $L^1$, $L^2$, and X are each as defined herein.

In certain embodiments, in Formula (I), (Ia), (Ib), (Ic) or (Id), $R^{Het}$ is

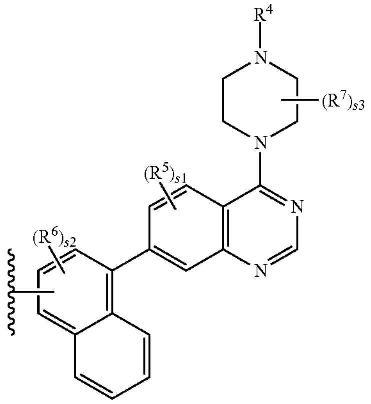

or

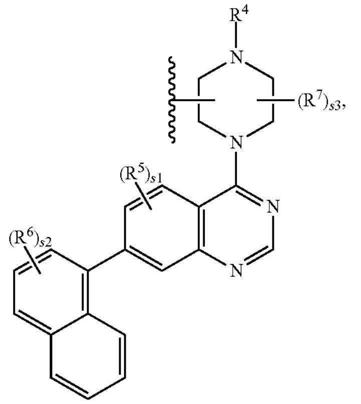

and wherein each $R^4$ is independently —C(O)$C_1$-$C_6$ alkyl, —C(O)$C_2$-$C_6$ alkenyl, —C(O)$C_3$-$C_8$ cycloalkyl, —C(O)($C_3$-$C_8$ cycloalkyl)$C_1$-$C_6$ alkyl, —C(O)—(3 to 7 membered heterocyclyl), or —C(O)$NH_2$; and wherein $R^5$, $R^6$, $R^7$, s1, s2, and s3 are each as defined herein. In certain embodiments, each $R^4$ is independently —C(O)$C_1$-$C_6$ alkyl, —C(O)$C_2$-$C_6$ alkenyl, —C(O)$C_3$-$C_8$ cycloalkyl, —C(O)($C_3$-$C_8$ cycloalkyl)$C_1$-$C_6$ alkyl, —C(O)—(3 to 7 membered heteroaryl), —C(O)—(3 to 7 membered heterocyclyl), or —C(O)$NH_2$. In certain embodiments, each $R^4$ is independently and optionally substituted with halogen or cyano. In certain embodiments, each $R^4$ is independently —C(O)$C_2$-$C_6$ alkenyl, optionally substituted with halogen or cyano. In certain embodiments, each $R^4$ is independently

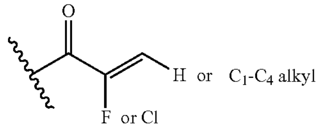

or

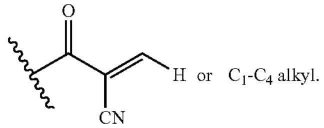

In certain embodiments, each $R^4$ is independently acetyl, propionoyl, 2-cyclopropylacetyl, acryloyl, 2-fluoroacryloyl, 2-chloroacryloyl, (Z)-2-chlorobut-2-enoyl, (Z)-2-chloropent-2-enoyl, (Z)-2-chloro-4-methylpent-2-enoyl, (E)-2-cyano-4-methylpent-2-enoyl, cyclopentylcarbonyl, imidaz-4-ylcarbonyl, oxetan-3-ylcarbonyl, tetrahydrofuran-3-ylcarbonyl, pyrrolidin-3-ylcarbonyl, tetrahydropyran-4-ylcarbonyl, carbamoyl, ethylsulfonyl, or ethenylsulfonyl.

In certain embodiments, each s1 is independently an integer of 1 or 2, and each $R^5$ is independently halogen, hydroxyl, or $C_1$-$C_6$ alkyl. In certain embodiments, s1 is an integer of 1; and $R^5$ is F or Cl. In certain embodiments, s1 is an integer of 3. In certain embodiments, s1 is an integer of 2; and each $R^5$ is independently F or Cl. In certain embodiments, s2 is an integer of 1 or 2; and each $R^6$ is independently halogen, hydroxyl, or $C_1$-$C_6$ alkyl. In certain embodiments, s2 is an integer of 1; and $R^6$ is independently F. In certain embodiments, s2 is an integer of 2 and each $R^6$ is independently F and —OH. In certain embodiments, s3 is 1 or 2, and each $R^7$ is independently $C_1$-$C_6$ alkyl. In certain embodiments, s3 is 1 or 2, and $R^7$ is methyl. In certain embodiments, s3 is 0.

In certain embodiments, in Formula (I), (Ia), (Ib), (Ic), or (Id), $R^{Het}$ is

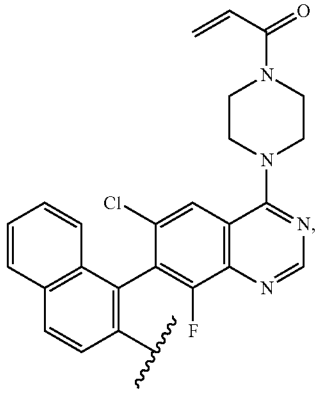

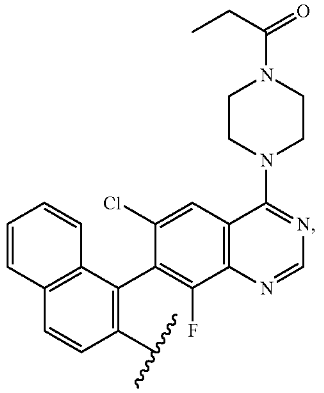

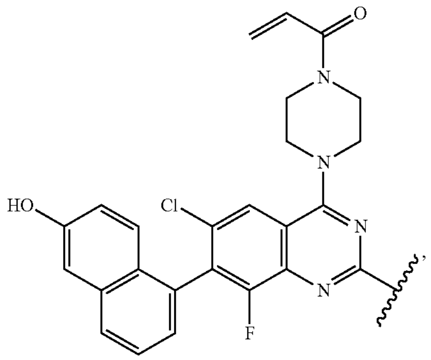

, or

-continued

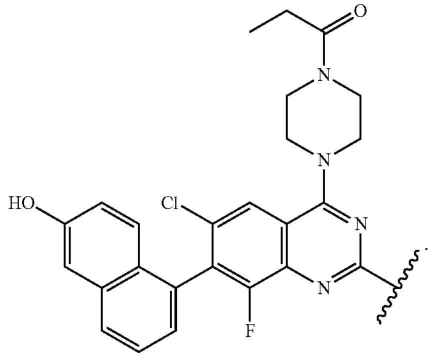

In certain embodiments, $R^{Het}$ is an R or S atropisomer, or a mixture thereof. In one embodiment, $R^{Het}$ is an R-atropisomer. In another embodiment, $R^{Het}$ is an S-atropisomer.

In certain embodiments, in Formula (I), (Ta), (Ib), (Ic) or (Id), $R^{Het}$ is

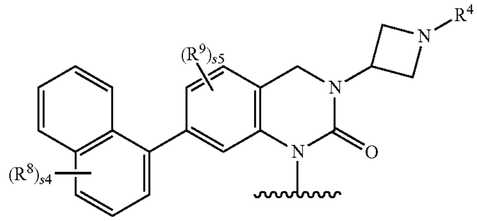

or

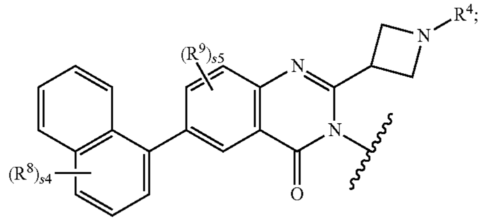

wherein $R^4$, $R^5$, $R^9$, s4 and s5 are each as defined herein. In certain embodiments, each $R^4$ is independently —C(O)$C_1$-$C_6$ alkyl (in one embodiment, —C(O)$CH_3$ or —C(O)$C_2H_5$), —C(O)$C_2$-$C_6$ alkenyl (in one embodiment, —C(O)CH=$CH_2$), —C(O)$C_3$-$C_5$ cycloalkyl, —C(O)($C_3$-$C_5$ cycloalkyl)$C_1$-$C_6$ alkyl, —C(O)—(3 to 7 membered heterocyclyl), or —C(O)$NH_2$. In certain embodiments, each $R^4$ is independently —C(O)$C_1$-$C_6$ alkyl, —C(O)$C_2$-$C_6$ alkenyl, —C(O)$C_3$-$C_5$ cycloalkyl, —C(O)($C_3$-$C_5$ cycloalkyl)$C_1$-$C_6$ alkyl, —C(O)—(3 to 7 membered heteroaryl), —C(O)—(3 to 7 membered heterocyclyl), or —C(O)$NH_2$. In certain embodiments, each $R^4$ is independently and optionally substituted with halogen or cyano. In certain embodiments, each $R^4$ is independently —C(O)$C_2$-$C_6$ alkenyl, optionally substituted with halogen or cyano. In certain embodiments, each $R^4$ is independently

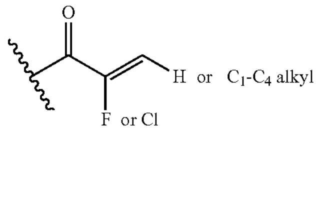

or

-continued

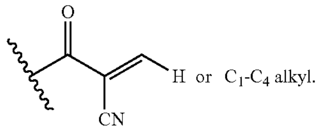

In certain embodiments, each $R^4$ is independently acetyl, propionoyl, 2-cyclopropylacetyl, acryloyl, 2-fluoroacryloyl, 2-chloroacryloyl, (Z)-2-chlorobut-2-enoyl, (Z)-2-chloropent-2-enoyl, (Z)-2-chloro-4-methylpent-2-enoyl, (E)-2-cyano-4-methylpent-2-enoyl, cyclopentylcarbonyl, imidaz-4-ylcarbonyl, oxetan-3-ylcarbonyl, tetrahydrofuran-3-ylcarbonyl, pyrrolidin-3-ylcarbonyl, tetrahydropyran-4-ylcarbonyl, carbamoyl, ethylsulfonyl, or ethenylsulfonyl.

In certain embodiments, each s4 is independently an integer of 1 or 2, and each $R^8$ is independently halogen, hydroxyl, or $C_1$-$C_6$ alkyl. In certain embodiments, s4 is 1 and $R^8$ is —OH. In certain embodiments, s5 is 0.

In certain embodiments, in Formula (I), (Ia), (Ib), (Ic), or (Id), $R^{Het}$ is:

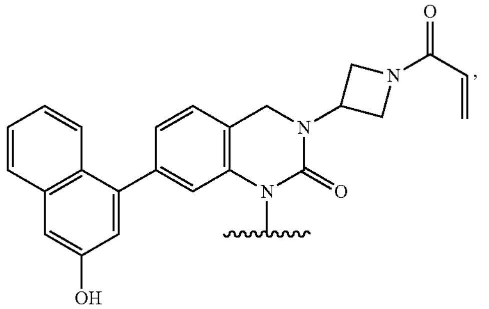

,

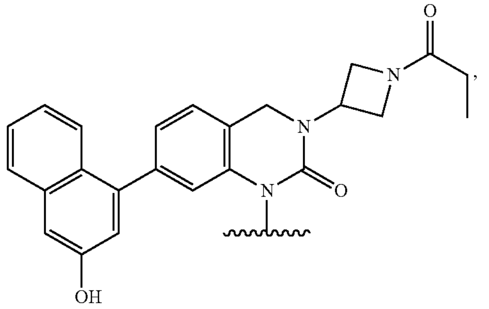

,

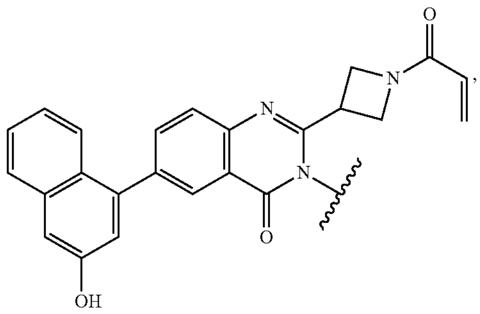

, or

-continued

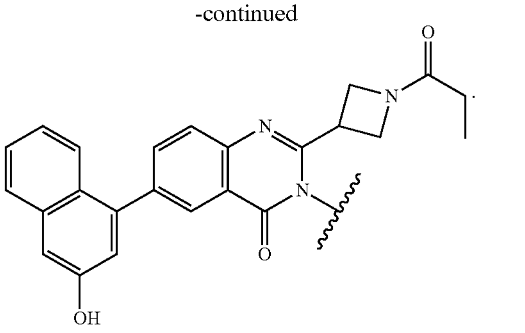

In one embodiment, provided herein is a compound of Formula (XXIV):

(XXIV)

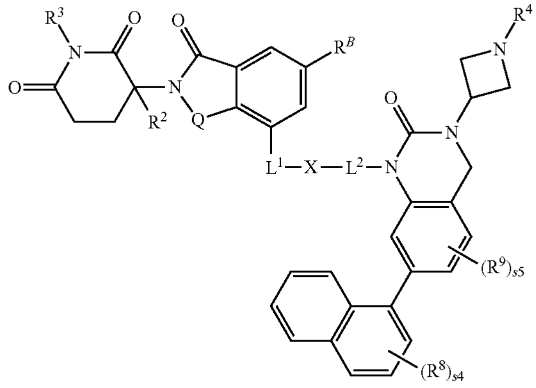

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^8$, $R^9$, $R^B$, $L^1$, $L^2$, Q, X, s4, and s5 are each as defined herein.

In another embodiment, provided herein is a compound of Formula (XXV):

(XXV)

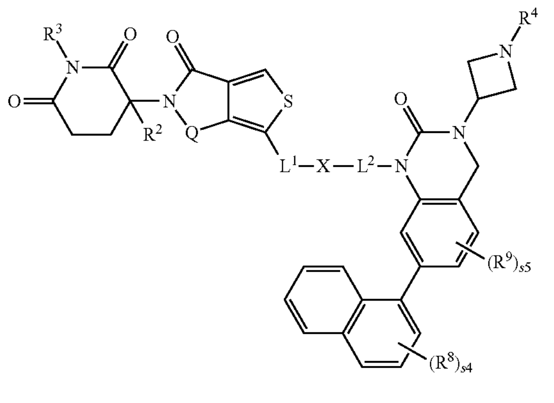

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^8$, $R^9$, $L^1$, $L^2$, Q, X, s4, and s5 are each as defined herein.

In yet another embodiment, provided herein is a compound of Formula (XXVI):

(XXVI)

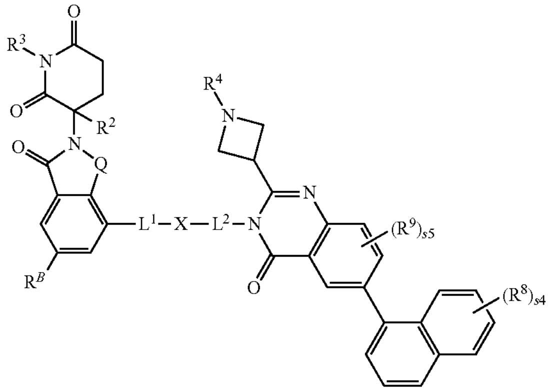

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^8$, $R^9$, $R^B$, $L^1$, $L^2$, Q, X, s4, and s5 are each as defined herein.

In still another embodiment, provided herein is a compound of Formula (XXVII):

(XXVII)

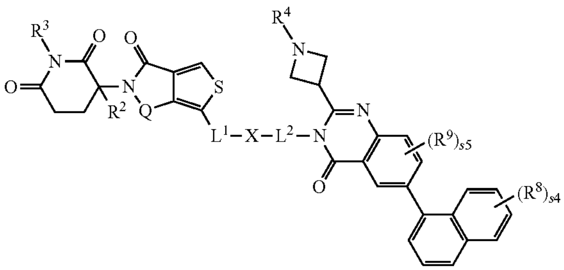

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^8$, $R^9$, $R^B$, $L^1$, $L^2$, Q, X, s4, and s5 are each as defined herein.

In one embodiment, in any one of Formulae (XXVI) to (XVII), $R^2$ and $R^3$ are each H;

$R^4$ is acetyl, propionoyl, 2-cyclopropylacetyl, acryloyl, 2-fluoroacryloyl, 2-chloroacryloyl, (Z)-2-chlorobut-2-enoyl, (Z)-2-chloropent-2-enoyl, (Z)-2-chloro-4-methylpent-2-enoyl, (E)-2-cyano-4-methylpent-2-enoyl, cyclopentylcarbonyl, imidaz-4-ylcarbonyl, oxetan-3-ylcarbonyl, tetrahydrofuran-3-ylcarbonyl, pyrrolidin-3-ylcarbonyl, tetrahydropyran-4-ylcarbonyl, carbamoyl, ethylsulfonyl, or ethenylsulfonyl;

$R^B$, if present, is H or fluoro;

$L^1$, if present, is a bond, —NH—, pyrrolidin-1,3-diyl, piperidin-1,3-diyl, piperidin-1,4-diyl,

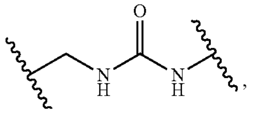,

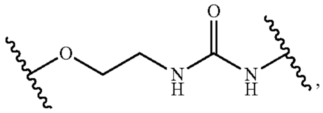,

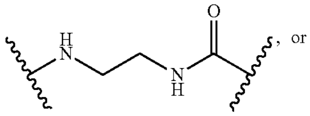, or

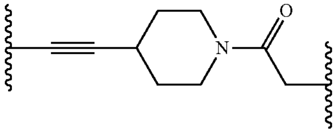;

$L^2$ is O;

Q is $CH_2$ or C(O);

X is pentan-1,5-diyl, hexan-1,6-diyl, heptan-1,7-diyl, octan-1,8-diyl, nonan-1,9-diyl, decan-1,10-diyl, undecan-1,11-diyl, piperazin-1,4-diyl

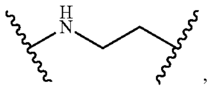,

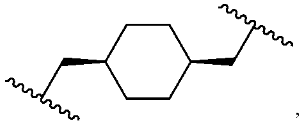,

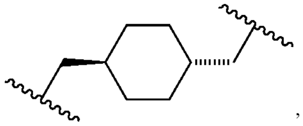,

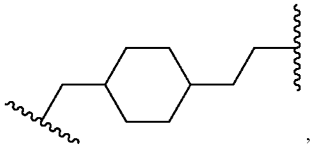,

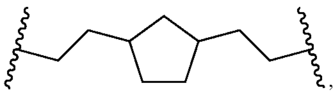,

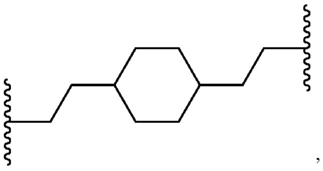,

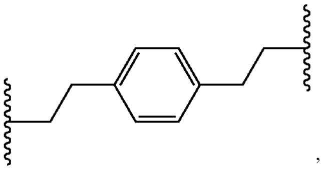,

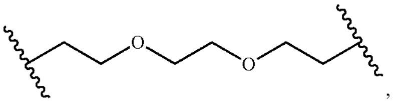,

-continued

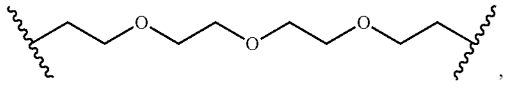,

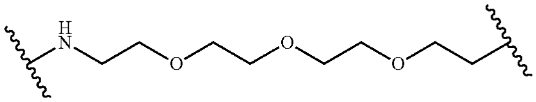,

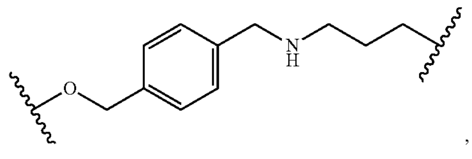,

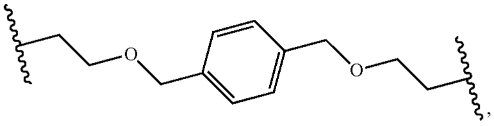,

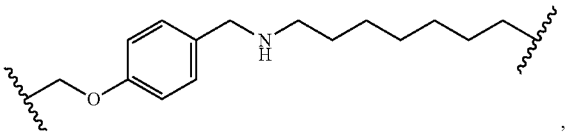,

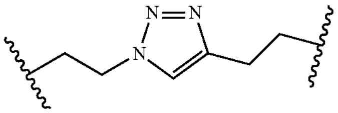, or

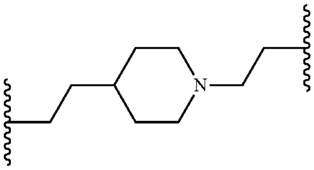;

and s4 and s5 are an integer of 0.

In certain embodiments, in Formula (I), (Ia), (Ib), (Ic) or (Id), $R^{Het}$ is

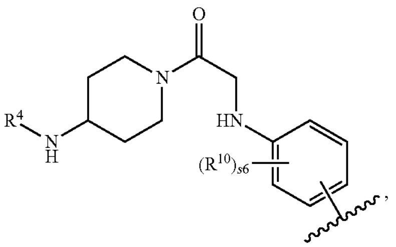, wherein $R^4$, $R^{10}$, and s6 are each as defined herein. In certain embodiments, $R^4$ is —$S(O)_2C_1$-$C_6$ alkyl (in one embodiment, —$S(O)_2CH_3$ or —$S(O)_2C_2H_5$), —$S(O)_2C_2$-$C_6$ alkenyl (in one embodiment, —$S(O)_2CH{=}CH_2$), or —$S(O)_2NH_2$. In certain embodiments, $R^4$ is optionally substituted with halogen or cyano. In certain embodiments, $R^4$ is —$S(O)_2C_2$-$C_6$ alkenyl optionally substituted with halogen or cyano. In certain embodiments, $R^4$ is

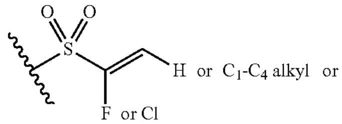

or

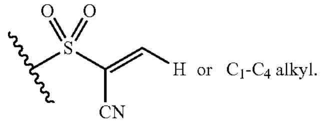

In certain embodiments, s6 is an integer of 1 or 2, and each $R^{10}$ is independently halogen, hydroxyl, or $C_1$-$C_6$ alkyl. In certain embodiments, s6 is 2, and each $R^{10}$ is independently F or Cl.

In certain embodiments, $R^{Het}$ is

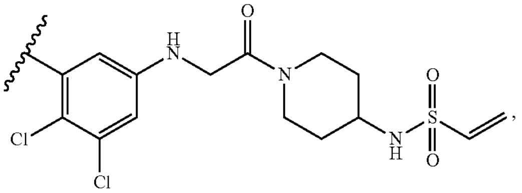

,

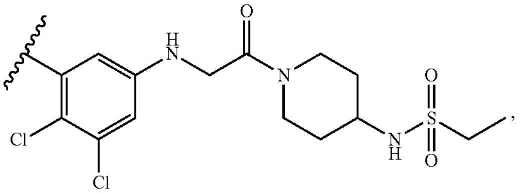

,

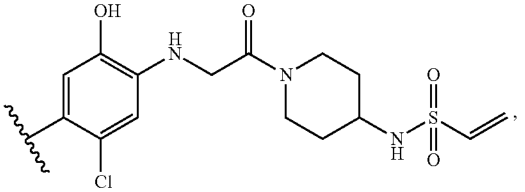

, or

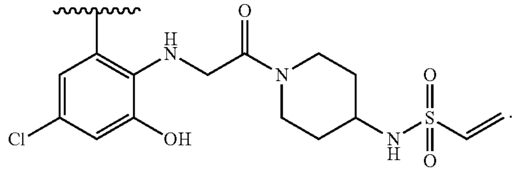

.

In certain embodiments, in Formula (I), (Ia), (Ib), (Ic) or (Id), $R^{Het}$ is

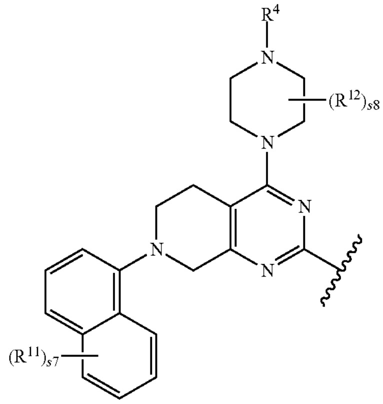

or

-continued

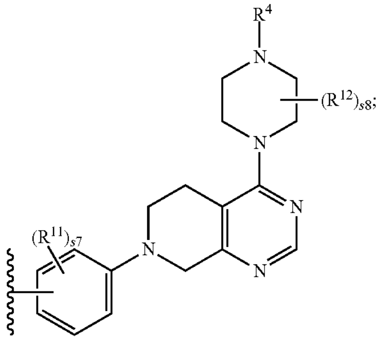

;

wherein $R^4$, $R^{11}$, $R^{12}$, s7, and s8 are each as defined herein. In certain embodiments, each $R^4$ is independently —C(O)$C_1$-$C_6$ alkyl (in one embodiment, —C(O)$CH_3$ or —C(O)$C_2H_5$), —C(O)$C_2$-$C_6$ alkenyl (in one embodiment, —C(O)CH═$CH_2$), —C(O)$C_3$-$C_5$ cycloalkyl, —C(O)($C_3$-$C_5$ cycloalkyl)$C_1$-$C_6$ alkyl, —C(O)—(3 to 7 membered heterocyclyl), or —C(O)$NH_2$. In certain embodiments, each $R^4$ is independently —C(O)$C_1$-$C_6$ alkyl, —C(O)$C_2$-$C_6$ alkenyl, —C(O)$C_3$-$C_5$ cycloalkyl, —C(O)($C_3$-$C_5$ cycloalkyl)$C_1$-$C_6$ alkyl, —C(O)—(3 to 7 membered heteroaryl), —C(O)—(3 to 7 membered heterocyclyl), or —C(O)$NH_2$. In certain embodiments, each $R^4$ is independently and optionally substituted with halogen or cyano. In certain embodiments, each $R^4$ is independently —C(O)$C_2$-$C_6$ alkenyl, optionally substituted with halogen or cyano. In certain embodiments, each $R^4$ is independently F or $C_1$ or

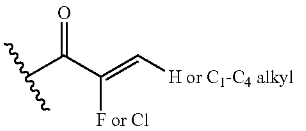

or

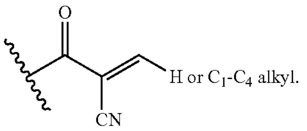

In certain embodiments, each $R^4$ is independently acetyl, propionoyl, 2-cyclopropylacetyl, acryloyl, 2-fluoroacryloyl, 2-chloroacryloyl, (Z)-2-chlorobut-2-enoyl, (Z)-2-chloropent-2-enoyl, (Z)-2-chloro-4-methylpent-2-enoyl, (E)-2-cyano-4-methylpent-2-enoyl, cyclopentylcarbonyl, imidaz-4-ylcarbonyl, oxetan-3-ylcarbonyl, tetrahydrofuran-3-ylcarbonyl, pyrrolidin-3-ylcarbonyl, tetrahydropyran-4-ylcarbonyl, carbamoyl, ethylsulfonyl, or ethenylsulfonyl.

In certain embodiments, each s7 is independently an integer of 1 or 2, and each $R^{11}$ is independently halogen, hydroxyl, or $C_1$-$C_6$ alkyl. In certain embodiments, s7 is 1 and each $R^8$ is independently $C_1$-$C_6$ alkyl (in one embodiment, methyl). In certain embodiments, each s8 is independently an integer of 0, 1, or 2; and each $R^{12}$ is independently optionally substituted $C_1$-$C_6$ alkyl. In certain embodiments, s8 is 2, and each $R^{12}$ is independently methyl or cyanomethyl.

In certain embodiments, $R^{Het}$ N
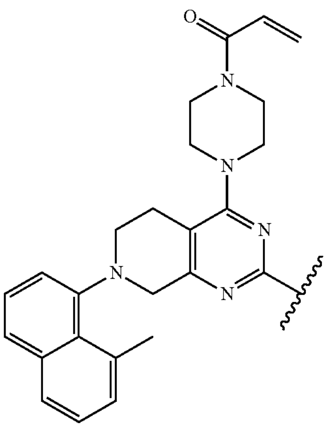
,
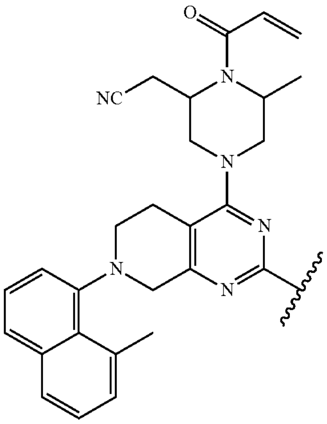
,
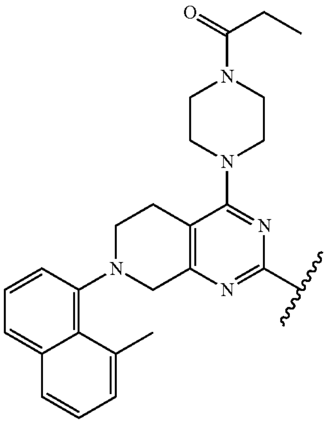
,
-continued
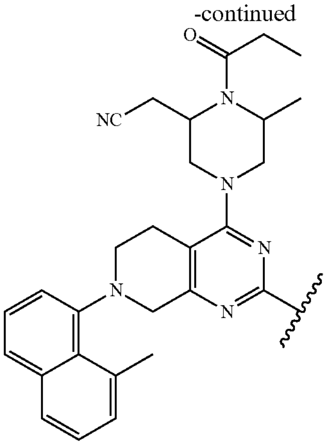
,
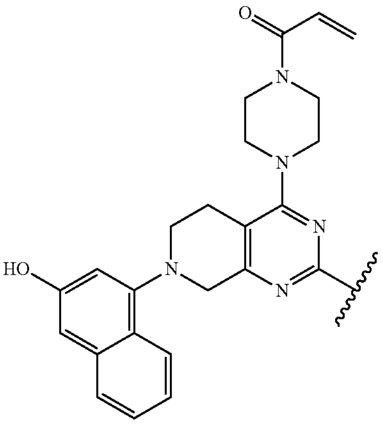
,
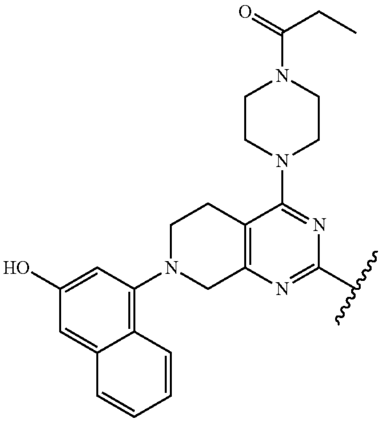
,
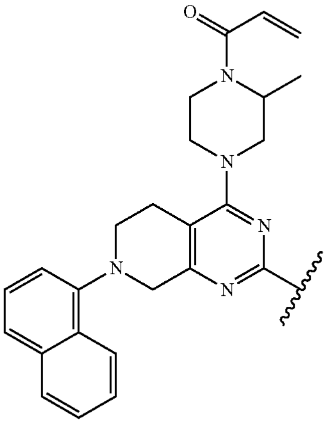
, -continued

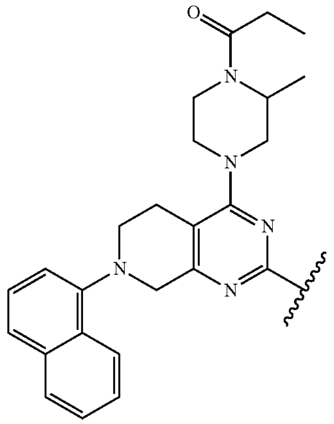

,

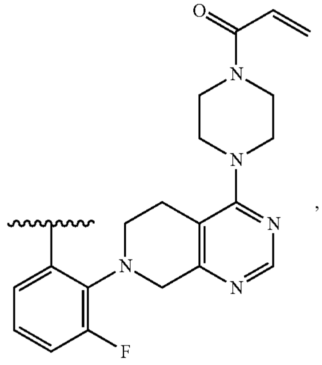

, or

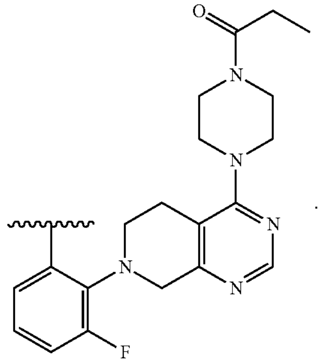

.

In certain embodiments, in Formula (I), (Ia), (Ib), (Ic) or (Id), $R^{Het}$ is

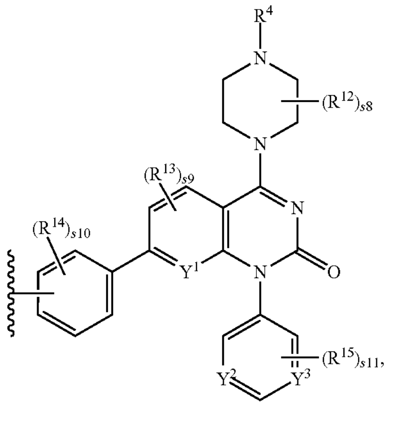

-continued

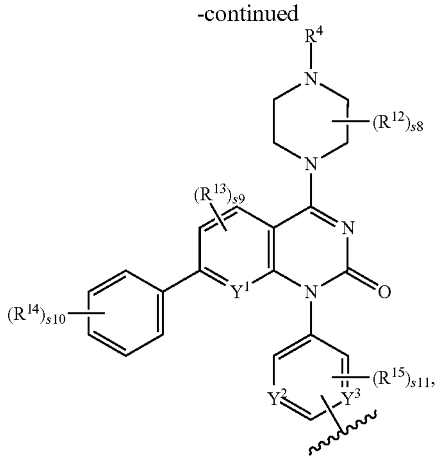

or

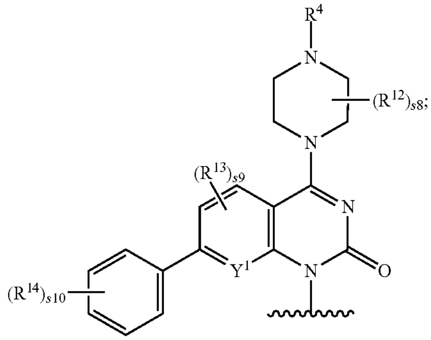

wherein $R^4$, $R^{12}$, $R^{13}$, $R^{14}$, $R^{15}$, $Y^1$, $Y^2$, $Y^3$, s9, s9, s10, and 211 are each as defined herein. In certain embodiments, each $R^4$ is independently —$C(O)C_1$-$C_6$ alkyl (in one embodiment, —$C(O)CH_3$ or —$C(O)C_2H_5$), —$C(O)C_2$-$C_6$ alkenyl (in one embodiment, —C(O)CH=$CH_2$), —$C(O)C_3$-$C_5$ cycloalkyl, —C(O)($C_3$-$C_5$ cycloalkyl)$C_1$-$C_6$ alkyl, —C(O)—(3 to 7 membered heterocyclyl), or —$C(O)NH_2$. In certain embodiments, each $R^4$ is independently —$C(O)C_1$-$C_6$ alkyl, —C(O)$C_2$-$C_6$ alkenyl, —$C(O)C_3$-$C_5$ cycloalkyl, —C(O)($C_3$-$C_5$ cycloalkyl)$C_1$-$C_6$ alkyl, —C(O)—(3 to 7 membered heteroaryl), —C(O)—(3 to 7 membered heterocyclyl), or —$C(O)NH_2$. In certain embodiments, each $R^4$ is independently and optionally substituted with halogen or cyano. In certain embodiments, each $R^4$ is independently —$C(O)C_2$-$C_6$ alkenyl, optionally substituted with halogen or cyano. In certain embodiments, each $R^4$ is independently

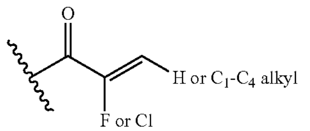

or

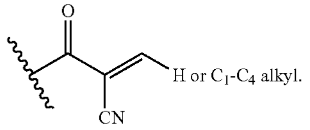

In certain embodiments, each $R^4$ is independently acetyl, propionoyl, 2-cyclopropylacetyl, acryloyl, 2-fluoroacryloyl, 2-chloroacryloyl, (Z)-2-chlorobut-2-enoyl, (Z)-2-chloropent-2-enoyl, (Z)-2-chloro-4-methylpent-2-enoyl, (E)-2-cyano-4-methylpent-2-enoyl, cyclopentylcarbonyl, imidaz-4-ylcarbonyl, oxetan-3-ylcarbonyl, tetrahydrofuran-3- ylcarbonyl, pyrrolidin-3-ylcarbonyl, tetrahydropyran-4-ylcarbonyl, carbamoyl, ethylsulfonyl, or ethenylsulfonyl.

In certain embodiments, $Y^1$ is N. In certain embodiments, $Y^2$ is N and $Y^3$ is CH. In certain embodiments, both $Y^2$ and $Y^3$ are N. In certain embodiments, both $Y^2$ and $Y^3$ are CH.

In certain embodiments, each s8 is independently an integer of 0, 1, or 2, and each $R^{12}$ is independently $C_1$-$C_6$ alky. In certain embodiments, each s8 is independently an integer of 1 or 2, and $R^{12}$ is methyl. In certain embodiments, s9 is 1, and each $R^{13}$ is independently halogen (in one embodiment, F or $C_1$). In certain embodiments, each s10 is independently an integer of 1 or 2, and each $R^{14}$ is independently halogen (in one embodiment, F or $C_1$), hydroxyl, amino, or $C_1$-$C_6$ alkyl (in one embodiment, methyl). In certain embodiments, each s11 is independently an integer of 1 or 2, and each $R^{15}$ is independently $C_1$-$C_6$ alkyl (in one embodiment, methyl, ethyl, and isopropyl).

In certain embodiments, in Formula (I), (Ia), (Ib), (Ic) or (Id), $R^{Het}$ is:

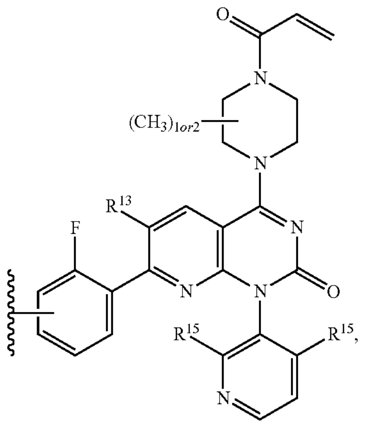

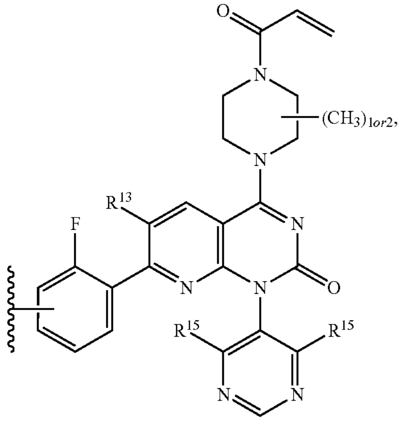

-continued

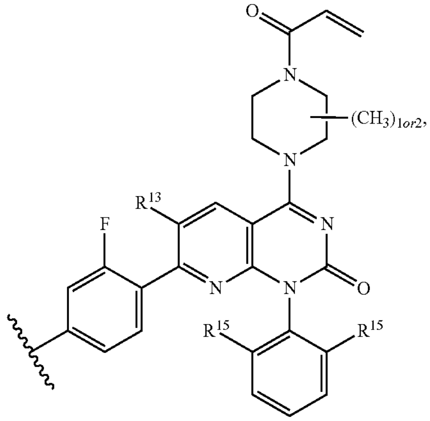

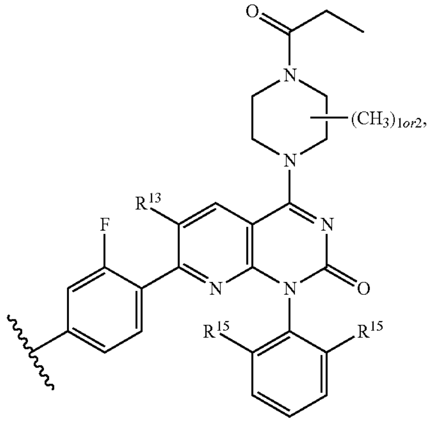

or

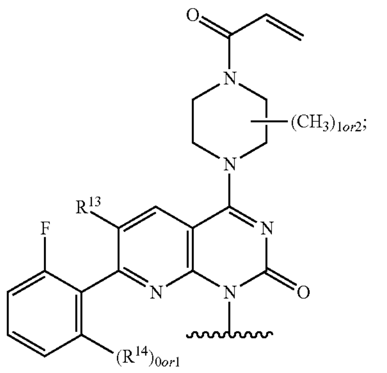

wherein each $R^{13}$ is independently F or $C_1$; $R^{14}$ is —OH or —$NH_2$; and each $R^{15}$ is independently methyl or isopropyl (in one embodiment, both are isopropyl, in another embodiment, one is methyl and the other is isopropyl).

In certain embodiments, $R^{Het}$ is an R or S atropisomer, or a mixture thereof. In one embodiment, $R^{Het}$ is an R-atropisomer. In another embodiment, $R^{Het}$ is an S-atropisomer.

In certain embodiments, in Formula (I), (Ia), (Ib), (Ic) or (Id), $R^{Het}$ is

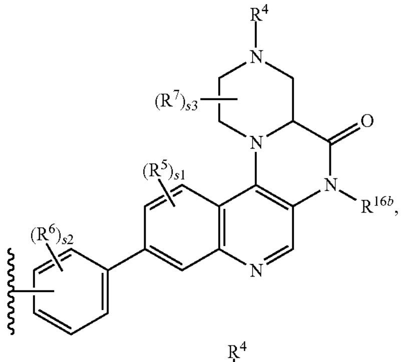

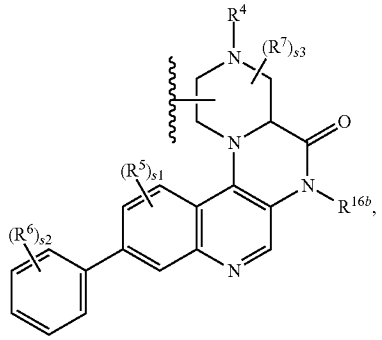

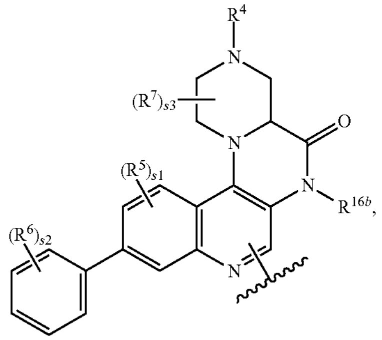

or

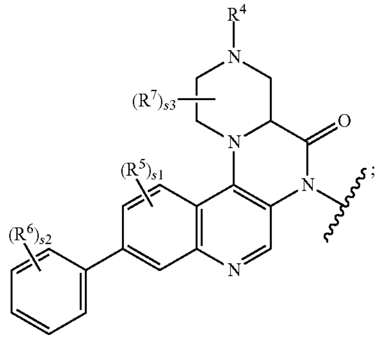

wherein $R^4$, $R^5$, $R^6$, $R^7$, $R^{16b}$, s1, s2, s3 are each as defined herein. In certain embodiments, each $R^4$ is independently —$C(O)C_1$-$C_6$ alkyl (in one embodiment, —$C(O)CH_3$ or —$C(O)C_2H_5$), —$C(O)C_2$-$C_6$ alkenyl (in one embodiment, —$C(O)CH{=}CH_2$), —$C(O)C_3$-$C_5$ cycloalkyl, —$C(O)(C_3$-$C_5$ cycloalkyl)$C_1$-$C_6$ alkyl, —C(O)—(3 to 7 membered heterocyclyl), or —$C(O)NH_2$. In certain embodiments, each $R^4$ is independently —$C(O)C_1$-$C_6$ alkyl, —$C(O)C_2$-$C_6$ alkenyl, —$C(O)C_3$-$C_5$ cycloalkyl, —$C(O)(C_3$-$C_5$ cycloalkyl)$C_1$-$C_6$ alkyl, —C(O)—(3 to 7 membered heteroaryl), —C(O)—(3 to 7 membered heterocyclyl), or —$C(O)NH_2$. In certain embodiments, each $R^4$ is independently and optionally substituted with halogen or cyano. In certain embodiments, each $R^4$ is independently —$C(O)C_2$-$C_6$ alkenyl, optionally substituted with halogen or cyano. In certain embodiments, each $R^4$ is independently

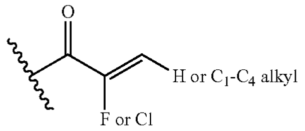

or

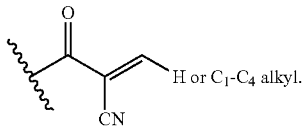

In certain embodiments, each $R^4$ is independently acetyl, propionoyl, 2-cyclopropylacetyl, acryloyl, 2-fluoroacryloyl, 2-chloroacryloyl, (Z)-2-chlorobut-2-enoyl, (Z)-2-chloropent-2-enoyl, (Z)-2-chloro-4-methylpent-2-enoyl, (E)-2-cyano-4-methylpent-2-enoyl, cyclopentylcarbonyl, imidaz-4-ylcarbonyl, oxetan-3-ylcarbonyl, tetrahydrofuran-3-ylcarbonyl, pyrrolidin-3-ylcarbonyl, tetrahydropyran-4-ylcarbonyl, carbamoyl, ethylsulfonyl, or ethenylsulfonyl.

In certain embodiments, each s1 is independently an integer of 1 or 2; and each $R^5$ is independently halogen, hydroxyl, or $C_1$-$C_6$ alkyl. In certain embodiments, s1 is an integer of 2, and each $R^5$ is independently F or Cl. In certain embodiments, each s2 is independently an integer of 1 or 2; and each $R^6$ is independently halogen, hydroxyl, or $C_1$-$C_6$ alkyl. In certain embodiments, s2 is an integer of 2 and each $R^6$ is independently F and —OH. In certain embodiments, each s3 is an integer of 1 or 2; and each $R^7$ is independently $C_1$-$C_6$ alkyl, in one embodiment, methyl. In certain other embodiments, s3 is an integer of 0.

In certain embodiments, in Formula (I), (Ia), (Ib), (Ic) or (Id), $R^{Het}$ is

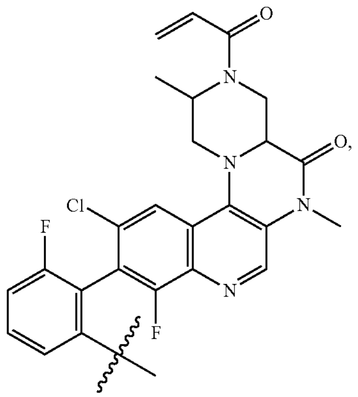

-continued
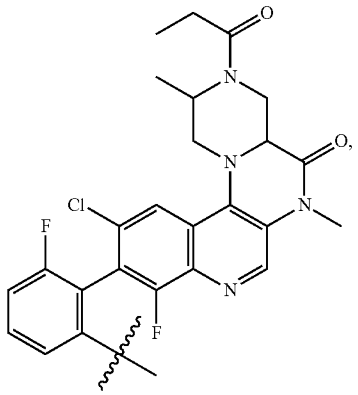
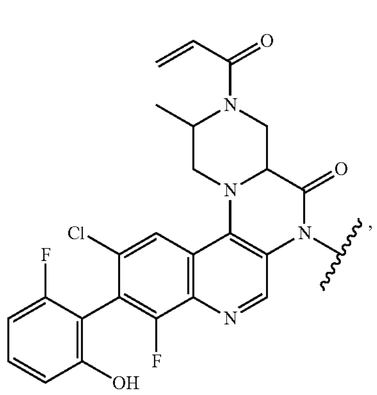
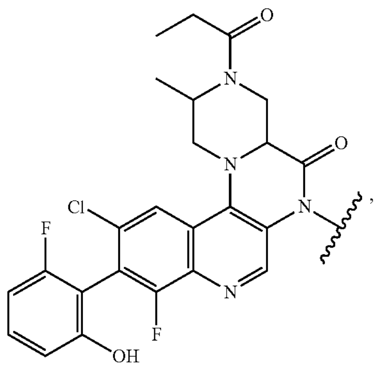
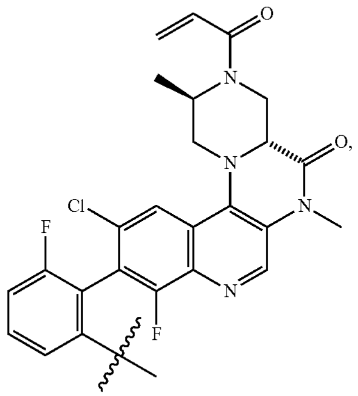
-continued
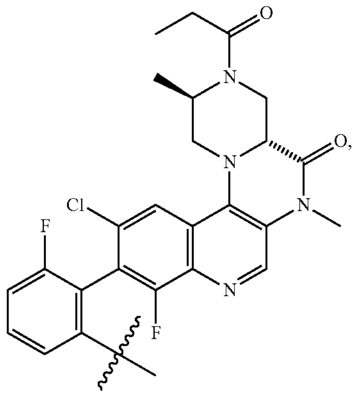
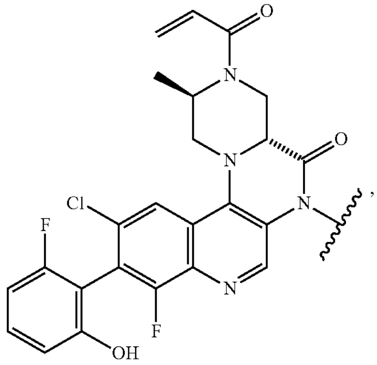
or
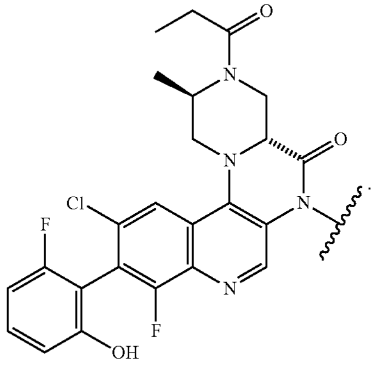
In certain embodiments, $R^{Het}$ is an R or S atropisomer, or a mixture thereof. In one embodiment, $R^{Het}$ is an R-atropisomer. In another embodiment, $R^{Het}$ is an S-atropisomer.
In certain embodiments, in Formula (I), $R^1$ is
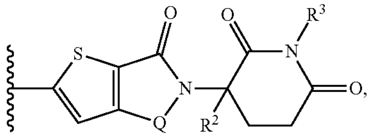
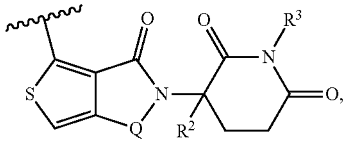

-continued

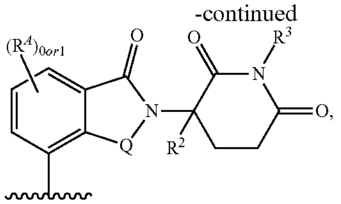

or

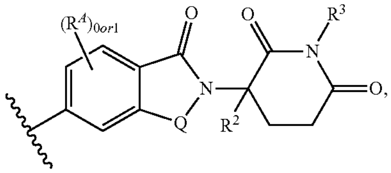

and $L^1$-X-$L^2$ is one listed in Table A; wherein $R^2$, $R^3$, $R^A$, and Q are each as defined herein. In certain embodiments, in Formula (I), $R^1$ is Q

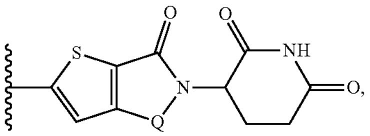

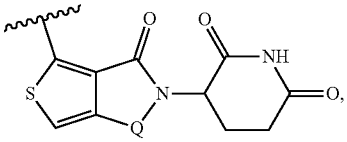

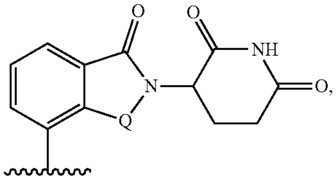

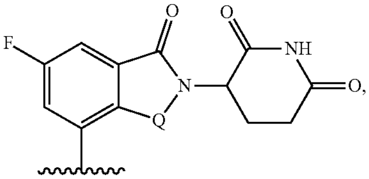

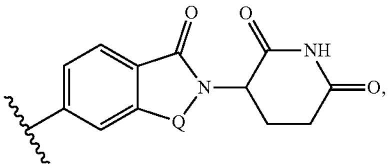

-continued

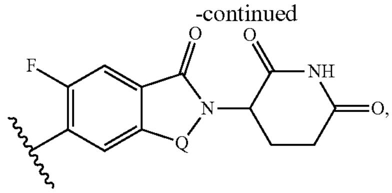

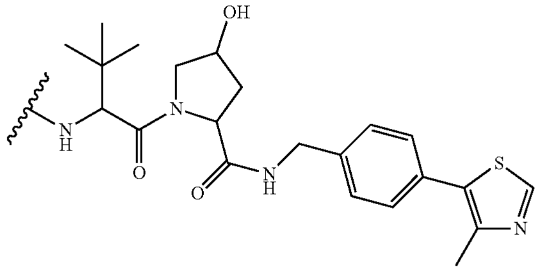

,

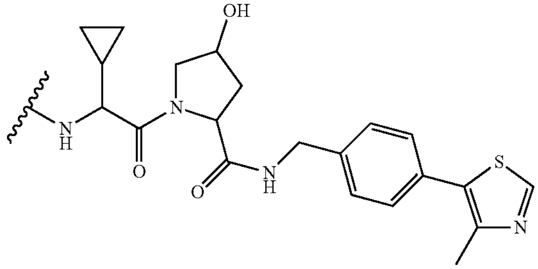

,

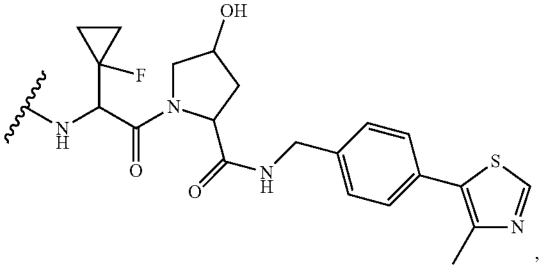

, or

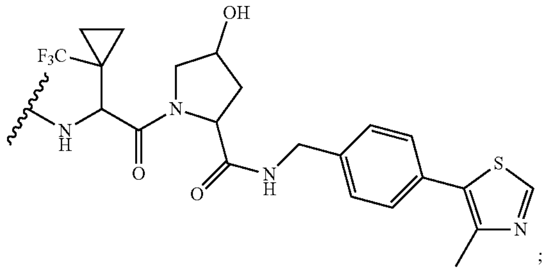 [SMILES: *NC(C(=O)N1CC(O)CC1C(=O)NCc1ccc(-c2scnc2C)cc1)C1(C(F)(F)F)CC1]

;

$L^1$-X-$L^2$ is one listed in Table A; wherein Q is as defined herein.

TABLE A

| —$L^1$—X—$L^2$— |
|---|
| —NH$(CH_2)_2$NHC(═O)$(CH_2CH_2O)_3$— |
| —NH$(CH_2)_2$NHC(═O)$(CH_2CH_2O)_2CH_2CH_2$— |
| —NH$(CH_2)_2$NHC(═O)$CH_2CH_2OCH_2CH_2$— |
| —NH$(CH_2CH_2O)_3CH_2CH_2$— |
| —NH$(CH_2CH_2O)_2CH_2CH_2$— |
| —NH$(CH_2CH_2O)_4$— |
| —NH$(CH_2CH_2O)_3$— |
| —NH$(CH_2)_6$O— |
| —NH$(CH_2)_7$O— |
| —NH$(CH_2)_8$O— |
| —O$(CH_2)_2$NHC(═O)$(CH_2CH_2O)_3$— |
| —O$(CH_2)_2$NHC(═O)$(CH_2CH_2O)_2CH_2CH_2$— |

TABLE A-continued
| $—L^1—X—L^2—$ |
| --- |
| $—O(CH_2)_2NHC(=O)CH_2CH_2OCH_2CH_2—$ |
| $—CH_2NHC(O)NH(CH_2)_5NHC(O)CH_2—$ |
| $—CH_2NHC(O)NH(CH_2)_7O—$ |
| 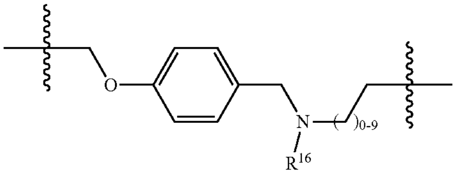 |
| 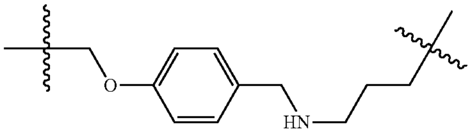 [SMILES: *CCCNCc1ccc(OC*)cc1] |
| 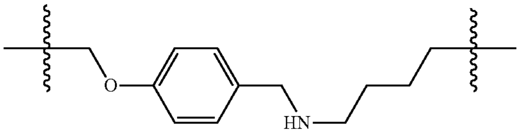 |
| 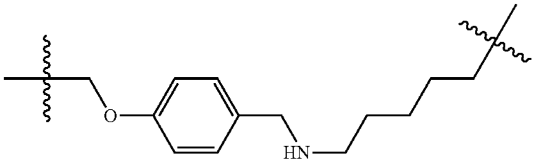 [SMILES: *CCCCCNCc1ccc(OC*)cc1] |
| 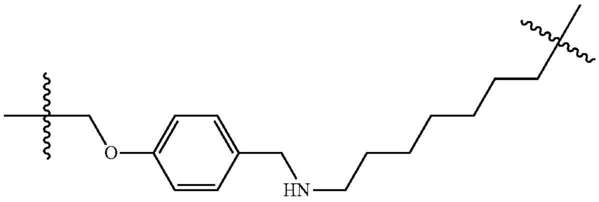 [SMILES: *CCCCCCCNCc1ccc(OC*)cc1] |
| 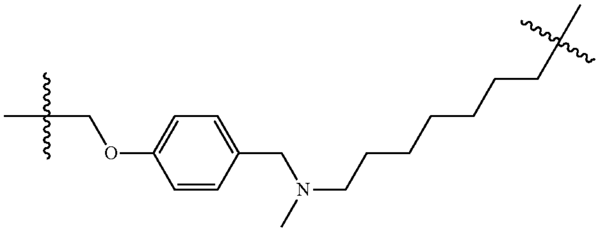 [SMILES: *CCCCCCCN(C)Cc1ccc(OC*)cc1] |
| 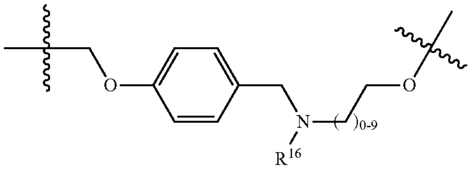 |
| 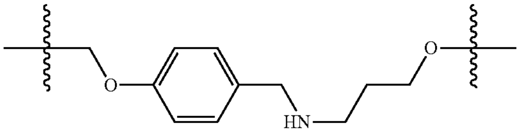 [SMILES: *COc1ccc(CNCCCO*)cc1] |

TABLE A-continued
| —$L^1$—X—$L^2$— |
|---|
| 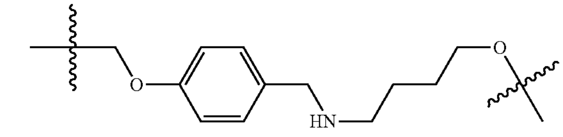 [SMILES: *COc1ccc(CNCCCCO*)cc1] |
| 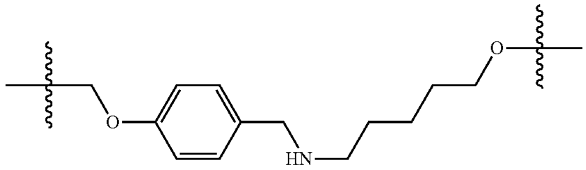 [SMILES: *COc1ccc(CNCCCCCO*)cc1] |
| 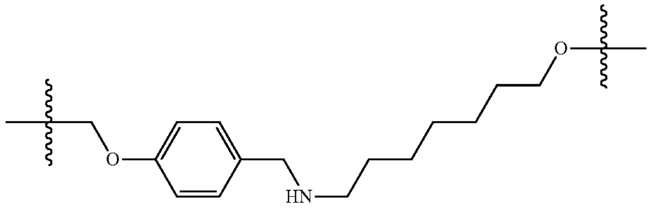 [SMILES: *COc1ccc(CNCCCCCCCO*)cc1] |
| 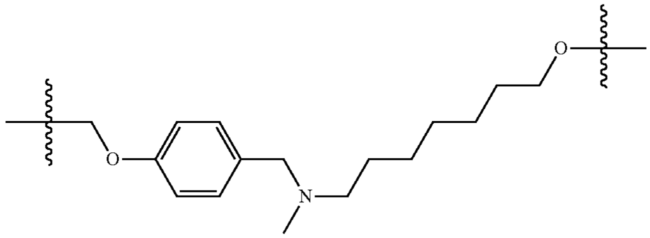 [SMILES: *COc1ccc(CN(C)CCCCCCCO*)cc1] |
| 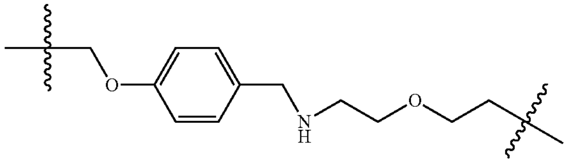 [SMILES: *CCOCCNCc1ccc(OC*)cc1] |
| 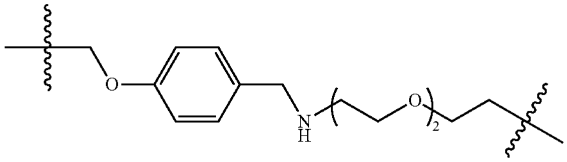 |
| 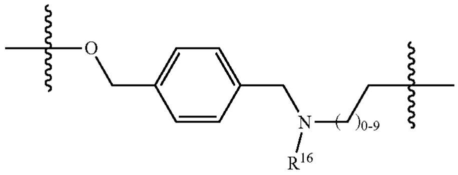 |
| 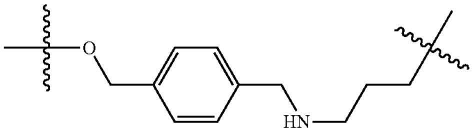 [SMILES: *CCCNCc1ccc(CO*)cc1] |

TABLE A-continued
| —$L^1$—X—$L^2$— |
| --- |
| 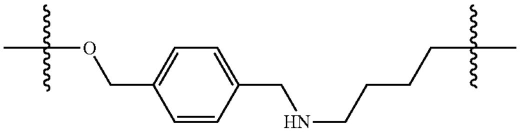 |
| 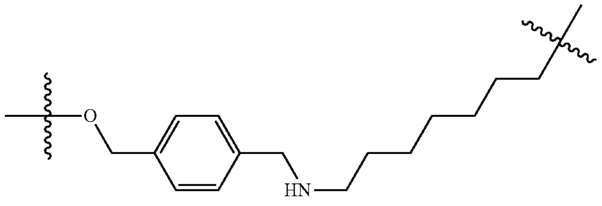 [SMILES: *CCCCCCCNCc1ccc(CO*)cc1] |
| 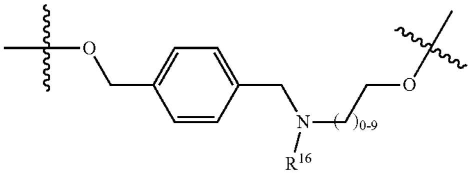 |
| 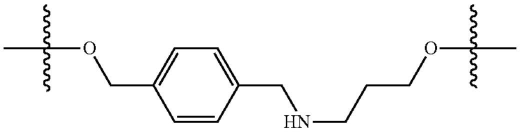 [SMILES: *OCCCNCc1ccc(CO*)cc1] |
| 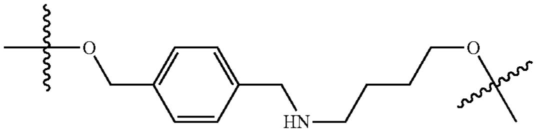 [SMILES: *OCCCCNCc1ccc(CO*)cc1] |
| 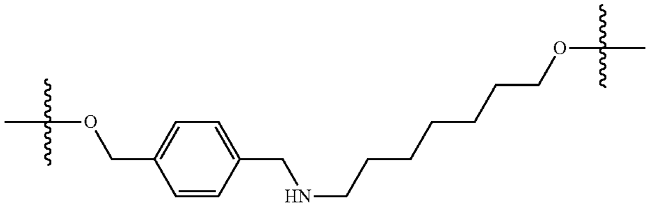 |
| 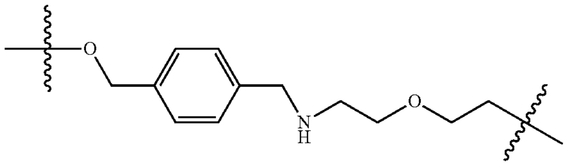 [SMILES: *CCOCCNCc1ccc(CO*)cc1] |
| 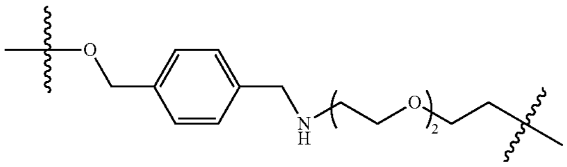 |
| 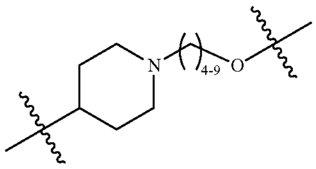 |

TABLE A-continued
| $—L^1—X—L^2—$ |
| --- |
| 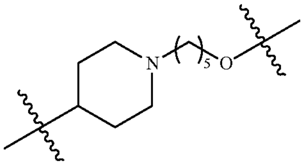 |
| 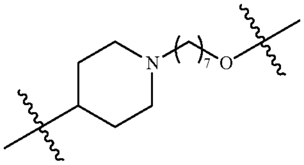 |
| 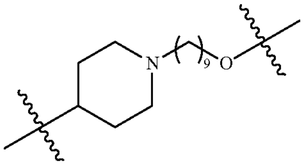 |
| 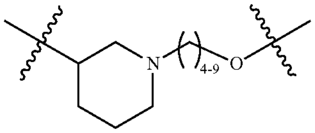 |
| 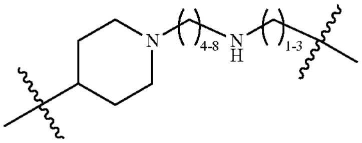 |
| 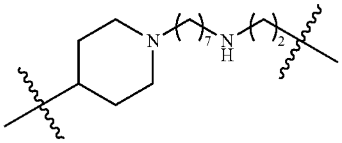 |
| 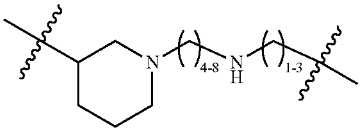 |
| 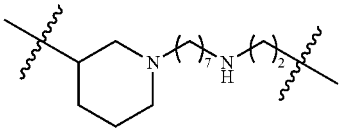 |
| 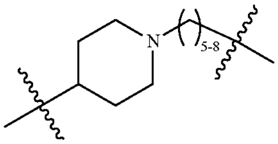 |

TABLE A-continued
| —L¹—X—L²— |
|---|
| 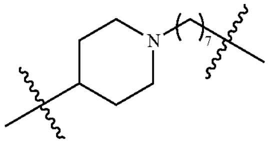 |
| 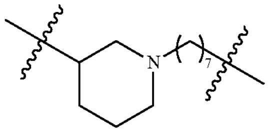 |
| 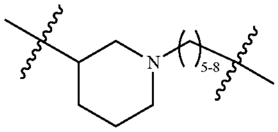 |
| 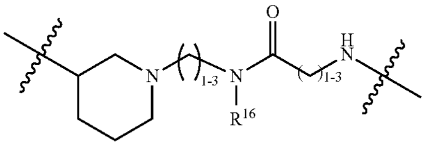 |
| 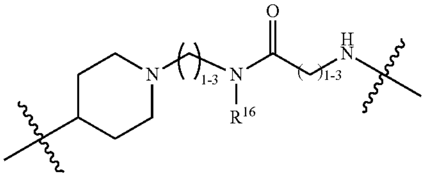 |
| 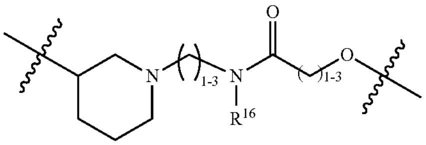 |
| 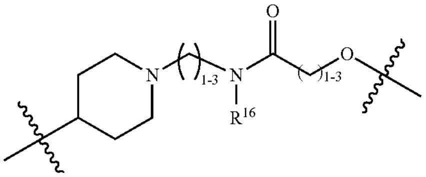 |
| 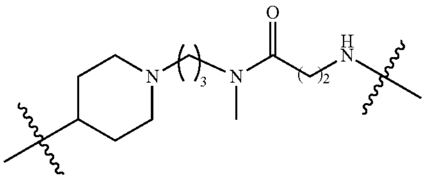 |
| 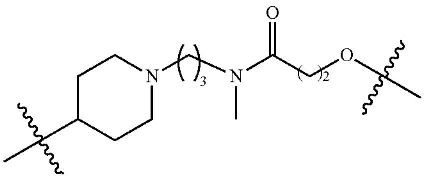 |

TABLE A-continued
| $-L^1-X-L^2-$ |
|---|
| 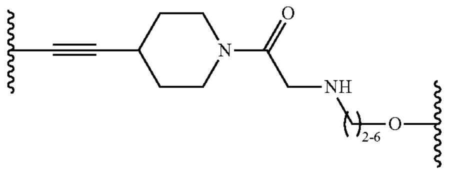 |
| 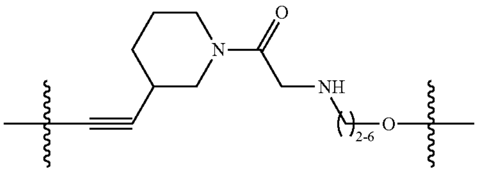 |
| 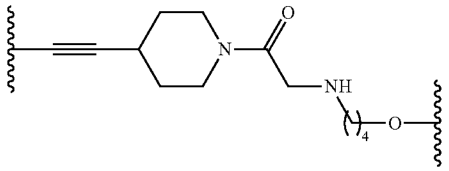 |
| 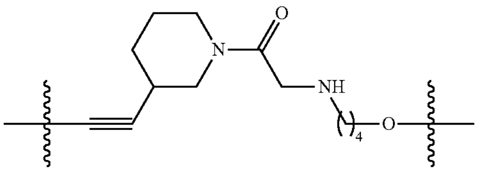 |
| 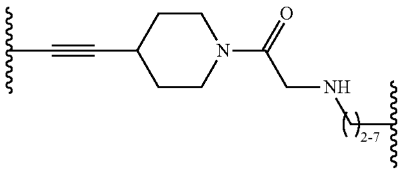 |
| 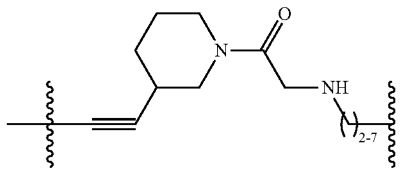 |
| 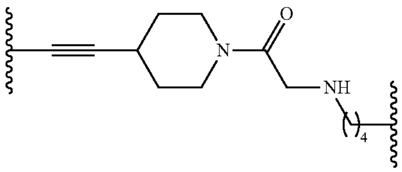 |
| 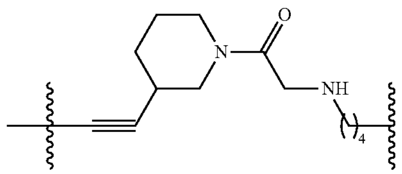 |
| $-C(O)(CH_2)_{4-10}-O-$ |
| $-C(O)(CH_2)_6-O-$ |
| $-C(O)(CH_2)_8-O-$ |
| $-C(O)(CH_2)_{10}-O-$ |
| $-C(O)(CH_2)_{4-10}-$ |
| $-C(O)(CH_2)_6-$ |

TABLE A-continued
| $—L^1—X—L^2—$ |
| --- |
| $—C(O)(CH_2)_8—$ |
| $—C(O)(CH_2)_{10}—$ |
| 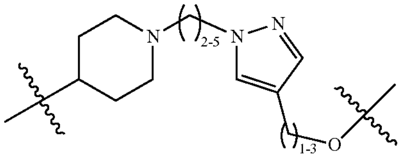 |
| 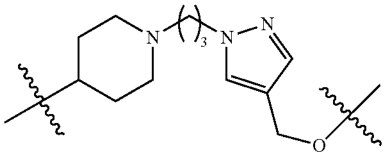 |
| 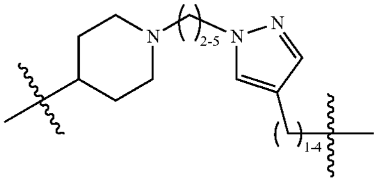 |
| 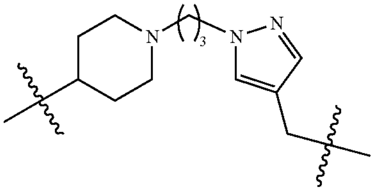 |
| 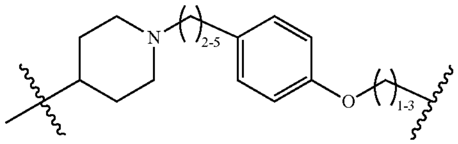 |
| 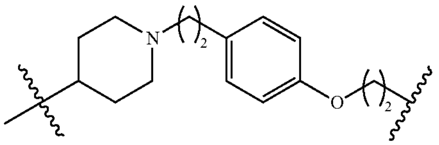 |
| 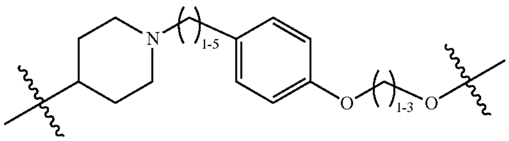 |
| 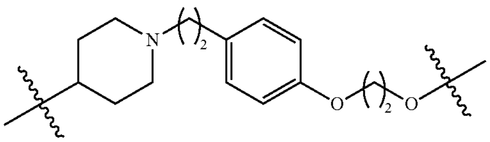 |
| 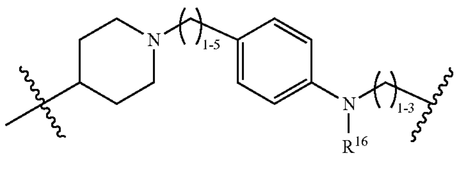 |

TABLE A-continued
| —L¹—X—L²— |
| --- |
| 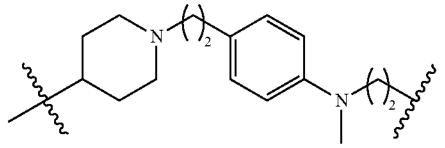 |
| 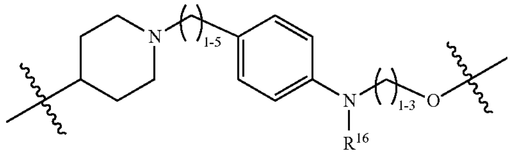 |
| 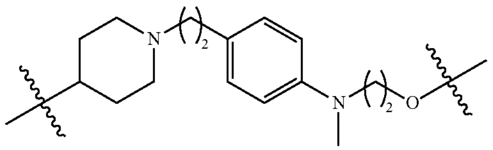 |
| 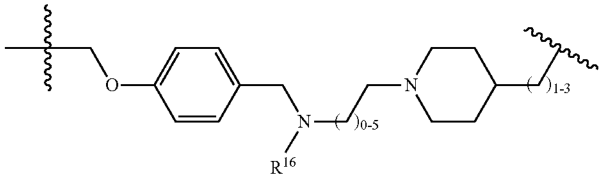 |
| 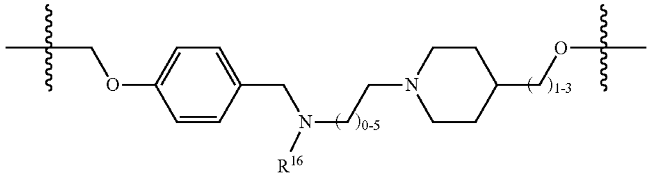 |
| 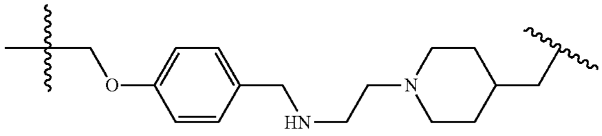 [SMILES: *COc1ccc(CNCCN2CCC(C*)CC2)cc1] |
| 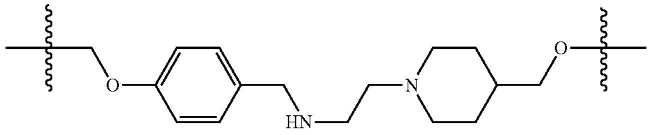 [SMILES: *COc1ccc(CNCCN2CCC(CO*)CC2)cc1] |
| 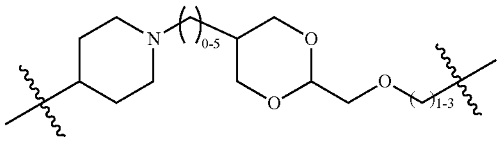 |
| 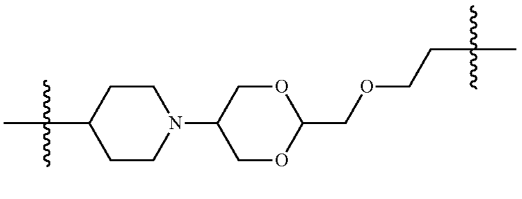 [SMILES: *CCOCC1OCC(N2CCC(*)CC2)CO1] |

TABLE A-continued

| $-L^1-X-L^2-$ |
| --- |
| 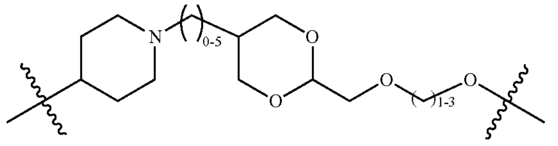 |
| 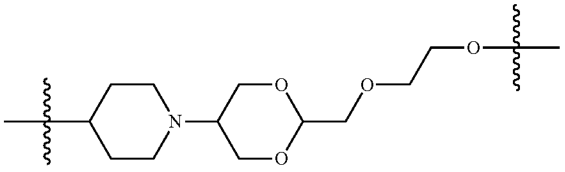 [SMILES: *OCCOCC1OCC(N2CCC(*)CC2)CO1] |
| 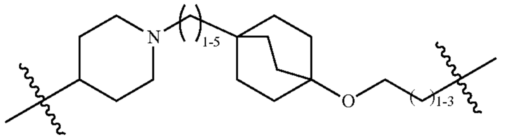 |
| 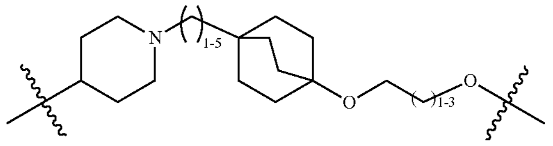 |
| 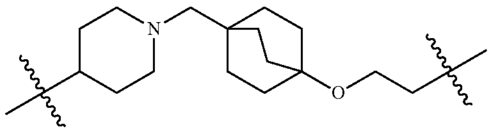 [SMILES: *CCOC12CCC(CN3CCC(*)CC3)(CC1)CC2] |
| 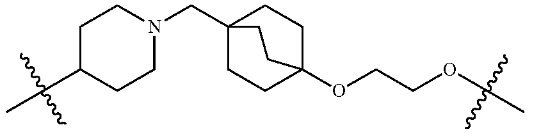 [SMILES: *OCCOC12CCC(CN3CCC(*)CC3)(CC1)CC2] |

In one embodiment, provided herein is:

3-(2-(2-(2-(4-(4-acryloylpiperazin-1-yl)-6-chloro-8-fluoroquinazolin-7-yl)-3-fluorophenoxy)ethoxy)ethoxy)-N-(2-((2-(2,6-dioxopiperidin-3-yl)-1,3-dioxoisoindolin-4-yl)amino)ethyl)propanamide 1;

3-(2-(2-(2-(4-(4-acryloylpiperazin-1-yl)-6-chloro-8-fluoroquinazolin-7-yl)-3-fluorophenoxy)ethoxy)ethoxy)-N-(2-((2-(2,6-dioxopiperidin-3-yl)-1,3-dioxoisoindolin-4-yl)oxy)ethyl)propanamide 3;

3-(2-(2-(2-(6-chloro-8-fluoro-4-(4-propionylpiperazin-1-yl)quinazolin-7-yl)-3-fluorophenoxy)ethoxy)ethoxy)-N-(2-((2-(2,6-dioxopiperidin-3-yl)-1,3-dioxoisoindolin-4-yl)amino)ethyl)propanamide 6;

3-(2-(2-(2-(6-chloro-8-fluoro-4-(4-propionylpiperazin-1-yl)quinazolin-7-yl)-3-fluorophenoxy)ethoxy)ethoxy)-N-(2-((2-(2,6-dioxopiperidin-3-yl)-1,3-dioxoisoindolin-4-yl)oxy)ethyl)propanamide 8;

4-((2-(2-(2-(2-(2-(6-chloro-8-fluoro-4-(4-propionylpiperazin-1-yl)quinazolin-7-yl)-3-fluorophenoxy)ethoxy)ethoxy)ethoxy)ethyl)amino)-2-(2,6-dioxopiperidin-3-yl)isoindoline-1,3-dione 9;

3-(4-(1-(8-(2-(8-chloro-6-fluoro-4-(4-propionylpiperazin-1-yl)quinazolin-7-yl)-3-fluorophenoxy)octyl)piperidin-4-yl)-6-fluoro-1-oxoisoindolin-2-yl)piperidine-2,6-dione 20;

4-((2-(2-(2-(2-(2-(4-(4-acryloylpiperazin-1-yl)-6-chloro-8-fluoroquinazolin-7-yl)-3-fluorophenoxy)ethoxy)ethoxy)ethoxy)ethyl)amino)-2-(2,6-dioxopiperidin-3-yl)isoindoline-1,3-dione 23;

(3S)-3-(1-((4-(((7-(2-(4-(4-acryloylpiperazin-1-yl)-6-chloro-8-fluoroquinazolin-7-yl)-3-fluorophenoxy)heptyl)amino)methyl)phenoxy)methyl)-4-oxo-4H-thieno[3,4-c]pyrrol-5(6H)-yl)piperidine-2,6-dione 24;

(3S)-3-(1-((4-(((7-(2-(6-chloro-8-fluoro-4-(4-propionylpiperazin-1-yl)quinazolin-7-yl)-3-fluorophenoxy)heptyl)amino)methyl)phenoxy)methyl)-4-oxo-4H-thieno[3,4-c]pyrrol-5(6H)-yl)piperidine-2,6-dione 25;

1-(7-(2-(4-(4-acryloylpiperazin-1-yl)-6-chloro-8-fluoroquinazolin-7-yl)-3-fluorophenoxy)heptyl)-3-((5-(2,6-dioxopiperidin-3-yl)-4-oxo-5,6-dihydro-4H-thieno[3,4-c]pyrrol-1-yl)methyl)urea 27;

1-(7-(2-(6-chloro-8-fluoro-4-(4-propionylpiperazin-1-yl)quinazolin-7-yl)-3-fluorophenoxy)heptyl)-3-((5-(2,6-dioxopiperidin-3-yl)-4-oxo-5,6-dihydro-4H-thieno[3,4-c]pyrrol-1-yl)methyl)urea 28;

3-(2-(2-(2-(4-(4-acryloylpiperazin-1-yl)-6-chloro-8-fluoroquinazolin-7-yl)-3-fluorophenoxy)ethoxy)ethoxy)-N-(2-((2-(2,6-dioxopiperidin-3-yl)-1-oxoisoindolin-4-yl)amino)ethyl)propanamide 29;

3-(2-(2-(2-(6-chloro-8-fluoro-4-(4-propionylpiperazin-1-yl)quinazolin-7-yl)-3-fluorophenoxy)ethoxy)ethoxy)-

N-(2-((2-(2,6-dioxopiperidin-3-yl)-1-oxoisoindolin-4-yl)amino)ethyl)propanamide 30;

4-((2-(2-(2-(2-(2-(4-(4-acetylpiperazin-1-yl)-6-chloro-8-fluoroquinazolin-7-yl)-3-fluorophenoxy)ethoxy)ethoxy)ethoxy)ethyl)amino)-2-(2,6-dioxopiperidin-3-yl)isoindoline-1,3-dione 31;

4-(6-chloro-7-(2-(2-(2-(2-(2-((2-(2,6-dioxopiperidin-3-yl)-1,3-dioxoisoindolin-4-yl)amino)ethoxy)ethoxy)ethoxy)ethoxy)-6-fluorophenyl)-8-fluoroquinazolin-4-yl)piperazine-1-carboxamide 32;

4-((8-(2-(6-chloro-8-fluoro-4-(4-propionylpiperazin-1-yl)quinazolin-7-yl)-3-fluorophenoxy)octyl)amino)-2-(2,6-dioxopiperidin-3-yl)isoindoline-1,3-dione 33;

4-((8-(2-(4-(4-acryloylpiperazin-1-yl)-6-chloro-8-fluoroquinazolin-7-yl)-3-fluorophenoxy)octyl)amino)-2-(2,6-dioxopiperidin-3-yl)isoindoline-1,3-dione 34;

3-(4-(1-(7-(2-(4-(4-acryloylpiperazin-1-yl)-6-chloro-8-fluoroquinazolin-7-yl)-3-fluorophenoxy)heptyl)piperidin-4-yl)-6-fluoro-1-oxoisoindolin-2-yl)piperidine-2,6-dione 36;

3-(4-(1-(7-(2-(6-chloro-8-fluoro-4-(4-propionylpiperazin-1-yl)quinazolin-7-yl)-3-fluorophenoxy)heptyl)piperidin-4-yl)-6-fluoro-1-oxoisoindolin-2-yl)piperidine-2,6-dione 37;

3-(2-(2-(3-(4-(4-acryloylpiperazin-1-yl)-6-chloro-8-fluoroquinazolin-7-yl)-4-fluorophenoxy)ethoxy)ethoxy)-N-(2-((2-(2,6-dioxopiperidin-3-yl)-1-oxoisoindolin-4-yl)amino)ethyl)propanamide 38;

3-(2-(2-((R)-3-(4-(4-acryloylpiperazin-1-yl)-6-chloro-8-fluoroquinazolin-7-yl)-4-fluorophenoxy)ethoxy)ethoxy)-N-(2-((2-(2,6-dioxopiperidin-3-yl)-1-oxoisoindolin-4-yl)amino)ethyl)propanamide 39;

3-(4-(1-(7-(2-(4-(4-(1H-imidazole-5-carbonyl)piperazin-1-yl)-6-chloro-8-fluoroquinazolin-7-yl)-3-fluorophenoxy)heptyl)piperidin-4-yl)-6-fluoro-1-oxoisoindolin-2-yl)piperidine-2,6-dione 41;

4-((2-(2-(2-(2-(2-(6-chloro-8-fluoro-4-(4-propionylpiperazin-1-yl)quinazolin-7-yl)-3-fluorophenoxy)ethoxy)ethoxy)ethoxy)ethyl)amino)-2-(2,6-dioxopiperidin-3-yl)isoindoline-1,3-dione 42;

3-(4-(1-(7-(2-(6-chloro-4-(4-(2-chloroacryloyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 43;

3-(4-(1-(8-((R)-2-(8-chloro-6-fluoro-4-(4-propionylpiperazin-1-yl)quinazolin-7-yl)-3-fluorophenoxy)octyl)piperidin-4-yl)-6-fluoro-1-oxoisoindolin-2-yl)piperidine-2,6-dione 49;

3-(4-(1-(7-(2-(6-chloro-4-(4-(cyclopentanecarbonyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 51;

3-(4-(1-(7-(2-(6-chloro-8-fluoro-4-(4-(tetrahydro-2H-pyran-4-carbonyl)piperazin-1-yl)quinazolin-7-yl)-3-fluorophenoxy)heptyl)piperidin-4-yl)-6-fluoro-1-oxoisoindolin-2-yl)piperidine-2,6-dione 52;

3-(4-(1-(7-(2-(6-chloro-4-(4-(2-cyclopropylacetyl)piperazin-1-yl)-8-fluoroquinazolin-7-yl)-3-fluorophenoxy)heptyl)piperidin-4-yl)-6- fluoro-1-oxoisoindolin-2-yl)piperidine-2,6-dione 53;

3-(4-(1-(7-(2-(6-chloro-8-fluoro-4-(4-(tetrahydrofuran-3-carbonyl)piperazin-1-yl)quinazolin-7-yl)-3-fluorophenoxy)heptyl)piperidin-4-yl)-6-fluoro-1-oxoisoindolin-2-yl)piperidine-2,6-dione 54;

4-((2-(2-(2-(2-((4-((2S,5R)-4-acryloyl-2,5-dimethylpiperazin-1-yl)-6-chloro-8-fluoro-7-(2-fluoro-6-hydroxyphenyl)quinazolin-2-yl)oxy)ethoxy)ethoxy)ethoxy)ethyl)amino)-2-(2,6-dioxopiperidin-3-yl)isoindoline-1,3-dione 58;

3-(4-(1-(7-(2-(6-chloro-4-(4-(ethylsulfonyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 59;

3-(4-(1-(5-(2-(6-chloro-8-fluoro-4-(4-propionylpiperazin-1-yl)quinazolin-7-yl)-3-fluorophenoxy)pentyl)piperidin-4-yl)-6-fluoro-1-oxoisoindolin-2-yl)piperidine-2,6-dione 60;

3-(4-(1-(9-(2-(6-chloro-8-fluoro-4-(4-propionylpiperazin-1-yl)quinazolin-7-yl)-3-fluorophenoxy)nonyl)piperidin-4-yl)-6-fluoro-1-oxoisoindolin-2-yl)piperidine-2,6-dione 61;

(3S)-3-(4-((4-(((3-(2-(4-(4-acryloylpiperazin-1-yl)-6-chloro-8-fluoroquinazolin-7-yl)-3-fluorophenoxy)propyl)amino)methyl)benzyl)oxy)-1-oxoisoindolin-2-yl)piperidine-2,6-dione 62;

(3S)-3-(4-((4-(((3-(2-(6-chloro-8-fluoro-4-(4-propionylpiperazin-1-yl)quinazolin-7-yl)-3-fluorophenoxy)propyl)amino)methyl)benzyl)oxy)-1-oxoisoindolin-2-yl)piperidine-2,6-dione 63;

3-(1-(1-(7-(2-(4-(4-acryloylpiperazin-1-yl)-6-chloro-8-fluoroquinazolin-7-yl)-3-fluorophenoxy)heptyl)piperidin-4-yl)-4-oxo-4H-thieno[3,4-c]pyrrol-5(6H)-yl)piperidine-2,6-dione 70;

3-(1-(1-(7-(2-(6-chloro-8-fluoro-4-(4-propionylpiperazin-1-yl)quinazolin-7-yl)-3-fluorophenoxy)heptyl)piperidin-4-yl)-4-oxo-4H-thieno[3,4-c]pyrrol-5(6H)-yl)piperidine-2,6-dione 71;

3-(4-(1-(7-(2-(6-chloro-8-fluoro-4-(4-(pyrrolidine-3-carbonyl)piperazin-1-yl)quinazolin-7-yl)-3-fluorophenoxy)heptyl)piperidin-4-yl)-6-fluoro-1-oxoisoindolin-2-yl)piperidine-2,6-dione 79;

(E)-2-(4-(6-chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoroquinazolin-4-yl)piperazine-1-carbonyl)-4-methylpent-2-enenitrile 80;

3-(4-(1-(7-(2-(6-chloro-8-fluoro-4-(4-(oxetane-3-carbonyl)piperazin-1-yl)quinazolin-7-yl)-3-fluorophenoxy)heptyl)piperidin-4-yl)-6-fluoro-1-oxoisoindolin-2-yl)piperidine-2,6-dione 81;

3-(4-(1-(7-(2-(6-chloro-8-fluoro-4-(4-(2-fluoroacryloyl)piperazin-1-yl)quinazolin-7-yl)-3-fluorophenoxy)heptyl)piperidin-4-yl)-6-fluoro-1-oxoisoindolin-2-yl)piperidine-2,6-dione 82;

4-(6-chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoroquinazolin-4-yl)piperazine-1-carboxamide 83;

3-(4-(1-(2-(4-(2-(2-(6-chloro-8-fluoro-4-(4-propionylpiperazin-1-yl)quinazolin-7-yl)-3-fluorophenoxy)ethyl)cyclohexyl)ethyl)piperidin-4-yl)-6-fluoro-1-oxoisoindolin-2-yl)piperidine-2,6-dione 84;

3-(4-(1-(7-(2-(6-chloro-8-fluoro-4-((S)-2-methyl-4-propionylpiperazin-1-yl)quinazolin-7-yl)-3-fluorophenoxy)heptyl)piperidin-4-yl)-6-fluoro-1-oxoisoindolin-2-yl)piperidine-2,6-dione 85;

3-((6-chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoro-4-(4-propionylpiperazin-1-yl)quinazolin-2-yl)amino)-N,N-dimethylpropanamide 86;

3-(4-(1-(7-(2-(6-chloro-8-fluoro-4-(4-propionylpiperazin-1-yl)quinazolin-7-yl)-3-fluorophenoxy)heptyl)piperidin-3-yl)-6-fluoro-1-oxoisoindolin-2-yl)piperidine-2,6-dione 87;

3-(4-(1-(7-(2-(4-(4-acryloylpiperazin-1-yl)-6-chloro-8-fluoro-2-(((S)-1-methylpyrrolidin-2-yl)methoxy)quinazolin-7-yl)-3-fluorophenoxy)heptyl)piperidin-4-yl)-6-fluoro-1-oxoisoindolin-2-yl)piperidine-2,6-dione 88;

3-(4-(1-(7-(2-(6-chloro-8-fluoro-2-(((S)-1-methylpyrrolidin-2-yl)methoxy)-4-(4-propionylpiperazin-1-yl)quinazolin-7-yl)-3-fluorophenoxy)heptyl)piperidin-4-yl)-6-fluoro-1-oxoisoindolin-2-yl)piperidine-2,6-dione 89;

3-(4-(1-(7-(3-(4-(4-acryloylpiperazin-1-yl)-6-chloro-8-fluoroquinazolin-7-yl)-4-fluorophenoxy)heptyl)piperidin-4-yl)-6-fluoro-1-oxoisoindolin-2-yl)piperidine-2,6-dione 90;

3-(4-(1-(7-(3-(6-chloro-8-fluoro-4-(4-propionylpiperazin-1-yl)quinazolin-7-yl)-4-fluorophenoxy)heptyl)piperidin-4-yl)-6-fluoro-1-oxoisoindolin-2-yl)piperidine-2,6-dione 91;

3-(4-(1-(2-(4-(2-(2-(6-chloro-8-fluoro-4-(4-propionylpiperazin-1-yl)quinazolin-7-yl)-3-fluorophenoxy)ethyl)-1H-1,2,3-triazol-1-yl)ethyl)piperidin-4-yl)-6-fluoro-1-oxoisoindolin-2-yl)piperidine-2,6-dione 92;

3-(5-(1-(7-(2-(6-chloro-8-fluoro-4-(4-propionylpiperazin-1-yl)quinazolin-7-yl)-3-fluorophenoxy)heptyl)piperidin-4-yl)-6-fluoro-1-oxoisoindolin-2-yl)piperidine-2,6-dione 93;

3-(5-(1-(7-(2-(4-(4-acryloylpiperazin-1-yl)-6-chloro-8-fluoroquinazolin-7-yl)-3-fluorophenoxy)heptyl)piperidin-4-yl)-6-fluoro-1-oxoisoindolin-2-yl)piperidine-2,6-dione 94;

(Z)-3-(4-(1-(7-(2-(6-chloro-4-(4-(2-chlorobut-2-enoyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 96;

(Z)-3-(4-(1-(7-(2-(6-chloro-4-(4-(2-chloro-4-methylpent-2-enoyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 97;

(Z)-3-(4-(1-(7-(2-(6-chloro-4-(4-(2-chloropent-2-enoyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 98;

3-(4-(1-(7-(2-(4-(4-acetylpiperazin-1-yl)-6-chloro-8-fluoroquinazolin-7-yl)-3-fluorophenoxy)heptyl)piperidin-4-yl)-6-fluoro-1-oxoisoindolin-2-yl)piperidine-2,6-dione 99;

3-(4-(1-(2-((4-((2-(2-(6-chloro-4-(4-(2-chloroacryloyl)piperazin-1-yl)-8-fluoroquinazolin-7-yl)-3-fluorophenoxy)ethoxy)methyl)benzyl)oxy)ethyl)piperidin-4-yl)-6-fluoro-1-oxoisoindolin-2-yl)piperidine-2,6-dione 101;

2-((2S)-4-(6-chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoroquinazolin-4-yl)-1-(2-chloroacryloyl)-piperazin-2-yl)acetonitrile 102;

3-(4-(1-(5-(2-(6-chloro-4-(4-(2-chloroacryloyl)piperazin-1-yl)-8-fluoroquinazolin-7-yl)-3-fluorophenoxy)pentyl)piperidin-4-yl)-6-fluoro-1-oxoisoindolin-2-yl)piperidine-2,6-dione 103;

3-(4-(1-(7-(2-(6-chloro-4-(4-(2-chloroacryloyl)piperazin-1-yl)quinazolin-7-yl)-3-fluorophenoxy)heptyl)piperidin-4-yl)-1-oxoisoindolin-2-yl)piperidine-2,6-dione 105;

3-(4-(1-(7-(2-(6-chloro-4-(4-(2-chloroacryloyl)piperazin-1-yl)-8-fluoroquinazolin-7-yl)-3-fluorophenoxy)heptyl)piperidin-3-yl)-6-fluoro-1-oxoisoindolin-2-yl)piperidine-2,6-dione 106;

3-(5-(1-(7-(2-(6-chloro-4-(4-(2-chloroacryloyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 107;

3-(4-(1-(7-(2-(6-chloro-4-(4-(2-chloroacryloyl)piperazin-1-yl)-8-fluoro-2-(((S)-1-methylpyrrolidin-2-yl)methoxy)quinazolin-7-yl)-3-fluorophenoxy)heptyl)piperidin-4-yl)-6-fluoro-1-oxoisoindolin-2-yl)piperidine-2,6-dione 108;

3-(4-(1-(2-((4-((2-(2-(6-chloro-8-fluoro-4-(4-propionylpiperazin-1-yl)quinazolin-7-yl)-3-fluorophenoxy)ethoxy)methyl)benzyl)oxy)ethyl)piperidin-4-yl)-6-fluoro-1-oxoisoindolin-2-yl)piperidine-2,6-dione 109;

3-(4-(1-(2-(4-(2-(2-(6-chloro-4-(4-(2-chloroacryloyl)piperazin-1-yl)-8-fluoroquinazolin-7-yl)-3-fluorophenoxy)ethyl)cyclohexyl)ethyl)piperidin-4-yl)-6-fluoro-1-oxoisoindolin-2-yl)piperidine-2,6-dione 110;

3-(4-(1-(4-(2-(2-(6-chloro-4-(4-(2-chloroacryloyl)piperazin-1-yl)-8-fluoroquinazolin-7-yl)-3-fluorophenoxy)ethyl)phenethyl)piperidin-4-yl)-6-fluoro-1-oxoisoindolin-2-yl)piperidine-2,6-dione 111;

3-(4-(1-(7-(2-(6-chloro-4-(4-(2-chloroacryloyl)piperazin-1-yl)-8-fluoroquinazolin-7-yl)-3-fluorophenoxy)heptyl)pyrrolidin-3-yl)-6-fluoro-1-oxoisoindolin-2-yl)piperidine-2,6-dione 112;

3-(4-(1-(9-(2-(6-chloro-4-(4-(2-chloroacryloyl)piperazin-1-yl)-8-fluoroquinazolin-7-yl)-3-fluorophenoxy)nonyl)piperidin-4-yl)-6-fluoro-1-oxoisoindolin-2-yl)piperidine-2,6-dione 113;

3-(4-(1-(11-(2-(6-chloro-4-(4-(2-chloroacryloyl)piperazin-1-yl)-8-fluoroquinazolin-7-yl)-3-fluorophenoxy)undecyl)piperidin-4-yl)-6-fluoro-1-oxoisoindolin-2-yl)piperidine-2,6-dione 114;

3-(4-(1-(7-(2-(6-chloro-4-(4-(2-chloroacryloyl)piperazin-1-yl)-2-(2-(dimethylamino)-ethoxy)-8-fluoroquinazolin-7-yl)-3-fluorophenoxy)heptyl)piperidin-4-yl)-6-fluoro-1-oxoisoindolin-2-yl)piperidine-2,6-dione 115;

3-(4-(1-(2-(4-(2-(2-(6-chloro-4-(4-(2-chloroacryloyl)piperazin-1-yl)-8-fluoroquinazolin-7-yl)-3-fluorophenoxy)ethyl)cyclohexyl)ethyl)piperidin-4-yl)-6-fluoro-1-oxoisoindolin-2-yl)piperidine-2,6-dione 116;

3-(4-(1-(((1r,4r)-4-((2-(6-chloro-4-(4-(2-chloroacryloyl)piperazin-1-yl)-8-fluoro-quinazolin-7-yl)-3-fluorophenoxy)methyl)cyclohexyl)methyl)piperidin-4-yl)-6-fluoro-1-oxoisoindolin-2-yl)piperidine-2,6-dione 117;

3-(4-(1-((4-(2-(2-(6-chloro-4-(4-(2-chloroacryloyl)piperazin-1-yl)-8-fluoroquinazolin-7-yl)-3-fluorophenoxy)ethyl)cyclohexyl)methyl)piperidin-4-yl)-6-fluoro-1-oxoisoindolin-2-yl)piperidine-2,6-dione 118;

3-(5-(1-(7-(2-(6-chloro-4-(4-(2-chloroacryloyl)piperazin-1-yl)-8-fluoroquinazolin-7-yl)-3-fluorophenoxy)heptyl)piperidin-3-yl)-6-fluoro-1-oxoisoindolin-2-yl)piperidine-2,6-dione 119;

3-(4-(1-(2-(1-(2-(2-(6-chloro-4-(4-(2-chloroacryloyl)piperazin-1-yl)-8-fluoroquinazolin-7-yl)-3-fluorophenoxy)ethyl)piperidin-4-yl)ethyl)piperidin-4-yl)-6-fluoro-1-oxoisoindolin-2-yl)piperidine-2,6-dione 120;

3-(4-(1-(3-(2-(6-chloro-4-(4-(2-chloroacryloyl)piperazin-1-yl)-8-fluoroquinazolin-7-yl)-3-fluorophenoxy)propyl)piperidin-4-yl)-6-fluoro-1-oxoisoindolin-2-yl)piperidine-2,6-dione 121;

2-((2R)-4-(6-chloro-7-(2-((7-(4-(2-(2,6-dioxopiperidin-3-yl)-6-fluoro-1-oxoisoindolin-5-yl)piperidin-1-yl)

heptyl)oxy)-6-fluorophenyl)-8-fluoroquinazolin-4-yl)-1-(2-chloroacryloyl)-piperazin-2-yl)acetonitrile 123;

3-(4-(1-(((1s,4s)-4-((2-(6-chloro-4-(4-(2-chloroacryloyl)piperazin-1-yl)-8-fluoro-quinazolin-7-yl)-3-fluorophenoxy)methyl)cyclohexyl)methyl)piperidin-4-yl)-6-fluoro-1-oxoisoindolin-2-yl)piperidine-2,6-dione 127;

2-((2R)-4-(6-chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoro-2-(((S)-1-methylpyrrolidin-2-yl)methoxy)quinazolin-4-yl)-1-(2-chloroacryloyl)piperazin-2-yl)acetonitrile 128;

2-((2R)-4-(6-chloro-7-(2-(2-(4-(2-(4-(2-(2,6-dioxopiperidin-3-yl)-6-fluoro-1-oxoisoindolin-4-yl)piperidin-1-yl)ethyl)cyclohexyl)ethoxy)-6-fluorophenyl)-8-fluoroquinazolin-4-yl)-1-(2-chloroacryloyl)piperazin-2-yl)acetonitrile 129;

3-(4-(1-(2-(3-(2-(2-(6-chloro-4-(4-(2-chloroacryloyl)piperazin-1-yl)-8-fluoroquinazolin-7-yl)-3-fluorophenoxy)ethyl)cyclopentyl)ethyl)piperidin-4-yl)-6-fluoro-1-oxoisoindolin-2-yl)piperidine-2,6-dione 130;

2-((2R)-4-(6-chloro-7-(2-(4-(2-(4-(2-(2,6-dioxopiperidin-3-yl)-6-fluoro-1-oxoisoindolin-4-yl)piperidin-1-yl)ethyl)phenethoxy)-6-fluorophenyl)-8-fluoroquinazolin-4-yl)-1-(2-chloroacryloyl)piperazin-2-yl)acetonitrile 131;

2-((2R)-4-(6-chloro-7-(2-((7-(4-(2-(2,6-dioxopiperidin-3-yl)-6-fluoro-1-oxoisoindolin-5-yl)piperidin-1-yl)heptyl)oxy)-6-fluorophenyl)-8-fluoro-2-(((S)-1-methylpyrrolidin-2-yl)methoxy)quinazolin-4-yl)-1-(2-chloroacryloyl)piperazin-2-yl)acetonitrile 132; or 3-(4-((1-((2-(2-(6-chloro-8-fluoro-4-(4-propionylpiperazin-1-yl)quinazolin-7-yl)-3-fluorophenoxy)ethyl)glycyl)piperidin-4-yl)-1$\lambda^5$-ethynyl)-1-oxoisoindolin-2-yl)piperidine-2,6-dione 133;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In another embodiment, provided herein is:

(2S,4R)-1-((2S)-2-(7-(2-(4-(4-acryloylpiperazin-1-yl)-6-chloro-8-fluoroquinazolin-7-yl)-3-fluorophenoxy)heptanamido)-3,3-dimethylbutanoyl)-4-hydroxy-N-(4-(4-methylthiazol-5-yl)benzyl)pyrrolidine-2-carboxamide 50;

(2S,4R)-1-((2S)-2-(11-(2-(4-(4-acryloylpiperazin-1-yl)-6-chloro-8-fluoroquinazolin-7-yl)-3-fluorophenoxy)undecanamido)-3,3-dimethylbutanoyl)-4-hydroxy-N-(4-(4-methylthiazol-5-yl)benzyl)pyrrolidine-2-carboxamide 76;

(2S,4R)-1-((2S)-2-(11-(2-(6-chloro-8-fluoro-4-(4-propionylpiperazin-1-yl)quinazolin-7-yl)-3-fluorophenoxy)undecanamido)-3,3-dimethylbutanoyl)-4-hydroxy-N-(4-(4-methylthiazol-5-yl)benzyl)pyrrolidine-2-carboxamide 77; or (2S,4R)-1-((2S)-2-(7-(2-(6-chloro-8-fluoro-4-(4-propionylpiperazin-1-yl)quinazolin-7-yl)-3-fluorophenoxy)heptanamido)-3,3-dimethylbutanoyl)-4-hydroxy-N-(4-(4-methylthiazol-5-yl)benzyl)pyrrolidine-2-carboxamide 78;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is 2-(4-acryloyl-1-(6-chloro-8-fluoro-7-(2-fluoro-6-hydroxyphenyl)quinazolin-4-yl)piperazin-2-yl)-N-(5-(3-((5-(2,6-dioxopiperidin-3-yl)-6-oxo-5,6-dihydro-4H-thieno[2,3-c]pyrrol-2-yl)methyl)ureido)pentyl)acetamide 13; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is:

4-((2-(2-(2-(2-(3-(1-acryloylazetidin-3-yl)-7-(3-hydroxynaphthalen-1-yl)-2-oxo-3,4-dihydroquinazolin-1(2H)-yl)ethoxy)ethoxy)ethoxy)ethyl)amino)-2-(2,6-dioxopiperidin-3-yl)isoindoline-1,3-dione 2;

3-(1-((4-(((2-(7-(3-hydroxynaphthalen-1-yl)-2-oxo-3-(1-propionylazetidin-3-yl)-3,4-dihydroquinazolin-1(2H)-yl)ethyl)amino)methyl)phenoxy)methyl)-4-oxo-4H-thieno[3,4-c]pyrrol-5(6H)-yl)piperidine-2,6-dione 4;

3-(1-((4-(((2-(2-(7-(3-hydroxynaphthalen-1-yl)-2-oxo-3-(1-propionylazetidin-3-yl)-3,4-dihydroquinazolin-1(2H)-yl)ethoxy)ethyl)amino)methyl)phenoxy)methyl)-4-oxo-4H-thieno[3,4-c]pyrrol-5(6H)-yl)piperidine-2,6-dione 5;

N-(2-((2-(2,6-dioxopiperidin-3-yl)-1,3-dioxoisoindolin-4-yl)oxy)ethyl)-3-(2-(2-(7-(3-hydroxynaphthalen-1-yl)-2-oxo-3-(1-propionylazetidin-3-yl)-3,4-dihydroquinazolin-1(2H)-yl)ethoxy)ethoxy)propanamide 7;

3-(2-(3-(1-acryloylazetidin-3-yl)-7-(3-hydroxynaphthalen-1-yl)-2-oxo-3,4-dihydroquinazolin-1(2H)-yl)ethoxy)-N-(2-((2-(2,6-dioxopiperidin-3-yl)-1,3-dioxoisoindolin-4-yl)oxy)ethyl)propanamide 10;

3-(2-(2-(3-(1-acryloylazetidin-3-yl)-7-(3-hydroxynaphthalen-1-yl)-2-oxo-3,4-dihydroquinazolin-1(2H)-yl)ethoxy)ethoxy)-N-(2-((2-(2,6-dioxopiperidin-3-yl)-1,3-dioxoisoindolin-4-yl)oxy)ethyl)propanamide 11;

2-(2,6-dioxopiperidin-3-yl)-4-((2-(2-(2-(2-(7-(3-hydroxynaphthalen-1-yl)-2-oxo-3-(1-propionylazetidin-3-yl)-3,4-dihydroquinazolin-1(2H)-yl)ethoxy)ethoxy)ethoxy)ethyl)amino)-isoindoline-1,3-dione 12;

(S)-3-(1-((4-(((4-(3-(1-acryloylazetidin-3-yl)-7-(3-hydroxynaphthalen-1-yl)-2-oxo-3,4-dihydroquinazolin-1(2H)-yl)butyl)amino)methyl)phenoxy)methyl)-4-oxo-4H-thieno[3,4-c]pyrrol-5(6H)-yl)piperidine-2,6-dione 16;

3-(1-((4-(((4-(3-(1-acryloylazetidin-3-yl)-7-(3-hydroxynaphthalen-1-yl)-2-oxo-3,4-dihydroquinazolin-1(2H)-yl)butyl)amino)methyl)phenoxy)methyl)-4-oxo-4H-thieno[3,4-c]pyrrol-5(6H)-yl)piperidine-2,6-dione 19;

(S)-3-(1-((4-(((2-(7-(3-hydroxynaphthalen-1-yl)-2-oxo-3-(1-propionylazetidin-3-yl)-3,4-dihydroquinazolin-1(2H)-yl)ethyl)amino)methyl)phenoxy)methyl)-4-oxo-4H-thieno[3,4-c]pyrrol-5(6H)-yl)piperidine-2,6-dione 22;

N-(7-(4-(2-(2,6-dioxopiperidin-3-yl)-6-fluoro-1-oxoisoindolin-4-yl)piperidin-1-yl)heptyl)-2-(7-(3-hydroxynaphthalen-1-yl)-2-oxo-3-(1-propionylazetidin-3-yl)-3,4-dihydroquinazolin-1(2H)-yl)acetamide 35;

5-((2-(2-(2-(2-(3-(1-acryloylazetidin-3-yl)-7-(3-hydroxynaphthalen-1-yl)-2-oxo-3,4-dihydroquinazolin-1(2H)-yl)ethoxy)ethoxy)ethoxy)ethyl)amino)-2-(2,6-dioxopiperidin-3-yl)isoindoline-1,3-dione 40;

3-(6-fluoro-4-(1-(7-(7-(3-hydroxynaphthalen-1-yl)-2-oxo-3-(1-propionylazetidin-3-yl)-3,4-dihydroquinazolin-1(2H)-yl)heptyl)piperidin-4-yl)-1-oxoisoindolin-2-yl)piperidine-2,6-dione 44;

4-((2-(2-(2-(3-(1-acryloylazetidin-3-yl)-7-(3-hydroxynaphthalen-1-yl)-2-oxo-3,4-dihydroquinazolin-1

(2H)-yl)ethoxy)ethoxy)ethyl)amino)-2-(2,6-dioxopiperidin-3-yl)isoindoline-1,3-dione 45; or 3-(6-fluoro-4-(1-(7-((2-(7-(3-hydroxynaphthalen-1-yl)-2-oxo-3-(1-propionylazetidin-3-yl)-3,4-dihydroquinazolin-1(2H)-yl)ethyl)amino)heptyl)piperidin-4-yl)-1-oxoisoindolin-2-yl)piperidine-2,6-dione 46;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is:

(S)-3-(1-((4-(((2-(2-(2-(2-(1-acryloylazetidin-3-yl)-6-(3-hydroxynaphthalen-1-yl)-4-oxoquinazolin-3(4H)-yl)ethoxy)ethoxy)ethyl)amino)methyl)phenoxy)methyl)-4-oxo-4H-thieno[3,4-c]pyrrol-5(6H)-yl)piperidine-2,6-dione 14;

(S)-3-(1-((4-(((2-(2-(1-acryloylazetidin-3-yl)-6-(3-hydroxynaphthalen-1-yl)-4-oxoquinazolin-3(4H)-yl)ethyl)amino)methyl)phenoxy)methyl)-4-oxo-4H-thieno[3,4-c]pyrrol-5(6H)-yl)piperidine-2,6-dione 15;

2-(2-(1-acryloylazetidin-3-yl)-6-(3-hydroxynaphthalen-1-yl)-4-oxoquinazolin-3(4H)-yl)-N-(2-(2-(2-(2-((2-(2,6-dioxopiperidin-3-yl)-1,3-dioxoisoindolin-4-yl)amino)ethoxy)ethoxy)ethoxy)-ethyl)acetamide 17;

3-(1-((4-(((2-(2-(1-acryloylazetidin-3-yl)-6-(3-hydroxynaphthalen-1-yl)-4-oxoquinazolin-3(4H)-yl)ethyl)amino)methyl)phenoxy)methyl)-4-oxo-4H-thieno[3,4-c]pyrrol-5(6H)-yl)piperidine-2,6-dione 18;

3-(1-((4-(((2-(2-(2-(1-acryloylazetidin-3-yl)-6-(3-hydroxynaphthalen-1-yl)-4-oxoquinazolin-3(4H)-yl)ethoxy)ethyl)amino)methyl)phenoxy)methyl)-4-oxo-4H-thieno[3,4-c]pyrrol-5(6H)-yl)piperidine-2,6-dione 21; or 3-(1-((4-(((2-(2-(6-(3-hydroxynaphthalen-1-yl)-4-oxo-2-(1-propionylazetidin-3-yl)quinazolin-3(4H)-yl)ethoxy)ethyl)amino)methyl)phenoxy)methyl)-4-oxo-4H-thieno[3,4-c]pyrrol-5(6H)-yl)piperidine-2,6-dione 26;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is:

4-((2-(2-(2-(2-((4-((R)-4-acryloyl-3-methylpiperazin-1-yl)-7-(naphthalen-1-yl)-5,6,7,8-tetrahydropyrido[3,4-d]pyrimidin-2-yl)oxy)ethoxy)ethoxy)ethoxy)ethyl)amino)-2-(2,6-dioxopiperidin-3-yl)isoindoline-1,3-dione 47;

2-(2,6-dioxopiperidin-3-yl)-4-((2-(2-(2-(2-((4-((R)-3-methyl-4-propionylpiperazin-1-yl)-7-(naphthalen-1-yl)-5,6,7,8-tetrahydropyrido[3,4-d]pyrimidin-2-yl)oxy)ethoxy)ethoxy)ethoxy)ethyl)-amino)isoindoline-1,3-dione 48; or 3-(4-(1-(7-((4-(4-acryloylpiperazin-1-yl)-7-(3-hydroxynaphthalen-1-yl)-5,6,7,8-tetrahydropyrido[3,4-d]pyrimidin-2-yl)oxy)heptyl)piperidin-4-yl)-6-fluoro-1-oxoisoindolin-2-yl)piperidine-2,6-dione 75;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is:

3-(4-(1-(7-(2-(4-((S)-4-acryloyl-2-methylpiperazin-1-yl)-6-fluoro-1-(2-isopropylphenyl)-2-oxo-1,2-dihydropyrido[2,3-d]pyrimidin-7-yl)-3-fluorophenoxy)heptyl)piperidin-4-yl)-6-fluoro-1-oxoisoindolin-2-yl)piperidine-2,6-dione 72;

3-(6-fluoro-4-(1-(7-(3-fluoro-2-(6-fluoro-1-(2-isopropylphenyl)-4-((S)-2-methyl-4-propionylpiperazin-1-yl)-2-oxo-1,2-dihydropyrido[2,3-d]pyrimidin-7-yl)phenoxy)heptyl)piperidin-4-yl)-1-oxoisoindolin-2-yl)piperidine-2,6-dione 73;

3-(4-(1-(7-(2-(4-((S)-4-(2-chloroacryloyl)-2-methylpiperazin-1-yl)-6-fluoro-1-(2-isopropylphenyl)-2-oxo-1,2-dihydropyrido[2,3-d]pyrimidin-7-yl)-3-fluorophenoxy)heptyl)piperidin-4-yl)-6-fluoro-1-oxoisoindolin-2-yl)piperidine-2,6-dione 100;

3-(4-(1-(7-(2-(4-((S)-4-(2-chloroacryloyl)-2-methylpiperazin-1-yl)-6-fluoro-1-(2-isopropyl-4-methylpyridin-3-yl)-2-oxo-1,2-dihydropyrido[2,3-d]pyrimidin-7-yl)-3-fluorophenoxy)heptyl)piperidin-4-yl)-6-fluoro-1-oxoisoindolin-2-yl)piperidine-2,6-dione 122; or 3-(4-(1-(7-(2-(4-((S)-4-acryloyl-2-methylpiperazin-1-yl)-6-fluoro-1-(2-isopropyl-4-methylpyridin-3-yl)-2-oxo-1,2-dihydropyrido[2,3-d]pyrimidin-7-yl)-3-fluorophenoxy)heptyl)-piperidin-4-yl)-6-fluoro-1-oxoisoindolin-2-yl)piperidine-2,6-dione 124;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is 3-(4-(1-(7-(4-(4-((S)-4-(2-Chloroacryloyl)-2-methylpiperazin-1-yl)-6-fluoro-7-(2-fluoro-6-hydroxyphenyl)-2-oxopyrido[2,3-d]pyrimidin-1(2H)-yl)-3-isopropylphenyl)heptyl)piperidin-4-yl)-6-fluoro-1-oxoisoindolin-2-yl)piperidine-2,6-dione 126; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is:

3-(4-(1-(7-(2-((2R,4aR)-3-acryloyl-11-chloro-9-fluoro-2,6-dimethyl-5-oxo-2,3,4,4a,5,6-hexahydro-1H-pyrazino[1',2':4,5]pyrazino[2,3-c]quinolin-10-yl)-3-fluorophenoxy)heptyl)piperidin-4-yl)-6-fluoro-1-oxoisoindolin-2-yl)piperidine-2,6-dione 64;

3-(4-(1-(7-(2-((2R,4aR)-11-chloro-9-fluoro-2,6-dimethyl-5-oxo-3-propionyl-2,3,4,4a,5,6-hexahydro-1H-pyrazino[1',2':4,5]pyrazino[2,3-c]quinolin-10-yl)-3-fluorophenoxy)heptyl)piperidin-4-yl)-6-fluoro-1-oxoisoindolin-2-yl)piperidine-2,6-dione 65; or 3-(4-(1-(7-(2-((2R,4aR)-11-chloro-3-(2-chloroacryloyl)-9-fluoro-2,6-dimethyl-5-oxo-2,3,4,4a,5,6-hexahydro-1H-pyrazino[1',2':4,5]pyrazino[2,3-c]quinolin-10-yl)-3-fluorophenoxy)-heptyl)piperidin-4-yl)-6-fluoro-1-oxoisoindolin-2-yl)piperidine-2,6-dione 104;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In still another embodiment, provided herein is:

3-(4-(1-(7-((2R,4aR)-3-acryloyl-11-chloro-9-fluoro-10-(2-fluoro-6-hydroxyphenyl)-2-methyl-5-oxo-1,2,3,4,4a,5-hexahydro-6H-pyrazino[1',2':4,5]pyrazino[2,3-c]quinolin-6-yl)heptyl)piperidin-4-yl)-6-fluoro-1-oxoisoindolin-2-yl)piperidine-2,6-dione 66;

3-(4-(1-(7-((2R,4aR)-11-chloro-9-fluoro-10-(2-fluoro-6-hydroxyphenyl)-2-methyl-5-oxo-3-propionyl-1,2,3,4, 4a,5-hexahydro-6H-pyrazino[1',2':4,5]pyrazino[2,3-c]quinolin-6-yl)heptyl)piperidin-4-yl)-6-fluoro-1-oxoisoindolin-2-yl)piperidine-2,6-dione 67;

2-((2R,4aR)-11-chloro-6-(7-(4-(2-(2,6-dioxopiperidin-3-yl)-6-fluoro-1-oxoisoindolin-4-yl)piperidin-1-yl)heptyl)-9-fluoro-2-methyl-5-oxo-3-propionyl-2,3,4,4a,5,6-hexahydro-1H-pyrazino[1',2':4,5]pyrazino[2,3-c]quinolin-10-yl)-3-fluorophenyl propionate 95; or 3-(4-(1-(7-((2R,4aR)-11-chloro-3-(2-chloroacryloyl)-9-fluoro-10-(2-fluoro-6-hydroxyphenyl)-2-methyl-5-oxo-1,2,3,4,4a,5-hexahydro-6H-pyrazino[11',2':4,5]pyrazino[2,3-c]quinolin-6-yl)heptyl)piperidin-4-yl)-6-fluoro-1-oxoisoindolin-2-yl)piperidine-2,6-dione 125;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In certain embodiments, a compound provided herein is isolated or purified. In certain embodiments, a compound provided herein has a purity of at least about 90%, at least about 95%, at least about 98%, at least about 99%, or at least about 99.5% by weight.

The compounds provided herein are intended to encompass all possible stereoisomers, unless a particular stereochemistry is specified. Where a compound provided herein contains an alkenyl group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contains an aromatic moiety. It follows that a single compound may exhibit more than one type of isomerism.

A compound provided herein can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a compound in its (R) form is equivalent, for the compound that undergoes epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When a compound provided herein contains an acidic or basic moiety, it can also be provided as a pharmaceutically acceptable salt. See, Berge et al., *J. Pharm. Sci.* 1977, 66, 1-19*; Handbook of Pharmaceutical Salts: Properties, Selection, and Use,* 2nd ed.; Stahl and Wermuth Eds.; John Wiley & Sons, 2011. In certain embodiments, a pharmaceutically acceptable salt of a compound provided herein is a solvate. In certain embodiments, a pharmaceutically acceptable salt of a compound provided herein is a hydrate.

Suitable acids for use in the preparation of pharmaceutically acceptable salts of a compound provided herein include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts of a compound provided herein include, but are not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

A compound provided herein may also be provided as a prodrug, which is a functional derivative of the compound and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis.

Uses or Methods of Treatment

In certain embodiments, provided herein is a method of inhibiting the activity of a RAS protein in a biological sample, comprising contacting one or more cells in the biological sample with an effective amount of a compound provided herein, e.g., a compound of Formula (I) or a pharmaceutically acceptable salt thereof.

In certain embodiments, provided herein is a method of decreasing cellular levels of a RAS protein in a cell, comprising contacting the cell with an effective amount of a compound provided herein, e.g., a compound of Formula (I) or a pharmaceutically acceptable salt thereof.

In certain embodiments, in a method provided herein, the cell is a cancer cell. In certain embodiments, the cancer cell is a small cell lung cancer cell, non-small cell lung cancer cell, breast cancer cell, prostate cancer cell, head and neck cancer cell, pancreatic cancer cell, colon cancer cell, rectal cancer cell, teratoma cell, gastric cancer cell, ovarian cancer cell, endometrial cancer cell, brain cancer cell, retinoblastoma cell, leukemia cell, skin cancer cell, melanoma cell, squamous cell carcinoma cell, liposarcoma cell, lymphoma cell, multiple myeloma cell, testicular cancer cell, liver cancer cell, esophageal cancer cell, kidney carcinoma cell, astrogliosis cell, relapsed/refractory multiple myeloma cell, or neuroblastoma cell. In certain embodiments, the cancer cell is a leukemia cell, lymphoma cell, or multiple myeloma cell. In certain embodiments, the cancer cell is a relapsed/refractory cancer cell.

In certain embodiments, provided herein is a method of treating or ameliorating a disease, disorder, or condition associated with RAS malfunction in a subject, comprising administering a therapeutically effective amount of a compound provided herein, e.g., a compound of Formula (I) or a pharmaceutically acceptable salt thereof, or a pharmaceutical composition thereof to the subject in need thereof. In certain embodiments, the disease, disorder, or condition is cancer.

In certain embodiments, provided herein is a method of treating or ameliorating cancer in a subject, comprising administering a therapeutically effective amount of a compound provided herein, e.g., a compound of Formula (I) or a pharmaceutically acceptable salt thereof, or a pharmaceutical composition thereof to the subject in need thereof. In certain embodiments, the cancer is mediated by a RAS mutation. In certain embodiments, the cancer is mediated by a RAS with a G12C mutation. In certain embodiments, the cancer is mediated by a KRAS, NRAS, or HRAS. In certain embodiments, the cancer is mediated by a KRAS with a G12C mutation. In certain embodiments, the cancer is mediated by an NRAS with a G12C mutation. In certain embodiments, the cancer is mediated by an HRAS with a G12C mutation.

In certain embodiments, in a method provided herein, the cancer is small cell lung cancer, non-small cell lung cancer, breast cancer, prostate cancer, head and neck cancer, pancreatic cancer, colon cancer, rectal cancer, teratoma, gastric cancer, ovarian cancer, endometrial cancer, brain cancer, retinoblastoma, leukemia, skin cancer, melanoma, squamous cell carcinoma, liposarcoma, lymphoma, multiple myeloma, testicular cancer, liver cancer, esophageal cancer, kidney carcinoma, astrogliosis, relapsed/refractory multiple myeloma, or neuroblastoma. In certain embodiments, the cancer is leukemia, lymphoma, or multiple myeloma. In certain embodiments, the cancer is relapsed or refractory.

In certain embodiments, the RAS protein is DIRAS1; DIRAS2; DIRAS3; ERAS; GEM; MRAS; NKIRAS1; NKIRAS2; NRAS; RALA; RALB; RAPlA; RAP1B; RAP2A; RAP2B; RAP2C; RASD1; RASD2; RASL10A; RASLiOB; RASLi1A; RASL11B; RASL12; REM1; REM2; RERG; RERGL; RRAD; RRAS, or RRAS2. In certain embodiments, the RAS protein is wild-type. In certain embodiments, the RAS protein is overexpressed. In certain embodiments, the RAS protein has a mutation.

Dosing Regimes

In certain embodiments, about 1 mg to about 5 grams, or any amount in between, of a compound provided herein, e.g., a compound of Formula (I) or a pharmaceutically acceptable salt thereof, is administered each day, each week, or each cycle of treatment.

In certain embodiments, a compound provided herein, e.g., a compound of Formula (I) or a pharmaceutically acceptable salt thereof, is administered once per day, twice per day, three times per day, four times per day, or more than four times per day. In certain embodiments, a compound provided herein, e.g., a compound of Formula (I) or a pharmaceutically acceptable salt thereof, is administered once per day, twice per day, three times per day, four times per day, or more than four times per cycle of treatment.

In certain embodiments, each cycle of treatment lasts from 1 day to 14 days, or any value in between. In certain embodiments, each cycle of treatment has from at least one day up to fourteen days, or any value in between. In certain embodiments, a compound provided herein, e.g., a compound of Formula (I) or a pharmaceutically acceptable salt thereof, is administered intravenously over about 10 minutes to over about 4 h, or any value in between.

Pharmaceutical Compositions

In certain embodiments, provided herein is a pharmaceutical composition comprising a compound provided herein, e.g., a compound of Formula (I) or a pharmaceutically acceptable salt thereof and a pharmaceutically acceptable carrier or excipient.

In certain embodiments, a compound provided herein is provided in the form of a pharmaceutically acceptable salt, active metabolite, or tautomer thereof. In certain embodiments, the pharmaceutical composition is formulated for intravenous injection, subcutaneous injection, oral administration, buccal administration, inhalation, nasal administration, topical administration, transdermal administration, ophthalmic administration, or otic administration. In certain embodiments, the pharmaceutical composition is provided in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

As used herein, an "excipient" refers to an essentially inert substances that is added to a pharmaceutical composition to provide, without limitation, bulk, consistency, stability, binding ability, lubrication, disintegrating ability etc., to the composition. For example, stabilizers such as antioxidants and metal-chelating agents are excipients. Excipients also include ingredients in a pharmaceutical composition that lack appreciable pharmacological activity but may be pharmaceutically necessary or desirable. For example, to increase the bulk of a potent drug whose mass is too small for manufacture and/or administration. It may also be a liquid for the dissolution of a drug to be administered by injection, ingestion, or inhalation. For example, a buffered aqueous solution such as, without limitation, phosphate buffered saline that mimics the pH and isotonicity of the human blood.

The pharmaceutical compositions described herein can be administered to a human patient per se, or in pharmaceutical compositions where they are mixed with other active ingredients, as in combination therapy, or excipients, or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, levigating, emulsifying, encapsulating, entrapping, or tableting processes. Many of the compounds used in the pharmaceutical combinations disclosed herein may be provided as salts with pharmaceutically compatible counterions.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections. In certain embodiments, a compound provided herein, e.g., a compound of Formula (I) or a pharmaceutically acceptable salt thereof, is administered orally.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical excipient may also be prepared, placed in an appropriate container, and labeled for treatment of an indicated condition.

Other objects, features, and advantages of the compounds, methods, and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: g (grams); mg (milligrams); mL (milliliters); μL (microliters); mM (millimolar); M (micromolar); mmol (millimoles); h (hour or hours); min (minute or minutes); ACN (acetonitrile); AcOH (acetic acid); DCM (dichloromethane); DMF (dimethylformamide); DMSO (dimethyl sulfoxide); EtOH (ethanol); MeOH (methanol); EtOAc (ethyl acetate); PE (petroleum ether); TEA (triethylamine); TFA (trifluoroacetic acid); THF (tetrahydrofuran); DIPEA (N,N-diisopropylethylamine); DMAP (4-dimethylaminopyridine); EDCI (1-ethyl-3-(3-dimethylaminopropyl)carbodiimide); $Et_3N$ (triethylamine); HOBt (1-hydroxybenzotriazole); NaOAc (sodium acetate); TEA (triethylamine); MS (mass spectrometry); and NMR (nuclear magnetic resonance).

For all of the following examples, standard work-up and purification methods known to those skilled in the art can be utilized. Unless otherwise indicated, all temperatures are expressed in ° C. (degrees Centigrade). All reactions are conducted at room temperature unless otherwise specified. Synthetic methodologies illustrated herein are intended to exemplify the applicable chemistry through the use of specific examples and are not indicative of the scope of the disclosure.

Example 1. 3-(2-(2-(2-(4-(4-Acryloylpiperazin-1-yl)-6-chloro-8-fluoroquinazolin-7-yl)-3-fluorophenoxy)ethoxy)ethoxy)-N-(2-((2-(2,6-dioxopiperidin-3-yl)-1,3-dioxoisoindolin-4-yl)amino)ethyl) propanamide 1

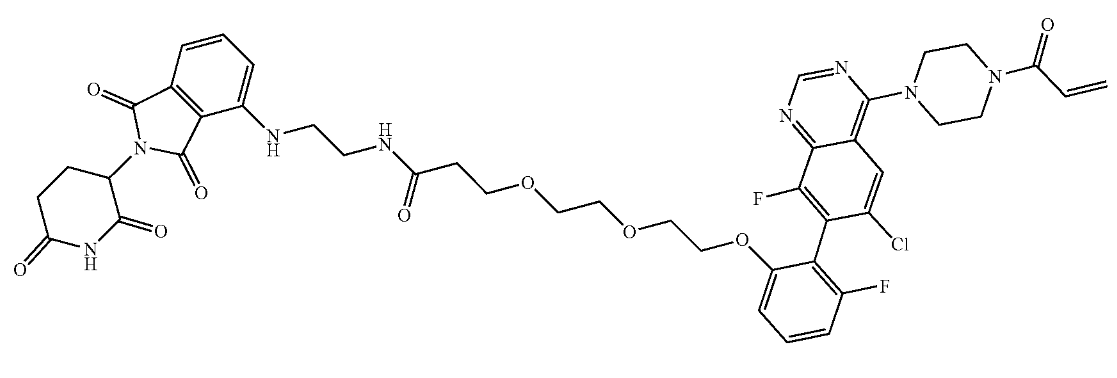

1

To a solution of 2-amino-4-bromo-3-fluorobenzoic acid 1a (1.00 g, 4.27 mmol) in DMF (20 mL) was added N-chlorosuccinimide (575 mg, 4.27 mmol). The mixture was heated at 70° C. overnight, and then poured into ice-water and filtered to give 2-amino-4-bromo-5-chloro-3-fluorobenzoic acid 1b (1.1 g) in 96% yield.

To a solution of compound 1b (1.1 g, 4.1 mmol) in EtOH (15 mL) was added formamidine acetate (5.1 g, 49.2 mmol). The mixture was heated at 80° C. overnight and concentrated. The residue was dissolved in $H_2O$ and extracted with EtOAc. The organic phase was separated and washed with brine, dried over anhydrous $Na_2SO_4$, concentrated, and purified using silica gel (DCM/MeOH, 50:1) to give 7-bromo-6-chloro-8-fluoroquinazolin-4(3H)-one 1c (580 mg) in 51% yield.

A mixture of compound 1c (580 mg, 2.10 mmol), thionyl chloride (20 mL), and DMF (3 drops) was heated at 80° C. overnight. The mixture was then concentrated to give 7-bromo-4,6-dichloro-8-fluoroquinazoline 1d (600 mg, crude).

To a solution of compound 1d (600 mg, 2.0 mmol, crude) in 1,4-dioxane (20 mL) were added DIPEA (1.6 mL) and tert-butyl piperazine-1-carboxylate (1.1 g, 6.0 mmol). The mixture was heated at 50° C. for 3 h, and then concentrated, diluted with water, and extracted with EtOAc. The organic phase was washed with brine, dried over anhydrous $Na_2SO_4$, concentrated, and purified using silica gel (DCM/MeOH, 50:1) to give tert-butyl 4-(7-bromo-6-chloro-8-fluoroquinazolin-4-yl)piperazine-1-carboxylate 1e (780 mg) in 86% yield.

To a solution of compound 1e (620 mg, 1.5 mmol) and (2-fluoro-6-methoxyphenyl)boronic acid (1.27 g, 7.5 mmol) in 1,4-dioxane (12 mL) and water (3 mL) were added $Na_2CO_3$ (800 mg, 7.5 mmol) and tetrakis(triphenylphosphine)palladium (345 mg, 0.3 mmol). After heating at 85° C. overnight, the mixture was concentrated, dissolved in water, and extracted with EtOAc. The organic phase was washed with brine, dried over anhydrous $Na_2SO_4$, concentrated, and purified using silica gel (PE/EtOAc, 3:1) to give tert-butyl 4-(6-chloro-8-fluoro-7-(2-fluoro-6-methoxyphenyl)quinazolin-4-yl)piperazine-1-carboxylate if (320 mg) in 43% yield.

To a solution of compound if (160 mg, 0.32 mmol) in MeOH (5 mL) was added HCl (MeOH solution, 5 mL). After stirring for 2 h, the mixture was concentrated to give 6-chloro-8-fluoro-7-(2-fluoro-6-methoxyphenyl)-4-(piperazin-1-yl)quinazoline as a solid, which was then dissolved in DCM (5 mL) and cooled to 0° C. TEA (160 mg, 1.6 mmol) and acryloyl chloride (45 mg, 0.48 mmol) were added. After 2 h at 0° C., the mixture was concentrated and purified by prep-TLC (EA) to give 1-(4-(6-chloro-8-fluoro-7-(2-fluoro-6-methoxyphenyl)quinazolin-4-yl)piperazin-1-yl)prop-2-en-1-one 1 g (60 mg) in 42% yield.

To a solution of compound 1 g (60 mg, 0.135 mmol) in DCM (5 mL) at −78° C. was dropwise added a solution of $BBr_3$ (170 mg, 0.675 mmol) in DCM. After 3 h at room temperature, the mixture was quenched with saturated aqueous $NaHCO_3$ and extracted with EtOAc. The organic phase was washed with brine, dried over anhydrous $Na_2SO_4$, concentrated, and purified by prep-TLC (EA) to give 1-(4-(6-chloro-8-fluoro-7-(2-fluoro-6-hydroxyphenyl)quinazolin-4-yl)piperazin-1-yl)prop-2-en-1-one A (13.3 mg) in 23% yield.

To a solution of compound A (70 mg, 0.163 mmol) in DMF (4 mL) were added $K_2CO_3$ (44.9 mg, 0.326 mmol) and tert-butyl 3-(2-(2-iodoethoxy)ethoxy)propanoate (84 mg, 0.244 mmol). After stirring overnight, the mixture was concentrated and purified by prep-TLC (EtOAc) to give tert-butyl 3-(2-(2-(2-(4-(4-acryloylpiperazin-1-yl)-6-chloro-8-fluoroquinazolin-7-yl)-3-fluorophenoxy)-ethoxy)ethoxy)propanoate (1 h) (67 mg) in 64% yield.

To a solution of compound 1h (50 mg, 0.075 mmol) in DCM (1 mL) was added TFA (1 mL). After 1 h, the mixture was concentrated to give 3-(2-(2-(2-(4-(4-acryloylpiperazin-1-yl)-6-chloro-8-fluoroquinazolin-7-yl)-3-fluorophenoxy)ethoxy)ethoxy)propanoic acid 1i (crude).

To a solution of tert-butyl (2-((2-(2,6-dioxopiperidin-3-yl)-1,3-dioxoisoindolin-4-yl)amino)ethyl)carbamate (50 mg, 0.12 mmol) in DCM (2 mL) was added TFA (0.5 mL). After 1 h, the mixture was concentrated to give 4-((2-aminoethyl)amino)-2-(2,6-dioxopiperidin-3-yl)isoindoline-1,3-dione 1j as a TFA salt (crude).

To a solution of compound 1i (0.075 mmol, crude) and compound 1j (0.12 mmol, crude) in DMF (5 mL) were added DIPEA (40 mg, 0.3 mmol), HOBt (20 mg, 0.15 mmol), and 1-(3-dimethylaminopropyl)-3-ethylcarbodiimide HCl (20 mg, 0.15 mmol). After stirring overnight, the mixture was quenched with saturated aqueous $NaHCO_3$ and extracted with EtOAc. The organic phase was washed with brine, dried over anhydrous $Na_2SO_4$, concentrated, and purified by prep-HPLC eluting with water (0.1% TFA) in ACN (0.1% TFA) with a gradient of 95 to 5% to afford compound 1 (23 mg) in 35% yield. $^1H$ NMR (400 MHz, DMSO-$d_6$) δ 11.09 (s, 1H), 8.69 (s, 1H), 8.03-8.04 (m, 2H), 7.53-7.58 (m, 2H), 7.08-7.15 (m, 2H), 6.99-7.04 (m, 2H), 6.78-6.85 (m, 1H), 6.70 (t, J=5.2 Hz, 1H), 6.17 (dd, J=1.6, 16.8 Hz, 1H), 5.73 (dd, J=1.6, 9.6 Hz, 1H), 5.05 (dd, J=5.2, 12.8 Hz, 1H), 4.10-4.16 (m, 2H), 3.77-3.92 (m, 8H), 3.55-3.56 (m, 2H), 3.43-3.46 (m, 4H), 3.22-3.28 (m, 6H), 2.84-2.92 (m, 1H), 2.53-2.61 (m, 2H), 2.22 (t, J=6.0 Hz, 2H), 2.00-2.03 (m, 1H); MS (ESI) m/z: 889.2 $[M+H]^+$.

Example 2. 4-((2-(2-(2-(2-(3-(1-Acryloylazetidin-3-yl)-7-(3-hydroxynaphthalen-1-yl)-2-oxo-3,4-dihydroquinazolin-1(2H)-yl)ethoxy)ethoxy)ethoxy)ethyl)amino)-2-(2,6-dioxopiperidin-3-yl)isoindoline-1,3-dione 2

2

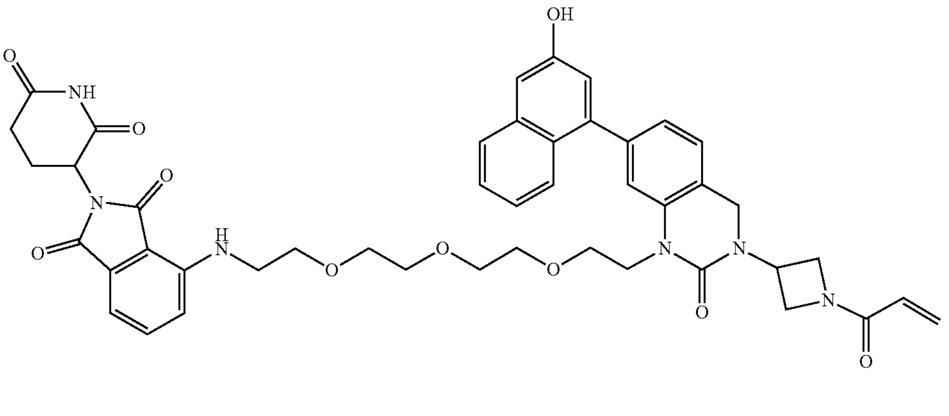

To 4-bromo-2-nitrobenzaldehyde (1.00 g, 4.35 mmol) in MeOH (16 mL) were added tert-butyl 3-aminoazetidine-1-carboxylate (898 mg, 5.22 mmol) and acetic acid (783 mg, 13.1 mmol). After 10 min, sodium cyanoborohydride (822 mg, 13.05 mmol) was added. The mixture was heated at 50° C. for 16 h and then concentrated. The residue was diluted with EtOAc, washed with saturated $NaHCO_3$ and then brine, dried over anhydrous $Na_2SO_4$, concentrated, and purified using silica gel (PE/EtOAc, 1:1) to give tert-butyl 3-((4-bromo-2-nitrobenzyl)amino)azetidine-1-carboxylate 2a (1.60 g) 95% yield.

A mixture of compound 2a (1.60 g, 4.15 mmol) and ammonium chloride (2.66 g, 49.80 mmol) in EtOH/$H_2O$ (50 mL:10 mL) was heated at 70° C. under $N_2$ for 1 h. Zinc (1.36 g, 20.75 mmol) was added. The mixture was heated at 70° C. for 1 h and then filtered. The filtrate was adjusted to pH 10 using 1N NaOH and then extracted with EtOAc. The organic phase was washed with brine, dried over anhydrous $Na_2SO_4$, filtered, and concentrated. The residue was purified using silica gel (PE/EtOAc, 1:1) to give tert-butyl 3-((2-amino-4-bromobenzyl)amino)azetidine-1-carboxylate 2b (1.42 g) in 96% yield.

To a mixture of compound 2b (1.42 g, 4.0 mmol) and TEA (6.1 mL, 44 mmol) in DCM (30 mL) was added 1,1'-carbonyldiimidazole (3.56 g, 22.0 mmol). After 16 h, the mixture was washed with brine and concentrated. The residue was purified using silica gel (PE/EtOAc, 2:1) to give tert-butyl 3-(7-bromo-2-oxo-1,2-dihydroquinazolin-3(4H)-yl)azetidine-1-carboxylate 2c (1.03 g) in 68% yield).

To a solution of compound 2c (13.5 g, 35.4 mmol) in DCM (50 mL) was added TFA (12 mL). After 2 h, the mixture was concentrated and the crude product was triturated with MTBE/PE (10:1) to give 3-(azetidin-3-yl)-7-bromo-3,4-dihydroquinazolin-2(1H)-one 2d as a TFA salt (12 g) in 85% yield.

To a solution of compound 2d (1.00 g, 2.53 mmol) in DCM (10 mL) were added TEA (1.5 mL) and acryloyl chloride (343 mg, 3.79 mmol). After 2 h, the mixture was concentrated and the residue was purified using silica gel (MeOH in DCM, 0 to 10%) to give 3-(1-acryloylazetidin-3-yl)-7-bromo-3,4-dihydroquinazolin-2(1H)-one 2e (368 mg) in 44% yield.

To a solution of compound 2e (200 mg, 0.597 mmol) in DMF (4 mL) were added tert-butyl (2-(2-(2-(2-iodoethoxy)ethoxy)ethoxy)ethyl)carbamate (481 mg, 1.19 mmol) and cesium carbonate (582 mg, 1.791 mmol). The mixture was heated at 100° C. under microwave for 4 h, and then filtered and concentrated. The residue was purified using silica gel (MeOH in DCM, 0 to 8%) to give tert-butyl (2-(2-(2-(2-(3-(1-acryloylazetidin-3-yl)-7-bromo-2-oxo-3,4-dihydroquinazolin-1(2H)-yl)ethoxy)ethoxy)ethoxy)ethyl)carbamate 2f (300 mg) in 82% yield.

To a solution of compound 2f (300 mg, 0.492 mmol) in 1,4-dioxane (4 mL) and $H_2O$ (1 mL) were added 4-(4,4,5,5-tetramethyl-1,3,2-dioxaborolan-2-yl)naphthalen-2-ol (136 mg, 0.492 mmol), $Pd(PPh_3)_4$(57 mg, 0.049 mmol), and $Na_2CO_3$ (104 mg, 0.984 mmol). The mixture was heated to 100° C. for 4 h and then filtered. The organic layer of the filtrate was concentrated and the residue was purified using silica gel (MeOH in DCM, 0 to 10%) to give tert-butyl (2-(2-(2-(2-(3-(1-acryloylazetidin-3-yl)-7-(3-hydroxynaphthalen-1-yl)-2-oxo-3,4-dihydroquinazolin-1(2H)-yl)ethoxy)ethoxy)ethoxy)ethyl)carbamate 2 g (180 mg) in 54% yield.

To a solution of compound 2 g (180 mg, 0.27 mmol) in DCM (4 mL) was added TFA (1 mL). After 1 h, the mixture was concentrated and the residue was purified using prep-TLC (DCM/MeOH, 10:1) to give 3-(1-acryloylazetidin-3-yl)-1-(2-(2-(2-(2-aminoethoxy)ethoxy)ethoxy)-ethyl)-7-(3-hydroxynaphthalen-1-yl)-3,4-dihydroquinazolin-2(1H)-one 2 h (76 mg) in 50% yield.

To a solution of compound 2h (76 mg, 0.13 mmol) and 2-(2,6-dioxopiperidin-3-yl)-4-fluoroisoindoline-1,3-dione (40 mg, 0.15 mmol) in DMF (3 mL) was added DIPEA (51 mg, 0.40 mmol). The mixture was heated at 150° C. under microwave for 1.5 h and then concentrated. The residue was purified using prep-TLC (DCM/MeOH, 10:1) to afford compound 2 (22 mg) in 20% yield. $^1H$ NMR (400 MHz, DMSO-$d_6$) δ 11.07 (s, 1H), 9.85 (s, 1H), 7.74 (d, J=8.4 Hz, 1H), 7.65 (d, J=8.4 Hz, 1H), 7.54 (t, J=8.0 Hz, 1H), 7.40-7.37 (m, 2H), 7.23-7.16 (m, 3H), 7.08-7.00 (m, 4H), 6.54 (t, J=5.6 Hz, 1H), 6.37-6.31 (m, 1H), 6.14-6.10 (m, 1H), 5.68 (d, J=10.4 Hz, 1H), 5.02 (dd, J=4.8, 12.4 Hz, 1H), 4.93 (t, J=7.2 Hz, 1H), 4.51-4.38 (m, 4H), 4.14 (d, J=6.8 Hz, 2H), 3.99-3.96 (m, 2H), 3.62-3.59 (m, 2H), 3.49-3.43 (m, 6H), 2.90-2.81 (m, 1H), 2.59-2.54 (m, 1H), 2.07-1.98 (m, 2H); MS (ESI) m/z: 831.0 $[M+H]^+$.

Example 3. 3-(1-((4-(((2-(7-(3-Hydroxynaphthalen-1-yl)-2-oxo-3-(1-propionylazetidin-3-yl)-3,4-dihydroquinazolin-1(2H)-yl)ethyl)amino)methyl)phenoxy)methyl)-4-oxo-4H-thieno[3,4-c]pyrrol-5(6H)-yl)piperidine-2,6-dione 4

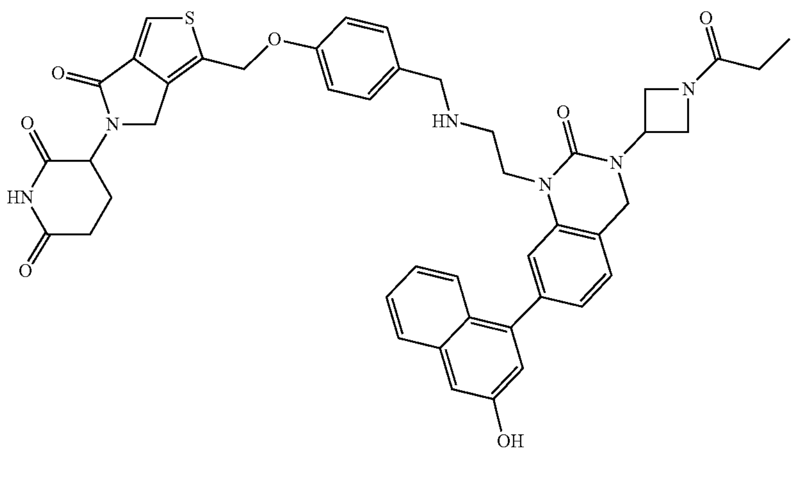

4

To a solution of 7-bromo-3-(1-propionylazetidin-3-yl)-3,4-dihydroquinazolin-2(1H)-one (150 mg, 0.44 mmol) in DMF (5 mL) were added tert-butyl (2-bromoethyl)carbamate (396 mg, 1.33 mmol) and $Cs_2CO_3$ (579 mg, 1.33 mmol). After 4 h at 80° C. under microwave, the mixture was concentrated and purified using silica gel eluting with EtOAc in PE from 10 to 70% to give tert-butyl (2-(7-bromo-2-oxo-3-(1-propionylazetidin-3-yl)-3,4-dihydroquinazolin-1(2H)-yl)ethyl)carbamate (110 mg) in 39% yield. MS (ESI) m/z: 481.2 $[M+H]^+$.

To a solution of tert-butyl (2-(7-bromo-2-oxo-3-(1-propionylazetidin-3-yl)-3,4-dihydroquinazolin-1(2H)-yl)ethyl) carbamate (110 mg, 0.23 mmol) in dioxane/$H_2O$ (5 mL:1 mL) were added 4-(4,4,5,5-tetramethyl-1,3,2-dioxaborolan-2-yl)naphthalen-2-ol (74 mg, 0.28 mmol), $Na_2CO_3$ (73 mg, 0.69 mmol), and $Pd(PPh_3)_4$(26 mg, 0.02 mmol). After 16 h at 90° C. under $N_2$, the mixture was concentrated and purified using silica gel eluting with EtOAc in PE from 10 to 100% to give tert-butyl (2-(7-(3-hydroxynaphthalen-1-yl)-2-oxo-3-(1-propionylazetidin-3-yl)-3,4-dihydroquinazolin-1(2H)-yl)ethyl)carbamate (90 mg) in 72% yield. MS (ESI) m/z: 545.2 $[M+H]^+$.

To a solution of tert-butyl (2-(7-(3-hydroxynaphthalen-1-yl)-2-oxo-3-(1-propionylazetidin-3-yl)-3,4-dihydroquinazolin-1(2H)-yl)ethyl)carbamate (90 mg, 0.16 mmol) in DCM (2 mL) at 0° C. was added TFA (1 mL). After 2 h, the solution was concentrated to give 1-(2-aminoethyl)-7-(3-hydroxynaphthalen-1-yl)-3-(1-propionylazetidin-3-yl)-3,4-dihydroquinazolin-2(1H)-one as a TFA salt (70 mg, crude). MS (ESI) m/z: 445.2 $[M+H]^+$.

To a solution of 1-(2-aminoethyl)-7-(3-hydroxynaphthalen-1-yl)-3-(1-propionylazetidin-3-yl)-3,4-dihydroquinazolin-2(1H)-one (70 mg, crude, 0.16 mmol) in DCM/MeOH (4 mL:1 mL) at 0° C. were added 4-((5-(2,6-dioxopiperidin-3-yl)-4-oxo-5,6-dihydro-4H-thieno[3,4-c]pyrrol-1-yl) methoxy)benzaldehyde (76 mg, 0.20 mmol), $NaBH_3CN$ (42 mg, 0.66 mmol), and AcOH (1 drop).

After 16 h at room temperature, the mixture was concentrated and the residue was purified using prep-HPLC eluting with water (0.1% TFA) in ACN (0.1% TFA) with a gradient of 95 to 5% to give 3-(1-((4-(((2-(7-(3-hydroxynaphthalen-1-yl)-2-oxo-3-(1-propionylazetidin-3-yl)-3,4-dihydroquinazolin-1(2H)-yl)ethyl)amino)methyl)phenoxy)-methyl)-4-oxo-4H-thieno[3,4-c]pyrrol-5(6H)-yl)piperidine-2,6-dione 4 (38 mg) in 28% yield. $^1H$ NMR (400 MHz, DMSO-$d_6$) δ 10.97 (s, 1H), 9.88 (s, 1H), 8.00 (s, 1H), 7.76 (d, J=8.0 Hz, 1H), 7.64-7.60 (m, 2H), 7.42-7.39 (m, 2H), 7.23-7.18 (m, 3H), 7.09-7.06 (m, 2H), 7.01-6.99 (m, 3H), 6.89-6.83 (m, 1H), 5.20 (s, 2H), 5.01 (dd, J=5.2, 13.6 Hz, 1H), 4.93-4.87 (m, 1H), 4.56-4.48 (m, 2H), 4.34-4.18 (m, 4H), 4.05-3.97 (m, 4H), 3.75-3.71 (m, 1H), 2.93-2.77 (m, 3H), 2.67-2.54 (m, 2H), 2.33-2.28 (m, 1H), 2.10 (q, J=7.6 Hz, 2H), 1.99-1.94 (m, 1H), 0.98 (t, J=7.6 Hz, 3H); MS (ESI) m/z: 813.2 $[M+H]^+$.

Example 4. (S)-3-(1-((4-(((2-(2-(2-(2-(1-Acryloylazetidin-3-yl)-6-(3-hydroxynaphthalen-1-yl)-4-oxoquinazolin-3(4H)-yl)ethoxy)ethoxy)ethyl)amino) methyl)phenoxy)methyl)-4-oxo-4H-thieno[3,4-c] pyrrol-5(6H)-yl)piperidine-2,6-dione 14

14

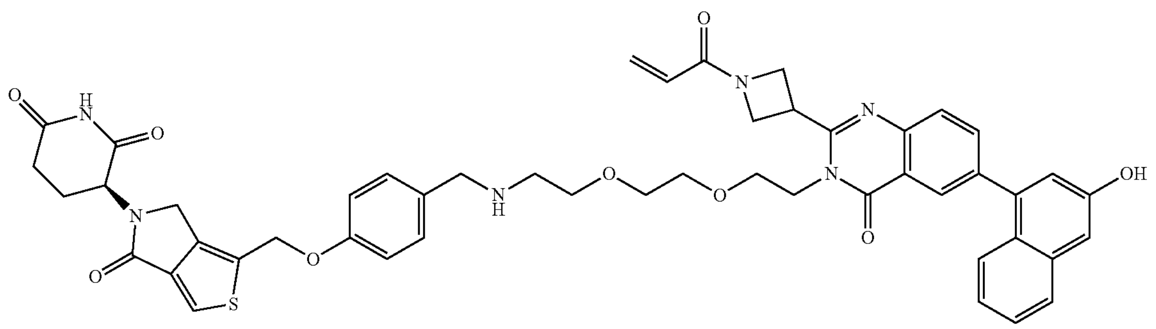

To a solution of 2-(1-acryloylazetidin-3-yl)-6-bromoquinazolin-4(3H)-one (300 mg, 0.9 mmol) in DMF (10 mL) were added tert-butyl (2-(2-(2-bromoethoxy)ethoxy)ethyl) carbamate (420 mg, 1.35 mmol) and cesium carbonate (590 mg, 1.8 mmol). After 16 h at 60° C., the mixture was diluted with $H_2O$ (10 mL) and extracted with DCM/MeOH (10:1). The organic phase was washed with brine, dried over anhydrous $Na_2SO_4$, filtered, and concentrated. The residue was purified using silica gel eluting with EtOAc to give tert-butyl (2-(2-(2-(2-(1-acryloylazetidin-3-yl)-6-bromo-4-oxoquinazolin-3(4H)-yl)ethoxy)ethoxy)ethyl)carbamate (500 mg). MS (ESI) m/z: 565.2 $[M+H]^+$.

To a solution of tert-butyl (2-(2-(2-(2-(1-acryloylazetidin-3-yl)-6-bromo-4-oxoquinazolin-3(4H)-yl)ethoxy)ethoxy) ethyl)carbamate (200 mg, 0.35 mmol) and 4-(4,4,5,5-tetramethyl-1,3,2-dioxaborolan-2-yl)naphthalen-2-ol (115 mg, 0.42 mmol) in 1,4-dioxane (10 mL) and water (2 mL) were added sodium carbonate (57 mg, 0.53 mmol) and tetrakis (triphenylphosphine)palladium (40 mg, 0.035 mmol). After 16 h at 90° C. under $N_2$, the mixture was concentrated and the residue was purified using silica gel eluting with DCM/MeOH (20:1) to give tert-butyl (2-(2-(2-(2-(1-acryloylazetidin-3-yl)-6-(3-hydroxynaphthalen-1-yl)-4-oxoquinazolin-3(4H)-yl)ethoxy)ethoxy)-ethyl)carbamate (100 mg) in 45% yield. MS (ESI) m/z: 629.3 $[M+H]^+$.

To a solution of tert-butyl (2-(2-(2-(2-(1-acryloylazetidin-3-yl)-6-(3-hydroxynaphthalen-1-yl)-4-oxoquinazolin-3 (4H)-yl)ethoxy)ethoxy)ethyl)carbamate (50 mg, 0.086 mmol) in DCM (2 mL) was added TFA (1 mL). After 1 h at room temperature, the mixture was concentrated to give 2-(1-acryloyl-azetidin-3-yl)-3-(2-(2-(2-aminoethoxy) ethoxy)ethyl)-6-(3-hydroxynaphthalen-1-yl)quinazolin-4 (3H)-one as a TFA salt (45 mg, crude). MS (ESI) m/z: 529.2 $[M+H]^+$.

To a solution of 2-(1-acryloylazetidin-3-yl)-3-(2-(2-(2-aminoethoxy)ethoxy)ethyl)-6-(3-hydroxynaphthalen-1-yl)

quinazolin-4(3H)-one (45 mg, 0.1 mmol) in DCM/MeOH (5 mL/0.5 mL) were added DIPEA (26 mg, 0.2 mmol), (S)-4-((5-(2,6-dioxopiperidin-3-yl)-4-oxo-5,6-dihydro-4H-thieno[3,4-c]pyrrol-1-yl)methoxy)benzaldehyde (45 mg, 0.12 mmol), sodium cyanoborohydride (50 mg, 0.8 mmol), and acetic acid (1 drop). After 16 h, the mixture was concentrated and the residue was purified using prep-HPLC to give (S)-3-(1-((4-(((2-(2-(2-(2-(1-acryloylazetidin-3-yl)-6-(3-hydroxynaphthalen-1-yl)-4-oxoquinazolin-3(4H)-yl)ethoxy)ethoxy)ethyl)amino)methyl)phenoxy)-methyl)-4-oxo-4H-thieno[3,4-c]pyrrol-5(6H)-yl)piperidine-2,6-dione 14 (32.8 mg) in 39% yield. $^1$H NMR (400 MHz, DMSO-$d_6$) δ 11.01 (brs, 1H), 9.94 (brs, 1H), 8.12-8.13 (m, 1H), 8.01-7.99 (m, 2H), 7.91-7.78 (m, 2H), 7.58 (t, J=8.8 Hz, 1H), 7.43 (t, J=7.6 Hz, 1H), 7.25-7.18 (m, 3H), 7.13-7.06 (m, 2H), 6.93-6.87 (m, 2H), 6.43-6.33 (m, 1H), 6.16-6.12 (m, 1H), 5.72-5.68 (m, 1H), 5.24-5.22 (m, 2H), 5.00 (dd, J=5.2, 13.2 Hz, 1H), 4.69-4.39 (m, 5H), 4.35-4.11 (m, 6H), 3.86-3.84 (m, 1H), 3.72-3.70 (m, 2H), 3.58-3.53 (m, 2H), 3.50-3.44 (m, 4H), 2.89-2.84 (m, 1H), 2.59-2.54 (m, 1H), 2.46-2.43 (m, 1H), 2.34-2.30 (m, 1H), 1.98-1.95 (m, 1H); MS (ESI) m/z: 897.2 [M+H]$^+$.

Example 5. 4-((2-(2-(2-(2-(2-(4-(4-Acryloylpiperazin-1-yl)-6-chloro-8-fluoroquinazolin-7-yl)-3-fluorophenoxy)ethoxy)ethoxy)ethoxy)ethyl)amino)-2-(2,6-dioxopiperidin-3-yl)isoindoline-1,3-dione 23

To a solution of tert-butyl (2-(2-(2-(2-(2-(4-(4-acryloylpiperazin-1-yl)-6-chloro-8-fluoroquinazolin-7-yl)-3-fluorophenoxy)ethoxy)ethoxy)ethoxy)ethyl)carbamate (155 mg, 0.22 mmol) in DCM (4 mL) was added TFA (1 mL). After 2 h at room temperature, the mixture was concentrated, and the residue was dissolved in DCM/MeOH (8:1, 5 mL) and neutralized to pH 7 using sodium bicarbonate. The mixture was filtered and concentrated. The residue was purified using prep-TLC eluting with DCM/MeOH (10:1) to give 1-(4-(7-(2-(2-(2-(2-(2-aminoethoxy)ethoxy)ethoxy)ethoxy)-6-fluorophenyl)-6-chloro-8-fluoroquinazolin-4-yl)piperazin-1-yl)prop-2-en-1-one (65 mg) in 49% yield. MS (ESI) m/z: 606.2 [M+H]$^+$.

To a solution of 1-(4-(7-(2-(2-(2-(2-(2-aminoethoxy)ethoxy)ethoxy)ethoxy)-6-fluorophenyl)-6-chloro-8-fluoroquinazolin-4-yl)piperazin-1-yl)prop-2-en-1-one (65 mg, 0.1 mmol) and (2-(2,6-dioxopiperidin-3-yl)-4-fluoroisoindoline-1,3-dione) (33 mg, 0.11 mmol) in 1-methyl-2-pyrrolidinone (2 mL) was added DIPEA (39 mg, 0.3 mmol). After purging with $N_2$, the mixture was heated at 150° C. for 2.5 h under microwave. The mixture was diluted with $H_2O$ and extracted with EtOAc. The organic phase was washed with

23

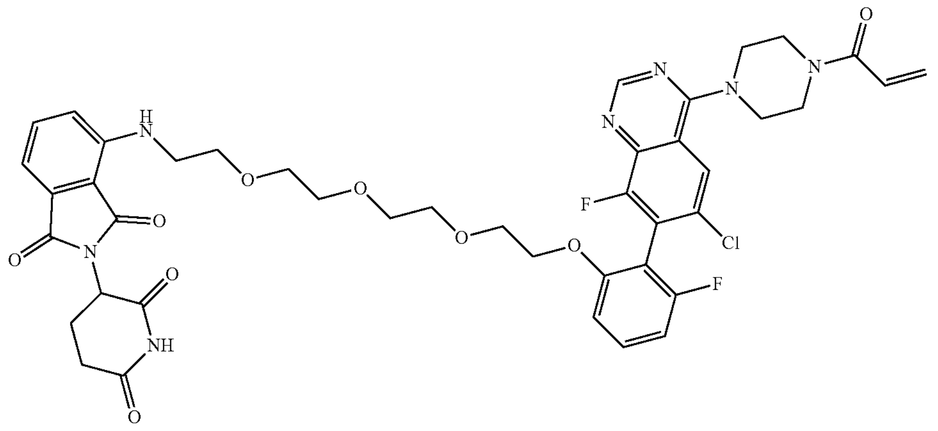

To a solution of 1-(4-(6-chloro-8-fluoro-7-(2-fluoro-6-hydroxyphenyl)quinazolin-4-yl)piperazin-1-yl)prop-2-en-1-one (100 mg, 0.23 mmol) and tert-butyl (2-(2-(2-(2-bromoethoxy)ethoxy)ethoxy)ethyl)carbamate (121 mg, 0.34 mmol) in DMF (4 mL) were added potassium carbonate (64 mg, 0.46 mmol) and potassium iodide (38 mg, 0.23 mmol). After 16 h, the mixture was quenched with water and extracted with EtOAc. The organic phase was washed with brine, dried over anhydrous $Na_2SO_4$, filtered, and concentrated. The residue was purified using prep-TLC (EtOAc) to give tert-butyl (2-(2-(2-(2-(2-(4-(4-acryloylpiperazin-1-yl)-6-chloro-8-fluoroquinazolin-7-yl)-3-fluorophenoxy)ethoxy)ethoxy)ethoxy)ethyl)carbamate (155 mg) in 95% yield. MS (ESI) m/z: 706.3 [M+H]$^+$.

brine, dried over anhydrous $Na_2SO_4$, filtered, and concentrated. The residue was purified using prep-HPLC to give 4-((2-(2-(2-(2-(2-(4-(4-acryloylpiperazin-1-yl)-6-chloro-8-fluoroquinazolin-7-yl)-3-fluorophenoxy)ethoxy)ethoxy)-ethoxy)ethyl)amino)-2-(2,6-dioxopiperidin-3-yl)isoindoline-1,3-dione 23 (6.9 mg) in 8% yield. $^1$H NMR (400 MHz, DMSO-$d_6$) δ 11.08 (s, 1H), 8.68 (s, 1H), 8.03 (s, 1H), 7.57-7.53 (m, 2H), 7.11-7.08 (m, 2H), 7.03-6.99 (m, 2H), 6.84-6.77 (m, 1H), 6.56 (t, J=5.6 Hz, 1H), 6.17 (dd, J=2.8, 16.4 Hz, 1H), 5.73 (dd, J=2.4, 10.4 Hz, 1H), 5.04 (dd, J=5.2, 12.8 Hz, 1H), 4.16-4.11 (m, 2H), 3.91-3.76 (m, 8H), 3.58-3.54 (m, 4H), 3.46-3.42 (m, 6H), 3.29-3.22 (m, 4H), 2.88-2.82 (m, 1H), 2.59-2.53 (m, 2H), 2.03-2.00 (m, 1H); MS (ESI) m/z: 862.1 [M+H]$^+$.

Example 6. 1-(7-(2-(4-(4-Acryloylpiperazin-1-yl)-6-chloro-8-fluoroquinazolin-7-yl)-3-fluorophenoxy)heptyl)-3-((5-(2,6-dioxopiperidin-3-yl)-4-oxo-5,6-dihydro-4H-thieno[3,4-c]pyrrol-1-yl)methyl)urea 27

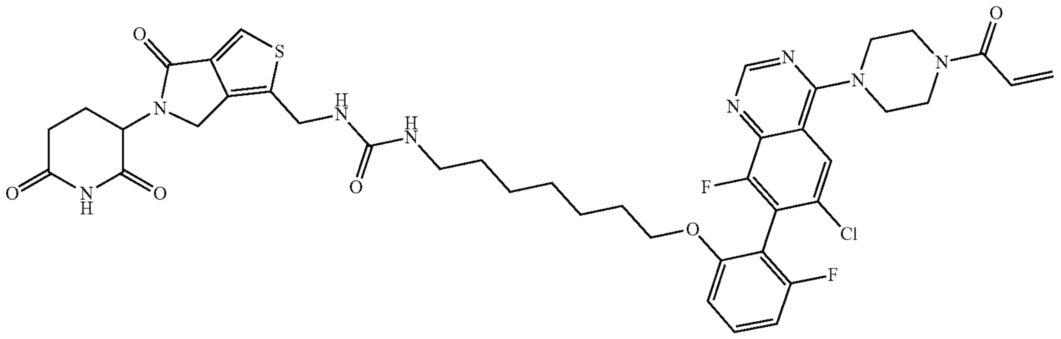

27

To a solution of 7-((tert-butoxycarbonyl)amino)heptanoic acid (490 mg, 2.00 mmol) in THF (10 mL) was dropwise added borane (1M solution in THF) (4 mL) at 0° C. After 2 h at 0° C., sodium hydroxide (1N, 10 mL) was added. After an an additional 1 h, the mixture was extracted with EtOAc. The organic phase was washed with brine, dried over anhydrous $Na_2SO_4$, filtered, and concentrated to give tert-butyl (7-hydroxyheptyl)carbamate (450 mg, crude).

To a solution of triphenylphosphine (768 mg, 2.922 mmol) in DCM (10 mL) were added imidazole (198 mg, 2.922 mmol) and diiodine (742 mg, 2.922 mmol). After 10 min, a solution of tert-butyl (7-hydroxyheptyl)carbamate (450 mg, crude) in DCM (2 mL) was added dropwise. After 1.5 h, the mixture was filtered and the filtrate was washed with sodium thiosulfate (aq.). The organic phase was washed with brine, dried over anhydrous $Na_2SO_4$, filtered, and concentrated. The residue was purified using silica gel eluting with EtOAc in PE from 0 to 20% to give tert-butyl (7-iodoheptyl)carbamate (906 mg) in 91% yield. MS (ESI) m/z: 342.1 $[M+H]^+$.

To a solution of 1-(4-(6-chloro-8-fluoro-7-(2-fluoro-6-hydroxyphenyl)quinazolin-4-yl)piperazin-1-yl)prop-2-en-1-one (100 mg, 0.232 mmol) in DMF (5 mL) were added tert-butyl (7-iodoheptyl)carbamate (95 mg, 0.279 mmol) and potassium carbonate (64 mg, 0.464 mmol). After 16 h, the mixture was filtered and concentrated. The residue was purified using silica gel eluting with EtOAc in PE from 15 to 80% to give tert-butyl (7-(2-(4-(4-acryloylpiperazin-1-yl)-6-chloro-8-fluoroquinazolin-7-yl)-3-fluorophenoxy)heptyl)carbamate (134 mg) in 90% yield. MS (ESI) m/z: 645.2 $[M+H]^+$.

To a solution of tert-butyl (7-(2-(4-(4-acryloylpiperazin-1-yl)-6-chloro-8-fluoroquinazolin-7-yl)-3-fluorophenoxy)heptyl)carbamate (70 mg, 0.108 mmol) in DCM (2 mL) was added TFA (0.5 mL). After 1 h, the solution was concentrated to give 1-(4-(7-(2-((7-aminoheptyl)oxy)-6-fluorophenyl)-6-chloro-8-fluoroquinazolin-4-yl)piperazin-1-yl)prop-2-en-1-one as a TFA salt (65 mg, crude). MS (ESI) m/z: 544.2 $[M+H]^+$.

To a solution of tert-butyl ((5-(2,6-dioxopiperidin-3-yl)-4-oxo-5,6-dihydro-4H-thieno[3,4-c]pyrrol-1-yl)methyl)carbamate (61 mg, 0.162 mmol) in DCM (2 mL) was added TFA (0.5 mL). After 1 h, the mixture was concentrated and the residue was dissolved in THF (5 mL). The solution was cooled to 0° C. and TEA (32.7 mg, 0.324 mmol) was added, followed by addition of 4-nitrophenyl carbonochloridate (32 mg, 0.162 mmol). The mixture was stirred at room temperature for 1 h. To a solution of 1-(4-(7-(2-((7-aminoheptyl)oxy)-6-fluorophenyl)-6-chloro-8-fluoroquinazolin-4-yl)piperazin-1-yl)prop-2-en-1-one in THF (5 mL) were added TEA (33 mg, 0.324 mmol) and the solution of 4-nitrophenyl ((5-(2,6-dioxopiperidin-3-yl)-4-oxo-5,6-dihydro-4H-thieno[3,4-c]pyrrol-1-yl)methyl)carbamate. After 1 h, the mixture was concentrated. The residue was purified using prep-TLC eluting with DCM/MeOH (10:1) and then prep-HPLC to give 1-(7-(2-(4-(4-acryloylpiperazin-1-yl)-6-chloro-8-fluoroquinazolin-7-yl)-3-fluorophenoxy)heptyl)-3-((5-(2,6-dioxopiperidin-3-yl)-4-oxo-5,6-dihydro-4H-thieno[3,4-c]pyrrol-1-yl)methyl)urea 27 (9.7 mg) in 11% yield. $^1H$ NMR (400 MHz, DMSO-$d_6$) δ 10.97 (s, 1H), 8.69 (s, 1H), 8.05 (s, 1H), 7.81 (s, 1H), 7.57-7.51 (m, 1H), 7.07 (d, J=8.4 Hz, 1H), 6.99 (t, J=8.8 Hz, 1H), 6.82 (dd, J=10.8, 16.8 Hz, 1H), 6.41 (t, J=6.4 Hz, 1H), 6.17 (dd, J=2.0, 16.4 Hz, 1H), 5.96 (t, J=5.6 Hz, 1H), 5.73 (dd, J=2.0, 10.0 Hz, 1H), 5.00 (dd, J=5.2, 13.2 Hz, 1H), 4.31 (d, J=6.0 Hz, 2H), 4.28-4.13 (m, 2H), 4.02-4.00 (m, 2H), 3.97-3.77 (m, 8H), 2.91-2.84 (m, 3H), 2.59-2.55 (m, 1H), 2.33-2.22 (m, 1H), 2.00-1.94 (m, 1H), 1.52-1.48 (m, 2H), 1.23-1.16 (m, 2H), 1.10-1.04 (m, 6H); MS (ESI) m/z: 850.8 $[M+H]^+$.

Example 7. 3-(2-(2-(2-(6-Chloro-8-fluoro-4-(4-propionylpiperazin-1-yl)quinazolin-7-yl)-3-fluorophenoxy)ethoxy)ethoxy)-N-(2-((2-(2,6-dioxopiperidin-3-yl)-1-oxoisoindolin-4-yl)amino)ethyl)propanamide 30

30

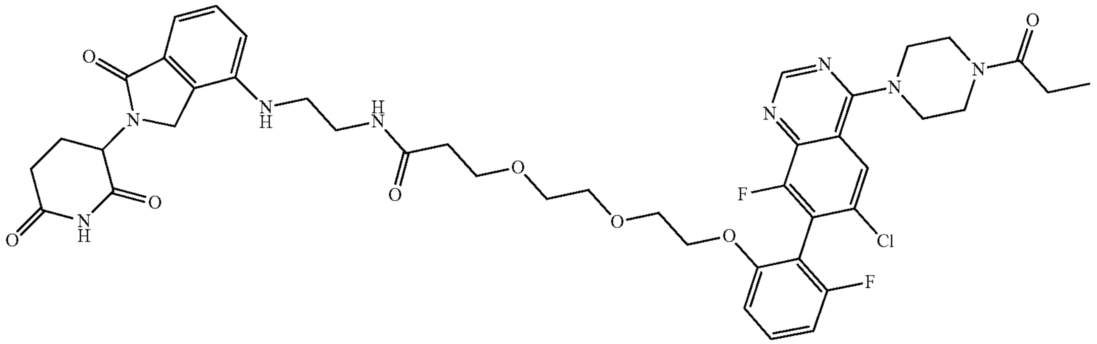

To a solution of 1-(4-(6-chloro-8-fluoro-7-(2-fluoro-6-hydroxyphenyl)quinazolin-4-yl)piperazin-1-yl)propan-1-one (150 mg, 0.34 mmol) in DMA (5 mL) were added $K_2CO_3$ (67 mg, 0.49 mmol) and tert-butyl 3-(2-(2-iodoethoxy)ethoxy)propanoate (167 mg, 0.49 mmol). After 16 h, the mixture was diluted with $H_2O$ and extracted with EtOAc. The organic phase was washed with $H_2O$, dried over anhydrous $Na_2SO_4$, filtered, and concentrated. The residue was purified using silica gel eluting with MeOH in DCM from 3 to 5% to give tert-butyl 3-(2-(2-(2-(6-chloro-8-fluoro-4-(4-propionylpiperazin-1-yl)quinazolin-7-yl)-3-fluorophenoxy)ethoxy)ethoxy)propanoate (192 mg) in 88% yield. MS (ESI) m/z: 649.1 $[M+H]^+$.

To a solution of tert-butyl 3-(2-(2-(2-(6-chloro-8-fluoro-4-(4-propionylpiperazin-1-yl)quinazolin-7-yl)-3-fluorophenoxy)ethoxy)ethoxy)propanoate (193 mg, 0.31 mmol) in DCM (3 mL) was added TFA (1 mL). After 1 h, the solution was concentrated to give 3-(2-(2-(2-(6-chloro-8-fluoro-4-(4-propionylpiperazin-1-yl)quinazolin-7-yl)-3-fluorophenoxy)ethoxy)-ethoxy)propanoic acid (93 mg) in 52% yield. MS (ESI) m/z: 593.1 $[M+H]^+$.

To a solution of 3-(2-(2-(2-(6-chloro-8-fluoro-4-(4-propionylpiperazin-1-yl)quinazolin-7-yl)-3-fluorophenoxy)ethoxy)ethoxy)propanoic acid (93.0 mg, 0.16 mmol) in DMF (4 mL) were added HOBt (31.1 mg, 0.23 mmol), EDCI (44.2 mg, 0.23 mmol), DIPEA (62 mg, 0.48 mmol), and 3-(4-((2-aminoethyl)amino)-1-oxoisoindolin-2-yl)piperidine-2,6-dione (71 mg, 0.23 mmol). After 16 h at room temperature, the mixture was concentrated and the residue was purified using prep-HPLC to give 3-(2-(2-(2-(6-chloro-8-fluoro-4-(4-propionylpiperazin-1-yl)quinazolin-7-yl)-3-fluorophenoxy)ethoxy)ethoxy)-N-(2-((2-(2,6-dioxopiperidin-3-yl)-1-oxoisoindolin-4-yl)amino)ethyl)propanamide 30 (70 mg) in 50% yield. $^1H$ NMR (400 MHz, DMSO-$d_6$) δ 11.00 (s, 1H), 8.68 (s, 1H), 8.04 (s, 1H), 7.97 (t, J=5.2 Hz, 1H), 7.57-7.51 (m, 1H), 7.28 (t, J=7.6 Hz, 1H), 7.08 (d, J=8.8 Hz, 1H), 7.02 (t, J=8.4 Hz, 1H), 6.94 (d, J=7.6 Hz, 1H), 6.80 (d, J=8.0 Hz, 1H), 5.65 (t, J=5.2 Hz, 1H), 5.10 (dd, J=4.8, 13.2 Hz, 1H), 4.23-3.91 (m, 5H), 3.90-3.86 (m, 5H), 3.69-3.51 (m, 6H), 3.25-3.17 (m, 8H), 2.96-2.87 (m, 1H), 2.64-2.59 (m, 1H), 2.40-2.28 (m, 3H), 2.24 (t, J=6.4 Hz, 2H) 2.05-1.99 (m, 1H), 1.02 (t, J=7.2 Hz, 3H); MS (ESI) m/z: 876.9 $[M+H]^+$.

Example 8. 3-(4-(1-(7-(2-(4-(4-Acryloylpiperazin-1-yl)-6-chloro-8-fluoroquinazolin-7-yl)-3-fluorophenoxy)heptyl)piperidin-4-yl)-6-fluoro-1-oxoisoindolin-2-yl)piperidine-2,6-dione 36

36

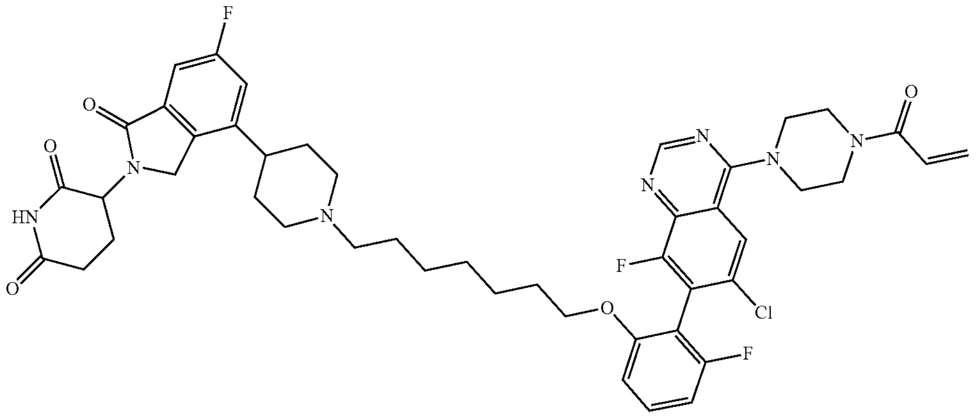

To a solution of 7-bromoheptanoic acid (2.0 g, 9.57 mmol) in DCM (20 mL) were added EDCI (2.74 g, 14.36 mmol), TEA (1.93 g, 19.14 mmol), N,O-dimethylhydroxylamine (1.12 g, 11.48 mmol), and N,N-dimethylpyridin-4-amine (116 mg, 0.957 mmol). After 16 h at room temperature, the mixture was diluted with $H_2O$ and extracted with DCM. The organic phase was dried over anhydrous $Na_2SO_4$, filtered, and concentrated. The residue was purified using silica gel eluting with EtOAc in PE from 10 to 30% to give 7-bromo-N-methoxy-N-methylheptanamide (991 mg) in 87% yield. MS (ESI) m/z: 252.1 [M+1]+, 254.1[M+3]+.

To a solution of 7-bromo-N-methoxy-N-methylheptanamide (366 mg, 1.46 mmol) in ACN (7 mL) was added NaI (262 mg, 1.75 mmol). After 16 h at room temperature, the mixture was diluted with $H_2O$ and extracted with EtOAc. The organic phase was dried over anhydrous $Na_2SO_4$, filtered, and concentrated. The residue was purified using silica gel eluting with EtOAc in PE from 10 to 35% to give 7-iodo-N-methoxy-N-methylheptanamide (316 mg) in 72% yield. MS (ESI) m/z: 300.1 $[M+1]^+$.

To a solution of tert-butyl 4-(6-chloro-8-fluoro-7-(2-fluoro-6-methoxyphenyl) quinazolin-4-yl)piperazine-1-carboxylate (1.10 g, 2.24 mmol) in DCM (20 mL) at −70° C. was added tribromoborane in DCM (7 mL, v/:v: ¼). After 2 h at room temperature, the mixture was cooled to 0° C. and quenched with saturated aqueous $NaHCO_3$. The organic phase was concentrated and the residue was purified using silica gel eluting with MeOH in DCM from 0 to 10% to give 2-(6-chloro-8-fluoro-4-(piperazin-1-yl)quinazolin-7-yl)-3-fluorophenol (801 mg) in 95% yield. MS (ESI) m/z: 377.1 $[M+H]^+$.

To a solution of 2-(6-chloro-8-fluoro-4-(piperazin-1-yl) quinazolin-7-yl)-3-fluorophenol (801 mg, 2.13 mmol) in DCM/MeOH (20 mL/2 mL) at 0° C. were added TEA (645 mg, 6.39 mmol) and $Boc_2O$ (543 mg, 2.56 mmol) in DCM (2 mL). After 1 h at 0° C., the mixture was diluted with $H_2O$ and extracted with DCM. The organic phase was dried over anhydrous $Na_2SO_4$, filtered, and concentrated. The residue was purified using silica gel eluting with MeOH in DCM from 0 to 10% to give tert-butyl 4-(6-chloro-8-fluoro-7-(2-fluoro-6-hydroxyphenyl)-quinazolin-4-yl)piperazine-1-carboxylate (743 mg) in 74% yield. MS (ESI) m/z: 477.1$[M+H]^+$.

To a solution of tert-butyl 4-(6-chloro-8-fluoro-7-(2-fluoro-6-hydroxyphenyl)quinazolin-4-yl)piperazine-1-carboxylate (305 mg, 0.641 mmol) in DMF (10 mL) were added 7-iodo-N-methoxy-N-methylheptanamide (673 mg, 2.24 mmol) and potassium carbonate (177 mg, 1.28 mmol). After 16 h at room temperature, the mixture was diluted with $H_2O$ and extracted with EtOAc. The organic phase was dried over anhydrous $Na_2SO_4$, filtered, and concentrated. The residue was purified using silica gel eluting with EtOAc in PE from 10 to 70% to give tert-butyl 4-(6-chloro-8-fluoro-7-(2-fluoro-6-((7-(methoxy(methyl)amino)-7-oxoheptyl)oxy)phenyl)quinazolin-4-yl)piperazine-1-carboxylate (397 mg) in 96% yield. MS (ESI) m/z: 648.2 $[M+H]^+$.

To a solution of tert-butyl 4-(6-chloro-8-fluoro-7-(2-fluoro-6-((7-(methoxy(methyl)amino)-7-oxoheptyl)oxy)phenyl)quinazolin-4-yl)piperazine-1-carboxylate (166 mg, 0.257 mmol) in THF (5 mL) at −70° C. under $N_2$ was added $LiAlH_4$ (0.5 mL, 1 M in THF) dropwise. After 1 h at −70° C., the mixture was quenched with saturated aqueous $NH_4Cl$ and extracted with EtOAc. The organic phase was dried over anhydrous $Na_2SO_4$, filtered, and concentrated to give tert-butyl 4-(6-chloro-8-fluoro-7-(2-fluoro-6-((7-oxoheptyl)oxy)phenyl)quinazolin-4-yl)piperazine-1-carboxylate (154 mg, crude). MS (ESI) m/z: 589.2 $[M+H]^+$.

To a solution of tert-butyl 4-(6-chloro-8-fluoro-7-(2-fluoro-6-((7-oxoheptyl)oxy)phenyl)-quinazolin-4-yl)piperazine-1-carboxylate (154 mg, 0.257 mmol) in DCM/MeOH (4 mL:1 mL) were added 3-(6-fluoro-1-oxo-4-(piperidin-4-yl)isoindolin-2-yl)piperidine-2,6-dione (143 mg, 0.257 mmol), DIPEA (33 mg, 0.257 mmol), $NaBH_3CN$ (64 mg, 1.02 mmol), and acetic acid (1 drop). After 16 h at room temperature, the mixture was concentrated and the residue was purified using silica gel eluting with MeOH in DCM from 0 to 8% to give tert-butyl 4-(6-chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoroquinazolin-4-yl)piperazine-1-carboxylate (141 mg) in 60% yield. MS (ESI) m/z: 918.4$[M+H]^+$.

To a solution of tert-butyl 4-(6-chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoroquinazolin-4-yl)piperazine-1-carboxylate (70 mg, 0.0763 mmol) in DCM (4 mL) was added TFA (1 mL). After 1 h, the solution was concentrated to give a TFA salt (75 mg, crude), which was dissolved in THF (4 mL) and cooled to 0° C. DIPEA (30 mg, 0.229 mmol) was added, followed by addition of acryloyl chloride (11 mg, 0.115 mmol). After 30 min at room temperature, the mixture was concentrated and the residue was purified using prep-HPLC to give 3-(4-(1-(7-(2-(4-(4-acryloylpiperazin-1-yl)-6-chloro-8-fluoroquinazolin-7-yl)-3-fluorophenoxy)heptyl)piperidin-4-yl)-6-fluoro-1-oxoisoindolin-2-yl)piperidine-2,6-dione 36 (12.1 mg) in 18% yield. $^1H$ NMR (400 MHz, DMSO-$d_6$) δ 11.00 (s, 1H), 8.71 (s, 1H), 8.05 (s, 1H), 7.57-7.51 (m, 1H), 7.39-7.35 (m, 2H), 7.07 (d, J=8.4 Hz, 1H), 7.00 (t, J=8.8 Hz, 1H), 6.82 (dd, J=10.4, 16.4 Hz, 1H), 6.17 (dd, J=2.4, 16.8 Hz, 1H), 5.73 (dd, J=2.4, 10.4 Hz, 1H), 5.13 (dd, J=4.8, 13.2 Hz, 1H), 4.53-4.32 (m, 2H), 4.03 (t, J=5.6 Hz, 2H), 3.93-3.91 (m, 4H), 3.88-3.65 (m, 9H), 2.97-2.87 (m, 2H), 2.63-2.58 (m, 2H), 2.45-2.38 (m, 1H), 2.23-2.17 (m, 1H), 2.03-1.95 (m, 2H), 1.74-1.67 (m, 3H), 1.53-1.50 (m, 2H), 1.31-1.26 (m, 2H), 1.14-1.03 (m, 5H); MS (ESI) m/z: 872.2 $[M+H]^+$.

Example 9. 3-(6-Fluoro-4-(1-(7-(7-(3-hydroxynaphthalen-1-yl)-2-oxo-3-(1-propionylazetidin-3-yl)-3,4-dihydroquinazolin-1(2H)-yl)heptyl)piperidin-4-yl)-1-oxoisoindolin-2-yl)piperidine-2,6-dione 44

44

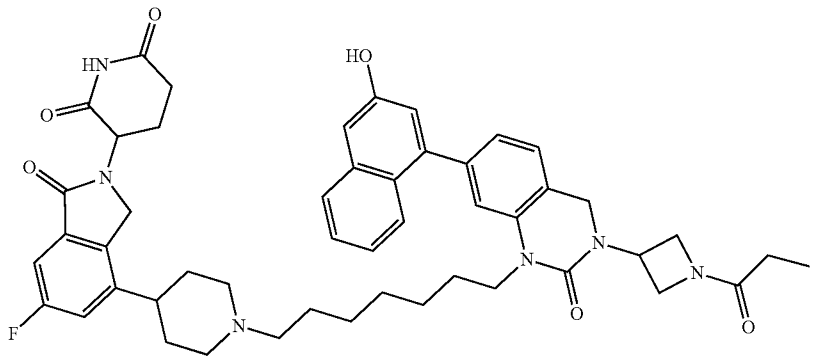

To a solution of 7-bromo-3-(1-propionylazetidin-3-yl)-3,4-dihydroquinazolin-2(1H)-one (400 mg, 1.2 mmol) in DMF (5 mL) were added $K_2CO_3$ (496.8 mg, 3.6 mmol) and 7-bromo-N-methoxy-N-methylheptanamide (376 mg, 1.5 mmol). After 16 h at 75° C., the mixture was diluted with $H_2O$ and extracted with EtOAc. The organic phase was washed with $H_2O$, dried over anhydrous $Na_2SO_4$, filtered, and concentrated. The residue was purified using silica gel eluting with EtOAc in PE from 40 to 60% to give 7-(7-bromo-2-oxo-3-(1-propionylazetidin-3-yl)-3,4-dihydroquinazolin-1(2H)-yl)-N-methoxy-N-methylheptanamide (164 mg) in 27% yield. MS (ESI) m/z: 509.2 $[M+H]^+$.

To a solution of 7-(7-bromo-2-oxo-3-(1-propionylazetidin-3-yl)-3,4-dihydroquinazolin-1(2H)-yl)-N-methoxy-N-methylheptanamide (164 mg, 0.32 mmol) in 1,4-dioxane/$H_2O$ (6 mL:1 mL) were added $Pd(PPh_3)_4$(104 mg, 0.38 mmol), $Na_2CO_3$ (101 mg, 0.96 mmol), and 4,4,5,5-tetramethyl-2-(3-methylnaphthalen-1-yl)-1,3,2-dioxaborolane (104 mg, 0.38 mmol). After 16 h at 90° C., the mixture was concentrated and the residue was purified using silica gel eluting with EtOAc in PE from 40 to 60% to give 7-(7-(3-hydroxynaphthalen-1-yl)-2-oxo-3-(1-propionylazetidin-3-yl)-3,4-dihydroquinazolin-1(2H)-yl)-N-methoxy-N-methylheptanamide (145 mg) in 79% yield. MS (ESI) m/z: 573.3 $[M+H]^+$.

To a solution of 7-(7-(3-hydroxynaphthalen-1-yl)-2-oxo-3-(1-propionylazetidin-3-yl)-3,4-dihydroquinazolin-1(2H)-yl)-N-methoxy-N-methylheptanamide (60 mg, 0.1 mmol) in THF (5 mL) was added lithium aluminum hydride (0.15 mL, 0.15 mmol, 1 M in THF) at −70° C. under $N_2$. After 30 min at −70° C., the mixture was quenched with saturated aqueous $NH_4Cl$ and extracted with EtOAc. The organic phase was dried over anhydrous $Na_2SO_4$, filtered, and concentrated to give 7-(7-(3-hydroxynaphthalen-1-yl)-2-oxo-3-(1-propionylazetidin-3-yl)-3,4-dihydroquinazolin-1(2H)-yl) heptanal (50 mg) in 97% yield. MS (ESI) m/z: 514.3 $[M+H]^+$.

To a solution of 3-(6-fluoro-1-oxo-4-(piperidin-4-yl) isoindolin-2-yl)piperidine-2,6-dione (34.5 mg, 0.1 mmol) in DCM/MeOH (2.5 mL:0.5 mL) were added DIPEA (12.9 mg, 0.1 mmol), 7-(7-(3-hydroxynaphthalen-1-yl)-2-oxo-3-(1-propionylazetidin-3-yl)-3,4-dihydroquinazolin-1(2H)-yl) heptanal (50 mg, 0.1 mmol), $NaBH_3CN$ (23.6 mg, 0.1 mmol), and acetic acid (1 drop). After 16 h at room temperature, the mixture was concentrated and the residue was purified using prep-HPLC to give 3-(6-fluoro-4-(1-(7-(7-(3-hydroxynaphthalen-1-yl)-2-oxo-3-(1-propionylazetidin-3-yl)-3,4-dihydroquinazolin-1(2H)-yl)heptyl)piperidin-4-yl)-1-oxoisoindolin-2-yl)piperidine-2,6-dione 44 (10.1 mg) in 12% yield. $^1$H NMR (400 MHz, DMSO-$d_6$) δ 11.04 (s, 1H), 9.89 (s, 1H), 7.77 (d, J=8.4 Hz, 1H), 7.67 (d, J=8.4 Hz, 1H), 7.44-7.40 (m, 3H), 7.31-7.18 (m, 3H), 7.08 (d, J=8.0 Hz, 1H), 7.03 (d, J=2.4 Hz, 1H), 7.00 (s, 1H), 5.17 (dd, J=5.2, 13.2 Hz, 1H), 4.93-4.86 (m, 1H), 4.56-4.49 (m, 3H), 4.39-4.29 (m, 3H), 4.06-4.04 (m, 2H), 3.84-3.81 (m, 2H), 3.57-3.49 (m, 1H), 2.99-2.89 (m, 4H), 2.65-2.61 (m, 1H), 2.37-2.33 (m, 1H), 2.13-1.97 (m, 8H), 1.61-1.59 (m, 4H), 1.35-1.23 (m, 8H), 0.98 (t, J=7.6 Hz, 3H); MS (ESI) m/z: 843.3 $[M+H]^+$.

Example 10. 4-((2-(2-(2-(2-((4-((R)-4-Acryloyl-3-methylpiperazin-1-yl)-7-(naphthalen-1-yl)-5,6,7,8-tetrahydropyrido[3,4-d]pyrimidin-2-yl)oxy)ethoxy)ethoxy)ethoxy)ethyl)amino)-2-(2,6-dioxopiperidin-3-yl)isoindoline-1,3-dione 47

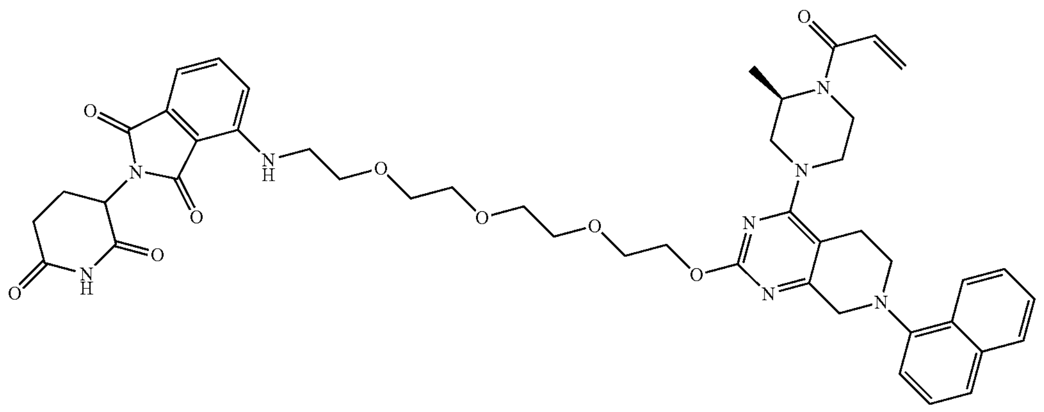

47

To a solution of 1-tert-butyl 4-ethyl 3-oxopiperidine-1,4-dicarboxylate (10 g, 37 mmol) in MeOH (200 mL) under $N_2$ were added NaOMe (10 g, 185 mmol) and methyl 2-methylisothiourea sulphate (9.3 g, 33 mmol). After 16 h at room temperature, the mixture was quenched with water, adjusted to pH 5 with 2N HCl, and concentrated. The residue was suspended in EtOAc (60 mL) and water (60 mL), The mixture was stirred vigorously, filtered, and dried to give tert-butyl 4-hydroxy-2-(methylthio)-5,6-dihydropyrido[3,4-d]pyrimidine-7(8H)-carboxylate (8.7 g) in 80% yield. MS (ESI) m/z: 242 [M-$^t$Bu+H]$^+$.

To a solution of tert-butyl 4-hydroxy-2-(methylthio)-5,6-dihydropyrido[3,4-d]pyrimidine-7(8H)-carboxylate (8.94 g, 30 mmol) in DCM (100 mL) under $N_2$ at 0° C. were added DIPEA (14.5 mL) and trifluoromethanesulfonic anhydride (12.69 g, 45 mmol). After 16 h at room temperature, the mixture was concentrated. The residue was purified using silica gel eluting with PE/EtOAc (10:1) to give tert-butyl 2-(methylthio)-4-(((trifluoromethyl)sulfonyl)oxy)-5,6-dihydropyrido[3,4-d]pyrimidine-7(8H)-carboxylate (2.85 g) in 22% yield. MS (ESI) m/z: 374.0 [M-$^t$Bu+H]$^+$.

To a solution of tert-butyl 2-(methylthio)-4-(((trifluoromethyl)sulfonyl)oxy)-5,6-dihydropyrido[3,4-d]pyrimidine-7(8H)-carboxylate (2.65 g, 6.18 mmol) in DMF (20 mL) under $N_2$ were added (R)-benzyl 2-methylpiperazine-1-carboxylate (1.59 g, 6.80 mmol) and DIPEA (2 mL).

After 1 h at 100° C., the mixture was concentrated and the residue was purified using silica gel eluting with PE/EtOAc (10:1) to afford (R)-tert-butyl 4-(4-((benzyloxy)carbonyl)-3-methylpiperazin-1-yl)-2-(methylthio)-5,6-dihydropyrido[3,4-d]pyrimidine-7(8H)-carboxylate (3.09 g) in 97% yield. MS (ESI) m/z: 514.3 [M+H]$^+$.

To a solution of (R)-tert-butyl 4-(4-((benzyloxy)carbonyl)-3-methylpiperazin-1-yl)-2-(methylthio)-5,6-dihydropyrido[3,4-d]pyrimidine-7(8H)-carboxylate (3.09 g, 6.0 mmol) in DCM (6 mL) was added TFA (6 mL). After 2 h, the mixture was concentrated and the residue was dissolved in 20 mL of EtOAc and 20 mL of water. The mixture was adjusted to pH 8 with $Na_2CO_3$. The organic phase was washed with water and brine, dried over anhydrous $Na_2SO_4$, filtered, and concentrated to give (R)-benzyl 2-methyl-4-(2-(methylthio)-5,6,7,8-tetrahydropyrido[3,4-d]pyrimidin-4-yl)piperazine-1-carboxylate as a TFA salt (3.02 g) in a quantitative yield. MS (ESI) m/z: 414.2 [M+H]$^+$.

A mixture of (R)-benzyl 2-methyl-4-(2-(methylthio)-5,6,7,8-tetrahydropyrido[3,4-d]pyrimidin-4-yl)piperazine-1-carboxylate (2.29 g, 5.55 mmol), 1-bromonaphthalene (1.43 g, 6.92 mmol), $Pd_2dba_3$ (552 mg, 0.56 mmol), BINAP (713 mg, 1.1 mmol), and NaOtBu (1.66 g, 17.3 mmol) in toluene (25 mL) was stirred under $N_2$ for 16 h at 100° C. The mixture was then concentrated and the residue was purified using silica gel eluting with PE/EtOAc from 5:1 to 3:1 to afford (R)-benzyl 2-methyl-4-(2-(methylthio)-7-(naphthalen-1-yl)-5,6,7,8-tetrahydropyrido[3,4-d]pyrimidin-4-yl)piperazine-1-carboxylate (2.34 g) in 78% yield. MS (ESI) m/z: 540.2 [M+H]$^+$.

To a solution of (R)-benzyl 2-methyl-4-(2-(methylthio)-7-(naphthalen-1-yl)-5,6,7,8-tetrahydropyrido[3,4-d]pyrimidin-4-yl)piperazine-1-carboxylate (2.34 g, 9.90 mmol) in DCM (50 mL) was added mCPBA (2.02 g, 9.90 mmol) in portions at 0° C. After 1 h at 0° C., the mixture was concentrated and the residue was purified using silica gel eluting with PE/EtOAc (5:1) to afford (2R)-benzyl 2-methyl-4-(2-(methylsulfinyl)-7-(naphthalen-1-yl)-5,6,7,8-tetrahydropyrido[3,4-d]pyrimidin-4-yl)piperazine-1-carboxylate (1.99 g) in 83% yield. MS (ESI) m/z: 556.2 [M+H]$^+$.

To a solution of (2R)-benzyl 2-methyl-4-(2-(methylsulfinyl)-7-(naphthalen-1-yl)-5,6,7,8-tetrahydropyrido[3,4-d]pyrimidin-4-yl)piperazine-1-carboxylate (1.81 g, 3.26 mmol) in THF (30 mL) were added NaOtBu (939 mg, 9.78 mmol) and tert-butyl (2-(2-(2-(2-hydroxyethoxy)ethoxy)-ethoxy)ethyl)carbamate (1.433 g, 4.89 mmol). After 3 h, the mixture was filtered and concentrated. The residue was purified using silica gel eluting with PE/EtOAc (5:1) to give (R)-benzyl 4-(2-((2,2-dimethyl-4-oxo-3,8,11,14-tetraoxa-5-azahexadecan-16-yl)oxy)-7-(naphthalen-1-yl)-5,6,7,8-tetrahydropyrido[3,4-d]pyrimidin-4-yl)-2-methylpiperazine-1-carboxylate (1.81 g) in 71% yield. MS (ESI) m/z: 785.4 [M+H]$^+$.

To a solution of (R)-benzyl 4-(2-((2,2-dimethyl-4-oxo-3,8,11,14-tetraoxa-5-azahexadecan-16-yl)oxy)-7-(naphthalen-1-yl)-5,6,7,8-tetrahydropyrido[3,4-d]pyrimidin-4-yl)-2-methylpiperazine-1-carboxylate (1.81 g) in DCM (4 mL) was added TFA (2 mL). After 2 h, the solution was concentrated to give (R)-benzyl 4-(2-(2-(2-(2-(2-aminoethoxy)ethoxy)ethoxy)ethoxy)-7-(naphthalen-1-yl)-5,6,7,8-tetrahydropyrido[3,4-d]pyrimidin-4-yl)-2-methylpiperazine-1-carboxylate as a TFA salt (1.49 g) in 94% yield. MS (ESI) m/z: 685.4 [M+H]$^+$.

A mixture of (R)-benzyl 4-(2-(2-(2-(2-(2-aminoethoxy)ethoxy)ethoxy)ethoxy)-7-(naphthalen-1-yl)-5,6,7,8-tetrahydropyrido[3,4-d]pyrimidin-4-yl)-2-methylpiperazine-1-carboxylate (604 mg, 1 mmol), 2-(2,6-dioxopiperidin-3-yl)-4-fluoroisoindoline-1,3-dione (276 mg, 1.0 mmol), and DIPEA (151 mg, 1.2 mmol) in NMP (2 mL) was heated at 180° C. under microwave for 2.5 h. The mixture was cooled to room temperature and EtOAc was then added. The mixture was washed with aqueous LiCl (1M) and brine in sequence, dried over anhydrous $Na_2SO_4$, filtered, and concentrated. The residue was purified using silica gel eluting with PE/EtOAc from 3:1 to 1:1 to afford (2R)-benzyl 4-(2-(2-(2-(2-(2-((2-(2,6-dioxopiperidin-3-yl)-1,3-dioxoisoindolin-4-yl)amino)ethoxy)ethoxy)ethoxy)ethoxy)-7-(naphthalen-1-yl)-5,6,7,8-tetrahydropyrido[3,4-d]pyrimidin-4-yl)-2-methylpiperazine-1-carboxylate (238 mg) in 87% yield. MS (ESI) m/z: 941.2 $[M+H]^+$.

A mixture of (2R)-benzyl 4-(2-(2-(2-(2-(2-((2-(2,6-dioxopiperidin-3-yl)-1,3-dioxoisoindolin-4-yl)amino)ethoxy)ethoxy)ethoxy)ethoxy)-7-(naphthalen-1-yl)-5,6,7,8-tetrahydropyrido[3,4-d]pyrimidin-4-yl)-2-methylpiperazine-1-carboxylate (238 mg, 0.25 mmol) and TFA (2 mL) was heated for 3 h at 80° C. The mixture was concentrated to afford 2-(2,6-dioxopiperidin-3-yl)-4-((2-(2-(2-(2-((4-((R)-3-methylpiperazin-1-yl)-7-(naphthalen-1-yl)-5,6,7,8-tetrahydropyrido[3,4-d]pyrimidin-2-yl)oxy)ethoxy)ethoxy)ethoxy)ethyl)amino)isoindoline-1,3-dione as a TFA salt (159 mg) in 78% yield. MS (ESI) m/z: 404.3 $[½M+H]^+$.

To a solution of 2-(2,6-dioxopiperidin-3-yl)-4-((2-(2-(2-(2-((4-((R)-3-methylpiperazin-1-yl)-7-(naphthalen-1-yl)-5,6,7,8-tetrahydropyrido[3,4-d]pyrimidin-2-yl)oxy)ethoxy)ethoxy)ethoxy)-ethyl)amino)isoindoline-1,3-dione (201 mg, 0.25 mmol) and DIPEA (95 mg, 0.75 mmol) in DCM (2 mL) at 0° C. was added acryloyl chloride (34 mg, 0.37 mmol). After 3 h at room temperature, the mixture was quenched with water (1 mL) and extracted with DCM. The organic phase was washed with brine, dried over anhydrous $Na_2SO_4$, filtered, and concentrated. The residue was purified using prep-HPLC to afford 4-((2-(2-(2-(2-((4-((R)-4-acryloyl-3-methylpiperazin-1-yl)-7-(naphthalen-1-yl)-5,6,7,8-tetrahydropyrido[3,4-d]pyrimidin-2-yl)oxy)ethoxy)ethoxy)ethoxy)ethyl)amino)-2-(2,6-dioxopiperidin-3-yl)isoindoline-1,3-dione 47 (142 mg) in 66% yield. $^1H$ NMR (400 MHz, DMSO-$d_6$) δ11.08 (s, 1H), 8.20-8.18 (m, 1H), 7.93-7.91 (m, 1H), 7.64 (d, J=8.0 Hz, 1H), 7.57-7.53 (m, 3H), 7.45 (t, J=8.0 Hz, 1H), 7.21-7.19 (m, 1H), 7.12 (d, J=8.4 Hz, 1H), 7.01 (d, J=7.2 Hz, 1H), 6.80 (dd, J=10.4, 16.4 Hz, 1H), 6.59 (t, J=6.0 Hz, 1H), 6.14 (d, J=17.2 Hz, 1H), 5.71 (dd, J=1.6 Hz, 10.0 Hz, 1H), 5.04 (dd, J=5.2 Hz, 12.8 Hz, 1H), 4.33 (t, J=4.4 Hz, 2H), 4.11 (s, 2H), 4.09-4.05 (m, 1H), 3.94 (d, J=12.0 Hz, 1H), 3.71 (t, J=5.2 Hz, 2H), 3.62 (t, J=5.6 Hz, 2H), 3.55-3.48 (m, 9H), 3.47-3.43 (m, 2H), 3.25-3.19 (m, 4H), 3.06-2.97 (m, 2H), 2.91-2.83 (m, 2H), 2.59-2.53 (m, 2H), 2.02-1.97 (m, 2H), 1.29-1.23 (m, 3H); MS (ESI) m/z: 861.3 $[M+H]^+$.

Example 11. (2S,4R)-1-((2S)-2-(7-(2-(4-(4-Acryloylpiperazin-1-yl)-6-chloro-8-fluoroquinazolin-7-yl)-3-fluorophenoxy)heptanamido)-3,3-dimethylbutanoyl)-4-hydroxy-N-(4-(4-methylthiazol-5-yl)benzyl)pyrrolidine-2-carboxamide 50

50

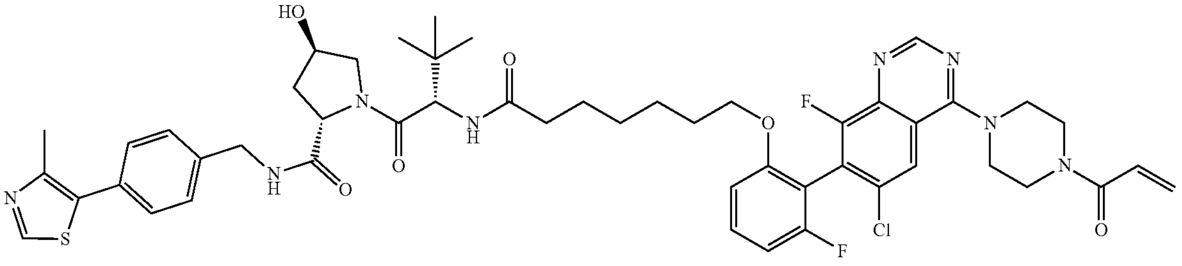

To a solution of 7-bromoheptanoic acid (5.0 g, 0.024 mol) in t-BuOH (50 mL) at 0° C. were added $Boc_2O$ (10.47 g, 0.048 mol) and DMAP (1.48 g, 0.012 mol). After 30 min at 0° C. and 16 h at room temperature, the mixture was concentrated. The residue was purified using silica gel eluting with EtOAc in PE from 0 to 10% to give tert-butyl 7-bromoheptanoate (2.6 g) in 41% yield. $^1$HNMR (400 MHz, $CDCl_3$) δ 3.40 (t, J=6.8 Hz, 2H), 2.21 (t, J=7.2 Hz, 2H), 1.89-1.83 (m, 2H), 1.61-1.55 (m, 3H), 1.47 (s, 1H), 1.44 (s, 9H), 1.37-1.31 (m, 2H).

To a solution of tert-butyl 7-bromoheptanoate (1.93 g, 7.26 mmol) in ACN (20 mL) was added NaI (2.18 g, 14.5 mmol). After 16 h, the mixture was diluted with $H_2O$ and extracted with EtOAc. The organic phase was dried over anhydrous $Na_2SO_4$, filtered, and concentrated to give tert-butyl 7-iodoheptanoate (2 g) in 88% yield. $^1$HNMR (400 MHz, $CDCl_3$) δ 3.18 (t, J=7.2 Hz, 2H), 2.21 (t, J=7.6 Hz, 2H), 1.86-1.80 (m, 2H), 1.61-1.49 (m, 4H), 1.44 (s, 9H), 1.37-1.31 (m, 2H).

To a solution of 1-(4-(6-chloro-8-fluoro-7-(2-fluoro-6-hydroxyphenyl)quinazolin-4-yl)piperazin-1-yl)prop-2-en-1-one (50 mg, 0.12 mmol) in DMF (2 mL) were added tert-butyl 7-iodoheptanoate (113 mg, 0.36 mmol) and potassium carbonate (33 mg, 0.24 mmol). After 16 h at room temperature, the mixture was diluted with $H_2O$ and extracted with EtOAc. The organic phase was dried over anhydrous $Na_2SO_4$, filtered, and concentrated. The residue was purified using prep-TLC eluting with PE/EtOAc (1:10) to give tert-butyl 7-(2-(4-(4-acryloylpiperazin-1-yl)-6-chloro-8-fluoroquinazolin-7-yl)-3-fluorophenoxy)heptanoate (64 mg) in 86% yield. MS (ESI) m/z: 615.3 $[M+H]^+$.

To a solution of tert-butyl 7-(2-(4-(4-acryloylpiperazin-1-yl)-6-chloro-8-fluoroquinazolin-7-yl)-3-fluorophenoxy)heptanoate (64 mg, 0.104 mmol) in DCM (1 mL) was added TFA (1 mL). After 16 h at room temperature, the solution was concentrated to give 7-(2-(4-(4-acryloylpiperazin-1-yl)-6-chloro-8-fluoroquinazolin-7-yl)-3-fluorophenoxy)heptanoic acid (60 mg, crude). MS (ESI) m/z: 559.2 $[M+H]^+$.

To a solution of 7-(2-(4-(4-acryloylpiperazin-1-yl)-6-chloro-8-fluoroquinazolin-7-yl)-3-fluorophenoxy)heptanoic acid (60 mg, crude) in DMF (3 mL) were added (2S,4R)-

1-((S)-2-amino-3,3-dimethylbutanoyl)-4-hydroxy-N-(4-(4-methylthiazol-5-yl)benzyl)pyrrolidine-2-carboxamide, DIPEA (40 mg, 0.312 mmol), 1-hydroxybenzotriazole (28 mg, 0.208 mmol), and 1-(3-dimethylaminopropyl)-3-ethyl-carbodiimide hydrochloride (40 mg, 0.208 mmol). After 16 h, the mixture was concentrated and the residue was purified using prep-HPLC to give (2S,4R)-1-((2S)-2-(7-(2-(4-(4-acryloylpiperazin-1-yl)-6-chloro-8-fluoroquinazolin-7-yl)-3-fluorophenoxy)-heptanamido)-3,3-dimethylbutanoyl)-4-hydroxy-N-(4-(4-methylthiazol-5-yl)benzyl)pyrrolidine-2-carboxamide 50 (20.7 mg) in 20% yield. $^1$H NMR (400 MHz, DMSO-$d_6$) δ 8.97 (d, J=1.6 Hz, 1H), 8.71 (d, J=11.2 Hz, 1H), 8.57-8.53 (m, 1H), 8.05 (s, 1H), 7.79 (dd, J=9.6, 17.2 Hz, 1H), 7.57-7.51 (m, 1H), 7.43-7.37 (m, 4H), 7.07 (d, J=8.4 Hz, 1H), 6.99 (t, J=8.8 Hz, 1H), 6.83 (dd, J=10.4, 16.4 Hz, 1H), 6.19 (dd, J=2.0, 16.4 Hz, 1H), 5.74 (dd, J=2.4, 10.4 Hz, 1H), 5.12 (s, 1H), 4.53 (dd, J=4.4, 9.6 Hz, 1H), 4.45-4.41 (m, 2H), 4.35 (s, 1H), 4.22 (dd, J=5.6, 16.0 Hz, 1H), 4.03-4.00 (m, 2H), 3.91-3.65 (m, 10H), 2.44 (d, J=3.6 Hz, 3H), 2.18-2.14 (m, 1H), 2.05-1.99 (m, 2H), 1.94-1.89 (m, 1H), 1.52-1.48 (m, 2H), 1.38-1.33 (m, 2H), 1.14-1.10 (m, 4H), 0.92 (s, 9H); MS (ESI) m/z: 971.3 [M+H]$^+$.

Example 12. (3S)-3-(4-((4-(((3-(2-(4-(4-Acryloylpiperazin-1-yl)-6-chloro-8-fluoroquinazolin-7-yl)-3-fluorophenoxy)propyl)amino)methyl)benzyl)oxy)-1-oxoisoindolin-2-yl)piperidine-2,6-dione 62

$K_2CO_3$ (96 mg, 0.696 mmol) and tert-butyl (3-iodopropyl) carbamate (132 mg 0.464 mmol). After 16 h at room temperature, the mixture was concentrated and the residue was purified using silica gel eluting with EtOAc in PE from 0 to 75% to give tert-butyl (3-(2-(4-(4-acryloylpiperazin-1-yl)-6-chloro-8-fluoroquinazolin-7-yl)-3-fluorophenoxy)propyl)carbamate (113 mg) in 83% yield. MS (ESI) m/z: 588.0 [M+1]$^+$.

To a solution of tert-butyl (3-(2-(4-(4-acryloylpiperazin-1-yl)-6-chloro-8-fluoroquinazolin-7-yl)-3-fluorophenoxy) propyl)carbamate (75 mg, 0.128 mmol) in DCM (3 mL) was added HCl-EtOAc (0.5 mL). After 30 min at room temperature, the solution was concentrated to give 1-(4-(7-(2-(3-aminopropoxy)-6-fluorophenyl)-6-chloro-8-fluoroquinazolin-4-yl)piperazin-1-yl)prop-2-en-1-one as a HCl salt (65 mg, crude). MS (ESI) m/z: 488.2 [M+1]$^+$.

To a solution of 1-(4-(7-(2-(3-aminopropoxy)-6-fluorophenyl)-6-chloro-8-fluoroquinazolin-4-yl)piperazin-1-yl) prop-2-en-1-one (65 mg, 0.128 mmol, crude) in DCM/MeOH (5 mL:1 mL) were added DIPEA (16 mg, 0.128 mmol), (S)-4-(((2-(2,6-dioxopiperidin-3-yl)-1-oxoisoindolin-4-yl)oxy)methyl)benzaldehyde (48 mg, 0.128 mmol), $NaBH_3CN$ (33 mg, 0.512 mmol), and acetic acid (a drop). After 16 h at room temperature, the mixture was concen-

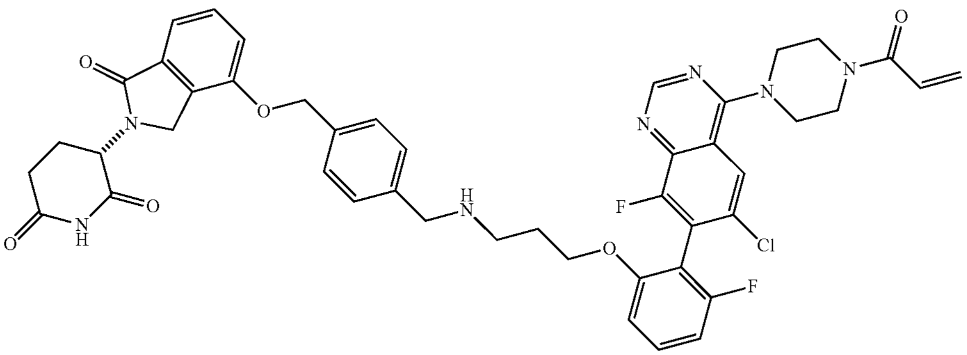

62

To a solution of imidazole (583 mg, 8.571 mmol) in DCM (25 mL) were added triphenylphosphine (2.245 g, 8.571 mmol) and 12(2.177 g, 8.571 mmol) at 0° C. After 10 min at room temperature, tert-butyl (3-hydroxypropyl)carbamate (1.0 g, 5.714 mmol) was added. After 16 h, the mixture was quenched with saturated aqueous $Na_2S203$ and extracted with EtOAc. The organic phase was concentrated and the residue was purified using silica gel eluting with EtOAc in PE from 0 to 40% to give tert-butyl (3-iodopropyl)carbamate (1.406 g) in 86% yield. MS (ESI) m/z: 285.1 [M+1]$^+$.

To a solution of 1-(4-(6-chloro-8-fluoro-7-(2-fluoro-6-hydroxyphenyl)quinazolin-4-yl) piperazin-1-yl)prop-2-en-1-one (100 mg, 0.232 mmol) in DMF (10 mL) were added trated and the residue was purified using prep-HPLC to give (3S)-3-(4-((4-(((3-(2-(4-(4-acryloylpiperazin-1-yl)-6-chloro-8-fluoroquinazolin-7-yl)-3-fluorophenoxy)propyl)amino)-methyl)benzyl)oxy)-1-oxoisoindolin-2-yl)piperidine-2,6-dione 62 (15.6 mg) in 14% yield. $^1$H NMR (400 MHz, DMSO-$d_6$) δ 10.96 (s, 1H), 8.76-8.61 (m, 3H), 8.06 (s, 1H), 7.58-7.41 (m, 5H), 7.33-7.24 (m, 2H), 7.09-7.03 (m, 3H), 6.80 (dd, J=10.4, 16.8 Hz, 1H), 6.17 (dd, J=2.4, 16.8 Hz, 1H), 5.74 (dd, J=2.0, 10.4 Hz, 1H), 5.29 (s, 2H), 5.11 (dd, J=5.2, 13.2 Hz, 1H), 4.45-4.25 (m, 2H), 4.16-4.14 (m, 2H), 4.04 (t, J=4.0 Hz, 2H), 3.96-3.91 (m, 4H), 3.81-3.76 (m, 4H), 2.92-2.85 (m, 3H), 2.60-2.56 (m, 1H), 2.44-2.41 (m, 1H), 2.01-1.91 (m, 3H); MS (ESI) m/z: 850.3 [M+1]$^+$.

Example 13. 3-(4-(1-(7-(2-((2R,4aR)-3-Acryloyl-11-chloro-9-fluoro-2,6-dimethyl-5-oxo-2,3,4,4a,5,6-hexahydro-1H-pyrazino[1',2':4,5]pyrazino[2,3-c]quinolin-10-yl)-3-fluorophenoxy)heptyl)piperidin-4-yl)-6-fluoro-1-oxoisoindolin-2-yl)piperidine-2,6-dione 64

64

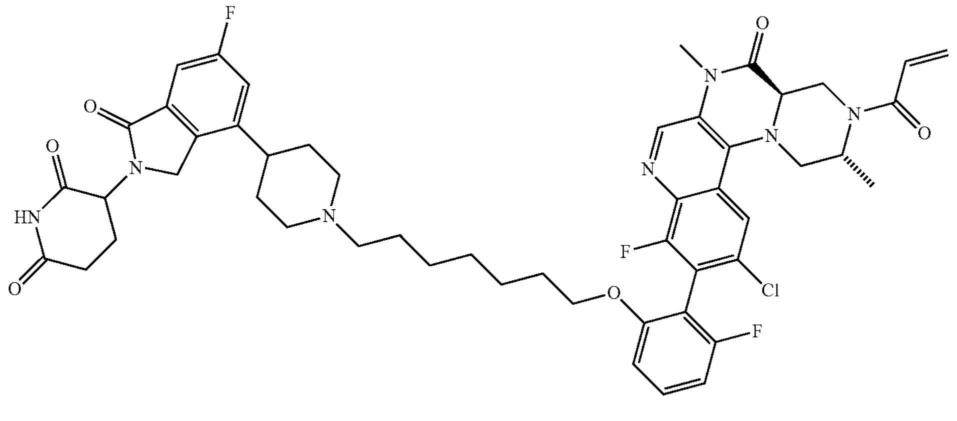

To a solution of 3-bromo-2-fluoroaniline (25 g, 132 mmol) in DMF (130 mL) was added N-chlorosuccinimide (18.5 g, 138.0 mmol). After 16 h, the mixture was poured into ice-water and extracted with EtOAc. The organic phase was washed with $H_2O$, dried over anhydrous $Na_2SO_4$, filtered, and concentrated. The residue was purified using silica gel eluting with EtOAc in PE from 0 to 5% to give 3-bromo-4-chloro-2-fluoroaniline (13.8 g) in 47% yield. MS (ESI) m/z: 225.9 $[M+H]^+$.

A solution of 2,2-dimethyl-1,3-dioxane-4,6-dione (11.5 g, 80.0 mmol) in trimethoxymethane (40 mL) was heated to 100° C. under $N_2$ for 10 min and then for 90 min at 85° C. 3-Bromo-4-chloro-2-fluoroaniline (13.79 g, 72.6 mmol) was added. After 1 h at 85° C., the mixture was filtered to give 5-(((3-bromo-4-chloro-2-fluorophenyl)amino)methylene)-2,2-dimethyl-1,3-dioxane-4,6-dione (18.53 g) in 67% yield. MS (ESI) m/z: 379.9 $[M+H]^+$.

A solution of 5-(((3-bromo-4-chloro-2-fluorophenyl)amino)methylene)-2,2-dimethyl-1,3-dioxane-4,6-dione (11 g, 29 mmol) in phenyl ether (130 mL) was heated at 210° C. for 2 h, and then the mixture was filtered. The residue was washed with PE to give 7-bromo-6-chloro-8-fluoroquinolin-4(1H)-one (5.378 g) in 67% yield. MS (ESI) m/z: 277.9 $[M+H]^+$.

To a solution of 7-bromo-6-chloro-8-fluoroquinolin-4(1H)-one (5.378 g, 19.6 mmol) in acetic acid (55 mL) was added nitric acid (2.46 g, 39.1 mmol). After 2 h at 125° C., the mixture was poured into ice-water. The solid was collected by filtration and washed with methyl tert-butyl ether to give 7-bromo-6-chloro-8-fluoro-3-nitroquinolin-4(1H)-one (3.42 g) in 55% yield. MS (ESI) m/z: 322.9$[M+H]^+$.

To a solution of 7-bromo-6-chloro-8-fluoro-3-nitroquinolin-4(1H)-one (3.42 g, 10.69 mmol) in thionyl chloride (45 mL) was added DMF (78 mg, 1.069 mmol). After 2 h at 80° C., the solution was concentrated to give 7-bromo-4, 6-dichloro-8-fluoro-3-nitroquinoline (3.9 g, crude). MS (ESI) m/z: 340.9 $[M+H]^+$.

To a solution of 7-bromo-4,6-dichloro-8-fluoro-3-nitroquinoline (3.90 g, 11.54 mmol) in THF (50 mL) was added (3R,6R)-1-tert-butyl 3-methyl 6-methylpiperazine-1,3-dicarboxylate (3.27 g, 12.7 mmol). After 3 h at 60° C., the mixture was diluted with $H_2O$ and extracted with EtOAc. The organic phase was dried over anhydrous $Na_2SO_4$, filtered, and concentrated. The residue was purified using silica gel eluting with DCM/MeOH (20:1) to give (3R,6R)-1-tert-butyl 3-methyl 4-(7-bromo-6-chloro-8-fluoro-3-nitroquinolin-4-yl)-6-methylpiperazine-1,3-dicarboxylate (5.47 g) in 89% yield. MS (ESI) m/z: 563.0 $[M+H]^+$.

To a solution of (3R,6R)-1-tert-butyl 3-methyl 4-(7-bromo-6-chloro-8-fluoro-3-nitroquinolin-4-yl)-6-methylpiperazine-1,3-dicarboxylate (5.47 g, 9.77 mmol) in acetic acid (80 mL) was added iron (2.19 g, 39.07 mmol). After 3 h at 80° C., the mixture was quenched using aqueous $NaHCO_3$ to pH 8. The mixture was extracted with DCM. The organic phase was dried over anhydrous $Na_2SO_4$, filtered, and concentrated. The residue was purified using silica gel eluting with DCM/MeOH (50:1) to give (2R,4aR)-tert-butyl 10-bromo-11-chloro-9-fluoro-2-methyl-5-oxo-4,4a,5,6-tetrahydro-1H-pyrazino[1',2':4,5]pyrazino[2,3-c]quinoline-3(2H)-carboxylate (4.41 g) in 91% yield. MS (ESI) m/z: 501.0 $[M+H]^+$.

To a solution of (2R,4aR)-tert-butyl 10-bromo-11-chloro-9-fluoro-2-methyl-5-oxo-4,4a,5,6-tetrahydro-1H-pyrazino[1',2',4,5]pyrazino[2,3-c]quinoline-3(2H)-carboxylate (4.00 g, 8.06 mmol) in acetone (50 mL) were added methyl iodide (11.44 g, 80.6 mmol) and potassium carbonate (2.23 g, 16.1 mmol). After 16 h at 40° C., the mixture was concentrated. The residue was diluted with $H_2O$ and extracted with DCM. The organic phase was dried over anhydrous $Na_2SO_4$, filtered, and concentrated. The residue was purified using silica gel eluting with DCM/MeOH (10:1) to give (2R,4aR)-tert-butyl 10-bromo-11-chloro-9-fluoro-2,6-dimethyl-5-oxo-4,4a,5,6-tetrahydro-1H-pyrazino[1',2':4,5]pyrazino[2,3-c]quinoline-3(2H)-carboxylate (2.89 g) in 66% yield. MS (ESI) m/z: 515.1 $[M+H]^+$.

To a solution of (2R,4aR)-tert-butyl 10-bromo-11-chloro-9-fluoro-2,6-dimethyl-5-oxo-4,4a,5,6-tetrahydro-1H-pyrazino[1',2':4,5]pyrazino[2,3-c]quinoline-3(2H)-carboxylate (2.5 g, 4.86 mmol) in 1,4-dioxane/water (25 mL, 4:1 (v/v)) at 95° C. were added (2-fluoro-6-hydroxyphenyl)-boronic acid (2.28 g, 14.6 mmol), potassium carbomate (1.67 g, 12.15 mmol), 2-dicyclohexyl-phosphino-2',6'-diisopropoxy-1,1'-biphenyl (445 mg, 0.97 mmol), and methanesulfonato(2-dicyclohexylphosphino-2',6'-di-i-propoxy-1,1'-biphenyl)(2'-amino-1,1'-biphenyl-2-yl)palladium(II) (837 mg, 0.20 mmol). After 16 h at 95° C. under $N_2$, water was added and the mixture was extracted with EtOAc. The organic phase was concentrated. The residue was purified using silica gel eluting with EtOAc in PE from 0 to 50% to give (2R,4aR)-tert-butyl 11-chloro-9-fluoro-10-(2-fluoro-6-hydroxyphenyl)-2,6-dimethyl-5-oxo-4,4a,5,6-tetrahydro-1H-pyrazino1',2':4,5]pyrazino[2,3-c]quinoline-3(2H)-carboxylate (535 mg) in 20% yield. MS (ESI) m/z: 545.2 $[M+H]^+$.

To a solution of (2R,4aR)-tert-butyl 11-chloro-9-fluoro-10-(2-fluoro-6-hydroxyphenyl)-2,6-dimethyl-5-oxo-4,4a,5,6-tetrahydro-1H-pyrazino[1',2',4,5]pyrazino[2,3-c]quinoline-3(2H)-carboxylate (535 mg, 0.98 mmol) in DMF (20 mL) were added 7-iodo-N-methoxy-N-methylheptanamide (587 mg, 1.96 mmol) and potassium carbonate (270 mg, 1.96 mmol). After 16 h at room temperature, the mixture was diluted with $H_2O$ and extracted with EtOAc. The organic phase was dried over anhydrous sodium sulfate, filtered, and concentrated. The residue was purified using silica gel eluting with MeOH in DCM from 0 to 5% to give (2R,4aR)-tert-butyl 11-chloro-9-fluoro-10-(2-fluoro-6-((7-(methoxy(methyl)amino)-7-oxoheptyl)oxy)phenyl)-2,6-dimethyl-5-oxo-4,4a,5,6-tetrahydro-1H-pyrazino[1',2':4,5]pyrazino[2,3-c]quinoline-3(2H)-carboxylate (565 mg) in 81% yield. MS (ESI) m/z: 716.3 $[M+H]^+$.

To a solution of (2R,4aR)-tert-butyl 11-chloro-9-fluoro-10-(2-fluoro-6-((7-(methoxy-(methyl)amino)-7-oxoheptyl)oxy)phenyl)-2,6-dimethyl-5-oxo-4,4a,5,6-tetrahydro-1H-pyrazino[1',2':4,5]pyrazino[2,3-c]quinoline-3(2H)-carboxylate (250 mg, 0.28 mmol) in THF (2 mL) at −78° C. under $N_2$ was added lithium aluminum hydride (0.4 mL, 1 M in THF) dropwise. After 1 h at −78° C. under $N_2$, the mixture was quenched with ammonium chloride (5 mL, aq.) and extracted with EtOAc. The organic phase was dried over anhydrous $Na_2SO_4$, filtered, and concentrated to give (2R,4aR)-tert-butyl 11-chloro-9-fluoro-10-(2-fluoro-6-((7-oxoheptyl)oxy)phenyl)-2,6-dimethyl-5-oxo-4,4a,5,6-tetrahydro-1H-pyrazino[1',2':4,5]pyrazino[2,3-c]quinoline-3(2H)-carboxylate (200 mg, crude). MS (ESI) m/z: 657.3 $[M+H]^+$.

To a solution of (2R,4aR)-tert-butyl 11-chloro-9-fluoro-10-(2-fluoro-6-((7-oxoheptyl)-oxy)phenyl)-2,6-dimethyl-5-oxo-4,4a,5,6-tetrahydro-1H-pyrazino[1',2':4,5]pyrazino[2,3-c]quinoline-3(2H)-carboxylate (200 mg, crude) in DCM/MeOH (2 mL:0.1 mL) were added 3-(6-fluoro-1-oxo-4-(piperidin-4-yl)isoindolin-2-yl)piperidine-2,6-dione (116 mg, 0.34 mmol) and sodium cyanoborohydride (35 mg, 0.56 mmol). After 16 h, the mixture was concentrated and the residue was purified using silica gel eluting with MeOH in DCM from 0 to 10% to give (2R,4aR)-tert-butyl 11-chloro-10-(2-((7-(4-(2-(2,6-dioxopiperidin-3-yl)-6-fluoro-1-oxoisoindolin-4-yl)piperidin-1-yl)heptyl)oxy)-6-fluorophenyl)-9-fluoro-2,6-dimethyl-5-oxo-4,4a,5,6-tetrahydro-1H-pyrazino[11',2':4,5]pyrazino[2,3-c]quinoline-3(2H)-carboxylate (223 mg) in 85% yield. MS (ESI) m/z: 986.4 $[M+H]^+$.

To a solution of (2R,4aR)-tert-butyl 11-chloro-10-(2-((7-(4-(2-(2,6-dioxopiperidin-3-yl)-6-fluoro-1-oxoisoindolin-4-yl)piperidin-1-yl)heptyl)oxy)-6-fluorophenyl)-9-fluoro-2,6-dimethyl-5-oxo-4,4a,5,6-tetrahydro-1H-pyrazino[1',2':4,5]pyrazino[2,3-c]quinoline-3(2H)-carboxylate (50 mg, 0.05 mmol) in DCM (2 mL) was added TFA (0.5 mL). After 1 h, the solution was concentrated to give 3-(4-(1-(7-(2-((2R,4aR)-11-chloro-9-fluoro-2,6-dimethyl-5-oxo-2,3,4,4a,5,6-hexahydro-1H-pyrazino[1',2':4,5]pyrazino[2,3-c]quinolin-10-yl)-3-fluorophenoxy)heptyl)piperidin-4-yl)-6-fluoro-1-oxoisoindolin-2-yl)piperidine-2,6-dione as a TFA salt (crude). MS (ESI) m/z: 886.4 $[M+H]^+$.

To a solution of 3-(4-(1-(7-(2-((2R,4aR)-11-chloro-9-fluoro-2,6-dimethyl-5-oxo-2,3,4,4a,5,6-hexahydro-1H-pyrazino[1',2':4,5]pyrazino[2,3-c]quinolin-10-yl)-3-fluorophenoxy)-heptyl)piperidin-4-yl)-6-fluoro-1-oxoisoindolin-2-yl)piperidine-2,6-dione (crude) in DCM (2 mL) were added acryloyl chloride (7 mg, 0.07 mmol) and TEA (0.02 mL, 0.15 mmol) at 0° C. After 2 h at room temperature, the mixture was concentrated and the residue was purified using prep-HPLC to give 3-(4-(1-(7-(2-((2R,4aR)-3-acryloyl-11-chloro-9-fluoro-2,6-dimethyl-5-oxo-2,3,4,4a,5,6-hexahydro-1H-pyrazino[1',2':4,5]pyrazino[2,3-c]quinolin-10-yl)-3-fluorophenoxy)-heptyl)piperidin-4-yl)-6-fluoro-1-oxoisoindolin-2-yl)piperidine-2,6-dione 64 (3.4 mg) in 7% yield. $^1H$ NMR (400 MHz, DMSO-$d_6$) δ 11.02 (s, 1H), 9.02 (s, 1H), 8.00 (s, 1H) 7.57-7.51 (m, 1H), 7.40-7.34 (m, 2H), 7.08 (d, J=8.4 Hz, 1H), 7.00 (t, J=8.4 Hz, 1H), 6.17-6.12 (m, 1H), 5.76 (d, J=10.4 Hz, 1H), 5.13 (dd, J=4.4, 12.4 Hz, 1H), 4.79-4.73 (m, 1H), 4.66 (d, J=14.0 Hz, 1H), 4.53-4.31 (m, 2H), 4.12-3.97 (m, 4H), 3.84-3.75 (m, 4H), 3.20-3.07 (m, 2H), 2.95-2.84 (m, 3H), 2.67-2.57 (m, 2H), 2.45-2.33 (m, 1H), 2.15-2.11 (m, 2H), 2.03-1.98 (m, 3H), 1.71-1.65 (m, 4H), 1.54-1.46 (m, 6H), 1.19-1.04 (m, 6H); MS (ESI) m/z: 940.4 $[M+H]^+$.

Example 14. 3-(1-(1-(7-(2-(6-Chloro-8-fluoro-4-(4-propionylpiperazin-1-yl)quinazolin-7-yl)-3-fluorophenoxy)heptyl)piperidin-4-yl)-4-oxo-4H-thieno[3,4-c]pyrrol-5(6H)-yl)piperidine-2,6-dione

71

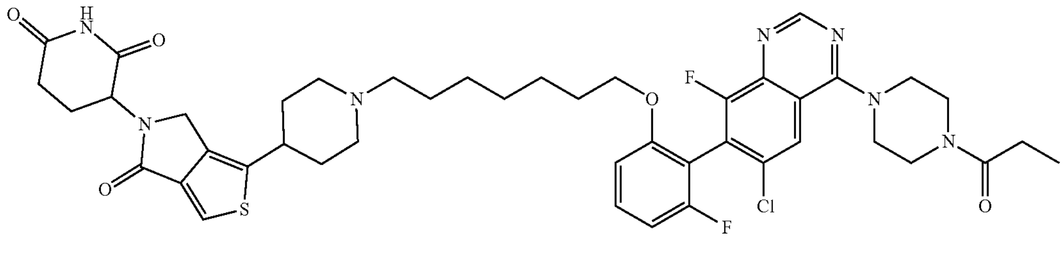

To a solution of 3-(1-bromo-4-oxo-4H-thieno[3,4-c]pyrrol-5(6H)-yl)piperidine-2,6-dione (1.0 g, 3.04 mmol) in DMF (20 mL) were added $K_2CO_3$, $Pd(dppf)Cl_2$, and tert-butyl 4-(4,4,5,5-tetramethyl-1,3,2-dioxaborolan-2-yl)-5,6-dihydropyridine-1(2H)-carboxylate (2.82 g, 9.12 mmol). After 16 h at 100° C. under $N_2$, the mixture was filtered. The filtrate was diluted with $H_2O$ and extracted with EtOAc. The organic phase was washed with $H_2O$, dried over anhydrous $Na_2SO_4$, filtered, and concentrated. The residue was purified using silica gel eluting with EtOAc in PE from 0 to 85% to give tert-butyl 4-(5-(2,6-dioxopiperidin-3-yl)-4-oxo-5,6-dihydro-4H-thieno[3,4-c]pyrrol-1-yl)-5,6-dihydropyridine-1(2H)-carboxylate (812 mg) in 62% yield. MS (ESI) m/z: 432.1 $[M+1]^+$.

To a solution of tert-butyl 4-(5-(2,6-dioxopiperidin-3-yl)-4-oxo-5,6-dihydro-4H-thieno[3,4-c]pyrrol-1-yl)-5,6-dihydropyridine-1(2H)-carboxylate (100 mg, 0.232 mmol) in MeOH (15 mL) was added Pd/C (200 mg). After 16 h under $H_2$, the mixture was filtered and the filtrate was concentrated to give tert-butyl 4-(5-(2,6-dioxopiperidin-3-yl)-4-oxo-5,6-dihydro-4H-thieno[3,4-c]pyrrol-1-yl)piperidine-1-carboxylate (65 mg) in 65% yield. MS (ESI) m/z: 388.1 [M−55]+.

To a solution of 1-(4-(6-chloro-8-fluoro-7-(2-fluoro-6-hydroxyphenyl)quinazolin-4-yl)piperazin-1-yl)propan-1-one (144 mg, 0.334 mmol) in DMF (5 mL) were added $K_2CO_3$ (138 mg, 1.00 mmol) and 7-iodo-N-methoxy-N-methylheptanamide (100 mg, 0.334 mmol). After 4 h at 75° C., the mixture was concentrated. The residue was purified using silica gel eluting with EtOAc in PE from 0 to 75% to give 7-(2-(6-chloro-8-fluoro-4-(4-propionylpiperazin-1-yl)quinazolin-7-yl)-3-fluorophenoxy)-N-methoxy-N-methylheptanamide (145 mg) in 72% yield. MS (ESI) m/z: 604.1 $[M+1]^+$.

To a solution of 7-(2-(6-chloro-8-fluoro-4-(4-propionylpiperazin-1-yl)quinazolin-7-yl)-3-fluorophenoxy)-N-methoxy-N-methylheptanamide (50 mg, 0.083 mmol) in THF (4 ml) at −78° C. was added $LiAlH_4$ (0.2 ml, 0.124 mmol) under $N_2$. After 1 h at −78° C. under $N_2$, the mixture was quenched with saturated aqueous $NH_4Cl$ (4 mL) and extracted with EtOAc. The organic phase was dried over anhydrous $Na_2SO_4$, filtered, and concentrated to give 7-(2-(6-chloro-8-fluoro-4-(4-propionylpiperazin-1-yl)quinazolin-7-yl)-3-fluorophenoxy)heptanal. MS (ESI) m/z: 545.2 $[M+1]^+$.

To a solution of tert-butyl 4-(5-(2,6-dioxopiperidin-3-yl)-4-oxo-5,6-dihydro-4H-thieno[3,4-c]pyrrol-1-yl)piperidine-1-carboxylate (36 mg, 0.083 mmol) in DCM (2 mL) was added HCl/EtOAc (0.5 mL). After 1 h, the solution was concentrated to give 3-(4-oxo-1-(piperidin-4-yl)-4H-thieno[3,4-c]pyrrol-5(6H)-yl)piperidine-2,6-dione as a HCl salt (30 mg, crude). MS (ESI) m/z: 334.1 $[M+1]^+$.

To a solution of 3-(4-oxo-1-(piperidin-4-yl)-4H-thieno[3,4-c]pyrrol-5(6H)-yl)piperidine-2,6-dione (26 mg, crude, 0.083 mmol) in DCM/MeOH (4 mL:1 mL) were added DIPEA (11 mg, 0.083 mmol), 7-(2-(6-chloro-8-fluoro-4-(4-propionylpiperazin-1-yl)quinazolin-7-yl)-3-fluorophenoxy)heptanal (30 mg, crude, 0.083 mmol), $NaBH_3CN$ (21 mg, 0.332 mmol), and acetic acid (a drop). After 16 h, the mixture was concentrated and the residue was purified using prep-HPLC to give 3-(1-(1-(7-(2-(6-chloro-8-fluoro-4-(4-propionylpiperazin-1-yl)quinazolin-7-yl)-3-fluorophenoxy)heptyl)piperidin-4-yl)-4-oxo-4H-thieno[3,4-c]pyrrol-5(6H)-yl)piperidine-2,6-dione 71 (4.1 mg) in 5.8% yield. $^1H$ NMR (400 MHz, DMSO-$d_6$) δ 10.99 (s, 1H), 9.46 (s, 1H), 8.71 (s, 1H), 8.07 (d, J=6.8 Hz, 1H), 7.90 (s, 1H), 7.57-7.52 (m, 1H), 7.07 (d, J=8.0 Hz, 1H), 7.01 (t, J=8.8 Hz, 1H), 5.15 (dd, J=4.4, 12.8 Hz, 1H), 4.39-4.18 (m, 2H), 4.04 (t, J=6.0 Hz, 2H), 3.94-3.87 (m, 4H), 3.70-3.66 (m, 4H), 3.54-3.51 (m, 2H), 3.23-3.10 (m, 1H), 2.99-2.94 (m, 4H), 2.67-2.61 (m, 3H), 2.44-2.27 (m, 4H), 2.21-2.18 (m, 1H), 2.03-1.96 (m, 4H), 1.59-1.52 (m, 2H), 1.47-1.43 (m, 1H), 1.23-1.17 (m, 4H), 1.03 (t, J=7.2 Hz, 3H); MS (ESI) m/z: 861.9 $[M+1]^+$.

Example 15. 3-(5-(1-(7-(2-(6-Chloro-8-fluoro-4-(4-propionylpiperazin-1-yl)quinazolin-7-yl)-3-fluorophenoxy)heptyl)piperidin-4-yl)-6-fluoro-1-oxoisoindolin-2-yl)piperidine-2,6-dione 93

93

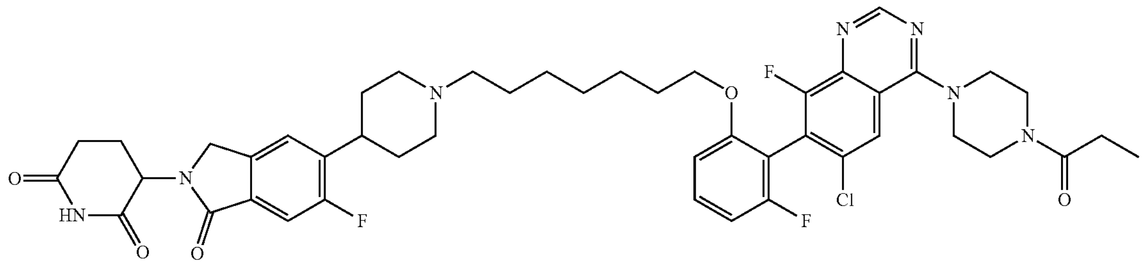

To a solution of 3-(5-bromo-6-fluoro-1-oxoisoindolin-2-yl)piperidine-2,6-dione (445 mg, 1.308 mmol) in DMF (10 mL) under $N_2$ were added tert-butyl 4-(4,4,5,5-tetramethyl-1,3,2-dioxaborolan-2-yl)-5,6-dihydropyridine-1(2H)-carboxylate (1.213 g, 3.926 mmol), $K_2CO_3$ (542 mg, 3.926 mmol), and Pd(dppf)$Cl_2$ (287 mg, 0.392 mmol). After 16 h at 100° C., the mixture was filtered and the filtrate was concentrated. The residue was purified using silica gel eluting with DCM in EtOAc from 10 to 50% to give tert-butyl 4-(2-(2,6-dioxopiperidin-3-yl)-6-fluoro-1-oxoisoindolin-5-yl)-5,6-dihydropyridine-1(2H)-carboxylate (180 mg) in 31% yield. MS (ESI) m/z: 444.2 $[M+H]^+$.

To a solution of tert-butyl 4-(2-(2,6-dioxopiperidin-3-yl)-6-fluoro-1-oxoisoindolin-5-yl)-5,6-dihydropyridine-1(2H)-carboxylate (180 mg, 0.406 mmol) in THF (6 mL) was added Pd/C (100 mg). After 16 h under $H_2$, the mixture was filtered and the filtrate was concentrated to give tert-butyl 4-(2-(2,6-dioxopiperidin-3-yl)-6-fluoro-1-oxoisoindolin-5-yl)piperidine-1-carboxylate (116 mg) in 64% yield. MS (ESI) m/z: 446.2 $[M+H]^+$.

To a solution of tert-butyl 4-(2-(2,6-dioxopiperidin-3-yl)-6-fluoro-1-oxoisoindolin-5-yl)piperidine-1-carboxylate (90 mg, 0.098 mmol) in DCM (4 mL) was added TFA (1 mL). After 1 h, the solution was concentrated to give 3-(6-fluoro-1-oxo-5-(piperidin-4-yl)isoindolin-2-yl)piperidine-2,6-dione as a TFA salt (90 mg, crude). MS (ESI) m/z: 346.2 $[M+H]^+$.

To a solution of tert-butyl 4-(6-chloro-8-fluoro-7-(2-fluoro-6-((7-(methoxy(methyl)amino)-7-oxoheptyl)oxy)phenyl)quinazolin-4-yl)piperazine-1-carboxylate (100 mg, 0.154 mmol) in THF (5 mL) at −78° C. under $N_2$ was added lithium aluminum hydride (0.3 mL, 1 M in THF) dropwise. After 1 h at −78° C. under $N_2$, the mixture was quenched with saturated aqueous $NH_4Cl$ (5 mL) and extracted with EtOAc. The organic phase was dried over anhydrous $Na_2SO_4$, filtered, and concentrated to give tert-butyl 4-(6- chloro-8-fluoro-7-(2-fluoro-6-((7-oxoheptyl)oxy)phenyl)-quinazolin-4-yl)piperazine-1-carboxylate (85 mg, crude). MS (ESI) m/z: 589.2 $[M+H]^+$.

To a solution of tert-butyl 4-(6-chloro-8-fluoro-7-(2-fluoro-6-((7-oxoheptyl)oxy)phenyl)-quinazolin-4-yl)piperazine-1-carboxylate (85 mg, crude) in DCM/MeOH (4 mL:0.5 mL) were added 3-(6-fluoro-1-oxo-5-(piperidin-4-yl)isoindolin-2-yl)piperidine-2,6-dione (41 mg, 0.119 mmol), sodium cyanoborohydride (15 mg, 0.238 mmol), and acetic acid (1 drop). After 16 h, the mixture was concentrated and the residue was purified using prep-TLC eluting with DCM/MeOH (10:1) to give tert-butyl 4-(6-chloro-7-(2-((7-(4-(2-(2,6-dioxopiperidin-3-yl)-6-fluoro-1-oxoisoindolin-5-yl)piperidin-1-yl)heptyl)oxy)-6-fluorophenyl)-8-fluoroquinazolin-4-yl)piperazine-1-carboxylate (90 mg) in 83% yield. MS (ESI) m/z: 918.4$[M+H]^+$.

To a solution of tert-butyl 4-(6-chloro-7-(2-((7-(4-(2-(2,6-dioxopiperidin-3-yl)-6-fluoro-1-oxoisoindolin-5-yl)piperidin-1-yl)heptyl)oxy)-6-fluorophenyl)-8-fluoroquinazolin-4-yl)piperazine-1-carboxylate (90 mg, 0.098 mmol) in DCM (4 mL) was added TFA (1 mL). After 1 h, the solution was concentrated to give 3-(5-(1-(7-(2-(6-chloro-8-fluoro-4-(piperazin-1-yl)quinazolin-7-yl)-3-fluorophenoxy)heptyl)piperidin-4-yl)-6-fluoro-1-oxoisoindolin-2-yl)piperidine-2,6-dione as a TFA salt (95 mg, crude). MS (ESI) m/z: 818.3 $[M+H]^+$.

To a solution 3-(5-(1-(7-(2-(6-chloro-8-fluoro-4-(piperazin-1-yl)quinazolin-7-yl)-3-fluorophenoxy)heptyl)piperidin-4-yl)-6-fluoro-1-oxoisoindolin-2-yl)piperidine-2,6-dione (95 mg, crude) in THF (4 mL) at 0° C. were added DIPEA (37.8 mg, 0.293 mmol) and acryloyl chloride (13.5 mg, 0.146 mmol). After 2 h, the mixture was concentrated and the residue was purified using prep-HPLC as previously described to give 3-(5-(1-(7-(2-(6-chloro-8-fluoro-4-(4-propionylpiperazin-1-yl)quinazolin-7-yl)-3-fluorophenoxy)heptyl)piperidin-4-yl)-6-fluoro-1-oxoisoindolin-2-yl)piperidine-2,6-dione 93 (31.2 mg) in 37% yield. $^1H$ NMR (400 MHz, DMSO-$d_6$) δ 10.98 (s, 1H), 8.70 (s, 1H), 8.15 (s, 1H), 8.04 (s, 1H), 7.59 (d, J=6.4 Hz, 1H), 7.57-7.51 (m, 1H), 7.47 (d, J=9.2 Hz, 1H), 7.07 (d, J=8.4 Hz, 1H), 7.00 (t, J=8.8 Hz, 1H), 5.11 (dd, J=5.2, 13.2 Hz, 1H), 4.44-4.27 (m, 2H), 4.03 (t, J=6.0 Hz, 2H), 3.92-3.87 (m, 4H), 3.71-3.69 (m, 4H), 3.12-3.09 (m, 3H), 2.94-2.87 (m, 3H), 2.62-2.57 (m, 1H), 2.41-2.39 (m, 6H), 2.21-2.15 (m, 2H), 2.02-1.97 (m, 1H), 1.77-1.73 (m, 4H), 1.53-1.51 (m, 1H), 1.33-1.29 (m, 2H), 1.14-1.08 (m, 4H), 1.01 (t, J=7.6 Hz, 3H); MS (ESI) m/z: 874.4 $[M+H]^+$.

Example 16. 3-(4-(1-(2-((4-((2-(2-(6-Chloro-4-(4-(2-chloroacryloyl)piperazin-1-yl)-8-fluoroquinazolin-7-yl)-3-fluorophenoxy)ethoxy)methyl)benzyl)oxy)ethyl)piperidin-4-yl)-6-fluoro-1-oxoisoindolin-2-yl)piperidine-2,6-dione 101

101

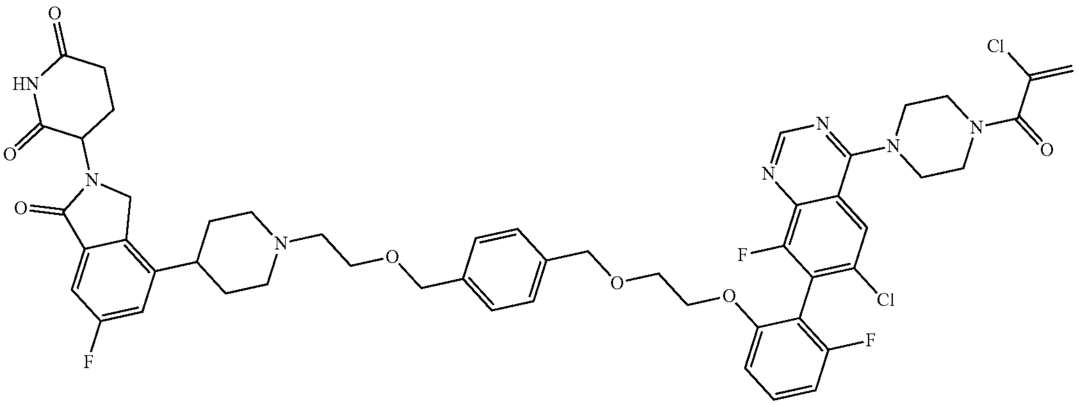

To a solution of imidazole (11.47 g, 45.2 mmol) in DCM (50 mL) at 0° C. were added $PPh_3$ (11.84 g, 45.2 mmol), 12(11.47 g, 45.2 mmol), and methyl 4-(hydroxymethyl) benzoate (5.0 g, 30.12 mmol). After 16 h at room temperature, the mixture was quenched with aqueous $Na_2S203$ and extracted with EtOAc. The organic phase was dried over anhydrous $Na_2SO_4$, filtered, and concentrated. The residue was purified using silica gel eluting with EtOAc in PE from 0 to 20% to give methyl 4-(iodomethyl)benzoate (4.76 g) in 57% yield. MS (ESI) m/z: 277.0 $[M+1]^+$.

To a solution of ethane-1,2-diol (3.72 g, 60 mmol) in DMF (20 mL) at 0° C. was added NaH (480 mg, 12 mmol) in portions. After 30 min at 0° C., a solution of methyl 4-(iodomethyl)-benzoate (2.76 g 10 mmol) in DMF (4 mL) was added. After 16 h at room temperature, the mixture was quenched with $H_2O$ and extracted with EtOAc. The organic phase was dried over anhydrous $Na_2SO_4$, filtered, and concentrated. The residue was purified using silica gel eluting with EtOAc in PE from 0 to 40% to give methyl 4-((2-hydroxyethoxy)methyl)benzoate (846 mg) in 40% yield. MS (ESI) m/z: 211.0 $[M+1]^+$.

To a solution of methyl 4-((2-hydroxyethoxy)methyl) benzoate (846 mg, 4.03 mmol) in DCM (20 mL) were added 3,4-dihydro-2H-pyran (508 mg, 6.10 mmol) and pyridinium p-toluenesulfonate (101 mg, 0.403 mmol). After 16 h at room temperature, the mixture was concentrated and the residue was purified using silica gel eluting with EtOAc in PE from 0 to 30% to give methyl 4-((2-((tetrahydro-2H-pyran-2-yl)oxy)ethoxy)methyl)benzoate (1.13 g) in 95% yield. MS (ESI) m/z: 295.1 $[M+1]^+$.

To a solution of methyl 4-((2-((tetrahydro-2H-pyran-2-yl) oxy)ethoxy)methyl)benzoate (1.13 g, 3.84 mmol) in THF (15 mL) at 0° C. was added $LiAlH_4$ (3.5 mL, 3.53 mmol, 1M in THF). After 3 h at 0° C., the mixture was quenched with saturated aqueous $NH_4Cl$ and extracted with EtOAc. The organic phase was dried over anhydrous $Na_2SO_4$, filtered, and concentrated. The residue was purified using silica gel eluting with EtOAc in PE from 0 to 30% to give (4-((2-((tetrahydro-2H-pyran-2-yl)oxy)ethoxy)methyl)phenyl) methanol (730 mg) in 72% yield.

To a solution of imidazole (575 mg, 8.46 mmol) in DCM (30 mL) were added $PPh_3$ (2.22 g, 8.46 mmol) and 12(2.15 g, 8.46 mmol) at 0° C. After 10 min, a solution of (4-((2-((tetrahydro-2H-pyran-2-yl)oxy)ethoxy)methyl)phenyl) methanol (1.2 g, 5.64 mmol) in DCM (5 mL) was added. After 16 h at room temperature, the mixture was quenched with aqueous $Na_2S203$ and extracted with EtOAc. The organic phase was dried over anhydrous $Na_2SO_4$, filtered, and concentrated. The residue was purified using silica gel eluting with EtOAc in PE from 0 to 20% to give 2-(2-((4-(iodomethyl)benzyl)oxy)ethoxy)tetrahydro-2H-pyran (1.43 g) in 54% yield. MS (ESI) m/z: 377.0 $[M+1]^+$.

To a solution of methyl 2-hydroxyacetate (1.64 g, 18.2 mmol) in DMF (20 mL) was added NaH (146 mg, 3.65 mmol) at 0° C. After 30 min, a solution of 2-(2-((4-(iodomethyl)benzyl)oxy)-ethoxy)tetrahydro-2H-pyran (1.43 g 10 mmol) in DMF (2 mL) was added. After 16 h at room temperature, the mixture was quenched with $H_2O$ and extracted with EtOAc. The organic phase was dried over anhydrous $Na_2SO_4$, filtered, and concentrated. The residue was purified using silica gel eluting with EtOAc in PE from 0 to 60% to give methyl 2-((4-((2-((tetrahydro-2H-pyran-2-yl)oxy)ethoxy)methyl)benzyl)oxy)acetate (928 mg) in 90% yield. MS (ESI) m/z: 339.2 $[M+1]^+$.

To a solution of methyl 2-((4-((2-((tetrahydro-2H-pyran-2-yl)oxy)ethoxy)methyl)benzyl)-oxy)acetate (928 mg, 2.75 mmol) in THF/water (20 mL, 3:1) was added LiOH (231 mg, 5.50 mmol). After 2 h, the mixture was adjusted to pH 6 with 1N HCl and extracted with EtOAc. The organic phase was concentrated to give 2-((4-((2-((tetrahydro-2H-pyran-2-yl)oxy)ethoxy)methyl)-benzyl)oxy)acetic acid (765 mg) in 90% yield. MS (ESI) m/z: 325.1 $[M+1]^+$.

To a solution of N,O-dimethylhydroxylamine (460 mg, 4.72 mmol) in DCM (20 mL) at 0° C. were added TEA (715 g, 7.08 mmol), EDCI (680 mg, 3.54 mmol), 2-((4-((2-((tetrahydro-2H-pyran-2-yl)oxy)ethoxy)methyl)benzyl) oxy)acetic acid (765 mg, 2.36 mmol), and DMAP (86 mg 0.708 mmol). After 16 h at room temperature, the mixture was concentrated and the residue was purified using silica gel eluting with EtOAc in PE from 0 to 70% to give N-methoxy-N-methyl-2-((4-((2-((tetrahydro-2H-pyran-2-yl)oxy)ethoxy)methyl)benzyl)oxy)acetamide (736 mg) in 85% yield. MS (ESI) m/z: 368.2 $[M+1]^+$.

To a solution of N-methoxy-N-methyl-2-((4-((2-((tetrahydro-2H-pyran-2-yl)oxy)ethoxy)-methyl)benzyl)oxy)acetamide (736 mg, 2.01 mmol) in EtOH (20 mL) was added pyridinium p-toluenesulfonate (28 mg, 7.08 mmol). After 2 h at 75° C., the mixture was concentrated and the residue was purified using silica gel eluting with EtOAc/PE from 0 to 70% to give 2-((4-((2-hydroxyethoxy)methyl)benzyl) oxy)-N-methoxy-N-methylacetamide (561 mg) in 99% yield. MS (ESI) m/z: 384.1 $[M+1]^+$.

To a solution of imidazole (202 mg, 2.97 mmol) in DCM (20 mL) at 0° C. were added $PPh_3$ (779 mg, 2.97 mmol) and 12(755 mg, 2.97 mmol). After 10 min at 0° C., a solution of 2-((4-((2-hydroxyethoxy)methyl)benzyl)oxy)-N-methoxy-N-methylacetamide (561 mg, 1.98 mmol) in DCM (2 mL) was added. After 16 h at room temperature, the mixture was quenched with aqueous $Na_2S203$ and extracted with EtOAc. The organic phase was dried over anhydrous $Na_2SO_4$, filtered, and concentrated. The residue was purified using silica gel eluting with EtOAc in PE from 0 to 20% to give 2-((4-((2-iodoethoxy)methyl)benzyl)oxy)-N-methoxy-N-methylacetamide (693 mg) in 75% yield. MS (ESI) m/z: 394.0 $[M+1]^+$.

To a solution of 2-((4-((2-iodoethoxy)methyl)benzyl) oxy)-N-methoxy-N-methylacetamide (340 mg, 0.86 mmol) in DMF (10 mL) were added $K_2CO_3$ (200 mg, 1.44 mmol) and tert-butyl 4-(6-chloro-8-fluoro-7-(2-fluoro-6-hydroxy-phenyl)quinazolin-4-yl)piperazine-1-carboxylate (343 mg, 0.72 mmol). After 16 h, the mixture was concentrated and the residue was purified using silica gel eluting with EtOAc in PE from 0 to 80% to give tert-butyl 4-(6-chloro-8-fluoro-7-(2-fluoro-6-(2-((4-((2-(methoxy(methyl)amino)-2-oxo-ethoxy)methyl)benzyl)oxy)ethoxy)phenyl)quinazolin-4-yl) piperazine-1-carboxylate (271 mg) in 51% yield. MS (ESI) m/z: 742.2 $[M+1]^+$.

To a solution of tert-butyl 4-(6-chloro-8-fluoro-7-(2-fluoro-6-(2-((4-((2-(methoxy(methyl)-amino)-2-oxoethoxy) methyl)benzyl)oxy)ethoxy)phenyl)quinazolin-4-yl)piperazine-1-carboxylate (90 mg, 0.121 mmol) in THF (3 mL) at −78° C. was added $LiAlH_4$ (0.16 mL, 0.158 mmol, 1 M). After 1 h at −78° C., the mixture was quenched with saturated aqueous $NH_4Cl$ and extracted with EtOAc. The organic phase was dried over anhydrous $Na_2SO_4$, filtered, and concentrated to give tert-butyl 4-(6-chloro-8-fluoro-7-(2-fluoro-6-(2-((4-((2-oxoethoxy)methyl)benzyl)oxy) ethoxy)phenyl)-quinazolin-4-yl)piperazine-1-carboxylate (85 mg, crude). MS (ESI) m/z: 683.2 $[M+1]^+$.

To a solution of tert-butyl 4-(2-(2, 6-dioxopiperidin-3-yl)-6-fluoro-1-oxoisoindolin-4-yl)piperidine-1-carboxylate (54 mg, 0.121 mmol) in DCM (2 mL) was added TFA (0.5 mL). After 1 h, the solution was concentrated to give 3-(6-fluoro-1-oxo-4-(piperidin-4-yl)isoindolin-2-yl)piperidine-2,6-dione as a TFA salt (55 mg, crude). MS (ESI) m/z: 346.1 $[M+1]^+$.

To a solution of 3-(6-fluoro-1-oxo-4-(piperidin-4-yl) isoindolin-2-yl)piperidine-2,6-dione (crude, 0.121 mmol) in DCM/MeOH (4 mL:1 mL) were added DIPEA (31 mg, 0.083 mmol), 7-(2-(6-chloro-8-fluoro-4-(4-propionylpiperazin-1-yl)quinazolin-7-yl)-3-fluorophenoxy)heptanal (crude, 0.121 mmol), $NaBH_3CN$ (16 mg, 0.242 mmol), and acetic acid (1 drop). After 16 h, the mixture was concentrated and the residue was purified using prep-HPLC as to give tert-butyl 4-(6-chloro-7-(2-(2-((4-((2-(4-(2-(2,6-dioxopiperidin-3-yl)-6-fluoro-1-oxoisoindolin-4-yl)piperidin-1-yl)ethoxy)methyl)-benzyl)oxy)ethoxy)-6-fluorophenyl)-8-fluoroquinazolin-4-yl)piperazine-1-carboxylate (75 mg) in 61% yield.

To a solution of tert-butyl 4-(6-chloro-7-(2-(2-((4-((2-(4-(2-(2,6-dioxopiperidin-3-yl)-6-fluoro-1-oxoisoindolin-4-yl) piperidin-1-yl)ethoxy)methyl)benzyl)oxy)ethoxy)-6-fluoro-phenyl)-8-fluoroquinazolin-4-yl)piperazine-1-carboxylate (75 mg, 0.0741 mmol) in DCM (3 mL) was added TFA (1 mL). After 1 h, the solution was concentrated to give 3-(4-(1-(2-((4-((2-(2-(6-chloro-8-fluoro-4-(piperazin-1-yl)quinazolin-7-yl)-3-fluorophenoxy)ethoxy)methyl)benzyl)oxy)ethyl)-piperidin-4-yl)-6-fluoro-1-oxoisoindolin-2-yl)piperidine-2,6-dione as a TFA salt (70 mg, crude). MS (ESI) m/z: 912.4 $[M+1]^+$.

To a solution of 2-chloroacrylic acid (16 mg, 0.148 mmol) in DCM (2 mL) was added $(COCl)_2$ (16 mg, 0.126 mmol) and the mixture was stirred at 0° C. for 2 h. To a solution of 3-(4-(1-(2-((4-((2-(2-(6-chloro-8-fluoro-4-(piperazin-1-yl)quinazolin-7-yl)-3-fluorophenoxy)ethoxy)-methyl)benzyl)oxy)ethyl)piperidin-4-yl)-6-fluoro-1-oxoisoindolin-2-yl)piperidine-2,6-dione (crude, 0.0741 mmol) in DCM (3 ml) 0° C. were added TEA (30 mg, 0.294 mmol) and the 2-chloroacryloyl chloride solution dropwise (11 mg, 0.083 mmol). After 30 min at 0° C., the mixture was concentrated and the residue was purified using prep-HPLC to give 3-(4-(1-(2-((4-((2-(2-(6-chloro-4-(4-(2-chloroacryloyl)piperazin-1-yl)-8-fluoroquinazolin-7-yl)-3-fluorophenoxy)ethoxy)methyl)-benzyl)oxy)ethyl)piperidin-4-yl)-6-fluoro-1-oxoisoindolin-2-yl)piperidine-2,6-dione 101 (14.9 mg) in 20% yield. $^1H$ NMR (400 MHz, DMSO-$d_6$) δ 11.00 (s, 1H), 8.73 (d, J=4.8 Hz, 1H), 8.07-7.85 (m, 1H), 7.59-7.50 (m, 1H), 7.41-7.35 (m, 2H), 7.12-6.92 (m, 6H), 5.83 (s, 1H), 5.80-5.78 (m, 1H), 5.13 (dd, J=4.8, 13.2 Hz, 1H), 4.54-4.33 (m, 5H), 4.29-4.17 (m, 4H), 3.86-3.80 (m, 4H), 3.68-3.51 (m, 9H), 3.11-3.09 (m, 2H), 2.95-2.89 (m, 1H), 2.69-2.67 (m, 2H), 2.62-2.58 (m, 1H), 2.43-2.40 (m, 1H), 2.29-2.23 (m, 1H), 2.02-1.99 (m, 1H), 1.78 (s, 4H); MS (ESI) m/z: 1000.3 $[M+H]^+$.

Example 17. 3-(4-(1-(7-(2-(6-Chloro-4-(4-(2-chloroacryloyl)piperazin-1-yl)-8-fluoro-2-(((S)-1-methylpyrrolidin-2-yl)methoxy)quinazolin-7-yl)-3-fluorophenoxy)heptyl)piperidin-4-yl)-6-fluoro-1-oxoisoindolin-2-yl)piperidine-2,6-dione 108

To a solution of 7-bromo-2,4,6-trichloro-8-fluoroquinazoline (crude, 17 mmol) in DCM (50 mL) were added DIPEA (6.58 g, 51 mmol) and tert-butyl piperazine-1-carboxylate (3.33 g, 17.85 mmol) at 0° C. After 1 h at room temperature, water was added and the mixture was then extracted with DCM. The organic phase was washed with brine, dried over anhydrous $Na_2SO_4$, filtered, and concentrated. The residue was purified using silica gel eluting with PE/EtOAc (5:1) to give tert-butyl 4-(7-bromo-2,6-dichloro-8-fluoroquinazolin-4-yl)piperazine-1-carboxylate (3.37 g) in 41% yield. MS (ESI) m/z: 479.2 $[M+H]^+$.

To a solution of tert-butyl 4-(7-bromo-2,6-dichloro-8-fluoroquinazolin-4-yl)piperazine-1-carboxylate (2.00 g, 4.16 mmol) and (S)-(1-methylpyrrolidin-2-yl)methanol (0.958 g, 8.33 mmol) in DMF (40 mL) was added potassium carbonate (1.725 g, 12.49 mmol). After 16 h at 80° C., $H_2O$ was added and the mixture was extracted with EtOAc. The organic phase was washed with $H_2O$, dried over anhydrous $Na_2SO_4$, filtered, and concentrated. The residue was purified using silica gel eluting with DCM/MeOH (10:1) to give (S)-tert-butyl 4-(7-bromo-6-chloro-8-fluoro-2-((1-methylpyrrolidin-2-yl)methoxy)quinazolin-4-yl)piperazine-1-carboxylate (1.175 g) in 50% yield. MS (ESI) m/z: 560.1 $[M+H]^+$.

To a solution of (S)-tert-butyl 4-(7-bromo-6-chloro-8-fluoro-2-((1-methylpyrrolidin-2-yl)methoxy)quinazolin-4-yl)piperazine-1-carboxylate (1.18 g, 2.10 mmol) and (2-fluoro-6-methoxyphenyl)boronic acid (1.79 g, 10.5 mmol) in 1,4-dioxane (63 mL) and water (7 mL) were added potassium carbonate (1.45 g, 10.5 mmol) and tetrakis(triphenylphosphine)palladium (486 mg, 0.42 mmol). After 16 h at 100° C., the mixture was concentrated and the residue was purified using silica gel eluting with DCM/MeOH (10:1) to

108

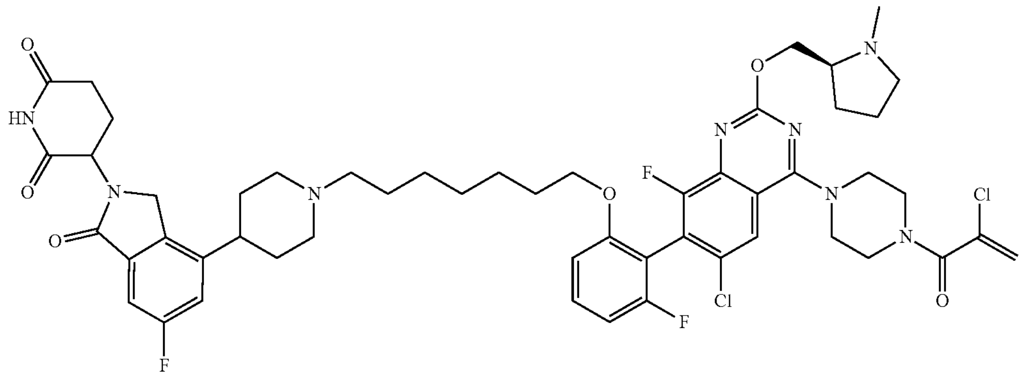

A mixture of 2-amino-4-bromo-5-chloro-3-fluorobenzoic acid (53.4 g, 0.2 mol) and urea (96 g, 1.6 mol) was heated at 202° C. for 3 h, The mixture was then cooled to room temperature and diluted with water (100 mL). The solid was collected by filtration and sequentially washed with water and tert-butyl methyl ether to give 7-bromo-6-chloro-8-fluoroquinazoline-2,4(1H,3H)-dione (47.6 g) in 81% yield. MS (ESI) m/z: 293.2 $[M+H]^+$.

To a solution of phosphorus oxychloride (50 mL) at 0° C. were added DIPEA (6.58 g, 51 mmol) and 7-bromo-6-chloro-8-fluoroquinazoline-2,4(1H,3H)-dione (5 g, 17 mmol). After 16 h at 105° C., the solution was concentrated to give 7-bromo-2,4,6-trichloro-8-fluoroquinazoline (7.0 g, crude). MS (ESI) m/z: 328.8 $[M+H]^+$.

give tert-butyl 4-(6-chloro-8-fluoro-7-(2-fluoro-6-methoxyphenyl)-2-(((S)-1-methylpyrrolidin-2-yl)methoxy)quinazolin-4-yl)piperazine-1-carboxylate (1.04 g) in 81% yield. MS (ESI) m/z: 604.2 $[M+H]^+$.

To a solution of tert-butyl 4-(6-chloro-8-fluoro-7-(2-fluoro-6-methoxyphenyl)-2-(((S)-1-methylpyrrolidin-2-yl)methoxy)quinazolin-4-yl)piperazine-1-carboxylate (518 mg, 0.859 mmol) in DCM (8 mL) at −78° C. was added boron tribromide (2.14 mL, 2M) dropwise. After 2 h at room temperature, the mixture was quenched with saturated aqueous $NaHCO_3$ and extracted with DCM. The organic phase was concentrated to give 2-(6-chloro-8-fluoro-2-(((S)-1-methylpyrrolidin-2-yl)methoxy)-4-(piperazin-1-yl)quinazolin-7-yl)-3-fluorophenol. MS (ESI) m/z: 490.2$[M+H]^+$.

To a solution of 2-(6-chloro-8-fluoro-2-(((S)-1-methylpyrrolidin-2-yl)methoxy)-4-(piperazin-1-yl)quinazolin-7-yl)-3-fluorophenol (crude, 0.859 mmol) in DCM/MeOH (9 mL:1 mL) at 0° C. were added TEA (260 mg, 2.58 mmol) and di-tert-butyl dicarbonate (168 mg, 0.773 mmol). After 1 h at 0° C., the the mixture was concentrated and the residue was purified using silica gel eluting with DCM/MeOH (25:1) to give tert-butyl 4-(6-chloro-8-fluoro-7-(2-fluoro-6-hydroxyphenyl)-2-(((S)-1-methylpyrrolidin-2-yl)methoxy) quinazolin-4-yl)piperazine-1-carboxylate (297 mg) in 29% yield. MS (ESI) m/z: 590.3[M+H]$^+$.

To a solution of tert-butyl 4-(6-chloro-8-fluoro-7-(2-fluoro-6-hydroxyphenyl)-2-(((S)-1-methylpyrrolidin-2-yl) methoxy)quinazolin-4-yl)piperazine-1-carboxylate (297 mg, 0.504 mmol) in DMF (10 mL) were added 7-iodo-N-methoxy-N-methylheptanamide (452 mg, 1.51 mmol) and potassium carbonate (208 mg, 1.512 mmol). After 16 h, $H_2O$ was added and the mixture was extracted with EtOAc. The organic phase was washed with $H_2O$, dried over anhydrous $Na_2SO_4$, filtered and concentrated. The residue was purified using silica gel eluting with DCM/MeOH (10:1) to give tert-butyl 4-(6-chloro-8-fluoro-7-(2-fluoro-6-((7-(methoxy (methyl)amino)-7-oxoheptyl)oxy)phenyl)-2-(((S)-1-methylpyrrolidin-2-yl)methoxy)quinazolin-4-yl)piperazine-1-carboxylate (203 mg) in 52% yield. MS (ESI) m/z: 761.5 [M+H]$^+$.

To a solution of tert-butyl 4-(6-chloro-8-fluoro-7-(2-fluoro-6-((7-(methoxy(methyl)amino)-7-oxoheptyl)oxy) phenyl)-2-(((S)-1-methylpyrrolidin-2-yl)methoxy)quinazolin-4-yl)piperazine-1-carboxylate (203 mg, 0.267 mmol) in THF (16 mL) at −78° C. under $N_2$ was added lithium aluminum hydride (0.4 mL, 1 M in THF) dropwise. After 30 min at −78° C., the mixture was quenched with saturated aqueous $NH_4Cl$ (5 mL) and extracted with EtOAc. The organic phase was washed with brine, dried over anhydrous $Na_2SO_4$, filtered, and concentrated to give tert-butyl 4-(6-chloro-8-fluoro-7-(2-fluoro-6-((7-oxoheptyl)oxy)phenyl)-2-(((S)-1-methylpyrrolidin-2-yl)methoxy)-quinazolin-4-yl) piperazine-1-carboxylate (187 mg, crude). MS (ESI) m/z: 702.3 [M+H]$^+$.

To a solution of tert-butyl 4-(6-chloro-8-fluoro-7-(2-fluoro-6-((7-oxoheptyl)oxy)phenyl)-2-(((S)-1-methylpyrrolidin-2-yl)methoxy)quinazolin-4-yl)piperazine-1-carboxylate (187 mg, 0.267 mmol) and 3-(6-fluoro-1-oxo-4-(piperidin-4-yl)isoindolin-2-yl)piperidine-2,6-dione (92.1 mg, 0.267 mmol) in DCM (20 mL) and MeOH (4 mL) were added sodium cyanoborohydride (84 mg, 1.33 mmol) and acetic acid (2 drops). After 16 h, the mixture was concentrated and the residue was purified using prep-TLC eluting with DCM/MeOH (10:1) to give tert-butyl 4-(6-chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoro-2-(((S)-1-methylpyrrolidin-2-yl)methoxy) quinazolin-4-yl)piperazine-1-carboxylate (233 mg) in 85% yield. MS (ESI) m/z: 516.2 [½M+H]$^+$.

A solution of tert-butyl 4-(6-chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoro-2-(((S)-1-methylpyrrolidin-2-yl)methoxy)quinazolin-4-yl)piperazine-1-carboxylate (90 mg, 0.087 mmol) in TFA/DCM (1 mL:4 mL) was stirred for 1 h and then concentrated to give 3-(4-(1-(7-(2-(6-chloro-8-fluoro-2-(((S)-1-methylpyrrolidin-2-yl)methoxy)-4-(piperazin-1-yl)quinazolin-7-yl)-3-fluorophenoxy)heptyl)-piperidin-4-yl)-6-fluoro-1-oxoisoindolin-2-yl)piperidine-2,6-dione as a TFA salt (81 mg, crude). MS (ESI) m/z: 466.0 [½M+H]$^+$.

To a solution of 3-(4-(1-(7-(2-(6-chloro-8-fluoro-2-(((S)-1-methylpyrrolidin-2-yl)methoxy)-4-(piperazin-1-yl)quinazolin-7-yl)-3-fluorophenoxy)heptyl)piperidin-4-yl)-6-fluoro-1-oxoisoindolin-2-yl)piperidine-2,6-dione (81 mg, 0.087 mmol) and 2-chloroacryloyl chloride (solution, 0.175 mmol) in DCM (4 mL) at 0° C. was added TEA (17.6 mg, 0.175 mmol). After 30 min at 0° C., the mixture was concentrated and the residue was purified using prep-TLC eluting with DCM/MeOH (10:1) and then prep-HPLC to give 3-(4-(1-(7-(2-(6-chloro-4-(4-(2-chloroacryloyl)-piperazin-1-yl)-8-fluoro-2-(((S)-1-methylpyrrolidin-2-yl) methoxy)quinazolin-7-yl)-3-fluoro-phenoxy)heptyl)piperidin-4-yl)-6-fluoro-1-oxoisoindolin-2-yl)piperidine-2,6-dione 108 (20.1 mg) in 22% yield. $^1H$ NMR (400 MHz, DMSO-$d_6$) δ 11.02 (s, 1H), 7.96 (s, 1H), 7.53-7.51 (m, 1H), 7.39-7.34 (m, 2H), 7.06 (d, J=8.4 Hz, 1H), 6.98 (t, J=8.4 Hz, 1H), 5.83 (s, 2H), 5.14 (dd, J=3.2, 12.4 Hz, 1H), 4.52-4.48 (m, 1H), 4.39-4.35 (m, 2H), 4.18-4.17 (m, 1H), 4.03-4.01 (m, 2H), 3.89-3.88 (m, 4H), 3.74-3.73 (m, 4H), 2.95-2.87 (m, 5H), 2.61-2.57 (m, 3H), 2.34-2.33 (m, 3H), 2.15-2.14 (m, 3H), 2.00-1.99 (m, 2H), 1.69-1.65 (m, 7H), 1.51-1.50 (m, 2H), 1.23-1.22 (m, 4H), 1.14-1.08 (m, 6H); MS (ESI) m/z: 1019.4 [M+H]$^+$.

Example 18. 3-(4-(1-(7-(2-(6-Chloro-4-(4-(2-chloroacryloyl)piperazin-1-yl)-8-fluoroquinazolin-7-yl)-3-fluorophenoxy)heptyl)pyrrolidin-3-yl)-6-fluoro-1-oxoisoindolin-2-yl)piperidine-2,6-dione 112

112

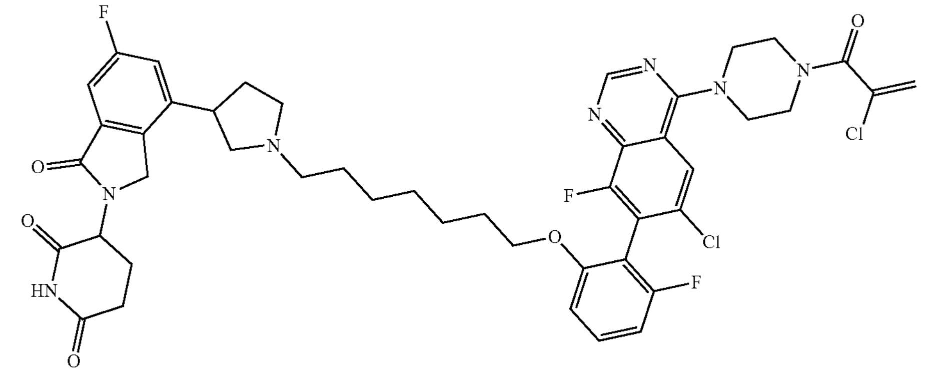

To a solution of 3-(4-bromo-6-fluoro-1-oxoisoindolin-2-yl)piperidine-2,6-dione (1.0 g, 2.9 mmol) in DMF (10 mL) under $N_2$ were added tert-butyl 3-(4,4,5,5-tetramethyl-1,3,2-dioxaborolan-2-yl)-2,5-dihydro-1H-pyrrole-1-carboxylate (1.71 g, 5.8 mmol), $K_2CO_3$ (800 mg, 5.80 mmol), and Pd(dppf)$C_{12}$ (424 mg, 0.58 mmol). After 16 h at 100° C., the mixture was filtered and the filtrate was concentrated. The residue was purified using silica gel eluting with DCM in EtOAc from 10 to 50% to give tert-butyl 3-(2-(2,6-dioxopiperidin-3-yl)-6-fluoro-1-oxoisoindolin-4-yl)-2,5-dihydro-1H-pyrrole-1-carboxylate (570 mg) in 48% yield. MS (ESI) m/z: 374 [M−55]+.

To a solution of tert-butyl 3-(2-(2,6-dioxopiperidin-3-yl)-6-fluoro-1-oxoisoindolin-4-yl)-2,5-dihydro-1H-pyrrole-1-carboxylate (389 mg, 0.9 mmol) in THF/$H_2O$ (10 mL:0.5 mL) was added Pd/C (300 mg). After 16 h under $H_2$, the mixture was filtered and the filtrate was concentrated to give tert-butyl 3-(2-(2,6-dioxopiperidin-3-yl)-6-fluoro-1-oxoisoindolin-4-yl)pyrrolidine-1-carboxylate (379 mg) in 95% yield. MS (ESI) m/z: 376 [M−55]+.

To a solution of tert-butyl 3-(2-(2,6-dioxopiperidin-3-yl)-6-fluoro-1-oxoisoindolin-4-yl)pyrrolidine-1-carboxylate (99 mg, 0.23 mmol) in DCM (2 mL) was added TFA (0.5 mL). After 1 h, the solution was concentrated to give 3-(6-fluoro-1-oxo-4-(pyrrolidin-3-yl)isoindolin-2-yl)piperidine-2,6-dione (90 mg, crude) as a TFA salt. MS (ESI) m/z: 332 $[M+H]^+$.

To a solution of tert-butyl 4-(6-chloro-8-fluoro-7-(2-fluoro-6-((7-(methoxy(methyl)amino)-7-oxoheptyl)oxy)phenyl)quinazolin-4-yl)piperazine-1-carboxylate (150 mg, 0.23 mmol) in THF (3 mL) at −70° C. under $N_2$ was added $LiAlH_4$ (0.345 mL, 1 M in THF) dropwise. After 1 h at −70° C. under $N_2$, the mixture was quenched with saturated aqueous $NH_4Cl$ (1 mL) and extracted with EtOAc. The organic phase was dried over anhydrous $Na_2SO_4$, filtered, and concentrated to give tert-butyl 4-(6-chloro-8-fluoro-7-(2-fluoro-6-((7-oxoheptyl)oxy)phenyl)quinazolin-4-yl)piperazine-1-carboxylate (135 mg, crude). MS (ESI) m/z: 589.2 $[M+H]^+$.

To a solution of tert-butyl 4-(6-chloro-8-fluoro-7-(2-fluoro-6-((7-oxoheptyl)oxy)phenyl)-quinazolin-4-yl)piperazine-1-carboxylate (135 mg, 0.23 mmol) in DCM/MeOH (4 mL:1 mL) were added 3-(6-fluoro-1-oxo-4-(pyrrolidin-3-yl)isoindolin-2-yl)piperidine-2,6-dione (76 mg, 0.23 mmol), $NaBH_3CN$ (29 mg, 0.46 mmol), and acetic acid (1 drop). After 16 h, the mixture was concentrated, and then diluted with $H_2O$ (10 mL) and extracted with EtOAc. The organic phase was dried over anhydrous $Na_2SO_4$, filtered, and concentrated. The residue was purified using silica gel eluting with MeOH in DCM from 0 to 10% to give tert-butyl 4-(6-chloro-7-(2-((7-(3-(2-(2,6-dioxopiperidin-3-yl)-6-fluoro-1-oxoisoindolin-4-yl)pyrrolidin-1-yl)heptyl)oxy)-6-fluorophenyl)-8-fluoroquinazolin-4-yl)piperazine-1-carboxylate (158 mg) in 76% yield. MS (ESI) m/z: 904.3$[M+H]^+$.

To a solution of tert-butyl 4-(6-chloro-7-(2-((7-(3-(2-(2,6-dioxopiperidin-3-yl)-6-fluoro-1-oxoisoindolin-4-yl)pyrrolidin-1-yl)heptyl)oxy)-6-fluorophenyl)-8-fluoroquinazolin-4-yl)piperazine-1-carboxylate (79 mg, 0.09 mmol) in DCM (2 mL) was added TFA (0.5 mL). After 1 h, the solution was concentrated to give 3-(4-(1-(7-(2-(6-chloro-8-fluoro-4-(piperazin-1-yl)quinazolin-7-yl)-3-fluorophenoxy)heptyl)pyrrolidin-3-yl)-6-fluoro-1-oxoisoindolin-2-yl)piperidine-2,6-dione as a TFA salt (72 mg, crude). MS (ESI) m/z: 804 $[M+H]^+$.

To a solution of 3-(4-(1-(7-(2-(6-chloro-8-fluoro-4-(piperazin-1-yl)quinazolin-7-yl)-3-fluorophenoxy)heptyl)pyrrolidin-3-yl)-6-fluoro-1-oxoisoindolin-2-yl)piperidine-2,6-dione (72 mg, 0.09 mmol) and 2-chloroacryloyl chloride (solution in DCM, 0.09 mmol) in DMF (3 mL) was added TEA (36 mg, 0.36 mmol) at 0° C. After 30 min at 0° C., water (10 mL) was added and the mixture was extracted with EtOAc. The organic phase was washed with brine, dried over anhydrous $Na_2SO_4$, filtered, and concentrated. The residue was purified using prep-HPLC to give 3-(4-(1-(7-(2-(6-chloro-4-(4-(2-chloroacryloyl)piperazin-1-yl)-8-fluoroquinazolin-7-yl)-3-fluorophenoxy)-heptyl)pyrrolidin-3-yl)-6-fluoro-1-oxoisoindolin-2-yl)piperidine-2,6-dione 112 (19.6 mg) in 25% yield. $^1$H NMR (400 MHz, DMSO-$d_6$) δ 11.00 (s, 1H), 8.72 (d, J=2.4 Hz, 1H), 8.04 (s, 1H), 7.57-7.51 (m, 1H), 7.43 (d, J=10.8 Hz, 1H), 7.34 (dd, J=2.4, 7.6 Hz, 1H), 7.07 (d, J=8.4 Hz, 1H), 7.00 (t, J=8.8 Hz, 1H), 5.84 (s, 2H), 5.14-5.10 (m, 1H), 4.51-4.23 (m, 2H), 4.03-4.02 (m, 2H), 3.96-3.87 (m, 4H), 3.78-3.71 (m, 4H), 2.97-2.88 (m, 1H), 2.77-2.73 (m, 2H), 2.63-2.58 (m, 2H), 2.41-2.25 (m, 4H), 2.07-1.99 (m, 2H), 1.79-1.72 (m, 1H), 1.53-1.47 (m, 2H), 1.29-1.27 (m, 3H), 1.15-1.13 (m, 6H); MS (ESI) m/z: 892.3 $[M+H]^+$.

Example 19. 3-(5-(1-(7-(2-(6-Chloro-4-(4-(2-chloroacryloyl)piperazin-1-yl)-8-fluoroquinazolin-7-yl)-3-fluorophenoxy)heptyl)piperidin-3-yl)-6-fluoro-1-oxoisoindolin-2-yl)piperidine-2,6-dione 119

119

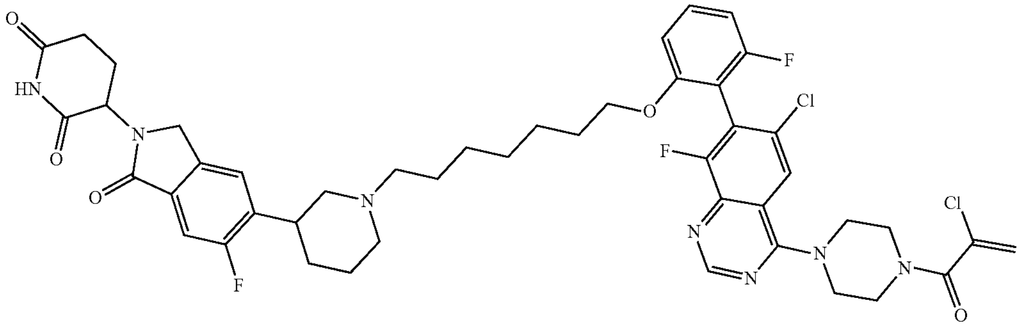

To a solution of tert-butyl 4-(6-chloro-8-fluoro-7-(2-fluoro-6-((7-(methoxy(methyl)amino)-7-oxoheptyl)oxy)phenyl)quinazolin-4-yl)piperazine-1-carboxylate (200 mg, 0.309 mmol) in THF (5 mL) at −78° C. under $N_2$ was added lithium aluminum hydride (0.6 mL, 1 M in THF) dropwise. After 1 h at −78° C. under $N_2$, the mixture was quenched with ammonium chloride (5 mL) and extracted with EtOAc.

The organic phase was dried over anhydrous $Na_2SO_4$, filtered, and concentrated to give tert-butyl 4-(6-chloro-8-fluoro-7-(2-fluoro-6-((7-oxoheptyl)oxy)phenyl)-quinazolin-4-yl)piperazine-1-carboxylate (182 mg, crude). MS (ESI) m/z: 589.2 $[M+H]^+$.

To a solution of tert-butyl 4-(6-chloro-8-fluoro-7-(2-fluoro-6-((7-oxoheptyl)oxy)phenyl)-quinazolin-4-yl)piperazine-1-carboxylate (113 mg, 0.192 mmol) in DCM/MeOH (4 mL:0.5 mL) were added 3-(6-fluoro-1-oxo-5-(piperidin-3-yl)isoindolin-2-yl)piperidine-2,6-dione (65.8 mg, 0.192 mmol), sodium cyanoborohydride (24 mg, 0.384 mmol), and acetic acid (1 drop). After 16 h, the mixture was concentrated and the residue was purified using prep-TLC eluting with DCM/MeOH (10:1) to give tert-butyl 4-(6-chloro-7-(2-((7-(3-(2-(2,6-dioxopiperidin-3-yl)-6-fluoro-1-oxoisoindolin-5-yl)piperidin-1-yl)heptyl)oxy)-6-fluorophenyl)-8-fluoroquinazolin-4-yl)piperazine-1-carboxylate (151 mg) in 86% yield. MS (ESI) m/z: 918.4 $[M+H]^+$.

To a solution of tert-butyl 4-(6-chloro-7-(2-((7-(3-(2-(2,6-dioxopiperidin-3-yl)-6-fluoro-1-oxoisoindolin-5-yl)piperidin-1-yl)heptyl)oxy)-6-fluorophenyl)-8-fluoroquinazolin-4-yl)piperazine-1-carboxylate (100 mg, 0.109 mmol) in DCM (4 mL) was added TFA (1 mL). After 1 h, the solution was concentrated to give 3-(5-(1-(7-(2-(6-chloro-8-fluoro-4-(piperazin-1-yl)quinazolin-7-yl)-3-fluorophenoxy)heptyl)piperidin-3-yl)-6-fluoro-1-oxoisoindolin-2-yl)piperidine-2,6-dione (89 mg, crude) as a TFA salt. MS (ESI) m/z: 818.3$[M+H]^+$.

To a solution 3-(5-(1-(7-(2-(6-chloro-8-fluoro-4-(piperazin-1-yl)quinazolin-7-yl)-3-fluorophenoxy)heptyl)piperidin-3-yl)-6-fluoro-1-oxoisoindolin-2-yl)piperidine-2,6-dione (89 mg, crude) in DCM (4 mL) were added DIPEA (22 mg, 0.218 mmol) and 2-chloroacryloyl chloride (27.2 mg, 0.218 mmol). After 2 h at room temperature, the mixture was concentrated and the residue was purified using prep-HPLC to give 3-(5-(1-(7-(2-(6-chloro-4-(4-(2-chloroacryloyl)piperazin-1-yl)-8-fluoroquinazolin-7-yl)-3-fluorophenoxy)heptyl)piperidin-3-yl)-6-fluoro-1-oxoisoindolin-2-yl)piperidine-2,6-dione 119 (38.4 mg) in 39% yield. $^1H$ NMR (400 MHz, DMSO-$d_6$) δ 11.00 (s, 1H), 9.79 (s, 1H), 8.71 (s, 1H), 8.04 (s, 1H), 7.64 (d, J=5.6 Hz, 1H), 7.57-7.51 (m, 2H), 7.07 (d, J=8.4 Hz, 1H), 7.00 (t, J=8.8 Hz, 1H), 5.85 (s, 2H), 5.12 (dd, J=4.8, 13.2 Hz, 1H), 4.42-4.30 (m, 2H), 4.02 (t, J=6.0 Hz, 2H), 3.93-3.87 (m, 4H), 3.74-3.71 (m, 4H), 3.50-3.49 (m, 1H), 3.19-3.10 (m, 1H), 2.98-2.87 (m, 4H), 2.62-2.58 (m, 1H), 2.49-2.38 (m, 2H), 2.01-1.86 (m, 5H), 1.59-1.51 (m, 4H), 1.22-1.15 (m, 6H); MS (ESI) m/z: 906.3 $[M+H]^+$.

Example 20. 3-(4-(1-(7-(2-(4-((S)-4-(2-Chloroacryloyl)-2-methylpiperazin-1-yl)-6-fluoro-1-(2-isopropyl-4-methylpyridin-3-yl)-2-oxo-1,2-dihydropyrido[2,3-d]pyrimidin-7-yl)-3-fluorophenoxy)heptyl)piperidin-4-yl)-6-fluoro-1-oxoisoindolin-2-yl)piperidine-2,6-dione 122

122

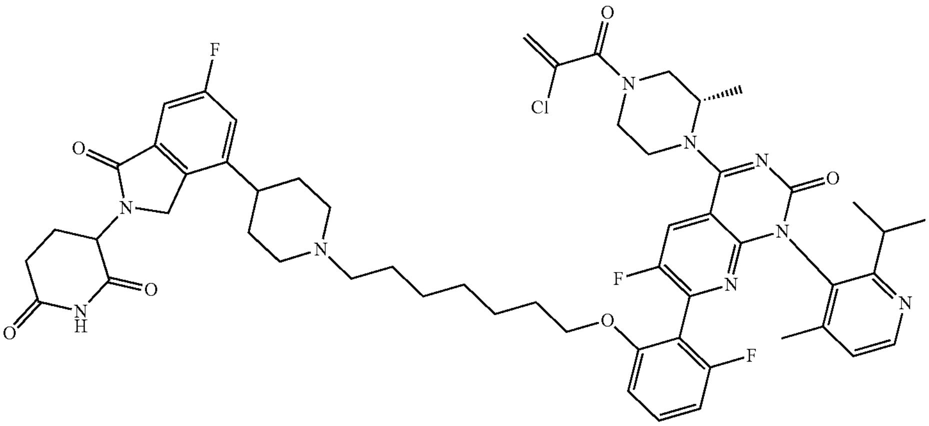

To a solution of 2,6-dichloro-5-fluoronicotinic acid (20 g, 95.7 mmol) in THF (160 mL) was added CDI (17 g, 105.3 mmol). The mixture was stirred for 15 min and then purged with $N_2$. After 2 h at 60° C., the mixture was diluted with toluene (40 mL) and concentrated to a half of the initial volume. The mixture was cooled to 0° C. and aqueous $NH_3$ (24 mL) was added slowly. The mixture was stirred for 1 h at room temperature, and then diluted with EtOAc and washed with $H_2O$. The organic phase was dried over anhydrous $Na_2SO_4$, filtered, and concentrated. The residue was purified using silica gel eluting with PE/EtOAc (3:1) to give 2,6-dichloro-5-fluoronicotinamide (13.5 g) in 69% yield. $^1H$ NMR (400 MHz, $CDCl_3$) δ 8.23 (d, J=8.0 Hz, 1H), 8.10 (s, 1H), 7.94 (s, 1H); MS (ESI) m/z: 208.9 $[M+1]^+$.

To a solution of 2-chloro-4-methyl-3-nitropyridine (16 g, 93.0 mmol), 4,4,5,5-tetramethyl-2-(prop-1-en-2-yl)-1,3,2-dioxaborolane (70.8 g, 416.0 mmol), and cesium carbonate (60.4 g, 184.0 mmol) in dioxane/$H_2O$ (5:1, 60 mL) under $N_2$ was added 1,1'-bis(diphenylphosphino)ferrocene dichloropalladium (II) (680 mg, 0.93 mmol). After 16 h at 100° C., the mixture was diluted with $H_2O$ and extracted with EtOAc. The organic phase was dried over anhydrous $Na_2SO_4$, filtered, and concentrated. The residue was purified using silica gel eluting with petroleum/EtOAc (100:1) to give 4-methyl-3-nitro-2-(prop-1-en-2-yl)pyridine (14.7 g) in 87% yield. $^1H$ NMR (400 MHz, $CDCl_3$) δ 8.65 (d, J=6.8 Hz, 1H), 7.52 (d, J=6.4 Hz, 1H), 5.38 (s, 1H), 5.10 (s, 1H), 2.36 (s, 3H), 2.14 (s, 3H).

To a solution of 4-methyl-3-nitro-2-(prop-1-en-2-yl)pyridine (15.8 g, 88.76 mmol) in MeOH (450 mL) was added Pd/C (1.6 g). After 16 h under $H_2$, the mixture was filtered. The filtrate was concentrated to give 2-isopropyl-4-methylpyridin-3-amine (10 g, crude). MS (ESI) m/z: 151.2 $[M+H]^+$.

To a solution of 2,6-dichloro-5-fluoronicotinamide (12 g, 57.69 mmol) in THF (200 mL) at 0° C. was added oxalyl chloride (8.1 g, 63.46 mmol) dropwise. After 2 h at 60° C., the mixture was cooled to −78° C. A solution of 2-isopropyl-4-methylpyridin-3-amine in THF (50 mL) was added dropwise at −78° C. After 1 h at room temperature, the mixture was diluted with $H_2O$ and extracted with EtOAc. The organic phase was dried over anhydrous $Na_2SO_4$, filtered, and concentrated.

EtOAc (50 mL) was added. The solid was collected and washed with EtOAc to afford 2,6-dichloro-5-fluoro-N-((2-isopropyl-4-methylpyridin-3-yl)carbamoyl)nicotinamide (16.9 g) in 76% yield. MS (ESI) m/z: 385.0[M+H]$^+$.

To a solution of 2,6-dichloro-5-fluoro-N-((2-isopropyl-4-methylpyridin-3-yl)carbamoyl)-nicotinamide (15.9 g, 41.40 mmol) in THF (350 mL) at 0° C. was added 1M KHMDS in THF (83 mL, 82.8 mmol) dropwise. After 4 h at room temperature, the mixture was quenched with saturated aqueous $NH_4Cl$ and extracted with EtOAc. The organic phase was dried over anhydrous $Na_2SO_4$, filtered, and concentrated. The residue was washed with DCM. The solid was collected, and the filtrate was concentrated and purified using silica gel eluting with PE/EtOAc (2:1), to give 7-chloro-6-fluoro-1-(2-isopropyl-4-methylpyridin-3-yl)pyrido[2,3-d]pyrimidine-2,4(1H,3H)-dione (11.0 g) in 76% yield. MS (ESI) m/z: 349.1 [M+H]$^+$.

To a solution of 7-chloro-6-fluoro-1-(2-isopropyl-4-methylpyridin-3-yl)pyrido[2,3-d]pyrimidine-2,4(1H,3H)-dione (2 g, 5.75 mmol) and DIPEA (1.48 g, 11.49 mmol) in toluene (20 mL) was added phosphorus oxychloride (1.32 g, 8.62 mmol). After 1 h at 50° C., the mixture was concentrated and the residue was dissolved in ACN (20 mL). DIPEA (1.48 g, 11.49 mmol) and (S)-tert-butyl 3-methylpiperazine-1-carboxylate were added. After 2 h, the mixture was diluted with $H_2O$ and extracted with EtOAc. The organic phase was dried over $Na_2SO_4$, filtered, and concentrated. The residue was purified using silica gel eluting with PE/EtOAc (1:1) to give (S)-tert-butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (2.7 g) in 88% yield. MS (ESI) m/z: 531.2 [M+H]$^+$.

To a mixture of (2-fluoro-6-hydroxyphenyl)boronic acid (500 mg, 3.18 mmol) in ACN (10 mL) was added $KF \cdot 2H_2O$ (1.2 g, 12.74 mmol) in $H_2O$ (1 mL). After 10 min, a solution of L-(+)-tartaric acid (1.2 g, 7.96 mmol) in THF (5 mL) was added slowly. After 1 h at room temperature, the solid was collected and washed with a small amount of THF. The filtrate was concentrated, cooled to −20° C., stirred for 12 h, and then warmed to room temperature. 2-Propanol (5 mL) was added and the resulting solid was collected by filtration and washed with 2-propanol to give (2-fluoro-6-hydroxyphenyl)potassium trifluoroborate (300 mg) in 55% yield. $^1H$ NMR (400 MHz, DMSO-$d_6$) δ 8.07 (q, J=14.4 Hz, 1H), 6.93 (q, J=8.0 Hz, 1H), 6.36-6.30 (m, 2H).

To a solution of (S)-tert-butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (200 mg, 0.377 mmol), (2-fluoro-6-hydroxyphenyl)potassium trifluoroborate (123 mg, 0.566 mmol), and potassium acetate (148 mg, 1.51 mmol) in dioxane/$H_2O$ (4:1, 3 mL) under $N_2$ was added 1,1'-bis(diphenyl-phosphino)ferrocene dichloropalladium (II) (28 mg, 0.038 mmol). After purged with $N_2$, the mixture was heated at 100° C. for 3 h. The mixture was diluted with $H_2O$ and extracted with EtOAc.

The organic phase was dried over anhydrous $Na_2SO_4$, filtered, and concentrated. The residue was purified using prep-TLC eluting with DCM/MeOH (30:1) to afford (3S)-tert-butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate (205 mg) in 89% yield. MS (ESI) m/z: 607.3[M+H]$^+$.

To a solution of 7-iodo-N-methoxy-N-methylheptanamide (600 mg, 2.01 mmol) in THF (70 mL) at −70° C. under $N_2$ was added $LiAlH_4$ (4.0 mL, 1 M in THF) dropwise. After 1 h at −70° C. under $N_2$, the mixture was quenched with saturated aqueous $NH_4Cl$ (30 mL) and extracted with EtOAc. The organic phase was dried over anhydrous $Na_2SO_4$, filtered, and concentrated to give 7-iodoheptanal (430 mg, crude).

To a solution of tert-butyl 4-(2-(2,6-dioxopiperidin-3-yl)-6-fluoro-1-oxoisoindolin-4-yl)piperidine-1-carboxylate (800 mg, 1.80 mmol) in DCM (9 mL) was added TFA (3 mL). After 1 h, the solution was concentrated to give 3-(6-fluoro-1-oxo-4-(piperidin-4-yl)isoindolin-2-yl)piperidine-2,6-dione (crude) as a TFA salt. MS (ESI) m/z: 346.1 [M+H]$^+$.

To a solution of 3-(6-fluoro-1-oxo-4-(piperidin-4-yl)isoindolin-2-yl)piperidine-2,6-dione (crude) in DCM/MeOH (3:1, 4 mL) at 0° C. was added DIPEA (700 mg, 5.40 mmol) dropwise. 7-Iodoheptanal in DCM/MeOH (3:1, 4 mL), acetic acid (0.3 mL) and sodium cyanoborohydride (454 mg, 7.20 mmol) were added at 0° C. After 16 h at room temperature, the mixture was concentrated and the residue was purified using silica gel eluting with DCM/MeOH (40:1) to give 3-(6-fluoro-4-(1-(7-iodoheptyl)piperidin-4-yl)-1-oxoisoindolin-2-yl)piperidine-2,6-dione (620 mg) in 54% yield. MS (ESI) m/z: 570.1[M+H]$^+$.

To a solution of (3S)-tert-butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate (170 mg, 0.281 mmol) in DMF (5 mL) were added 3-(6-fluoro-4-(1-(7-iodoheptyl)piperidin-4-yl)-1-oxoisoindolin-2-yl)piperidine-2,6-dione (400 mg, 0.701 mmol) and potassium carbonate (97 mg, 0.701 mmol). After 16 h at 30° C., the mixture was diluted with $H_2O$ and extracted with EtOAc. The organic phase was dried over anhydrous $Na_2SO_4$, filtered, and concentrated. The residue was purified using prep-TLC eluting with DCM/MeOH (30:1) to give (3S)-tert-butyl 4-(7-(2-((7-(4-(2-(2,6-dioxopiperidin-3-yl)-6-fluoro-1-oxoisoindolin-4-yl)piperidin-1-yl)heptyl)oxy)-6-fluorophenyl)-6-fluoro-1-(2-isopropyl-4-methylpyridin-3-yl)-2-oxo-1,2-dihydropyrido[2,3-d]pyrimidin-4-yl)-3-methylpiperazine-1-carboxylate (180 mg, crude).

To a solution of (3S)-tert-butyl 4-(7-(2-((7-(4-(2-(2,6-dioxopiperidin-3-yl)-6-fluoro-1-oxoisoindolin-4-yl)piperidin-1-yl)heptyl)oxy)-6-fluorophenyl)-6-fluoro-1-(2-isopropyl-4-methylpyridin-3-yl)-2-oxo-1,2-dihydropyrido[2,3-d]pyrimidin-4-yl)-3-methylpiperazine-1-carboxylate (180 mg, crude) in DCM (1.5 mL) was added TFA (0.5 mL). After 1 h, the mixture was concentrated. The residue was dissolved in THF (2 mL) and potassium carbonate (70 mg, 0.515 mmol) was added. After 30 min, the mixture was concentrated and the residue was purified using prep-TLC eluting with DCM/MeOH (10:1) to give (3-(6-fluoro-4-(1-(7-(3-fluoro-2-(6-fluoro-1-(2-isopropyl-4-methylpyridin-3-yl)-4-((S)-2-methylpiperazin-1-yl)-2-oxo-1,2-dihydropyrido[2,3-d]pyrimidin-7-yl)phenoxy)heptyl)piperidin-4-yl)-1-oxoisoindolin-2-yl)piperidine-2,6-dione (80 mg) in 50% yield. MS (ESI) m/z: 948.5[M+H]$^+$.

To a solution of 2-chloroacrylic acid (30 mg, 0.28 mmol) in DCM (1 mL) at 0° C. were added oxalyl chloride (30 mg, 0.24 mmol) and DMF (1 drop). The solution was stirred for 2 h at room temperature. To a solution of (3-(6-fluoro-4-(1-(7-(3-fluoro-2-(6-fluoro-1-(2-isopropyl-4-methylpyridin-3-yl)-4-((S)-2-methylpiperazin-1-yl)-2-oxo-1,2-dihydropyrido[2,3-d]pyrimidin-7-yl)phenoxy)heptyl)piperidin-4-yl)-1-oxoisoindolin-2-yl)piperidine-2,6-dione (80 mg, 0.084 mmol) in DCM (1 mL) at 0° C. were added the 2-chloroacryloyl chloride solution and TEA (25 mg, 0.25 mmol). After 20 min at 0° C., the mixture was quenched with saturated aqueous $NaHCO_3$(5 mL) and extracted with DCM. The organic phase was washed with brine, dried over anhydrous $Na_2SO_4$, filtered, and concentrated. The residue was purified using prep-HPLC to give 3-(4-(1-(7-(2-(4-((S)-4-(2-chloroacryloyl)-2-methylpiperazin-1-yl)-6-fluoro-1-

(2-isopropyl-4-methylpyridin-3-yl)-2-oxo-1,2-dihydropyrido[2,3-d]pyrimidin-7-yl)-3-fluorophenoxy)heptyl)piperidin-4-yl)-6-fluoro-1-oxoisoindolin-2-yl)piperidine-2,6-dione 122 (37.1 mg) in 43% yield. $^1$H NMR (400 MHz, DMSO-$d_6$) δδ11.00 (s, 1H), 8.40-8.37 (m, 2H), 8.15 (d, J=3.2 Hz, 1H), 7.46-7.34 (m, 3H), 7.19 (dd, J=4.0, 12.8 Hz, 1H), 6.96 (d, J=8.8 Hz, 1H), 6.86 (t, J=8.8 Hz, 1H), 5.87-5.84 (m, 2H), 5.13 (dd, J=5.6, 13.2 Hz, 1H), 5.01-4.85 (m, 1H), 4.54-4.26 (m, 4H), 3.95-3.91 (m, 2H), 3.80-3.66 (m, 2H), 2.96-2.92 (m, 3H), 2.69-2.62 (m, 1H), 2.44-2.38 (m, 2H), 2.27-2.21 (m, 3H), 2.01-1.88 (m, 7H), 1.75-1.72 (m, 4H), 1.51-1.46 (m, 2H), 1.37-1.34 (m, 5H), 1.17-1.13 (m, 5H), 1.07 (d, J=6.4 Hz, 3H), 0.94 (d, J=6.4 Hz, 2H), 0.85 (d, J=5.2 Hz, 2H).

Example 21. 2-((2R)-4-(6-Chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoro-2-(((S)-1-methylpyrrolidin-2-yl)methoxy)quinazolin-4-yl)-1-(2-chloroacryloyl)piperazin-2-yl)acetonitrile 128

(cyanomethyl)piperazine-1-carboxylate (1.25 g) in 23% yield. MS (ESI) m/z: 631.1 $[M+H]^+$.

To a solution of (R)-benzyl 4-(7-bromo-6-chloro-8-fluoro-2-(((S)-1-methylpyrrolidin-2-yl)methoxy)quinazolin-4-yl)-2-(cyanomethyl)piperazine-1-carboxylate (1.25 g, 1.98 mmol) and (2-fluoro-6-hydroxyphenyl)boronic acid (1.54 g, 10 mmol) in 1,4-dioxane (45 mL) and water (5 mL) were added potassium carbonate (820 mg, 6 mmol) and tetrakis(triphenylphosphine)palladium (458 mg, 0. 4 mmol). After 16 h at 100° C., the mixture was concentrated and the residue was purified using silica gel eluting with DCM/MeOH (10:1) to give (2R)-benzyl 4-(6-chloro-8-fluoro-7-(2-fluoro-6-hydroxyphenyl)-2-(((S)-1-methylpyrrolidin-2-yl)methoxy)quinazolin-4-yl)-2-(cyanomethyl)piperazine-1-carboxylate (800 mg) in 61% yield. MS (ESI) m/z: 663.2 $[M+H]^+$.

To a solution of (2R)-benzyl 4-(6-chloro-8-fluoro-7-(2-fluoro-6-hydroxyphenyl)-2-(((S)-1-methylpyrrolidin-2-yl)methoxy)quinazolin-4-yl)-2-(cyanomethyl)piperazine-1-carboxylate (530 mg, 0.8 mmol) in DMF (10 mL) were added 7-iodo-N-methoxy-N-methylheptanamide (480 mg,

128

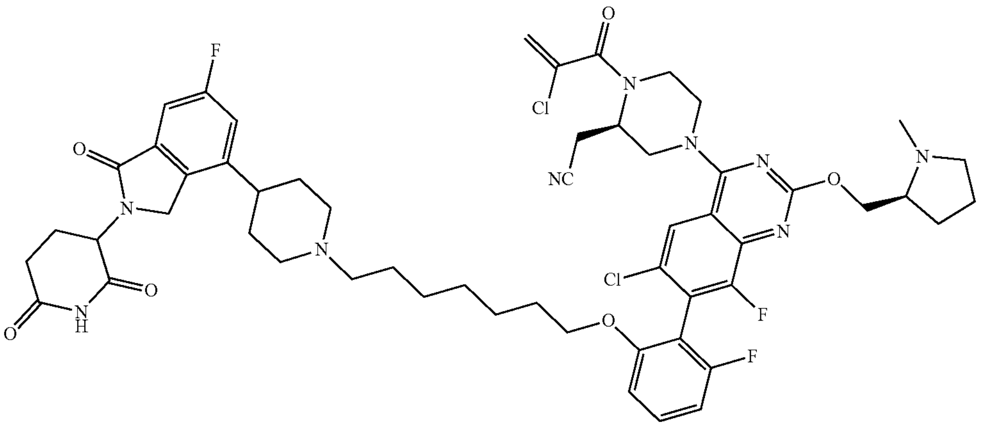

To a solution of phosphorus oxychloride (50 mL) at 0° C. were added DIPEA (6.6 g, 54 mmol) and 7-bromo-6-chloro-8-fluoroquinazoline-2,4(1H,3H)-dione (5.5 g, 18 mmol). After 16 h at 105° C., the solution was concentrated to give 7-bromo-2,4,6-trichloro-8-fluoroquinazoline (crude). MS (ESI) m/z: 328.8 $[M+H]^+$.

To a solution of 7-bromo-2,4,6-trichloro-8-fluoroquinazoline (18 mmol, crude) in DCM (20 mL) at 0° C. were added DIPEA (8.5 mL) and (R)-benzyl 2-(cyanomethyl)piperazine-1-carboxylate (19.5 mmol). After 1 h for room temperature, water was added and the mixture was extracted with DCM. The organic phase was washed with brine, dried over anhydrous $Na_2SO_4$, filtered, and concentrated. The residue was purified using silica gel eluting with PE/EtOAc (3:1) to give (R)-benzyl 4-(7-bromo-2,6-dichloro-8-fluoroquinazolin-4-yl)-2-(cyanomethyl)-piperazine-1-carboxylate (4.8 g) in 48% yield. MS (ESI) m/z: 553.9 $[M+H]^+$.

To a solution of (R)-benzyl 4-(7-bromo-2,6-dichloro-8-fluoroquinazolin-4-yl)-2-(cyanomethyl)piperazine-1-carboxylate (4.8 g, 8.68 mmol) and (S)-(1-methylpyrrolidin-2-yl)methanol (2 g, 17 mmol) in DMF (40 mL) was added potassium carbonate (3.6 g, 26 mmol). After 16 h at 80° C., water was added and the mixture was extracted with EtOAc. The organic phase was washed with brine, dried over anhydrous $Na_2SO_4$, filtered, and concentrated. The residue was purified using silica gel eluting with DCM/MeOH (10:1) to give (R)-benzyl 4-(7-bromo-6-chloro-8-fluoro-2-(((S)-1-methylpyrrolidin-2-yl)methoxy)quinazolin-4-yl)-2-

1.6 mmol) and potassium carbonate (221 mg, 1.6 mmol). After 16 h, the mixture was diluted with water and extracted with EtOAc. The organic phase was washed with brine, dried over anhydrous $Na_2SO_4$, filtered, and concentrated. The residue was purified using silica gel eluting with DCM/MeOH (10:1) to give (2R)-benzyl 4-(6-chloro-8-fluoro-7-(2-fluoro-6-((7-(methoxy(methyl)amino)-7-oxoheptyl)oxy)phenyl)-2-(((S)-1-methylpyrrolidin-2-yl)methoxy)-quinazolin-4-yl)-2-(cyanomethyl)piperazine-1-carboxylate (310 mg) in 47% yield. MS (ESI) m/z: 834.4 $[M+H]^+$.

To a solution of (2R)-benzyl 4-(6-chloro-8-fluoro-7-(2-fluoro-6-((7-(methoxy(methyl)-amino)-7-oxoheptyl)oxy)phenyl)-2-(((S)-1-methylpyrrolidin-2-yl)methoxy)quinazolin-4-yl)-2-(cyanomethyl)piperazine-1-carboxylate (80 mg, 0.09 mmol) in THF (2 mL) at −78° C. under $N_2$ was dropwise added lithium aluminum hydride (1 M in THF, 0.18 mL). After 1 h at −78° C., the mixture was quenched with saturated aqueous $NH_4Cl$ (5 mL) and extracted with EtOAc. The organic phase was washed with brine, dried over anhydrous $Na_2SO_4$, filtered, and concentrated to give (2R)-benzyl 4-(6-chloro-8-fluoro-7-(2-fluoro-6-((7-oxoheptyl)oxy)phenyl)-2-(((S)-1-methylpyrrolidin-2-yl)methoxy)quinazolin-4-yl)-2-(cyanomethyl)piperazine-1-carboxylate (70 mg, crude). MS (ESI) m/z: 775.2 $[M+H]^+$.

To a solution of (2R)-benzyl 4-(6-chloro-8-fluoro-7-(2-fluoro-6-((7-oxoheptyl)oxy)-phenyl)-2-(((S)-1-methylpyrrolidin-2-yl)methoxy)quinazolin-4-yl)-2-(cyanomethyl)piperazine-1-carboxylate (0.09 mmol) and 3-(6-fluoro-1-oxo-4-(piperidin-4-yl)isoindolin-2-yl)piperidine-2,6-dione (0.09 mmol) in DCM (2 mL) and MeOH (0.5 mL) were added sodium cyanoborohydride (12 mg, 0.18 mmol) and acetic acid (1 drop). After 16 h, the mixture was concentrated and the residue was purified using prep-TLC eluting with DCM/MeOH (10:1) to give (2R)-benzyl 4-(6-chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoro-2-(((S)-1-methylpyrrolidin-2-yl)methoxy)quinazolin-4-yl)-2-(cyanomethyl)piperazine-1-carboxylate (88 mg) in 89% yield. MS (ESI) m/z: 553.2 [½M+H]$^+$.

A solution of (2R)-benzyl 4-(6-chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoro-2-(((S)-1-methylpyrrolidin-2-yl)methoxy)quinazolin-4-yl)-2-(cyanomethyl)piperazine-1-carboxylate (88 mg, 0.08 mmol) in TFA (4 mL) was heated at 80° C. for 1 h. The solution was concentrated to give (2R)-benzyl 4-(6-chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoro-2-(((S)-1-methylpyrrolidin-2-yl)methoxy)quinazolin-4-yl)-2-(cyanomethyl)piperazine-1-carboxylate (77 mg, crude). MS (ESI) m/z: 486.0 [½M+H]$^+$.

To a solution of (2R)-benzyl 4-(6-chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoro-2-(((S)-1-methyl-pyrrolidin-2-yl)methoxy)quinazolin-4-yl)-2-(cyanomethyl)piperazine-1-carboxylate (77 mg, 0.08 mmol) in DCM (2 mL) at 0° C. were added TEA (20 mg, 0.32 mmol) and 2-chloroacryloyl chloride (0.16 mmol). After 30 min at 0° C., the mixture was concentrated and the residue was purified using prep-TLC eluting with DCM/MeOH (5:1) and then prep-HPLC to give 2-((2R)-4-(6-chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoro-2-(((S)-1-methylpyrrolidin-2-yl)methoxy)quinazolin-4-yl)-1-(2-chloro-acryloyl)piperazin-2-yl)acetonitrile 128 (6.1 mg). $^1$H NMR (400 MHz, DMSO-$d_6$) δ 11.06 (s, 1H), 9.74 (brs, 1H), 9.25 (brs, 1H), 8.09 (s, 1H), 7.56 (q, J=7.6 Hz, 1H), 7.46 (dd, J=2.0, 7.2 Hz, 1H), 7.31 (dd, J=2.0, 10.8 Hz, 1H), 7.09 (d, J=8.4 Hz, 1H), 7.01 (t, J=8.8 Hz, 1H), 5.92-5.86 (m, 2H), 5.19 (dd, J=4.8, 12.8 Hz, 1H), 4.78-4.33 (m, 6H), 4.06-4.05 (m, 2H), 3.84 (brs, 1H), 3.59-3.56 (m, 4H), 3.05-2.97 (m, 12H), 2.68-2.62 (m, 3H), 2.34-2.27 (m, 3H), 2.04-1.93 (m, 11H), 1.62-1.54 (m, 4H), 1.32-1.24 (m, 4H); MS (ESI) m/z=1058.4 [M+H]$^+$.

The following compounds were prepared similarly.

3-(2-(2-(2-(4-(4-Acryloylpiperazin-1-yl)-6-chloro-8-fluoroquinazolin-7-yl)-3-fluorophenoxy)ethoxy)ethoxy)-N-(2-((2-(2,6-dioxopiperidin-3-yl)-1,3-dioxoisoindolin-4-yl)oxy)ethyl)propanamide 3. MS (ESI) m/z: 890.2 [M+H]$^+$.

3

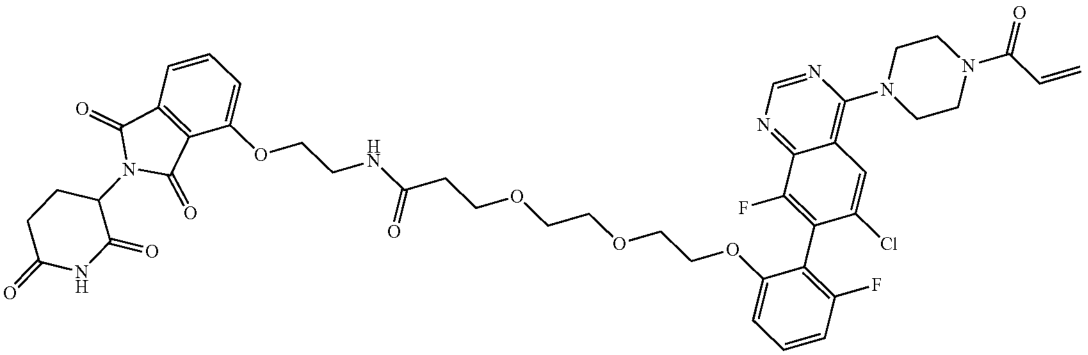

3-(1-((4-(((2-(2-(7-(3-Hydroxynaphthalen-1-yl)-2-oxo-3-(1-propionylazetidin-3-yl)-3,4-dihydroquinazolin-1(2H)-yl)ethoxy)ethyl)amino)methyl)phenoxy)methyl)-4-oxo-4H-thieno[3,4-c]pyrrol-5(6H)-yl)piperidine-2,6-dione 5. MS (ESI) m/z: 857.2 [M+H]$^+$.

5

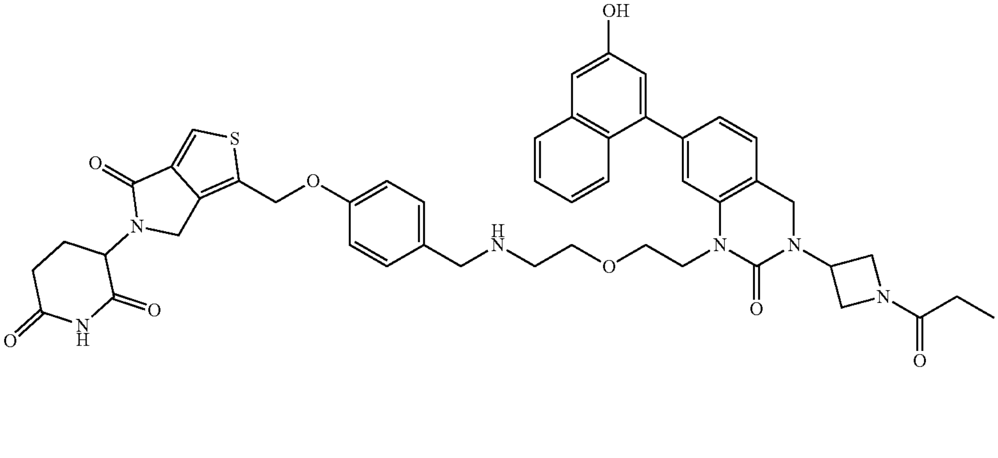

3-(2-(2-(2-(6-Chloro-8-fluoro-4-(4-propionylpiperazin-1-yl)quinazolin-7-yl)-3-fluorophenoxy)ethoxy)ethoxy)-N-(2-((2-(2,6-dioxopiperidin-3-yl)-1,3-dioxoisoindolin-4-yl)amino)ethyl)propanamide 6. $^{1}$H NMR (400 MHz, DMSO-$d_6$) δ11.08 (s, 1H), 8.69 (d, J=2.8 Hz, 1H), 8.05-8.03 (m, 2H), 7.58-7.53 (m, 2H), 7.15 (d, J=8.4 Hz, 1H), 7.09 (d, J=8.4 Hz, 1H), 7.04-6.99 (m, 2H), 6.71 (t, J=5.6 Hz, 1H), 5.06 (dd, J=5.2, 12.4 Hz, 1H), 4.16-4.10 (m, 2H), 3.92-3.83 (m, 4H), 3.70-3.65 (m, 4H), 3.55 (t, J=4.4 Hz, 2H), 3.45 (t, J=6.4 Hz, 4H), 3.28-3.22 (m, 6H), 2.93-2.84 (m, 1H), 2.61-2.53 (m, 2H), 2.39-2.33 (m, 2H), 2.24-2.21 (m, 2H), 2.03-1.97 (m, 1H), 1.03-0.97 (m, 3H); MS (ESI) m/z: 891.2 $[M+H]^+$.

6

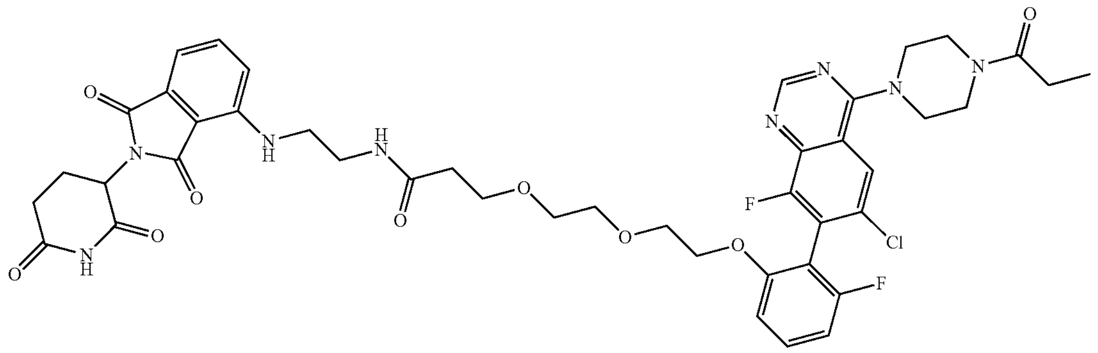

N-(2-((2-(2,6-Dioxopiperidin-3-yl)-1,3-dioxoisoindolin-4-yl)oxy)ethyl)-3-(2-(2-(7-(3-hydroxynaphthalen-1-yl)-2-oxo-3-(1-propionylazetidin-3-yl)-3,4-dihydroquinazolin-1(2H)-yl)ethoxy)ethoxy)propanamide 7. $^{1}$H NMR (400 MHz, DMSO-$d_6$) δ 11.08 (s, 1H), 9.84 (s, 1H), 8.00-7.98 (m, 1H), 7.95 (t, J=5.6 Hz, 1H), 7.78-7.74 (m, 1H), 7.68 (d, J=8.4 Hz, 1H), 7.59-7.57 (m, 1H), 7.53-7.48 (m, 1H), 7.44-7.38 (m, 3H), 7.25-7.21 (m, 1H), 7.16 (d, J=2.4 Hz, 1H), 7.06-7.05 (m, 1H), 7.05-7.03 (m, 1H), 5.07 (dd, J=5.6, 12.8 Hz, 1H), 4.95-4.93 (m, 1H), 4.79-4.77 (m, 2H), 4.53-4.52 (m, 2H), 4.19 (t, J=6.0 Hz, 2H), 3.95-3.91 (m, 2H), 3.55 (t, J=6.0 Hz, 2H), 3.48-3.38 (m, 8H), 2.86-2.84 (m, 1H), 2.67-2.66 (m, 1H), 2.59-2.57 (m, 1H), 2.33-2.3 (m, 1H), 2.21 (t, J=6.4 Hz, 2H), 2.07-1.99 (m, 4H), 0.93 (t, J=7.6 Hz, 3H); MS (ESI) m/z: 861.2 $[M+H]^+$.

7

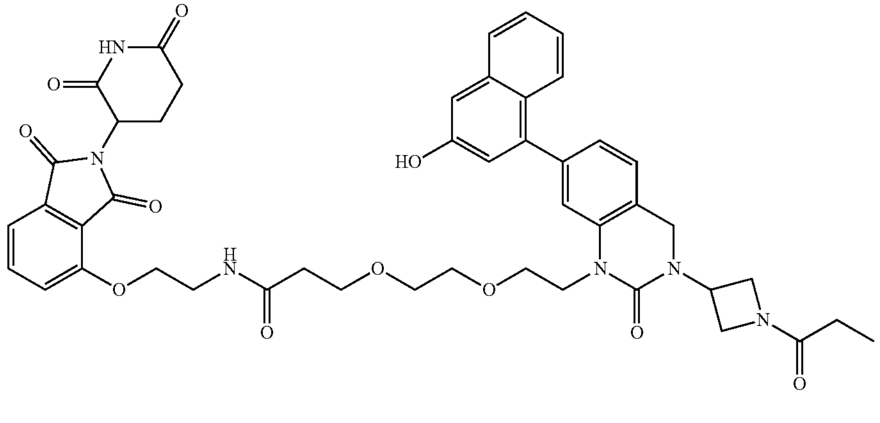

3-(2-(2-(2-(6-Chloro-8-fluoro-4-(4-propionylpiperazin-1-yl)quinazolin-7-yl)-3-fluorophenoxy)ethoxy)ethoxy)-N-(2-((2-(2,6-dioxopiperidin-3-yl)-1,3-dioxoisoindolin-4-yl)oxy)ethyl)propanamide 8. $^{1}$H NMR (400 MHz, DMSO-$d_6$) δ 11.10 (s, 1H), 8.68 (d, J=2.8 Hz, 1H), 8.05 (t, J=4.8 Hz, 2H), 7.82-7.77 (m, 1H), 7.57-7.50 (m, 2H), 7.45 (d, J=6.8 Hz, 1H), 7.09 (d, J=8.4 Hz, 1H), 7.04-6.99 (m, 1H), 5.08 (dd, J=5.6, 12.8 Hz, 1H), 4.22 (t, J=5.6 Hz, 2H), 4.17-4.09 (m, 2H), 3.91-3.79 (m, 4H), 3.69-3.65 (m, 4H), 3.54 (t, J=4.0 Hz, 2H), 3.45-3.40 (m, 4H), 3.27 (d, J=6.4 Hz, 4H), 2.93-2.84 (m, 1H), 2.61-2.53 (m, 2H), 2.38-2.34 (m, 2H), 2.27-2.25 (m, 2H), 2.03-2.01 (m, 1H), 1.04-0.99 (m, 3H); MS (ESI) m/z: 892.2 [M+H]$^+$.

8

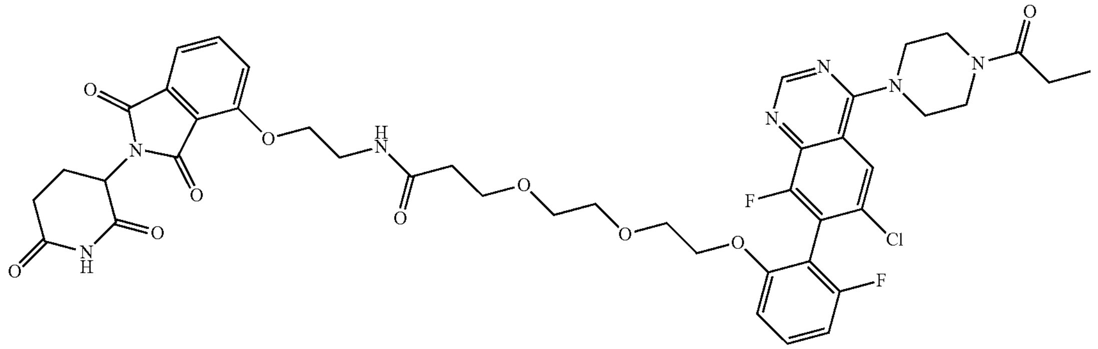

4-((2-(2-(2-(2-(2-(6-Chloro-8-fluoro-4-(4-propionylpiperazin-1-yl)quinazolin-7-yl)-3-fluorophenoxy)ethoxy)ethoxy)ethoxy)ethyl)amino)-2-(2,6-dioxopiperidin-3-yl)isoindoline-1,3-dione 9. $^{1}$H NMR (400 MHz, DMSO-$d_6$) δ 11.08 (s, 1H), 8.67 (s, 1H), 8.02 (s, 1H), 7.57-7.51 (m, 2H), 7.09 (t, J=8.4 Hz, 2H), 7.03-7.01 (m, 2H), 6.57 (t, J=5.6 Hz, 1H), 5.04 (dd, J=5.2, 12.4 Hz, 1H), 4.19-4.08 (m, 2H), 3.90-3.82 (m, 4H), 3.71-3.68 (m, 4H), 3.58-3.54 (m, 4H), 3.46-3.35 (m, 10H), 2.94-2.82 (m, 1H), 2.59-2.53 (m, 1H), 2.49-2.45 (m, 1H), 2.35 (q, J=7.2 Hz, 2H), 2.02-1.99 (m, 1H), 1.28 (t, J=7.2 Hz, 3H); MS (ESI) m/z: 864.2 [M+H]$^+$.

9

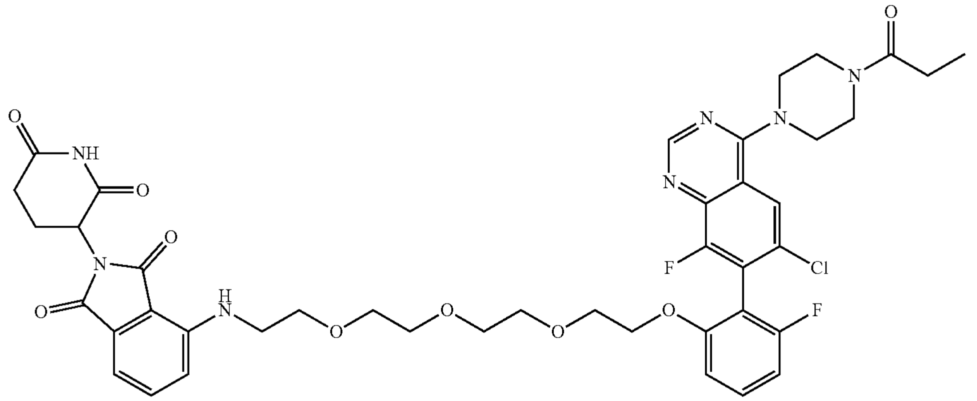

3-(2-(3-(1-Acryloylazetidin-3-yl)-7-(3-hydroxynaphthalen-1-yl)-2-oxo-3,4-dihydroquinazolin-1(2H)-yl)ethoxy)-N-(2-((2-(2,6-dioxopiperidin-3-yl)-1,3-dioxoisoindolin-4-yl)oxy)ethyl)propanamide 10. $^{1}$H NMR (400 MHz, DMSO-$d_6$) δ 11.08 (s, 1H), 9.87 (s, 1H), 7.98 (t, J=4.0 Hz, 1H), 7.81-7.71 (m, 2H), 7.65 (d, J=8.8 Hz, 1H), 7.51-7.34 (m, 4H), 7.23 (t, J=7.4 Hz, 1H), 7.17-7.13 (m, 1H), 7.12-7.04 (m, 2H), 7.03-6.99 (m, 1H), 6.34 (dd, J=16.8, 10.0 Hz, 1H), 6.12 (dd, J=1.6, 16.8 Hz, 1H), 5.69 (dd, J=1.6, 10.0 Hz, 1H), 5.06 (dd, J=12.8, 4.8 Hz, 1H), 4.98-4.88 (m, 1H), 4.56-4.35 (m, 4H), 4.23-4.08 (m, 4H), 4.04-3.91 (m, 2H), 3.62-3.53 (m, 4H), 3.01-2.94 (m, 1H), 2.89-2.81 (m, 1H), 2.62-2.54 (m, 2H), 2.27 (t, J=6.2 Hz, 2H), 2.04-1.93 (m, 2H); MS (ESI) m/z: 815.2 [M+H]$^+$.

10

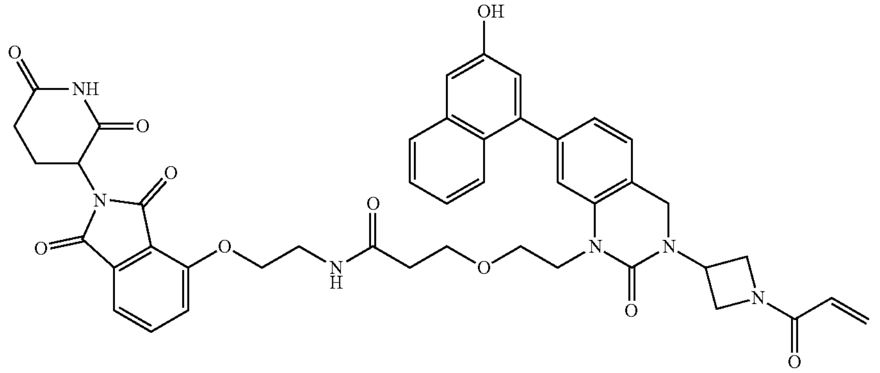

3-(2-(2-(3-(1-Acryloylazetidin-3-yl)-7-(3-hydroxynaphthalen-1-yl)-2-oxo-3,4-dihydroquinazolin-1(2H)-yl)ethoxy)ethoxy)-N-(2-((2-(2,6-dioxopiperidin-3-yl)-1,3-dioxoisoindolin-4-yl)oxy)ethyl)propanamide 11. $^1$H NMR (400 MHz, DMSO-$d_6$) δ 11.10 (s, 1H), 9.88 (s, 1H), 8.02 (t, J=5.6 Hz, 1H), 7.79-7.74 (m, 2H), 7.65 (d, J=8.4 Hz, 1H), 7.51 (d, J=8.8 Hz, 1H), 7.45-7.38 (m, 3H), 7.22 (t, J=7.6 Hz, 1H), 7.16 (d, J=2.4 Hz, 1H), 7.14 (s, 1H), 7.07 (d, J=7.6 Hz, 1H), 7.01 (d, J=2.4 Hz, 1H), 6.35 (dd, J=10.0, 16.8 Hz, 1H), 6.12 (dd, J=2.4, 16.8 Hz, 1H), 5.69 (dd, J=2.0, 10.0 Hz, 1H), 5.07 (dd, J=5.6, 12.4 Hz, 1H), 4.97-4.91 (m, 1H), 4.55-4.41 (m, 4H), 4.20 (t, J=5.6 Hz, 2H), 4.14 (d, J=7.6 Hz, 2H), 3.98 (t, J=5.6 Hz, 2H), 3.59 (t, J=5.6 Hz, 2H), 3.46-3.41 (m, 8H), 2.88-2.84 (m, 1H), 2.59-2.55 (m, 1H), 2.48-2.44 (m, 1H), 2.21 (t, J=6.4 Hz, 2H), 2.01-1.97 (m, 1H); MS (ESI) m/z: 881.2 [M+Na]+.

11

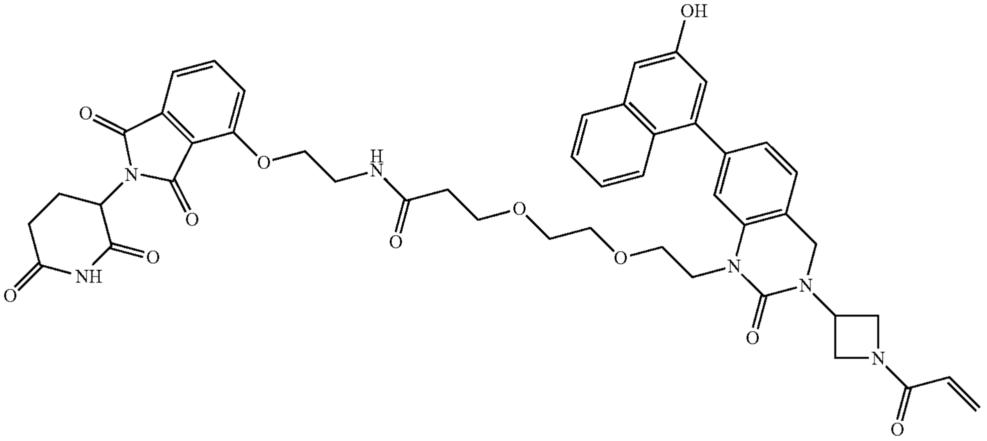

2-(2,6-Dioxopiperidin-3-yl)-4-((2-(2-(2-(2-(7-(3-hydroxynaphthalen-1-yl)-2-oxo-3-(1-propionylazetidin-3-yl)-3,4-dihydroquinazolin-1(2H)-yl)ethoxy)ethoxy)ethoxy)ethyl)amino)-isoindoline-1,3-dione 12. $^1$H NMR (400 MHz, DMSO-$d_6$) δ 11.07 (s, 1H), 9.85 (s, 1H), 7.74 (d, J=8.4 Hz, 1H), 7.66 (d, J=8.4 Hz, 1H), 7.54 (t, J=8.0 Hz, 1H), 7.41-7.37 (m, 2H), 7.22 (d, J=7.6 Hz, 1H), 7.16 (s, 2H), 7.08-7.00 (m, 4H), 6.54 (t, J=5.6 Hz, 1H), 5.03 (dd, J=5.2, 12.8 Hz, 1H), 4.88 (t, J=6.4 Hz, 1H), 4.52-4.44 (m, 2H), 4.33-4.25 (m, 2H), 4.05-4.03 (m, 2H), 3.97 (t, J=6.0 Hz, 2H), 3.61-3.48 (m, 14H), 2.90-2.83 (m, 1H), 2.59-2.50 (m, 2H), 2.09 (q, J=7.6 Hz, 2H), 2.01-1.91 (m, 1H), 0.98 (t, J–7.6 Hz, 3H); MS (ESI) m/z: 833.2 [M+H]$^+$.

12

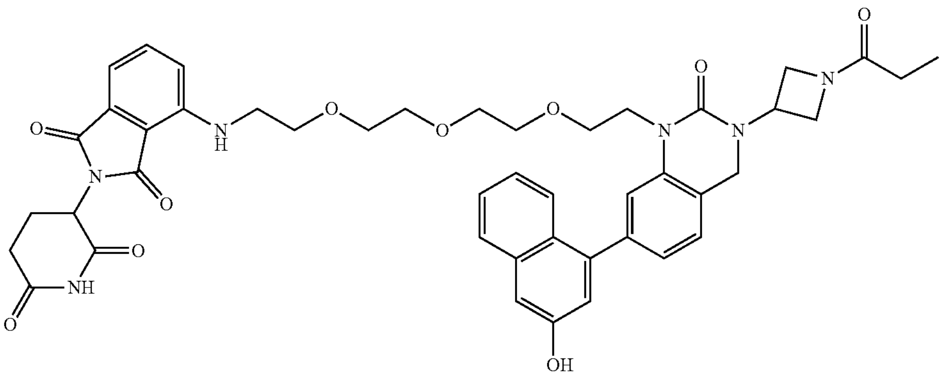

2-(4-Acryloyl-1-(6-chloro-8-fluoro-7-(2-fluoro-6-hydroxyphenyl)quinazolin-4-yl)piperazin-2-yl)-N-(5-(3-((5-(2,6-dioxopiperidin-3-yl)-6-oxo-5,6-dihydro-4H-thieno[2,3-c]pyrrol-2-yl)methyl)ureido)pentyl)acetamide 13. $^1H$ NMR (400 MHz, DMSO-$d_6$) δ 10.93 (s, 1H), 10.29 (brs, 1H), 8.68 (s, 1H), 8.04-8.02 (m, 2H), 7.39-7.33 (m, 1H), 7.03 (s, 1H), 6.87-6.75 (m, 3H), 6.49-6.45 (m, 1H), 6.19 (dd, J=2.0, 16.8 Hz, 1H), 6.03-5.98 (m, 1H), 5.75-5.73 (m, 1H), 5.18-5.11 (m, 1H), 4.96 (dd, J=5.2, 13.6 Hz, 1H), 4.47-4.12 (m, 6H), 3.76-3.57 (m, 4H), 3.17-3.13 (m, 1H), 2.96-2.83 (m, 5H), 2.73-2.72 (m, 1H), 2.60-2.55 (m, 1H), 2.38-2.28 (m, 1H), 2.03-1.96 (m, 1H), 1.28-1.16 (m, 6H); MS (ESI) m/z: 878.2 $[M+H]^+$.

13

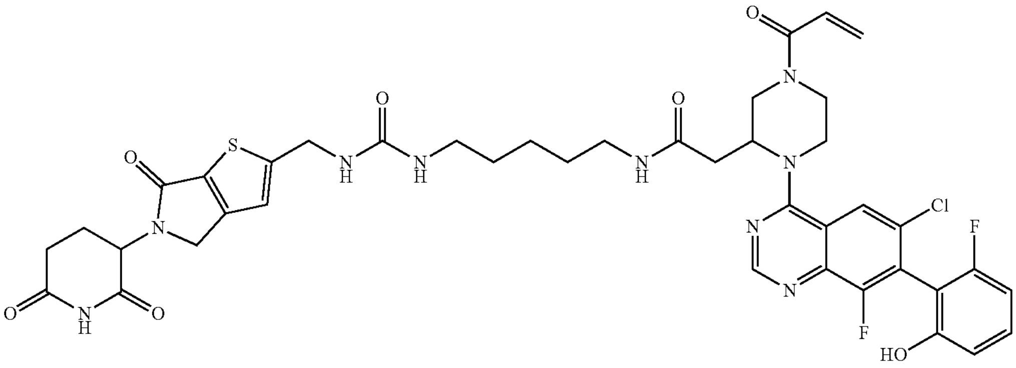

(S)-3-(1-((4-(((2-(2-(1-Acryloylazetidin-3-yl)-6-(3-hydroxynaphthalen-1-yl)-4-oxoquinazolin-3(4H)-yl)ethyl)amino)methyl)phenoxy)methyl)-4-oxo-4H-thieno[3,4-c]pyrrol-5(6H)-yl)piperidine-2,6-dione 15. $^1H$ NMR (400 MHz, DMSO-$d_6$) δ 10.93 (s, 1H), 9.94 (s, 1H), 8.10 (s, 1H), 7.99 (s, 1H), 7.92 (dd, J=2.0, 8.0 Hz, 1H), 7.85-7.78 (m, 2H), 7.61 (d, J=8.4 Hz, 1H), 7.43 (t, J=7.2 Hz, 1H), 7.27-7.18 (m, 4H), 7.07 (d, J=2.0 Hz, 1H), 6.88 (d, J=8.4 Hz, 2H), 6.38 (dd, J=10.4, 17.2 Hz, 1H), 6.15 (dd, J=2.4, 17.2 Hz, 1H), 5.71 (dd, J=2.4, 10.4 Hz, 1H), 5.22 (s, 2H), 4.99 (dd, J=4.0, 13.2 Hz, 1H), 4.68 (t, J=7.2 Hz, 1H), 4.58 (t, J=7.6 Hz, 1H), 4.48-4.39 (m, 2H), 4.33-4.15 (m, 4H), 3.98 (t, J=6.0 Hz, 2H), 3.65 (s, 2H), 3.57-3.54 (m, 1H), 2.91-2.83 (m, 1H), 2.78 (t, J=5.6 Hz, 2H), 2.60-2.55 (m, 1H), 2.36-2.24 (m, 1H), 2.01-1.95 (m, 1H); MS (ESI) m/z: 809.2 $[M+H]^+$.

15

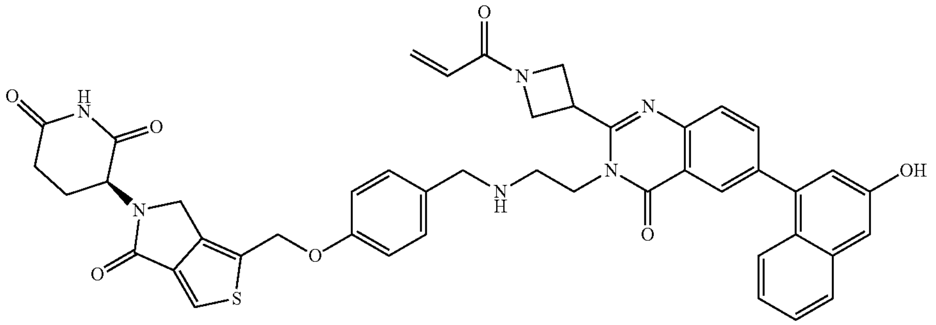

(S)-3-(1-((4-(((4-(3-(1-Acryloylazetidin-3-yl)-7-(3-hydroxynaphthalen-1-yl)-2-oxo-3,4-dihydroquinazolin-1(2H)-yl)butyl)amino)methyl)phenoxy)methyl)-4-oxo-4H-thieno[3,4-c]pyrrol-5(6H)-yl)piperidine-2,6-dione 16. $^{1}$H NMR (400 MHz, DMSO-$d_6$) δ 10.97 (s, 1H), 9.90 (s, 1H), 8.01 (s, 1H), 7.76 (d, J=8.4 Hz, 1H), 7.65 (d, J=8.4 Hz, 1H), 7.41-7.32 (m, 4H), 7.22-7.17 (m, 2H), 7.08 (d, J=7.6 Hz, 1H), 7.04-7.01 (m, 4H), 6.34 (dd, J=10.4, 17.2 Hz, 1H), 6.14 (dd, J=2.4, 17.2 Hz, 1H), 5.69 (dd, J=2.0, 10.0 Hz, 1H), 5.30 (s, 2H), 5.01 (dd, J=5.2, 13.2 Hz, 1H), 4.97-4.89 (m, 1H), 4.58-4.51 (m, 2H), 4.47-4.41 (m, 2H), 4.37-4.19 (m, 2H), 4.14 (d, J=6.8 Hz, 2H), 3.89-3.86 (m, 4H), 2.93-2.84 (m, 1H), 2.79-2.76 (m, 2H), 2.60-2.55 (m, 1H), 2.34-2.31 (m, 1H), 2.02-1.97 (m, 2H), 1.60 (s, 4H); MS (ESI) m/z: 839.2 $[M+H]^+$.

16

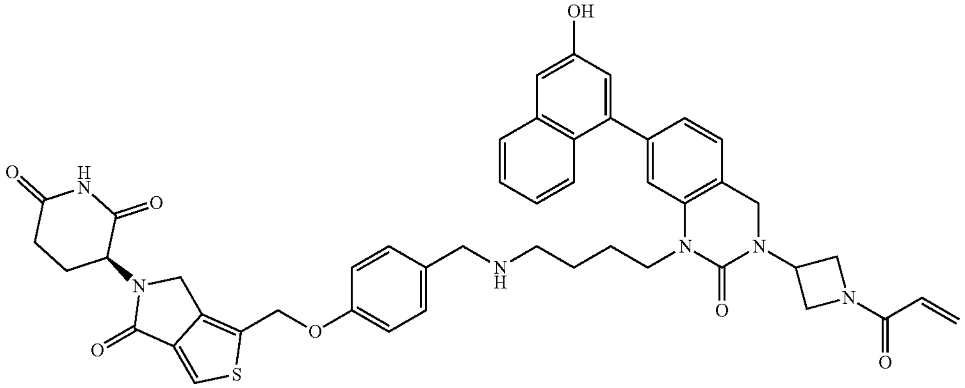

2-(2-(1-Acryloylazetidin-3-yl)-6-(3-hydroxynaphthalen-1-yl)-4-oxoquinazolin-3(4H)-yl)-N-(2-(2-(2-(2-((2-(2,6-dioxopiperidin-3-yl)-1,3-dioxoisoindolin-4-yl)amino)ethoxy)ethoxy)ethoxy)-ethyl)acetamide 17. $^{1}$H NMR (400 MHz, DMSO-$d_6$) δ 11.08 (s, 1H), 9.94 (s, 1H), 8.42 (t, J=5.2 Hz, 1H), 8.11 (d, J=1.6 Hz, 1H), 7.93 (dd, J=2.0, 8.0 Hz, 1H), 7.87-7.79 (m, 2H), 7.80-7.78 (m, 1H), 7.61-7.55 (m, 2H), 7.44 (t, J=7.6 Hz, 1H), 7.26 (t, J=7.2 Hz, 1H), 7.22 (d, J=2.0 Hz, 1H), 7.12 (d, J=8.4 Hz, 1H), 7.07 (d, J=2.4 Hz, 1H), 7.02 (d, J=7.2 Hz, 1H), 6.58 (t, J=5.2 Hz, 1H), 6.37 (dd, J=10.4, 16.8 Hz, 1H), 6.14 (dd, J=2.0, 16.8 Hz, 1H), 5.71 (dd, J=2.0, 10.8 Hz, 1H), 5.04 (dd, J=5.6, 13.2 Hz, 1H), 4.71-4.66 (m, 3H), 4.56 (t, J=8.8 Hz, 1H), 4.37-4.28 (m, 1H), 4.27 (t, J=8.8 Hz, 1H), 4.16-4.10 (m, 1H), 3.74-3.53 (m, 13H), 2.90-2.83 (m, 1H), 2.59-2.50 (m, 1H), 2.49-2.47 (m, 1H), 2.04-1.98 (m, 2H), 1.47-1.43 (m, 1H); MS (ESI) m/z: 886.2 $[M+H]^+$.

17

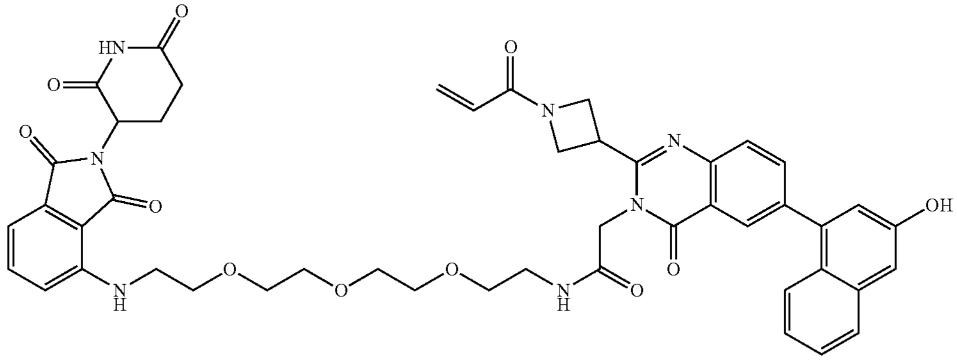

3-(1-((4-(((2-(2-(1-Acryloylazetidin-3-yl)-6-(3-hydroxynaphthalen-1-yl)-4-oxoquinazolin-3(4H)-yl)ethyl) amino)methyl)phenoxy)methyl)-4-oxo-4H-thieno[3,4-c] pyrrol-5(6H)-yl)piperidine-2,6-dione 18. $^{1}$H NMR (400 MHz, DMSO-$d_6$) δ 10.93 (s, 1H), 9.91 (s, 1H), 8.10 (d, J=2.0 Hz, 1H), 7.99 (s, 1H), 7.92 (dd, J=6.0, 8.4 Hz, 1H), 7.85-7.78 (m, 2H), 7.60 (d, J=8.8 Hz, 1H), 7.43 (t, J=7.2 Hz, 1H), 7.26-7.19 (m, 4H), 7.06 (d, J=2.4 Hz, 1H), 6.90 (d, J=8.4 Hz, 2H), 6.38 (dd, J=10.4, 16.8 Hz, 1H), 6.15 (dd, J=2.0, 16.8 Hz, 1H), 5.72 (dd, J=2.4, 10.4 Hz, 1H), 5.23 (s, 2H), 5.00 (dd, J=5.2, 13.6 Hz, 1H), 4.71-4.67 (m, 1H), 4.58 (t, J=8.0 Hz, 1H), 4.46-4.38 (m, 2H), 4.32-4.16 (m, 4H), 4.01-3.96 (m, 2H), 3.68 (s, 2H), 3.51-3.49 (m, 1H), 2.91-2.81 (m, 2H), 2.59-2.51 (m, 1H), 2.35-2.24 (m, 1H), 2.01-1.96 (m, 1H); MS (ESI) m/z: 809.2 $[M+H]^+$.

18

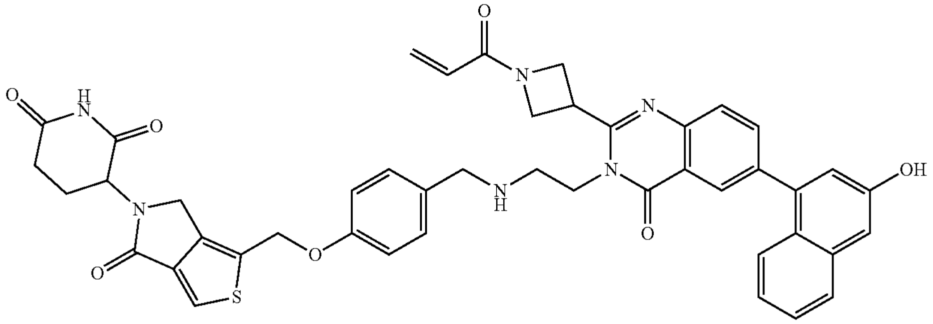

3-(1-((4-(((4-(3-(1-Acryloylazetidin-3-yl)-7-(3-hydroxynaphthalen-1-yl)-2-oxo-3,4-dihydroquinazolin-1(2H)-yl)butyl)amino)methyl)phenoxy)methyl)-4-oxo-4H-thieno [3,4-c]pyrrol-5(6H)-yl)piperidine-2,6-dione 19. $^{1}$H NMR (400 MHz, DMSO-$d_6$) δ 10.96 (s, 1H), 9.90 (s, 1H), 8.01 (s, 1H), 7.76 (d, J=8.8 Hz, 1H), 7.65 (d, J=8.4 Hz, 1H), 7.41-7.36 (m, 4H), 7.22-7.17 (m, 2H), 7.09-7.03 (m, 5H), 6.35 (dd, J=10.4, 16.8 Hz, 1H), 6.14 (dd, J=2.0, 16.8 Hz, 1H), 5.69 (dd, J=2.4, 10.4 Hz, 1H), 5.31 (s, 2H), 5.02 (dd, J=5.2, 13.2 Hz, 1H), 4.95-4.91 (m, 1H), 4.57-4.48 (m, 2H), 4.45-4.16 (m, 2H), 4.37-4.20 (m, 2H), 4.15 (d, J=7.2 Hz, 2H), 3.94-3.86 (m, 4H), 2.88-2.81 (m, 3H), 2.60-2.55 (m, 1H), 2.34-2.30 (m, 1H), 2.01-1.95 (m, 2H), 1.61 (s, 4H); MS (ESI) m/z: 839.1 $[M+H]^+$.

19

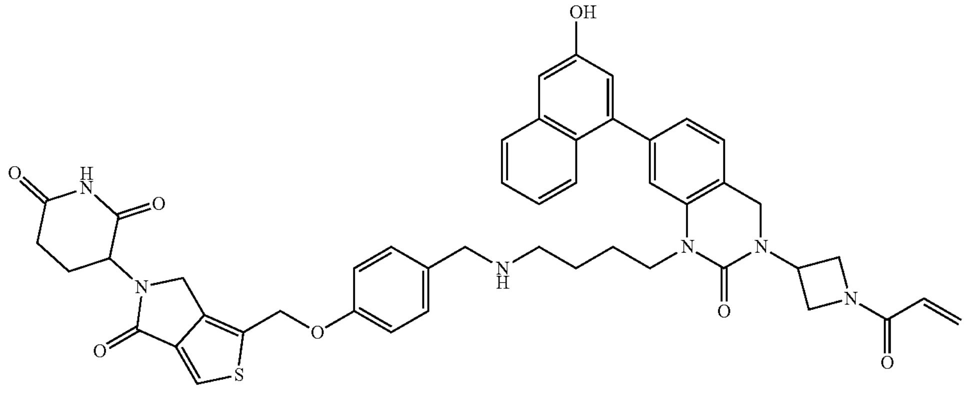

3-(4-(1-(8-(2-(8-Chloro-6-fluoro-4-(4-propionylpiperazin-1-yl)quinazolin-7-yl)-3-fluorophenoxy)octyl)piperidin-4-yl)-6-fluoro-1-oxoisoindolin-2-yl)piperidine-2,6-dione 20. $^{1}H$ NMR (400 MHz, DMSO-$d_6$) δ 11.04 (s, 1H), 9.51 (brs, 1H), 8.71 (s, 1H), 8.05 (s, 1H), 7.55-7.54 (m, 1H), 7.44-7.43 (m, 1H), 7.31-7.28 (m, 1H), 7.15-7.02 (m, 3H), 5.18-5.16 (m, 1H), 4.56-4.35 (m, 2H), 4.03-4.01 (m, 2H), 3.89-3.87 (m, 4H), 3.70-3.68 (m, 4H), 3.60-3.57 (m, 5H), 3.02-2.91 (m, 5H), 2.65-2.61 (m, 1H), 2.38-2.37 (m, 2H), 2.02-1.84 (m, 4H), 1.59-1.53 (m, 4H), 1.14-0.85 (m, 11H); MS (ESI) m/z: 888.3 $[M+H]^+$.

20

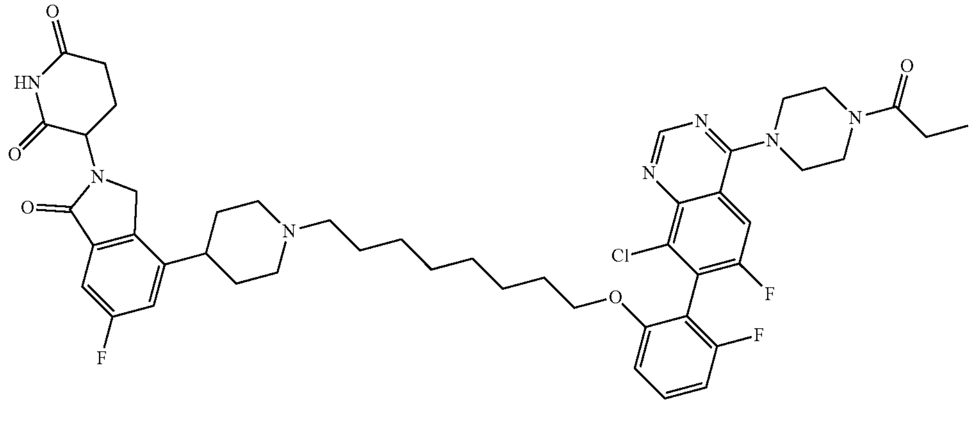

3-(1-((4-(((2-(2-(2-(1-Acryloylazetidin-3-yl)-6-(3-hydroxynaphthalen-1-yl)-4-oxoquinazolin-3(4H)-yl)ethoxy)ethyl)amino)methyl)phenoxy)methyl)-4-oxo-4H-thieno[3,4-c]pyrrol-5(6H)-yl)piperidine-2,6-dione 21. $^{1}H$ NMR (400 MHz, DMSO-$d_6$) δ 10.93 (brs, 1H), 9.90 (s, 1H), 8.13 (s, 1H), 8.02-7.60 (m, 4H), 7.56 (t, J=8.8 Hz, 1H), 7.43 (t, J=7.2 Hz, 1H), 7.23-7.06 (m, 5H), 6.92-6.82 (m, 2H), 6.40-6.33 (m, 1H), 6.17-6.12 (m, 1H), 5.71-5.69 (m, 1H), 5.24-5.22 (m, 2H), 5.00 (dd, J=4.8, 12.8 Hz, 1H), 4.70-4.56 (m, 3H), 4.42-4.28 (m, 4H), 4.22-4.11 (m, 3H), 3.85-3.83 (m, 1H), 3.70-3.66 (m, 2H), 3.59-3.46 (m, 5H), 2.92-2.83 (m, 1H), 2.62-2.54 (m, 2H), 2.36-2.26 (m, 1H), 1.99-1.97 (m, 1H); MS (ESI) m/z; 853.2 [MtH]E.

21

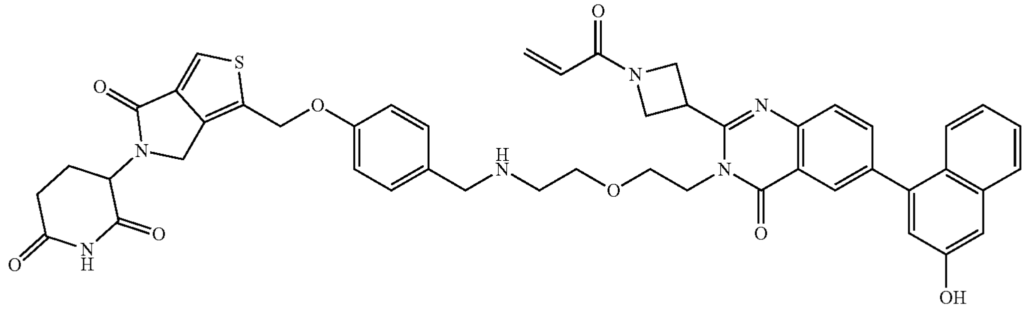

(S)-3-(1-((4-(((2-(7-(3-Hydroxynaphthalen-1-yl)-2-oxo-3-(1-propionylazetidin-3-yl)-3,4-dihydroquinazolin-1(2H)-yl)ethyl)amino)methyl)phenoxy)methyl)-4-oxo-4H-thieno[3,4-c]pyrrol-5(6H)-yl)piperidine-2,6-dione 22. MS (ESI) m/z: 813.2 $[M+H]^+$.

22

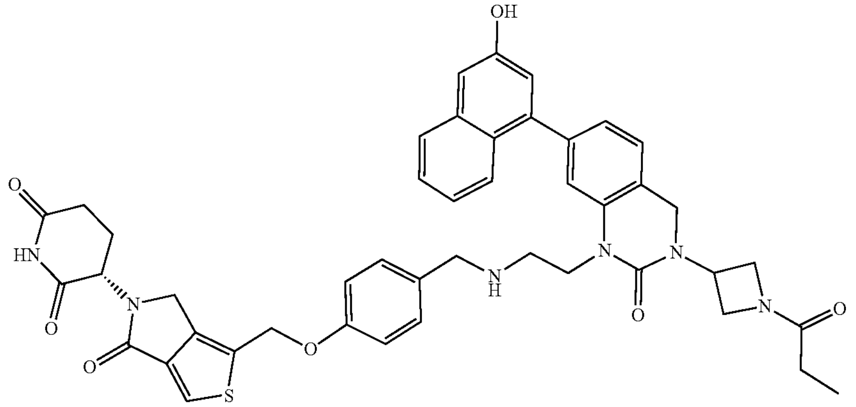

(3S)-3-(1-((4-(((7-(2-(4-(4-Acryloylpiperazin-1-yl)-6-chloro-8-fluoroquinazolin-7-yl)-3-fluorophenoxy)heptyl)amino)methyl)phenoxy)methyl)-4-oxo-4H-thieno[3,4-c]pyrrol-5(6H)-yl)piperidine-2,6-dione 24. $^1H$ NMR (400 MHz, DMSO-$d_6$) δ 8.69 (s, 1H), 8.04-8.01 (m, 2H), 7.56-7.51 (m, 1H), 7.28-7.23 (m, 2H), 7.06 (d, J=8.0 Hz, 2H), 6.99-6.98 (m, 3H), 6.85-6.78 (m, 1H), 6.17 (dd, J=2.4, 17.2 Hz, 1H), 5.73 (dd, J=2.4, 10.4 Hz, 1H), 5.29 (s, 2H), 5.02 (dd, J=4.0, 12.4 Hz, 1H), 4.37-4.20 (m, 2H), 4.02 (t, J=4.0 Hz, 2H), 3.89-3.75 (m, 10H), 2.88-2.84 (m, 1H), 2.67-2.55 (m, 3H), 2.35-2.29 (m, 2H), 2.00-1.94 (m, 1H), 1.53-1.47 (m, 2H), 1.29-1.23 (m, 2H), 1.14-0.99 (m, 6H); MS (ESI) m/z: 912.2 $[M+H]^+$.

24

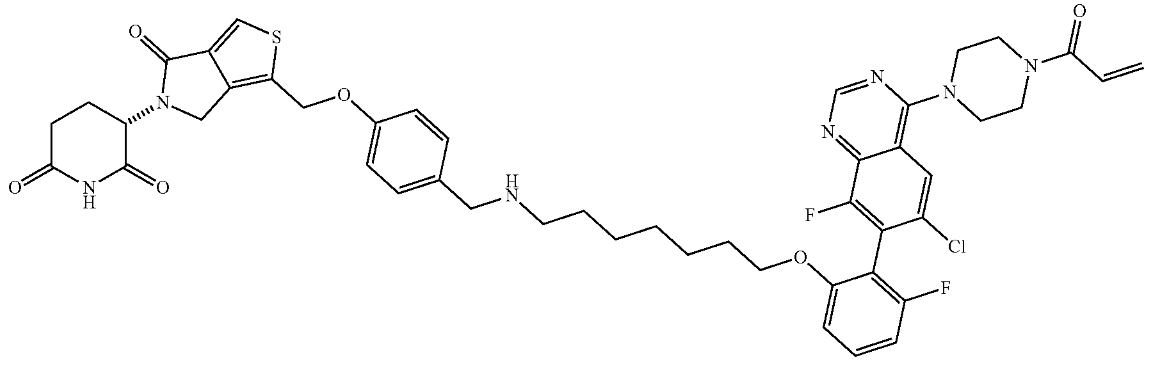

(3S)-3-(1-((4-(((7-(2-(6-Chloro-8-fluoro-4-(4-propionylpiperazin-1-yl)quinazolin-7-yl)-3-fluorophenoxy)heptyl)amino)methyl)phenoxy)methyl)-4-oxo-4H-thieno[3,4-c]pyrrol-5(6H)-yl)piperidine-2,6-dione 25. $^1$H NMR (400 MHz, DMSO-$d_6$) δ 8.67 (s, 1H), 8.03 (s, 1H), 8.01 (s, 1H), 7.54-7.52 (m, 1H), 7.23 (d, J=8.4 Hz, 2H), 7.07-6.94 (m, 4H), 5.30 (s, 2H), 5.02 (dd, J=4.8, 13.2 Hz, 1H), 4.37-4.20 (m, 4H), 4.01-3.96 (m, 2H), 3.89-3.84 (m, 6H), 3.67-3.60 (m, 4H), 2.93-2.83 (m, 1H), 2.60-2.58 (m, 1H), 2.38-2.32 (m, 5H), 2.01-1.97 (m, 2H), 1.50-1.46 (m, 2H), 1.07-1.03 (m, 6H), 1.01 (t, J=7.6 Hz, 3H); MS (ESI) m/z: 914.2 $[M+H]^+$.

25

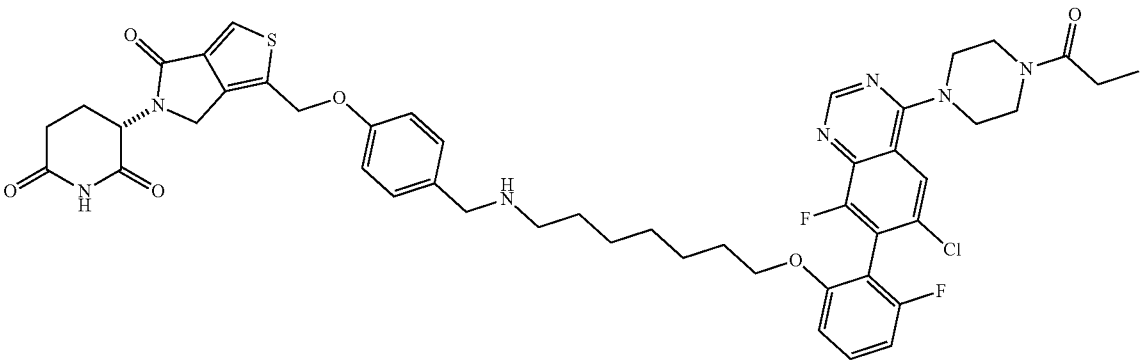

3-(1-((4-(((2-(2-(6-(3-Hydroxynaphthalen-1-yl)-4-oxo-2-(1-propionylazetidin-3-yl)quinazolin-3(4H)-yl)ethoxy)ethyl)amino)methyl)phenoxy)methyl)-4-oxo-4H-thieno[3,4-c]pyrrol-5(6H)-yl)piperidine-2,6-dione 26. $^1$H NMR (400 MHz, DMSO-$d_6$) δ 11.00 (s, 1H), 10.07 (s, 1H), 8.13 (s, 1H), 8.02-8.01 (m, 3H), 7.79 (d, J=8.4 Hz, 1H), 7.56 (d, J=8.8 Hz, 1H), 7.42 (t, J=7.2 Hz, 1H), 7.25-7.20 (m, 4H), 7.13 (s, 1H), 6.89 (d, J=8.4 Hz, 2H), 5.25 (s, 2H), 5.01 (dd, J=5.2, 13.2 Hz, 1H), 4.74-4.72 (m, 2H), 4.54 (t, J=8.4 Hz, 1H), 4.48-4.44 (m, 1H), 4.36-4.19 (m, 4H), 4.13-4.07 (m, 1H), 3.88 (t, J=4.0 Hz, 2H), 3.79 (s, 2H), 3.67 (t, J=4.8 Hz, 2H), 2.93-2.81 (m, 4H), 2.60-2.56 (m, 1H), 2.34-2.31 (m, 1H), 2.12 (q, J=7.6 Hz, 2H), 2.01-1.95 (m, 1H), 1.39-1.28 (m, 1H), 1.00 (t, J=7.6 Hz, 3H); MS (ESI) m/z: 855.2 $[M+H]^+$.

26

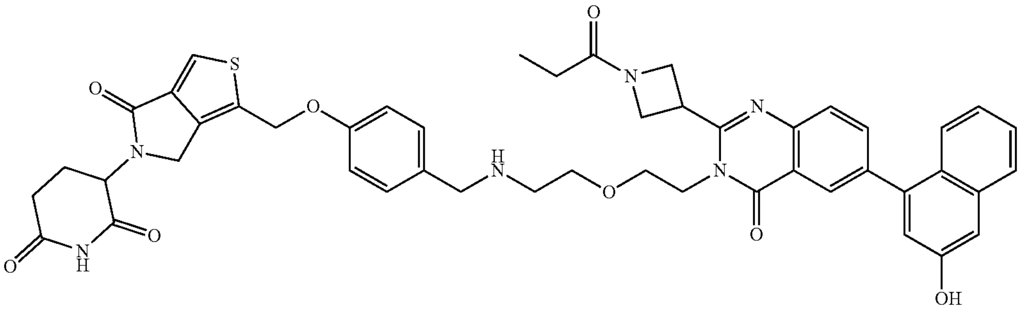

1-(7-(2-(6-Chloro-8-fluoro-4-(4-propionylpiperazin-1-yl)quinazolin-7-yl)-3-fluorophenoxy)heptyl)-3-((5-(2,6-dioxopiperidin-3-yl)-4-oxo-5,6-dihydro-4H-thieno[3,4-c]pyrrol-1-yl)methyl)urea 28. $^1$H NMR (400 MHz, DMSO-$d_6$) δ 10.97 (s, 1H), 8.69 (s, 1H), 8.04 (t, J=1.2 Hz, 1H), 7.82 (s, 1H), 7.57-7.51 (m, 1H), 7.07 (d, J=8.4 Hz, 1H), 6.98 (t, J=8.8 Hz, 1H), 6.41 (t, J=6.0 Hz, 1H), 5.96 (t, J=5.6 Hz, 1H), 5.01 (dd, J=5.2, 13.2 Hz, 1H), 4.31 (d, J=6.0 Hz, 2H), 4.28-4.13 (m, 2H), 4.03-3.99 (m, 2H), 3.92-3.65 (m, 8H), 2.93-2.84 (m, 3H), 2.59-2.50 (m, 1H), 2.37 (q, J=7.6 Hz, 2H), 2.33-2.23 (m, 1H), 1.99-1.95 (m, 1H), 1.51-1.48 (m, 2H), 1.23-1.16 (m, 2H), 1.10-1.07 (m, 6H), 1.02 (t, J=7.2 Hz, 3H); MS (ESI) m/z: 851.2 $[M+H]^+$.

28

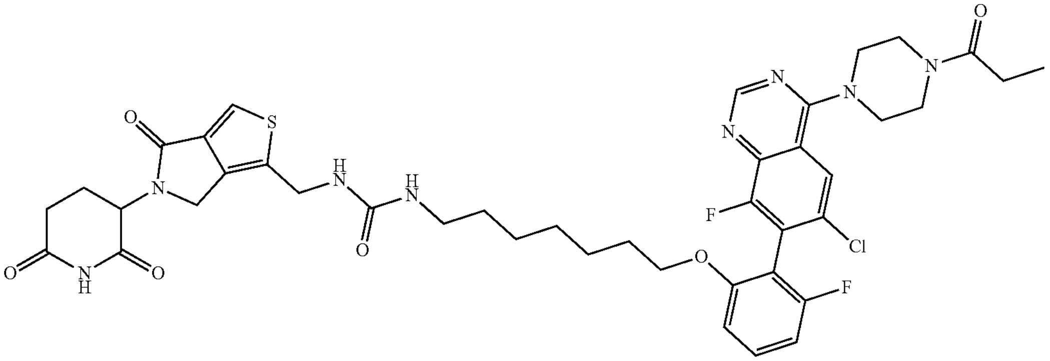

3-(2-(2-(2-(4-(4-Acryloylpiperazin-1-yl)-6-chloro-8-fluoroquinazolin-7-yl)-3-fluorophenoxy)ethoxy)ethoxy)-N-(2-((2-(2,6-dioxopiperidin-3-yl)-1-oxoisoindolin-4-yl)amino)ethyl)propanamide 29. $^{1}$H NMR (400 MHz, DMSO-$d_6$) δ 10.98 (s, 1H), 8.69 (s, 1H), 8.04 (d, J=0.8 Hz, 1H), 7.95 (t, J=8.4 Hz, 1H), 7.54 (q, J=8.4 Hz, 1H), 7.27 (t, J=7.6 Hz, 1H), 7.08 (d, J=8.4 Hz, 1H), 7.02 (t, J=8.8 Hz, 1H), 6.93 (d, J=7.6 Hz, 1H), 6.86-6.78 (m, 2H), 6.17 (dd, J=2.4 Hz, 16.8 Hz, 1H), 5.73 (dd, J=2.4, 10.4 Hz, 1H), 5.65 (t, J=5.2 Hz, 1H), 5.10 (dd, J=5.2, 13.2 Hz, 1H), 4.23-4.06 (m, 4H), 3.94-3.76 (m, 8H), 3.53 (t, J=4.8 Hz, 2H), 3.46 (t, J=6.4 Hz, 2H), 3.29-3.17 (m, 8H), 2.96-2.87 (m, 1H), 2.64-2.58 (m, 1H), 2.34-2.20 (m, 3H), 2.05-1.99 (m, 1H); MS (ESI) m/z: 875.2 $[M+H]^+$.

29

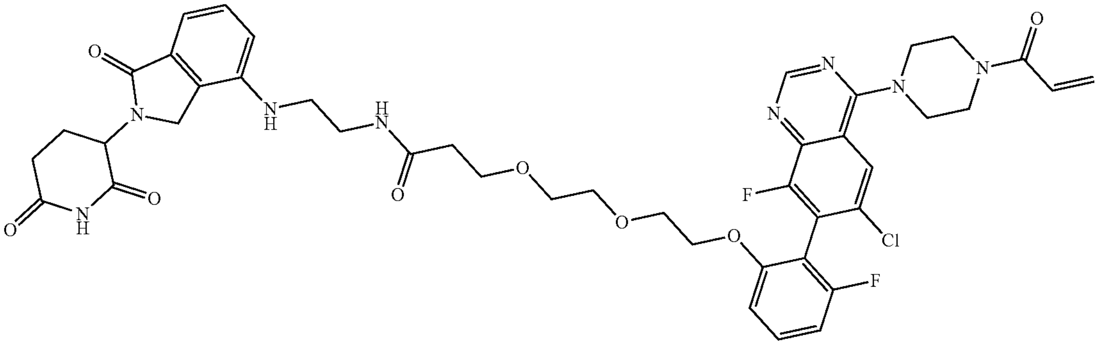

4-((2-(2-(2-(2-(2-(4-(4-Acetylpiperazin-1-yl)-6-chloro-8-fluoroquinazolin-7-yl)-3-fluorophenoxy)ethoxy)ethoxy)ethoxy)ethyl)amino)-2-(2,6-dioxopiperidin-3-yl)isoindoline-1,3-dione 31. $^{1}$H NMR (400 MHz, DMSO-$d_6$) δ 11.08 (s, 1H), 8.68 (s, 1H), 8.02 (s, 1H), 7.57-7.46 (m, 2H), 7.12-6.96 (m, 4H), 6.56 (t, J=5.6 Hz, 1H), 5.04 (dd, J=5.2, 12.8 Hz, 1H), 4.16-4.10 (m, 2H), 3.91-3.79 (m, 4H), 3.67-3.62 (m, 4H), 3.58-3.54 (m, 4H), 3.46-3.42 (m, 4H), 3.37-3.35 (m, 2H), 3.32-3.29 (m, 4H), 2.91-2.85 (m, 1H), 2.59-2.51 (m, 2H), 2.04 (s, 3H), 2.03-1.97 (m, 1H); MS (ESI) m/z: 850.2 $[M+H]^+$.

31

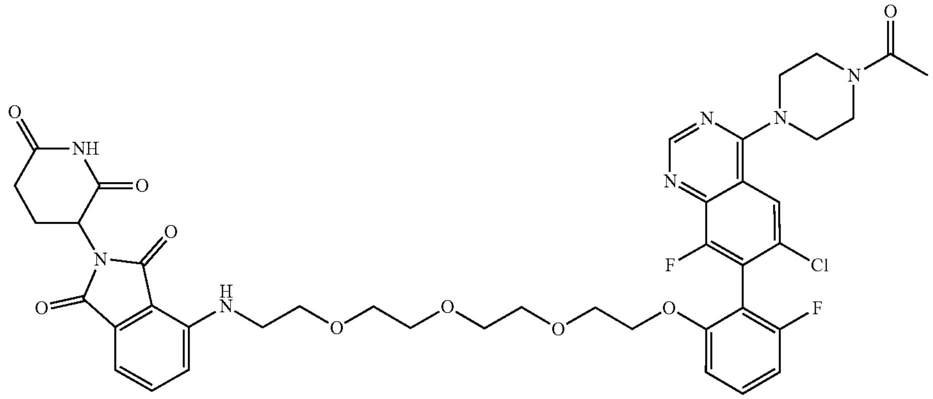

4-(6-Chloro-7-(2-(2-(2-(2-(2-((2-(2,6-dioxopiperidin-3-yl)-1,3-dioxoisoindolin-4-yl)amino)ethoxy)ethoxy)ethoxy)ethoxy)-6-fluorophenyl)-8-fluoroquinazolin-4-yl)piperazine-1-carboxamide 32. $^1$H NMR (400 MHz, DMSO-$d_6$) δ 11.08 (s, 1H), 8.67 (s, 1H), 8.01 (s, 1H), 8.57-7.51 (m, 2H), 7.11-6.99 (m, 4H), 6.56 (t, J=5.2 Hz, 1H), 6.07 (s, 2H), 5.04 (dd, J=5.2, 12.8 Hz, 1H), 4.19-4.08 (m, 2H), 3.87-3.75 (m, 4H), 3.58-3.53 (m, 10H), 3.47-3.43 (m, 4H), 3.31-3.29 (m, 4H), 2.91-2.82 (m, 1H), 2.62-2.55 (m, 2H), 2.07-1.99 (m, 1H); MS (ESI) m/z: 851.2 $[M+H]^+$.

32

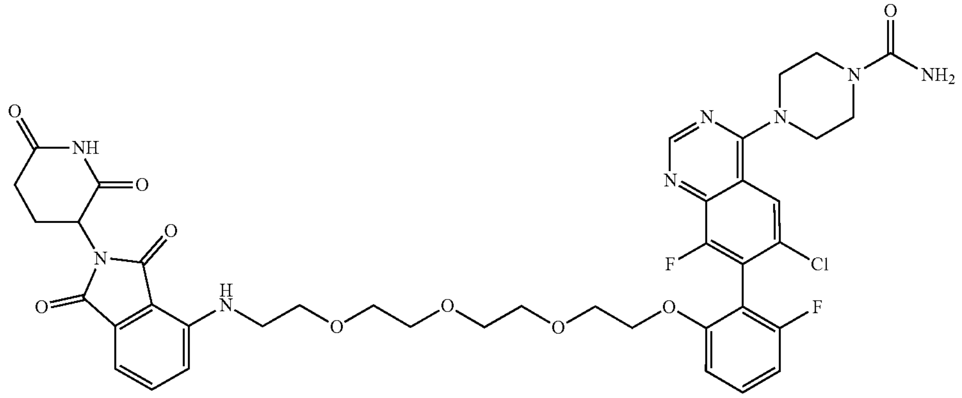

4-((8-(2-(6-Chloro-8-fluoro-4-(4-propionylpiperazin-1-yl)quinazolin-7-yl)-3-fluorophenoxy)octyl)amino)-2-(2,6-dioxopiperidin-3-yl)isoindoline-1,3-dione 33. $^1$H NMR (400 MHz, DMSO-$d_6$) δ 11.09 (s, 1H), 8.68 (s, 1H), 8.04 (s, 1H), 7.60-7.51 (m, 2H), 7.08-6.98 (m, 4H), 6.50-6.47 (m, 1H), 5.05 (dd, J=5.2, 12.8 Hz, 1H), 4.04-3.99 (m, 2H), 3.88-3.85 (m, 4H), 3.72-3.63 (m, 4H), 3.21 (q, J=6.4 Hz, 2H), 2.93-2.84 (m, 1H), 2.61-2.51 (m, 2H), 2.34 (q, J=7.2 Hz, 2H), 2.06-2.00 (m, 1H), 1.55-1.42 (m, 4H), 1.24-1.11 (m, 8H), 1.01 (t, J=7.6 Hz, 3H); MS (ESI) m/z: 816.2 $[M+H]^+$.

33

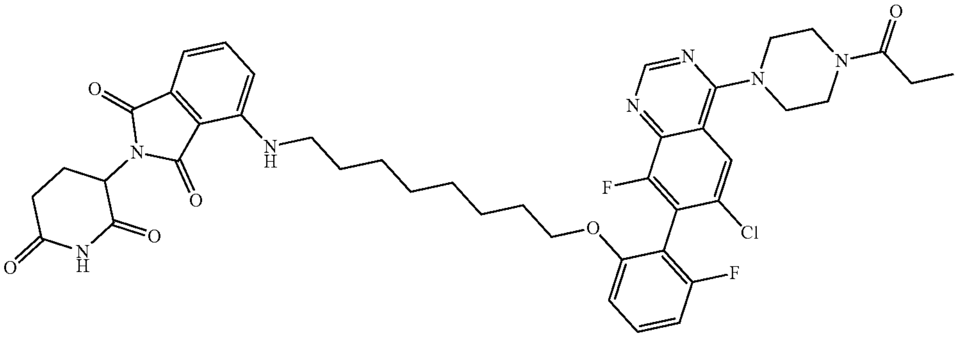

4-((8-(2-(4-(4-Acryloylpiperazin-1-yl)-6-chloro-8-fluoroquinazolin-7-yl)-3-fluorophenoxy)octyl)amino)-2-(2,6-dioxopiperidin-3-yl)isoindoline-1,3-dione 34. MS (ESI) m/z: 814.2 $[M+H]^+$.

34

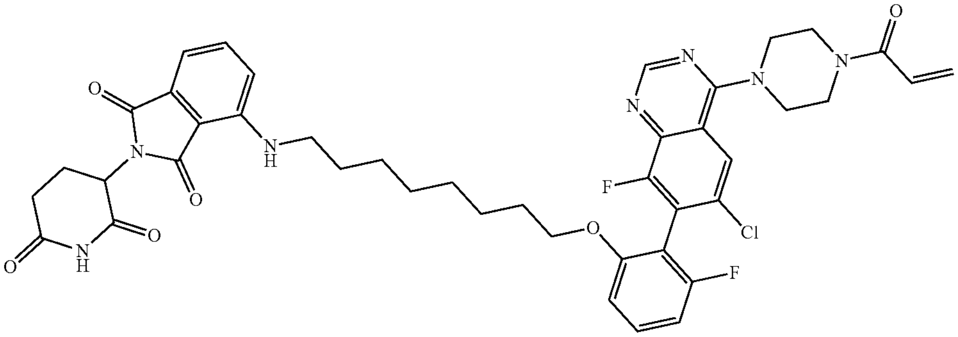

N-(7-(4-(2-(2,6-Dioxopiperidin-3-yl)-6-fluoro-1-oxoisoindolin-4-yl)piperidin-1-yl)heptyl)-2-(7-(3-hydroxynaphthalen-1-yl)-2-oxo-3-(1-propionylazetidin-3-yl)-3,4-dihydroquinazolin-1(2H)-yl)acetamide 35. $^1$H NMR (400 MHz, DMSO-$d_6$) δ 11.05 (s, 1H), 9.86 (s, 1H), 9.12 (s, 1H), 7.96 (s, 1H), 7.76 (d, J=8.8 Hz, 1H), 7.65 (d, J=10.4 Hz, 1H), 7.45-7.38 (m, 3H), 7.29 (d, J=10.0 Hz, 1H), 7.22-7.18 (m, 1H), 7.16 (d, J=2.0 Hz, 1H), 7.09 (d, J=8.0 Hz, 1H), 6.97 (d, J=2.4 Hz, 1H), 6.77 (s, 1H), 5.18 (dd, J=4.4, 13.6 Hz, 1H), 4.94 (t, J=6.8 Hz, 1H), 4.57-4.51 (m, 3H), 4.40-4.32 (m, 5H), 4.07 (d, J=6.8 Hz, 2H), 3.59-3.55 (m, 1H), 3.03-2.95 (m, 9H), 2.66-2.61 (m, 1H), 2.35-2.32 (m, 1H), 2.11 (q, J=7.2 Hz, 2H), 2.05-1.97 (m, 5H), 1.57-1.45 (m, 2H), 1.31-1.27 (m, 4H), 1.15 (s, 4H), 0.99 (t, J=7.2 Hz, 3H); MS (ESI) m/z: 900.3 $[M+H]^+$.

35

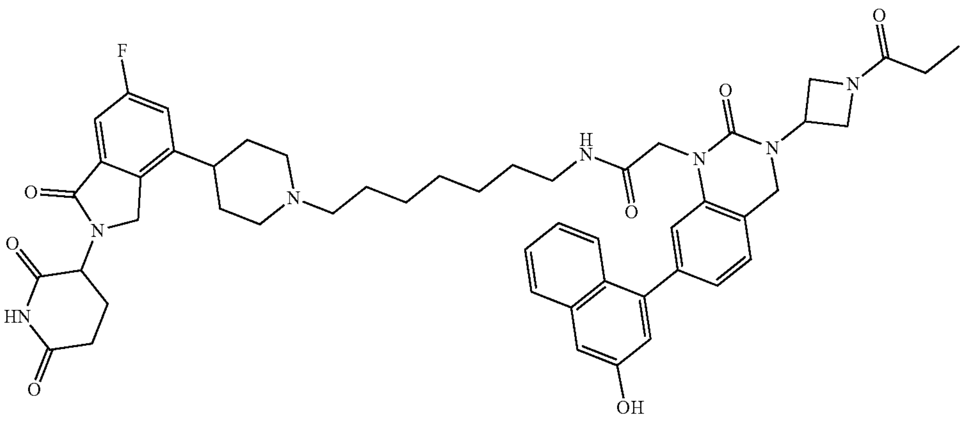

3-(4-(1-(7-(2-(6-Chloro-8-fluoro-4-(4-propionylpiperazin-1-yl)quinazolin-7-yl)-3-fluorophenoxy)heptyl)piperidin-4-yl)-6-fluoro-1-oxoisoindolin-2-yl)piperidine-2,6-dione 37. $^1$H NMR (400 MHz, DMSO-$d_6$) δ 11.00 (s, 1H), 8.70 (s, 1H), 8.04 (s, 1H), 7.57-7.51 (m, 1H), 7.40-7.35 (m, 2H), 7.07 (d, J=8.4 Hz, 1H), 6.99 (t, J=8.8 Hz, 1H), 5.14 (dd, J=4.8, 13.2 Hz, 1H), 4.53-4.32 (m, 2H), 4.03 (t, J=5.2 Hz, 2H), 3.91-3.87 (m, 4H), 3.70-3.64 (m, 4H), 2.95-2.89 (m, 3H), 2.62-2.58 (m, 2H), 2.45-2.34 (m, 3H), 2.23-2.15 (m, 2H), 2.03-1.99 (m, 3H), 1.73-1.66 (m, 4H), 1.53-1.49 (m, 2H), 1.29-1.23 (m, 3H), 1.14-1.08 (m, 5H), 1.02 (t, J=7.2 Hz, 3H); MS (ESI) m/z: 874.2 [M+H]$^+$.

37

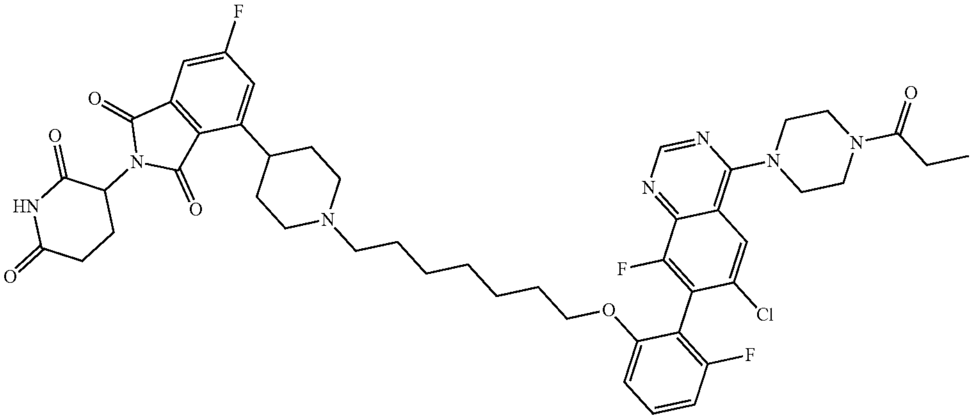

3-(2-(2-(3-(4-(4-Acryloylpiperazin-1-yl)-6-chloro-8-fluoroquinazolin-7-yl)-4-fluorophenoxy)ethoxy)ethoxy)-N-(2-((2-(2,6-dioxopiperidin-3-yl)-1-oxoisoindolin-4-yl)amino)ethyl)propanamide 38. $^1$H NMR (400 MHz, DMSO-$d_6$) δ 10.99 (s, 1H), 8.70 (s, 1H), 8.05 (s, 1H), 7.99 (t, J=5.6 Hz, 1H), 7.86 (s, 1H), 7.30-7.25 (m, 2H), 7.10-7.06 (m, 2H), 6.93 (d, J=7.2 Hz, 1H), 6.82-6.75 (m, 2H), 6.15 (dd, J=2.4, 16.8 Hz, 1H), 5.71 (dd, J=2.4, 10.4 Hz, 1H), 5.65 (t, J=5.6 Hz, 1H), 5.10 (dd, J=5.2, 13.2 Hz, 1H), 4.23-4.09 (m, 4H), 3.92-3.91 (m, 4H), 3.78-3.76 (m, 2H), 3.73-3.70 (m, 4H), 3.60 (t, J=6.4 Hz, 2H), 3.55-3.45 (m, 4H), 3.26-3.17 (m, 4H), 2.96-2.87 (m, 1H), 2.64-2.59 (m, 1H), 2.32 (t, J=6.4 Hz, 3H), 2.06-2.00 (m, 1H); MS (ESI) m/z: 875.2 [M+H]$^+$.

38

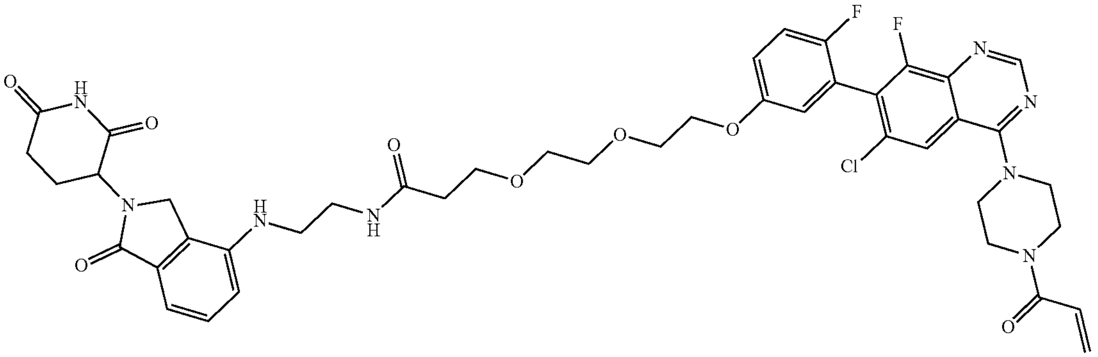

3-(2-(2-((R)-3-(4-(4-Acryloylpiperazin-1-yl)-6-chloro-8-fluoroquinazolin-7-yl)-4-fluorophenoxy)ethoxy)ethoxy)-N-(2-((2-(2,6-dioxopiperidin-3-yl)-1-oxoisoindolin-4-yl)amino)ethyl)propanamide 39. $^1$H NMR (400 MHz, DMSO-$d_6$) δ 10.98 (s, 1H), 8.70 (s, 1H), 8.05 (s, 1H), 7.99 (t, J=5.2 Hz, 1H), 7.33 (t, J=8.8 Hz, 1H), 7.27 (t, J=7.6 Hz, 1H), 7.15-7.11 (m, 1H), 7.07-7.05 (m, 1H), 6.93 (d, J=7.6 Hz, 1H), 6.85-6.79 (m, 2H), 6.18 (dd, J=2.0, 16.8 Hz, 1H), 5.74 (dd, J=2.4, 10.4 Hz, 1H), 5.65 (t, J=5.2 Hz, 1H), 5.11 (dd, J=4.8, 13.2 Hz, 1H), 4.23-4.13 (m, 4H), 3.92-3.90 (m, 4H), 3.83-3.76 (m, 4H), 3.72-3.70 (m, 2H), 3.60 (t, J=6.4 Hz, 2H), 3.55-3.48 (m, 4H), 3.25-3.17 (m, 4H), 2.96-2.87 (m, 1H), 2.63-2.59 (m, 1H), 2.32 (t, J=6.4 Hz, 3H), 2.06-2.01 (m, 1H); MS (ESI) m/z: 875.2 [M+H]$^+$.

39

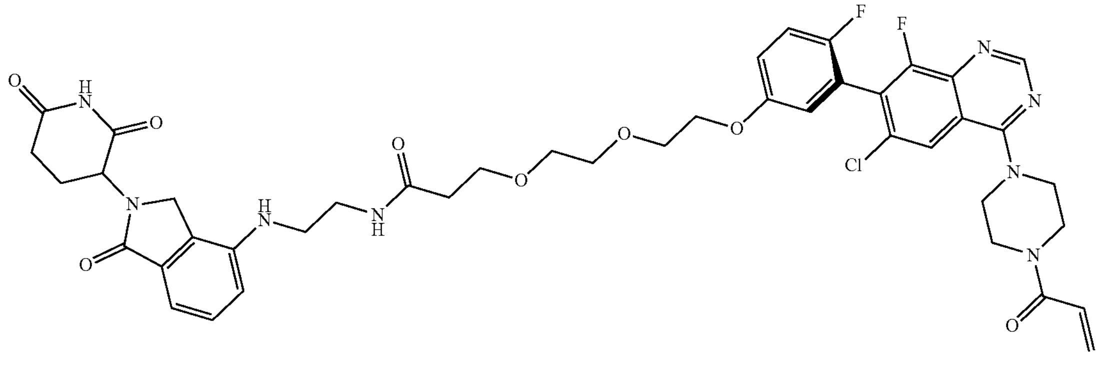

5-((2-(2-(2-(2-(3-(1-Acryloylazetidin-3-yl)-7-(3-hydroxynaphthalen-1-yl)-2-oxo-3,4-dihydroquinazolin-1(2H)-yl)ethoxy)ethoxy)ethoxy)ethyl)amino)-2-(2,6-dioxopiperidin-3-yl)isoindoline-1,3-dione 40. $^1$H NMR (400 MHz, DMSO-$d_6$) δ 11.04 (s, 1H), 9.85 (s, 1H), 7.74 (d, J=8.0 Hz, 1H), 7.65 (d, J=8.0 Hz, 1H), 7.54 (d, J=8.0 Hz, 1H), 7.41-7.37 (m, 2H), 7.23-7.20 (m, 2H), 7.16 (s, 1H), 7.10-7.06 (m, 2H), 7.01 (d, J=2.8 Hz, 1H), 6.97 (d, J=1.6 Hz, 1H), 6.84 (dd, J=1.2, 8.0 Hz, 1H), 6.37-6.31 (m, 1H), 6.13 (dd, J=2.0, 17.2 Hz, 1H), 5.69 (dd, J=2.0, 8.4 Hz, 1H), 5.02 (dd, J=5.2, 12.8 Hz, 1H), 4.93 (t, J=6.8 Hz, 1H), 4.51-4.40 (m, 3H), 4.15-4.13 (m, 1H), 3.99-3.96 (m, 1H), 3.62-3.59 (m, 4H), 2.99-2.86 (m, 1H), 2.33-2.26 (m, 1H), 2.07-2.00 (m, 2H), 1.50-1.44 (m, 5H), 0.87-0.83 (m, 6H); MS (ESI) m/z: 831.2 $[M+H]^+$.

40

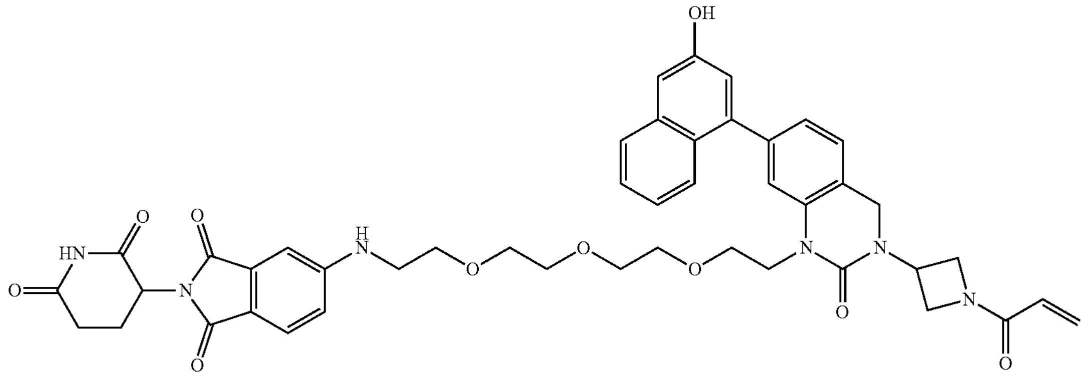

3-(4-(1-(7-(2-(4-(4-(1H-Imidazole-5-carbonyl)piperazin-1-yl)-6-chloro-8-fluoroquinazolin-7-yl)-3-fluorophenoxy)heptyl)piperidin-4-yl)-6-fluoro-1-oxoisoindolin-2-yl)piperidine-2,6-dione 41. $^1$H NMR (400 MHz, DMSO-$d_6$) δ 11.05 (s, 1H), 9.43 (s, 1H), 8.73 (s, 1H), 8.65 (s, 1H), 8.09 (s, 1H), 7.99 (s, 1H), 7.59-7.53 (m, 1H), 7.44 (dd, J=2.4, 7.6 Hz, 1H), 7.29 (t, J=2.0, 10.4 Hz, 1H), 7.10 (t, J=8.8 Hz, 1H), 7.01 (t, J=8.4 Hz, 1H), 5.17 (dd, J=4.8, 13.2 Hz, 1H), 4.55-4.34 (m, 2H), 4.21-4.03 (m, 8H), 4.22-4.15 (m, 1H), 4.04 (t, J=6.0 Hz, 2H), 3.94-3.85 (m, 4H), 3.59-3.52 (m, 5H), 3.44-3.40 (m, 2H), 3.00-2.90 (m, 7H), 2.65-2.61 (m, 1H), 2.34-2.32 (m, 1H), 2.06-1.89 (m, 6H), 1.63-1.51 (m, 4H), 1.23-1.19 (m, 8H); MS (ESI) m/z: 912.3 $[M+H]^+$.

41

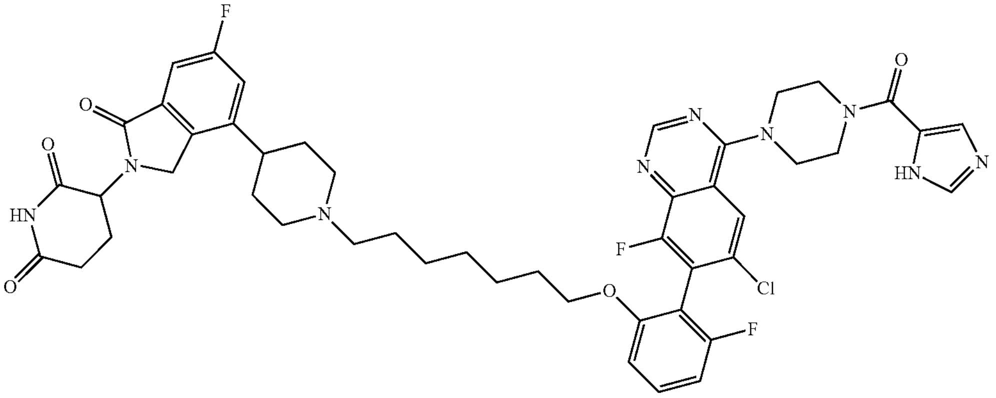

4-((2-(2-(2-(2-(2-(6-Chloro-8-fluoro-4-(4-propionylpiperazin-1-yl)quinazolin-7-yl)-3-fluorophenoxy)ethoxy)ethoxy)ethoxy)ethyl)amino)-2-(2,6-dioxopiperidin-3-yl)isoindoline-1,3-dione 42. MS (ESI) m/z: 864.2 [M+H]$^+$.

42

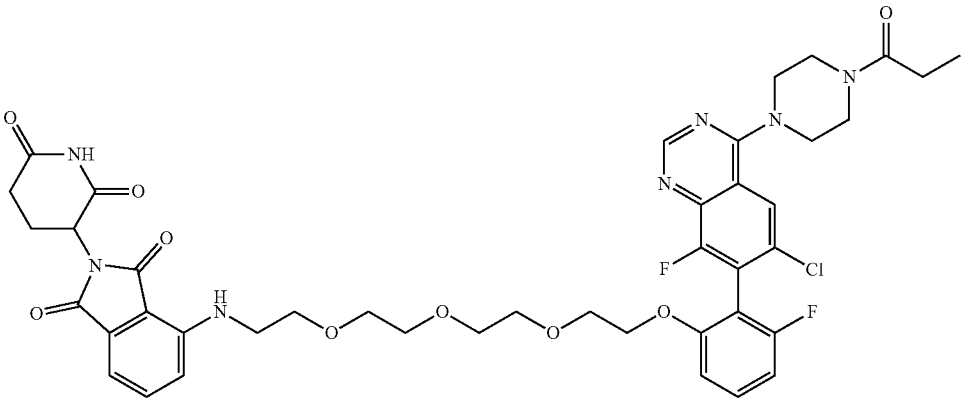

3-(4-(1-(7-(2-(6-Chloro-4-(4-(2-chloroacryloyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 43. $^1$H NMR (400 MHz, DMSO-$d_6$) δ 11.05 (s, 1H), 9.28 (s, 1H), 8.75 (s, 1H), 8.07 (s, 1H), 7.58-7.52 (m, 1H), 7.42 (d, J=7.2 Hz, 1H), 7.31 (d, J=10.0 Hz, 1H), 7.08 (d, J=8.4 Hz, 1H), 7.01 (t, J=8.8 Hz, 1H), 5.84 (s, 2H), 5.16 (dd, J=4.8, 13.6 Hz, 1H), 4.55-4.34 (m, 2H), 4.04 (t, J=5.6 Hz, 2H), 3.98-3.89 (m, 4H), 3.75 (s, 4H), 3.16-2.89 (m, 4H), 2.67-2.59 (m, 1H), 2.36-2.33 (m, 1H), 2.05-1.97 (m, 8H), 1.56-1.45 (m, 5H), 1.23-1.17 (m, 6H); MS (ESI) m/z: 906.3 [M+H]$^+$.

43

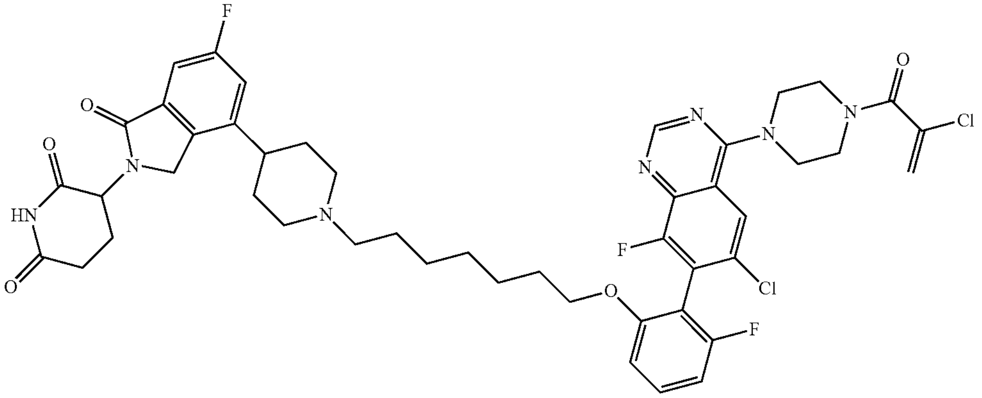

4-((2-(2-(2-(3-(1-Acryloylazetidin-3-yl)-7-(3-hydroxynaphthalen-1-yl)-2-oxo-3,4-dihydroquinazolin-1(2H)-yl)ethoxy)ethoxy)ethyl)amino)-2-(2,6-dioxopiperidin-3-yl)isoindoline-1,3-dione 45. $^{1}$H NMR (400 MHz, DMSO-$d_6$) δ 11.07 (s, 1H), 9.83 (s, 1H), 7.72 (d, J=8.0 Hz, 1H), 7.64 (d, J=8.8 Hz, 1H), 7.51 (dd, J=7.2, 8.0 Hz, 1H), 7.37-7.34 (m, 2H), 7.23-6.96 (m, 6H), 6.45 (t, J=5.6 Hz, 1H), 6.34 (dd, J=10.4, 17.2 Hz, 1H), 6.12 (dd, J=2.0, 17.2 Hz, 1H), 5.68 (dd, J=2.4, 10.4 Hz, 1H), 5.01 (dd, J=5.2 Hz, 12.0 Hz, 1H), 4.97-4.89 (m, 1H), 4.51-4.34 (m, 4H), 4.13 (t, J=7.2 Hz, 2H), 3.97 (t, J=5.6 Hz, 2H), 3.64 (t, J=8.4 Hz, 2H), 3.51-3.33 (m, 7H), 3.24-3.19 (m, 2H), 2.90-2.80 (m, 1H), 2.58-2.56 (m, 1H), 2.50-2.42 (m, 1H), 2.03-1.95 (m, 1H); MS (ESI) m/z: 787.3 $[M+H]^+$.

45

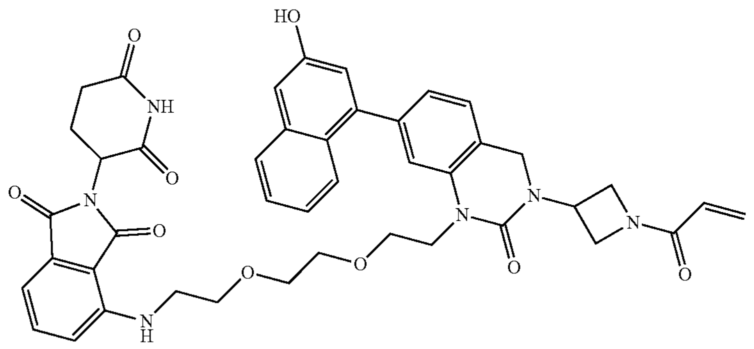

3-(6-Fluoro-4-(1-(7-((2-(7-(3-hydroxynaphthalen-1-yl)-2-oxo-3-(1-propionylazetidin-3-yl)-3,4-dihydroquinazolin-1(2H)-yl)ethyl)amino)heptyl)piperidin-4-yl)-1-oxoisoindolin-2-yl)piperidine-2,6-dione 46. $^{1}$H NMR (400 MHz, DMSO-$d_6$) δ 11.05 (s, 1H), 9.94 (s, 1H), 9.77 (s, 1H), 8.06 (t, J=5.2 Hz, 1H), 7.77 (d, J=8.4 Hz, 1H), 7.64 (d, J=8.8 Hz, 1H), 7.45-7.40 (m, 3H), 7.33-7.19 (m, 4H), 7.13 (s, 1H), 7.02 (d, J=2.4 Hz, 1H), 5.17 (dd, J=4.8 Hz, 13.2 Hz, 1H), 4.68 (s, 2H), 4.56-4.35 (m, 2H), 4.16-4.08 (m, 3H), 3.95-3.90 (m, 2H), 3.72-3.58 (m, 5H), 3.48-3.27 (m, 8H), 3.10-2.91 (m, 5H), 2.65-2.60 (m, 1H), 2.40-2.31 (m, 1H), 2.10-1.97 (m, 5H), 1.70 (s, 3H), 1.40-1.25 (m, 5H), 0.93 (t, J=7.2 Hz, 3H); MS (ESI) m/z: 886.4 $[M+H]^+$.

46

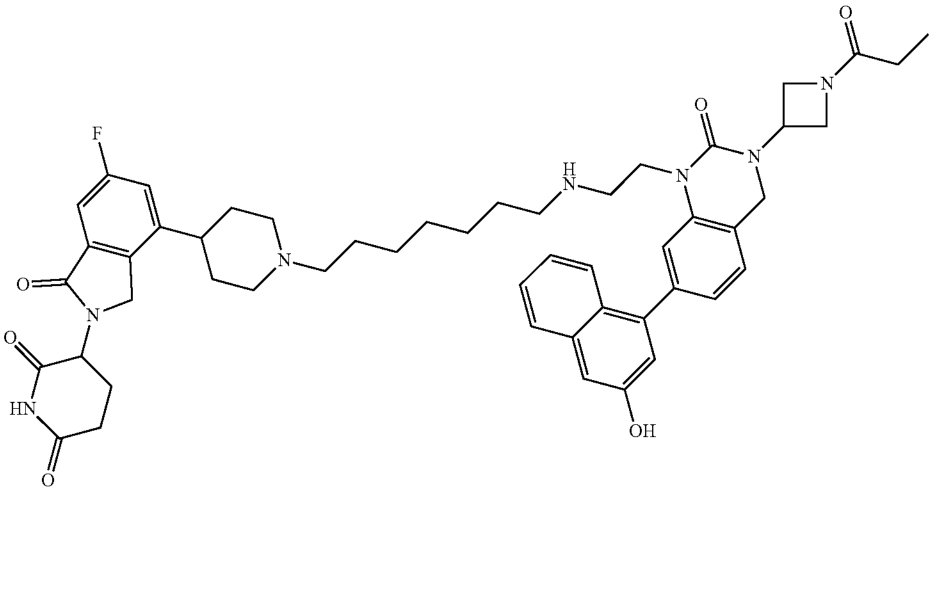

2-(2,6-Dioxopiperidin-3-yl)-4-((2-(2-(2-(2-((4-((R)-3-methyl-4-propionylpiperazin-1-yl)-7-(naphthalen-1-yl)-5,6,7,8-tetrahydropyrido[3,4-d]pyrimidin-2-yl)oxy)ethoxy)ethoxy)ethoxy)ethyl)-amino)isoindoline-1,3-dione 48. $^1$H NMR (400 MHz, DMSO-$d_6$) δ 11.08 (s, 1H), 8.22-8.16 (m, 1H), 7.95-7.89 (m, 1H), 7.64 (d, J=8.0 Hz, 1H), 7.58-7.50 (m, 3H), 7.45 (t, J=8.0 Hz, 1H), 7.21 (d, J=7.2 Hz, 1H), 7.12 (d, J=8.8 Hz, 1H), 7.15 (d, J=6.8 Hz, 1H), 6.60 (t, J=5.2 Hz, 1H), 5.04 (dd, J=4.8, 12.8 Hz, 1H), 4.32 (t, J=4.4 Hz, 2H), 4.11 (s, 2H), 4.06-4.01 (m, 1H), 3.93-3.89 (m, 1H), 3.71-3.69 (m, 2H), 3.62 (t, J=5.6 Hz, 2H), 3.55-3.50 (m, 8H), 3.47-3.45 (m, 2H), 3.24-3.11 (m, 2H), 3.03-2.98 (m, 2H), 2.91-2.80 (m, 2H), 2.59-2.55 (m, 1H), 2.40-2.27 (m, 1H), 2.03-1.98 (m, 2H), 1.29-1.23 (m, 6H), 1.15-1.10 (m, 2H), 1.01 (t, J=6.8 Hz, 3H); MS (ESI) m/z: 863.4 [M+H]$^+$.

48

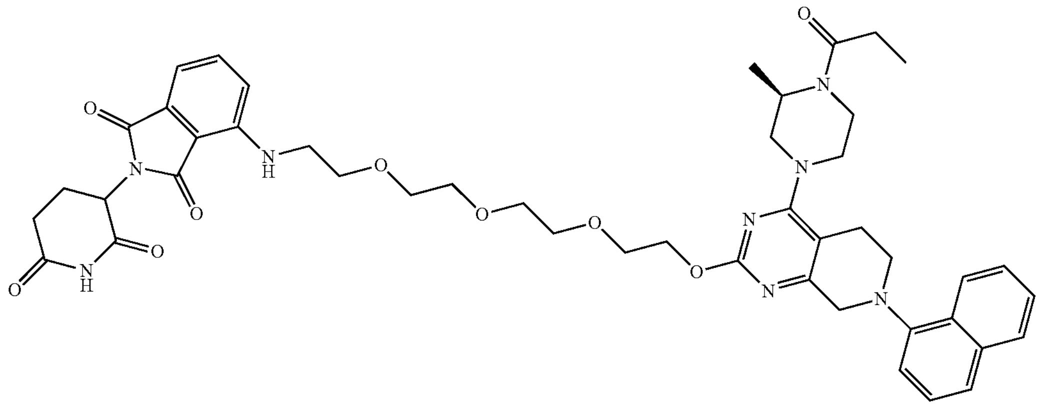

3-(4-(1-(8-((R)-2-(8-Chloro-6-fluoro-4-(4-propionylpiperazin-1-yl)quinazolin-7-yl)-3-fluorophenoxy)octyl)piperidin-4-yl)-6-fluoro-1-oxoisoindolin-2-yl)piperidine-2,6-dione 49. $^1$H NMR (400 MHz, DMSO-$d_6$) δ 11.04 (s, 1H), 9.38 (brs, 1H), 8.71 (s, 1H), 8.05 (s, 1H), 7.58-7.52 (m, 1H), 7.43 (d, J=6.0 Hz, 1H), 7.29 (t, J=10.4 Hz, 1H), 7.13-6.99 (m, 3H), 5.18 (dd, J=4.4, 12.8 Hz, 1H), 4.56-4.35 (m, 2H), 4.03-4.01 (m, 2H), 3.91-3.88 (m, 4H), 3.70-3.68 (m, 4H), 3.60-3.57 (m, 3H), 3.02-2.91 (m, 5H), 2.65-2.61 (m, 1H), 2.40-2.32 (m, 3H), 2.06-1.92 (m, 5H), 1.59-1.53 (m, 4H), 1.20-1.14 (m, 8H), 1.02 (t, J=7.2 Hz, 3H); MS (ESI) m/z: 888.3 [M+H]$^+$.

49

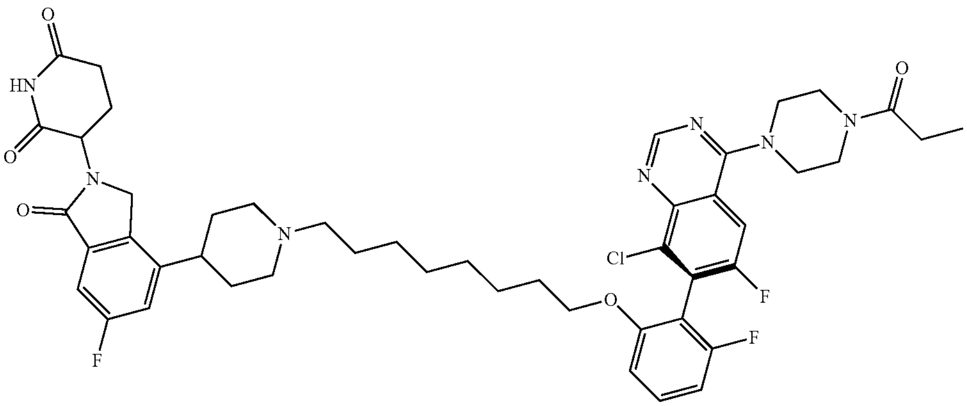

3-(4-(1-(7-(2-(6-Chloro-4-(4-(cyclopentanecarbonyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 51. $^1$H NMR (400 MHz, DMSO-$d_6$) δ 11.02 (s, 1H), 8.71 (s, 1H), 8.05 (s, 1H), 7.58-7.52 (m, 1H), 7.38-7.34 (m, 2H), 7.07 (d, J=8.4 Hz, 1H), 7.00 (t, J=8.8 Hz, 1H), 5.15 (dd, J=4.8, 13.2 Hz, 1H), 4.54-4.33 (m, 2H), 4.03 (t, J=6.0 Hz, 2H), 3.89-3.86 (m, 4H), 3.77-3.64 (m, 4H), 3.06-2.86 (m, 5H), 2.67-2.59 (m, 1H), 2.42-2.33 (m, 4H), 2.04-1.98 (m, 2H), 1.81-1.51 (m, 16H), 1.65-1.07 (m, 6H); MS (ESI) m/z: 914.3 [M+H]$^+$.

51

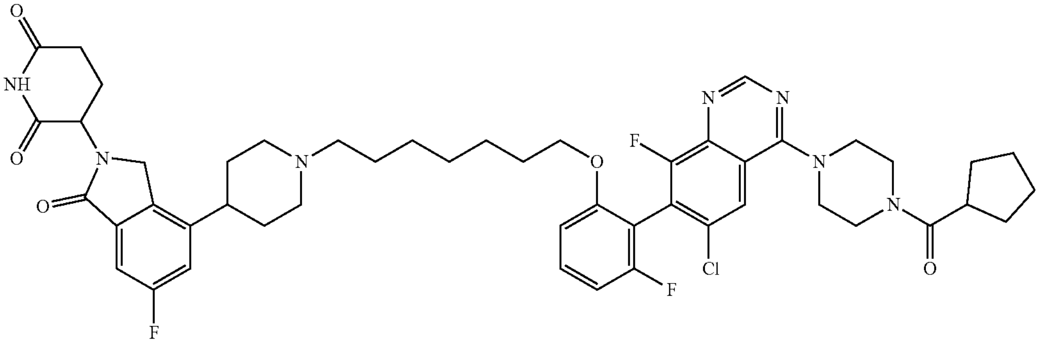

3-(4-(1-(7-(2-(6-Chloro-8-fluoro-4-(4-(tetrahydro-2H-pyran-4-carbonyl)piperazin-1-yl)quinazolin-7-yl)-3-fluorophenoxy)heptyl)piperidin-4-yl)-6-fluoro-1-oxoisoindolin-2-yl)piperidine-2,6-dione 52. $^1$H NMR (400 MHz, DMSO-$d_6$) δ 11.05 (s, 1H), 9.06 (brs, 1H), 8.72 (s, 1H), 7.56-7.54 (m, 1H), 7.45 (dd, J=2.0, 7.2 Hz, 1H), 7.30 (d, J=10.4 Hz, 1H), 7.09-7.07 (m, 1H), 7.01 (t, J=8.8 Hz, 1H), 5.17 (dd, J=5.2, 13.2 Hz, 1H), 4.55-4.35 (m, 2H), 4.04 (t, J=6.0 Hz, 2H), 3.88-3.77 (m, 8H), 3.69-3.56 (m, 4H), 3.01-2.92 (m, 7H), 2.67-2.61 (m, 2H), 2.35-2.30 (m, 2H), 2.07-2.03 (m, 5H), 1.64-1.50 (m, 8H), 1.21-1.12 (m, 6H); MS (ESI) m/z: 930.3 [M+H]$^+$.

52

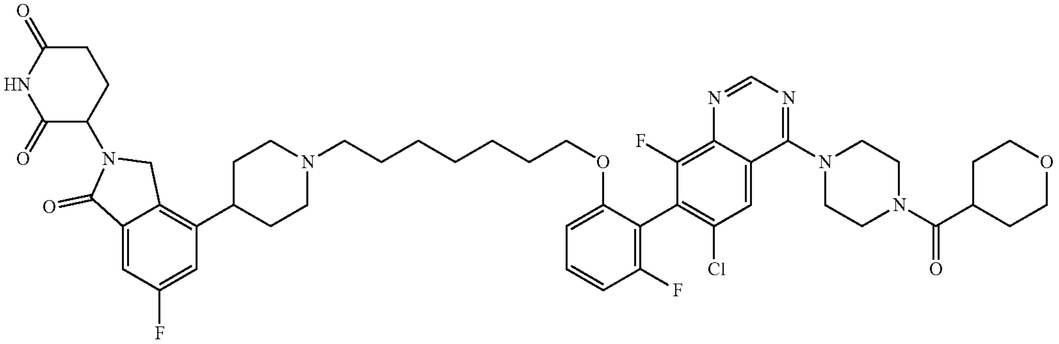

3-(4-(1-(7-(2-(6-Chloro-4-(4-(2-cyclopropylacetyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 53. $^1$H NMR (400 MHz, DMSO-$d_6$) δ 11.04 (s, 1H), 9.11 (brs, 1H), 8.71 (s, 1H), 8.05 (s, 1H), 7.44-7.30 (m, 2H), 7.07 (d, J=8.4 Hz, 1H), 7.01 (t, J=8.8 Hz, 1H), 5.19-5.14 (m, 1H), 4.54-4.34 (m, 2H), 4.04 (t, J=4.8 Hz, 2H), 3.95-3.82 (m, 5H), 3.73-3.65 (m, 6H), 3.04-2.88 (m, 6H), 2.67-2.59 (m, 2H), 2.41-2.31 (m, 4H), 2.05-1.94 (m, 4H), 1.58-1.49 (m, 4H), 1.23-1.09 (m, 4H), 1.01-0.97 (m, 1H), 0.46 (d, J=8.0 Hz, 2H), 0.14 (d, J=4.8 Hz, 2H); MS (ESI) m/z: 900.3 [M+H]$^+$.

53

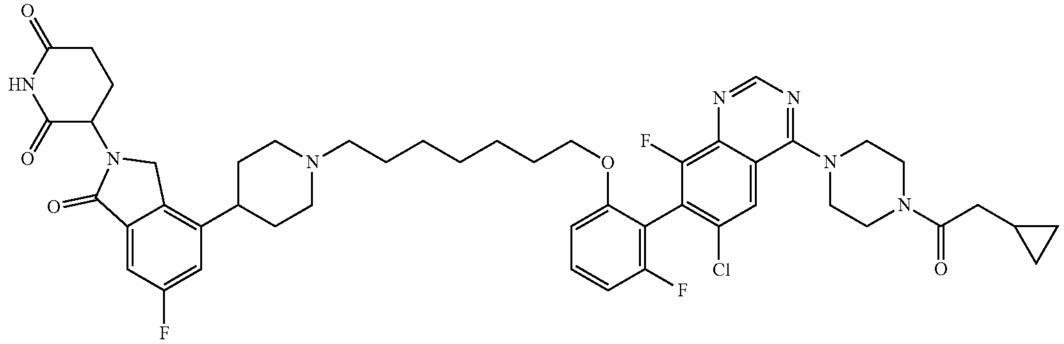

3-(4-(1-(7-(2-(6-Chloro-8-fluoro-4-(4-(tetrahydrofuran-3-carbonyl)piperazin-1-yl)quinazolin-7-yl)-3-fluorophenoxy)heptyl)piperidin-4-yl)-6-fluoro-1-oxoisoindolin-2-yl)piperidine-2,6-dione 54. $^{1}$H NMR (400 MHz, DMSO-$d_6$) δ 11.04 (s, 1H), 9.09 (s, 1H), 8.72 (s, 1H), 8.05 (s, 1H), 7.58-7.52 (m, 1H), 7.43 (d, J=6.4 Hz, 1H), 7.33-7.30 (m, 1H), 7.08 (d, J=8.4 Hz, 1H), 7.01 (t, J=8.8 Hz, 1H), 5.17 (dd, J=4.4, 12.8 Hz, 1H), 4.55-4.34 (m, 2H), 4.04 (t, J=4.8 Hz, 2H), 3.98-3.84 (m, 5H), 3.77-3.68 (m, 8H), 3.51-3.49 (m, 2H), 2.98-2.91 (m, 3H), 2.65-2.61 (m, 1H), 2.40-2.29 (m, 1H), 2.07-1.87 (m, 8H), 1.59-1.47 (m, 4H), 1.23-1.18 (m, 8H); MS (ESI) m/z: 900.3 $[M+H]^+$.

54

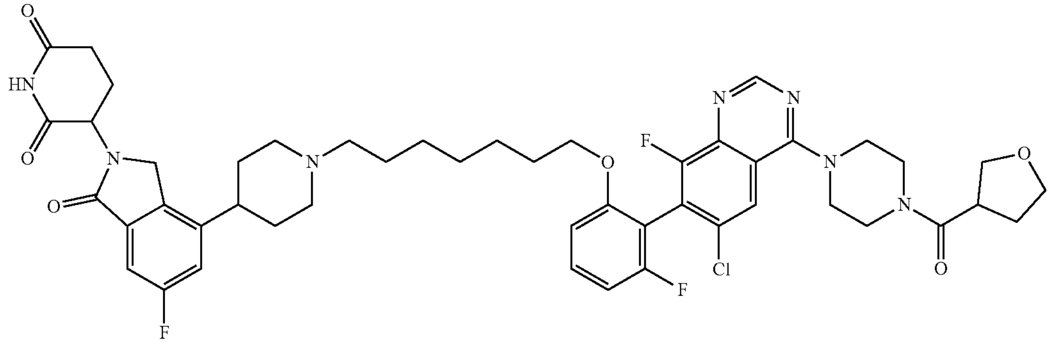

4-((2-(2-(2-(2-((4-((2S,5R)-4-Acryloyl-2,5-dimethylpiperazin-1-yl)-6-chloro-8-fluoro-7-(2-fluoro-6-hydroxyphenyl)quinazolin-2-yl)oxy)ethoxy)ethoxy)ethoxy)ethyl)amino)-2-(2,6-dioxopiperidin-3-yl)isoindoline-1,3-dione 58. $^{1}$H NMR (400 MHz, DMSO-$d_6$) δ 11.08 (s, 1H), 10.26 (d, J=8.4 Hz 1H), 7.88 (s, 1H), 7.54 (dd, J=7.2, 8.4 Hz, 1H), 7.38-7.34 (m, 1H), 7.09 (d, J=6.8 Hz, 1H), 7.01 (d, J=6.8 Hz, 1H), 6.87-6.83 (m, 1H), 6.81-6.78 (m, 1H), 6.59 (t, J=4.8 Hz, 1H), 6.17 (dd, J=2.4, 15.6 Hz, 1H), 5.73 (dd, J=2.4, 10.4 Hz, 1H), 5.04 (dd, J=12.4, 7.6 Hz, 1H), 4.78-4.70 (m, 2H), 4.45 (t, J=3.6 Hz, 2H), 4.10-4.01 (m, 2H), 3.89-3.82 (m, 2H), 3.76-3.74 (m, 2H), 3.61 (t, J=5.6 Hz, 2H), 3.57-3.56 (m, 2H), 3.55-3.54 (m, 4H), 3.46-3.43 (m, 4H), 2.92-2.83 (m, 1H), 2.60-2.54 (m, 2H), 2.03-1.99 (m, 3H), 1.28-1.20 (m, 6H); MS (ESI) m/z: 906.2 $[M+H]^+$.

58

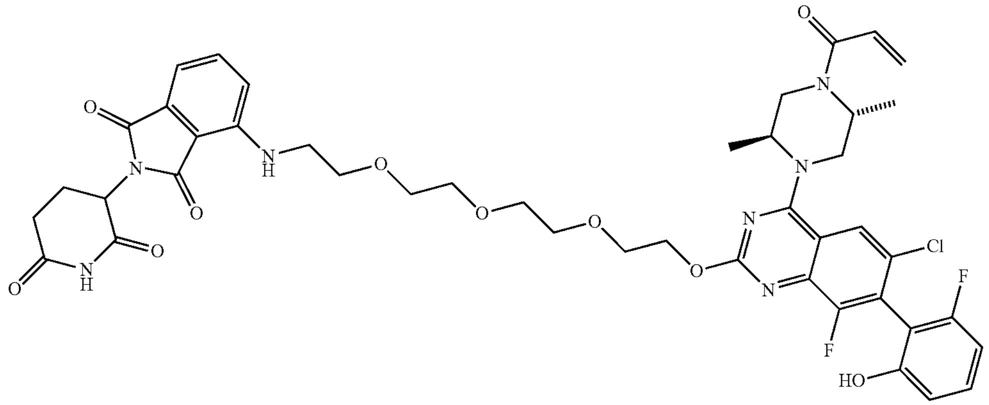

3-(4-(1-(7-(2-(6-Chloro-4-(4-(ethylsulfonyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 59. $^{1}H$ NMR (400 MHz, DMSO-$d_6$) δ 11.03 (s, 1H), 8.75 (s, 1H), 8.02 (s, 1H), 7.58-7.52 (m, 1H), 7.41 (d, J=6.8 Hz, 1H), 7.34-7.31 (m, 1H), 7.08 (d, J=8.4 Hz, 1H), 7.01 (t, J=8.0 Hz, 1H), 5.16 (dd, J=4.8, 13.2 Hz, 1H), 4.55-4.34 (m, 2H), 4.04 (t, J=5.6 Hz, 2H), 3.95-3.84 (m, 5H), 3.56-3.43 (m, 3H), 3.15-3.10 (m, 4H), 2.97-2.87 (m, 4H), 2.65-2.60 (m, 1H), 2.38-2.33 (m, 1H), 1.99-1.90 (m, 10H), 1.54-1.46 (m, 4H), 1.24-1.17 (m, 6H); MS (ESI) m/z: 911.4 $[M+H]^+$.

59

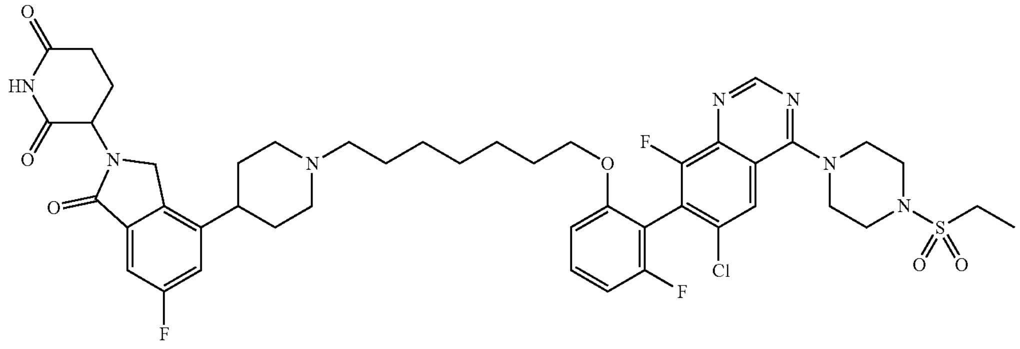

3-(4-(1-(5-(2-(6-Chloro-8-fluoro-4-(4-propionylpiperazin-1-yl)quinazolin-7-yl)-3-fluorophenoxy)pentyl)piperidin-4-yl)-6-fluoro-1-oxoisoindolin-2-yl)piperidine-2,6-dione 60. $^{1}H$ NMR (400 MHz, DMSO-$d_6$) δ 11.02 (s, 1H), 8.70 (s, 1H), 8.06-8.05 (m, 1H), 7.56-7.52 (m, 1H), 7.39-7.38 (m, 2H), 7.09 (d, J=8.4 Hz, 1H), 7.01 (t, J=8.8 Hz, 1H), 5.15 (dd, J=4.8, 13.2 Hz, 1H), 4.54-4.33 (m, 2H), 4.05 (t, J=6.0 Hz, 2H), 3.92-3.83 (m, 4H), 3.69-3.64 (m, 4H), 3.50-3.49 (m, 1H), 2.97-2.89 (m, 4H), 2.63-2.59 (m, 2H), 2.39-2.34 (m, 3H), 2.05-1.95 (m, 3H), 1.57-1.55 (m, 3H), 1.27-1.19 (m, 7H), 1.01 (t, J=7.2 Hz, 3H); MS (ESI) m/z: 846.3 $[M+H]^+$.

60

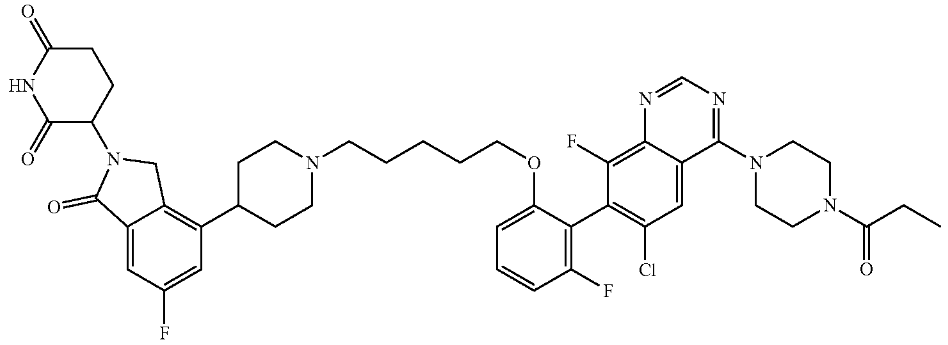

3-(4-(1-(9-(2-(6-Chloro-8-fluoro-4-(4-propionylpiperazin-1-yl)quinazolin-7-yl)-3-fluorophenoxy)nonyl)piperidin-4-yl)-6-fluoro-1-oxoisoindolin-2-yl)piperidine-2,6-dione 61. $^1H$ NMR (400 MHz, DMSO-$d_6$) δ 11.05 (s, 1H), 9.19 (brs, 1H), 8.71 (s, 1H), 8.04 (s, 1H), 7.58-7.52 (q, J=8.4 Hz, 1H), 7.44 (dd, J=2.4, 7.2 Hz, 1H), 7.30 (dd, J=2.4, 10.4 Hz, 1H), 7.07 (d, J=8.4 Hz, 1H), 7.01 (t, J=8.8 Hz, 1H), 5.18 (dd, J=4.8, 13.2 Hz, 1H), 4.55-4.35 (m, 2H), 4.03 (t, J=6.0 Hz, 2H), 3.96-3.88 (m, 4H), 3.73-3.67 (m, 4H), 3.62-3.57 (m, 2H), 3.08-2.90 (m, 7H), 2.69-2.63 (m, 1H), 2.42-2.34 (m, 3H), 2.07-1.97 (m, 6H), 1.65-1.58 (m, 2H), 1.55-1.48 (m, 2H), 1.18-1.10 (m, 8H), 1.02 (t, J=7.6 Hz, 3H); MS (ESI) m/z: 902.4 $[M+H]^+$.

61

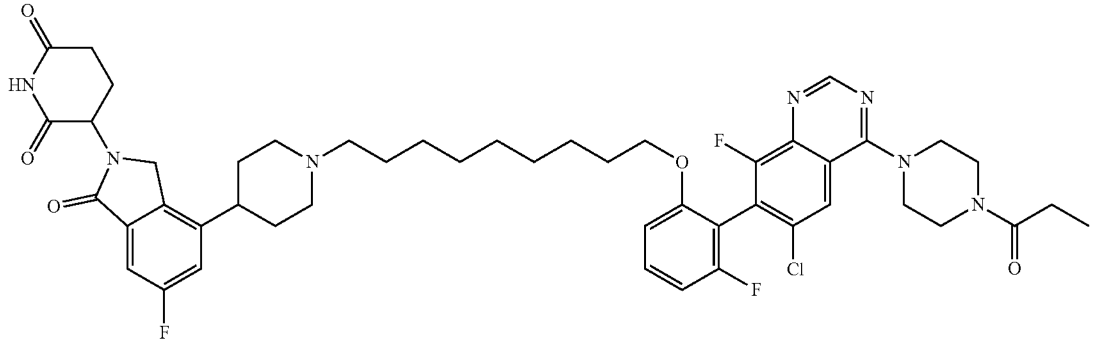

(3S)-3-(4-((4-(((3-(2-(6-Chloro-8-fluoro-4-(4-propionylpiperazin-1-yl)quinazolin-7-yl)-3-fluorophenoxy)propyl)amino)methyl)benzyl)oxy)-1-oxoisoindolin-2-yl)piperidine-2,6-dione 63. $^1H$ NMR (400 MHz, DMSO-$d_6$) δ 10.98 (brs, 1H), 8.69 (s, 1H), 8.03 (s, 1H), 7.57-7.51 (m, 1H), 7.49-7.46 (m, 1H), 7.36-7.31 (m, 4H), 7.24-7.22 (m, 2H), 7.09-7.07 (d, J=8.4 Hz, 1H), 7.00 (t, J=8.8 Hz, 1H), 5.20 (s, 2H), 5.10 (dd, J=5.2, 13.2 Hz, 1H), 4.42-4.03 (m, 2H), 4.22-4.09 (m, 2H), 3.96-3.82 (m, 4H), 3.70-3.63 (m, 4H), 3.56-3.49 (m, 2H), 2.96-2.86 (m, 1H), 2.45-2.39 (m, 3H), 2.37-2.32 (m, 3H), 2.04-1.94 (m, 2H), 1.71-1.66 (m, 2H), 1.01 (t, J=7.2 Hz, 3H); MS (ESI) m/z: 852.3 $[M+H]^+$.

63

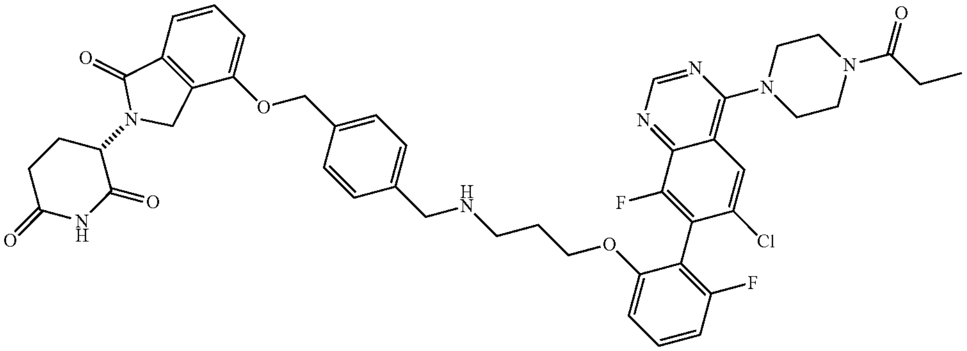

3-(4-(1-(7-(2-((2R,4aR)-11-Chloro-9-fluoro-2,6-dimethyl-5-oxo-3-propionyl-2,3,4,4a,5,6-hexahydro-1H-pyrazino[11',2':4,5]pyrazino[2,3-c]quinolin-10-yl)-3-fluorophenoxy)heptyl)piperidin-4-yl)-6-fluoro-1-oxoisoindolin-2-yl)piperidine-2,6-dione 65. $^{1}$H NMR (400 MHz, DMSO-$d_6$) δ 11.00 (s, 1H), 9.01 (s, 1H), 7.99 (s, 1H) 7.55-7.53 (m, 1H), 7.46-7.34 (m, 2H), 7.07 (d, J=8.0 Hz, 1H), 7.01 (t, J=8.0 Hz, 1H), 5.15-5.11 (m, 1H), 4.78-4.72 (m, 1H), 4.51-4.31 (m, 3H), 4.03 (t, J=6.4 Hz, 2H), 3.95 (m, 1H), 3.72-3.68 (m, 1H), 3.51-3.49 (m, 4H), 3.15-3.05 (m, 2H), 2.92-2.87 (m, 4H), 2.80-2.62 (m, 2H), 2.62-2.58 (m, 2H), 2.46-2.40 (m, 1H), 2.16-2.14 (m, 2H), 2.03-1.97 (m, 3H), 1.91-1.85 (m, 4H), 1.70-1.68 (m, 4H), 1.53-1.46 (m, 5H), 1.07-1.00 (m, 5H); MS (ESI) m/z: 942.4 $[M+H]^+$.

65

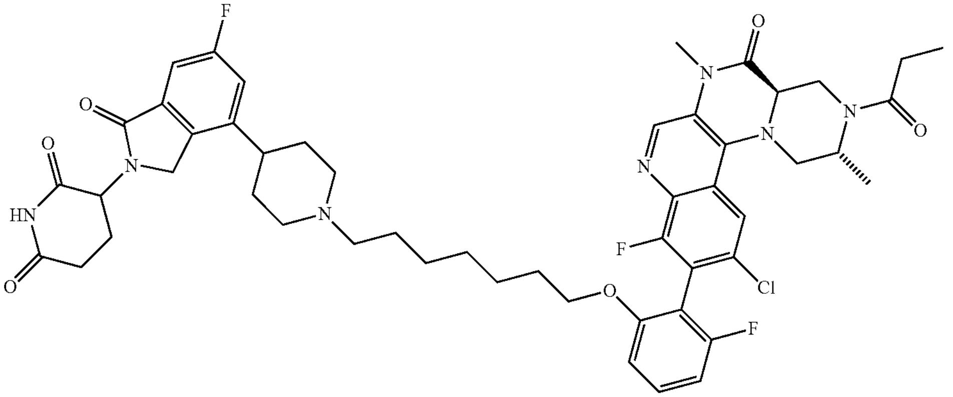

3-(4-(1-(7-((2R,4aR)-3-Acryloyl-11-chloro-9-fluoro-10-(2-fluoro-6-hydroxyphenyl)-2-methyl-5-oxo-1,2,3,4,4a,5-hexahydro-6H-pyrazino[1',2':4,5]pyrazino[2,3-c]quinolin-6-yl)heptyl)piperidin-4-yl)-6-fluoro-1-oxoisoindolin-2-yl) piperidine-2,6-dione 66. $^{1}$H NMR (400 MHz, DMSO-$d_6$) δ 11.02 (s, 1H), 9.05 (s, 1H), 7.98 (s, 1H), 7.44-7.33 (m, 3H), 7.01 (dd, J=10.4, 16.0 Hz, 1H), 6.86 (d, J=8.0 Hz, 1H), 6.81 (t, J=8.8 Hz, 1H), 6.15 (d, J=16.8 Hz, 1H), 5.80-5.70 (m, 1H), 5.12 (dd, J=4.8, 13.2 Hz, 1H), 4.76 (s, 1H), 4.64 (d, J=14.0 Hz, 1H), 4.52-4.30 (m, 3H), 4.25-3.90 (m, 4H), 3.75 (dd, J=2.8, 14.0 Hz, 2H), 2.99-2.79 (m, 4H), 2.60 (d, J=16.0 Hz, 2H), 2.45-2.35 (m, 1H), 2.24 (t, J=6.8 Hz, 2H), 2.05-1.97 (m, 5H), 1.71 (s, 4H), 1.60-1.51 (m, 4H), 1.45-1.30 (m, 6H); MS (ESI) m/z: 926.4 $[M+H]^+$.

66

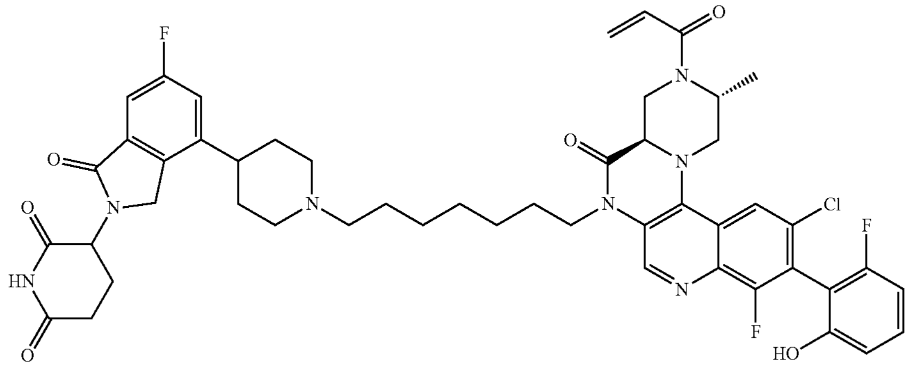

3-(4-(1-(7-((2R,4aR)-11-Chloro-9-fluoro-10-(2-fluoro-6-hydroxyphenyl)-2-methyl-5-oxo-3-propionyl-1,2,3,4,4a,5-hexahydro-6H-pyrazino[11',2':4,5]pyrazino[2,3-c]quinolin-6-yl)heptyl)piperidin-4-yl)-6-fluoro-1-oxoisoindolin-2-yl)piperidine-2,6-dione 67. $^{1}$H NMR (400 MHz, DMSO-$d_6$) δ 11.04 (s, 1H), 10.26 (s, 1H), 9.38 (s, 1H), 9.06 (s, 1H), 7.98 (s, 1H), 7.43-7.25 (m, 3H), 6.87 (d, J=8.0 Hz, 1H), 6.81 (t, J=8.8 Hz, 1H), 5.17 (dd, J=4.8, 13.2 Hz, 1H), 4.73 (s, 1H), 4.56-4.46 (m, 2H), 4.40-4.34 (m, 1H), 4.30-3.80 (m, 9H), 3.71 (d, J=10.4 Hz, 2H), 3.58 (d, J=11.2 Hz, 2H), 3.20-2.90 (m, 7H), 2.80-2.60 (m, 4H), 2.45-2.31 (m, 1H), 2.10-1.90 (m, 6H), 1.70-1.45 (m, 6H), 1.05 (t, J=7.2 Hz, 3H); MS (ESI) m/z: 928.4 $[M+H]^+$.

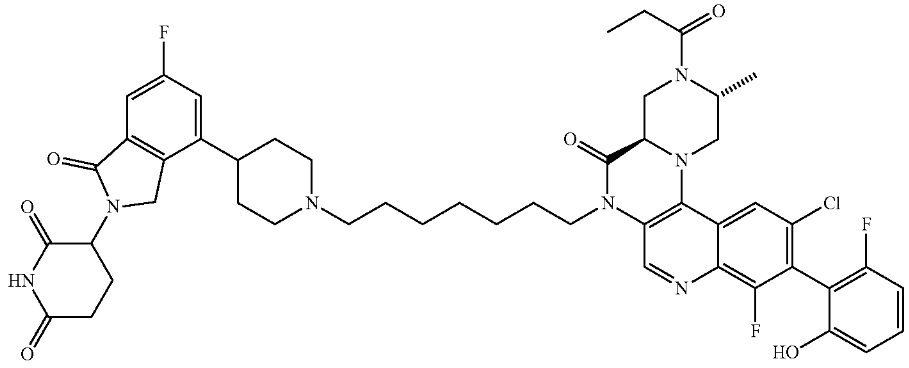 [SMILES: CCC(=O)N1C[C@@H]2C(=O)N(CCCCCCCN3CCC(c4cc(F)cc5c4CN(C4CCC(=O)NC4=O)C5=O)CC3)c3cnc4c(F)c(-c5c(O)cccc5F)c(Cl)cc4c3N2C[C@H]1C]

3-(1-(1-(7-(2-(4-(4-Acryloylpiperazin-1-yl)-6-chloro-8-fluoroquinazolin-7-yl)-3-fluorophenoxy)heptyl)piperidin-4-yl)-4-oxo-4H-thieno[3,4-c]pyrrol-5(6H)-yl)piperidine-2,6-dione 70. $^{1}$H NMR (400 MHz, DMSO-$d_6$) δ 10.96 (s, 1H), 8.70 (s, 1H), 8.04 (s, 1H), 7.81 (s, 1H), 7.57-7.51 (m, 1H), 7.07 (d, J=8.8 Hz, 1H), 7.00 (t, J=8.4 Hz, 1H), 6.85-6.79 (m, 1H), 6.16 (dd, J=2.4, 16.8 Hz, 1H), 5.73 (dd, J=2.0, 10.4 Hz, 1H), 5.00 (dd, J=5.2, 13.2 Hz, 1H), 4.38-4.16 (m, 2H), 4.02 (t, J=5.6 Hz, 2H), 3.94-3.90 (m, 4H), 3.84-3.77 (m, 4H), 2.90-2.87 (m, 1H), 2.84-2.81 (m, 2H), 2.59-2.55 (m, 1H), 2.37-2.32 (m, 1H), 2.12 (t, J=7.2 Hz, 2H), 2.02-1.96 (m, 4H), 1.63-1.57 (m, 2H), 1.53-1.44 (m, 4H), 1.15-1.04 (m, 8H); MS (ESI) m/z: 860.3 $[M+H]^+$.

70

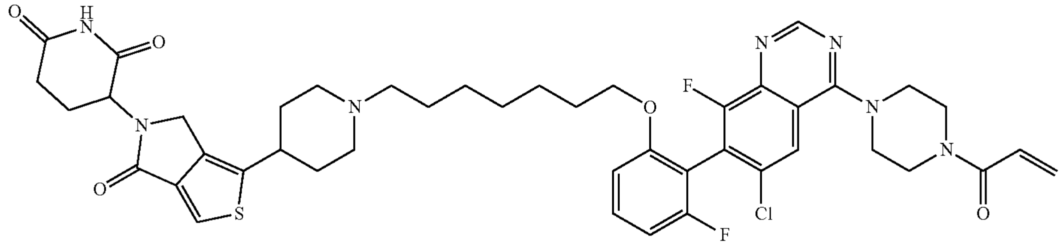

3-(4-(1-(7-(2-(4-((S)-4-Acryloyl-2-methylpiperazin-1-yl)-6-fluoro-1-(2-isopropylphenyl)-2-oxo-1,2-dihydropyrido[2,3-d]pyrimidin-7-yl)-3-fluorophenoxy)heptyl)piperidin-4-yl)-6-fluoro-1-oxoisoindolin-2-yl)piperidine-2,6-dione 72. $^1$H NMR (400 MHz, DMSO-$d_6$) δ 11.06 (s, 1H), 9.28 (s, 1H), 8.27 (s, 1H), 7.45-7.20 (m, 6H), 7.12-7.03 (m, 1H), 6.96 (d, J=4.4 Hz, 1H), 6.90-6.83 (m, 1H), 6.65 (s, 1H), 6.21 (d, J=16.8 Hz, 1H), 5.77 (d, J=11.6 Hz, 1H), 5.33 (t, J=4.8 Hz, 1H), 5.18 (dd, J=4.4 Hz, 12.8 Hz, 1H), 4.90 (s, 1H), 4.57-4.35 (m, 3H), 4.30-4.12 (m, 2H), 3.96-3.90 (m, 3H), 3.80-3.70 (m, 2H), 3.64-3.56 (m, 4H), 3.10-2.92 (m, 5H), 2.68-2.60 (m, 2H), 2.40-2.31 (m, 2H), 2.10-1.95 (m, 5H), 1.64 (s, 1H), 1.56-1.42 (m, 3H), 1.38-1.30 (m, 4H), 1.10-1.02 (m, 4H), 0.96 (d, J=6.8 Hz, 1H), 0.86 (t, J=6.8 Hz, 3H); MS (ESI) m/z: 987.4 $[M+H]^+$.

72

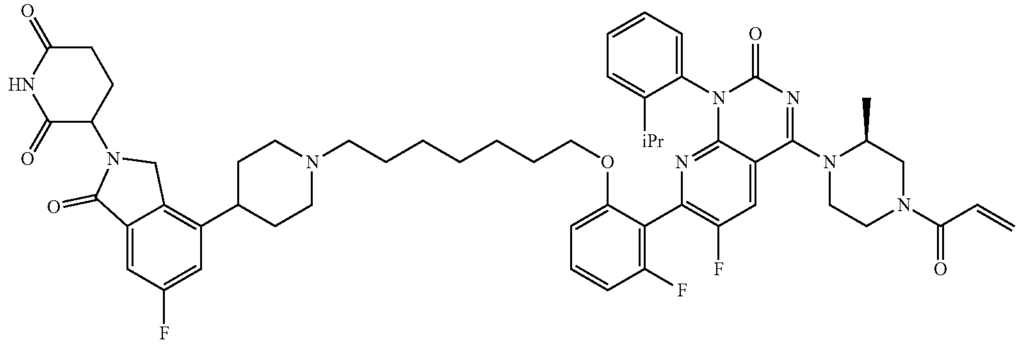

3-(6-Fluoro-4-(1-(7-(3-fluoro-2-(6-fluoro-1-(2-isopropylphenyl)-4-((S)-2-methyl-4-propionylpiperazin-1-yl)-2-oxo-1,2-dihydropyrido[2,3-d]pyrimidin-7-yl)phenoxy)heptyl)piperidin-4-yl)-1-oxoisoindolin-2-yl)piperidine-2,6-dione 73. $^1$H NMR (400 MHz, DMSO-$d_6$) δ 11.05 (s, 1H), 9.48 (s, 1H), 8.27-8.25 (m, 1H), 7.50-6.50 (m, 9H), 5.33 (t, J=4.8 Hz, 1H), 5.16 (dd, J=4.8, 13.6 Hz, 1H), 4.91 (s, 1H), 4.60-4.30 (m, 3H), 4.30-4.00 (m, 2H), 4.00 (s, 4H), 3.90-3.70 (m, 5H), 3.10-2.90 (m, 5H), 2.66-2.55 (m, 2H), 2.50-2.45 (m, 2H), 2.10-1.90 (m, 5H), 1.63 (s, 1H), 1.58-1.42 (m, 3H), 1.40-1.23 (m, 10H), 1.10-1.00 (m, 4H), 0.85 (t, J=6.0 Hz, 3H); MS (ESI) m/z: 989.5 $[M+H]^+$.

73

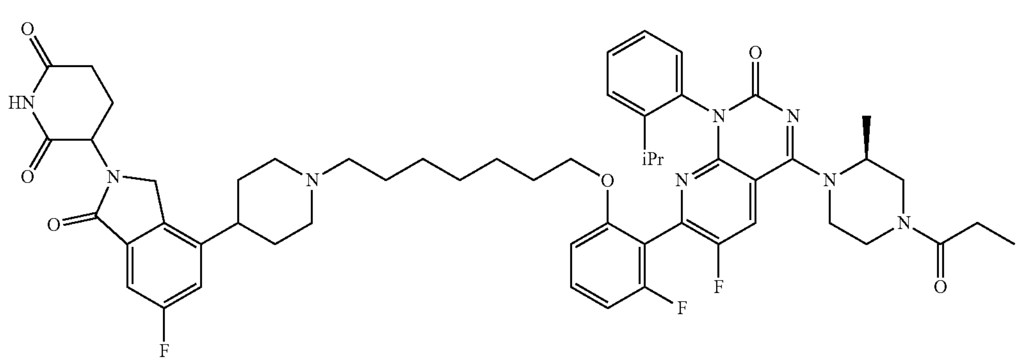

3-(4-(1-(7-((4-(4-Acryloylpiperazin-1-yl)-7-(3-hydroxynaphthalen-1-yl)-5,6,7,8-tetrahydropyrido[3,4-d]pyrimidin-2-yl)oxy)heptyl)piperidin-4-yl)-6-fluoro-1-oxoisoindolin-2-yl)piperidine-2,6-dione 75. $^{1}$H NMR (400 MHz, DMSO-$d_6$) δ 10.99 (s, 1H), 9.96 (s, 1H), 9.65 (s, 1H), 8.66 (s, 1H), 7.94 (d, J=8.2 Hz, 1H), 7.60 (d, J=8.0 Hz, 1H), 7.38-7.16 (m, 4H), 6.80-6.71 (m, 3H), 6.08 (dd, J=1.6, 16.8 Hz, 1H), 5.67 (dd, J=2.0, 11.2 Hz, 1H), 5.11 (dd, J=4.8, 13.2 Hz, 1H), 4.50-4.29 (m, 2H), 4.18-4.16 (m, 2H), 4.01 (s, 2H), 3.65-3.46 (m, 10H), 3.11-2.84 (m, 10H), 2.58-2.54 (m, 1H), 2.29-2.27 (m, 1H), 1.99-1.91 (m, 6H), 1.68-1.62 (m, 4H), 1.33-1.31 (m, 4H); MS (ESI) m/z: 873.5 $[M+H]^+$.

75

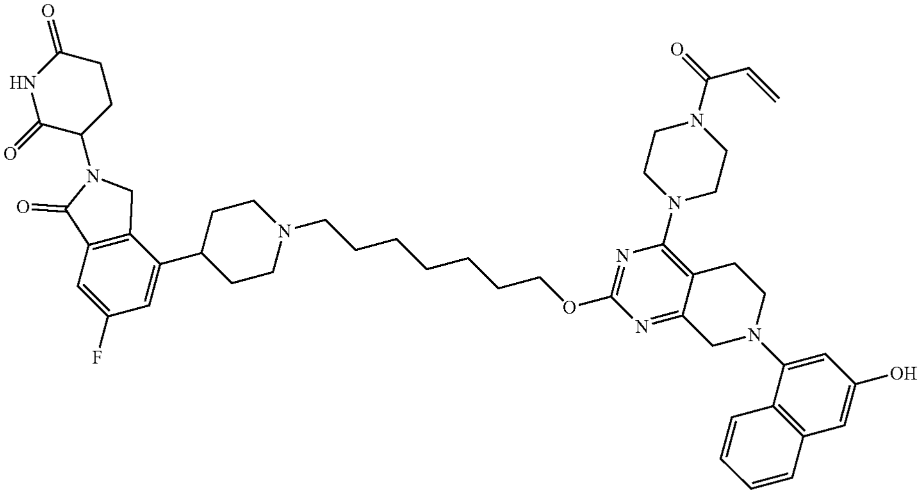

(2S,4R)-1-((2S)-2-(11-(2-(4-(4-Acryloylpiperazin-1-yl)-6-chloro-8-fluoroquinazolin-7-yl)-3-fluorophenoxy)undecanamido)-3,3-dimethylbutanoyl)-4-hydroxy-N-(4-(4-methylthiazol-5-yl)benzyl)pyrrolidine-2-carboxamide 76. $^{1}$H NMR (400 MHz, DMSO-$d_6$) δ 8.97 (s, 1H), 8.69 (s, 1H), 8.54 (t, J=6.0 Hz, 1H), 8.04 (s, 1H), 7.81 (d, J=5.6 Hz, 1H), 7.53 (q, J=8.4 Hz, 1H), 7.43-7.37 (m, 4H), 7.06 (d, J=8.4 Hz, 1H), 6.99 (t, J=8.4 Hz, 1H), 6.85-6.78 (m, 1H), 6.17 (dd, J=2.4, 16.8 Hz, 1H), 5.73 (dd, J=2.4, 10.8 Hz, 1H), 5.11 (d, J=3.6 Hz, 1H), 4.53 (d, J=9.2 Hz, 1H), 4.46-4.40 (m, 2H), 4.36-4.34 (m, 1H), 4.21 (dd, J=5.6, 16.0 Hz, 1H), 4.01 (t, J=8.8 Hz, 2H), 3.99-3.65 (m, 10H), 2.44 (s, 3H), 2.26-2.20 (m, 1H), 2.11-1.88 (m, 4H), 1.51-1.38 (m, 5H), 1.29-1.24 (m, 4H), 1.19-1.13 (m, 6H), 0.92 (s, 9H); MS (ESI) m/z: 1027.4 $[M+H]^+$.

76

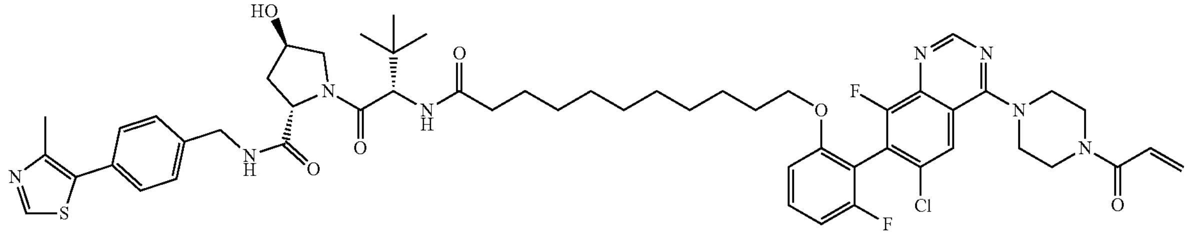

(2S,4R)-1-((2S)-2-(11-(2-(6-Chloro-8-fluoro-4-(4-propionylpiperazin-1-yl)quinazolin-7-yl)-3-fluorophenoxy)undecanamido)-3,3- dimethylbutanoyl)-4-hydroxy-N-(4-(4-methylthiazol-5-yl)benzyl)pyrrolidine-2-carboxamide 77. $^1$H NMR (400 MHz, DMSO-$d_6$) δ 8.97 (s, 1H), 8.69 (s, 1H), 8.54 (t, J=6.0 Hz, 1H), 8.03 (s, 1H), 7.81 (d, J=5.2 Hz, 1H), 7.53 (q, J=7.6 Hz, 1H), 7.43-7.37 (m, 4H), 7.06 (d, J=8.4 Hz, 1H), 6.99 (t, J=8.8 Hz, 1H), 5.11 (d, J=3.2 Hz, 1H), 4.54 (d, J=9.2 Hz, 1H), 4.46-4.40 (m, 2H), 4.35-4.34 (m, 1H), 4.21 (dd, J=5.6, 16.0 Hz, 1H), 4.01 (t, J=8.8 Hz, 2H), 3.90-3.86 (m, 4H), 3.99-3.65 (m, 6H), 2.44 (s, 3H), 2.37 (q, J=7.6 Hz, 2H), 2.26-2.20 (m, 1H), 2.11-1.87 (m, 3H), 1.51-1.40 (m, 4H), 1.13-0.97 (m, 15H), 0.92 (s, 9H); MS (ESI) m/z: 1029.4 $[M+H]^+$.

77

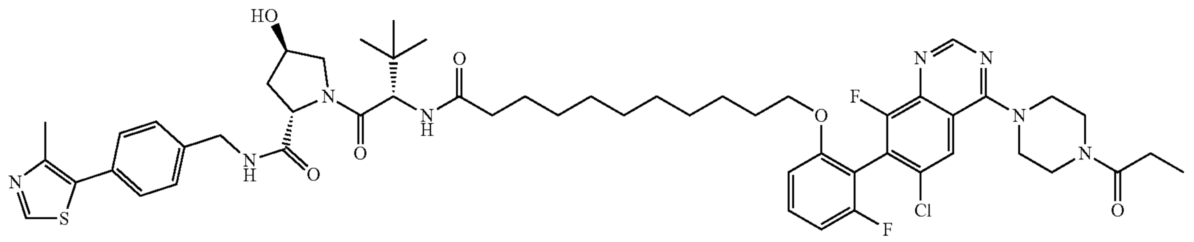

(2S,4R)-1-((2S)-2-(7-(2-(6-Chloro-8-fluoro-4-(4-propionylpiperazin-1-yl)quinazolin-7-yl)-3-fluorophenoxy)heptanamido)-3,3-dimethylbutanoyl)-4-hydroxy-N-(4-(4-methylthiazol-5-yl)benzyl)pyrrolidine-2-carboxamide 78. $^1$H NMR (400 MHz, DMSO-$d_6$) δ 8.97 (d, J=1.6 Hz, 1H), 8.70 (d, J=11.6 Hz, 1H), 8.56-8.53 (m, 1H), 8.04 (s, 1H), 7.79 (q, J=9.2 Hz, 1H), 7.53 (q, J=8.4 Hz, 1H), 7.43-7.47 (m, 4H), 7.07 (d, J=8.4 Hz, 1H), 6.99 (t, J=8.4 Hz, 1H), 5.12 (s, 1H), 4.52 (dd, J=4.4, 9.2 Hz, 1H), 4.46-4.41 (m, 2H), 4.35 (s, 1H), 4.22 (dd, J=5.2, 15.6 Hz, 1H), 4.04-4.00 (m, 2H), 3.91-3.86 (m, 4H), 3.70-3.65 (m, 6H), 2.43 (d, J=4.0 Hz, 3H), 2.37 (q, J=7.6 Hz, 2H), 2.17-2.13 (m, 1H), 2.03-1.99 (m, 2H), 1.94-1.87 (m, 1H), 1.52-1.48 (m, 2H), 1.38-1.33 (m, 2H), 1.15-1.14 (m, 4H), 1.02 (t, J=7.6 Hz, 3H), 0.92 (s, 9H); MS (ESI) m/z: 973.3 $[M+H]^+$.

78

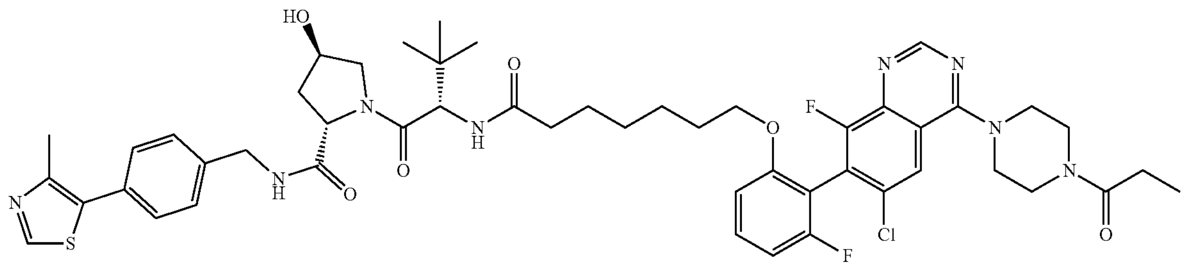

3-(4-(1-(7-(2-(6-Chloro-8-fluoro-4-(4-(pyrrolidine-3-carbonyl)piperazin-1-yl)quinazolin-7-yl)-3-fluorophenoxy)heptyl)piperidin-4-yl)-6-fluoro-1-oxoisoindolin-2-yl)piperidine-2,6-dione 79. $^1$H NMR (400 MHz, DMSO-$d_6$) δ 11.03 (s, 1H), 9.21 (s, 1H), 8.82 (s, 2H), 8.72 (s, 1H), 8.05 (s, 1H), 7.56-7.52 (m, 1H), 7.44 (dd, J=2.4, 5.8 Hz, 1H), 7.29 (dd, J=2.4, 4.4 Hz, 1H), 7.08 (d, J=8.4 Hz, 1H), 7.00 (t, J=9.2 Hz, 1H), 5.17 (dd, J=4.8, 13.2 Hz, 1H), 4.55-4.34 (m, 2H), 4.05 (t, J=6.4 Hz, 1H), 3.94-3.65 (m, 7H), 3.22-3.18 (m, 2H), 3.04-2.93 (m, 9H), 2.67-2.60 (m, 2H), 2.35-2.31 (m, 2H), 2.28-2.24 (m, 2H), 2.08-1.94 (m, 7H), 1.60-1.52 (m, 5H), 1.21-1.14 (m, 4H); MS (ESI) m/z: 915.3 [M+H]$^+$.

79

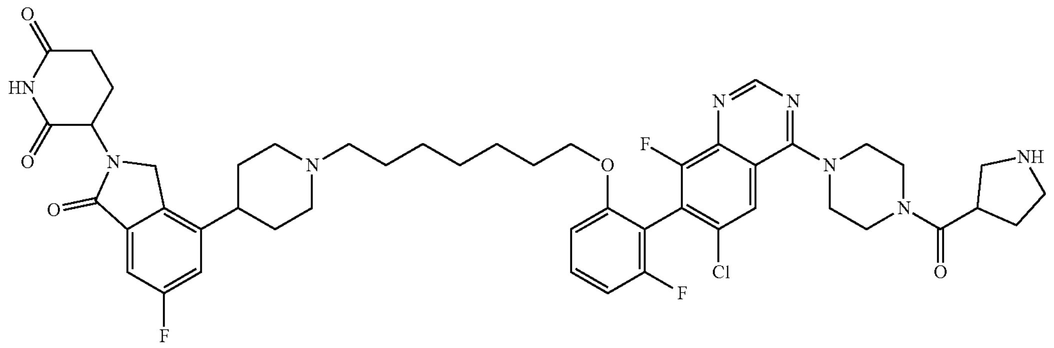

(E)-2-(4-(6-Chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoroquinazolin-4-yl)piperazine-1-carbonyl)-4-methylpent-2-enenitrile 80. $^1$H NMR (400 MHz, DMSO-$d_6$) δ 11.05 (s, 1H), 9.40 (s, 1H), 8.74 (d, J=6.4 Hz, 1H), 8.07 (s, 1H), 7.58-7.53 (m, 1H), 7.43 (d, J=6.0 Hz, 1H), 7.30 (d, J=6.0 Hz, 1H), 7.09 (d, J=8.4 Hz, 1H), 7.03-6.95 (m, 2H), 5.17 (dd, J=4.4, 13.2 Hz, 1H), 4.56-4.35 (m, 2H), 4.04-3.92 (m, 6H), 3.84-3.78 (m, 6H), 3.59-3.51 (m, 3H), 3.01-2.91 (m, 5H), 2.65-2.61 (m, 1H), 2.39-2.29 (m, 1H), 2.06-1.89 (m, 5H), 1.55-1.54 (m, 3H), 1.23-1.11 (m, 12H); MS (ESI) m/z: 938.9 [M+H]$^+$.

80

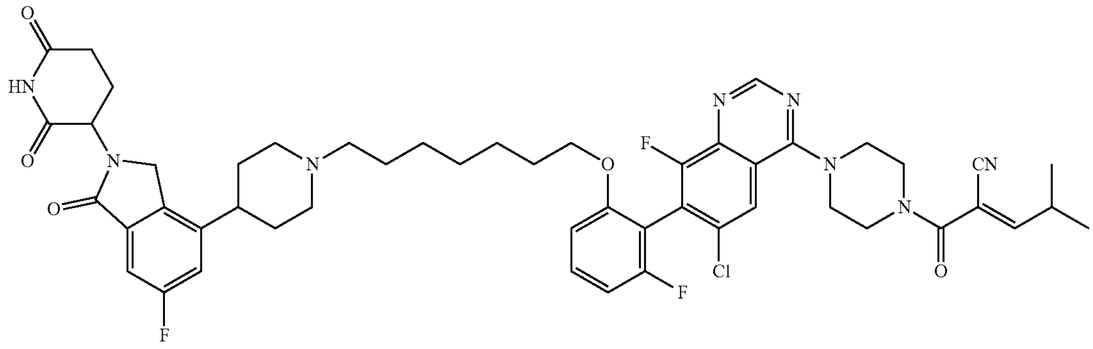

3-(4-(1-(7-(2-(6-Chloro-8-fluoro-4-(4-(oxetane-3-carbonyl)piperazin-1-yl)quinazolin-7-yl)-3-fluorophenoxy)heptyl)piperidin-4-yl)-6-fluoro-1-oxoisoindolin-2-yl)piperidine-2,6-dione 81. $^1$H NMR (400 MHz, DMSO-$d_6$) δ 11.05 (s, 1H), 9.41 (s, 1H), 8.72 (s, 1H), 8.04 (s, 1H), 7.58-7.52 (m, 1H), 7.43 (dd, J=2.0, 7.2 Hz, 1H), 7.30 (dd, J=2.0, 10.4 Hz, 1H), 7.08 (d, J=8.4 Hz, 1H), 7.01 (t, J=8.8 Hz, 1H), 5.17 (dd, J=5.6, 13.2 Hz, 1H), 4.75-4.69 (m, 4H), 4.56-4.35 (m, 2H), 4.22-4.15 (m, 1H), 4.04 (t, J=6.0 Hz, 2H), 3.94-3.85 (m, 4H), 3.59-3.52 (m, 5H), 3.44-3.40 (m, 2H), 3.01-2.90 (m, 6H), 2.65-2.61 (m, 1H), 2.39-2.28 (m, 1H), 2.06-1.92 (m, 5H), 1.63-1.54 (m, 4H), 1.22-1.19 (m, 5H); MS (ESI) m/z: 901.9 [M+H]$^+$.

81

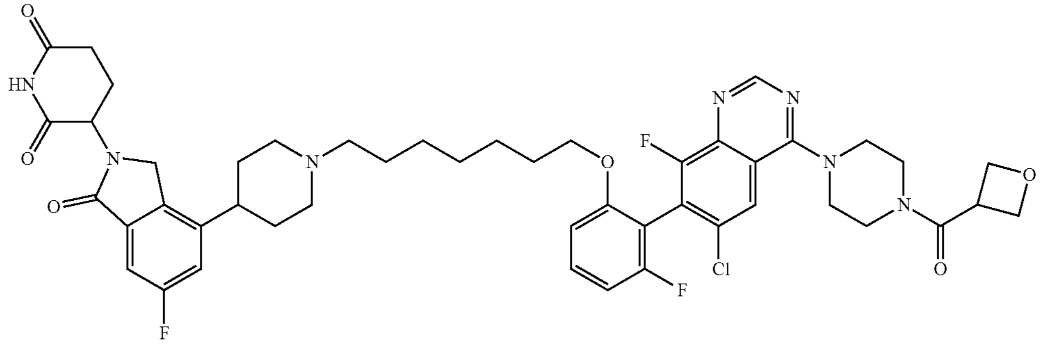

3-(4-(1-(7-(2-(6-Chloro-8-fluoro-4-(4-(2-fluoroacryloyl)piperazin-1-yl)quinazolin-7-yl)-3-fluorophenoxy)heptyl)piperidin-4-yl)-6-fluoro-1-oxoisoindolin-2-yl)piperidine-2,6-dione 82. $^{1}H$ NMR (400 MHz, DMSO-$d_6$) δ 11.07 (s, 1H), 9.48 (s, 1H), 8.74 (d, J=3.6 Hz, 1H), 8.07 (s, 1H), 7.59-7.52 (m, 1H), 7.45 (d, J=6.8 Hz, 1H), 7.32 (d, J=2.4 Hz, 1H), 7.09 (dd, J=3.2, 8.8 Hz, 1H), 7.05-7.00 (m, 1H), 5.40-5.17 (m, 3H), 4.57-4.36 (m, 2H), 4.05-3.92 (m, 6H), 3.86-3.71 (m, 4H), 3.60-3.57 (m, 3H), 3.32-3.24 (m, 1H), 3.07-2.93 (m, 6H), 2.66-2.61 (m, 1H), 2.40-2.28 (m, 1H), 2.10-1.95 (m, 5H), 1.60-1.50 (m, 4H), 1.32-1.24 (m, 4H); MS (ESI) m/z: 889.9 [M+H]$^+$.

82

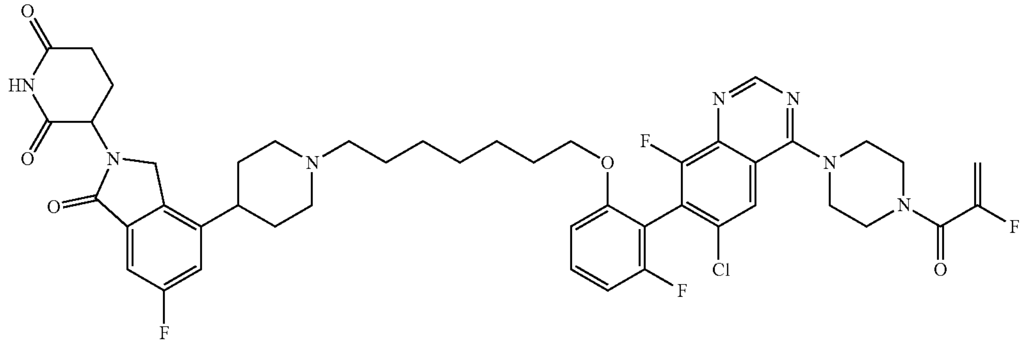

4-(6-Chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoroquinazolin-4-yl)piperazine-1-carboxamide 83. $^{1}H$ NMR (400 MHz, DMSO-$d_6$) δ 11.08 (s, 1H), 9.19 (s, 1H), 8.71 (s, 1H), 8.05 (s, 1H), 7.58-7.52 (m, 1H), 7.45 (dd, J=2.0, 7.2 Hz, 1H), 7.31 (dd, J=2.4, 10.8 Hz, 1H), 7.08 (d, J=8.8 Hz, 1H), 7.02 (t, J=8.8 Hz, 1H), 6.11 (s, 2H), 5.17 (dd, J=4.8, 13.2 Hz, 1H), 4.56-4.35 (m, 2H), 4.07-4.00 (m, 2H), 3.90-3.81 (m, 4H), 3.59-3.52 (m, 8H), 3.04-2.92 (m, 6H), 2.67-2.59 (m, 1H), 2.35-2.32 (m, 1H), 2.06-1.97 (m, 5H), 1.59-1.43 (m, 4H), 1.20-1.14 (m, 4H); MS (ESI) m/z: 861.9[M+H]$^+$.

83

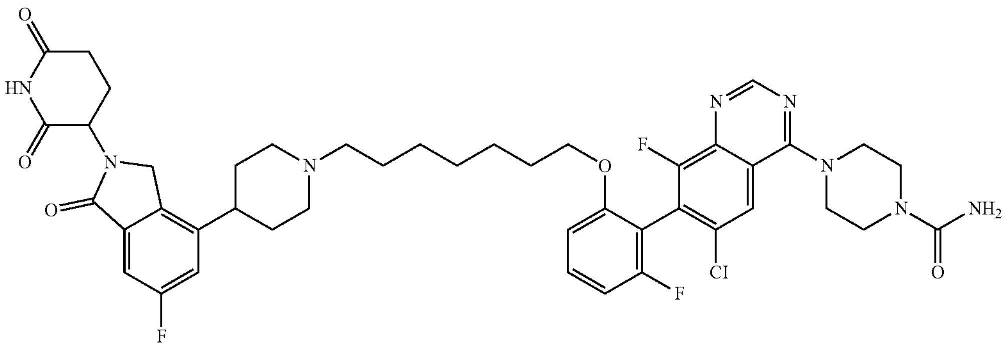

3-(4-(1-(2-(4-(2-(2-(6-Chloro-8-fluoro-4-(4-propionylpiperazin-1-yl)quinazolin-7-yl)-3-fluorophenoxy)ethyl)cyclohexyl)ethyl)piperidin-4-yl)-6-fluoro-1-oxoisoindolin-2-yl)piperidine-2,6-dione 84. $^1$H NMR (400 MHz, DMSO-$d_6$) δ 10.97 (brs, 1H), 8.69 (s, 1H), 8.04 (s, 1H), 7.54-7.34 (m, 3H), 7.08-7.00 (m, 2H), 5.14-5.12 (m, 1H), 4.53-4.32 (m, 2H), 4.53-4.48 (m, 2H), 4.36-4.32 (m, 4H), 4.04-3.90 (m, 4H), 2.95-2.92 (m, 3H), 2.62-2.58 (m, 2H), 2.36-2.35 (m, 3H), 2.23-2.16 (m, 2H), 2.02-1.87 (m, 7H), 1.72-1.70 (m, 4H), 1.49-1.47 (m, 5H), 1.42-1.38 (m, 5H), 1.02-1.01 (m, 3H); MS (ESI) m/z: 914.5 [M+H]$^+$.

84

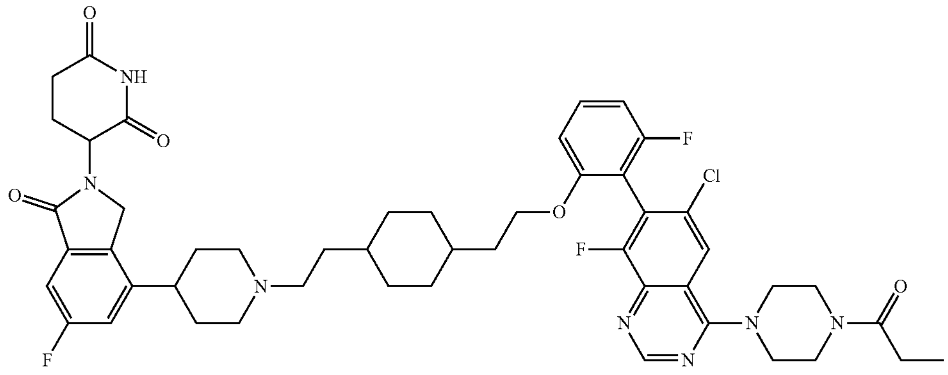

3-(4-(1-(7-(2-(6-Chloro-8-fluoro-4-((S)-2-methyl-4-propionylpiperazin-1-yl)quinazolin-7-yl)-3-fluorophenoxy)heptyl)piperidin-4-yl)-6-fluoro-1-oxoisoindolin-2-yl)piperidine-2,6-dione 85. $^1$H NMR (400 MHz, DMSO-$d_6$) δ 11.03 (s, 1H), 8.72 (d, J=2.0 Hz, 1H), 7.97-7.93 (m, 1H), 7.55 (q, J=8.4 Hz, 1H), 7.41-7.29 (m, 2H), 7.08 (d, J=8.8 Hz, 1H), 7.01 (t, J=8.4 Hz, 1H), 5.16 (dd, J=4.8, 13.2 Hz, 1H), 4.79-4.71 (m, 1H), 4.55-4.33 (m, 2H), 4.21-4.18 (m, 2H), 4.03 (t, J=5.6 Hz, 2H), 3.80-3.50 (m, 4H), 3.03-2.89 (m, 5H), 2.67-2.59 (m, 2H), 2.44-2.33 (m, 3H), 2.05-1.88 (m, 5H), 1.53-1.47 (m, 4H), 1.38-1.27 (m, 5H), 1.23-1.17 (m, 5H), 1.05-1.00 (m, 4H); MS (ESI) m/z: 888.4 [M+H]$^+$.

85

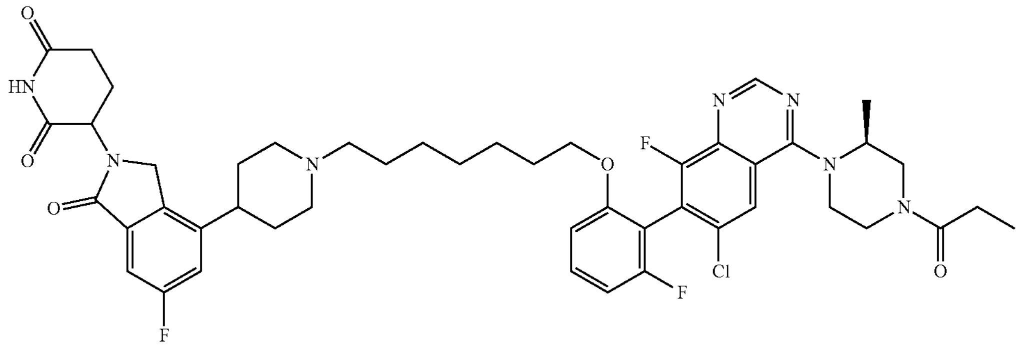

3-((6-Chloro-7-(2-((7-(4-(2-(2,6-dioxopiperidin-3-yl)-6-fluoro-1-oxoisoindolin-4-yl)piperidin-1-yl)heptyl)oxy)-6-fluorophenyl)-8-fluoro-4-(4-propionylpiperazin-1-yl)quinazolin-2-yl)amino)-N,N-dimethylpropanamide 86.

86

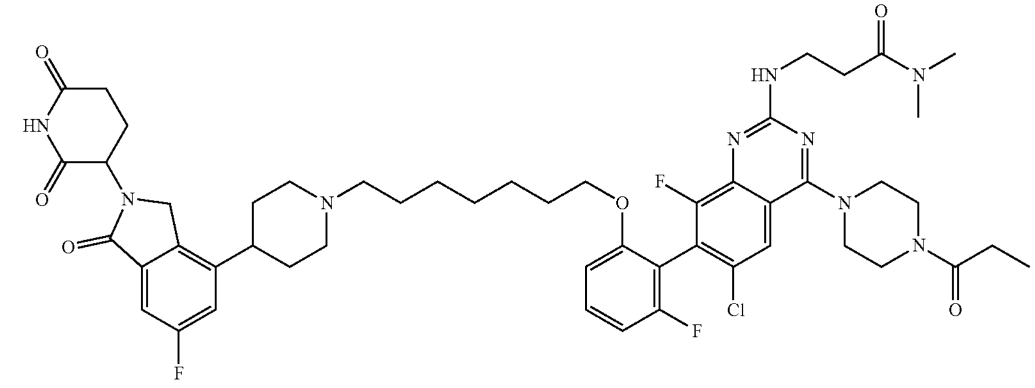

3-(4-(1-(7-(2-(6-Chloro-8-fluoro-4-(4-propionylpiperazin-1-yl)quinazolin-7-yl)-3-fluorophenoxy)heptyl)piperidin-3-yl)-6-fluoro-1-oxoisoindolin-2-yl)piperidine-2,6-dione 87.

87

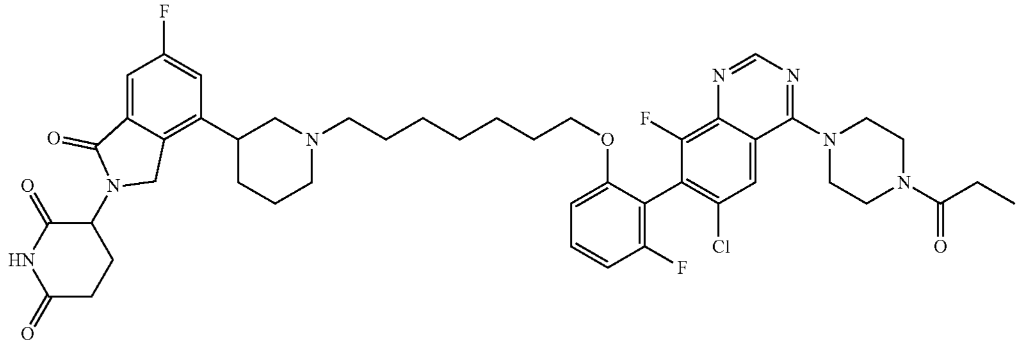

3-(4-(1-(7-(2-(4-(4-Acryloylpiperazin-1-yl)-6-chloro-8-fluoro-2-(((S)-1-methylpyrrolidin-2-yl)methoxy)quinazolin-7-yl)-3-fluorophenoxy)heptyl)piperidin-4-yl)-6-fluoro-1-oxoisoindolin-2-yl)piperidine-2,6-dione 88. $^{1}H$ NMR (400 MHz, DMSO-$d_6$) δ 11.00 (s, 1H), 7.96 (s, 1H), 7.55-7.49 (m, 1H), 7.38-7.34 (m, 2H), 7.06 (d, J=8.4 Hz, 1H), 6.98 (t, J=8.4 Hz, 1H), 6.81 (dd, J=10.0, 16.4 Hz, 1H), 6.16 (d, J=17.2 Hz, 1H), 5.73 (d, J=10.4 Hz, 1H), 5.13 (dd, J=5.2, 13.2 Hz, 1H), 4.53-4.31 (m, 3H), 4.21-4.19 (m, 1H), 4.03-4.00 (m, 2H), 3.89-3.77 (m, 8H), 2.95-2.92 (m, 4H), 2.62-2.58 (m, 2H), 2.40-2.37 (m, 4H), 2.21-2.17 (m, 3H), 2.03-1.95 (m, 4H), 1.73-1.66 (m, 7H), 1.53-1.51 (m, 2H), 1.23-1.15 (m, 2H), 1.15-1.10 (m, 7H); MS (ESI) m/z: 985.5 $[M+H]^+$.

88

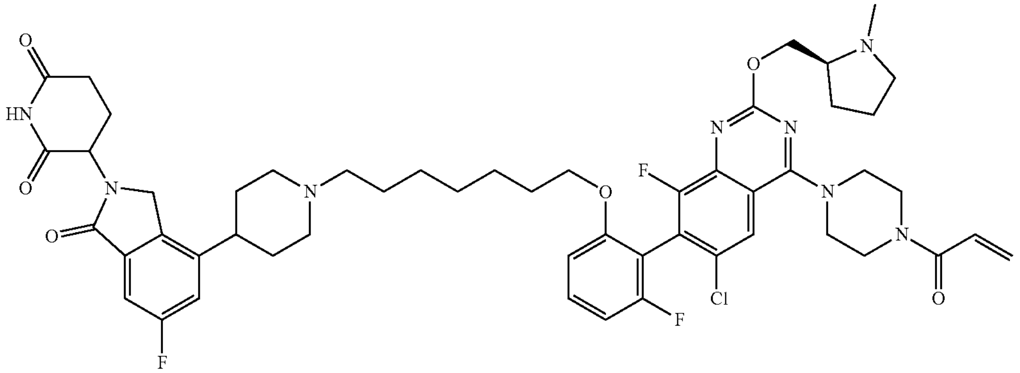

3-(4-(1-(7-(2-(6-Chloro-8-fluoro-2-(((S)-1-methylpyrrolidin-2-yl)methoxy)-4-(4-propionylpiperazin-1-yl)quinazolin-7-yl)-3-fluorophenoxy)heptyl)piperidin-4-yl)-6-fluoro-1-oxoisoindolin-2-yl)piperidine-2,6-dione 89. $^1$H NMR (400 MHz, DMSO-$d_6$) δ 10.99 (s, 1H), 7.95 (s, 1H), 7.53 (q, J=4.2 Hz, 1H), 7.39-7.33 (m, 2H), 7.06 (d, J=8.0 Hz, 1H), 6.98 (t, J=8.4 Hz, 1H), 5.14 (dd, J=5.2, 13.2 Hz, 1H), 4.52-4.31 (m, 3H), 4.18-4.17 (m, 1H), 4.02 (t, J=6.0 Hz, 2H), 3.88-3.84 (m, 4H), 3.70-3.69 (m, 4H), 2.95-2.87 (m, 4H), 2.62-2.57 (m, 3H), 2.45-2.40 (m, 1H), 2.37-2.33 (m, 5H), 2.17-2.14 (m, 3H), 2.02-2.00 (m, 1H), 1.91-1.90 (m, 5H), 1.70-1.65 (m, 7H), 1.53-1.50 (m, 2H), 1.23-1.09 (m, 6H), 1.01 (t, J=7.2 Hz, 3H); MS (ESI) m/z: 987.5 $[M+H]^+$.

89

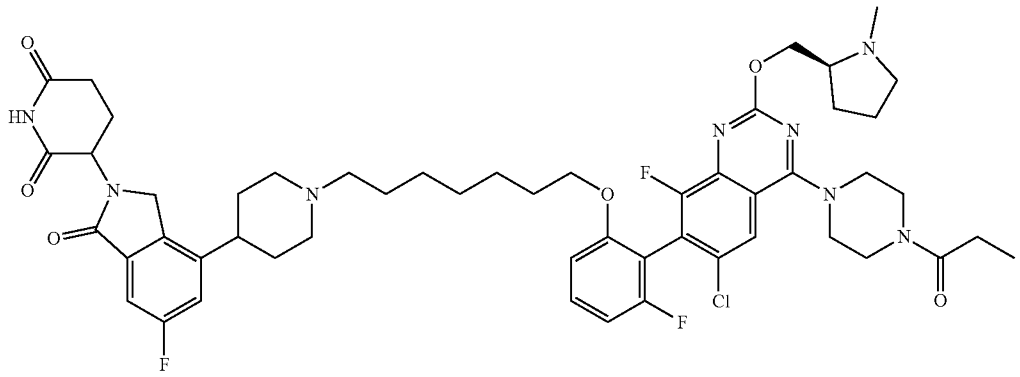

3-(4-(1-(7-(3-(4-(4-Acryloylpiperazin-1-yl)-6-chloro-8-fluoroquinazolin-7-yl)-4-fluorophenoxy)heptyl)piperidin-4-yl)-6-fluoro-1-oxoisoindolin-2-yl)piperidine-2,6-dione 90. $^1$H NMR (400 MHz, DMSO-$d_6$) δ 10.99 (s, 1H), 8.69 (s, 1H), 8.05 (s, 1H), 7.39-7.33 (m, 3H), 7.12 (m, 1H), 7.05 (s, 1H), 6.82 (dd, J=10.4, 16.4 Hz, 1H), 6.17 (dd, J=1.6, 16.0 Hz, 1H), 5.74 (dd, J=2.0, 10.0 Hz, 1H), 5.13 (dd, J=5.2, 13.2 Hz, 1H), 4.56-4.30 (m, 2H), 3.99 (t, J=6.4 Hz, 2H), 3.93-3.83 (m, 4H), 3.78-3.62 (m, 4H), 2.97-2.95 (m, 3H), 2.26-2.57 (m, 3H), 2.44-2.41 (m, 1H), 2.32-2.27 (m, 2H), 2.01-1.91 (m, 3H), 1.79-1.66 (m, 5H), 1.45-1.43 (m, 5H), 1.32-1.20 (m, 3H); MS (ESI) m/z: 872.2 $[M+H]^+$.

90

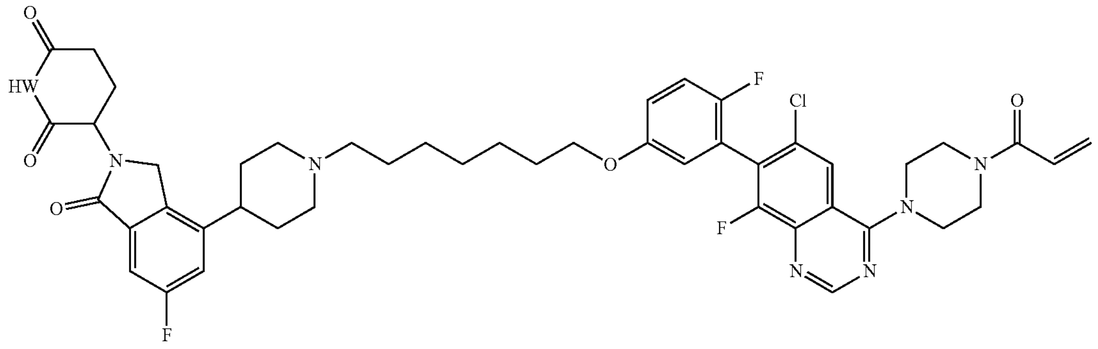

3-(4-(1-(7-(3-(6-Chloro-8-fluoro-4-(4-propionylpiperazin-1-yl)quinazolin-7-yl)-4-fluorophenoxy)heptyl)piperidin-4-yl)-6-fluoro-1-oxoisoindolin-2-yl)piperidine-2,6-dione 91. $^1$H NMR (400 MHz, DMSO-$d_6$) δ 10.99 (s, 1H), 8.69 (s, 1H), 8.04 (s, 1H), 7.39-7.31 (m, 3H), 7.14-7.10 (m, 1H), 7.04 (dd, J=3.2, 9.6 Hz, 1H), 5.13 (dd, J=5.2, 13.2 Hz, 1H), 4.52-4.31 (m, 2H), 3.99 (t, J=6.4 Hz, 2H), 3.91-3.88 (m, 4H), 3.69 (s, 4H), 2.97-2.95 (m, 3H), 2.61-2.58 (m, 2H), 2.37 (q, J=7.2 Hz, 2H), 2.32-2.28 (m, 2H), 2.02-1.91 (m, 3H), 1.72-1.70 (m, 6H), 1.45-1.43 (m, 3H), 1.38-1.29 (m, 6H), 1.02 (t, J=7.6 Hz, 3H); MS (ESI) m/z: 874.3 $[M+H]^+$.

91

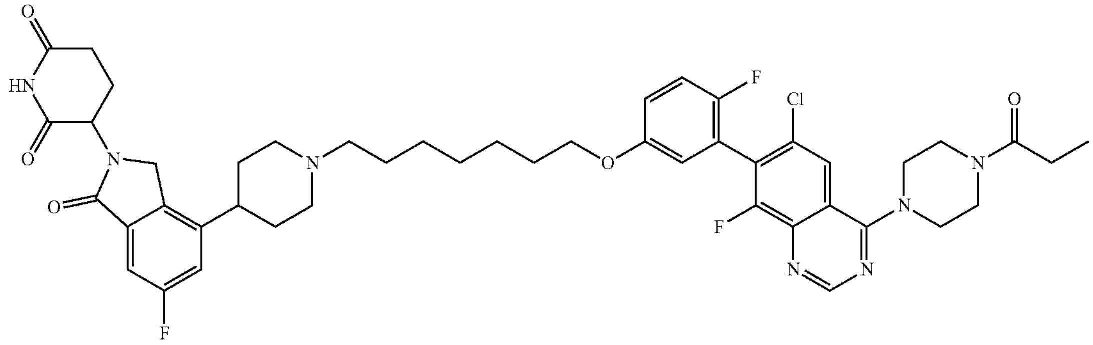

3-(4-(1-(2-(4-(2-(2-(6-Chloro-8-fluoro-4-(4-propionylpiperazin-1-yl)quinazolin-7-yl)-3-fluorophenoxy)ethyl)-1H-1,2,3-triazol-1-yl)ethyl)piperidin-4-yl)-6-fluoro-1-oxoisoindolin-2-yl)piperidine-2,6-dione 92. $^1$H NMR (400 MHz, DMSO-$d_6$) δ 11.00 (s, 1H), 8.71 (s, 1H), 8.01 (s, 1H), 7.61-7.51 (m, 3H), 7.36 (d, J=8.8 Hz, 2H), 7.11 (d, J=8.4 Hz, 1H), 7.01 (t, J=8.8 Hz, 1H), 5.14 (dd, J=5.2, 13.2 Hz, 1H), 4.53-4.27 (m, 6H), 3.92-3.89 (m, 4H), 3.70-3.64 (m, 4H), 2.95-2.90 (m, 5H), 2.67-2.58 (m, 4H), 2.40-2.34 (m, 3H), 2.10-1.99 (m, 3H), 1.72-1.67 (m, 4H), 1.01 (t, J=7.6 Hz, 3H); MS (ESI) m/z: 899.4 [M+H]$^+$.

92

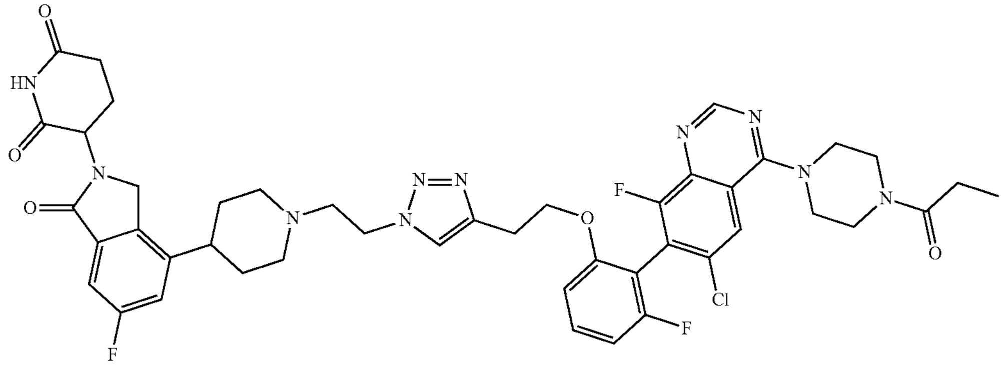

3-(5-(1-(7-(2-(4-(4-Acryloylpiperazin-1-yl)-6-chloro-8-fluoroquinazolin-7-yl)-3-fluorophenoxy)heptyl)piperidin-4-yl)-6-fluoro-1-oxoisoindolin-2-yl)piperidine-2,6-dione 94. $^1$H NMR (400 MHz, DMSO-$d_6$) δ 10.99 (s, 1H), 8.71 (s, 1H), 8.06 (s, 1H), 7.58-7.50 (m, 3H), 7.08 (d, J=8.4 Hz, 1H), 7.01 (t, J=8.8 Hz, 1H), 6.83 (dd, J=10.4, 16.8 Hz, 1H), 6.17 (dd, J=1.6, 16.8 Hz, 1H), 5.74 (dd, J=2.0, 10.4 Hz, 1H), 5.12 (dd, J=4.8, 13.2 Hz, 1H), 4.46-4.29 (m, 2H), 4.05 (t, J=6.4 Hz, 2H), 3.94-3.85 (m, 4H), 3.78-3.71 (m, 4H), 2.95-2.59 (m, 7H), 2.03-2.01 (m, 1H), 1.99-1.91 (m, 6H), 1.53-1.48 (m, 5H), 1.23-1.16 (m, 6H); MS (ESI) m/z: 872.4 [M+H]$^+$.

94

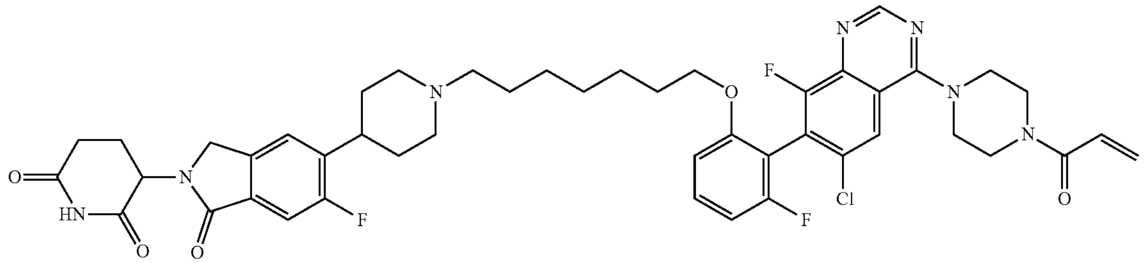

2-((2R,4aR)-11-Chloro-6-(7-(4-(2-(2,6-dioxopiperidin-3-yl)-6-fluoro-1-oxoisoindolin-4-yl)piperidin-1-yl)heptyl)-9-fluoro-2-methyl-5-oxo-3-propionyl-2,3,4,4a,5,6-hexahydro-1H-pyrazino[1',2':4,5]pyrazino[2,3-c]quinolin-10-yl)-3-fluorophenyl propionate 95. $^1$H NMR (400 MHz, DMSO-$d_6$) δ 11.04 (s, 1H), 9.83 (s, 1H), 9.07 (d, J=3.6 Hz, 1H), 8.03 (d, J=26.0 Hz, 1H), 7.75-7.62 (m, 1H), 7.45-7.25 (m, 3H), 5.17 (dd, J=4.8, 12.8 Hz, 1H), 4.80-4.30 (m, 4H), 4.25-4.05 (m, 2H), 4.00-3.94 (m, 1H), 3.76-3.50 (m, 3H), 3.20-2.89 (m, 6H), 2.80-2.60 (m, 3H), 2.35-2.20 (m, 5H), 2.02 (s, 4H), 1.65-1.55 (m, 4H), 1.50-1.45 (m, 3H), 1.40-1.25 (m, 7H), 1.05 (t, J=7.2 Hz, 3H), 0.78 (t, J=7.6 Hz, 3H); MS (ESI) m/z: 984.3 [M+H]$^+$.

95

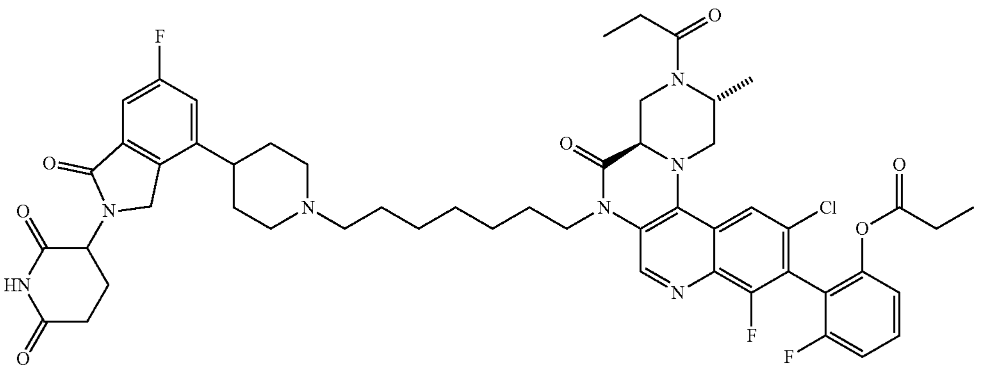

(Z)-3-(4-(1-(7-(2-(6-Chloro-4-(4-(2-chlorobut-2-enoyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 96. $^1$H NMR (400 MHz, DMSO-$d_6$) δ 11.04 (s, 1H), 9.76 (s, 1H), 8.73 (s, 1H), 8.05 (s, 1H), 7.58-7.52 (m, 1H), 7.43 (d, J=7.2 Hz, 1H), 7.30 (d, J=9.6 Hz, 1H), 7.08 (d, J=8.4 Hz, 1H), 7.01 (t, J=8.8 Hz, 1H), 6.27 (dd, J=6.8, 13.2 Hz, 1H), 5.17 (dd, J=5.2, 13.2 Hz, 1H), 4.56-4.35 (m, 2H), 4.04 (t, J=6.0 Hz, 2H), 3.97-3.86 (m, 4H), 3.74-3.69 (m, 4H), 3.57-3.55 (m, 2H), 2.98-2.90 (m, 5H), 2.65-2.61 (m, 1H), 2.36-2.32 (m, 1H), 2.06-2.03 (m, 5H), 1.82 (d, J=6.8 Hz, 3H), 1.59-1.53 (m, 4H), 1.23-1.19 (m, 6H); MS (ESI) m/z: 920.3 [M+H]$^+$.

96

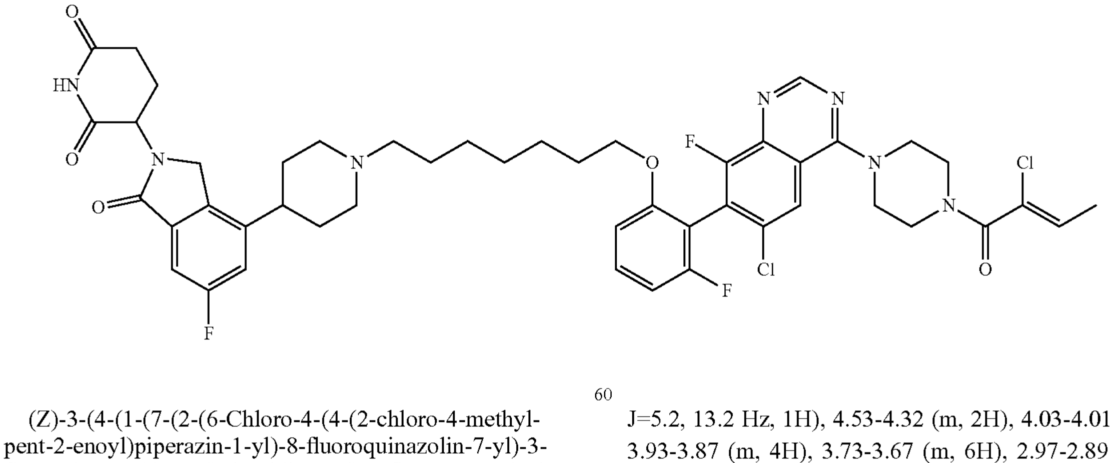

(Z)-3-(4-(1-(7-(2-(6-Chloro-4-(4-(2-chloro-4-methylpent-2-enoyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 97. $^1$H NMR (400 MHz, DMSO-$d_6$) δ11.00 (s, 1H), 8.72 (s, 1H), 8.05 (s, 1H), 7.54 (q, J=8.0 Hz, 1H), 7.39-7.34 (m, 2H), 7.27 (d, J=8.4 Hz, 1H), 6.99 (t, J=8.8 Hz, 1H), 6.03 (d, J=9.2 Hz, 1H), 5.17 (dd, J=5.2, 13.2 Hz, 1H), 4.53-4.32 (m, 2H), 4.03-4.01 (m, 2H), 3.93-3.87 (m, 4H), 3.73-3.67 (m, 6H), 2.97-2.89 (m, 3H), 2.77-2.72 (m, 1H), 2.62-2.58 (m, 2H), 2.45-2.41 (m, 1H), 2.17 (t, J=7.2 Hz, 2H), 2.03-2.00 (m, 1H), 1.91-1.89 (m, 2H), 1.75-1.72 (m, 3H), 1.52-1.49 (m, 2H), 1.25-1.23 (m, 2H), 1.13-1.02 (m, 11H); MS (ESI) m/z: 948.4 [M+H]$^+$.

97

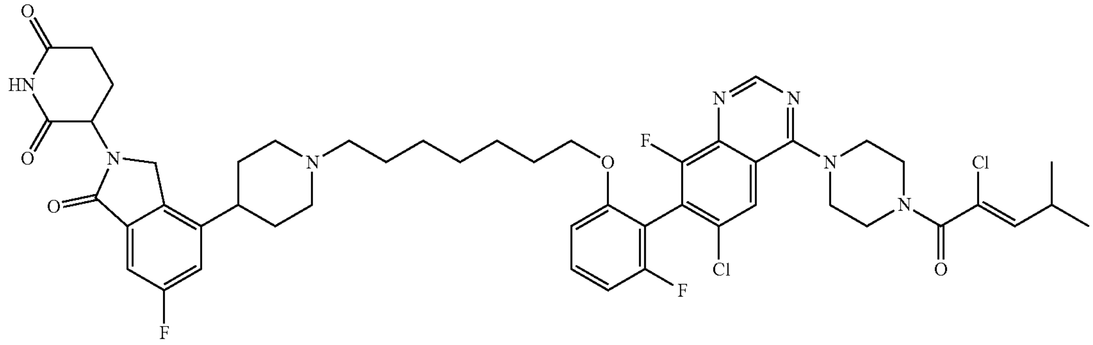

(Z)-3-(4-(1-(7-(2-(6-Chloro-4-(4-(2-chloropent-2-enoyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 98. $^{1}$H NMR (400 MHz, DMSO-$d_6$) δ 11.04 (s, 1H), 9.11 (s, 1H), 8.75 (s, 1H), 8.07 (s, 1H), 7.56 (q, J=8.4 Hz, 1H), 7.44 (d, J=5.2 Hz, 1H), 7.30 (d, J=10.8 Hz, 1H), 7.08 (d, J=8.4 Hz, 1H), 7.01 (t, J=8.4 Hz, 1H), 6.21 (t, J=7.2 Hz, 1H), 5.17 (dd, J=5.2, 13.2 Hz, 1H), 4.55-4.35 (m, 2H), 4.39-4.35 (m, 2H), 4.06-4.03 (m, 4H), 3.99-3.91 (m, 4H), 3.30-3.28 (m, 1H), 3.03-2.95 (m, 5H), 2.65-2.61 (m, 1H), 2.34-2.23 (m, 3H), 2.06-2.01 (m, 3H), 1.94-1.86 (m, 2H), 1.55-1.54 (m, 4H), 1.23-1.19 (m, 8H), 1.03 (t, J=7.6 Hz, 3H); MS (ESI) m/z: 934.4 $[M+H]^+$.

98

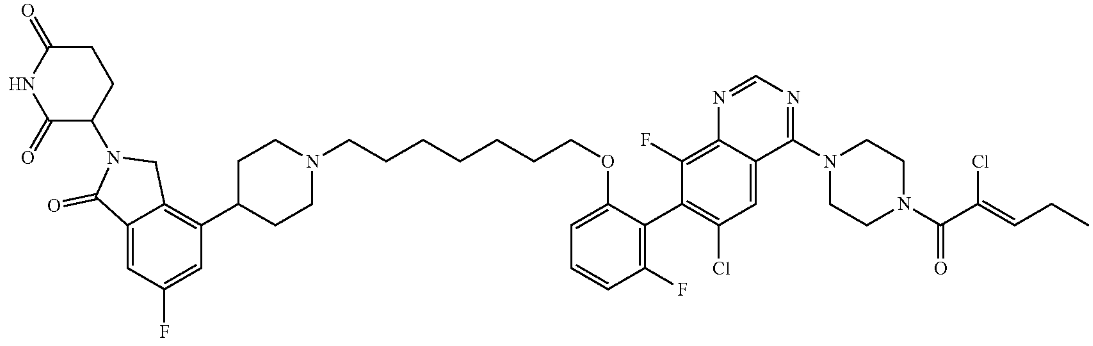

3-(4-(1-(7-(2-(4-(4-Acetylpiperazin-1-yl)-6-chloro-8-fluoroquinazolin-7-yl)-3-fluorophenoxy)heptyl)piperidin-4-yl)-6-fluoro-1-oxoisoindolin-2-yl)piperidine-2,6-dione 99. $^{1}$H NMR (400 MHz, DMSO-$d_6$) δ 11.00 (s, 1H), 8.70 (s, 1H), 8.04 (s, 1H), 7.59-7.51 (m, 1H), 7.39-7.35 (m, 2H), 7.07 (d, J=8.4 Hz, 1H), 7.00 (t, J=4, 8.4 Hz, 1H), 5.14 (dd, J=12.8 Hz, 1H), 4.54-4.33 (m, 2H), 4.03 (m, 2H), 3.91-3.87 (m, 4H), 3.69 (s, 4H), 2.93-2.88 (m, 3H), 2.62-2.59 (m, 2H), 2.45-2.42 (m, 1H), 2.2 (s, 2H), 2.05-1.96 (m, 5H), 1.73-1.51 (m, 6H), 1.24-1.09 (m, 9H); MS (ESI) m/z: 860.4 $[M+H]^+$.

99

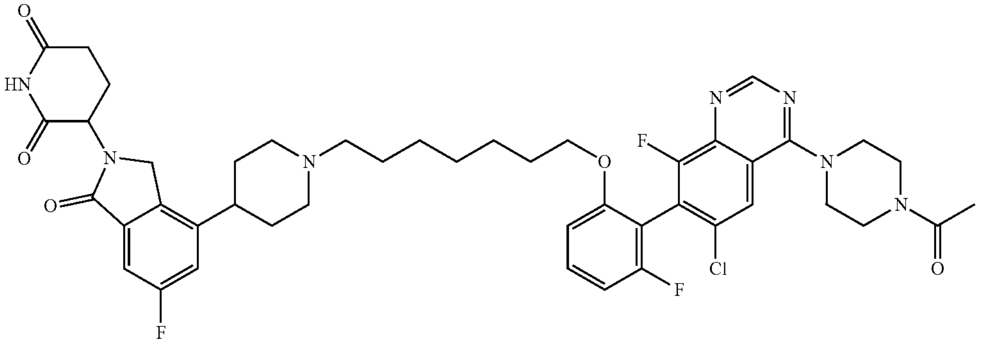

3-(4-(1-(7-(2-(4-((S)-4-(2-Chloroacryloyl)-2-methylpiperazin-1-yl)-6-fluoro-1-(2-isopropylphenyl)-2-oxo-1,2-dihydropyrido[2,3-d]pyrimidin-7-yl)-3-fluorophenoxy)heptyl)piperidin-4-yl)-6-fluoro-1-oxoisoindolin-2-yl) piperidine-2,6-dione 100. $^{1}$H NMR (400 MHz, DMSO-$d_6$) δ 11.00 (s, 1H), 8.35-8.20 (m, 1H), 7.46-7.32 (m, 5H), 7.27-7.19 (m, 1H), 7.11-7.02 (m, 1H), 6.95 (d, J=8.8 Hz, 1H), 6.84 (q, J=8.4 Hz, 1H), 5.85 (s, 2H), 5.13 (dd, J=4.8, 12.8 Hz, 1H), 4.90 (s, 1H), 4.51 (d, J=16.8 Hz, 1H), 4.40-4.15 (m, 3H), 3.92 (d, J=5.6 Hz, 2H), 3.80-3.59 (m, 2H), 3.00-2.87 (m, 2H), 2.59 (d, J=15.6 Hz, 2H), 2.49-2.35 (m, 2H), 2.30-2.18 (m, 2H), 2.05-1.93 (m, 2H), 1.72 (s, 4H), 1.60-1.40 (m, 2H), 1.40-1.33 (m, 5H), 1.21 (d, J=15.2 Hz, 6H), 1.06 (d, J=6.4 Hz, 3H), 0.96 (d, J=6.4 Hz, 2H), 0.86 (d, J=6.4 Hz, 2H); MS (ESI) m/z: 1021.5 $[M+H]^+$.

100

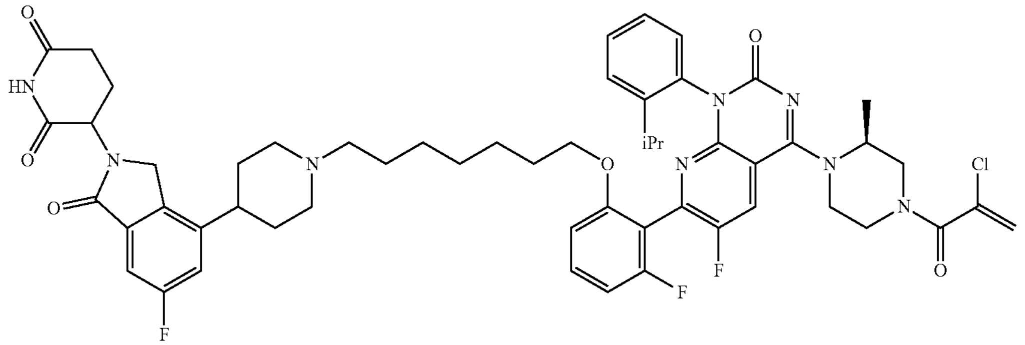

2-((2R)-4-(6-Chloro-7-(2-((7-(4-(2-(2,6-dioxopiperidin-3-yl)-6-fluoro-1-oxoisoindolin-4-yl)piperidin-1-yl)heptyl) oxy)-6-fluorophenyl)-8-fluoroquinazolin-4-yl)-1-(2-chloroacryloyl)-piperazin-2-yl)acetonitrile 102. $^{1}$H NMR (400 MHz, DMSO-$d_6$) δ 11.04 (s, 1H), 9.24 (s, 1H), 8.75 (d, J=6.0 Hz, 1H), 8.14 (d, J=9.2 Hz, 1H), 7.59-7.53 (m, 1H), 7.43 (dd, J=2.0, 7.2 Hz, 1H), 7.30 (dd, J=1.6, 10.4 Hz, 1H), 7.09 (d, J=8.4 Hz, 1H), 7.01 (t, J=8.8 Hz, 1H), 5.90 (s, 1H), 5.86 (s, 1H), 5.17 (dd, J=5.2, 13.6 Hz, 1H), 4.55-4.30 (m, 4H), 4.05 (t, J=6.4 Hz, 2H), 3.94-3.83 (m, 1H), 3.79-3.73 (m, 4H), 3.45-3.37 (m, 3H), 3.09-2.95 (m, 7H), 2.65-2.61 (m, 1H), 2.38-2.27 (m, 1H), 2.07-1.86 (m, 6H), 1.61-1.54 (m, 4H), 1.23-1.20 (m, 5H); MS (ESI) m/z: 945.3 $[M+H]^+$.

102

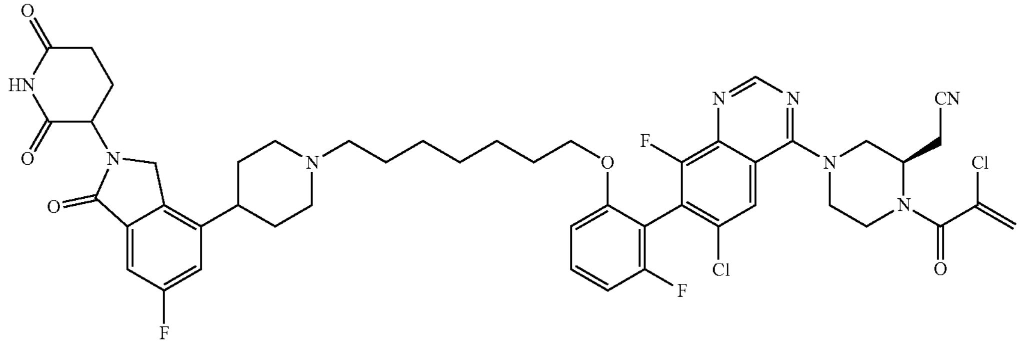

3-(4-(1-(5-(2-(6-Chloro-4-(4-(2-chloroacryloyl)piperazin-1-yl)-8-fluoroquinazolin-7-yl)-3-fluorophenoxy)pentyl)piperidin-4-yl)-6-fluoro-1-oxoisoindolin-2-yl)piperidine-2,6-dione 103. $^{1}$H NMR (400 MHz, DMSO-$d_6$) δ 11.01 (s, 1H), 8.72 (d, J=4.0 Hz, 1H), 8.50-8.43 (m, 1H), 7.58-7.47 (m, 1H), 7.38-7.35 (m, 2H), 7.10-6.98 (m, 2H), 5.83 (d, J=9.2 Hz, 2H), 5.14 (dd, J=5.2, 13.2 Hz, 1H), 4.52-4.31 (m, 2H), 3.94-3.87 (m, 4H), 3.74-3.70 (m, 4H), 2.97-2.86 (m, 4H), 2.63-2.58 (m, 2H), 2.11-2.06 (m, 2H), 2.03-1.99 (m, 2H), 1.73-1.65 (m, 3H), 1.54-1.53 (m, 2H), 1.30-1.24 (m, 4H), 1.20-1.16 (m, 2H); MS (ESI) m/z: 878.3 $[M+H]^+$.

103

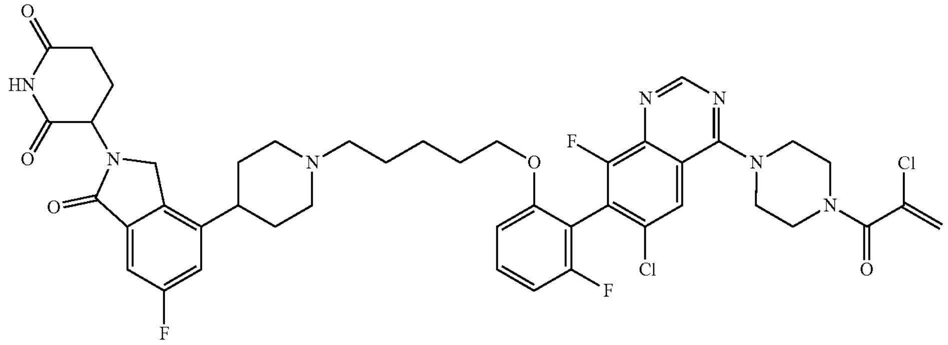

3-(4-(1-(7-(2-((2R,4aR)-11-Chloro-3-(2-chloroacryloyl)-9-fluoro-2,6-dimethyl-5-oxo-2,3,4,4a,5,6-hexahydro-1H-pyrazino[1',2':4,5]pyrazino[2,3-c]quinolin-10-yl)-3-fluoro-phenoxy)-heptyl)piperidin-4-yl)-6-fluoro-1-oxoisoindolin-2-yl)piperidine-2,6-dione 104. $^1$H NMR (400 MHz, DMSO-$d_6$) δ 11.01 (s, 1H), 9.03 (s, 1H), 7.99 (s, 1H), 7.55-7.53 (m, 1H), 7.39-7.34 (m, 3H), 7.07 (d, J=8.4 Hz, 1H), 6.99 (t, J=8.4 Hz, 1H), 5.93 (s, 1H), 5.12 (dd, J=5.2, 13.6 Hz, 1H), 4.57-4.31 (m, 2H), 4.04-3.97 (m, 3H), 3.50 (s, 3H), 2.92-2.90 (m, 5H), 2.67-2.58 (m, 3H), 2.19 (m, 2H), 1.99-1.91 (m, 3H), 1.75-1.71 (m, 6H), 1.54-1.51 (m, 6H), 1.14-1.06 (m, 8H); MS (ESI) m/z: 974.2 $[M+H]^+$.

104

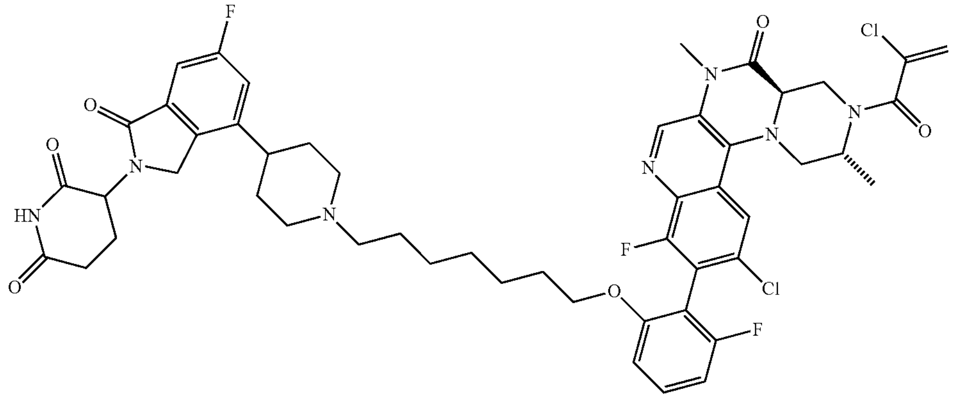

3-(4-(1-(7-(2-(6-Chloro-4-(4-(2-chloroacryloyl)piperazin-1-yl)quinazolin-7-yl)-3-fluorophenoxy)heptyl)piperidin-4-yl)-1-oxoisoindolin-2-yl)piperidine-2,6-dione 105. $^1$H NMR (400 MHz, DMSO-$d_6$) δ 11.02 (s, 1H), 8.73 (s, 1H), 8.05 (s, 1H), 7.61-7.51 (m, 4H), 7.08 (d, J=8.4 Hz, 1H), 7.01 (t, J=8.4 Hz, 1H), 5.85 (s, 2H), 5.16 (dd, J=5.2, 14 Hz, 1H), 4.56-4.34 (m, 2H), 4.05-4.02 (m, 2H), 3.98-3.88 (m, 4H), 3.76-3.75 (m, 4H), 2.99-2.91 (m, 2H), 2.67-2.58 (m, 2H), 2.42-2.33 (m, 4H), 2.02-1.97 (m, 4H), 1.83-1.81 (m, 2H), 1.55-1.43 (m, 4H), 1.17-1.02 (m, 8H); MS (ESI) m/z: 870.8 $[M+H]^+$.

105

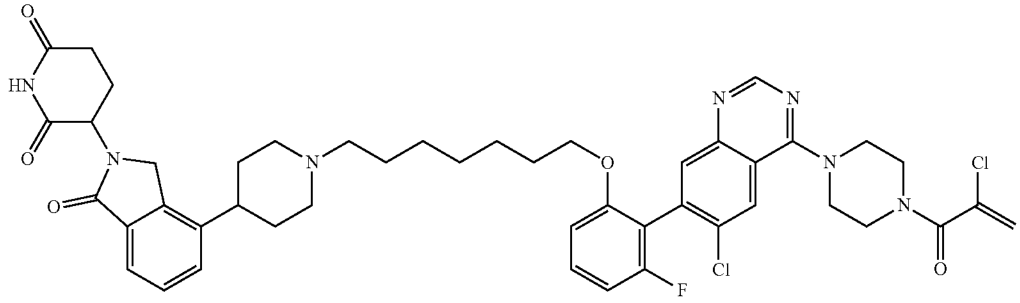

3-(4-(1-(7-(2-(6-Chloro-4-(4-(2-chloroacryloyl)piperazin-1-yl)-8-fluoroquinazolin-7-yl)-3-fluorophenoxy)heptyl)piperidin-3-yl)-6-fluoro-1-oxoisoindolin-2-yl)piperidine-2,6-dione 106. $^1$H NMR (400 MHz, DMSO-$d_6$) δ 11.06 (s, 1H), 9.33-9.20 (m, 1H), 8.72-8.65 (m, 1H), 8.04 (m, 1H), 7.57-7.46 (m, 3H), 7.06 (d, J=9.2 Hz, 2H), 7.01 (t, J=8.4 Hz, 1H), 5.85 (s, 2H), 5.20-5.13 (m, 1H), 4.61-4.30 (m, 2H), 4.02 (t, J=5.6 Hz, 2H), 3.94-3.87 (m, 3H), 3.74-3.71 (m, 4H), 3.12-3.11 (m, 2H), 2.98-2.89 (m, 4H), 2.67-2.60 (m, 1H), 2.36-2.31 (m, 1H), 2.01-1.99 (m, 2H), 1.92-1.90 (m, 1H), 1.81-1.76 (m, 2H), 1.57-1.51 (m, 4H), 1.26-1.24 (m, 3H), 1.20-1.11 (m, 6H); MS (ESI) m/z: 906.3 [M+H]$^+$.

106

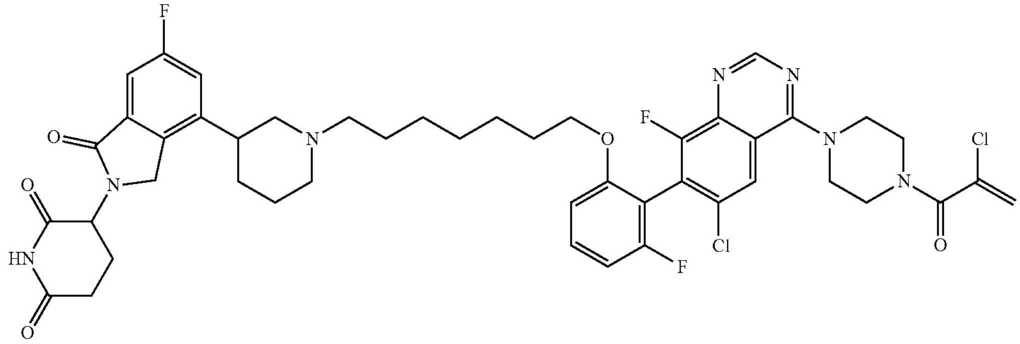

3-(5-(1-(7-(2-(6-Chloro-4-(4-(2-chloroacryloyl)piperazin-1-yl)-8-fluoroquinazolin-7-yl)-3-fluorophenoxy)heptyl)piperidin-4-yl)-6-fluoro-1-oxoisoindolin-2-yl)piperidine-2,6-dione 107. $^1$H NMR (400 MHz, DMSO-$d_6$) δ 10.99 (s, 1H), 8.74 (s, 1H), 8.06 (s, 1H), 7.58-7.49 (m, 3H), 7.08 (d, J=8.8 Hz, 1H), 7.01 (t, J=8.8 Hz, 1H), 5.85 (s, 2H), 5.11 (dd, J=4.8, 13.2 Hz,1H), 4.46-4.28 (m, 2H), 4.04 (t, J=6.4 Hz, 2H), 3.96-3.91 (m, 4H), 3.76-3.71 (m, 4H), 3.51-3.43 (m, 1H), 3.11-3.09 (m, 1H), 2.95-2.87 (m, 2H), 2.67-2.58 (m, 1H), 2.40-2.33 (m, 1H), 2.01-1.99 (m, 2H), 1.91-1.86 (m, 3H), 1.53-1.46 (m, 4H), 1.26-1.24 (m, 3H), 1.21-1.11 (m, 6H); MS (ESI) m/z: 906.3 [M+H]$^+$.

107

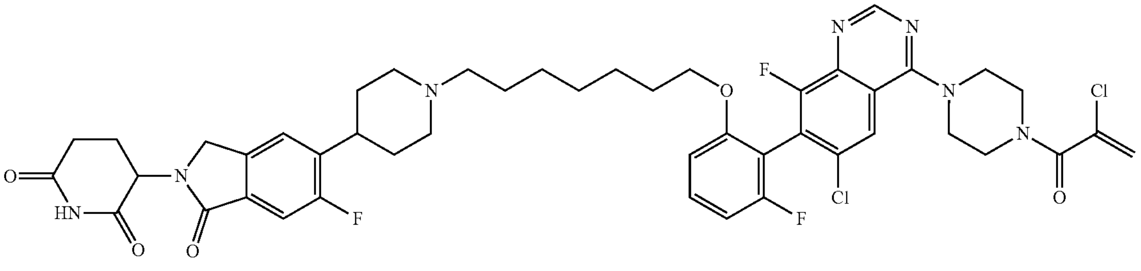

3-(4-(1-(2-((4-((2-(2-(6-Chloro-8-fluoro-4-(4-propionylpiperazin-1-yl)quinazolin-7-yl)-3-fluorophenoxy)ethoxy)methyl)benzyl)oxy)ethyl)piperidin-4-yl)-6-fluoro-1-oxoisoindolin-2-yl)piperidine-2,6-dione 109. $^1$H NMR (400 MHz, DMSO-$d_6$) δ 11.05 (s, 1H), 8.71-8.70 (m, 1H), 8.07-7.84 (m, 1H), 7.59-7.50 (m, 1H), 7.42 (d, J=6.8 Hz, 1H), 7.34-7.32 (m, 1H), 7.14-7.08 (m, 3H), 7.05-6.98 (m, 2H), 6.93 (d, J=7.6 Hz, 1H), 5.17 (dd, J=5.2, 14.0 Hz, 1H), 4.66 (s, 1H), 4.55-4.38 (m, 4H), 4.29-4.17 (m, 4H), 3.86-3.71 (m, 6H), 3.63-3.51 (m, 8H), 3.51 (s, 1H), 2.98-2.89 (m, 3H), 2.67-2.59 (m, 1H), 2.38-2.29 (m, 4H), 2.05-1.96 (m, 6H), 1.47-1.44 (m, 1H), 1.01 (t, J=7.6 Hz, 3H); MS (ESI) m/z: 968.4 [M+H]$^+$.

109

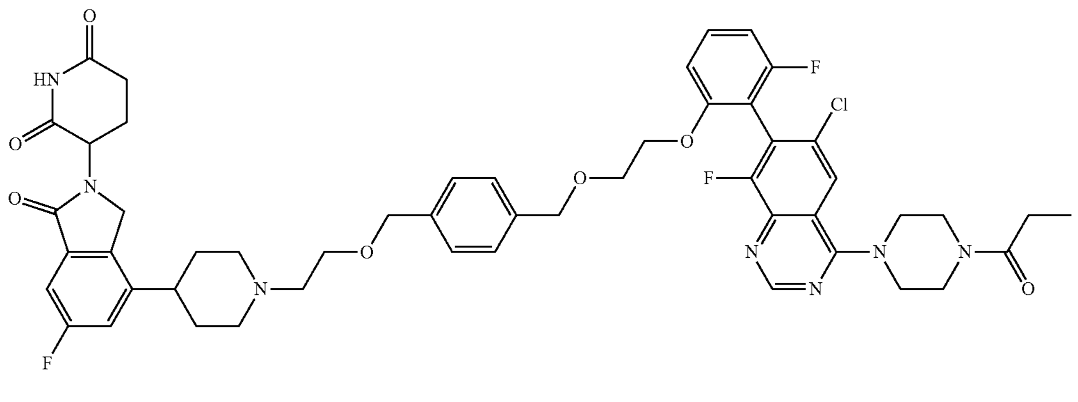

3-(4-(1-(2-(4-(2-(2-(6-Chloro-4-(4-(2-chloroacryloyl)piperazin-1-yl)-8-fluoroquinazolin-7-yl)-3-fluorophenoxy)ethyl)cyclohexyl)ethyl)piperidin-4-yl)-6-fluoro-1-oxoisoindolin-2-yl)piperidine-2,6-dione 110. $^1$H NMR (400 MHz, DMSO-$d_6$) δ11.00 (s, 1H), 8.73 (s, 1H), 8.06 (s, 1H), 7.55-7.35 (m, 3H), 7.09-6.98 (m, 2H), 5.84-5.81 (m, 2H), 5.14 (dd, J=4.8, 13.2 Hz, 1H), 4.53-4.32 (m, 2H), 4.04-4.00 (m, 2H), 3.92-3.88 (m, 4H), 3.76-3.70 (m, 4H), 2.95-2.89 (m, 3H), 2.63-2.59 (m, 2H), 2.45-2.42 (m, 1H), 2.27-2.20 (m, 2H), 2.03-1.99 (m, 3H), 1.75-1.73 (m, 4H), 1.48-1.38 (m, 5H), 1.23-1.06 (m, 7H), 0.70-0.58 (m, 2H); MS (ESI) m/z: 946.3 [M+H]$^+$.

110

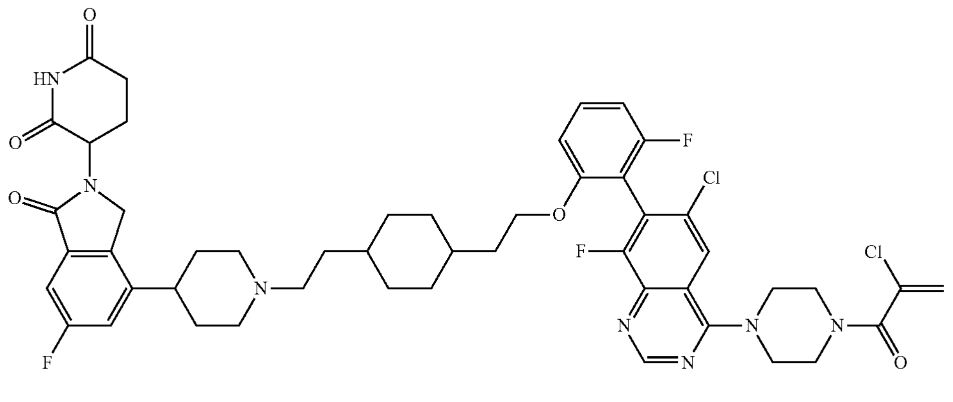

3-(4-(1-(4-(2-(2-(6-Chloro-4-(4-(2-chloroacryloyl)piperazin-1-yl)-8-fluoroquinazolin-7-yl)-3-fluorophenoxy)ethyl)phenethyl)piperidin-4-yl)-6-fluoro-1-oxoisoindolin-2-yl)piperidine-2,6-dione 111. $^1$H NMR (400 MHz, DMSO-$d_6$) δ 11.00 (s, 1H), 8.77 (s, 1H), 8.03 (s, 1H), 7.54-7.42 (m, 1H), 7.39-7.35 (m, 2H), 7.09-6.96 (m, 2H), 6.82-6.78 (m, 4H), 5.84-5.80 (m, 2H), 5.14 (dd, J=5.2, 13.2 Hz, 1H), 4.54-4.33 (m, 2H), 4.20-4.15 (m, 2H), 3.97-3.93 (m, 2H), 3.86-3.85 (m, 2H), 3.79-3.76 (m, 2H), 3.71-3.69 (m, 2H), 3.04-3.02 (m, 2H), 2.97-2.88 (m, 1H), 2.79-2.75 (m, 2H), 2.62-2.59 (m, 4H), 2.46-2.42 (m, 3H), 2.08-1.99 (m, 3H), 1.75-1.69 (m, 4H); MS (ESI) m/z: 942.3 [M+H]$^+$.

111

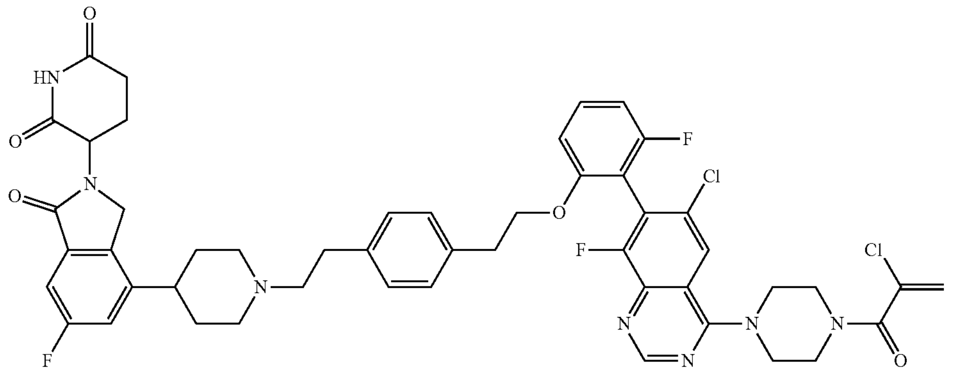

3-(4-(1-(9-(2-(6-Chloro-4-(4-(2-chloroacryloyl)piperazin-1-yl)-8-fluoroquinazolin-7-yl)-3-fluorophenoxy)nonyl)piperidin-4-yl)-6-fluoro-1-oxoisoindolin-2-yl)piperidine-2,6-dione 113. $^{1}H$ NMR (400 MHz, DMSO-$d_6$) δ 11.01 (s, 1H), 8.72 (s, 1H), 8.04-7.84 (m, 1H), 7.56-7.48 (m, 1H), 7.37-7.36 (m, 2H), 7.00 (m, 2H), 5.83 (d, J=12 Hz, 2H), 5.14 (dd, J=5.2, 13.2 Hz, 1H), 4.49-4.36 (m, 2H), 4.02-3.93 (m, 2H), 3.92-3.91 (m, 4H), 3.88-3.87 (m, 2H), 3.76-3.57 (m, 2H), 3.06-2.96 (m, 1H), 2.67-2.62 (m, 2H), 2.45-2.33 (m, 2H), 2.02-1.91 (m, 3H), 1.78-1.74 (m, 4H), 1.51-1.49 (m, 3H), 1.29-1.02 (m, 14H); MS (ESI) m/z: 934.3 $[M+H]^+$.

113

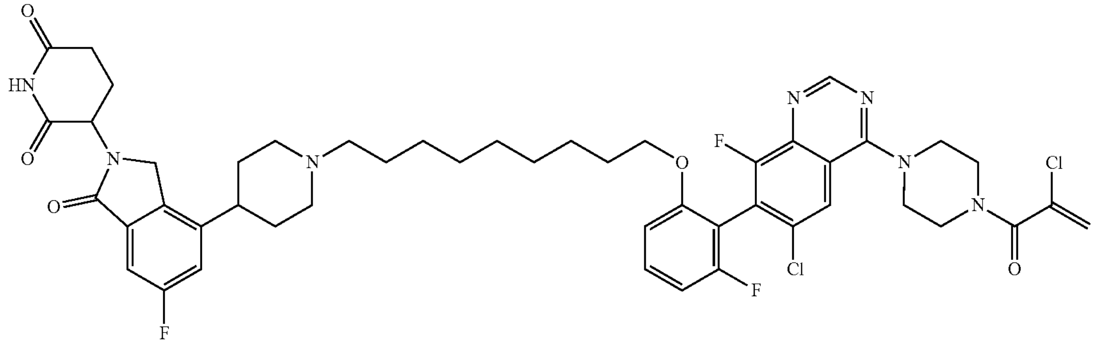

3-(4-(1-(11-(2-(6-Chloro-4-(4-(2-chloroacryloyl)piperazin-1-yl)-8-fluoroquinazolin-7-yl)-3-fluorophenoxy)undecyl)piperidin-4-yl)-6-fluoro-1-oxoisoindolin-2-yl)piperidine-2,6-dione 114. $^{1}H$ NMR (400 MHz, DMSO-$d_6$) δ 11.02 (s, 1H), 8.72 (s, 1H), 8.16 (s, 1H), 8.04 (s, 1H), 7.57-7.51 (m, 1H), 7.40-7.36 (m, 2H), 7.07 (d, J=8.4 Hz, 1H), 7.00 (t, J=8.4 Hz, 1H), 5.84 (s, 2H), 5.15 (dd, J=4.4, 12.8 Hz, 1H), 4.53-4.32 (m, 2H), 4.01-4.00 (m, 2H), 3.93-3.90 (m, 5H), 3.75-3.71 (m, 5H), 3.08-3.05 (m, 3H), 2.96-2.88 (m, 2H), 2.67-2.58 (m, 2H), 2.43-2.39 (m, 3H), 2.17-2.11 (m, 2H), 2.03-2.00 (m, 1H), 1.78-1.72 (m, 4H), 1.50-1.45 (m, 4H), 1.23-1.04 (m, 10H); MS (ESI) m/z: 962.4 $[M+H]^+$.

114

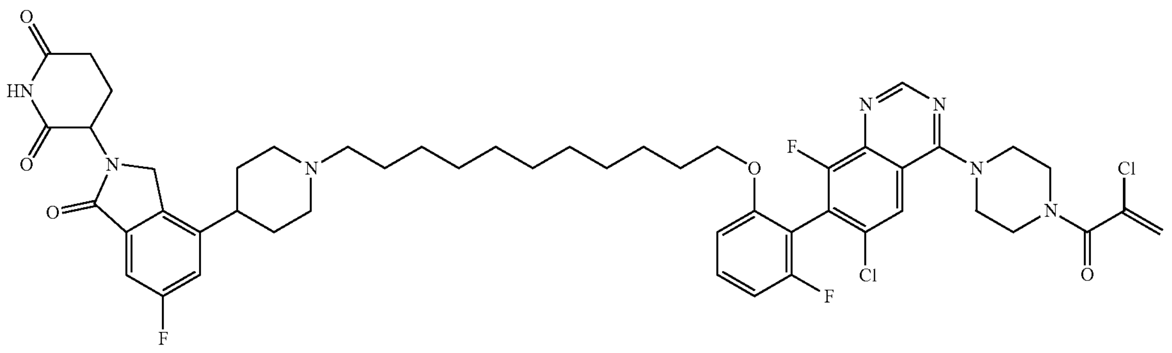

3-(4-(1-(7-(2-(6-Chloro-4-(4-(2-chloroacryloyl)piperazin-1-yl)-2-(2-(dimethylamino)-ethoxy)-8-fluoroquinazolin-7-yl)-3-fluorophenoxy)heptyl)piperidin-4-yl)-6-fluoro-1-oxoisoindolin-2-yl)piperidine-2,6-dione 115. $^1$H NMR (400 MHz, DMSO-$d_6$) δ 11.04 (s, 1H), 9.68 (brs, 2H), 8.01 (s, 1H), 7.54 (q, J=8.0 Hz, 1H), 7.44-7.43 (m, 1H), 7.30-7.28 (m, 1H), 7.08 (d, J=8.4 Hz, 1H), 6.99 (t, J=8.4 Hz, 1H), 5.86-5.84 (m, 2H), 5.17 (dd, J=4.8, 12.8 Hz, 1H), 4.71-4.66 (m, 2H), 4.54-4.34 (m, 2H), 4.05-3.99 (m, 2H), 3.96-3.94 (m, 4H), 3.78-3.76 (m, 4H), 3.57-3.55 (m, 4H), 3.02-2.94 (m, 5H), 2.88-2.87 (m, 6H), 2.65-2.60 (m, 1H), 2.34-2.30 (m, 2H), 2.06-1.93 (m, 5H), 1.61-1.55 (m, 4H), 1.26-1.24 (m, 6H); MS (ESI) m/z: 993.4 $[M+H]^+$.

115

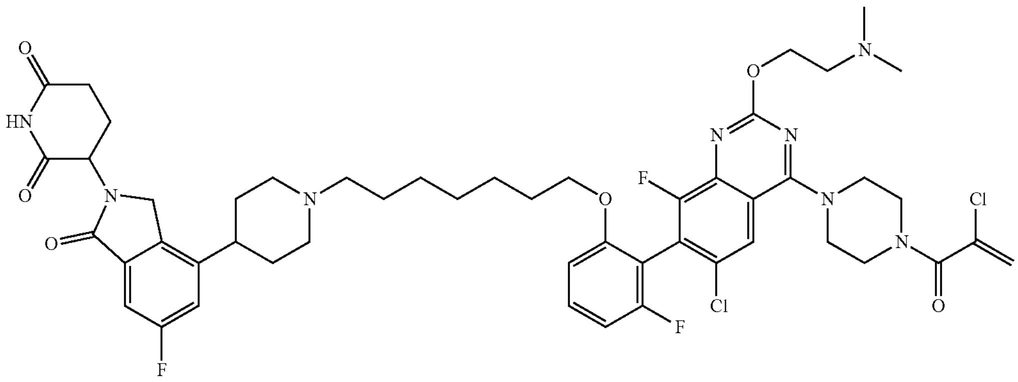

3-(4-(1-(2-(4-(2-(2-(6-Chloro-4-(4-(2-chloroacryloyl)piperazin-1-yl)-8-fluoroquinazolin-7-yl)-3-fluorophenoxy)ethyl)cyclohexyl)ethyl)piperidin-4-yl)-6-fluoro-1-oxoisoindolin-2-yl)piperidine-2,6-dione 116. $^1$H NMR (400 MHz, DMSO-$d_6$) δ 11.02 (s, 1H), 8.11 (s, 1H), 8.06 (s, 1H), 7.57-7.49 (m, 1H), 7.41-7.34 (m, 2H), 7.06 (d, J=8.8 Hz, 1H), 7.00 (t, J=8.4 Hz, 1H), 5.85 (s, 2H), 5.14 (dd, J=5.2, 13.2 Hz, 1H), 4.52-4.31 (m, 2H), 3.94-3.82 (m, 6H), 3.76-3.71 (m, 4H), 2.98-2.89 (m, 3H), 2.67-2.58 (m, 1H), 2.46-2.41 (m, 2H), 2.33-2.27 (m, 2H), 2.19-2.15 (m, 1H), 2.03-1.98 (m, 3H), 1.77-1.68 (m, 4H), 1.61-1.54 (m, 3H), 1.49-1.41 (m, 1H), 1.48-1.43 (m, 4H), 1.30-1.24 (m, 3H); MS (ESI) m/z: 932.3 $[M+H]^+$.

116

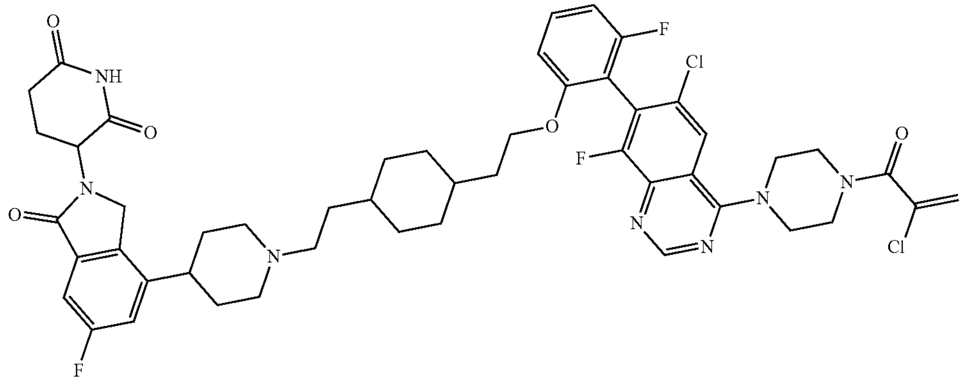

3-(4-(1-(((1r,4r)-4-((2-(6-Chloro-4-(4-(2-chloroacryloyl)piperazin-1-yl)-8-fluoro-quinazolin-7-yl)-3-fluorophenoxy)methyl)cyclohexyl)methyl)piperidin-4-yl)-6-fluoro-1-oxoisoindolin-2-yl)piperidine-2,6-dione 117. $^1$H NMR (400 MHz, DMSO-$d_6$) δ 11.01 (s, 1H), 8.72 (s, 1H), 8.06 (s, 1H), 7.54 (q, J=8.4 Hz, 1H), 7.40 (dd, J=2.0, 10.8 Hz, 1H), 7.34 (dd, J=2.4, 7.6 Hz, 1H), 7.05 (d, J=8.4 Hz, 1H), 7.00 (t, J=9.2 Hz, 1H), 5.83-5.82 (m, 2H), 5.15 (dd, J=5.6, 13.6 Hz, 1H), 4.52-4.31 (m, 2H), 3.95-3.83 (m, 6H), 3.75-3.74 (m, 4H), 2.92-2.87 (m, 1H), 2.81-2.80 (m, 2H), 2.62-2.58 (m, 2H), 2.44-2.41 (m, 1H), 2.01-2.00 (m, 3H), 1.88-1.86 (m, 1H), 1.71-1.65 (m, 6H), 1.62-1.51 (m, 3H), 1.26-1.16 (m, 2H), 0.88-0.80 (m, 2H), 0.74-0.68 (m, 2H); MS (ESI) m/z: 918.3 $[M+H]^+$.

117

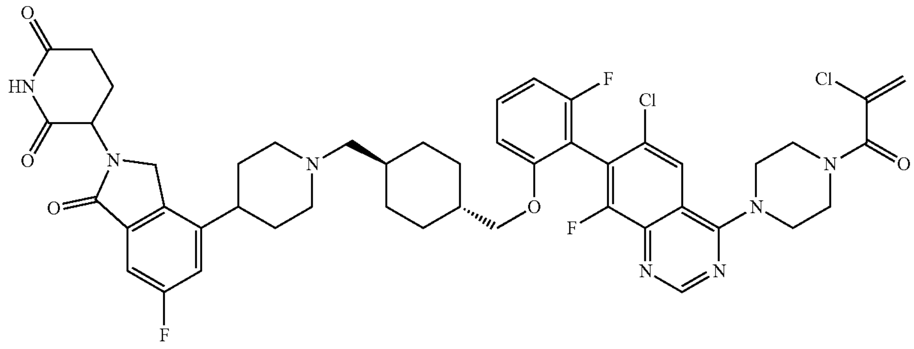

3-(4-(1-((4-(2-(2-(6-Chloro-4-(4-(2-chloroacryloyl)piperazin-1-yl)-8-fluoroquinazolin-7-yl)-3-fluorophenoxy)ethyl)cyclohexyl)methyl)piperidin-4-yl)-6-fluoro-1-oxoisoindolin-2-yl)piperidine-2,6-dione 118. $^1$H NMR (400 MHz, DMSO-$d_6$) δ 11.02 (s, 1H), 8.73 (s, 1H), 8.06 (s, 1H), 7.57-7.51 (m, 1H), 7.42-7.39 (m, 1H), 7.36-7.34 (m, 1H), 7.07 (dd, J=3.2, 8.4 Hz, 1H), 7.01 (t, J=8.8 Hz, 1H), 5.84 (s, 2H), 5.14 (dd, J=5.2, 13.6 Hz, 1H), 4.52-4.31 (m, 2H), 4.05 (t, J=5.6 Hz, 2H), 3.93-3.88 (m, 4H), 3.76-3.71 (m, 4H), 2.97-2.88 (m, 3H), 2.67-2.58 (m, 2H), 2.46-2.39 (m, 2H), 2.02-1.99 (m, 4H), 1.74-1.68 (m, 4H), 1.60-1.56 (m, 2H), 1.50-1.46 (m, 2H), 1.41-1.38 (m, 2H), 1.29-1.23 (m, 4H), 1.14-1.08 (m, 2H); MS (ESI) m/z: 933.3 $[M+H]^+$.

118

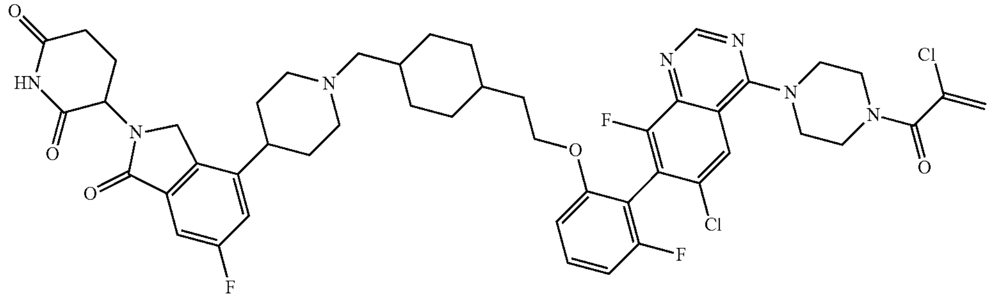

3-(4-(1-(2-(1-(2-(2-(6-Chloro-4-(4-(2-chloroacryloyl)piperazin-1-yl)-8-fluoroquinazolin-7-yl)-3-fluorophenoxy)ethyl)piperidin-4-yl)ethyl)piperidin-4-yl)-6-fluoro-1-oxoisoindolin-2-yl)piperidine-2,6-dione 120. $^{1}$H NMR (400 MHz, DMSO-$d_6$) δ11.05 (s, 1H), 9.55 (brs, 2H), 8.75 (s, 1H), 8.07 (s, 1H), 7.66-7.60 (m, 1H), 7.46-7.44 (m, 1H), 7.33-7.30 (m, 1H), 7.17-7.10 (m, 2H), 5.86-5.82 (m, 2H), 5.18 (dd, J=4.8, 12.8 Hz, 1H), 4.56-4.35 (m, 4H), 4.00-3.97 (m, 4H), 3.92-3.88 (m, 4H), 3.62-3.60 (m, 3H), 3.35-3.26 (m, 5H), 3.06-2.92 (m, 6H), 2.74-2.61 (m, 3H), 2.34-2.32 (m, 1H), 2.06-1.95 (m, 5H), 1.66-1.56 (m, 3H), 1.36-1.23 (m, 2H); MS (ESI) m/z: 947.3 $[M+H]^+$.

120

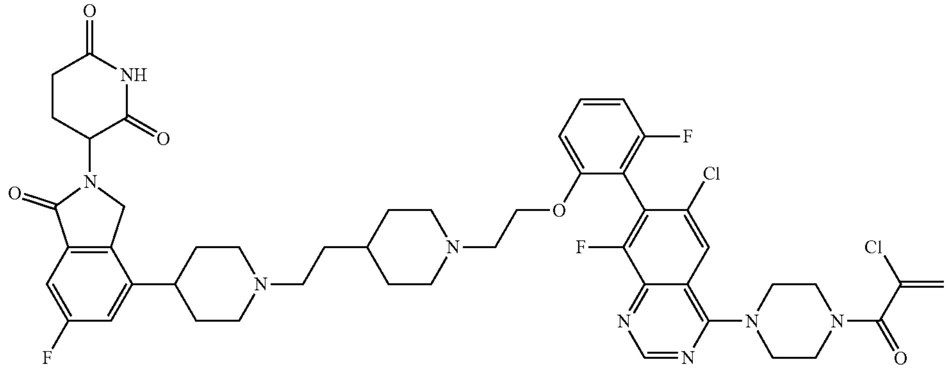

3-(4-(1-(3-(2-(6-Chloro-4-(4-(2-chloroacryloyl)piperazin-1-yl)-8-fluoroquinazolin-7-yl)-3-fluorophenoxy)propyl)piperidin-4-yl)-6-fluoro-1-oxoisoindolin-2-yl)piperidine-2,6-dione 121. $^{1}$H NMR (400 MHz, DMSO-$d_6$) δ 11.05 (s, 1H), 9.32 (s, 1H), 8.73 (s, 1H), 8.07 (s, 1H), 7.63-7.57 (m, 1H), 7.44 (dd, J=2.4, 7.6 Hz, 1H), 7.26 (dd, J=2.0, 10.4 Hz, 1H), 7.12 (d, J=8.4 Hz, 1H), 7.07 (t, J=9.2 Hz, 1H), 5.84-5.79 (m, 2H), 5.17 (dd, J=5.2, 12.8 Hz, 1H), 4.54-4.33 (m, 2H), 4.16 (t, J=5.6 Hz, 2H), 3.99-3.83 (m, 4H), 3.77-3.69 (m, 4H), 3.28-3.19 (m, 1H), 3.03-2.84 (m, 6H), 2.65-2.62 (m, 1H), 2.39-2.34 (m, 1H), 2.04-1.96 (m, 6H), 1.90-1.78 (m, 2H); MS (ESI) m/z: 850.3 $[M+H]^+$.

121

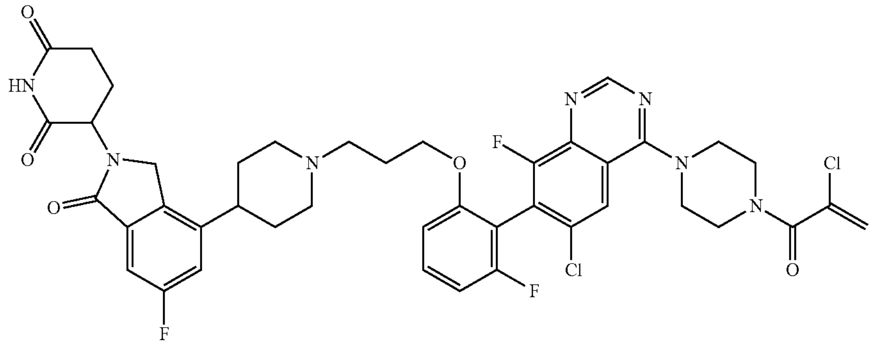

2-((2R)-4-(6-Chloro-7-(2-((7-(4-(2-(2,6-dioxopiperidin-3-yl)-6-fluoro-1-oxoisoindolin-5-yl)piperidin-1-yl)heptyl)oxy)-6-fluorophenyl)-8-fluoroquinazolin-4-yl)-1-(2-chloro-acryloyl)-piperazin-2-yl)acetonitrile 123. $^{1}H$ NMR (400 MHz, DMSO-$d_6$) δ 10.99 (s, 1H), 9.26 (s, 1H), 8.75 (d, J=6.0 Hz, 1H), 8.14 (d, J=9.6 Hz, 1H), 7.57-7.52 (m, 3H), 7.09 (d, J=8.4 Hz, 1H), 7.01 (t, J=8.8 Hz, 1H), 5.90 (s, 1H), 5.86 (s, 1H), 5.11 (dd, J=4.8, 13.2 Hz, 1H), 4.47-4.30 (m, 5H), 4.05 (t, J=6.4 Hz, 2H), 3.94-3.80 (m, 8H), 3.25-2.92 (m, 8H), 2.63-2.59 (m, 1H), 2.41-2.33 (m, 1H), 2.07-1.94 (m, 4H), 1.62-1.49 (m, 4H), 1.22-1.13 (m, 5H); MS (ESI) m/z: 945.3 $[M+H]^+$.

123

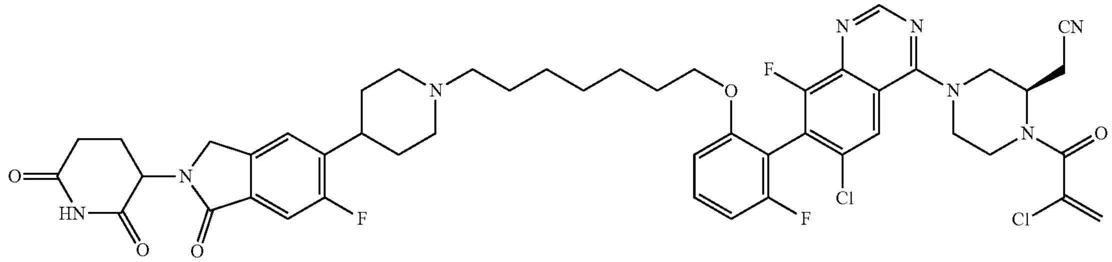

3-(4-(1-(7-(2-(4-((S)-4-Acryloyl-2-methylpiperazin-1-yl)-6-fluoro-1-(2-isopropyl-4-methylpyridin-3-yl)-2-oxo-1,2-dihydropyrido[2,3-d]pyrimidin-7-yl)-3-fluorophenoxy)heptyl)-piperidin-4-yl)-6-fluoro-1-oxoisoindolin-2-yl)piperidine-2,6-dione 124. $^{1}H$ NMR (400 MHz, DMSO-$d_6$) δ11.00 (s, 1H), 8.39-8.33 (m, 2H), 7.45-7.33 (m, 3H), 7.19 (dd, J=3.2 Hz, 12.0 Hz, 2H), 6.96 (d, J=16.0 Hz, 2H), 6.90-6.80 (m, 2H), 6.20 (d, J=16.0 Hz, 2H), 5.75 (dd, J=2.0, 10.4 Hz, 1H), 5.13 (dd, J=5.2, 13.2 Hz, 1H), 4.92 (s, 4H), 4.53-4.25 (m, 4H), 4.03-3.92 (m, 2H), 3.80-3.60 (m, 1H), 3.20-3.10 (m, 1H), 2.95-2.85 (m, 3H), 2.70-2.55 (m, 3H), 2.45-2.30 (m, 2H), 2.23 (s, 2H), 2.05-1.93 (m, 4H), 1.88 (s, 2H), 1.80-1.65 (m, 4H), 1.48 (s, 2H), 1.40-1.28 (m, 5H), 1.17 (s, 6H), 1.07 (d, J=6.0 Hz, 3H), 0.95 (d, J=6.4 Hz, 2H), 0.85 (d, J=4.8 Hz, 2H); MS (ESI) m/z: 1003.4 $[M+H]^+$.

124

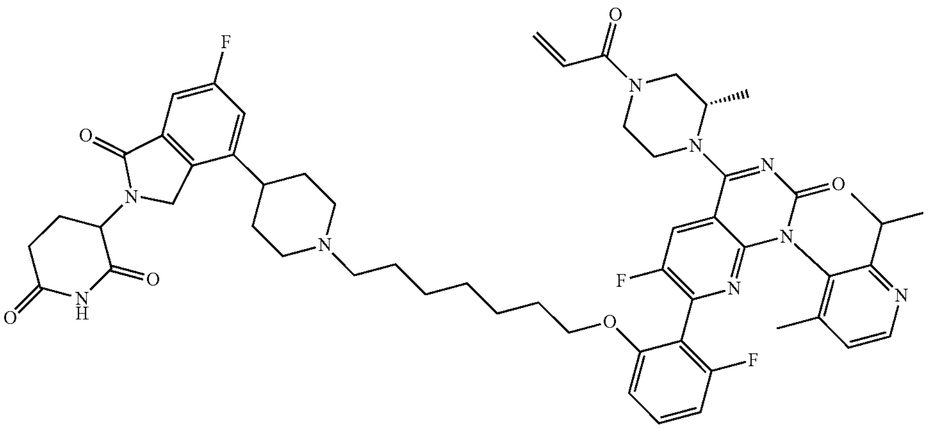

3-(4-(1-(7-((2R,4aR)-11-Chloro-3-(2-chloroacryloyl)-9-fluoro-10-(2-fluoro-6-hydroxyphenyl)-2-methyl-5-oxo-1,2,3,4,4a,5-hexahydro-6H-pyrazino[1',2':4,5]pyrazino[2,3-c]quinolin-6-yl)heptyl)piperidin-4-yl)-6-fluoro-1-oxoisoindolin-2-yl)piperidine-2,6-dione 125. $^{1}H$ NMR (400 MHz, DMSO-$d_6$) δ 10.99 (s, 1H), 10.20 (s, 1H), 9.06 (s, 1H), 7.97 (s, 1H), 7.40-7.31 (m, 3H), 6.86 (d, J=8.0 Hz, 1H), 6.81 (t, J=8.4 Hz, 1H), 5.97-5.70 (m, 2H), 5.13 (dd, J=5.2, 13.2 Hz, 1H), 4.63-3.78 (m, 8H), 2.98-2.80 (m, 4H), 2.67-2.54 (m, 2H), 2.49-2.37 (m, 1H), 2.24 (t, J=7.2 Hz, 2H), 2.06-1.92 (m, 3H), 1.76-1.55 (m, 9H), 1.46-1.20 (m, 9H); MS (ESI) m/z: 960.3 $[M+H]^+$.

125

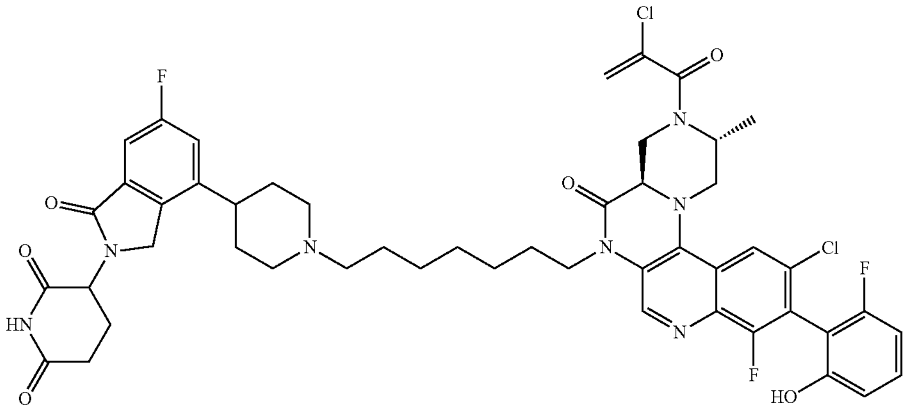

3-(4-(1-(7-(4-(4-((S)-4-(2-Chloroacryloyl)-2-methylpiperazin-1-yl)-6-fluoro-7-(2-fluoro-6-hydroxyphenyl)-2-oxopyrido[2,3-d]pyrimidin-1(2H)-yl)-3-isopropylphenyl)heptyl)piperidin-4-yl)-6-fluoro-1-oxoisoindolin-2-yl)piperidine-2,6-dione 126. $^{1}H$ NMR (400 MHz, DMSO-$d_6$) δ 11.00 (s, 1H), 8.25-8.18 (m, 1H), 7.40-7.34 (m, 2H), 7.29-7.23 (m, 1H), 7.19 (s, 1H), 7.05-6.96 (m, 2H), 6.72 (d, J=8.4 Hz, 1H), 6.67 (t, J=9.2 Hz, 1H), 5.84 (s, 2H), 5.14 (dd, J=4.4, 13.2 Hz, 1H), 4.95-4.80 (m, 1H), 4.53-4.31 (m, 2H), 4.19-4.13 (m, 2H), 3.94-3.88 (m, 2H), 2.95-2.87 (m, 2H), 2.61-2.59 (m, 4H), 2.40-2.32 (m, 2H), 2.00-1.97 (m, 4H), 1.76-1.75 (m, 4H), 1.60-1.59 (m, 2H), 1.46-1.45 (m, 3H), 1.36-1.31 (m, 7H), 1.23-1.22 (m, 6H), 1.06-1.04 (m, 3H), 0.98-0.94 (m, 3H); MS (ESI) m/z: 1021.4 $[M+H]^+$.

126

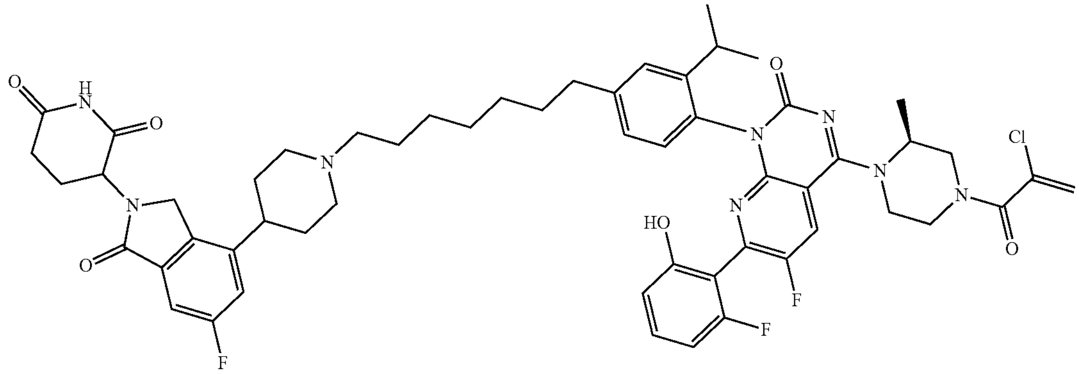

3-(4-(1-(((1s,4s)-4-((2-(6-Chloro-4-(4-(2-chloroacryloyl)piperazin-1-yl)-8-fluoro-quinazolin-7-yl)-3-fluorophenoxy)methyl)cyclohexyl)methyl)piperidin-4-yl)-6-fluoro-1-oxoisoindolin-2-yl)piperidine-2,6-dione 127. $^{1}$H NMR (400 MHz, DMSO-$d_6$) δ 11.00 (s, 1H), 8.72 (s, 1H), 8.06 (s, 1H), 7.56-7.51 (m, 1H), 7.41-7.34 (m, 2H), 7.06-6.97 (m, 2H), 5.83-5.80 (m, 2H), 5.15 (dd, J=4.0, 12.8 Hz, 1H), 4.51-4.36 (m, 2H), 3.92-3.85 (m, 5H), 3.74-3.71 (m, 3H), 2.95-2.89 (m, 3H), 2.67-2.57 (m, 2H), 2.39-2.36 (m, 1H), 2.02-1.98 (m, 4H), 1.70-1.68 (m, 7H), 1.50-1.44 (m, 2H), 1.35-1.23 (m, 4H), 0.85-0.83 (m, 2H), 0.72-0.69 (m, 2H); MS (ESI) m/z: 918.3 $[M+H]^+$.

127

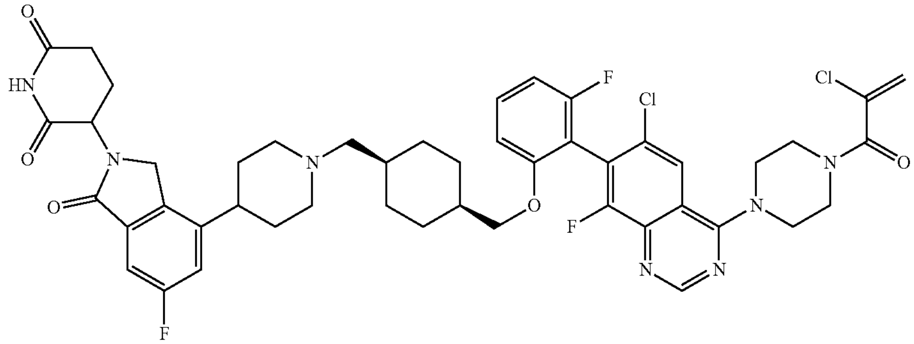

2-((2R)-4-(6-Chloro-7-(2-(2-(4-(2-(4-(2-(2,6-dioxopiperidin-3-yl)-6-fluoro-1-oxoisoindolin-4-yl)piperidin-1-yl)ethyl)cyclohexyl)ethoxy)-6-fluorophenyl)-8-fluoroquinazolin-4-yl)-1-(2-chloroacryloyl)piperazin-2-yl)acetonitrile 129. $^{1}$H NMR (400 MHz, DMSO-$d_6$) δ 11.05 (s, 1H), 9.26 (s, 1H), 8.77-8.74 (m, 1H), 8.15 (s, 1H), 7.58-7.52 (m, 1H), 7.45-7.43 (m, 1H), 7.32-7.30 (m, 1H), 7.09-7.07 (m, 1H), 7.01 (t, J=8.4 Hz, 1H), 5.90-5.85 (m, 2H), 5.16 (dd, J=5.2, 13.2 Hz, 1H), 4.56-4.29 (m, 5H), 4.06-4.00 (m, 2H), 3.90-3.88 (m, 1H), 3.61-3.59 (m, 4H), 3.09-2.90 (m, 8H), 2.65-2.61 (m, 2H), 2.35-2.29 (m, 1H), 2.07-2.03 (m, 4H), 1.57-1.41 (m, 8H), 1.19-1.10 (m, 3H), 0.86-0.69 (m, 4H); MS (ESI) m/z: 985.4 $[M+H]^+$.

129

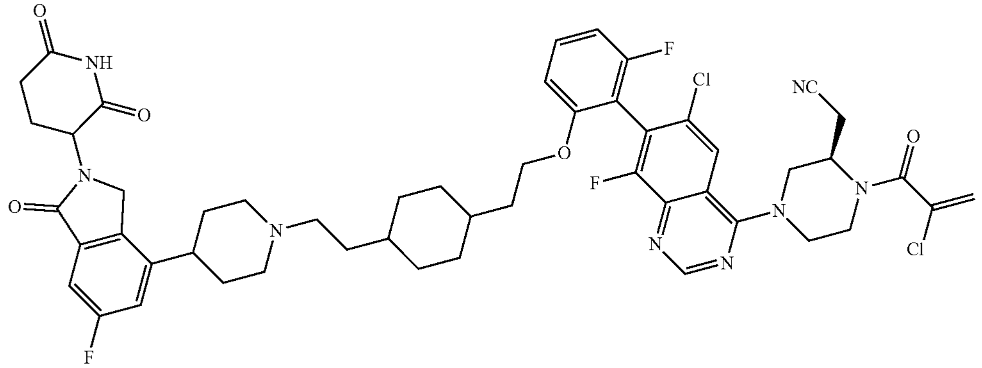

3-(4-(1-(2-(3-(2-(2-(6-Chloro-4-(4-(2-chloroacryloyl)piperazin-1-yl)-8-fluoroquinazolin-7-yl)-3-fluorophenoxy)ethyl)cyclopentyl)ethyl)piperidin-4-yl)-6-fluoro-1-oxoisoindolin-2-yl)piperidine-2,6-dione 130. $^{1}$H NMR (400 MHz, DMSO-$d_6$) δ 11.05 (s, 1H), 9.13 (s, 1H), 8.74-8.73 (m, 1H), 8.06 (s, 1H), 7.56-7.51 (m, 1H), 7.45-7.43 (m, 1H), 7.31-7.29 (m, 1H), 7.07 (dd, J=2.0, 8.0 Hz, 1H), 7.01 (t, J=8.8 Hz, 1H), 5.85 (s, 2H), 5.17 (dd, J=5.2, 13.2 Hz, 1H), 4.55-4.35 (m, 2H), 4.05-4.03 (m, 2H), 3.96-3.88 (m, 4H), 3.76-3.73 (m, 4H), 3.59-3.56 (m, 4H), 3.04-2.91 (m, 6H), 2.66-2.61 (m, 1H), 2.49-2.33 (m, 1H), 2.07-2.02 (m, 3H), 1.95-1.78 (m, 4H), 1.66-1.56 (m, 6H), 1.11-1.06 (m, 2H); MS (ESI) m/z: 932.3 $[M+H]^+$.

130

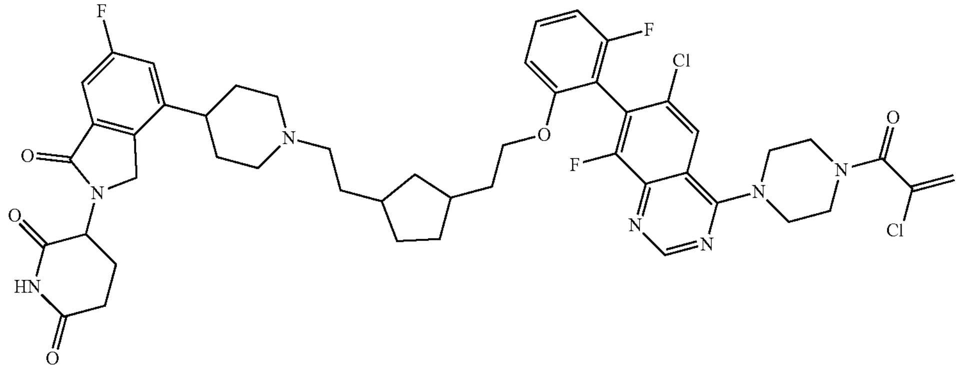

2-((2R)-4-(6-Chloro-7-(2-(4-(2-(4-(2-(2,6-dioxopiperidin-3-yl)-6-fluoro-1-oxoisoindolin-4-yl)piperidin-1-yl)ethyl)phenethoxy)-6-fluorophenyl)-8-fluoroquinazolin-4-yl)-1-(2-chloroacryloyl)piperazin-2-yl)acetonitrile 131.

131

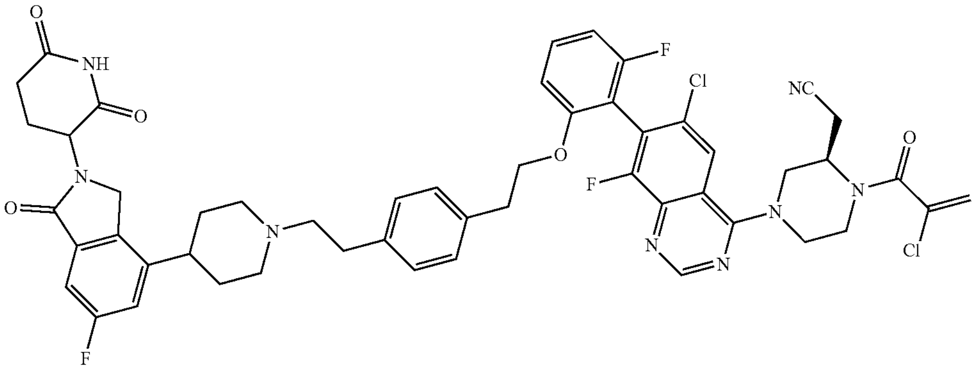

2-((2R)-4-(6-Chloro-7-(2-((7-(4-(2-(2,6-dioxopiperidin-3-yl)-6-fluoro-1-oxoisoindolin-5-yl)piperidin-1-yl)heptyl)oxy)-6-fluorophenyl)-8-fluoro-2-(((S)-1-methylpyrrolidin-2-yl)methoxy)quinazolin-4-yl)-1-(2-chloroacryloyl)piperazin-2-yl)acetonitrile 132.

132

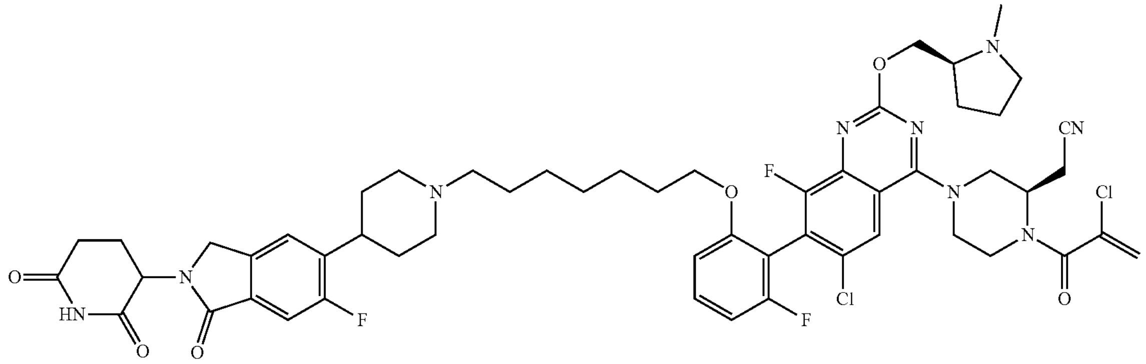

3-(4-((1-((2-(2-(6-Chloro-8-fluoro-4-(4-propionylpiperazin-1-yl)quinazolin-7-yl)-3-fluorophenoxy)ethyl)glycyl)piperidin-4-yl)-1λ$^5$-ethynyl)-1-oxoisoindolin-2-yl)piperidine-2,6-dione 133. Compound 133 was prepared according to the procedures described in U.S. Pat. Appl. Publ. 2020/0109149 A1, the disclosure of which is incorporated herein by reference in its entirety. $^1$H NMR (400 MHz, DMSO-$d_6$) δ 10.98 (s, 1H), 8.67 (s, 1H), 8.03 (s, 1H), 7.72 (d, J=7.2 Hz, 1H), 7.65 (d, J=7.6 Hz, 1H), 7.56-7.51 (m, 2H), 7.09 (d, J=8.4 Hz, 1H), 7.01 (t, J=8.8 Hz, 1H), 5.12 (dd, J=4.8, 13.2 Hz, 1H), 4.47-4.30 (m, 2H), 4.11-4.05 (m, 2H), 3.90-3.87 (m, 4H), 3.87-3.68 (m, 6H), 3.28-3.21 (m, 3H), 3.13-3.07 (m, 2H), 2.95-2.91 (m, 2H), 2.71 (t, J=4.2 Hz, 2H), 2.61-2.57 (m, 1H), 2.50-2.45 (m, 1H), 2.35-2.33 (m, 2H), 2.03-1.99 (m, 1H), 1.90-1.89 (m, 2H), 1.79-1.78 (m, 2H), 1.00 (t, J=7.6 Hz, 3H); MS (ESI) m/z: 867.3 [M+H]$^+$.

133

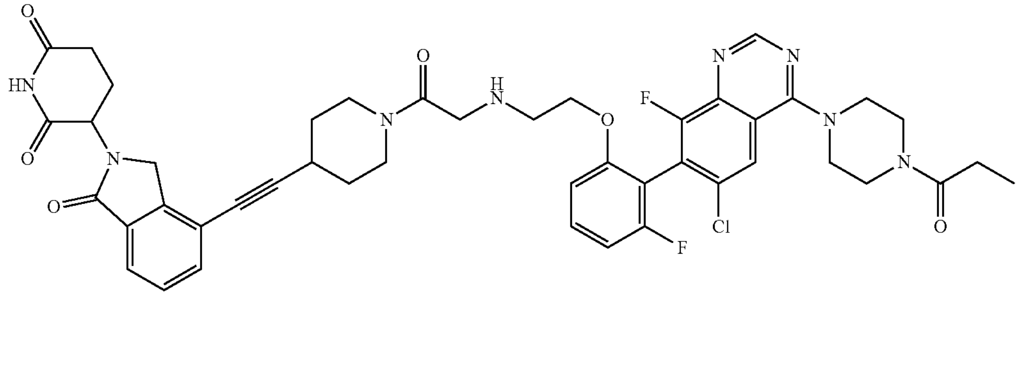

The following compounds are prepared similarly.

N-(1-((5-Chloro-4-(4-((4-((5-(2,6-dioxopiperidin-3-yl)-4-oxo-5,6-dihydro-4H-thieno[3,4-c]pyrrol-1-yl)methoxy)benzyl)amino)butyl)-2-hydroxyphenyl)glycyl)piperidin-4-yl)ethene-sulfonamide 55.

55

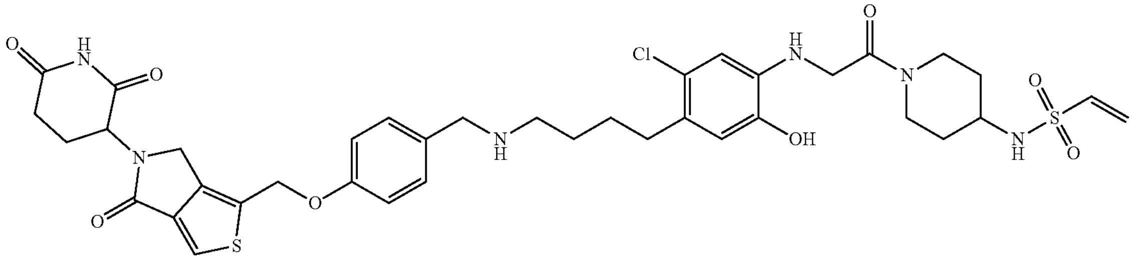

N-(1-((5-Chloro-4-(3-(3-((4-((5-(2,6-dioxopiperidin-3-yl)-4-oxo-5,6-dihydro-4H-thieno[3,4-c]pyrrol-1-yl)methoxy)benzyl)amino)propoxy)propyl)-2-hydroxyphenyl)glycyl)-piperidin-4-yl)ethenesulfonamide 56.

56

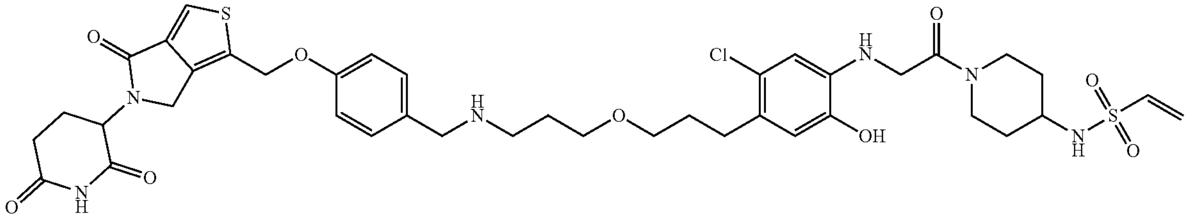

N-(1-((4-Chloro-2-(2-(2-(2-(2-((2-(2,6-dioxopiperidin-3-yl)-1,3-dioxoisoindolin-4-yl)amino)ethoxy)ethoxy)ethoxy)ethyl)-6-hydroxyphenyl)glycyl)piperidin-4-yl)ethenesulfonamide 57.

57

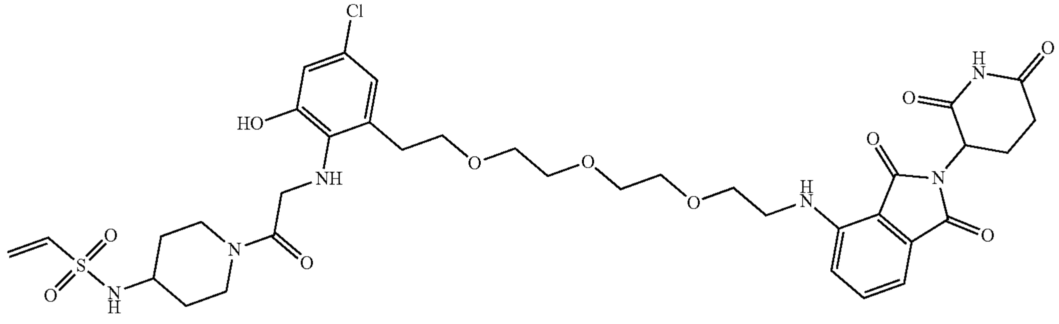

3-((4-(4-Acryloylpiperazin-1-yl)-6-chloro-7-(3-hydroxynaphthalen-1-yl)quinazolin-2-yl)amino)-N-(3-(4-(2-(2,6-dioxopiperidin-3-yl)-6-fluoro-1-oxoisoindolin-4-yl)piperidin-1-yl)propyl)-N-methylpropanamide 68.

68
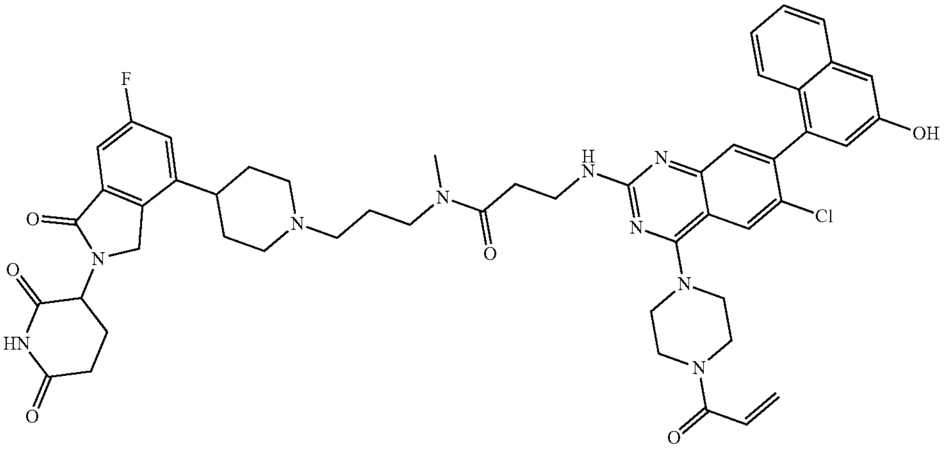
3-((6-Chloro-7-(3-hydroxynaphthalen-1-yl)-4-(4-propionylpiperazin-1-yl)quinazolin-2-yl)amino)-N-(3-(4-(2-(2,6-dioxopiperidin-3-yl)-6-fluoro-1-oxoisoindolin-4-yl)piperidin-1-yl)propyl)-N-methylpropanamide 69.
69
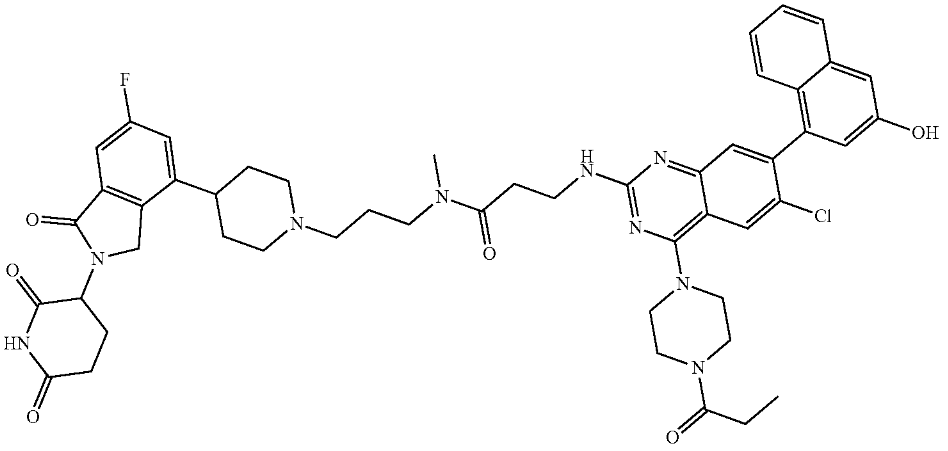
3-(4-(1-(7-(2-(4-(4-Acryloylpiperazin-1-yl)-5,8-dihydropyrido[3,4-d]pyrimidin-7(6H)-yl)-3-fluorophenoxy)heptyl)piperidin-4-yl)-6-fluoro-1-oxoisoindolin-2-yl)piperidine-2,6-dione 74.
74
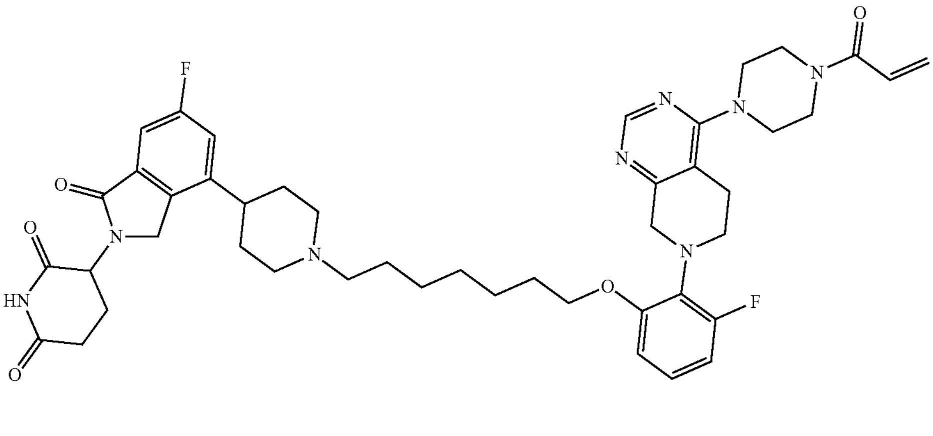

3-(4-((1-((4-(2-(4-(4-Acryloylpiperazin-1-yl)-6-chloro-8-fluoroquinazolin-7-yl)-3-fluorophenoxy)butyl)glycyl)piperidin-4-yl)-1λ$^5$-ethynyl)-1-oxoisoindolin-2-yl)piperidine-2,6-dione 134.

134

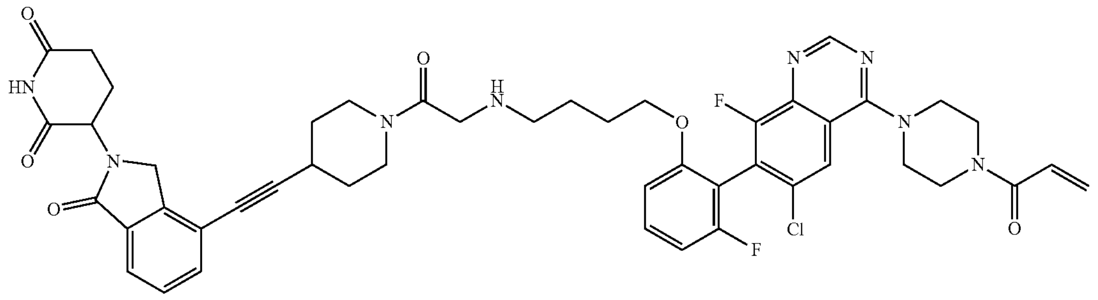

3-(4-((1-((4-(2-(6-Chloro-8-fluoro-4-(4-propionylpiperazin-1-yl)quinazolin-7-yl)-3-fluorophenoxy)butyl)glycyl)piperidin-4-yl)-1λ$^5$-ethynyl)-1-oxoisoindolin-2-yl)piperidine-2,6-dione 135.

135

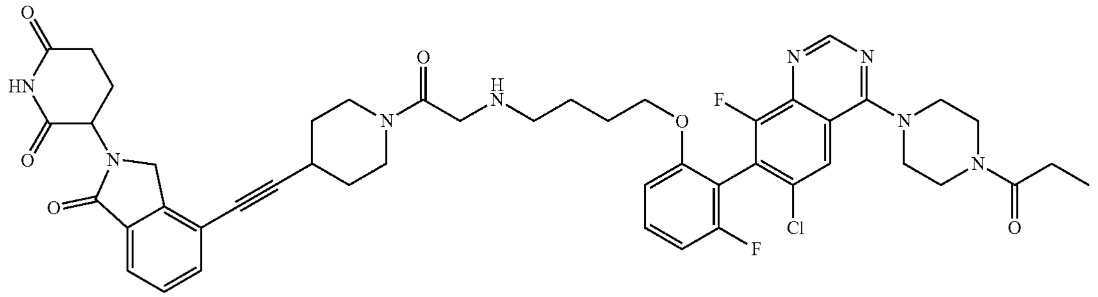

3-(4-((1-((2-(2-(6-Chloro-8-fluoro-4-(4-propionylpiperazin-1-yl)quinazolin-7-yl)-3-fluorophenoxy)ethyl)glycyl)piperidin-4-yl)-1λ$^5$-ethynyl)-1-oxoisoindolin-2-yl)piperidine-2,6-dione 136.

136

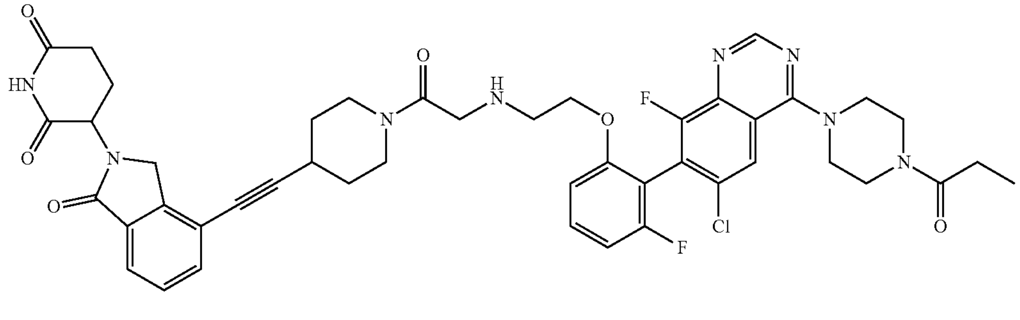

3-(1-((4-(((7-(2-((2R,4aR)-3-Acryloyl-11-chloro-9-fluoro-2,6-dimethyl-5-oxo-2,3,4,4a,5,6-hexahydro-1H-pyrazino[1',2':4,5]pyrazino[2,3-c]quinolin-10-yl)-3-fluorophenoxy)heptyl)amino)-methyl)phenoxy)methyl)-4-oxo-4H-thieno[3,4-c]pyrrol-5(6H)-yl)piperidine-2,6-dione 137.

137

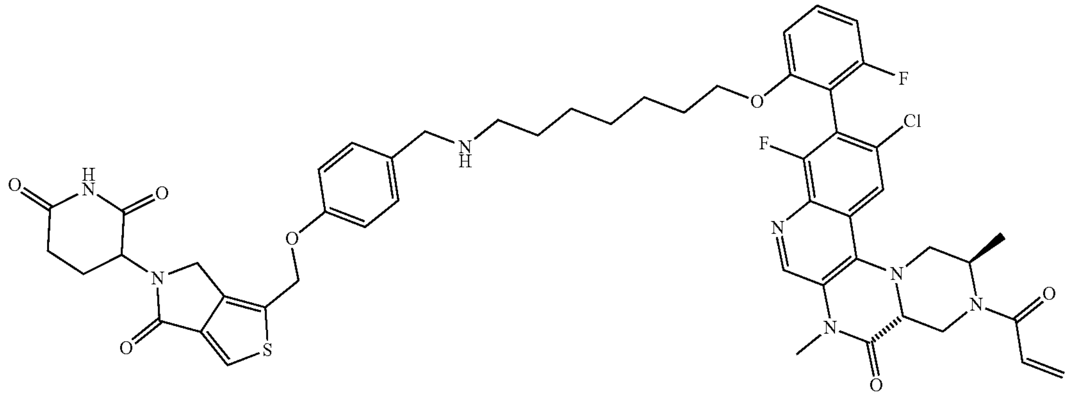

3-(1-((4-(((7-(2-((2R,4aR)-11-Chloro-9-fluoro-2,6-dimethyl-5-oxo-3-propionyl-2,3,4,4a,5,6-hexahydro-1H-pyrazino[1',2':4,5]pyrazino[2,3-c]quinolin-10-yl)-3-fluoro-phenoxy)-heptyl)amino)methyl)phenoxy)methyl)-4-oxo-4H-thieno[3,4-c]pyrrol-5(6H)-yl)piperidine-2,6-dione 138.

138

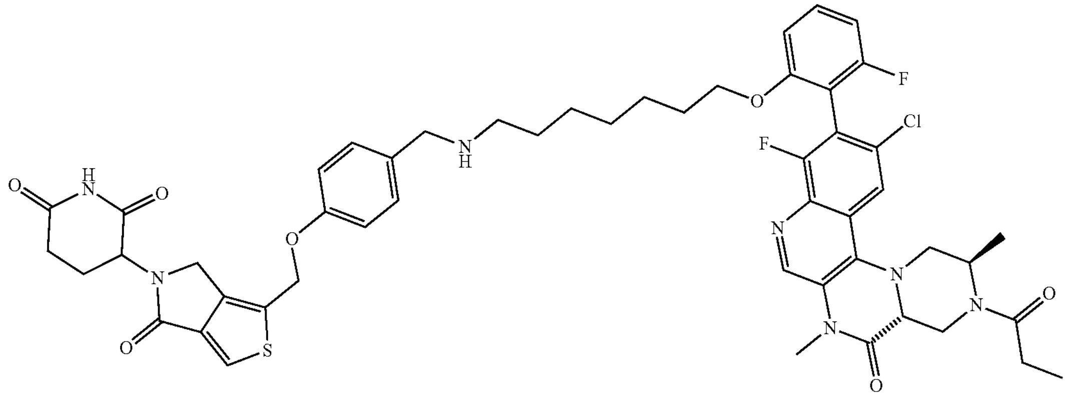

Example B1. Cell Viability Assays

MOLM-13 cells, MV-4-11 cells, H23, and H358 cells were independently cultured in RPMI 1640 media supplemented with 10% fetal bovine serum, streptomycin and penicillin. The cells were plated in white walled 96-well plates at 4,000 cells/well. The cells were incubated in DMSO (control) or a compound for 3 days at 37° C. under 5% $CO_2$. A CELLTITER-GLO® reagent (100 μL) was then added to each well. After a 10 min incubation with shaking, luminescence was measured using an ENVISION® multi-mode plate reader.

The results are summarized in Tables 1 to 4. In Tables 1 and 2, each compound was tested at 10 μM; and in Table 3, each compound was tested at 1 μM. In Tables 1 to 3, the cell viability values as % DMSO are reported as "A," "B," "C," or "D;" where "A" represents a % viability value of less than 10%; "B" represents a % viability value of no less than 10% and less than 25%; "C" represents a % viability value of no less than 25% and less than 50%; and "D" represents a % viability value of no less than 50%. Compound A is

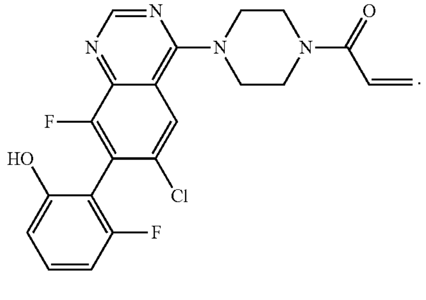 [SMILES: C=CC(=O)N1CCN(c2ncnc3c(F)c(-c4c(O)cccc4F)c(Cl)cc23)CC1]

.

TABLE 1

Effect on MOLM-13, MV-4-11, and H358 Cell Viability

| Compound No. | MOLM-13 | MV-4-11 | H358 |
|---|---|---|---|
| A | C | C | C |
| 1 | C | B | C |
| 2 | B | A | B |

TABLE 2

| Effect on MOLM-13 Cell Viability | |
|---|---|
| Compound No. | MOLM-13 |
| 11 | D |
| 12 | D |
| 13 | D |
| 14 | D |
| 15 | D |
| 16 | D |
| 17 | D |
| 18 | D |
| 19 | D |
| 20 | A |
| 21 | D |
| 23 | A |
| 24 | A |
| 25 | A |
| 26 | D |
| 27 | A |
| 28 | A |
| 29 | A |
| 30 | D |
| 31 | D |
| 32 | D |
| 33 | C |
| 34 | B |
| 35 | B |
| 36 | A |
| 37 | A |
| 38 | D |
| 39 | D |
| 40 | A |
| 41 | A |
| 42 | D |
| 43 | A |
| 44 | A |
| 45 | D |
| 46 | D |
| 58 | A |
| 59 | A |
| 61 | A |
| 62 | A |
| 63 | B |
| 64 | A |
| 65 | A |
| 66 | A |
| 67 | A |
| 70 | A |
| 71 | A |
| 72 | A |
| 73 | B |
| 75 | C |
| 76 | A |
| 77 | D |
| 78 | A |
| 79 | A |
| 80 | A |
| 81 | D |
| 82 | A |
| 83 | A |
| 84 | A |
| 85 | A |
| 87 | A |
| 88 | A |
| 89 | A |
| 90 | A |
| 91 | A |
| 92 | D |
| 93 | A |
| 94 | A |
| 95 | A |
| 96 | A |
| 97 | A |
| 98 | C |
| 99 | A |
| 100 | A |
| 101 | A |
| 102 | A |
| 103 | A |

TABLE 2-continued

| Effect on MOLM-13 Cell Viability | |
|---|---|
| Compound No. | MOLM-13 |
| 104 | A |
| 105 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | A |
| 130 | A |
| 133 | D |

$IC_{50}$ values are summarized in Table 4, where "A" represents an $IC_{50}$ value of no greater than 1 μM, "B" represents an $IC_{50}$ value of greater than 1 μM and no greater than 5 μM, "C" represents an $IC_{50}$ value of greater than 5 μM and no greater than 10 μM, and "D" represents an $IC_{50}$ value of greater than 10 μM.

TABLE 3

| Effect on MOLM-13 Cell Viability | |
|---|---|
| Compound No. | MOLM-13 |
| A | D |
| 1 | D |
| 3 | D |
| 4 | B |
| 5 | D |
| 6 | D |
| 7 | D |
| 8 | D |
| 9 | D |
| 10 | D |

TABLE 4

| Inhibition of H358 and H23 Cells | | |
|---|---|---|
| Compound No. | H358 | H23 |
| A | 0.99 μM | 4.3 μM |
| 1 | C' | C' |
| 20 | B' | B' |
| 23 | B' | B' |
| 24 | B' | B' |
| 36 | A' | A' |
| 37 | B' | B' |
| 38 | D' | D' |
| 39 | D' | D' |
| 40 | B' | B' |
| 41 | B' | B' |
| 42 | D' | D' |
| 43 | A' | A' |

TABLE 4-continued

| Inhibition of H358 and H23 Cells | | |
|---|---|---|
| Compound No. | H358 | H23 |
| 44 | C' | B' |
| 45 | C' | B' |
| 46 | D' | D' |
| 47 | C' | B' |
| 48 | D' | D' |
| 49 | B' | B' |
| 50 | A' | B' |
| 51 | B' | B' |
| 52 | C' | B' |
| 53 | B' | B' |
| 54 | C' | B' |
| 58 | B' | B' |
| 59 | B' | B' |
| 60 | D' | C' |
| 61 | B' | B' |
| 62 | B' | B' |
| 63 | C' | C' |
| 64 | B' | A' |
| 65 | B' | B' |
| 66 | A' | B' |
| 67 | B' | B' |
| 70 | A' | B' |
| 71 | B' | B' |
| 72 | A' | B' |
| 73 | B' | B' |
| 75 | C' | B' |
| 76 | B' | B' |
| 77 | C' | D' |
| 78 | B' | C' |
| 79 | B' | B' |
| 80 | B' | B' |
| 81 | C' | C' |
| 82 | B' | B' |
| 83 | B' | B' |
| 84 | B' | B' |
| 85 | B' | B' |
| 86 | B' | B' |
| 87 | B' | B' |
| 88 | A' | B' |
| 89 | B' | B' |
| 90 | B' | B' |
| 91 | B' | B' |
| 92 | C' | D' |
| 93 | B' | B' |
| 94 | B' | B' |
| 95 | B' | B' |
| 96 | B' | B' |
| 97 | B' | B' |
| 98 | B' | B' |
| 99 | B' | B' |
| 100 | A' | A' |
| 101 | A' | A' |
| 102 | A' | A' |
| 103 | A' | A' |
| 104 | B' | B' |
| 105 | A' | A' |
| 106 | A' | A' |
| 107 | A' | A' |
| 108 | A' | A' |
| 109 | B' | B' |
| 110 | B' | A' |
| 111 | B' | A' |
| 112 | B' | A' |
| 113 | B' | B' |
| 114 | B' | B' |
| 115 | B' | A' |
| 116 | A' | A' |
| 117 | A' | A' |
| 118 | A' | A' |
| 119 | B' | A' |
| 120 | B' | B' |
| 121 | B' | B' |
| 122 | A' | A' |
| 123 | A' | A' |
| 124 | A' | B' |
| 125 | B' | B' |

TABLE 4-continued

| Inhibition of H358 and H23 Cells | | |
|---|---|---|
| Compound No. | H358 | H23 |
| 126 | B' | B' |
| 127 | A' | A' |
| 128 | A' | A' |
| 129 | A' | B' |
| 130 | B' | A' |
| 131 | A' | A' |
| 132 | B' | B' |
| 133 | D' | D' |

Example B2. Protein Degradation Assay

H358 cells were grown in RPMI 1640 media supplemented with 10% fetal bovine serum, streptomycin, and penicillin. The cells were plated in 10 cm plates in the growth media. The next day, the cells were rinsed in 1× PBS with the media replaced by RPMI1640 supplemented with 2.5% fetal bovine serum, streptomycin, and penicillin. The cells were then treated with 1 μM of a compound for 24 h. Whole cell extracts were prepared using an immunoprecipitation (IP) lysis buffer. Briefly, the cells were washed once in PBS, and the cell pellets were resuspended in the IP lysis buffer and incubated for 15 min on ice. Cells debris was removed by centrifugation and the cleared whole cell lysates were transferred to new tubes for further analysis.

For a western blot analysis, the whole cell protein extracts were separated on 12% SDS-polyacrylamide gels, transferred to nitrocellulose, and probed with primary antibodies. Membranes were subsequently washed and probed with IRDYE® secondary antibodies. The signals were detected using an ODYSSEY® Imaging System. The antibodies used in the assay included anti-KRAS; β-actin mouse monoclonal antibody; IRDYE® 680RD goat anti-rabbit antibody; and IRDYE® 800CW goat anti-mouse antibody. It was determined that treating the cells with compound 36 or 37 at 1 μM resulted in about 60% and 30% degradation of KRAS protein, respectively.

The examples set forth above are provided to give those of ordinary skill in the art with a complete disclosure and description of how to make and use the claimed embodiments and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula (I):

$$R^{Het}\text{-}L^2\text{-}X\text{-}L^1\text{-}R^1 \quad (I)$$

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof; wherein:
$R^1$ is
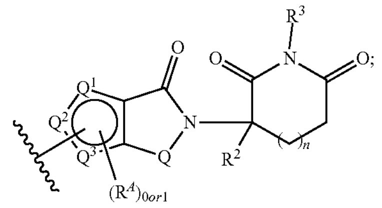
$R^{Het}$ is
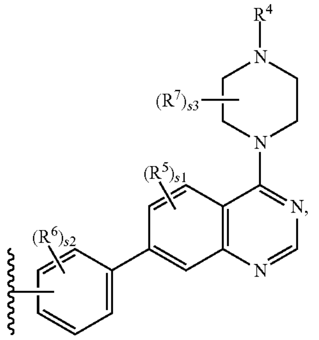
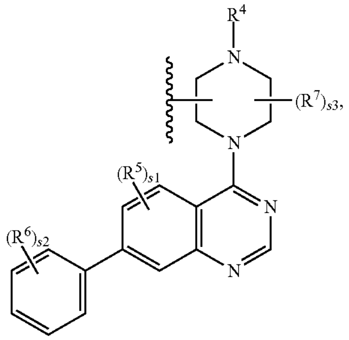
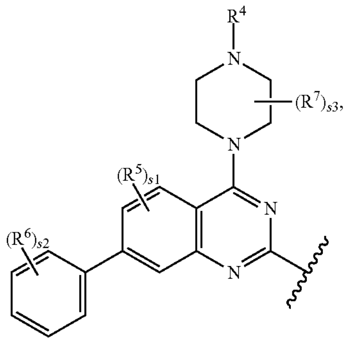
-continued
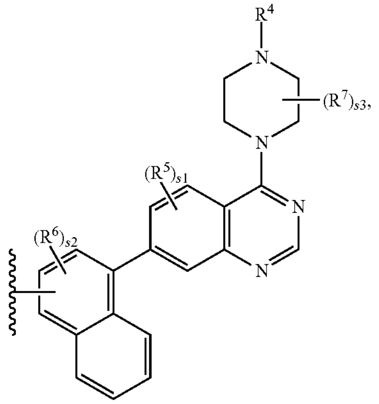
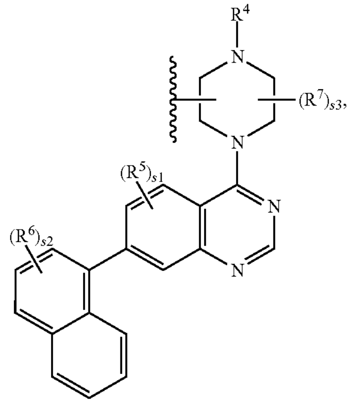
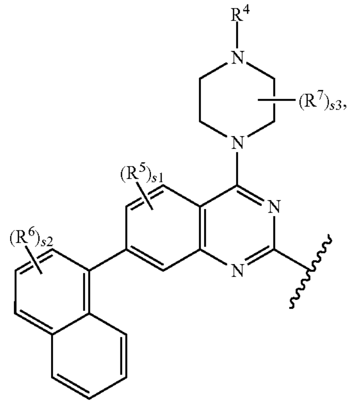
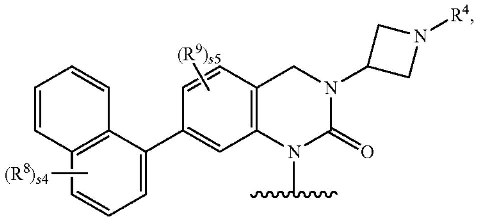
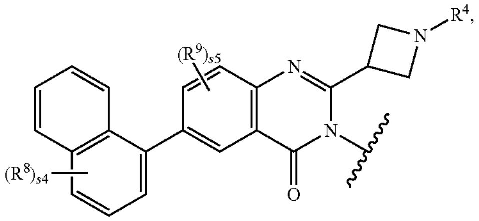

-continued
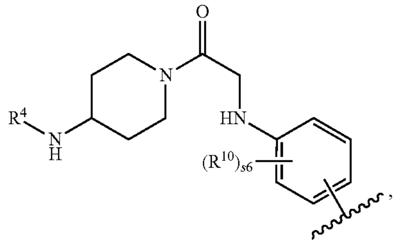
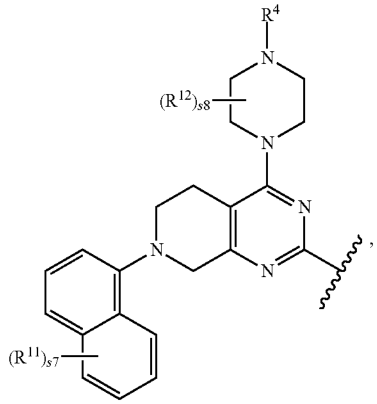
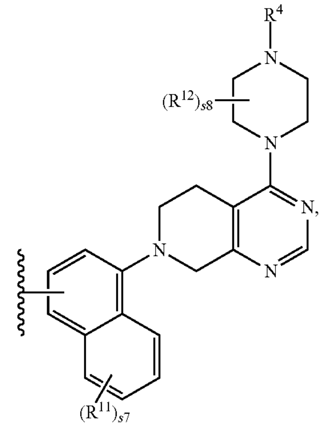
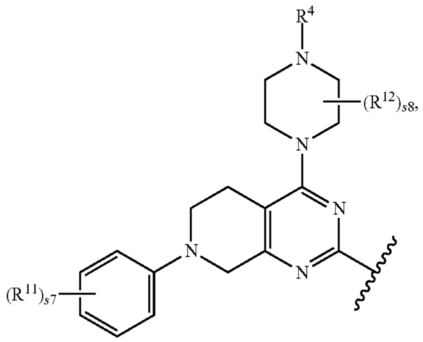
-continued
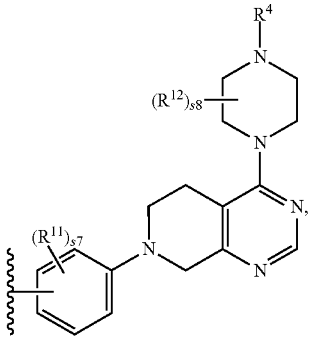
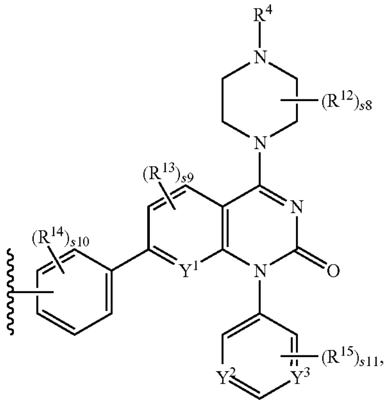
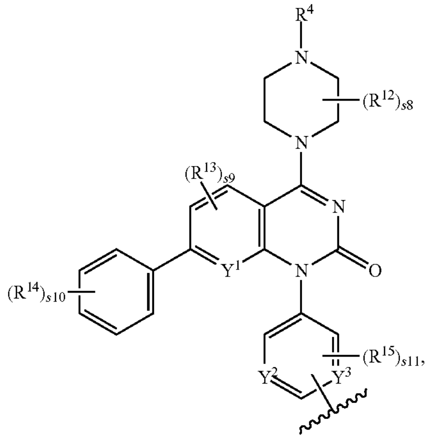
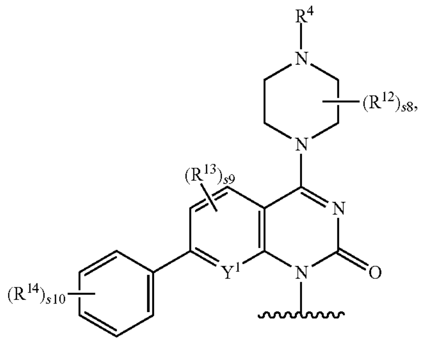

-continued

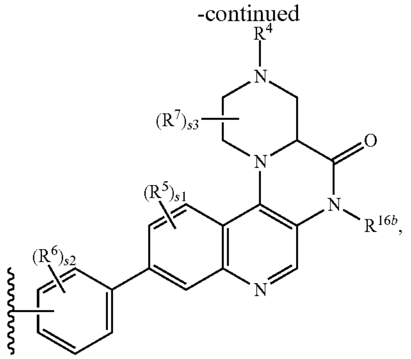

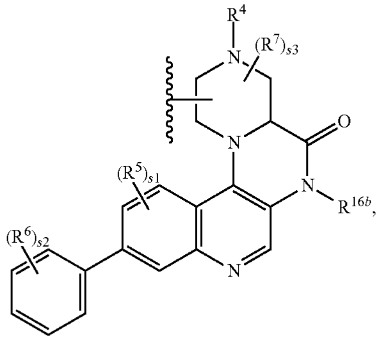

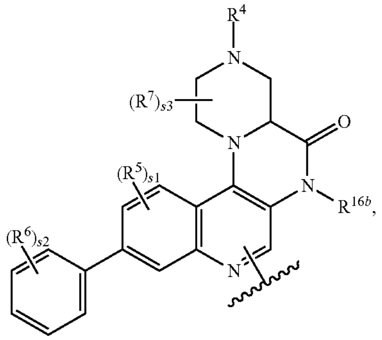

or

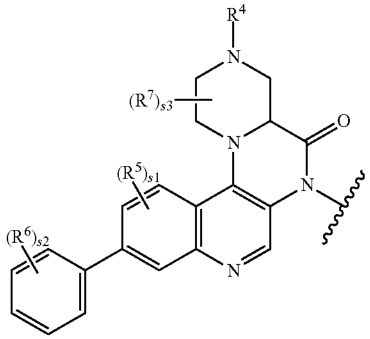

;

X is $C_1$-$C_{15}$ alkylene, heteroalkylene, $C_2$-$C_{10}$ alkenylene, $C_2$-$C_{10}$ alkynylene, phenylene, five to six membered heteroarylene, five to six membered heterocyclylene, or $C_3$-$C_8$ cycloalkylene, each of which is optionally substituted with one or more $R^{18}$; or X is $C_1$-$C_{15}$ alkylene, heteroalkylene, $C_2$-$C_{10}$ alkenylene, or $C_2$-$C_{10}$ alkynylene, wherein one or more methylene repeating units is replaced by a ring structure, each ring structure independently selected from the group consisting of phenylene, five to six membered heteroarylene, five to six membered heterocyclylene, and $C_3$-$C_8$ cycloalkylene, and wherein each ring structure is independently and optionally substituted with one or more $R^{18}$;

$L^1$ is

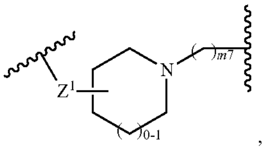

,

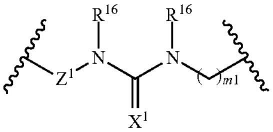

,

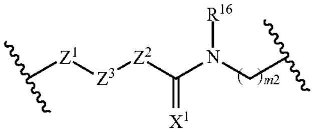

,

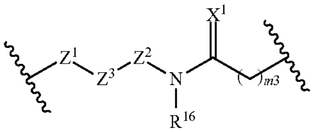

,

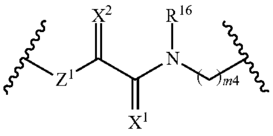

,

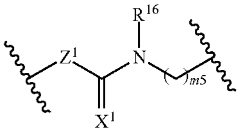

,

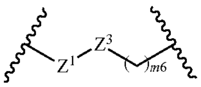

,

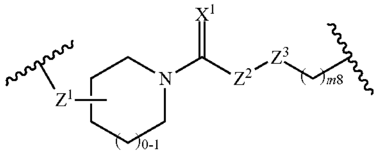

,

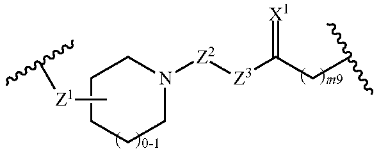

,

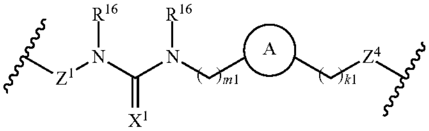

,

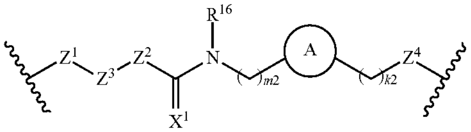

,

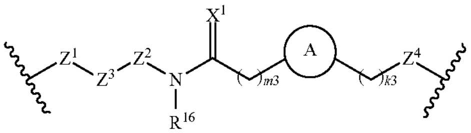

,

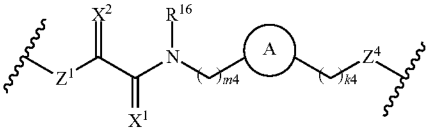

,

-continued

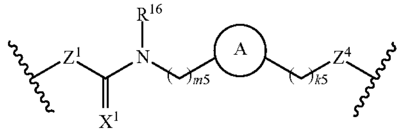

,

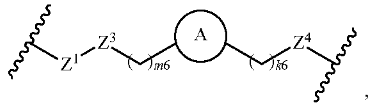

,

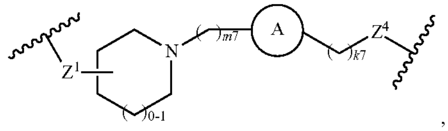

,

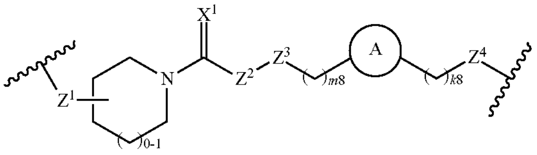

,

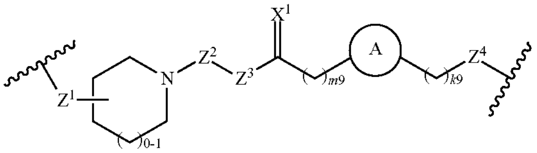

, or a bond;

$L^2$ is a bond, —O—, —S—, —$NR^{16a}$—, —$(CH_2)_{1-3}$—, —C(═O)—, or —$(CH_2)_{0-3}C(═O)\ NR^{16a}$—;

each of $Q^1$, $Q^2$, and $Q^3$ is independently S or CH, provided that one of $Q^1$, $Q^2$, and $Q^3$ is S;

Q is $CH_2$ or C(O);

n is an integer of 0, 1, or 2;

each $R^A$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, (amino) $C_1$-$C_6$ alkyl, —(C═O) $NR^{17a}R^{17b}$, ($C_1$-$C_6$ alkoxy) $C_1$-$C_6$ alkyl, —O—($C_1$-$C_6$ alkoxy) $C_1$-$C_6$ alkyl, or optionally substituted $C_3$-$C_7$ cycloalkyl;

$R^2$ is H, deuterium, halogen, or $C_1$-$C_6$ alkyl;

each $R^3$ is independently H, deuterium, $C_1$-$C_6$ alkyl,

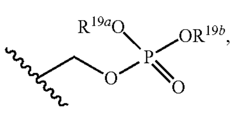

, or

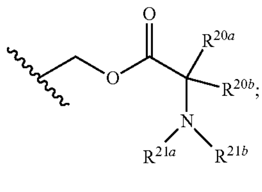

;

each $R^4$ is independently H, $C_1$-$C_6$ alkyl, —C(O) $C_1$-$C_6$ alkyl, —C(O) $C_2$-$C_6$ alkenyl, —C(O) $C_3$-$C_8$ cycloalkyl, —C(O) ($C_3$-$C_8$ cycloalkyl) $C_1$-$C_6$ alkyl, —C(O)— (3 to 7 membered heteroaryl), —C(O)-(3 to 7 membered heterocyclyl), —C(O)-(3 to 7 membered heterocyclyl) $C_1$-$C_6$ alkyl, —C(O) $NR^{17a}R^{17b}$, —$S(O)_2C_1$-$C_6$ alkyl, —$S(O)_2C_2$-$C_6$ alkenyl, —$S(O)_2C_3$-$C_8$ cycloalkyl, —$S(O)_2$ ($C_3$-$C_8$ cycloalkyl) $C_1$-$C_6$ alkyl, —$S(O)_2$-(3 to 7 membered heterocyclyl), —$S(O)_2$-(3 to 7 membered heterocyclyl) $C_1$-$C_6$ alkyl, or —$S(O)_2NR^{17a}R^{17b}$, wherein, when $R^4$ is not H, $R^4$ is optionally substituted with one or more $R^{18}$;

each of $R^5$, $R^6$, $R^7$, $R^8$, $R^9$, $R^{10}$, $R^{11}$, $R^{12}$, $R^{13}$, $R^{14}$, and $R^{15}$ is independently halogen, hydroxyl, cyano, nitro, optionally substituted $C_1$-$C_6$ alkyl, optionally substituted $C_1$-$C_6$ haloalkyl, optionally substituted $C_1$-$C_6$ alkoxy, optionally substituted $C_1$-$C_6$ haloalkoxy, optionally substituted amino, ($C_1$-$C_6$ alkoxy) $C_1$-$C_6$ alkyl, —O—($C_1$-$C_6$ alkoxy) $C_1$-$C_6$ alkyl, or optionally substituted $C_3$-$C_7$ cycloalkyl;

each of $R^{16}$, $R^{16a}$, and R 16b is independently H or $C_1$-$C_6$ alkyl;

each $R^{17a}$ and $R^{17b}$ is independently H or $C_1$-$C_6$ alkyl; or $R^{17a}$ and $R^{17b}$ together with the nitrogen atom to which they are attached form 5 or 6 membered heterocyclyl, each optionally substituted with one or more $R^{18}$;

each $R^{18}$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy) $C_1$-$C_6$ alkyl, —O—($C_1$-$C_6$ alkoxy) $C_1$-$C_6$ alkyl, optionally substituted amino, halogen, or cyano; or two geminal $R^{18}$ form oxo;

each of $R^{19a}$ and $R^{19b}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each of $R^{20a}$ and $R^{20b}$ is independently H, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl;

each of $R^{21a}$ and $R^{21b}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl;

each of s1, s2, s3, s4, s5, s6, s7, s8, s9, s10, and s11 is independently an integer of 0, 1, 2 or 3;

each of $Y^1$, $Y^2$, and $Y^3$ is independently N or CH;

each $Z^1$ is independently a bond, —$(CR^aR^b)_{q1}$—, —C(═O)—, —CH═CH—, or —C≡C—;

each $Z^2$ is independently-$(CR^cR^d)_{q2}$—;

each of $Z^3$ and $Z^4$ is independently $NR^{16}$, O, S, or a bond;

each of $R^a$, $R^b$, $R^c$, and $R^d$ is independently H, halogen, hydroxyl, $C_1$-$C_6$ alkyl, $C_1$-$C_6$ haloalkyl, $C_1$-$C_6$ alkoxy, $C_1$-$C_6$ haloalkoxy, or optionally substituted $C_3$-$C_6$ cycloalkyl;

q1 and q2 are each independently an integer of 1, 2, or 3;

each of $X^1$ and $X^2$ is independently O or S;

each ring A is independently phenylene, five to six membered heteroarylene, five to six membered heterocyclylene, or $C_3$-$C_8$ cycloalkylene, each of which is optionally substituted with one or more $R^{18}$; and each of m1, m2, m3, m4, m5, m6, m7, m8, m9, k1, k2, k3, k4, k5, k6, k7, k8, and k9 is independently an integer of 0, 1, 2, 3, 4, or 5.

2. The compound of claim 1, wherein $R^1$ is

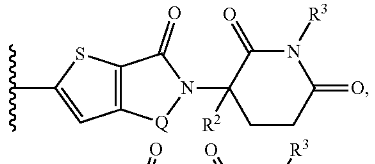

,

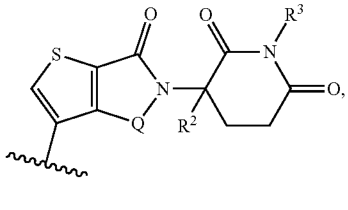

-continued

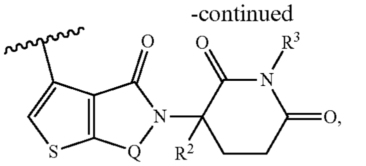

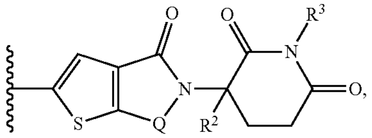

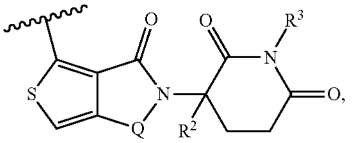

or

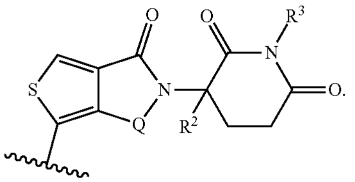

3. The compound of claim 1, wherein $R^{Het}$ is

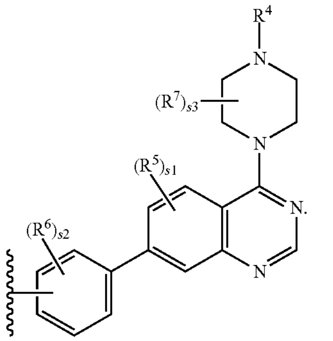

4. The compound of claim 1, having the structure of Formula (III):

(III)

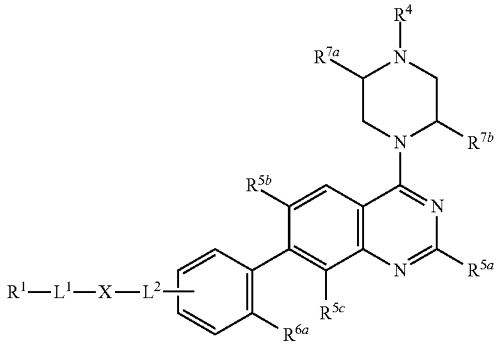

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or thereof; wherein:

$R^{5a}$, $R^{5b}$, and $R^{5c}$ are each independently H or $R^5$;

$R^{6a}$ is H or $R^6$; and $R^{7a}$ and $R^{7b}$ are each independently H or $R^7$.

5. The compound of claim 4, having the structure of Formula (XVI):

(XVI)

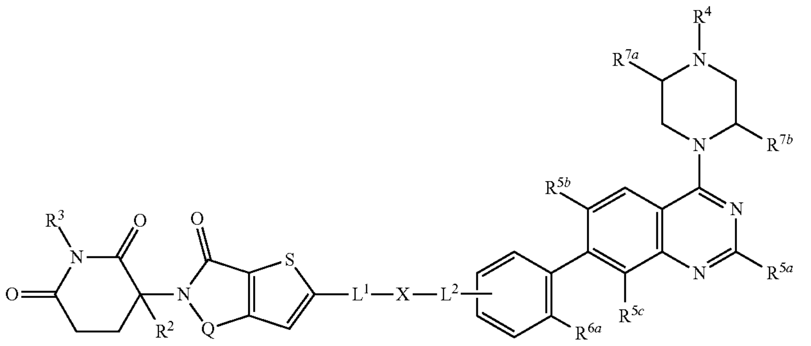

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

6. The compound of claim 4, having the structure of Formula (XVIII):

(XVIII)

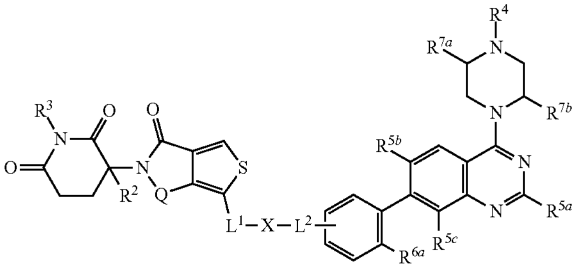

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

7. The compound of claim 6, having the structure of Formula (XIX):

(XIX)

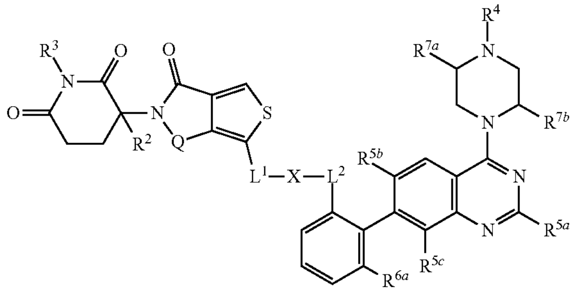

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

8. The compound of claim 4, having the structure of Formula (XX):

(XX)

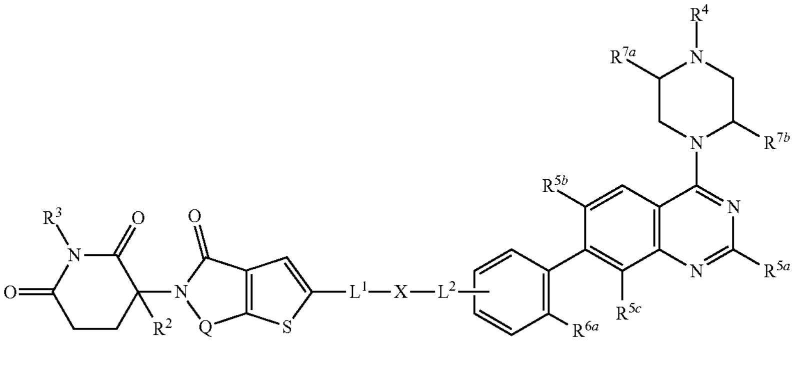

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

9. The compound of claim 1, wherein $R^2$ is H.

10. The compound of claim 1, wherein $R^3$ is H.

11. The compound of claim 1, wherein Q is $CH_2$.

12. The compound of claim 1, wherein Q is C(O).

13. The compound of claim 4, wherein $R^{5a}$ is H, optionally substituted $C_1$-$C_6$ alkoxy, or optionally substituted amino; or wherein $R^{5a}$ is H, 2-dimethylamino-ethoxy, (S)-1-methylpyrrolidin-2-ylmethoxy, or 2-dimethylcarbamoyl-ethylamino.

14. The compound of claim 4, wherein $R^{5b}$ is halogen; or wherein $R^{5b}$ is fluoro or chloro.

15. The compound of claim 4, wherein $R^{5c}$ is H or halogen; or wherein $R^{5c}$ is H, fluoro, or chloro.

16. The compound of claim 4, wherein $R^{6a}$ is halogen or fluoro.

17. The compound of claim 4, wherein $R^{7a}$ is H or optionally substituted $C_1$-$C_6$ alkyl; or wherein $R^{7a}$ is H, methyl, or cyanomethyl.

18. The compound of claim 4, wherein $R^{7b}$ is H or optionally substituted $C_1$-$C_6$ alkyl; or wherein $R^{7b}$ is H or methyl.

19. The compound of claim 1, having the structure of Formula (XXV):

(XXV)

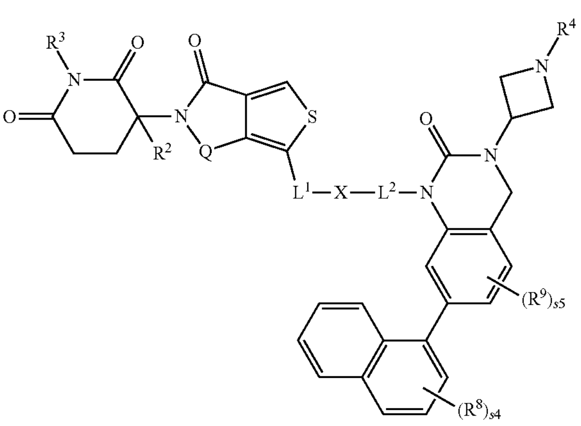

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

20. The compound of claim 1, having the structure of Formula (XXVII):

(XXVII)

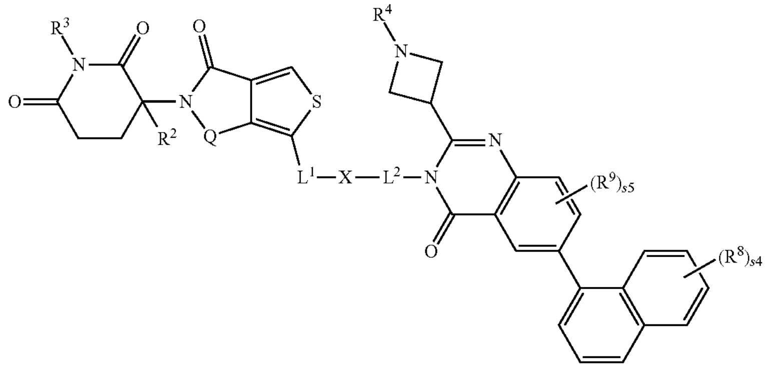

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

21. The compound of claim 1, wherein $R^1$ is

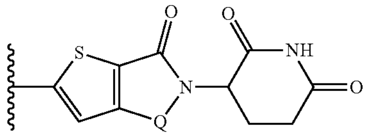

or

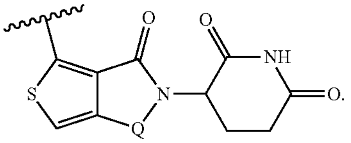

22. The compound of claim 1, wherein $L^1$ is a bond,

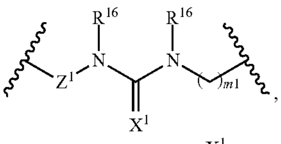

,

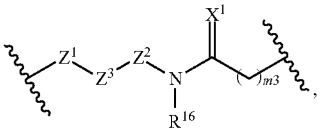

,

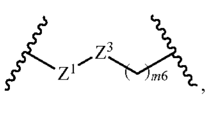

,

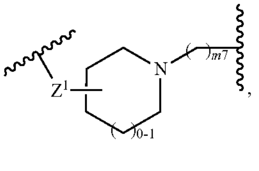

, or

-continued

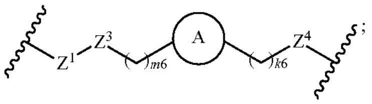

;

or wherein $L^1$ is a bond, —NH—, pyrrolidin-1,3-diyl, piperidin-1,3-diyl, piperidin-1,4-diyl,

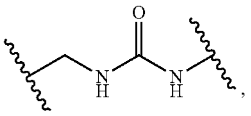

,

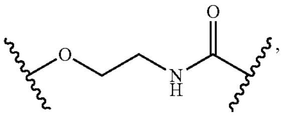

,

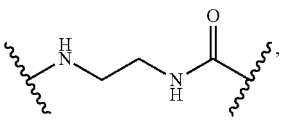

,

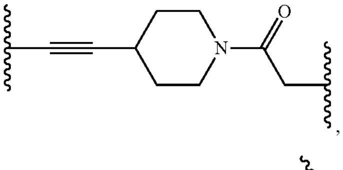

,

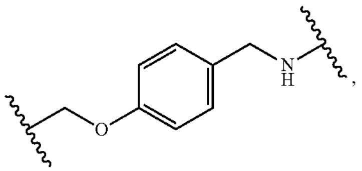

, or

-continued

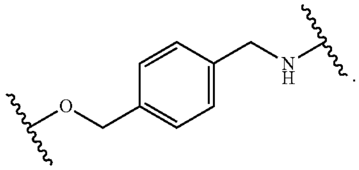.

23. The compound of claim 1, wherein $L^2$ is a bond or O.

24. The compound of claim 1, wherein X is $C_1$-$C_{15}$ alkylene or heteroalkylene; or wherein X is $C_1$-$C_{15}$ alkylene or heteroalkylene, where one or more methylene repeating units is replaced by a ring structure, each ring structure independently selected from the group consisting of phenylene, five to six membered heteroarylene, five to six membered heterocyclylene, and $C_3$-$C_8$ cycloalkylene.

25. The compound of claim 1, wherein X is pentan-1,5-diyl, hexan-1,6-diyl, heptan-1,7-diyl, octan-1,8-diyl, nonan-1,9-diyl, decan-1,10-diyl, undecan-1,11-diyl, piperazin-1,4-diyl,

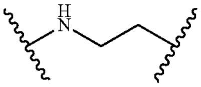,

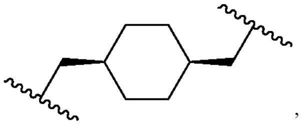,

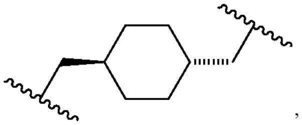,

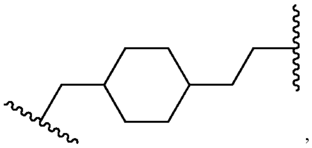,

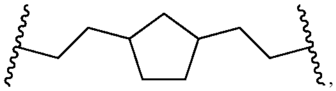,

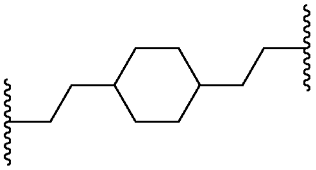,

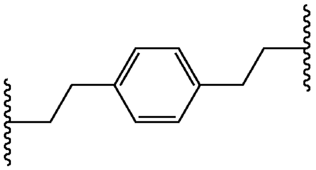,

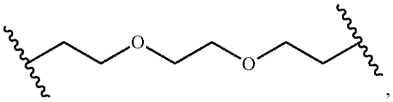,

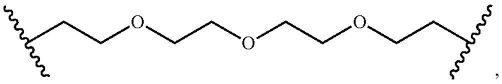,

-continued

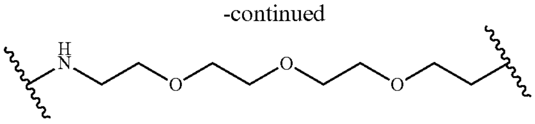,

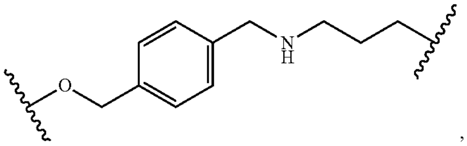,

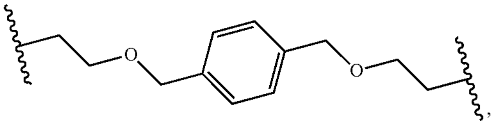,

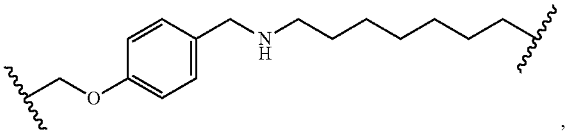,

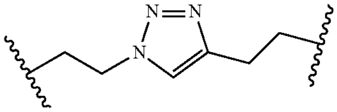, or

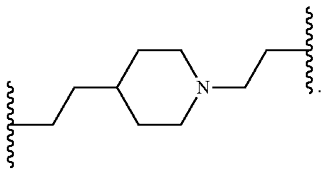.

26. A compound selected from:

3-(2-(2-(2-(4-(4-acryloylpiperazin-1-yl)-6-chloro-8-fluoroquinazolin-7-yl)-3-fluoro-phenoxy) ethoxy) ethoxy)-N-(2-((2-(2,6-dioxopiperidin-3-yl)-1,3-dioxoisoindolin-4-yl)amino)-ethyl) propanamide 1;

3-(2-(2-(2-(4-(4-acryloylpiperazin-1-yl)-6-chloro-8-fluoroquinazolin-7-yl)-3-fluoro-phenoxy) ethoxy) ethoxy)-N-(2-((2-(2,6-dioxopiperidin-3-yl)-1,3-dioxoisoindolin-4-yl)oxy)-ethyl) propanamide 3;

3-(2-(2-(2-(6-chloro-8-fluoro-4-(4-propionylpiperazin-1-yl) quinazolin-7-yl)-3-fluoro-phenoxy) ethoxy) ethoxy)-N-(2-((2-(2,6-dioxopiperidin-3-yl)-1,3-dioxoisoindolin-4-yl)amino)-ethyl) propanamide 6;

3-(2-(2-(2-(6-chloro-8-fluoro-4-(4-propionylpiperazin-1-yl) quinazolin-7-yl)-3-fluoro-phenoxy) ethoxy) ethoxy)-N-(2-((2-(2,6-dioxopiperidin-3-yl)-1,3-dioxoisoindolin-4-yl)oxy)-ethyl) propanamide 8;

4-((2-(2-(2-(2-(2-(6-chloro-8-fluoro-4-(4-propionylpiperazin-1-yl) quinazolin-7-yl)-3-fluorophenoxy) ethoxy) ethoxy) ethoxy)ethyl)amino)-2-(2,6-dioxopiperidin-3-yl) isoindoline-1,3-dione 9;

3-(4-(1-(8-(2-(8-chloro-6-fluoro-4-(4-propionylpiperazin-1-yl) quinazolin-7-yl)-3-fluorophenoxy) octyl) piperidin-4-yl)-6-fluoro-1-oxoisoindolin-2-yl) piperidine-2,6-dione 20;

4-((2-(2-(2-(2-(2-(4-(4-acryloylpiperazin-1-yl)-6-chloro-8-fluoroquinazolin-7-yl)-3-fluorophenoxy) ethoxy) ethoxy) ethoxy)ethyl)amino)-2-(2,6-dioxopiperidin-3-yl) isoindoline-1,3-dione 23;

(3S)-3-(1-((4-(((7-(2-(4-(4-acryloylpiperazin-1-yl)-6-chloro-8-fluoroquinazolin-7-yl)-3-fluorophenoxy) heptyl)amino)methyl) phenoxy)methyl)-4-oxo-4H-thieno [3,4-c]pyrrol-5 (6H)-yl)-piperidine-2,6-dione 24;

(3S)-3-(1-((4-(((7-(2-(6-chloro-8-fluoro-4-(4-propionylpiperazin-1-yl) quinazolin-7-yl)-3-fluorophenoxy) heptyl)amino)methyl) phenoxy)methyl)-4-oxo-4H-thieno[3,4-c]pyrrol-5 (6H)-yl) piperidine-2,6-dione 25;

1-(7-(2-(4-(4-acryloylpiperazin-1-yl)-6-chloro-8-fluoro-quinazolin-7-yl)-3-fluoro-phenoxy) heptyl)-3-((5-(2,6-dioxopiperidin-3-yl)-4-oxo-5,6-dihydro-4H-thieno[3,4-c]pyrrol-1-yl)methyl) urea 27;

1-(7-(2-(6-chloro-8-fluoro-4-(4-propionylpiperazin-1-yl) quinazolin-7-yl)-3-fluoro-phenoxy) heptyl)-3-((5-(2,6-dioxopiperidin-3-yl)-4-oxo-5,6-dihydro-4H-thieno[3,4-c]pyrrol-1-yl)methyl) urea 28;

3-(2-(2-(2-(4-(4-acryloylpiperazin-1-yl)-6-chloro-8-fluoroquinazolin-7-yl)-3-fluoro-phenoxy) ethoxy) ethoxy)-N-(2-((2-(2,6-dioxopiperidin-3-yl)-1-oxoisoindolin-4-yl)amino) ethyl)-propanamide 29;

3-(2-(2-(2-(6-chloro-8-fluoro-4-(4-propionylpiperazin-1-yl) quinazolin-7-yl)-3-fluoro-phenoxy) ethoxy) ethoxy)-N-(2-((2-(2,6-dioxopiperidin-3-yl)-1-oxoisoindolin-4-yl)amino) ethyl)-propanamide 30;

4-((2-(2-(2-(2-(2-(4-(4-acetylpiperazin-1-yl)-6-chloro-8-fluoroquinazolin-7-yl)-3-fluorophenoxy) ethoxy) ethoxy) ethoxy)ethyl)amino)-2-(2,6-dioxopiperidin-3-yl) isoindoline-1,3-dione 31;

4-(6-chloro-7-(2-(2-(2-(2-(2-((2-(2,6-dioxopiperidin-3-yl)-1,3-dioxoisoindolin-4-yl)-amino) ethoxy) ethoxy) ethoxy) ethoxy)-6-fluorophenyl)-8-fluoroquinazolin-4-yl) piperazine-1-carboxamide 32;

4-((8-(2-(6-chloro-8-fluoro-4-(4-propionylpiperazin-1-yl) quinazolin-7-yl)-3-fluoro-phenoxy) octyl)amino)-2-(2,6-dioxopiperidin-3-yl) isoindoline-1,3-dione 33;

4-((8-(2-(4-(4-acryloylpiperazin-1-yl)-6-chloro-8-fluoro-quinazolin-7-yl)-3-fluoro-phenoxy) octyl)amino)-2-(2,6-dioxopiperidin-3-yl) isoindoline-1,3-dione 34;

3-(4-(1-(7-(2-(4-(4-acryloylpiperazin-1-yl)-6-chloro-8-fluoroquinazolin-7-yl)-3-fluoro-phenoxy) heptyl) piperidin-4-yl)-6-fluoro-1-oxoisoindolin-2-yl) piperidine-2,6-dione 36;

3-(4-(1-(7-(2-(6-chloro-8-fluoro-4-(4-propionylpiperazin-1-yl) quinazolin-7-yl)-3-fluorophenoxy) heptyl) piperidin-4-yl)-6-fluoro-1-oxoisoindolin-2-yl) piperidine-2,6-dione 37;

3-(2-(2-(3-(4-(4-acryloylpiperazin-1-yl)-6-chloro-8-fluoroquinazolin-7-yl)-4-fluoro-phenoxy) ethoxy) ethoxy)-N-(2-((2-(2,6-dioxopiperidin-3-yl)-1-oxoisoindolin-4-yl)amino)-ethyl) propanamide 38;

3-(2-(2-((R)-3-(4-(4-acryloylpiperazin-1-yl)-6-chloro-8-fluoroquinazolin-7-yl)-4-fluorophenoxy) ethoxy) ethoxy)-N-(2-((2-(2,6-dioxopiperidin-3-yl)-1-oxoisoindolin-4-yl)amino)-ethyl) propanamide 39;

3-(4-(1-(7-(2-(4-(4-(1H-imidazole-5-carbonyl) piperazin-1-yl)-6-chloro-8-fluoro-quinazolin-7-yl)-3-fluorophenoxy) heptyl) piperidin-4-yl)-6-fluoro-1-oxoisoindolin-2-yl)-piperidine-2,6-dione 41;

4-((2-(2-(2-(2-(2-(6-chloro-8-fluoro-4-(4-propionylpiperazin-1-yl) quinazolin-7-yl)-3-fluorophenoxy) ethoxy) ethoxy) ethoxy)ethyl)amino)-2-(2,6-dioxopiperidin-3-yl) isoindoline-1,3-dione 42;

3-(4-(1-(7-(2-(6-chloro-4-(4-(2-chloroacryloyl) piperazin-1-yl)-8-fluoroquinazolin-7-yl)-3-fluorophenoxy) heptyl) piperidin-4-yl)-6-fluoro-1-oxoisoindolin-2-yl) piperidine-2,6-dione 43;

3-(4-(1-(8-((R)-2-(8-chloro-6-fluoro-4-(4-propionylpiperazin-1-yl) quinazolin-7-yl)-3-fluorophenoxy) octyl) piperidin-4-yl)-6-fluoro-1-oxoisoindolin-2-yl) piperidine-2,6-dione 49;

3-(4-(1-(7-(2-(6-chloro-4-(4-(cyclopentanecarbonyl) piperazin-1-yl)-8-fluoroquinazolin-7-yl)-3-fluorophenoxy) heptyl) piperidin-4-yl)-6-fluoro-1-oxoisoindolin-2-yl) piperidine-2,6-dione 51;

3-(4-(1-(7-(2-(6-chloro-8-fluoro-4-(4-(tetrahydro-2H-pyran-4-carbonyl) piperazin-1-yl)-quinazolin-7-yl)-3-fluorophenoxy) heptyl) piperidin-4-yl)-6-fluoro-1-oxoisoindolin-2-yl)-piperidine-2,6-dione 52;

3-(4-(1-(7-(2-(6-chloro-4-(4-(2-cyclopropylacetyl) piperazin-1-yl)-8-fluoroquinazolin-7-yl)-3-fluorophenoxy) heptyl) piperidin-4-yl)-6-fluoro-1-oxoisoindolin-2-yl) piperidine-2,6-dione 53;

3-(4-(1-(7-(2-(6-chloro-8-fluoro-4-(4-(tetrahydrofuran-3-carbonyl) piperazin-1-yl)-quinazolin-7-yl)-3-fluorophenoxy) heptyl) piperidin-4-yl)-6-fluoro-1-oxoisoindolin-2-yl)-piperidine-2,6-dione 54;

4-((2-(2-(2-(2-((4-((2S,5R)-4-acryloyl-2,5-dimethylpiperazin-1-yl)-6-chloro-8-fluoro-7-(2-fluoro-6-hydroxyphenyl) quinazolin-2-yl)oxy) ethoxy) ethoxy) ethoxy) ethyl)amino)-2-(2,6-dioxopiperidin-3-yl) isoindoline-1,3-dione 58;

3-(4-(1-(7-(2-(6-chloro-4-(4-(ethylsulfonyl) piperazin-1-yl)-8-fluoroquinazolin-7-yl)-3-fluorophenoxy) heptyl) piperidin-4-yl)-6-fluoro-1-oxoisoindolin-2-yl) piperidine-2,6-dione 59;

3-(4-(1-(5-(2-(6-chloro-8-fluoro-4-(4-propionylpiperazin-1-yl) quinazolin-7-yl)-3-fluorophenoxy) pentyl) piperidin-4-yl)-6-fluoro-1-oxoisoindolin-2-yl) piperidine-2,6-dione 60;

3-(4-(1-(9-(2-(6-chloro-8-fluoro-4-(4-propionylpiperazin-1-yl) quinazolin-7-yl)-3-fluorophenoxy) nonyl) piperidin-4-yl)-6-fluoro-1-oxoisoindolin-2-yl) piperidine-2,6-dione 61;

(3S)-3-(4-((4-(((3-(2-(4-(4-acryloylpiperazin-1-yl)-6-chloro-8-fluoroquinazolin-7-yl)-3-fluorophenoxy) propyl)amino)methyl)benzyl)oxy)-1-oxoisoindolin-2-yl) piperidine-2,6-dione 62;

(3S)-3-(4-((4-(((3-(2-(6-chloro-8-fluoro-4-(4-propionylpiperazin-1-yl) quinazolin-7-yl)-3-fluorophenoxy) propyl)amino)methyl)benzyl)oxy)-1-oxoisoindolin-2-yl) piperidine-2,6-dione 63;

3-(1-(1-(7-(2-(4-(4-acryloylpiperazin-1-yl)-6-chloro-8-fluoroquinazolin-7-yl)-3-fluoro-phenoxy) heptyl) piperidin-4-yl)-4-oxo-4H-thieno[3,4-c]pyrrol-5 (6H)-yl) piperidine-2,6-dione 70;

3-(1-(1-(7-(2-(6-chloro-8-fluoro-4-(4-propionylpiperazin-1-yl) quinazolin-7-yl)-3-fluorophenoxy) heptyl) piperidin-4-yl)-4-oxo-4H-thieno[3,4-c]pyrrol-5 (6H)-yl) piperidine-2,6-dione 71;

3-(4-(1-(7-(2-(6-chloro-8-fluoro-4-(4-(pyrrolidine-3-carbonyl) piperazin-1-yl)-quinazolin-7-yl)-3-fluorophenoxy) heptyl) piperidin-4-yl)-6-fluoro-1-oxoisoindolin-2-yl)-piperidine-2,6-dione 79;

(E)-2-(4-(6-chloro-7-(2-((7-(4-(2-(2,6-dioxopiperidin-3-yl)-6-fluoro-1-oxoisoindolin-4-yl) piperidin-1-yl) heptyl)oxy)-6-fluorophenyl)-8-fluoroquinazolin-4-yl) piperazine-1-carbonyl)-4-methylpent-2-enenitrile 80;

3-(4-(1-(7-(2-(6-chloro-8-fluoro-4-(4-(oxetane-3-carbonyl) piperazin-1-yl) quinazolin-7-yl)-3-fluorophenoxy) heptyl) piperidin-4-yl)-6-fluoro-1-oxoisoindolin-2-yl) piperidine-2,6-dione 81;

3-(4-(1-(7-(2-(6-chloro-8-fluoro-4-(4-(2-fluoroacryloyl) piperazin-1-yl) quinazolin-7-yl)-3-fluorophenoxy) heptyl) piperidin-4-yl)-6-fluoro-1-oxoisoindolin-2-yl) piperidine-2,6-dione 82;

4-(6-chloro-7-(2-((7-(4-(2-(2,6-dioxopiperidin-3-yl)-6-fluoro-1-oxoisoindolin-4-yl)-piperidin-1-yl) heptyl) oxy)-6-fluorophenyl)-8-fluoroquinazolin-4-yl) piperazine-1-carboxamide 83;

3-(4-(1-(2-(4-(2-(2-(6-chloro-8-fluoro-4-(4-propionylpiperazin-1-yl) quinazolin-7-yl)-3-fluorophenoxy)ethyl) cyclohexyl)ethyl) piperidin-4-yl)-6-fluoro-1-oxoisoindolin-2-yl) piperidine-2,6-dione 84;

3-(4-(1-(7-(2-(6-chloro-8-fluoro-4-((S)-2-methyl-4-propionylpiperazin-1-yl) quinazolin-7-yl)-3-fluorophenoxy) heptyl) piperidin-4-yl)-6-fluoro-1-oxoisoindolin-2-yl) piperidine-2,6-dione 85;

3-((6-chloro-7-(2-((7-(4-(2-(2,6-dioxopiperidin-3-yl)-6-fluoro-1-oxoisoindolin-4-yl)-piperidin-1-yl) heptyl) oxy)-6-fluorophenyl)-8-fluoro-4-(4-propionylpiperazin-1-yl) quinazolin-2-yl)amino)-N,N-dimethylpropanamide 86;

3-(4-(1-(7-(2-(6-chloro-8-fluoro-4-(4-propionylpiperazin-1-yl) quinazolin-7-yl)-3-fluorophenoxy) heptyl) piperidin-3-yl)-6-fluoro-1-oxoisoindolin-2-yl) piperidine-2,6-dione 87;

3-(4-(1-(7-(2-(4-(4-acryloylpiperazin-1-yl)-6-chloro-8-fluoro-2-(((S)-1-methyl-pyrrolidin-2-yl) methoxy) quinazolin-7-yl)-3-fluorophenoxy) heptyl) piperidin-4-yl)-6-fluoro-1-oxoisoindolin-2-yl) piperidine-2,6-dione 88;

3-(4-(1-(7-(2-(6-chloro-8-fluoro-2-(((S)-1-methylpyrrolidin-2-yl) methoxy)-4-(4-propionylpiperazin-1-yl) quinazolin-7-yl)-3-fluorophenoxy) heptyl) piperidin-4-yl)-6-fluoro-1-oxoisoindolin-2-yl) piperidine-2,6-dione 89;

3-(4-(1-(7-(3-(4-(4-acryloylpiperazin-1-yl)-6-chloro-8-fluoroquinazolin-7-yl)-4-fluoro-phenoxy) heptyl) piperidin-4-yl)-6-fluoro-1-oxoisoindolin-2-yl) piperidine-2,6-dione 90;

3-(4-(1-(7-(3-(6-chloro-8-fluoro-4-(4-propionylpiperazin-1-yl) quinazolin-7-yl)-4-fluorophenoxy) heptyl) piperidin-4-yl)-6-fluoro-1-oxoisoindolin-2-yl) piperidine-2,6-dione 91;

3-(4-(1-(2-(4-(2-(2-(6-chloro-8-fluoro-4-(4-propionylpiperazin-1-yl) quinazolin-7-yl)-3-fluorophenoxy)ethyl)-1H-1,2,3-triazol-1-yl)ethyl) piperidin-4-yl)-6-fluoro-1-oxoisoindolin-2-yl)-piperidine-2,6-dione 92;

3-(5-(1-(7-(2-(6-chloro-8-fluoro-4-(4-propionylpiperazin-1-yl) quinazolin-7-yl)-3-fluorophenoxy) heptyl) piperidin-4-yl)-6-fluoro-1-oxoisoindolin-2-yl) piperidine-2,6-dione 93;

3-(5-(1-(7-(2-(4-(4-acryloylpiperazin-1-yl)-6-chloro-8-fluoroquinazolin-7-yl)-3-fluoro-phenoxy) heptyl) piperidin-4-yl)-6-fluoro-1-oxoisoindolin-2-yl) piperidine-2,6-dione 94;

(Z)-3-(4-(1-(7-(2-(6-chloro-4-(4-(2-chlorobut-2-enoyl) piperazin-1-yl)-8-fluoro-quinazolin-7-yl)-3-fluorophenoxy) heptyl) piperidin-4-yl)-6-fluoro-1-oxoisoindolin-2-yl)-piperidine-2,6-dione 96;

(Z)-3-(4-(1-(7-(2-(6-chloro-4-(4-(2-chloro-4-methylpent-2-enoyl) piperazin-1-yl)-8-fluoroquinazolin-7-yl)-3-fluorophenoxy) heptyl) piperidin-4-yl)-6-fluoro-1-oxoisoindolin-2-yl)-piperidine-2,6-dione 97;

(Z)-3-(4-(1-(7-(2-(6-chloro-4-(4-(2-chloropent-2-enoyl) piperazin-1-yl)-8-fluoro-quinazolin-7-yl)-3-fluorophenoxy) heptyl) piperidin-4-yl)-6-fluoro-1-oxoisoindolin-2-yl)-piperidine-2,6-dione 98;

3-(4-(1-(7-(2-(4-(4-acetylpiperazin-1-yl)-6-chloro-8-fluoroquinazolin-7-yl)-3-fluoro-phenoxy) heptyl) piperidin-4-yl)-6-fluoro-1-oxoisoindolin-2-yl) piperidine-2,6-dione 99;

3-(4-(1-(2-((4-((2-(2-(6-chloro-4-(4-(2-chloroacryloyl) piperazin-1-yl)-8-fluoro-quinazolin-7-yl)-3-fluorophenoxy) ethoxy)methyl)benzyl)oxy) ethyl) piperidin-4-yl)-6-fluoro-1-oxoisoindolin-2-yl) piperidine-2,6-dione 101;

2-((2S)-4-(6-chloro-7-(2-((7-(4-(2-(2,6-dioxopiperidin-3-yl)-6-fluoro-1-oxoisoindolin-4-yl) piperidin-1-yl) heptyl)oxy)-6-fluorophenyl)-8-fluoroquinazolin-4-yl)-1-(2-chloroacryloyl)-piperazin-2-yl) acetonitrile 102;

3-(4-(1-(5-(2-(6-chloro-4-(4-(2-chloroacryloyl) piperazin-1-yl)-8-fluoroquinazolin-7-yl)-3-fluorophenoxy) pentyl) piperidin-4-yl)-6-fluoro-1-oxoisoindolin-2-yl) piperidine-2,6-dione 103;

3-(4-(1-(7-(2-(6-chloro-4-(4-(2-chloroacryloyl) piperazin-1-yl) quinazolin-7-yl)-3-fluorophenoxy) heptyl) piperidin-4-yl)-1-oxoisoindolin-2-yl) piperidine-2,6-dione 105;

3-(4-(1-(7-(2-(6-chloro-4-(4-(2-chloroacryloyl) piperazin-1-yl)-8-fluoroquinazolin-7-yl)-3-fluorophenoxy) heptyl) piperidin-3-yl)-6-fluoro-1-oxoisoindolin-2-yl) piperidine-2,6-dione 106;

3-(5-(1-(7-(2-(6-chloro-4-(4-(2-chloroacryloyl) piperazin-1-yl)-8-fluoroquinazolin-7-yl)-3-fluorophenoxy) heptyl) piperidin-4-yl)-6-fluoro-1-oxoisoindolin-2-yl) piperidine-2,6-dione 107;

3-(4-(1-(7-(2-(6-chloro-4-(4-(2-chloroacryloyl) piperazin-1-yl)-8-fluoro-2-(((S)-1-methylpyrrolidin-2-yl) methoxy) quinazolin-7-yl)-3-fluorophenoxy) heptyl) piperidin-4-yl)-6-fluoro-1-oxoisoindolin-2-yl) piperidine-2,6-dione 108;

3-(4-(1-(2-((4-((2-(2-(6-chloro-8-fluoro-4-(4-propionylpiperazin-1-yl) quinazolin-7-yl)-3-fluorophenoxy) ethoxy)methyl)benzyl)oxy) ethyl) piperidin-4-yl)-6-fluoro-1-oxoisoindolin-2-yl) piperidine-2,6-dione 109;

3-(4-(1-(2-(4-(2-(2-(6-chloro-4-(4-(2-chloroacryloyl) piperazin-1-yl)-8-fluoro-quinazolin-7-yl)-3-fluorophenoxy)ethyl)cyclohexyl)ethyl) piperidin-4-yl)-6-fluoro-1-oxo-isoindolin-2-yl) piperidine-2,6-dione 110;

3-(4-(1-(4-(2-(2-(6-chloro-4-(4-(2-chloroacryloyl) piperazin-1-yl)-8-fluoroquinazolin-7-yl)-3-fluorophenoxy) ethyl) phenethyl) piperidin-4-yl)-6-fluoro-1-oxoisoindolin-2-yl) piperidine-2,6-dione 111;

3-(4-(1-(7-(2-(6-chloro-4-(4-(2-chloroacryloyl) piperazin-1-yl)-8-fluoroquinazolin-7-yl)-3-fluorophenoxy) heptyl) pyrrolidin-3-yl)-6-fluoro-1-oxoisoindolin-2-yl) piperidine-2,6-dione 112;

3-(4-(1-(9-(2-(6-chloro-4-(4-(2-chloroacryloyl) piperazin-1-yl)-8-fluoroquinazolin-7-yl)-3-fluorophenoxy) nonyl) piperidin-4-yl)-6-fluoro-1-oxoisoindolin-2-yl) piperidine-2,6-dione 113;

3-(4-(1-(11-(2-(6-chloro-4-(4-(2-chloroacryloyl) piperazin-1-yl)-8-fluoroquinazolin-7-yl)-3-fluorophenoxy) undecyl) piperidin-4-yl)-6-fluoro-1-oxoisoindolin-2-yl) piperidine-2,6-dione 114;

3-(4-(1-(7-(2-(6-chloro-4-(4-(2-chloroacryloyl) piperazin-1-yl)-2-(2-(dimethylamino)-ethoxy)-8-fluoroquinazolin-7-yl)-3-fluorophenoxy) heptyl) piperidin-4-yl)-6-fluoro-1-oxo-isoindolin-2-yl) piperidine-2,6-dione 115;

3-(4-(1-(2-(4-(2-(2-(6-chloro-4-(4-(2-chloroacryloyl) piperazin-1-yl)-8-fluoro-quinazolin-7-yl)-3-fluorophenoxy)ethyl)cyclohexyl)ethyl) piperidin-4-yl)-6-fluoro-1-oxo-isoindolin-2-yl) piperidine-2,6-dione 116;

3-(4-(1-(((1r,4r)-4-((2-(6-chloro-4-(4-(2-chloroacryloyl) piperazin-1-yl)-8-fluoro-quinazolin-7-yl)-3-fluorophenoxy)methyl)cyclohexyl)methyl) piperidin-4-yl)-6-fluoro-1-oxo-isoindolin-2-yl) piperidine-2,6-dione 117;

3-(4-(1-((4-(2-(2-(6-chloro-4-(4-(2-chloroacryloyl) piperazin-1-yl)-8-fluoroquinazolin-7-yl)-3-fluorophenoxy) ethyl)cyclohexyl)methyl) piperidin-4-yl)-6-fluoro-1-oxoisoindolin-2-yl)-piperidine-2,6-dione 118;

3-(5-(1-(7-(2-(6-chloro-4-(4-(2-chloroacryloyl) piperazin-1-yl)-8-fluoroquinazolin-7-yl)-3-fluorophenoxy) heptyl) piperidin-3-yl)-6-fluoro-1-oxoisoindolin-2-yl) piperidine-2,6-dione 119;

3-(4-(1-(2-(1-(2-(2-(6-chloro-4-(4-(2-chloroacryloyl) piperazin-1-yl)-8-fluoro-quinazolin-7-yl)-3-fluorophenoxy)ethyl) piperidin-4-yl)ethyl) piperidin-4-yl)-6-fluoro-1-oxo-isoindolin-2-yl) piperidine-2,6-dione 120;

3-(4-(1-(3-(2-(6-chloro-4-(4-(2-chloroacryloyl) piperazin-1-yl)-8-fluoroquinazolin-7-yl)-3-fluorophenoxy) propyl) piperidin-4-yl)-6-fluoro-1-oxoisoindolin-2-yl) piperidine-2,6-dione 121;

2-((2R)-4-(6-chloro-7-(2-((7-(4-(2-(2,6-dioxopiperidin-3-yl)-6-fluoro-1-oxoisoindolin-5-yl) piperidin-1-yl) heptyl)oxy)-6-fluorophenyl)-8-fluoroquinazolin-4-yl)-1-(2-chloroacryloyl)-piperazin-2-yl) acetonitrile 123;

3-(4-(1-(((1s,4s)-4-((2-(6-chloro-4-(4-(2-chloroacryloyl) piperazin-1-yl)-8-fluoro-quinazolin-7-yl)-3-fluorophenoxy)methyl)cyclohexyl)methyl) piperidin-4-yl)-6-fluoro-1-oxo-isoindolin-2-yl) piperidine-2,6-dione 127;

2-((2R)-4-(6-chloro-7-(2-((7-(4-(2-(2,6-dioxopiperidin-3-yl)-6-fluoro-1-oxoisoindolin-4-yl) piperidin-1-yl) heptyl)oxy)-6-fluorophenyl)-8-fluoro-2-(((S)-1-methylpyrrolidin-2-yl)-methoxy) quinazolin-4-yl)-1-(2-chloroacryloyl) piperazin-2-yl) acetonitrile 128;

2-((2R)-4-(6-chloro-7-(2-(2-(4-(2-(4-(2-(2,6-dioxopiperidin-3-yl)-6-fluoro-1-oxo-isoindolin-4-yl) piperidin-1-yl)ethyl)cyclohexyl) ethoxy)-6-fluorophenyl)-8-fluoroquinazolin-4-yl)-1-(2-chloroacryloyl) piperazin-2-yl) acetonitrile 129;

3-(4-(1-(2-(3-(2-(2-(6-chloro-4-(4-(2-chloroacryloyl) piperazin-1-yl)-8-fluoro-quinazolin-7-yl)-3-fluorophenoxy)ethyl)cyclopentyl)ethyl) piperidin-4-yl)-6-fluoro-1-oxo-isoindolin-2-yl) piperidine-2,6-dione 130;

2-((2R)-4-(6-chloro-7-(2-(4-(2-(4-(2-(2,6-dioxopiperidin-3-yl)-6-fluoro-1-oxo-isoindolin-4-yl) piperidin-1-yl)ethyl) phenethoxy)-6-fluorophenyl)-8-fluoroquinazolin-4-yl)-1-(2-chloroacryloyl) piperazin-2-yl) acetonitrile 131;

2-((2R)-4-(6-chloro-7-(2-((7-(4-(2-(2,6-dioxopiperidin-3-yl)-6-fluoro-1-oxoisoindolin-5-yl) piperidin-1-yl) heptyl)oxy)-6-fluorophenyl)-8-fluoro-2-(((S)-1-methylpyrrolidin-2-yl)-methoxy) quinazolin-4-yl)-1-(2-chloroacryloyl) piperazin-2-yl) acetonitrile 132;

3-(4-((1-((2-(2-(6-chloro-8-fluoro-4-(4-propionylpiperazin-1-yl) quinazolin-7-yl)-3-fluorophenoxy)ethyl) glycyl) piperidin-4-yl)-125-ethynyl)-1-oxoisoindolin-2-yl) piperidine-2,6-dione 133;

(2S,4R)-1-((2S)-2-(7-(2-(4-(4-acryloylpiperazin-1-yl)-6-chloro-8-fluoroquinazolin-7-yl)-3-fluorophenoxy) heptanamido)-3,3-dimethylbutanoyl)-4-hydroxy-N-(4-(4-methylthiazol-5-yl)benzyl) pyrrolidine-2-carboxamide 50;

(2S,4R)-1-((2S)-2-(11-(2-(4-(4-acryloylpiperazin-1-yl)-6-chloro-8-fluoroquinazolin-7-yl)-3-fluorophenoxy) undecanamido)-3,3-dimethylbutanoyl)-4-hydroxy-N-(4-(4-methylthiazol-5-yl)benzyl) pyrrolidine-2-carboxamide 76;

(2S,4R)-1-((2S)-2-(11-(2-(6-chloro-8-fluoro-4-(4-propionylpiperazin-1-yl) quinazolin-7-yl)-3-fluorophenoxy) undecanamido)-3,3-dimethylbutanoyl)-4-hydroxy-N-(4-(4-methylthiazol-5-yl)benzyl) pyrrolidine-2-carboxamide 77;

(2S,4R)-1-((2S)-2-(7-(2-(6-chloro-8-fluoro-4-(4-propionylpiperazin-1-yl) quinazolin-7-yl)-3-fluorophenoxy) heptanamido)-3,3-dimethylbutanoyl)-4-hydroxy-N-(4-(4-methylthiazol-5-yl)benzyl) pyrrolidine-2-carboxamide 78;

2-(4-acryloyl-1-(6-chloro-8-fluoro-7-(2-fluoro-6-hydroxyphenyl) quinazolin-4-yl)-piperazin-2-yl)-N-(5-(3-((5-(2,6-dioxopiperidin-3-yl)-6-oxo-5,6-dihydro-4H-thieno[2,3-c]pyrrol-2-yl)methyl) ureido) pentyl) acetamide 13;

4-((2-(2-(2-(2-(3-(1-acryloylazetidin-3-yl)-7-(3-hydroxynaphthalen-1-yl)-2-oxo-3,4-dihydroquinazolin-1 (2H)-yl) ethoxy) ethoxy) ethoxy)ethyl)amino)-2-(2,6-dioxopiperidin-3-yl)-isoindoline-1,3-dione 2;

3-(1-((4-(((2-(7-(3-hydroxynaphthalen-1-yl)-2-oxo-3-(1-propionylazetidin-3-yl)-3,4-dihydroquinazolin-1 (2H)-yl)ethyl)amino) methyl) phenoxy)methyl)-4-oxo-4H-thieno[3,4-c]-pyrrol-5 (6H)-yl) piperidine-2,6-dione 4;

3-(1-((4-(((2-(2-(7-(3-hydroxynaphthalen-1-yl)-2-oxo-3-(1-propionylazetidin-3-yl)-3,4-dihydroquinazolin-1 (2H)-yl) ethoxy)ethyl)amino) methyl) phenoxy) methyl)-4-oxo-4H-thieno[3,4-c]pyrrol-5 (6H)-yl) piperidine-2,6-dione 5;

N-(2-((2-(2,6-dioxopiperidin-3-yl)-1,3-dioxoisoindolin-4-yl)oxy)ethyl)-3-(2-(2-(7-(3-hydroxynaphthalen-1-yl)-2-oxo-3-(1-propionylazetidin-3-yl)-3,4-dihydroquinazolin-1 (2H)-yl)-ethoxy) ethoxy) propanamide 7;

3-(2-(3-(1-acryloylazetidin-3-yl)-7-(3-hydroxynaphthalen-1-yl)-2-oxo-3,4-dihydro-quinazolin-1 (2H)-yl) ethoxy)-N-(2-((2-(2,6-dioxopiperidin-3-yl)-1,3-dioxoisoindolin-4-yl)oxy)-ethyl) propanamide 10;

3-(2-(2-(3-(1-acryloylazetidin-3-yl)-7-(3-hydroxynaphthalen-1-yl)-2-oxo-3,4-dihydro-quinazolin-1 (2H)-yl) ethoxy) ethoxy)-N-(2-((2-(2,6-dioxopiperidin-3-yl)-1,3-dioxoisoindolin-4-yl)oxy)ethyl) propanamide 11;

2-(2,6-dioxopiperidin-3-yl)-4-((2-(2-(2-(2-(7-(3-hydroxynaphthalen-1-yl)-2-oxo-3-(1-propionylazetidin-3-yl)-3,4-dihydroquinazolin-1 (2H)-yl) ethoxy) ethoxy) ethoxy)ethyl)amino)-isoindoline-1,3-dione 12;

(S)-3-(1-((4-(((4-(3-(1-acryloylazetidin-3-yl)-7-(3-hydroxynaphthalen-1-yl)-2-oxo-3,4-dihydroquinazolin-1 (2H)-yl)butyl)amino) methyl) phenoxy)methyl)-4-oxo-4H-thieno[3,4-c]-pyrrol-5 (6H)-yl) piperidine-2,6-dione 16;

3-(1-((4-(((4-(3-(1-acryloylazetidin-3-yl)-7-(3-hydroxynaphthalen-1-yl)-2-oxo-3,4-dihydroquinazolin-1 (2H)-yl)butyl)amino) methyl) phenoxy)methyl)-4-oxo-4H-thieno[3,4-c]-pyrrol-5 (6H)-yl) piperidine-2,6-dione 19;

(S)-3-(1-((4-(((2-(7-(3-hydroxynaphthalen-1-yl)-2-oxo-3-(1-propionylazetidin-3-yl)-3,4-dihydroquinazolin-1 (2H)-yl)ethyl)amino) methyl) phenoxy)methyl)-4-oxo-4H-thieno[3,4-c]-pyrrol-5 (6H)-yl) piperidine-2,6-dione 22;

N-(7-(4-(2-(2,6-dioxopiperidin-3-yl)-6-fluoro-1-oxoisoindolin-4-yl) piperidin-1-yl)-heptyl)-2-(7-(3-hydroxynaphthalen-1-yl)-2-oxo-3-(1-propionylazetidin-3-yl)-3,4-dihydro-quinazolin-1 (2H)-yl) acetamide 35;

5-((2-(2-(2-(2-(3-(1-acryloylazetidin-3-yl)-7-(3-hydroxynaphthalen-1-yl)-2-oxo-3,4-dihydroquinazolin-1 (2H)-yl) ethoxy) ethoxy) ethoxy)ethyl)amino)-2-(2,6-dioxopiperidin-3-yl)-isoindoline-1,3-dione 40;

3-(6-fluoro-4-(1-(7-(7-(3-hydroxynaphthalen-1-yl)-2-oxo-3-(1-propionylazetidin-3-yl)-3,4-dihydroquinazolin-1 (2H)-yl) heptyl) piperidin-4-yl)-1-oxoisoindolin-2-yl) piperidine-2,6-dione 44;

4-((2-(2-(2-(3-(1-acryloylazetidin-3-yl)-7-(3-hydroxynaphthalen-1-yl)-2-oxo-3,4-dihydro-quinazolin-1 (2H)-yl) ethoxy) ethoxy)ethyl)amino)-2-(2,6-dioxopiperidin-3-yl)-isoindoline-1,3-dione 45;

3-(6-fluoro-4-(1-(7-((2-(7-(3-hydroxynaphthalen-1-yl)-2-oxo-3-(1-propionylazetidin-3-yl)-3,4-dihydroquinazolin-1 (2H)-yl)ethyl)amino) heptyl) piperidin-4-yl)-1-oxoisoindolin-2-yl)-piperidine-2,6-dione 46;

(S)-3-(1-((4-(((2-(2-(2-(2-(1-acryloylazetidin-3-yl)-6-(3-hydroxynaphthalen-1-yl)-4-oxoquinazolin-3 (4H)-yl) ethoxy) ethoxy)ethyl)amino) methyl) phenoxy) methyl)-4-oxo-4H-thieno[3,4-c]pyrrol-5 (6H)-yl) piperidine-2,6-dione 14;

(S)-3-(1-((4-(((2-(2-(1-acryloylazetidin-3-yl)-6-(3-hydroxynaphthalen-1-yl)-4-oxo-quinazolin-3 (4H)-yl) ethyl)amino) methyl) phenoxy)methyl)-4-oxo-4H-thieno[3,4-c]pyrrol-5 (6H)-yl) piperidine-2,6-dione 15;

2-(2-(1-acryloylazetidin-3-yl)-6-(3-hydroxynaphthalen-1-yl)-4-oxoquinazolin-3 (4H)-yl)-N-(2-(2-(2-(2-((2-(2,6-dioxopiperidin-3-yl)-1,3-dioxoisoindolin-4-yl) amino) ethoxy) ethoxy)-ethoxy)-ethyl) acetamide 17;

3-(1-((4-(((2-(2-(1-acryloylazetidin-3-yl)-6-(3-hydroxynaphthalen-1-yl)-4-oxo-quinazolin-3 (4H)-yl) ethyl)amino) methyl) phenoxy)methyl)-4-oxo-4H-thieno[3,4-c]pyrrol-5 (6H)-yl) piperidine-2,6-dione 18;

3-(1-((4-(((2-(2-(2-(1-acryloylazetidin-3-yl)-6-(3-hydroxynaphthalen-1-yl)-4-oxo-quinazolin-3 (4H)-yl) ethoxy)ethyl)amino) methyl) phenoxy)methyl)-4-oxo-4H-thieno[3,4-c]-pyrrol-5 (6H)-yl) piperidine-2,6-dione 21;

3-(1-((4-(((2-(2-(6-(3-hydroxynaphthalen-1-yl)-4-oxo-2-(1-propionylazetidin-3-yl)-quinazolin-3 (4H)-yl) ethoxy)ethyl)amino) methyl) phenoxy)methyl)-4-oxo-4H-thieno[3,4-c]-pyrrol-5 (6H)-yl) piperidine-2,6-dione 26;

4-((2-(2-(2-(2-((4-((R)-4-acryloyl-3-methylpiperazin-1-yl)-7-(naphthalen-1-yl)-5,6,7,8-tetrahydropyrido[3,4-d]pyrimidin-2-yl)oxy) ethoxy) ethoxy) ethoxy)ethyl) amino)-2-(2,6-dioxo-piperidin-3-yl) isoindoline-1,3-dione 47;

2-(2,6-dioxopiperidin-3-yl)-4-((2-(2-(2-(2-((4-((R)-3-methyl-4-propionylpiperazin-1-yl)-7-(naphthalen-1-yl)-5,6,7,8-tetrahydropyrido[3,4-d]pyrimidin-2-yl) oxy) ethoxy) ethoxy) ethoxy)-ethyl)amino) isoindoline-1,3-dione 48;

3-(4-(1-(7-((4-(4-acryloylpiperazin-1-yl)-7-(3-hydroxynaphthalen-1-yl)-5,6,7,8-tetrahydropyrido[3,4-d] pyrimidin-2-yl)oxy) heptyl) piperidin-4-yl)-6-fluoro-1-oxoisoindolin-2-yl) piperidine-2,6-dione 75;

3-(4-(1-(7-(2-(4-((S)-4-acryloyl-2-methylpiperazin-1-yl)-6-fluoro-1-(2-isopropyl-phenyl)-2-oxo-1,2-dihydro-pyrido[2,3-d]pyrimidin-7-yl)-3-fluorophenoxy) heptyl) piperidin-4-yl)-6-fluoro-1-oxoisoindolin-2-yl) piperidine-2,6-dione 72;

3-(6-fluoro-4-(1-(7-(3-fluoro-2-(6-fluoro-1-(2-isopropylphenyl)-4-((S)-2-methyl-4-propionylpiperazin-1-yl)-2-oxo-1,2-dihydropyrido[2,3-d]pyrimidin-7-yl) phenoxy) heptyl)-piperidin-4-yl)-1-oxoisoindolin-2-yl) piperidine-2,6-dione 73;

3-(4-(1-(7-(2-(4-((S)-4-(2-chloroacryloyl)-2-methylpiperazin-1-yl)-6-fluoro-1-(2-isopropylphenyl)-2-oxo-1,2-dihydropyrido[2,3-d]pyrimidin-7-yl)-3-fluorophenoxy) heptyl)-piperidin-4-yl)-6-fluoro-1-oxoisoindolin-2-yl) piperidine-2,6-dione 100;

3-(4-(1-(7-(2-(4-((S)-4-(2-chloroacryloyl)-2-methylpiperazin-1-yl)-6-fluoro-1-(2-isopropyl-4-methylpyridin-3-yl)-2-oxo-1,2-dihydropyrido[2,3-d]pyrimidin-7-yl)-3-fluoro-phenoxy) heptyl) piperidin-4-yl)-6-fluoro-1-oxoisoindolin-2-yl) piperidine-2,6-dione 122;

3-(4-(1-(7-(2-(4-((S)-4-acryloyl-2-methylpiperazin-1-yl)-6-fluoro-1-(2-isopropyl-4-methylpyridin-3-yl)-2-oxo-1,2-dihydropyrido[2,3-d]pyrimidin-7-yl)-3-fluorophenoxy) heptyl)-piperidin-4-yl)-6-fluoro-1-oxoisoindolin-2-yl) piperidine-2,6-dione 124;

3-(4-(1-(7-(4-(4-((S)-4-(2-Chloroacryloyl)-2-methylpiperazin-1-yl)-6-fluoro-7-(2-fluoro-6-hydroxyphenyl)-2-oxopyrido[2,3-d]pyrimidin-1 (2H)-yl)-3-isopropylphenyl) heptyl)-piperidin-4-yl)-6-fluoro-1-oxoisoindolin-2-yl) piperidine-2,6-dione 126;

3-(4-(1-(7-(2-((2R,4aR)-3-acryloyl-11-chloro-9-fluoro-2,6-dimethyl-5-oxo-2,3,4,4a,5,6-hexahydro-1H-pyrazino[1',2': 4,5]pyrazino[2,3-c]quinolin-10-yl)-3-fluorophenoxy) heptyl)-piperidin-4-yl)-6-fluoro-1-oxoisoindolin-2-yl) piperidine-2,6-dione 64;

3-(4-(1-(7-(2-((2R,4aR)-11-chloro-9-fluoro-2,6-dimethyl-5-oxo-3-propionyl-2,3,4,4a,5,6-hexahydro-1H-pyrazino[1',2': 4,5]pyrazino[2,3-c]quinolin-10-yl)-3-fluorophenoxy)-heptyl) piperidin-4-yl)-6-fluoro-1-oxoisoindolin-2-yl) piperidine-2,6-dione 65;

3-(4-(1-(7-(2-((2R,4aR)-11-chloro-3-(2-chloroacryloyl)-9-fluoro-2,6-dimethyl-5-oxo-2,3,4,4a,5,6-hexahydro-1H-pyrazino[11,2': 4,5]pyrazino[2,3-c]quinolin-10-yl)-3-fluorophenoxy)-heptyl) piperidin-4-yl)-6-fluoro-1-oxoisoindolin-2-yl) piperidine-2,6-dione 104;

3-(4-(1-(7-((2R,4aR)-3-acryloyl-11-chloro-9-fluoro-10-(2-fluoro-6-hydroxyphenyl)-2-methyl-5-oxo-1,2,3,4,4a,5-hexahydro-6H-pyrazino[1',2': 4,5]pyrazino[2,3-c] quinolin-6-yl)-heptyl) piperidin-4-yl)-6-fluoro-1-oxoisoindolin-2-yl) piperidine-2,6-dione 66;

3-(4-(1-(7-((2R,4aR)-11-chloro-9-fluoro-10-(2-fluoro-6-hydroxyphenyl)-2-methyl-5-oxo-3-propionyl-1,2,3,4,4a,5-hexahydro-6H-pyrazino[1',2': 4,5]pyrazino[2,3-c] quinolin-6-yl)-heptyl) piperidin-4-yl)-6-fluoro-1-oxoisoindolin-2-yl) piperidine-2,6-dione 67;

2-((2R,4aR)-11-chloro-6-(7-(4-(2-(2,6-dioxopiperidin-3-yl)-6-fluoro-1-oxoisoindolin-4-yl) piperidin-1-yl) heptyl)-9-fluoro-2-methyl-5-oxo-3-propionyl-2,3,4,4a,5,6-hexahydro-1H-pyrazino[1',2': 4,5]pyrazino[2,3-c] quinolin-10-yl)-3-fluorophenyl propionate 95; or 3-(4-(1-(7-((2R,4aR)-11-chloro-3-(2-chloroacryloyl)-9-fluoro-10-(2-fluoro-6-hydroxy-phenyl)-2-methyl-5-oxo-1,2,3,4,4a,5-hexahydro-6H-pyrazino[1',2': 4,5] pyrazino[2,3-c]quinolin-6-yl) heptyl) piperidin-4-yl)-6-fluoro-1-oxoisoindolin-2-yl) piperidine-2,6-dione 125;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

27. A pharmaceutical composition comprising a compound of claim 1, and a pharmaceutically acceptable excipient.

28. A method of inhibiting the activity of RAS in a biological sample, comprising contacting one or more cells in the biological sample with an effective amount of a compound of claim 1.

29. A method of treating or ameliorating a disease, disorder, or condition associated with a RAS, comprising administering to a subject in need thereof a therapeutically effective amount of a compound of claim 1.

* * * * *